(12) United States Patent
Hanan et al.

(10) Patent No.: US 11,279,735 B2
(45) Date of Patent: Mar. 22, 2022

(54) CYCLIC PEPTIDE ANTIBIOTICS

(71) Applicant: Genentech, Inc., South San Francisco, CA (US)

(72) Inventors: Emily J. Hanan, South San Francisco, CA (US); Georgette Castanedo, South San Francisco, CA (US); Marie Gabrielle Braun, South San Francisco, CA (US); Keira Garland, South San Francisco, CA (US); Peter Andrew Smith, South San Francisco, CA (US); Richard Pastor, South San Francisco, CA (US); Paul Gibbons, South San Francisco, CA (US); Yunxing Cheng, Beijing (CN); Guosheng Wu, Beijing (CN); Yuhong Fu, Beijing (CN); Po-Wai Yuen, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/816,969

(22) Filed: Mar. 12, 2020

(65) Prior Publication Data
US 2020/0331968 A1 Oct. 22, 2020

Related U.S. Application Data

(63) Continuation of application No. PCT/CN2018/105821, filed on Sep. 14, 2018.

(60) Provisional application No. 62/559,244, filed on Sep. 15, 2017.

(51) Int. Cl.
*C07K 11/02* (2006.01)
*A61K 38/00* (2006.01)

(52) U.S. Cl.
CPC .............. *C07K 11/02* (2013.01); *A61K 38/00* (2013.01)

(58) Field of Classification Search
CPC ....... A61K 38/00; A61P 31/00; C07D 273/00; C07D 413/12; C07K 11/02
See application file for complete search history.

(56) References Cited

U.S. PATENT DOCUMENTS

| 5,384,309 A | 1/1995 | Barker et al. |
| 10,787,490 B2 * | 9/2020 | Bhandari ................. A61P 1/04 |

FOREIGN PATENT DOCUMENTS

| JP | S53-141202 A | 8/1978 |
| JP | S55-47644 A | 4/1980 |

OTHER PUBLICATIONS

"International Preliminary Report on Patentability—PCT/CN2018/105821" (dated Mar. 17, 2020), pp. 1-8 (dated Mar. 26, 2020).
"International Search Report—PCT/CN2018/105821":pp. 1-6 (dated Dec. 18, 2018).
Kiho, T., et al., "Synthesis and Antimicrobial Activity of Novel Globomycin Analogues" Bioorg Med Chem Lett 13(14):2315-2318 (Jul. 21, 2003).
Kiho, T., et al., "Total synthesis and NMR conformational study of signal peptidase II inhibitors, globomycin and SF-1902 A5" Tetrahedron 59(10):1685-1697 (Mar. 3, 2003).
Sarabia, F., et al., "Solid Phase Synthesis of Globomycin and SF-1902 A5" J Org Chem 87(7):2132-2144 (Apr. 1, 2011).

\* cited by examiner

*Primary Examiner* — Marcela M Cordero Garcia
(74) *Attorney, Agent, or Firm* — Robert C. Hall

(57) ABSTRACT

Provided herein are antibacterial compounds, wherein the compounds in some embodiments have broad spectrum bioactivity. In various embodiments, the compounds act by inhibition of lipoprotein signal peptidase II (LspA), a key protein in bacteria. Pharmaceutical compositions and methods for treatment using the compounds described herein are also provided.

28 Claims, No Drawings

CYCLIC PEPTIDE ANTIBIOTICS

CROSS REFERENCE TO RELATED APPLICATIONS

This application is a continuation of International Patent Application No. International Patent Application No. PCT/CN 2018/105821 filed on Sep. 14, 2018, and is entitled to the benefit of International Patent Application No. PCT/CN2018/101004 filed on Aug. 17, 2018 and U.S. Provisional Application No. 62/559,244 filed on Sep. 15, 2017, the disclosures of which are incorporated herein by reference.

BACKGROUND OF THE INVENTION

Antibiotic resistance is a serious and growing phenomenon in contemporary medicine and has emerged as a major public health concern of the 21st century. Therefore, novel classes of broad-spectrum antibiotics, especially those that target novel mechanisms of action, are needed to treat multidrug-resistant pathogens. The Type II signal peptidase LspA plays a critical role in the biosynthesis of Gram-negative bacterial lipoproteins. Blocking of lipoprotein synthesis via inhibition of LspA function not only depletes essential as well as virulence-associated lipoproteins but can also lead to accumulation of mislocalized unprocessed liporptoeins, all of which leads to bacterial cell death. LspA inhibitors thus offer a novel approach to combatting Gram-negative bacterial infection.

SUMMARY OF THE INVENTION

Described herein are novel macrocyclic compounds for the treatment of microbial infections, such as for the treatment of bacterial infections. In various embodiments, the present disclosure provides cyclic peptide, depsipeptide and peptide-containing compounds for the treatment of bacterial infections. In various embodiments, the present disclosure provides classes and subclasses of chemical compounds structurally related to globomycin for the treatment of bacterial infections. In various embodiments, the cyclic peptide, depsipeptide and peptide containing compounds act by inhibition of lipoprotein signal peptidase II (IspA), a key enzyme involved in the posttranslational processing of lipoproteins in bacteria.

Disclosed herein is a compound of Formula (I):

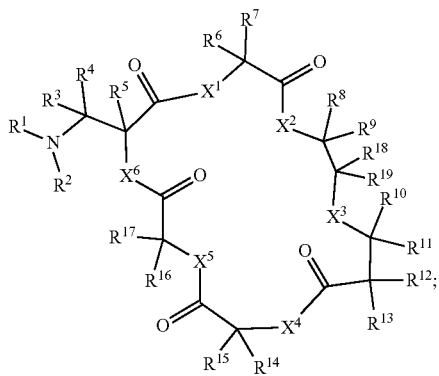

Formula (I)

wherein:
$X^1$ is —O— or —$NR^{1a}$—;
$X^2$ is —O— or —$NR^{2a}$—;
$X^3$ is —O— or —$NR^{3a}$—;
$X^4$ is —O— or —$NR^{4a}$—;
$X^5$ is —O— or —$NR^{5a}$—;
$X^6$ is —O— or —$NR^{6a}$—;
provided that at least one of $X^1$, $X^2$, $X^3$, $X^4$, $X^5$, or $X^6$ is —O—; $R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2R^a$, —S(=O)$_2NR^bR^c$, —C(=O)$R^a$, —C(=O)O$R^b$, —C(=O)N$R^bR^c$, or —(C=N$R^b$)N$R^bR^c$;
or $R^1$ and $R^2$ are taken together with the nitrogen atom to which they are attached to form an optionally substituted heterocycloalkyl;
$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
or $R^3$ and $R^4$ are taken together with the carbon atom to which they are attached to form an oxo;
$R^5$ is hydrogen, halogen, optionally substituted $C_1$-$C_6$ alkyl, optionally substituted $C_2$-$C_6$ alkenyl, or optionally substituted $C_2$-$C_6$ alkynyl;
$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{10}$ and $R^{12}$ are taken together to form an optionally substituted cycloalkyl or an optionally substituted cycloalkenyl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

Also disclosed herein is a compound of Formula (II):

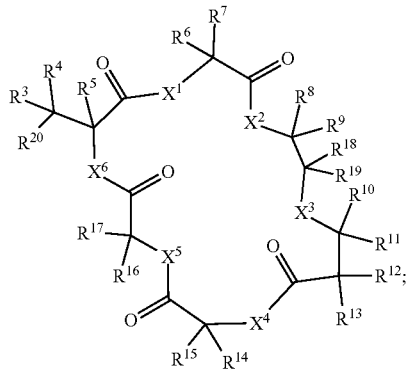

Formula (II)

wherein:
$X^1$ is —O— or —$NR^{1a}$—;
$X^2$ is —O— or —$NR^{2a}$—;
$X^3$ is —O— or —$NR^{3a}$—;
$X^4$ is —O— or —$NR^{4a}$—;
$X^5$ is —O— or —$NR^{5a}$—;
$X^6$ is —O— or —$NR^{6a}$—;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;

$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$R^a$, —S(=O)$_2$$NR^bR^c$, —C(=O)$R^a$, —C(=O)$OR^b$, —C(=O)$NR^bR^c$, or —(C=$NR^b$)$NR^bR^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{10}$ and $R^{12}$ are taken together to form an optionally substituted cycloalkyl or an optionally substituted cycloalkenyl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{20}$ is —$NR^1R^2$ or —OH;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

Also disclosed herein is a compound of Formula (III):

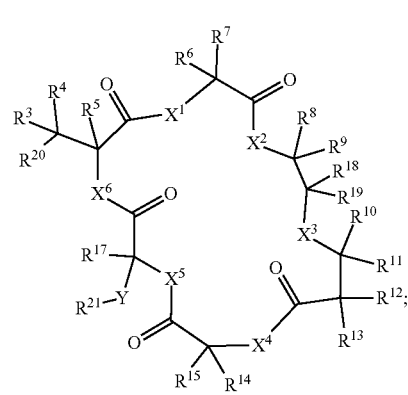

Formula (III)

wherein:
$X^1$ is —O— or —$NR^{1a}$—;
$X^2$ is —O— or —$NR^{2a}$—;
$X^3$ is —O— or —$NR^{3a}$—;
$X^4$ is —O— or —$NR^{4a}$—;
$X^5$ is —O— or —$NR^{5a}$—;
$X^6$ is —O— or —$NR^{6a}$—;
provided that at least one of $X^1$, $X^2$, $X^3$, $X^4$, $X^5$, or $X^6$ is —O—;

Y is a bond or optionally substituted $C_1$-$C_6$ alkylene;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;

$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, optionally substituted ($C_1$-$C_6$ alkyl)heteroaryl, —S(=O)$_2$$R^a$, —S(=O)$_2$$NR^bR^c$, —C(=O)$R^a$, —C(=O)$OR^b$, or —C(=O)$NR^bR^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted heterocycloalkyl, optionally substituted (C$_1$-C$_6$ alkyl)aryl, or optionally substituted (C$_1$-C$_6$ alkyl)heteroaryl;

R$^8$ and R$^9$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted (C$_1$-C$_6$ alkyl)heterocycloalkyl, optionally substituted (C$_1$-C$_6$ alkyl)aryl, or optionally substituted (C$_1$-C$_6$ alkyl)heteroaryl;

R$^{10}$ and R$^{11}$ are each independently hydrogen, halogen, optionally substituted C$_1$-C$_{20}$ alkyl, optionally substituted C$_2$-C$_{20}$ alkenyl, optionally substituted C$_2$-C$_{20}$ alkynyl, optionally substituted cycloalkyl, optionally substituted (C$_1$-C$_6$ alkyl)cycloalkyl, optionally substituted (C$_1$-C$_6$ alkyl)heterocycloalkyl, optionally substituted (C$_1$-C$_6$ alkyl)aryl, or optionally substituted (C$_1$-C$_6$ alkyl)heteroaryl;

R$^{12}$ and R$^{13}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted (C$_1$-C$_6$ alkyl)heterocycloalkyl, optionally substituted (C$_1$-C$_6$ alkyl)aryl, or optionally substituted (C$_1$-C$_6$ alkyl)heteroaryl;

or R$^{10}$ and R$^{12}$ are taken together to form an optionally substituted cycloalkyl or an optionally substituted cycloalkenyl;

R$^{14}$ and R$^{15}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted (C$_1$-C$_6$ alkyl)heterocycloalkyl, optionally substituted (C$_1$-C$_6$ alkyl)aryl, or optionally substituted (C$_1$-C$_6$ alkyl)heteroaryl;

or R$^{14}$ and R$^{4a}$ are taken together with the atoms to which they are attached to form an optionally substituted heterocycloalkyl;

R$^{17}$ is hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted (C$_1$-C$_6$ alkyl)heterocycloalkyl, optionally substituted (C$_1$-C$_6$ alkyl)aryl, or optionally substituted (C$_1$-C$_6$ alkyl)heteroaryl;

R$^{18}$ and R$^{19}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

or R$^{18}$ and R$^{19}$ are taken together with the carbon atom to which they are attached to form an oxo;

R$^{20}$ is hydroxyl or —NR$^1$R$^2$;

R$^{21}$ is optionally substituted cycloalkyl;

each R$^a$ is independently optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, or optionally substituted heteroaryl;

each R$^b$ and R$^c$ is independently hydrogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, or optionally substituted heteroaryl;

or R$^b$ and R$^c$ are taken together with the nitrogen atom to which they are attached to form an optionally substituted heterocycloalkyl;

or a pharmaceutically acceptable salt, solvate, or stereoisomer thereof.

Also disclosed herein is a compound of Formula (IV):

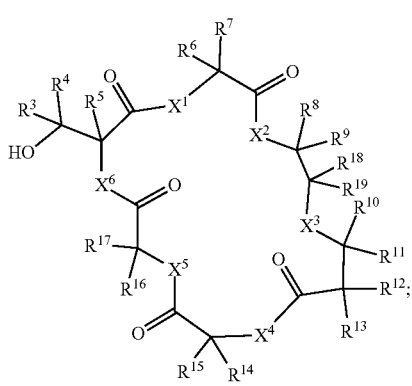

Formula (IV)

wherein:

X$^1$ is —O— or —NR$^{1a}$—;
X$^2$ is —O— or —NR$^{2a}$—;
X$^3$ is —O— or —NR$^{3a}$—;
X$^4$ is —O— or —NR$^{4a}$—;
X$^5$ is —O— or —NR$^{5a}$—;
X$^6$ is —O— or —NR$^{6a}$—;

provided that at least one of X$^1$, X$^2$, X$^3$, X$^4$, X$^5$, or X$^6$ is —O—;

R$^{1a}$, R$^{2a}$, R$^{3a}$, R$^{4a}$, R$^{5a}$, and R$^{6a}$ are each independently hydrogen or optionally substituted C$_1$-C$_6$ alkyl;

R$^3$ and R$^4$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, or optionally substituted heteroaryl;

or R$^3$ and R$^4$ are taken together with the carbon atom to which they are attached to form an oxo;

R$^5$ is hydrogen, halogen, optionally substituted C$_1$-C$_6$ alkyl, optionally substituted C$_2$-C$_6$ alkenyl, or optionally substituted C$_2$-C$_6$ alkynyl;

R$^6$ and R$^7$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

R$^8$ and R$^9$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

R$^{10}$ is optionally substituted branched C$_3$-C$_{20}$ alkyl or optionally substituted C$_{10}$-C$_{20}$ alkyl;

R$^{11}$ is hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

R$^{12}$ is optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

R$^{13}$ is hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl) heteroaryl;

R$^{14}$ and R$^{15}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

or R$^{14}$ and R$^{4a}$ are taken together with the atoms to which they are attached to form an optionally substituted heterocycloalkyl;

R$^{16}$ and R$^{17}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

R$^{18}$ and R$^{19}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, optionally substituted heteroaryl, or optionally substituted (C$_1$-C$_6$ alkyl)heteroaryl;

or R$^{18}$ and R$^{19}$ are taken together with the carbon atom to which they are attached to form an oxo;

each R$^a$ is independently optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, or optionally substituted heteroaryl;

each R$^b$ and R$^c$ is independently hydrogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, or optionally substituted heteroaryl;

or R$^b$ and R$^c$ are taken together with the nitrogen atom to which they are attached to form an optionally substituted heterocycloalkyl;

or a pharmaceutically acceptable salt, solvate, or stereoisomer thereof;

provided that the compound of Formula (IV) is not:

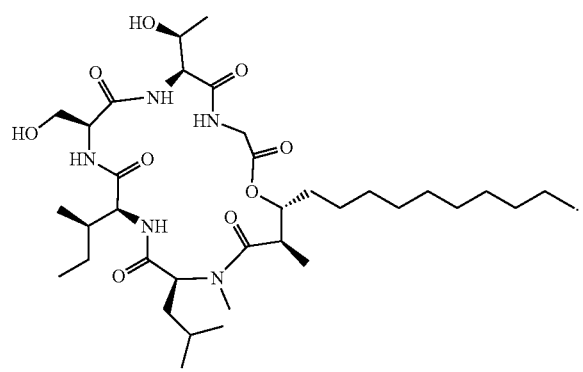 [SMILES: CCCCCCCCCC[C@H]1OC(=O)CNC(=O)[C@H]([C@H](C)O)NC(=O)[C@H](CO)NC(=O)[C@H]([C@H](C)CC)NC(=O)[C@H](CC(C)C)N(C)C(=O)[C@@H]1C]

Also disclosed herein is a compound of Formula (V):

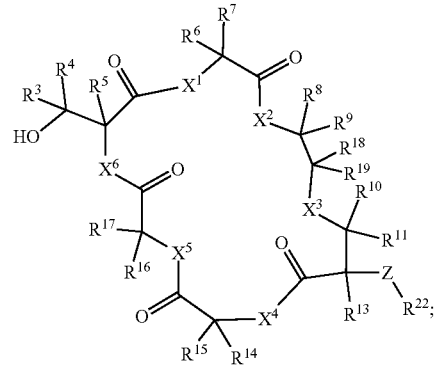

Formula (V)

wherein:
X$^1$ is —O— or —NR$^{1a}$—;
X$^2$ is —O— or —NR$^{2a}$—;
X$^3$ is —O— or —NR$^{3a}$—;
X$^4$ is —O— or —NR$^{4a}$—;
X$^5$ is —O— or —NR$^{5a}$—;
X$^6$ is —O— or —NR$^{6a}$—;
R$^{1a}$, R$^{2a}$, R$^{3a}$, R$^{4a}$, R$^{5a}$, and R$^{6a}$ are each independently hydrogen or optionally substituted C$_1$-C$_6$ alkyl;
R$^3$ and R$^4$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted cycloalkyl, optionally substituted heterocycloalkyl, optionally substituted aryl, or optionally substituted heteroaryl;
or R$^3$ and R$^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ is optionally substituted $C_2$-$C_{20}$ alkyl;

$R^{11}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

Z is —$CR^{23}R^{24}$—, —O—, or —$NR^{25}$—; $R^{22}$ is optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{23}$, $R^{24}$, and $R^{25}$ are each independently hydrogen or optionally substituted $C_1$-$C_6$ alkyl;

$R^{13}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

Also disclosed herein is a pharmaceutical composition comprising the compound disclosed herein, or a pharmaceutically acceptable salt, solvate, or stereoisomer thereof, and a pharmaceutically acceptable excipient.

Also disclosed herein is the use of a compound disclosed herein, or a pharmaceutically acceptable salt, solvate, or stereoisomer thereof, for preparation of a medicament for treatment of a bacterial infection in a patient.

Also disclosed herein is a method of treatment of a bacterial infection in a mammal, comprising administering to the mammal an effective amount of a compound disclosed herein, or a pharmaceutically acceptable salt, solvate, or stereoisomer thereof, to the mammal at a frequency and for a duration sufficient to provide a beneficial effect to the mammal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to an optionally substituted straight-chain, or optionally substituted branched-chain saturated hydrocarbon monoradical having from one to about ten carbon atoms, or from one to six carbon atoms, wherein a sp3-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein a sp2-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkenyl is optionally substituted with oxo, halogen, —CN, —$CF_3$, —OH, —OMe, —$NH_2$, or —$NO_2$. In some embodiments, an alkenyl is optionally substituted with oxo, halogen, —CN, —$CF_3$, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkynyl is optionally substituted with oxo, halogen, —CN, —$CF_3$, —OH, —OMe, —$NH_2$, or —$NO_2$. In some embodiments, an alkynyl is optionally substituted with oxo, halogen, —CN, —$CF_3$, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen or methyl. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen or methyl. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, phosphorous and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen or methyl. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl. Unless stated otherwise specifically in the specification, a Heteroalkyl is optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiopheny 1), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrroly 1, phenazinyl, phenothiazinyl, phenoxazinyl, phthalazinyl, pteridinyl, pminyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen or methyl. In some embodiments, the heteroaryl is optionally substituted with halogen.

The term "oxo" means =O.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease, in some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The terms "disease" or "disorder" are used interchangeably, and are used to refer to diseases or conditions wherein a bacterial signal peptidase plays a role in the biochemical mechanisms involved in the disease or disorder such that a therapeutically beneficial effect can be achieved by acting on the enzyme. "Acting on" signal peptidase can include binding to signal peptidase and/or inhibiting the bioactivity of an signal peptidase.

Compounds

In one aspect described herein are compounds of Formula (I):

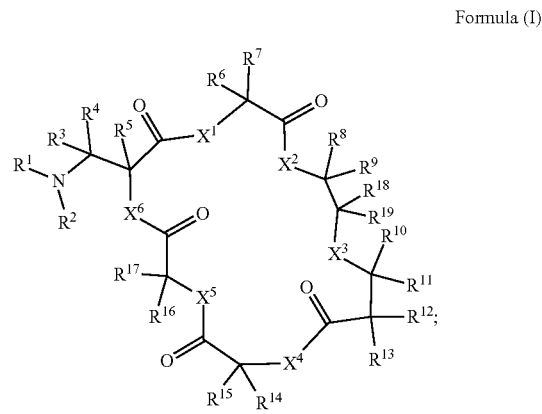

Formula (I)

wherein:
X$^1$ is —O— or —NR$^{1a}$—;
X$^2$ is —O— or —NR$^{2a}$—;
X$^3$ is —O— or —NR$^{3a}$—;
X$^4$ is —O— or —NR$^{4a}$—;
X$^5$ is —O— or —NR$^{5a}$—;
X$^6$ is —O— or —NR$^{6a}$—;
provided that at least one of X$^1$, X$^2$, X$^3$, X$^4$, X$^5$, or X$^6$ is —O—;

$R^{1a}$, $R^{2a}$, $R^{3a}$, $R^{4a}$, $R^{5a}$, and $R^{6a}$ are each independently hydrogen or optionally substituted $C_1$-$C_6$ alkyl;

$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, $-S(=O)_2R^a$, $-S(=O)_2NR^bR^c$, $-C(=O)R^a$, $-C(=O)OR^b$, $-C(=O)NR^bR^c$, or $-(C=NR^b)NR^bR^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{10}$ and $R^{12}$ are taken together to form an optionally substituted cycloalkyl or an optionally substituted cycloalkenyl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

In some embodiments of a compound of Formula (I), $R^{18}$ and $R^{19}$ are taken together with the carbon atom to which they are attached to form an oxo.

In some embodiments of a compound of Formula (I), $R^{18}$ and $R^{19}$ are each independently hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (I), $R^{18}$ and $R^{19}$ are each independently hydrogen, halogen, or optionally substituted $C_1$-$C_6$ alkyl. In some embodiments of a compound of Formula (I), $R^{18}$ and $R^{19}$ are each independently hydrogen or $C_1$-$C_6$ alkyl. In some embodiments of a compound of Formula (I), $R^{18}$ and $R^{19}$ are hydrogen.

In some embodiments the compound of Formula (I) has the structure of Formula (Ia):

Formula (Ia)

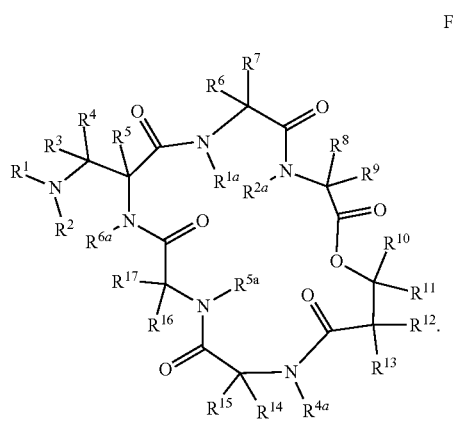

Formula (Ib)

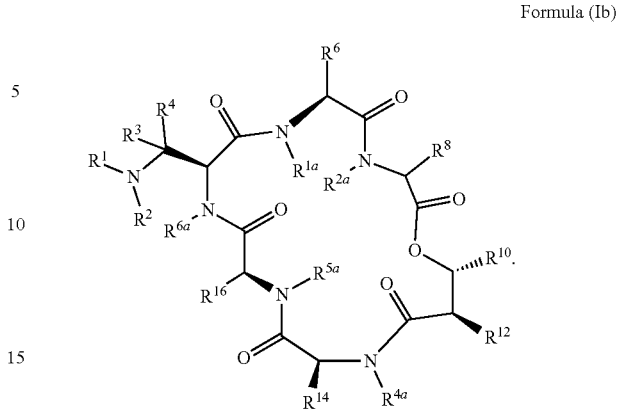

In some embodiments of a compound of Formula (I) or (Ia), $R^5$ is hydrogen or optionally substituted $C_1$-$C_6$ alkyl. In some embodiments of a compound of Formula (I) or (Ia), $R^5$ is hydrogen or $C_1$-$C_6$ alkyl. In some embodiments of a compound of Formula (I) or (Ia), $R^5$ is hydrogen.

In some embodiments of a compound of Formula (I) or (Ia), $R^7$ is hydrogen or optionally substituted $C_1$-$C_6$ alkyl. In some embodiments of a compound of Formula (I) or (Ia), $R^7$ is hydrogen or $C_1$-$C_6$ alkyl. In some embodiments of a compound of Formula (I) or (Ia), $R^7$ is hydrogen.

In some embodiments of a compound of Formula (I) or (Ia), $R^9$ is hydrogen or optionally substituted $C_1$-$C_6$ alkyl. In some embodiments of a compound of Formula (I) or (Ia), $R^9$ is hydrogen or $C_1$-$C_6$ alkyl. In some embodiments of a compound of Formula (I) or (Ia), $R^9$ is hydrogen.

In some embodiments of a compound of Formula (I) or (Ia), $R^{11}$ is hydrogen or optionally substituted $C_1$-$C_6$ alkyl. In some embodiments of a compound of Formula (I) or (Ia), $R^{11}$ is hydrogen or $C_1$-$C_6$ alkyl. In some embodiments of a compound of Formula (I) or (Ia), $R^{11}$ is hydrogen.

In some embodiments of a compound of Formula (I) or (Ia), $R^{13}$ is hydrogen or optionally substituted $C_1$-$C_6$ alkyl. In some embodiments of a compound of Formula (I) or (Ia), $R^{13}$ is hydrogen or $C_1$-$C_6$ alkyl. In some embodiments of a compound of Formula (I) or (Ia), $R^{13}$ is hydrogen.

In some embodiments of a compound of Formula (I) or (Ia), $R^{15}$ is hydrogen or optionally substituted $C_1$-$C_6$ alkyl. In some embodiments of a compound of Formula (I) or (Ia), $R^{15}$ is hydrogen or $C_1$-$C_6$ alkyl. In some embodiments of a compound of Formula (I) or (Ia), $R^{15}$ is hydrogen.

In some embodiments of a compound of Formula (I) or (Ia), $R^{17}$ is hydrogen or optionally substituted $C_1$-$C_6$ alkyl. In some embodiments of a compound of Formula (I) or (Ia), $R^{17}$ is hydrogen or $C_1$-$C_6$ alkyl. In some embodiments of a compound of Formula (I) or (Ia), $R^{17}$ is hydrogen.

In some embodiments the compound of Formula (I) or (Ia) has the structure of Formula (Ib):

In some embodiments of a compound of Formula (I), (Ia), or (Ib), $R^{1a}$ is hydrogen or $C_1$-$C_6$ alkyl. In some embodiments of a compound of Formula (I), (Ia), or (Ib), $R^{1a}$ is hydrogen. In some embodiments of a compound of Formula (I), (Ia), or (Ib), $R^{1a}$ is $C_1$-$C_6$ alkyl.

In some embodiments of a compound of Formula (I), (Ia), or (Ib), $R^{2a}$ is hydrogen or $C_1$-$C_6$ alkyl. In some embodiments of a compound of Formula (I), (Ia), or (Ib), $R^{2a}$ is hydrogen. In some embodiments of a compound of Formula (I), (Ia), or (Ib), $R^{2a}$ is $C_1$-$C_6$ alkyl.

In some embodiments of a compound of Formula (I), (Ia), or (Ib), $R^{5a}$ is hydrogen or $C_1$-$C_6$ alkyl. In some embodiments of a compound of Formula (I), (Ia), or (Ib), $R^{5a}$ is hydrogen. In some embodiments of a compound of Formula (I), (Ia), or (Ib), $R^{5a}$ is $C_1$-$C_6$ alkyl.

In some embodiments of a compound of Formula (I), (Ia), or (Ib), $R^{6a}$ is hydrogen or $C_1$-$C_6$ alkyl. In some embodiments of a compound of Formula (I), (Ia), or (Ib), $R^{6a}$ is hydrogen. In some embodiments of a compound of Formula (I), (Ia), or (Ib), $R^{6a}$ is $C_1$-$C_6$ alkyl.

In some embodiments the compound of Formula (I), (Ia), or (Ib) has the structure of Formula (Ic):

Formula (Ic)

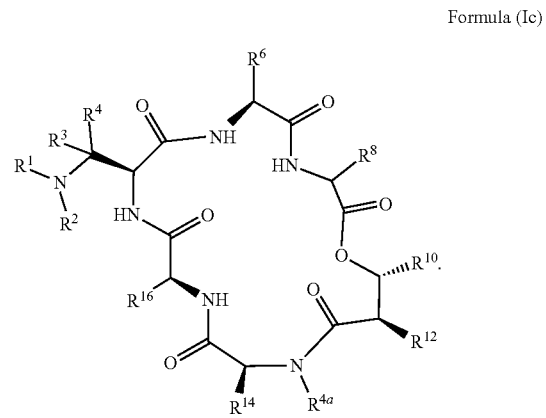

In some embodiments of a compound of Formula (I), (Ia), (Ib), or (Ic), $R^{4a}$ is hydrogen or $C_1$-$C_6$ alkyl. In some embodiments of a compound of Formula (I), (Ia), (Ib), or (Ic), $R^{4a}$ is hydrogen. In some embodiments of a compound of Formula (I), (Ia), (Ib), or (Ic), $R^{4a}$ is $C_1$-$C_6$ alkyl.

In some embodiments of a compound of Formula (I), (Ia), (Ib), or (Ic), $R^{14}$ and $R^{4a}$ are taken together with the atoms to which they are attached to form an optionally substituted 5- or 6-membered heterocycloalkyl. In some embodiments of a compound of Formula (I), (Ia), (Ib), or (Ic), $R^{14}$ and $R^{4a}$ are taken together with the atoms to which they are attached to form an optionally substituted 5-membered heterocycloalkyl. In some embodiments of a compound of Formula (I), (Ia), (Ib), or (Ic), $R^{14}$ and $R^{4a}$ are taken together with the atoms to which they are attached to form an optionally substituted 6-membered heterocycloalkyl.

In some embodiments of a compound of Formula (I), (Ia), (Ib), or (Ic), each $R^3$ and $R^4$ are independently hydrogen or optionally substituted $C_1$-$C_6$ alkyl. In some embodiments of a compound of Formula (I), (Ia), (Ib), or (Ic), each $R^3$ and $R^4$ are independently hydrogen or $C_1$-$C_6$ alkyl. In some embodiments of a compound of Formula (I), (Ia), (Ib), or (Ic), each $R^3$ and $R^4$ are hydrogen. In some embodiments of a compound of Formula (I), (Ia), (Ib), or (Ic), $R^3$ is hydrogen and $R^4$ is $C_1$-$C_6$ alkyl.

In some embodiments of a compound of Formula (I), (Ia), (Ib), or (Ic), $R^6$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (I), (Ia), (Ib), or (Ic), $R^6$ is hydrogen, optionally substituted $C_1$-$C_6$ alkyl, or optionally substituted heterocycloalkyl. In some embodiments of a compound of Formula (I), (Ia), (Ib), or (Ic), $R^6$ is optionally substituted $C_1$-$C_6$ alkyl or optionally substituted heterocycloalkyl. In some embodiments of a compound of Formula (I), (Ia), (Ib), or (Ic), $R^6$ is optionally substituted heterocycloalkyl selected from aziridinyl, azetidinyl, pyrrolidinyl, piperidinyl, or piperazinyl. In some embodiments of a compound of Formula (I), (Ia), (Ib), or (Ic), $R^6$ is $C_1$-$C_6$ alkyl optionally substituted with one, two, or three halogen, —$OR^b$, —$NR^bR^c$, —NC(=$NR^b$)$NR^bR^c$, —S(=O)$_2R^a$, —$NR^bS$(=O)$_2R^a$, —S(=O)$_2NR^bR^c$, —C(=O)$R^a$, —OC(=O)$R^a$, —C(=O)$OR^a$, —OC(=O)$OR^b$, —C(=O)$NR^bR^c$, —$NR^bC$(=O)[($R^d$)$_2$]$_{1-4}NR^bR^c$, —OC[($R^d$)$_2$]$_{2-4}OR^b$, —OC[($R^d$)$_2$]$_{2-4}NR^bR^c$, —OC[($R^d$)$_2$]$_{2-4}OC$[($R^d$)$_2$]$_{2-4}NR^bR^c$, —OC[($R^d$)$_2$]$_{2-4}NC$(=$NR^b$)$NR^bR^c$, —OC(=O)$NR^bR^c$, —$NR^bC$(=O)$NR^bR^c$, —$NR^bC$(=O)$R^a$, —$NR^bC$(=O)$OR^b$, —O-(optionally substituted heterocycloalkyl), —O-(optionally substituted aryl), or heteroaryl; and each $R^d$ is independently hydrogen, halogen, —OH, —OCH$_3$, or $C_1$-$C_6$ alkyl. In some embodiments of a compound of Formula (I), (Ia), (Ib), or (Ic), $R^6$ is $C_1$-$C_6$ alkyl optionally substituted with halogen, —$OR^b$, —$NR^bR^c$, —S(=O)$_2R^a$, —$NR^bS$(=O)$_2R^a$, —S(=O)$_2NR^bR^c$, —C(=O)$R^a$, —OC(=O)$R^a$, —C(=O)$OR^a$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, or heteroaryl. In some embodiments of a compound of Formula (I), (Ia), (Ib), or (Ic), $R^6$ is $C_1$-$C_6$ alkyl optionally substituted with one, two, or three —$OR^b$. In some embodiments of a compound of Formula (I), (Ia), (Ib), or (Ic), $R^6$ is selected from:

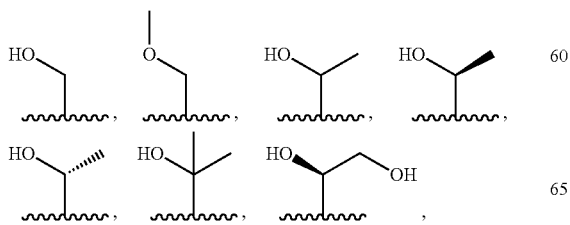

-continued

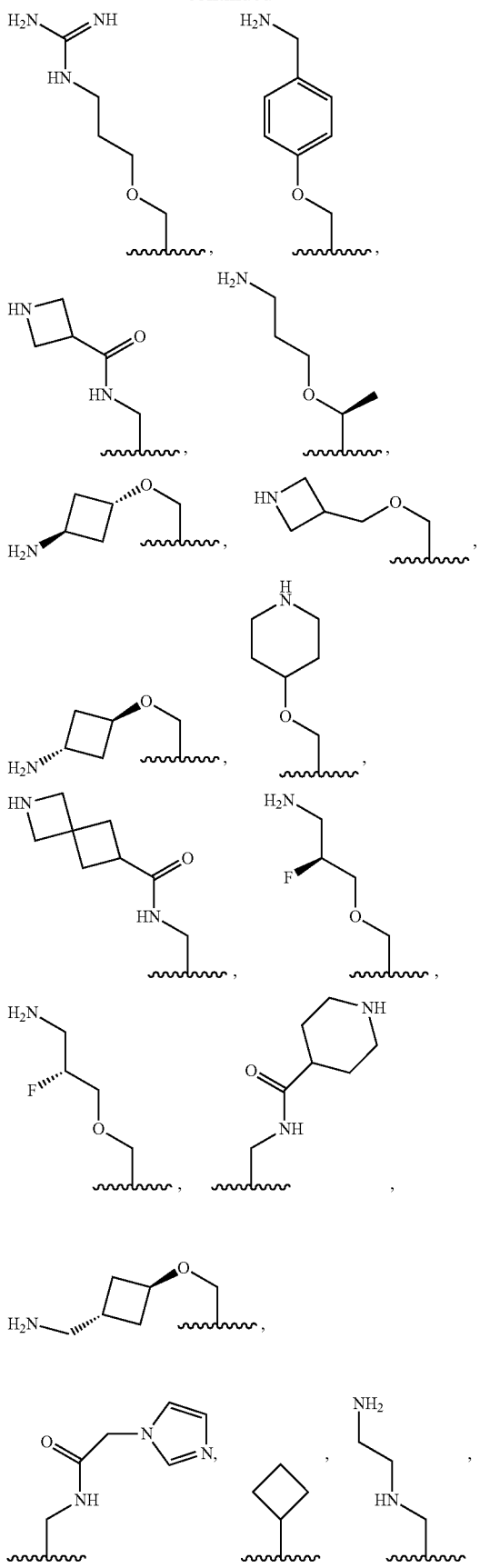

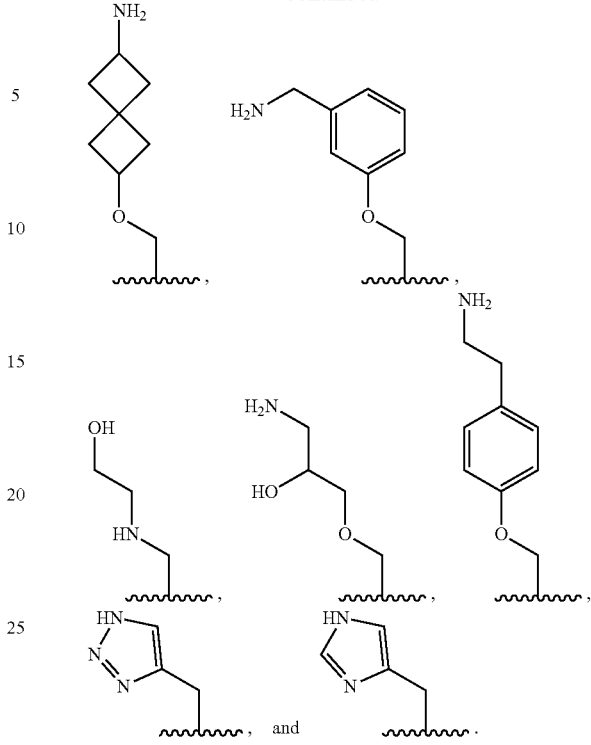

In some embodiments of a compound of Formula (I), (Ia), (Ib), or (Ic), $R^8$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (I), (Ia), (Ib), or (Ic), $R^8$ is hydrogen or $C_1$-$C_6$ alkyl. In some embodiments of a compound of Formula (I), (Ia), (Ib), or (Ic), $R^8$ is hydrogen. In some embodiments of a compound of Formula (I), (Ia), (Ib), or (Ic), $R^8$ is $C_1$-$C_6$ alkyl.

In some embodiments of a compound of Formula (I), (Ia), (Ib), or (Ic), $R^{10}$ is optionally substituted $C_1$-$C_{20}$ alkyl, optionally substituted $C_2$-$C_{20}$ alkenyl, or optionally substituted ($C_1$-$C_6$ alkyl)cycloalkyl. In some embodiments of a compound of Formula (I), (Ia), (Ib), or (Ic), $R^{10}$ is hydrogen, halogen, optionally substituted $C_1$-$C_{20}$ alkyl, optionally substituted cycloalkyl, optionally substituted heterocycloalkyl, optionally substituted aryl, or optionally substituted heteroaryl. In some embodiments of a compound of Formula (I), (Ia), (Ib), or (Ic), $R^{10}$ is hydrogen or optionally substituted $C_1$-$C_{20}$ alkyl. In some embodiments of a compound of Formula (I), (Ia), (Ib), or (Ic), $R^{10}$ is optionally substituted $C_1$-$C_{20}$ alkyl. In some embodiments of a compound of Formula (I), (Ia), (Ib), or (Ic), $R^{10}$ is $C_1$-$C_{20}$ alkyl optionally substituted with one, two, or three halogen, —OH, —OCH$_3$, cycloalkyl, or aryl. In some embodiments of a compound of Formula (I), (Ia), (Ib), or (Ic), $R^{10}$ is $C_1$-$C_{20}$ alkyl optionally substituted with one, two, or three halogen, —OH, or —OCH$_3$. In some embodiments of a compound of Formula (I), (Ia), (Ib), or (Ic), $R^{10}$ is $C_1$-$C_{20}$ alkyl optionally substituted with one aryl or one cycloalkyl. In some embodiments of a compound of Formula (I), (Ia), (Ib), or (Ic), $R^{10}$ is optionally substituted $C_8$-$C_{12}$ alkyl. In some embodiments of a compound of Formula (I), (Ia), (Ib), or (Ic), $R^{10}$ is $C_8$-$C_{12}$ alkyl optionally substituted with one, two, or three halogen, —OH, or —OCH$_3$. In some embodiments of a compound of Formula (I), (Ia), (Ib), or (Ic), $R^{10}$ is optionally substituted $C_1$-$C_8$ alkyl. In some embodiments of a compound of Formula (I), (Ia), (Ib), or (Ic), $R^{10}$ is $C_1$-$C_8$ alkyl optionally substituted with one, two, or three halogen, —OH, —OCH$_3$, cycloalkyl, or aryl. In some embodiments of a compound of Formula (I), (Ia), (Ib), or (Ic), $R^{10}$ is $C_1$-$C_8$ alkyl optionally substituted with one, two, or three halogen, —OH, or —OCH$_3$. In some embodiments of a compound of Formula (I), (Ia), (Ib), or (Ic), $R^{10}$ is $C_1$-$C_8$ alkyl optionally substituted with one aryl or one cycloalkyl. In some embodiments of a compound of Formula (I), (Ia), (Ib), or (Ic), $R^{10}$ is optionally substituted $C_{11}$-$C_{20}$ alkyl. In some embodiments of a compound of Formula (I), (Ia), (Ib), or (Ic), $R^{10}$ is optionally substituted $C_6$-$C_{12}$ alkyl. In some embodiments of a compound of Formula (I), (Ia), (Ib), or (Ic), $R^{10}$ is optionally substituted $C_8$-$C_{15}$ alkyl. In some embodiments of a compound of Formula (I), (Ia), (Ib), or (Ic), $R^{10}$ is $C_1$-$C_{20}$ alkyl. In some embodiments of a compound of Formula (I), (Ia), (Ib), or (Ic), $R^{10}$ is $C_8$-$C_{12}$ alkyl. In some embodiments of a compound of Formula (I), (Ia), (Ib), or (Ic), $R^{10}$ is $C_{11}$-$C_{20}$ alkyl. In some embodiments of a compound of Formula (I), (Ia), (Ib), or (Ic), $R^{10}$ is $C_6$-$C_{12}$ alkyl. In some embodiments of a compound of Formula (I), (Ia), (Ib), or (Ic), $R^{10}$ is $C_8$-$C_{15}$ alkyl. In some embodiments of a compound of Formula (I), (Ia), (Ib), or (Ic), $R^{10}$ is hydrogen.

In some embodiments of a compound of Formula (I), (Ia), (Ib), or (Ic), $R^{10}$ is

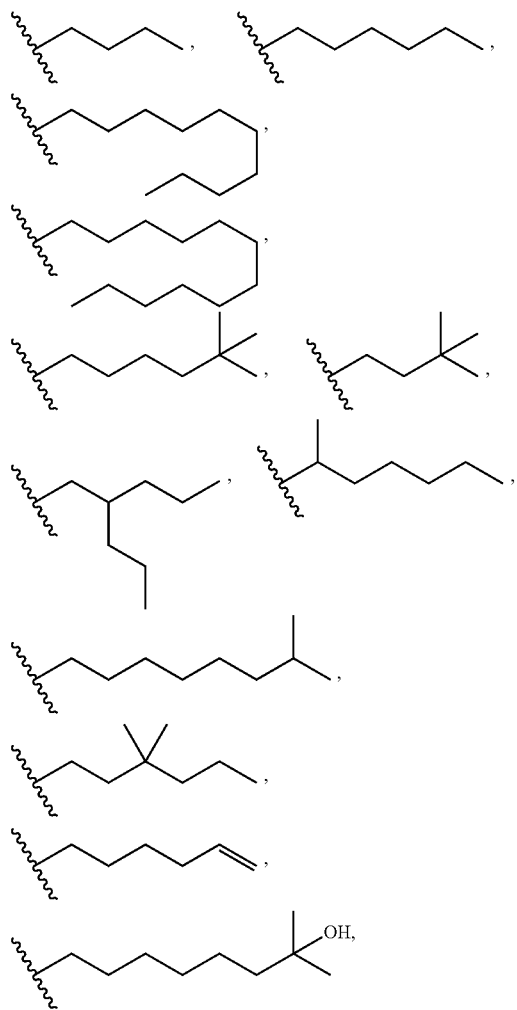

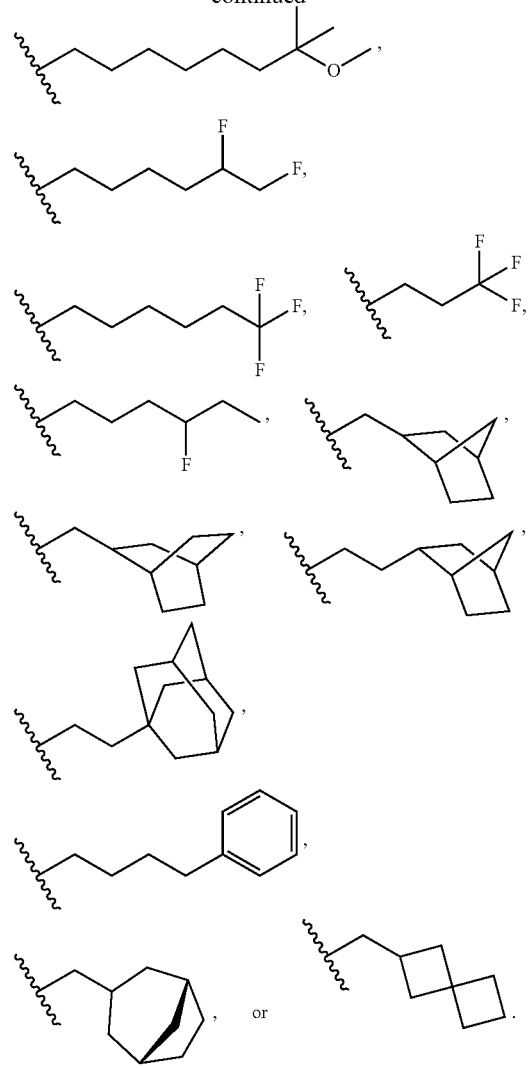

In some embodiments of a compound of Formula (I), (Ia), (Ib), or (Ic), $R^{12}$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (I), (Ia), (Ib), or (Ic), $R^{12}$ is halogen, optionally substituted $C_1$-$C_6$ alkyl, optionally substituted ($C_1$-$C_6$ alkyl)aryl, or optionally substituted ($C_1$-$C_6$ alkyl)cycloalkyl. In some embodiments of a compound of Formula (I), (Ia), (Ib), or (Ic), $R^{12}$ is $C_1$-$C_6$ alkyl, $C_1$-$C_6$ haloalkyl, ($C_1$-$C_6$ alkyl)aryl, or ($C_1$-$C_6$ alkyl)cycloalkyl; wherein the aryl is optionally substituted with one, two, or three halogen, $C_1$-$C_6$ alkyl, $C_1$-$C_6$ haloalkyl, —OH, —OCH$_3$, or aryl. In some embodiments of a compound of Formula (I), (Ia), (Ib), or (Ic), $R^{12}$ is hydrogen or optionally substituted $C_1$-$C_6$ alkyl. In some embodiments of a compound of Formula (I), (Ia), (Ib), or (Ic), $R^{12}$ is optionally substituted $C_1$-$C_6$ alkyl. In some embodiments of a compound of Formula (I), (Ia), (Ib), or (Ic), $R^{12}$ is $C_1$-$C_6$ alkyl. In some embodiments of a compound of Formula (I), (Ia), (Ib), or (Ic), $R^{12}$ is methyl or ethyl. In some embodiments of a compound of Formula (I), (Ia), (Ib), or (Ic), $R^{12}$ is methyl. In some embodiments of a compound of Formula (I), (Ia), (Ib), or (Ic), $R^{12}$ is hydrogen.

In some embodiments of a compound of Formula (I), (Ia), (Ib), or (Ic), $R^{12}$ is

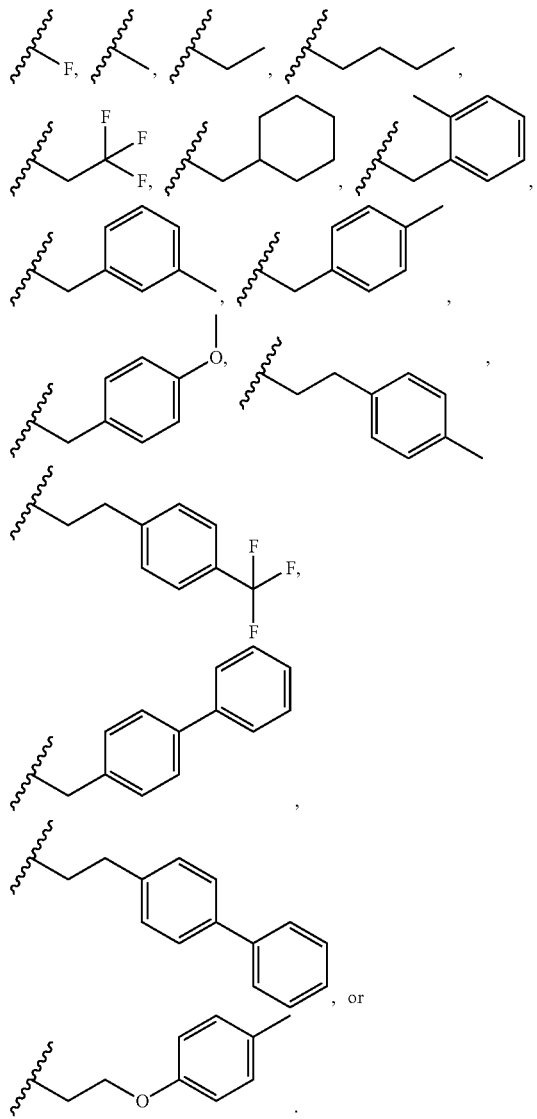

In some embodiments of a compound of Formula (I), (Ia), (Ib), or (Ic), $R^{10}$ and $R^{12}$ are taken together to form an optionally substituted cycloalkyl. In some embodiments of a compound of Formula (I), (Ia), (Ib), or (Ic), the cycloalkyl is cycloheptane. In some embodiments of a compound of Formula (I), (Ia), (Ib), or (Ic), the cycloalkyl is cyclooctane. In some embodiments of a compound of Formula (I), (Ia), (Ib), or (Ic), $R^{10}$ and $R^{12}$ are taken together to form an optionally substituted cycloalkenyl group. In some embodiments of a compound of Formula (I), (Ia), (Ib), or (Ic), the cycloalkenyl group is cycloheptene. In some embodiments of a compound of Formula (I), (Ia), (Ib), or (Ic), the cycloalkenyl group is cyclooctene.

In some embodiments of a compound of Formula (I), (Ia), (Ib), or (Ic), $R^{14}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, or optionally substituted heteroaryl. In some embodiments of a compound of Formula (I), (Ia), (Ib), or (Ic), $R^{14}$ is hydrogen, optionally substituted $C_1$-$C_6$ alkyl, optionally substituted cycloalkyl, or optionally substituted ($C_1$-$C_6$ alkyl)cycloalkyl. In some embodiments of a compound of Formula (I), (Ia), (Ib), or (Ic), $R^{14}$ is optionally substituted $C_1$-$C_6$ alkyl or optionally substituted ($C_1$-$C_6$ alkyl)cycloalkyl. In some embodiments of a compound of Formula (I), (Ia), (Ib), or (Ic), $R^{14}$ is $C_1$-$C_6$ alkyl, $C_1$-$C_6$ haloalkyl, or ($C_1$-$C_6$ alkyl)cycloalkyl. In some embodiments of a compound of Formula (I), (Ia), (Ib), or (Ic), $R^{14}$ is selected from:

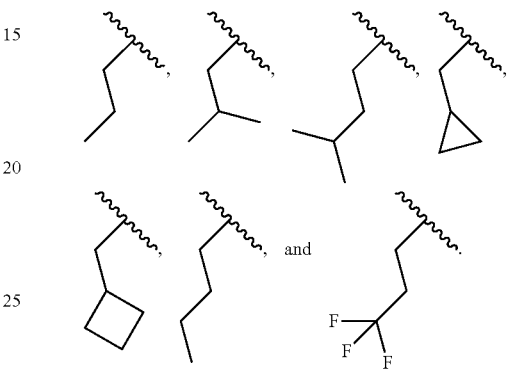

In some embodiments of a compound of Formula (I), (Ia), (Ib), or (Ic), $R^{16}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, or optionally substituted heteroaryl. In some embodiments of a compound of Formula (I), (Ia), (Ib), or (Ic), $R^{16}$ is optionally substituted $C_1$-$C_6$ alkyl, optionally substituted ($C_1$-$C_6$ alkyl)cycloalkyl, optionally substituted cycloalkyl, optionally substituted ($C_1$-$C_6$ alkyl)aryl, or optionally substituted aryl. In some embodiments of a compound of Formula (I), (Ia), (Ib), or (Ic), $R^{16}$ is optionally substituted $C_1$-$C_6$ alkyl, optionally substituted ($C_1$-$C_6$ alkyl)cycloalkyl, or optionally substituted cycloalkyl. In some embodiments of a compound of Formula (I), (Ia), (Ib), or (Ic), $R^{16}$ is optionally substituted $C_1$-$C_6$ alkyl, optionally substituted ($C_1$-$C_6$ alkyl)cycloalkyl, or optionally substituted cycloalkyl. In some embodiments of a compound of Formula (I), (Ia), (Ib), or (Ic), $R^{16}$ is $C_1$-$C_6$ alkyl, ($C_1$-$C_6$ alkyl)cycloalkyl, cycloalkyl, ($C_1$-$C_6$ alkyl)aryl, or aryl, each optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl. In some embodiments of a compound of Formula (I), (Ia), (Ib), or (Ic), $R^{16}$ is $C_1$-$C_6$ alkyl, ($C_1$-$C_6$ alkyl)cycloalkyl, or cycloalkyl, each optionally substituted with halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl. In some embodiments of a compound of Formula (I), (Ia), (Ib), or (Ic), $R^{16}$ is $C_3$-$C_7$ cycloalkyl. In some embodiments of a compound of Formula (I), (Ia), (Ib), or (Ic), $R^{16}$ is cyclobutyl, cyclopentyl, cyclohexyl, or cycloheptyl. In some embodiments of a compound of Formula (I), (Ia), (Ib), or (Ic), $R^{16}$ is cyclohexyl. In some embodiments of a compound of Formula (I), (Ia), (Ib), or (Ic), $R^{16}$ is cycloheptyl. In some embodiments of a compound of Formula (I), (Ia), (Ib), or (Ic), $R^{16}$ is selected from:

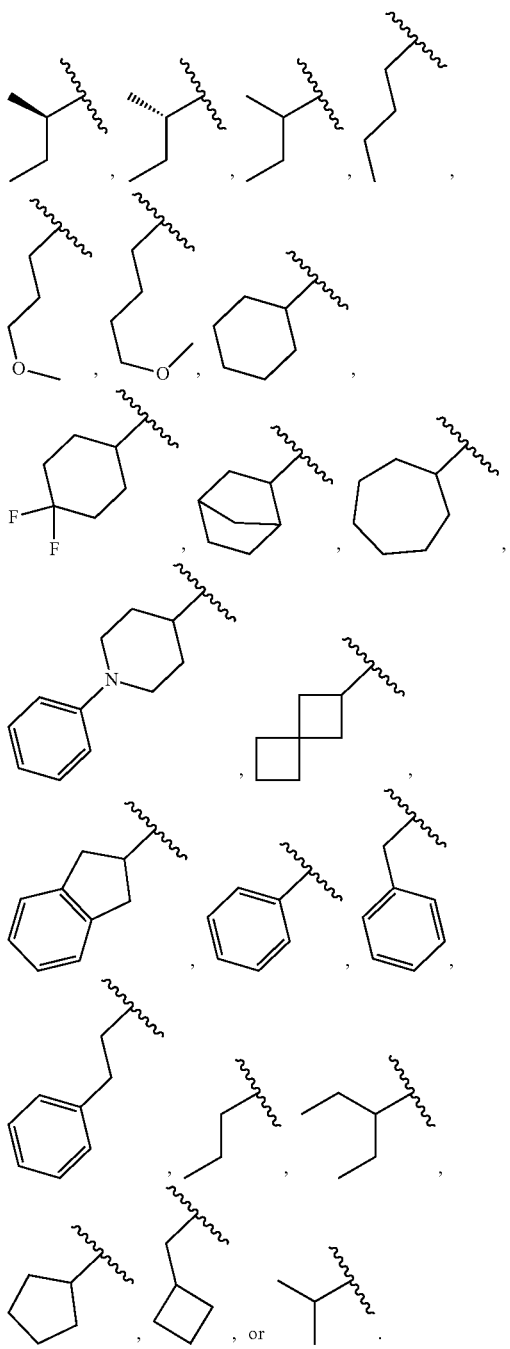

In some embodiments of a compound of Formula (I), (Ia), (Ib), or (Ic), $R^1$ and $R^2$ are each independently hydrogen, optionally substituted $C_1$-$C_6$ alkyl, optionally substituted $C_2$-$C_6$ alkynyl, optionally substituted cycloalkyl, optionally substituted heterocycloalkyl, optionally substituted aryl, optionally substituted heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$. In some embodiments of a compound of Formula (I), (Ia), (Ib), or (Ic), $R^1$ and $R^2$ are each independently hydrogen, optionally substituted $C_1$-$C_6$ alkyl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$. In some embodiments of a compound of Formula (I), (Ia), (Ib), or (Ic), $R^1$ and $R^2$ are each independently hydrogen, optionally substituted $C_1$-$C_6$ alkyl, or —(C=NR$^b$)NR$^b$R$^c$. In some embodiments of a compound of Formula (I), (Ia), (Ib), or (Ic), $R^1$ and $R^2$ are each independently hydrogen or optionally substituted $C_1$-$C_6$ alkyl. In some embodiments of a compound of Formula (I), (Ia), (Ib), or (Ic), $R^1$ and $R^2$ are each independently hydrogen or $C_1$-$C_6$ alkyl. In some embodiments of a compound of Formula (I), (Ia), (Ib), or (Ic), $R^1$ is hydrogen. In some embodiments of a compound of Formula (I), (Ia), (Ib), or (Ic), $R^2$ is hydrogen.

In some embodiments of a compound of Formula (I), (Ia), (Ib), or (Ic), each $R^a$ is independently $C_1$-$C_6$ alkyl. In some embodiments of a compound of Formula (I), (Ia), (Ib), or (Ic), each $R^b$ and $R^c$ is independently hydrogen or $C_1$-$C_6$ alkyl. In some embodiments of a compound of Formula (I), (Ia), (Ib), or (Ic), each $R^b$ and $R^c$ is hydrogen.

Also disclosed herein are compounds of Formula (II):

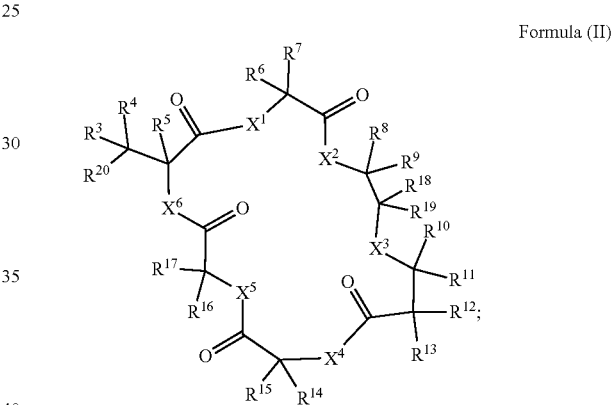

Formula (II)

wherein:

$X^1$ is —O— or —NR$^{1a}$—;
$X^2$ is —O— or —NR$^{2a}$—;
$X^3$ is —O— or —NR$^{3a}$—;
$X^4$ is —O— or —NR$^{4a}$—;
$X^5$ is —O— or —NR$^{5a}$—;
$X^6$ is —O— or —NR$^{6a}$—;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$;
or $R^1$ and $R^2$ are taken together with the nitrogen atom to which they are attached to form an optionally substituted heterocycloalkyl;
$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{10}$ and $R^{12}$ are taken together to form an optionally substituted cycloalkyl or an optionally substituted cycloalkenyl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{20}$ is —$NR^1R^2$ or —OH;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

In some embodiments of a compound of Formula (II), $R^{18}$ and $R^{19}$ are each independently hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (II), $R^{18}$ and $R^{19}$ are each independently hydrogen, halogen, or optionally substituted $C_1$-$C_6$ alkyl. In some embodiments of a compound of Formula (II), $R^{18}$ and $R^{19}$ are each independently hydrogen or $C_1$-$C_6$ alkyl. In some embodiments of a compound of Formula (II), $R^{18}$ and $R^{19}$ are hydrogen.

In some embodiments the compound of Formula (II) has the structure of Formula (IIa):

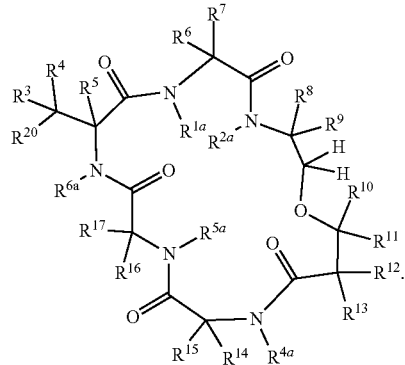

Formula (IIa)

In some embodiments of a compound of Formula (II) or (IIa), $R^7$ is hydrogen or optionally substituted $C_1$-$C_6$ alkyl. In some embodiments of a compound of Formula (II) or (IIa), $R^7$ is hydrogen or $C_1$-$C_6$ alkyl. In some embodiments of a compound of Formula (II) or (IIa), $R^7$ is hydrogen.

In some embodiments of a compound of Formula (II) or (IIa), $R^9$ is hydrogen or optionally substituted $C_1$-$C_6$ alkyl. In some embodiments of a compound of Formula (II) or (IIa), $R^9$ is hydrogen or $C_1$-$C_6$ alkyl. In some embodiments of a compound of Formula (II) or (IIa), $R^9$ is hydrogen.

In some embodiments of a compound of Formula (II) or (IIa), $R^{11}$ is hydrogen or optionally substituted $C_1$-$C_6$ alkyl. In some embodiments of a compound of Formula (II) or (IIa), $R^{11}$ is hydrogen or $C_1$-$C_6$ alkyl. In some embodiments of a compound of Formula (II) or (IIa), $R^{11}$ is hydrogen.

In some embodiments of a compound of Formula (II) or (IIa), $R^{13}$ is hydrogen or optionally substituted $C_1$-$C_6$ alkyl. In some embodiments of a compound of Formula (II) or (IIa), $R^{13}$ is hydrogen or $C_1$-$C_6$ alkyl. In some embodiments of a compound of Formula (II) or (IIa), $R^{13}$ is hydrogen.

In some embodiments of a compound of Formula (II) or (IIa), $R^{15}$ is hydrogen or optionally substituted $C_1$-$C_6$ alkyl. In some embodiments of a compound of Formula (II) or (IIa), $R^{15}$ is hydrogen or $C_1$-$C_6$ alkyl. In some embodiments of a compound of Formula (II) or (IIa), $R^{15}$ is hydrogen.

In some embodiments of a compound of Formula (II) or (IIa), $R^{17}$ is hydrogen or optionally substituted $C_1$-$C_6$ alkyl. In some embodiments of a compound of Formula (II) or (IIa), $R^{17}$ is hydrogen or $C_1$-$C_6$ alkyl. In some embodiments of a compound of Formula (II) or (IIa), $R^{17}$ is hydrogen.

In some embodiments the compound of Formula (II) or (IIa) has the structure of Formula (IIb):

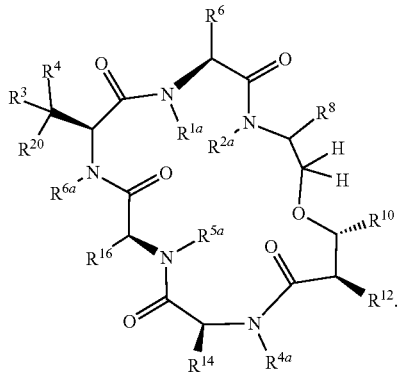

Formula (IIb)

In some embodiments of a compound of Formula (II), (IIa), or (IIb), $R^{1a}$ is hydrogen or $C_1$-$C_6$ alkyl. In some embodiments of a compound of Formula (II), (IIa), or (IIb), $R^{1a}$ is hydrogen. In some embodiments of a compound of Formula (II), (IIa), or (IIb), $R^{1a}$ is $C_1$-$C_6$ alkyl.

In some embodiments of a compound of Formula (II), (IIa), or (IIb), $R^{2a}$ is hydrogen or $C_1$-$C_6$ alkyl. In some embodiments of a compound of Formula (II), (IIa), or (IIb), $R^{2a}$ is hydrogen. In some embodiments of a compound of Formula (II), (IIa), or (IIb), $R^{2a}$ is $C_1$-$C_6$ alkyl.

In some embodiments of a compound of Formula (II), (IIa), or (IIb), $R^{5a}$ is hydrogen or $C_1$-$C_6$ alkyl. In some embodiments of a compound of Formula (II), (IIa), or (IIb), $R^{5a}$ is hydrogen. In some embodiments of a compound of Formula (II), (IIa), or (IIb), $R^{5a}$ is $C_1$-$C_6$ alkyl.

In some embodiments of a compound of Formula (II), (IIa), or (IIb), $R^{6a}$ is hydrogen or $C_1$-$C_6$ alkyl. In some embodiments of a compound of Formula (II), (IIa), or (IIb), $R^{6a}$ is hydrogen. In some embodiments of a compound of Formula (II), (IIa), or (IIb), $R^{6a}$ is $C_1$-$C_6$ alkyl.

In some embodiments the compound of Formula (II), (IIa), or (IIb) has the structure of Formula (IIc):

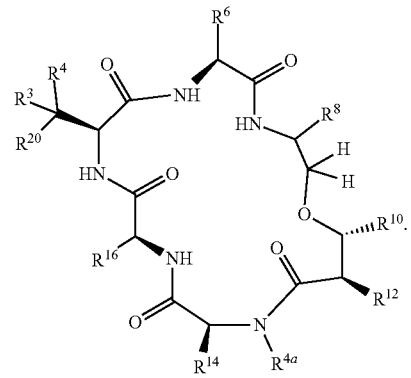

Formula (IIc)

In some embodiments of a compound of Formula (II), (IIa), (IIb), or (IIc), $R^{4a}$ is hydrogen or $C_1$-$C_6$ alkyl. In some embodiments of a compound of Formula (II), (IIa), (IIb), or (IIc), $R^{4a}$ is hydrogen. In some embodiments of a compound of Formula (II), (IIa), (IIb), or (IIc), $R^{4a}$ is $C_1$-$C_6$ alkyl.

In some embodiments of a compound of Formula (II), (IIa), (IIb), or (IIc), $R^{14}$ and $R^{4a}$ are taken together with the atoms to which they are attached to form an optionally substituted 5- or 6-membered heterocycloalkyl. In some embodiments of a compound of Formula (II), (IIa), (IIb), or (IIc), $R^{14}$ and $R^{4a}$ are taken together with the atoms to which they are attached to form an optionally substituted 5-membered heterocycloalkyl. In some embodiments of a compound of Formula (II), (IIa), (IIb), or (IIc), $R^{14}$ and $R^{4a}$ are taken together with the atoms to which they are attached to form an optionally substituted 6-membered heterocycloalkyl.

In some embodiments of a compound of Formula (II), (IIa), (IIb), or (IIc), each $R^3$ and $R^4$ are independently hydrogen or optionally substituted $C_1$-$C_6$ alkyl. In some embodiments of a compound of Formula (II), (IIa), (IIb), or (IIc), each $R^3$ and $R^4$ are independently hydrogen or $C_1$-$C_6$ alkyl. In some embodiments of a compound of Formula (II), (IIa), (IIb), or (IIc), each $R^3$ and $R^4$ are hydrogen. In some embodiments of a compound of Formula (II), (IIa), (IIb), or (IIc), $R^3$ is hydrogen and $R^4$ is $C_1$-$C_6$ alkyl.

In some embodiments of a compound of Formula (II), (IIa), (IIb), or (IIc), $R^6$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (II), (IIa), (IIb), or (IIc), $R^6$ is hydrogen, optionally substituted $C_1$-$C_6$ alkyl, or optionally substituted heterocycloalkyl. In some embodiments of a compound of Formula (II), (IIa), (IIb), or (IIc), $R^6$ is optionally substituted $C_1$-$C_6$ alkyl or optionally substituted heterocycloalkyl. In some embodiments of a compound of Formula (II), (IIa), (IIb), or (IIc), $R^6$ is optionally substituted heterocycloalkyl selected from aziridinyl, azetidinyl, pyrrolidinyl, piperidinyl, or piperazinyl. In some embodiments of a compound of Formula (II), (IIa), (IIb), or (IIc), $R^6$ is $C_1$-$C_6$ alkyl optionally substituted with one, two, or three halogen, $-OR^b$, $-NR^bR^c$, $-NC(=NR^b)NR^bR^c$, $-S(=O)_2R^a$, $-NR^bS(=O)_2R^a$, $-S(=O)_2NR^bR^c$, $-C(=O)R^a$, $-OC(=O)R^a$, $-C(=O)OR^a$, $-OC(=O)OR^b$, $-C(=O)NR^bR^c$, $-NR^bC(=O)[(R^d)_2]_{1-4}NR^bR^c$, $-OC[(R^d)_2]_{2-4}OR^b$, $-OC[(R^d)_2]_{2-4}NR^bR^c$, $-OC[(R^d)_2]_{2-4}OC[(R^d)_2]_{2-4}NR^bR^c$, $-OC[(R^d)_2]_{2-4}NC(=NR^b)NR^bR^c$, $-OC(=O)NR^bR^c$, $-NR^bC(=O)NR^bR^c$, —NR$^b$C(=O)R$^a$, —NR$^b$C(=O)OR$^b$, —O-(optionally substituted heterocycloalkyl), —O-(optionally substituted aryl), or heteroaryl; and each R$^d$ is independently hydrogen, halogen, —OH, —OCH$_3$, or C$_1$-C$_6$ alkyl. In some embodiments of a compound of Formula (II), (IIa), (IIb), or (IIc), R$^6$ is C$_1$-C$_6$ alkyl optionally substituted with one, two, or three halogen, —OR$^b$, —NR$^b$R$^c$, —S(=O)$_2$R$^a$, —NR$^b$S(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, or heteroaryl. In some embodiments of a compound of Formula (II), (IIa), (IIb), or (IIc), R$^6$ is C$_1$-C$_6$ alkyl optionally substituted with one, two, or three —OR$^b$. In some embodiments of a compound of Formula (II), (IIa), (IIb), or (IIc), R$^6$ is selected from:

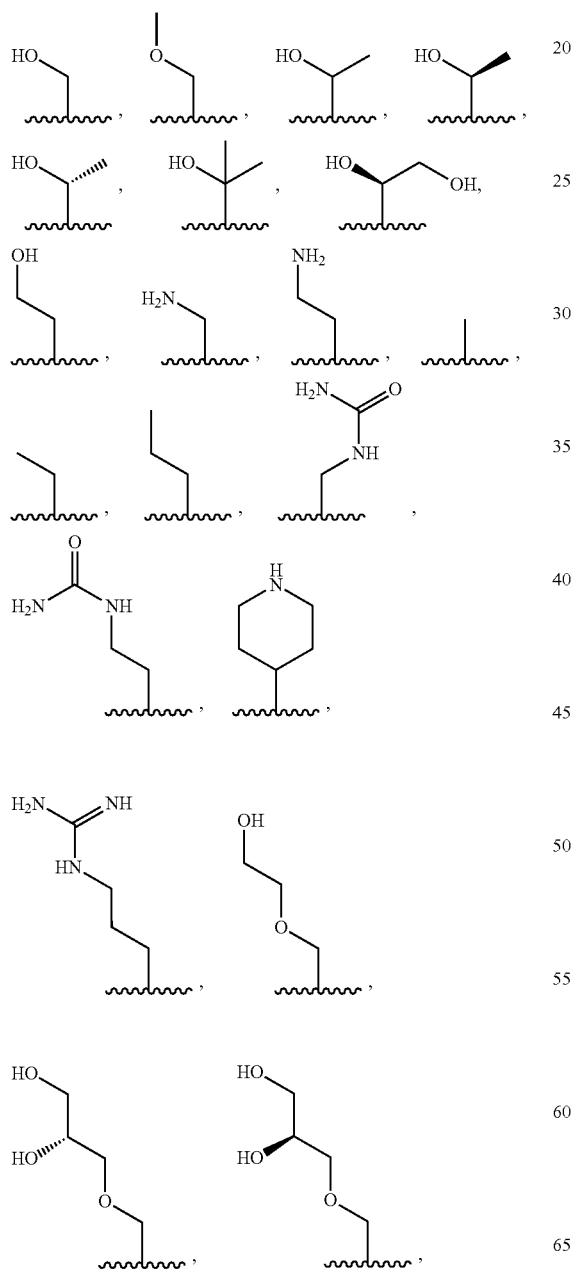

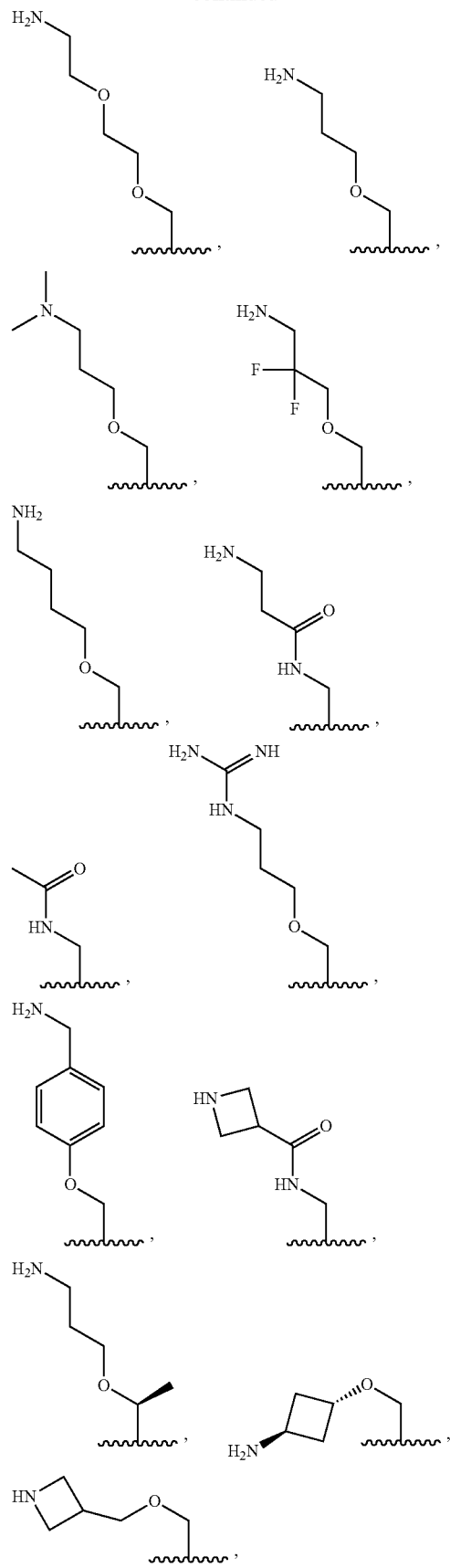

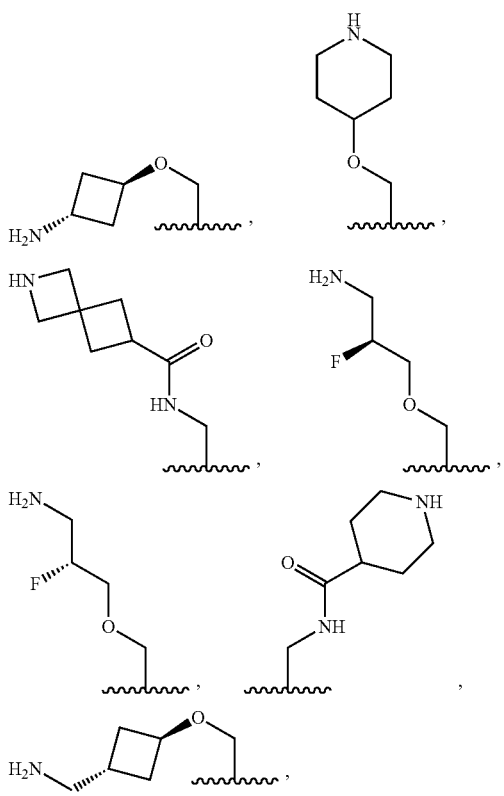

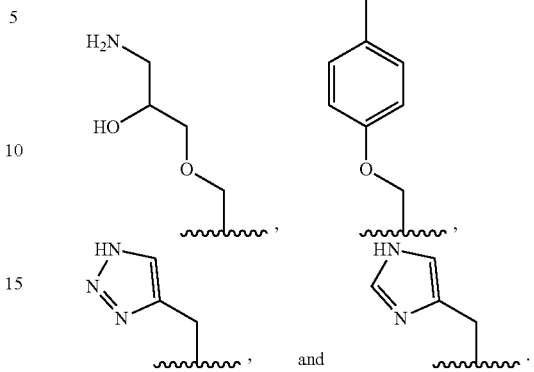

In some embodiments of a compound of Formula (II), (IIa), (IIb), or (IIc), $R^8$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (II), (IIa), (IIb), or (IIc), $R^8$ is hydrogen or $C_1$-$C_6$ alkyl. In some embodiments of a compound of Formula (II), (IIa), (IIb), or (IIc), $R^8$ is hydrogen. In some embodiments of a compound of Formula (II), (IIa), (IIb), or (IIc), $R^8$ is $C_1$-$C_6$ alkyl.

In some embodiments of a compound of Formula (II), (IIa), (IIb), or (IIc), $R^{10}$ is optionally substituted $C_1$-$C_{20}$ alkyl, optionally substituted $C_2$-$C_{20}$ alkenyl, or optionally substituted ($C_1$-$C_6$ alkyl)cycloalkyl. In some embodiments of a compound of Formula (II), (IIa), (IIb), or (IIc), $R^{10}$ is hydrogen, halogen, optionally substituted $C_1$-$C_{20}$ alkyl, optionally substituted cycloalkyl, optionally substituted heterocycloalkyl, optionally substituted aryl, or optionally substituted heteroaryl. In some embodiments of a compound of Formula (II), (IIa), (IIb), or (IIc), $R^{10}$ is hydrogen or optionally substituted $C_1$-$C_{20}$ alkyl. In some embodiments of a compound of Formula (II), (IIa), (IIb), or (IIc), $R^{10}$ is $C_1$-$C_{20}$ alkyl optionally substituted with one, two, or three halogen, —OH, —OCH$_3$, cycloalkyl, or aryl. In some embodiments of a compound of Formula (II), (IIa), (IIb), or (IIc), $R^{10}$ is $C_1$-$C_{20}$ alkyl optionally substituted with one, two, or three halogen, —OH, or —OCH$_3$. In some embodiments of a compound of Formula (II), (IIa), (IIb), or (IIc), $R^{10}$ is $C_1$-$C_{20}$ alkyl optionally substituted with one aryl or one cycloalkyl. In some embodiments of a compound of Formula (II), (IIa), (IIb), or (IIc), $R^{10}$ is optionally substituted $C_1$-$C_{20}$ alkyl. In some embodiments of a compound of Formula (II), (IIa), (IIb), or (IIc), $R^{10}$ is optionally substituted $C_8$-$C_{12}$ alkyl optionally substituted with one, two, or three halogen, —OH, or —OCH$_3$. In some embodiments of a compound of Formula (II), (IIa), (IIb), or (IIc), $R^{10}$ is optionally substituted $C_1$-$C_8$ alkyl. In some embodiments of a compound of Formula (II), (IIa), (IIb), or (Ic), $R^{10}$ is $C_1$-$C_8$ alkyl optionally substituted with one, two, or three halogen, —OH, —OCH$_3$, cycloalkyl, or aryl. In some embodiments of a compound of Formula (II), (IIa), (IIb), or (IIc), $R^{10}$ is $C_1$-$C_8$ alkyl optionally substituted with one, two, or three halogen, —OH, or —OCH$_3$. In some embodiments of a compound of Formula (II), (IIa), (IIb), or (IIc), $R^{10}$ is $C_1$-$C_8$ alkyl optionally substituted with one aryl or one cycloalkyl. In some embodiments of a compound of Formula (II), (IIa), (IIb), or (IIc), $R^{10}$ is optionally substituted $C_8$-$C_{12}$ alkyl. In some embodiments of a compound of Formula (II), (IIa), (IIb), or (IIc), $R^{10}$ is optionally substituted $C_{11}$-$C_{20}$ alkyl. In some embodiments of a compound of Formula (II), (IIa), (IIb), or (IIc), $R^{10}$ is optionally substituted $C_6$-$C_{12}$ alkyl. In some embodiments of a compound of Formula (II), (IIa), (IIb), or (IIc), $R^{10}$ is optionally substituted $C_8$-$C_{15}$ alkyl. In some embodiments of a compound of Formula (II), (IIa), (IIb), or (IIc), $R^{10}$ is $C_1$-$C_{20}$ alkyl. In some embodiments of a compound of Formula (II), (IIa), (IIb), or (IIc), $R^{10}$ is $C_8$-$C_{12}$ alkyl. In some embodiments of a compound of Formula (II), (IIa), (IIb), or (IIc), $R^{10}$ is $C_{11}$-$C_{20}$ alkyl. In some embodiments of a compound of Formula (II), (IIa), (IIb), or (IIc), $R^{10}$ is $C_6$-$C_{12}$ alkyl. In some embodiments of a compound of Formula (II), (IIa), (IIb), or (IIc), $R^{10}$ is $C_8$-$C_{15}$ alkyl. In some embodiments of a compound of Formula (II), (IIa), (IIb), or (IIc), R is hydrogen.

In some embodiments of a compound of Formula (II), (IIa), (IIb), or (IIc), $R^{10}$ is

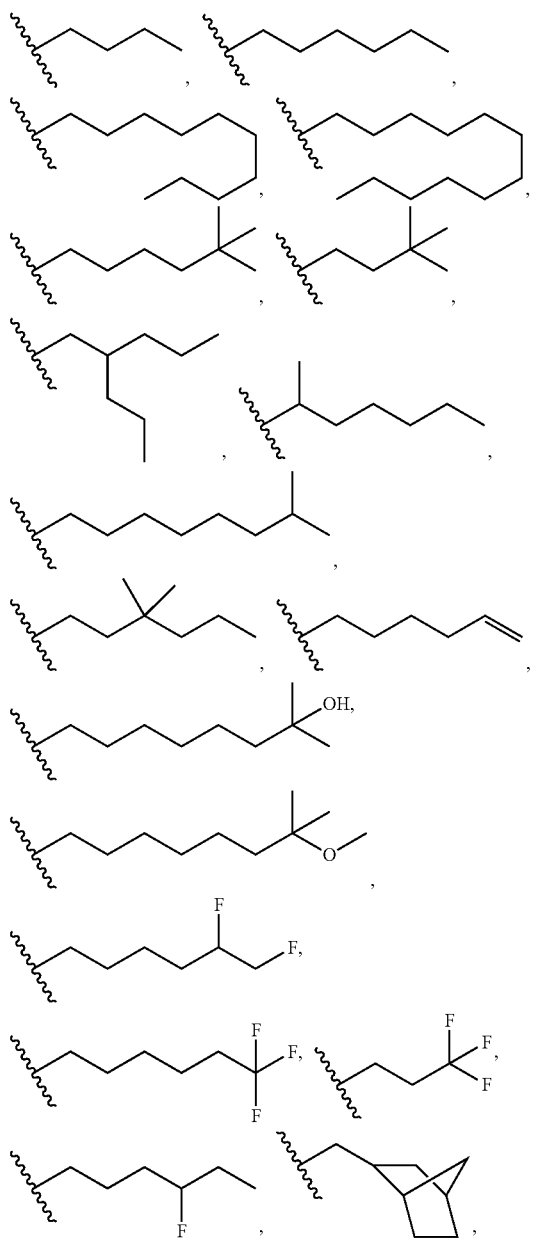

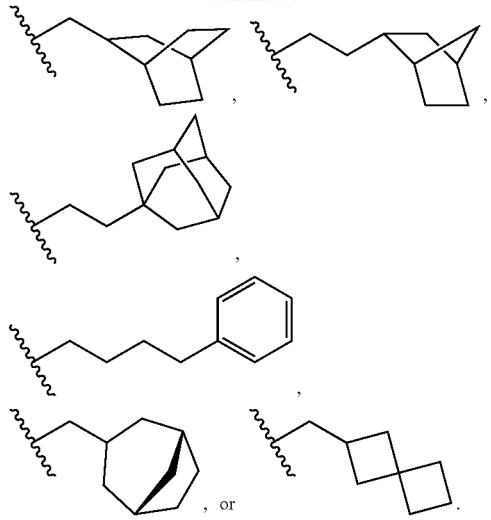

In some embodiments of a compound of Formula (II), (IIa), (IIb), or (IIc), $R^{12}$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (II), (IIa), (IIb), or (IIc), $R^{12}$ is halogen, optionally substituted $C_1$-$C_6$ alkyl, optionally substituted ($C_1$-$C_6$ alkyl)aryl, or optionally substituted ($C_1$-$C_6$ alkyl)cycloalkyl. In some embodiments of a compound of Formula (II), (IIa), (IIb), or (IIc), $R^{12}$ is $C_1$-$C_6$ alkyl, $C_1$-$C_6$ haloalkyl, (CV $C_6$ alkyl)aryl, or ($C_1$-$C_6$ alkyl)cycloalkyl; wherein the aryl is optionally substituted with one, two, or three halogen, $C_1$-$C_6$ alkyl, $C_1$-$C_6$ haloalkyl, —OH, —OCH$_3$, or aryl. In some embodiments of a compound of Formula (II), (IIa), (IIb), or (IIc), $R^{12}$ is hydrogen or optionally substituted $C_1$-$C_6$ alkyl. In some embodiments of a compound of Formula (II), (IIa), (IIb), or (IIc), $R^{12}$ is optionally substituted $C_1$-$C_6$ alkyl. In some embodiments of a compound of Formula (II), (IIa), (IIb), or (IIc), $R^{12}$ is $C_1$-$C_6$ alkyl. In some embodiments of a compound of Formula (II), (IIa), (IIb), or (IIc), $R^{12}$ is methyl or ethyl. In some embodiments of a compound of Formula (II), (IIa), (IIb), or (IIc), $R^{12}$ is methyl. In some embodiments of a compound of Formula (II), (IIa), (IIb), or (IIc), $R^{12}$ is hydrogen.

In some embodiments of a compound of Formula (II), (IIa), (IIb), or (IIc), $R^{10}$ and $R^{12}$ are taken together to form an optionally substituted cycloalkyl. In some embodiments of a compound of Formula (II), (IIa), (IIb), or (IIc), the cycloalkyl is cycloheptane. In some embodiments of a compound of Formula (II), (IIa), (IIb), or (IIc), the cycloalkyl is cyclooctane. In some embodiments of a compound of Formula (II), (IIa), (IIb), or (IIc), $R^{10}$ and $R^{12}$ are taken together to form an optionally substituted cycloalkenyl group. In some embodiments of a compound of Formula (II), (IIa), (IIb), or (IIc), the cycloalkenyl group is cycloheptene. In some embodiments of a compound of Formula (II), (IIa), (IIb), or (IIc), the cycloalkenyl group is cyclooctene.

In some embodiments of a compound of Formula (II), (IIa), (IIb), or (IIc), $R^{12}$ is

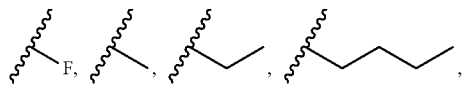

In some embodiments of a compound of Formula (II), (IIa), (IIb), or (IIc), $R^{14}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, or optionally substituted heteroaryl. In some embodiments of a compound of Formula (II), (IIa), (IIb), or (IIc), $R^{14}$ is hydrogen, optionally substituted $C_1$-$C_6$ alkyl, optionally substituted cycloalkyl, or optionally substituted ($C_1$-$C_6$ alkyl)cycloalkyl. In some embodiments of a compound of Formula (II), (IIa), (IIb), or (IIc), $R^{14}$ is optionally substituted $C_1$-$C_6$ alkyl or optionally substituted ($C_1$-$C_6$ alkyl)cycloalkyl. In some embodiments of a compound of Formula (II), (IIa), (IIb), or (IIc), $R^{14}$ is $C_1$-$C_6$ alkyl, $C_1$-$C_6$ haloalkyl, or ($C_1$-$C_6$ alkyl)cycloalkyl. In some embodiments of a compound of Formula (II), (IIa), (IIb), or (IIc), $R^{14}$ is selected from:

In some embodiments of a compound of Formula (II), (IIa), (IIb), or (IIc), $R^{16}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, or optionally substituted heteroaryl. In some embodiments of a compound of Formula (II), (IIa), (IIb), or (IIc), $R^{16}$ is optionally substituted $C_1$-$C_6$ alkyl, optionally substituted ($C_1$-$C_6$ alkyl)cycloalkyl, optionally substituted cycloalkyl, optionally substituted ($C_1$-$C_6$ alkyl)aryl, or optionally substituted aryl. In some embodiments of a compound of Formula (II), (IIa), (IIb), or (IIc), $R^{16}$ is optionally substituted $C_1$-$C_6$ alkyl, optionally substituted ($C_1$-$C_6$ alkyl)cycloalkyl, or optionally substituted cycloalkyl. In some embodiments of a compound of Formula (II), (IIa), (IIb), or (IIc), $R^{16}$ is optionally substituted $C_1$-$C_6$ alkyl, optionally substituted ($C_1$-$C_6$ alkyl)cycloalkyl, or optionally substituted cycloalkyl. In some embodiments of a compound of Formula (II), (IIa), (IIb), or (IIc), $R^{16}$ is $C_1$-$C_6$ alkyl, ($C_1$-$C_6$ alkyl)cycloalkyl, cycloalkyl, ($C_1$-$C_6$ alkyl)aryl, or aryl, each optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl. In some embodiments of a compound of Formula (II), (IIa), (IIb), or (IIc), $R^{16}$ is $C_1$-$C_6$ alkyl, ($C_1$-$C_6$ alkyl)cycloalkyl, or cycloalkyl, each optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl. In some embodiments of a compound of Formula (II), (IIa), (IIb), or (IIc), $R^{16}$ is $C_3$-$C_7$ cycloalkyl. In some embodiments of a compound of Formula (II), (IIa), (IIb), or (IIc), $R^{16}$ is cyclobutyl, cyclopentyl, cyclohexyl, or cycloheptyl. In some embodiments of a compound of Formula (II), (IIa), (IIb), or (IIc), $R^{16}$ is cyclohexyl. In some embodiments of a compound of Formula (I), (Ia), (Ib), or (Ic), $R^{16}$ is cycloheptyl. In some embodiments of a compound of Formula (II), (IIa), (IIb), or (IIc), $R^{16}$ is selected from:

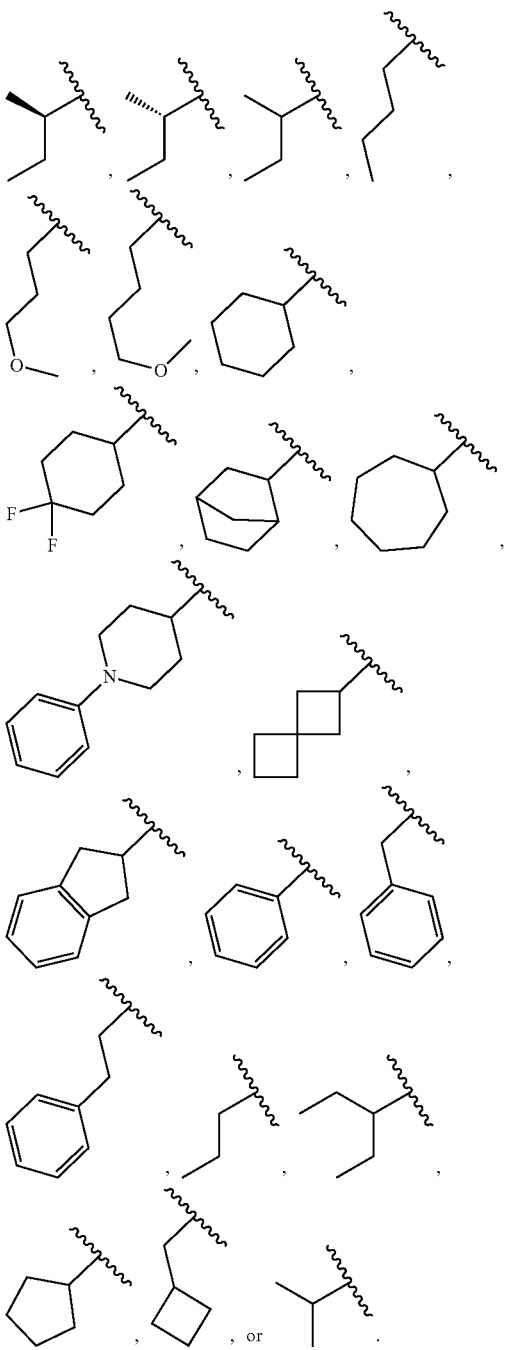

In some embodiments of a compound of Formula (II), (IIa), (IIb), or (IIc), $R^{20}$ is —OH.

In some embodiments of a compound of Formula (II), (IIa), (IIb), or (IIc), $R^{20}$ is —$NR^1R^2$.

In some embodiments of a compound of Formula (II), (IIa), (IIb), or (IIc), $R^1$ and $R^2$ are each independently hydrogen, optionally substituted $C_1$-$C_6$ alkyl, optionally substituted $C_2$-$C_6$ alkynyl, optionally substituted cycloalkyl, optionally substituted heterocycloalkyl, optionally substituted aryl, optionally substituted heteroaryl, —S(=O)$_2$$R^a$, —S(=O)$_2$$NR^bR^c$, —C(=O)$R^a$, —C(=O)$OR^b$, —C(=O)$NR^bR^c$, or —(C=$NR^b$)$NR^bR^c$. In some embodiments of a compound of Formula (II), (IIa), (IIb), or (IIc), $R^1$ and $R^2$ are each independently hydrogen, optionally substituted $C_1$-$C_6$ alkyl, —S(=O)$_2$$R^a$, —S(=O)$_2$$NR^bR^c$, —C(=O)$R^a$, —C(=O)$OR^b$, —C(=O)$NR^bR^c$, or —(C=$NR^b$)$NR^bR^c$. In some embodiments of a compound of Formula (II), (IIa), (IIb), or (IIc), $R^1$ and $R^2$ are each independently hydrogen, optionally substituted $C_1$-$C_6$ alkyl, or —(C=$NR^b$)$NR^bR^c$. In some embodiments of a compound of Formula (II), (IIa), (IIb), or (IIc), $R^1$ and $R^2$ are each independently hydrogen or optionally substituted $C_1$-$C_6$ alkyl. In some embodiments of a compound of Formula (II), (IIa), (IIb), or (IIc), $R^1$ and $R^2$ are each independently hydrogen or $C_1$-$C_6$ alkyl. In some embodiments of a compound of Formula (II), (IIa), (IIb), or (IIc), $R^1$ is hydrogen. In some embodiments of a compound of Formula (II), (IIa), (IIb), or (IIc), $R^2$ is hydrogen.

In some embodiments of a compound of Formula (II), (IIa), (IIb), or (IIc), each $R^a$ is independently $C_1$-$C_6$ alkyl. In some embodiments of a compound of Formula (II), (IIa), (IIb), or (IIc), each $R^b$ and $R^c$ is independently hydrogen or $C_1$-$C_6$ alkyl. In some embodiments of a compound of Formula (II), (IIa), (IIb), or (IIc), each $R^b$ and $R^c$ is hydrogen.

Also disclosed herein are compounds of Formula (III):

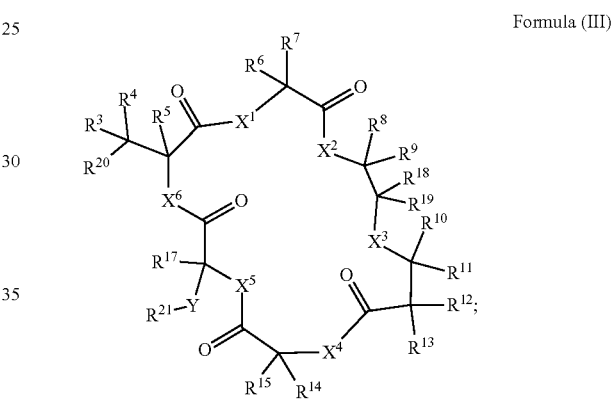

Formula (III)

wherein:
$X^1$ is —O— or —$NR^{1a}$—;
$X^2$ is —O— or —$NR^{2a}$—;
$X^3$ is —O— or —$NR^{3a}$—;
$X^4$ is —O— or —$NR^{4a}$—;
$X^5$ is —O— or —$NR^{5a}$—;
$X^6$ is —O— or —$NR^{6a}$—;
provided that at least one of $X^1$, $X^2$, $X^3$, $X^4$, $X^5$, or $X^6$ is —O—;
Y is a bond or optionally substituted $C_1$-$C_6$ alkylene;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, optionally substituted ($C_1$-$C_6$ alkyl)heteroaryl, —S(=O)$_2$$R^a$, —S(=O)$_2$$NR^bR^c$, —C(=O)$R^a$, —C(=O)$OR^b$, or —C(=O)$NR^bR^c$;
or $R^1$ and $R^2$ are taken together with the nitrogen atom to which they are attached to form an optionally substituted heterocycloalkyl;
$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
or $R^3$ and $R^4$ are taken together with the carbon atom to which they are attached to form an oxo;
$R^5$ is hydrogen, halogen, optionally substituted $C_1$-$C_6$ alkyl, optionally substituted $C_2$-$C_6$ alkenyl, or optionally substituted $C_2$-$C_6$ alkynyl;
$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted heterocycloalkyl, optionally substituted ($C_1$-$C_6$ alkyl)aryl, or optionally substituted ($C_1$-$C_6$ alkyl)heteroaryl;
$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;
$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;
$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;
or $R^{10}$ and $R^{12}$ are taken together to form an optionally substituted cycloalkyl or an optionally substituted cycloalkenyl;
$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;
or $R^{14}$ and $R^{4a}$ are taken together with the atoms to which they are attached to form an optionally substituted heterocycloalkyl;
$R^{17}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;
$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
or $R^{18}$ and $R^{19}$ are taken together with the carbon atom to which they are attached to form an oxo;
$R^{20}$ is hydroxyl or —$NR^1R^2$;
$R^{21}$ is optionally substituted cycloalkyl;
each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
or $R^b$ and $R^c$ are taken together with the nitrogen atom to which they are attached to form an optionally substituted heterocycloalkyl;
or a pharmaceutically acceptable salt, solvate, or stereoisomer thereof.

In some embodiments of a compound of Formula (III), $R^{18}$ and $R^{19}$ are taken together with the carbon atom to which they are attached to form an oxo.

In some embodiments of a compound of Formula (III), $R^{18}$ and $R^{19}$ are each independently hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (III), $R^{18}$ and $R^{19}$ are each independently hydrogen, halogen, or optionally substituted $C_1$-$C_6$ alkyl. In some embodiments of a compound of Formula (III), $R^{18}$ and $R^{19}$ are each independently hydrogen or $C_1$-$C_6$ alkyl. In some embodiments of a compound of Formula (III), $R^{18}$ and $R^{19}$ are hydrogen.

In some embodiments the compound of Formula (III) has the structure of Formula (IIIa):

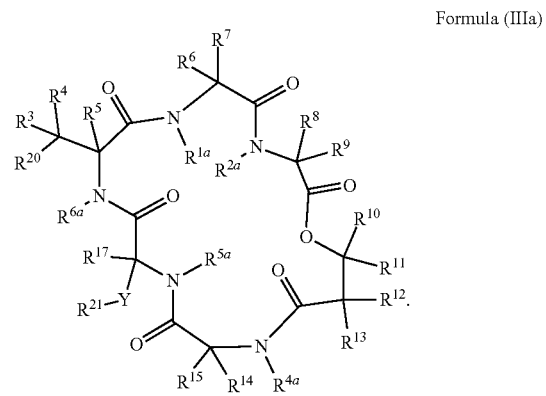

Formula (IIIa)

In some embodiments of a compound of Formula (III) or (IIIa), $R^5$ is hydrogen or optionally substituted $C_1$-$C_6$ alkyl. In some embodiments of a compound of Formula (III) or (IIIa), $R^5$ is hydrogen or $C_1$-$C_6$ alkyl. In some embodiments of a compound of Formula (III) or (IIIa), $R^5$ is hydrogen.

In some embodiments of a compound of Formula (III) or (IIIa), $R^7$ is hydrogen or optionally substituted $C_1$-$C_6$ alkyl. In some embodiments of a compound of Formula (III) or (IIIa), $R^7$ is hydrogen or $C_1$-$C_6$ alkyl. In some embodiments of a compound of Formula (III) or (IIIa), $R^7$ is hydrogen.

In some embodiments of a compound of Formula (III) or (IIIa), $R^9$ is hydrogen or optionally substituted $C_1$-$C_6$ alkyl. In some embodiments of a compound of Formula (III) or (IIIa), $R^9$ is hydrogen or $C_1$-$C_6$ alkyl. In some embodiments of a compound of Formula (III) or (IIIa), $R^9$ is hydrogen.

In some embodiments of a compound of Formula (III) or (IIIa), $R^{11}$ is hydrogen or optionally substituted $C_1$-$C_6$ alkyl. In some embodiments of a compound of Formula (III) or (IIIa), $R^{11}$ is hydrogen or $C_1$-$C_6$ alkyl. In some embodiments of a compound of Formula (III) or (IIIa), $R^{11}$ is hydrogen.

In some embodiments of a compound of Formula (III) or (IIIa), $R^{13}$ is hydrogen or optionally substituted $C_1$-$C_6$ alkyl. In some embodiments of a compound of Formula (III) or (IIIa), $R^{13}$ is hydrogen or $C_1$-$C_6$ alkyl. In some embodiments of a compound of Formula (III) or (IIIa), $R^{13}$ is hydrogen.

In some embodiments of a compound of Formula (III) or (IIIa), $R^{15}$ is hydrogen or optionally substituted $C_1$-$C_6$ alkyl. In some embodiments of a compound of Formula (III) or (IIIa), $R^{15}$ is hydrogen or $C_1$-$C_6$ alkyl. In some embodiments of a compound of Formula (III) or (IIIa), $R^{15}$ is hydrogen.

In some embodiments of a compound of Formula (III) or (IIIa), $R^{17}$ is hydrogen or optionally substituted $C_1$-$C_6$ alkyl. In some embodiments of a compound of Formula (III) or (IIIa), $R^{17}$ is hydrogen or $C_1$-$C_6$ alkyl. In some embodiments of a compound of Formula (III) or (IIIa), $R^{17}$ is hydrogen.

In some embodiments the compound of Formula (III) or (IIIa) has the structure of Formula (IIIb):

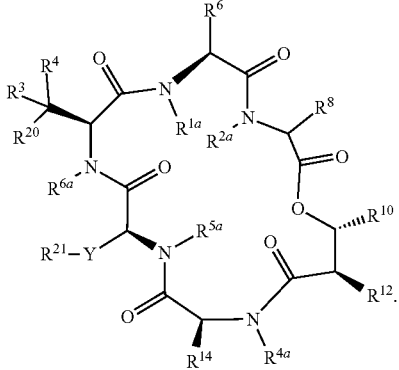

Formula (IIIb)

In some embodiments of a compound of Formula (III), (IIIa), or (IIIb), $R^{1a}$ is hydrogen or $C_1$-$C_6$ alkyl. In some embodiments of a compound of Formula (III), (IIIa), or (IIIb), $R^{1a}$ is hydrogen. In some embodiments of a compound of Formula (III), (IIIa), or (IIIb), $R^{1a}$ is $C_1$-$C_6$ alkyl.

In some embodiments of a compound of Formula (III), (IIIa), or (IIIb), $R^{2a}$ is hydrogen or $C_1$-$C_6$ alkyl. In some embodiments of a compound of Formula (III), (IIIa), or (IIIb), $R^{2a}$ is hydrogen. In some embodiments of a compound of Formula (III), (IIIa), or (IIIb), $R^{2a}$ is $C_1$-$C_6$ alkyl.

In some embodiments of a compound of Formula (III), (IIIa), or (IIIb), $R^{5a}$ is hydrogen or $C_1$-$C_6$ alkyl. In some embodiments of a compound of Formula (III), (IIIa), or (IIIb), $R^{5a}$ is hydrogen. In some embodiments of a compound of Formula (III), (IIIa), or (IIIb), $R^{5a}$ is $C_1$-$C_6$ alkyl.

In some embodiments of a compound of Formula (III), (IIIa), or (IIIb), $R^{6a}$ is hydrogen or $C_1$-$C_6$ alkyl. In some embodiments of a compound of Formula (III), (IIIa), or (IIIb), $R^{6a}$ is hydrogen. In some embodiments of a compound of Formula (III), (IIIa), or (IIIb), $R^{6a}$ is $C_1$-$C_6$ alkyl.

In some embodiments the compound of Formula (III), (IIIa), or (IIIb) has the structure of Formula (IIIc):

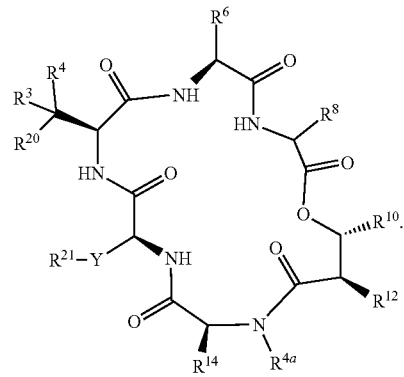

Formula (IIIc)

In some embodiments of a compound of Formula (III), (IIIa), (IIIb), or (IIIc), $R^{4a}$ is hydrogen or $C_1$-$C_6$ alkyl. In some embodiments of a compound of Formula (III), (IIIa), (IIIb), or (IIIc), $R^{4a}$ is hydrogen. In some embodiments of a compound of Formula (III), (IIIa), (IIIb), or (IIIc), $R^{4a}$ is $C_1$-$C_6$ alkyl.

In some embodiments of a compound of Formula (III), (IIIa), (IIIb), or (IIIc), $R^{14}$ and $R^{4a}$ are taken together with the atoms to which they are attached to form an optionally substituted 5- or 6-membered heterocycloalkyl. In some embodiments of a compound of Formula (III), (IIIa), (IIIb), or (IIIc), $R^{14}$ and $R^{4a}$ are taken together with the atoms to which they are attached to form an optionally substituted 5-membered heterocycloalkyl. In some embodiments of a compound of Formula (III), (IIIa), (IIIb), or (IIIc), $R^{14}$ and $R^{4a}$ are taken together with the atoms to which they are attached to form an optionally substituted 6-membered heterocycloalkyl.

In some embodiments of a compound of Formula (III), (IIIa), (IIIb), or (IIIc), each $R^3$ and $R^4$ are independently hydrogen or optionally substituted $C_1$-$C_6$ alkyl. In some embodiments of a compound of Formula (III), (IIIa), (IIIb), or (IIIc), each $R^3$ and $R^4$ are independently hydrogen or $C_1$-$C_6$ alkyl. In some embodiments of a compound of Formula (III), (IIIa), (IIIb), or (IIIc), each $R^3$ and $R^4$ are hydrogen. In some embodiments of a compound of Formula (III), (IIIa), (IIIb), or (IIIc), $R^3$ is hydrogen and $R^4$ is $C_1$-$C_6$ alkyl.

In some embodiments of a compound of Formula (III), (IIIa), (IIIb), or (IIIc), $R^6$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (III), (IIIa), (IIIb), or (IIIc), $R^6$ is hydrogen, optionally substituted $C_1$-$C_6$ alkyl, or optionally substituted heterocycloalkyl. In some embodiments of a compound of Formula (III), (IIIa), (IIIb), or (IIIc), $R^6$ is optionally substituted $C_1$-$C_6$ alkyl or optionally substituted heterocycloalkyl. In some embodiments of a compound of Formula (III), (IIIa), (IIIb), or (IIIc), $R^6$ is optionally substituted heterocycloalkyl selected from aziridinyl, azetidinyl, pyrrolidinyl, piperidinyl, or piperazinyl. In some embodiments of a compound of Formula (III), (IIIa), (IIIb), or (IIIc), $R^6$ is $C_1$-$C_6$ alkyl optionally substituted with one, two, or three halogen, —OR$^b$, —NR$^b$R$^c$, —NC(=NR$^b$)NR$^b$R$^c$, —S(=O)$_2$R$^a$, —NR$^b$S(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —NR$^b$C(=O)[(R$^d$)$_2$]$_{1-4}$NR$^b$R$^c$, —OC[(R$^d$)$_2$]$_{2-4}$OR$^b$, —OC[(R$^d$)$_2$]$_{2-4}$NR$^b$R$^c$, —OC[(R$^d$)$_2$]$_{2-4}$OC[(R$^d$)$_2$]$_{2-4}$NR$^b$R$^c$, —OC[(R$^d$)$_2$]$_{2-4}$NC(=NR$^b$)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, —O-(optionally substituted heterocycloalkyl), —O-(optionally substituted aryl), or heteroaryl; and each R$^d$ is independently hydrogen, halogen, —OH, —OCH$_3$, or C$_1$-C$_6$ alkyl. In some embodiments of a compound of Formula (III), (IIIa), (IIIb), or (IIIc), R$^6$ is C$_1$-C$_6$ alkyl optionally substituted with one, two, or three halogen, —OR$^b$, —NR$^b$R$^c$, —S(=O)$_2$R$^a$, —NR$^b$S(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, or heteroaryl. In some embodiments of a compound of Formula (III), (IIIa), (IIIb), or (IIIc), R$^6$ is C$_1$-C$_6$ alkyl optionally substituted with one, two, or three —OR$^b$. In some embodiments of a compound of Formula (III), (IIIa), (IIIb), or (IIIc), R$^6$ is selected from:

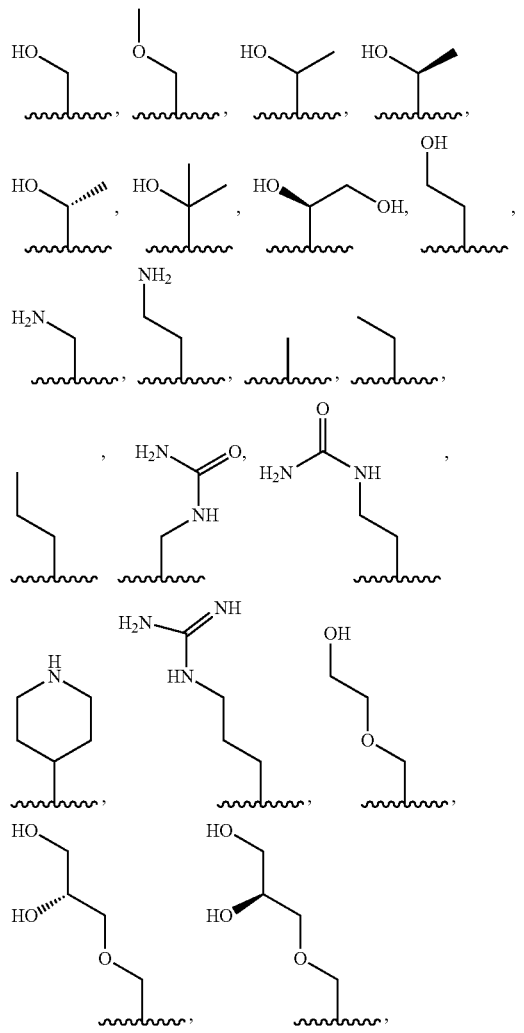

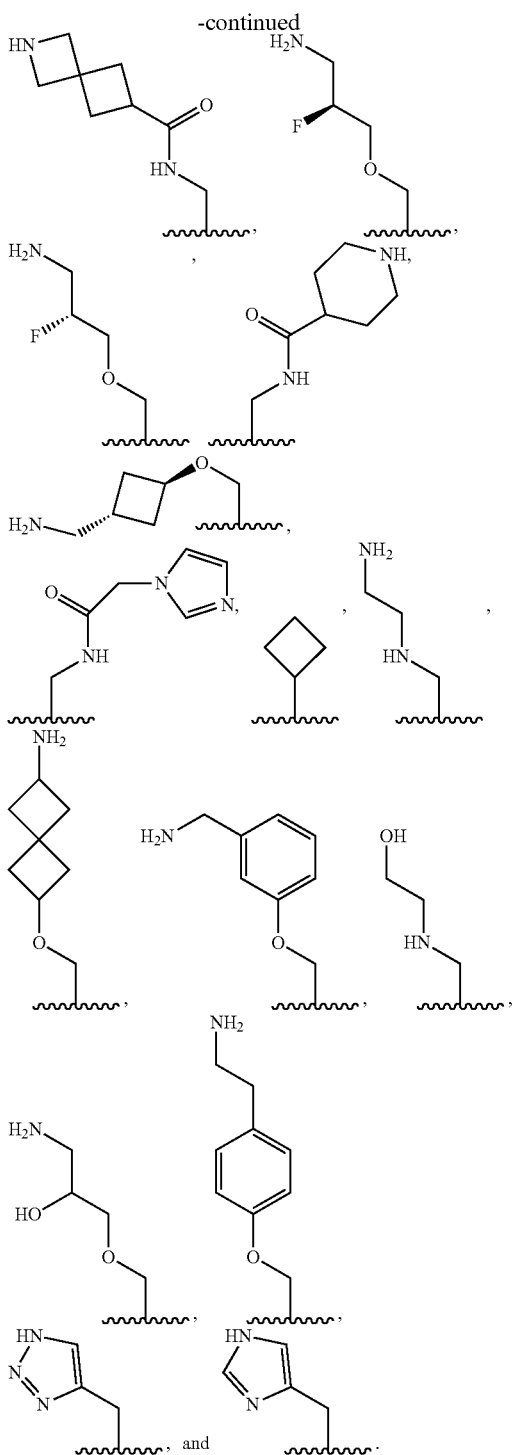

In some embodiments of a compound of Formula (III), (IIIa), (IIIb), or (IIIc), $R^8$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (III), (IIIa), (IIIb), or (IIIc), $R^8$ is hydrogen or $C_1$-$C_6$ alkyl. In some embodiments of a compound of Formula (III), (IIIa), (IIIb), or (IIIc), $R^8$ is hydrogen. In some embodiments of a compound of Formula (III), (IIIa), (IIIb), or (IIIc), $R^8$ is $C_1$-$C_6$ alkyl.

In some embodiments of a compound of Formula (III), (IIIa), (IIIb), or (IIIc), $R^{10}$ is optionally substituted $C_1$-$C_{20}$ alkyl, optionally substituted $C_2$-$C_{20}$ alkenyl, or optionally substituted ($C_1$-$C_6$ alkyl)cycloalkyl. In some embodiments of a compound of Formula (III), (IIIa), (IIIb), or (IIIc), $R^{10}$ is hydrogen, halogen, optionally substituted $C_1$-$C_{20}$ alkyl, optionally substituted cycloalkyl, optionally substituted heterocycloalkyl, optionally substituted aryl, or optionally substituted heteroaryl. In some embodiments of a compound of Formula (III), (IIIa), (IIIb), or (IIIc), $R^{10}$ is hydrogen or optionally substituted $C_1$-$C_{20}$ alkyl. In some embodiments of a compound of Formula (III), (IIIa), (IIIb), or (IIIc), $R^{10}$ is $C_1$-$C_{20}$ alkyl optionally substituted with one, two, or three halogen, —OH, —OCH$_3$, cycloalkyl, or aryl. In some embodiments of a compound of Formula (III), (IIIa), (IIIb), or (IIIc), $R^{10}$ is $C_1$-$C_{20}$ alkyl optionally substituted with one, two, or three halogen, —OH, or —OCH$_3$. In some embodiments of a compound of Formula (III), (IIIa), (IIIb), or (IIIc), $R^{10}$ is $C_1$-$C_{20}$ alkyl optionally substituted with one aryl or one cycloalkyl. In some embodiments of a compound of Formula (III), (IIIa), (IIIb), or (IIIc), $R^{10}$ is optionally substituted $C_1$-$C_{20}$ alkyl. In some embodiments of a compound of Formula (III), (IIIa), (IIIb), or (IIIc), $R^{10}$ is optionally substituted $C_8$-$C_{12}$ alkyl optionally substituted with one, two, or three halogen, —OH, or —OCH$_3$. In some embodiments of a compound of Formula (III), (IIIa), (IIIb), or (IIIc), $R^{10}$ is optionally substituted $C_1$-$C_8$ alkyl. In some embodiments of a compound of Formula (III), (IIIa), (IIIb), or (IIIc), $R^{10}$ is $C_1$-$C_8$ alkyl optionally substituted with one, two, or three halogen, —OH, —OCH$_3$, cycloalkyl, or aryl. In some embodiments of a compound of Formula (III), (IIIa), (IIIb), or (IIIc), $R^{10}$ is $C_1$-$C_8$ alkyl optionally substituted with one, two, or three halogen, —OH, or —OCH$_3$. In some embodiments of a compound of Formula (III), (IIIa), (IIIb), or (IIIc), $R^{10}$ is $C_1$-$C_8$ alkyl optionally substituted with one aryl or one cycloalkyl. In some embodiments of a compound of Formula (III), (IIIa), (IIIb), or (IIIc), $R^{10}$ is optionally substituted $C_8$-$C_{12}$ alkyl. In some embodiments of a compound of Formula (III), (IIIa), (IIIb), or (IIIc), $R^{10}$ is optionally substituted $C_{11}$-$C_{20}$ alkyl. In some embodiments of a compound of Formula (III), (IIIa), (IIIb), or (IIIc), $R^{10}$ is optionally substituted $C_6$-$C_{12}$ alkyl. In some embodiments of a compound of Formula (III), (IIIa), (IIIb), or (IIIc), $R^{10}$ is optionally substituted $C_8$-$C_{15}$ alkyl. In some embodiments of a compound of Formula (III), (IIIa), (IIIb), or (IIIc), $R^{10}$ is $C_1$-$C_{20}$ alkyl. In some embodiments of a compound of Formula (III), (IIIa), (IIIb), or (IIIc), $R^{10}$ is $C_8$-$C_{12}$ alkyl. In some embodiments of a compound of Formula (III), (IIIa), (IIIb), or (IIIc), $R^{10}$ is $C_{11}$-$C_{20}$ alkyl. In some embodiments of a compound of Formula (III), (IIIa), (IIIb), or (IIIc), $R^{10}$ is $C_6$-$C_{12}$ alkyl. In some embodiments of a compound of Formula (III), (IIIa), (IIIb), or (IIIc), $R^{10}$ is $C_8$-$C_{15}$ alkyl. In some embodiments of a compound of Formula (III), (IIIa), (IIIb), or (IIIc), $R^{10}$ is hydrogen.

In some embodiments of a compound of Formula (III), (IIIa), (IIIb), or (IIIc), $R^{10}$ is

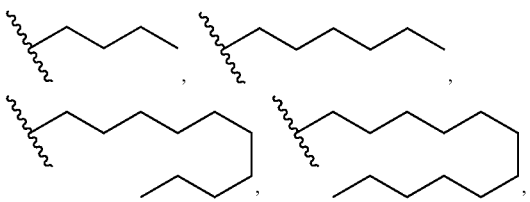

-continued

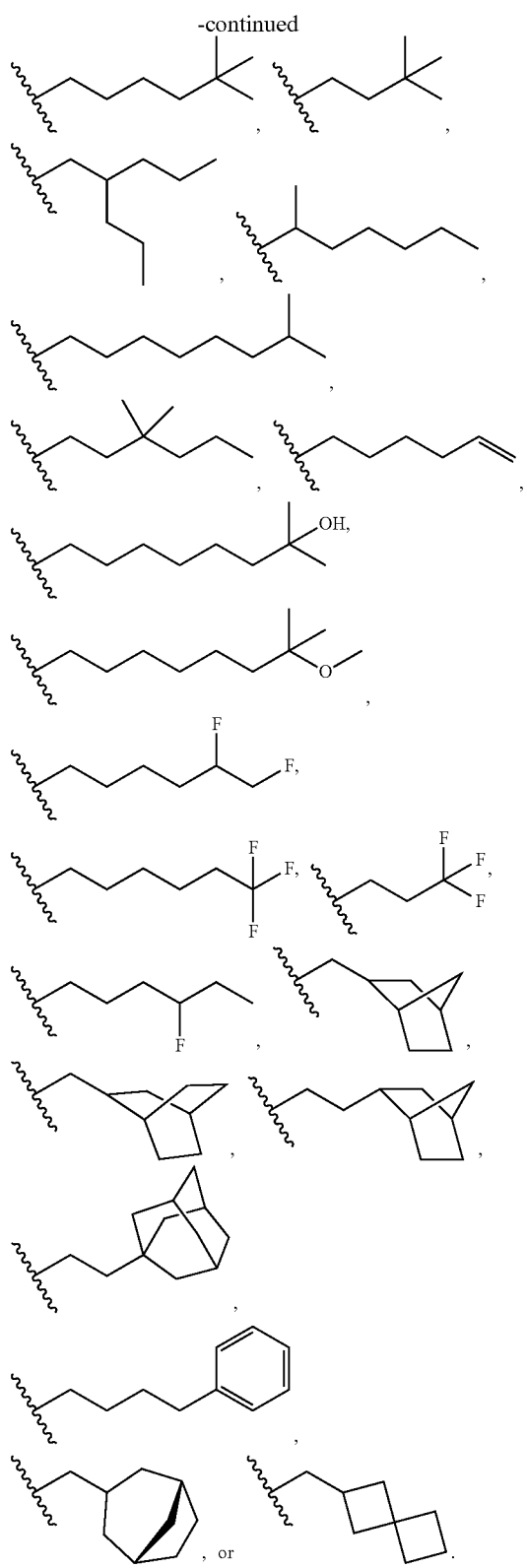

In some embodiments of a compound of Formula (III), (IIIa), (IIIb), or (IIIc), $R^{12}$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (III), (IIIa), (IIIb), or (IIIc), $R^{12}$ is halogen, optionally substituted $C_1$-$C_6$ alkyl, optionally substituted ($C_1$-$C_6$ alkyl)aryl, or optionally substituted ($C_1$-$C_6$ alkyl)cycloalkyl. In some embodiments of a compound of Formula (III), (IIIa), (IIIb), or (IIIc), $R^{12}$ is $C_1$-$C_6$ alkyl, $C_1$-$C_6$ haloalkyl, ($C_1$-$C_6$ alkyl)aryl, or ($C_1$-$C_6$ alkyl)cycloalkyl; wherein the aryl is optionally substituted with one, two, or three halogen, $C_1$-$C_6$ alkyl, $C_1$-$C_6$ haloalkyl, —OH, —OCH$_3$, or aryl. In some embodiments of a compound of Formula (III), (IIIa), (IIIb), or (IIIc), $R^{12}$ is hydrogen or optionally substituted $C_1$-$C_6$ alkyl. In some embodiments of a compound of Formula (III), (IIIa), (IIIb), or (IIIc), $R^{12}$ is optionally substituted $C_1$-$C_6$ alkyl. In some embodiments of a compound of Formula (III), (IIIa), (IIIb), or (IIIc), $R^{12}$ is $C_1$-$C_6$ alkyl. In some embodiments of a compound of Formula (III), (IIIa), (IIIb), or (IIIc), $R^{12}$ is ethyl or methyl. In some embodiments of a compound of Formula (III), (IIIa), (IIIb), or (IIIc), $R^{12}$ is methyl. In some embodiments of a compound of Formula (III), (IIIa), (IIIb), or (IIIc), $R^{12}$ is hydrogen.

In some embodiments of a compound of Formula (III), (IIIa), (IIIb), or (IIIc), $R^{12}$ is

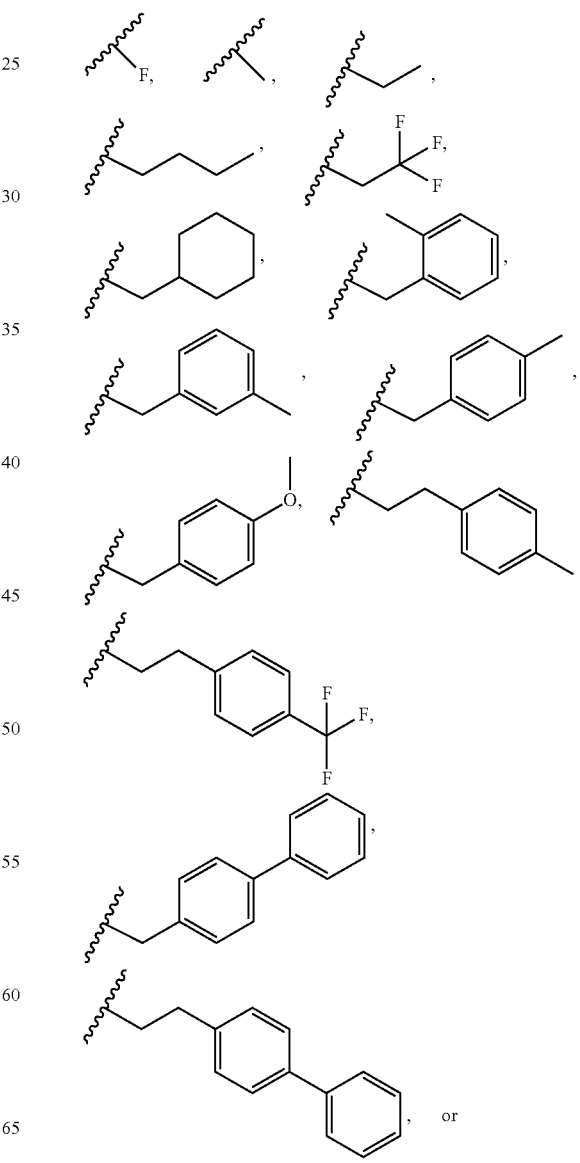

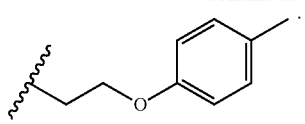

In some embodiments of a compound of Formula (III), (IIIa), (IIIb), or (IIIc), $R^{10}$ and $R^{12}$ are taken together to form an optionally substituted cycloalkyl. In some embodiments of a compound of Formula (III), (IIIa), (IIIb), or (IIIc), the cycloalkyl is cycloheptane. In some embodiments of a compound of Formula (III), (IIIa), (IIIb), or (IIIc), the cycloalkyl is cyclooctane. In some embodiments of a compound of Formula (III), (IIIa), (IIIb), or (IIIc), $R^{10}$ and $R^{12}$ are taken together to form an optionally substituted cycloalkenyl group. In some embodiments of a compound of Formula (III), (IIIa), (IIIb), or (IIIc), the cycloalkenyl group is cycloheptene. In some embodiments of a compound of Formula (III), (IIIa), (IIIb), or (IIIc), the cycloalkenyl group is cyclooctene.

In some embodiments of a compound of Formula (III), (IIIa), (IIIb), or (IIIc), $R^{14}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, or optionally substituted heteroaryl. In some embodiments of a compound of Formula (III), (IIIa), (IIIb), or (IIIc), $R^{14}$ is hydrogen, optionally substituted $C_1$-$C_6$ alkyl, optionally substituted cycloalkyl, or optionally substituted ($C_1$-$C_6$ alkyl)cycloalkyl. In some embodiments of a compound of Formula (III), (IIIa), (IIIb), or (IIIc), $R^{14}$ is optionally substituted $C_1$-$C_6$ alkyl or optionally substituted ($C_1$-$C_6$ alkyl)cycloalkyl. In some embodiments of a compound of Formula (III), (IIIa), (IIIb), or (IIIc), $R^{14}$ is $C_1$-$C_6$ alkyl, $C_1$-$C_6$ haloalkyl, or ($C_1$-$C_6$ alkyl)cycloalkyl. In some embodiments of a compound of Formula (III), (IIIa), (IIIb), or (IIIc), $R^{14}$ is selected from:

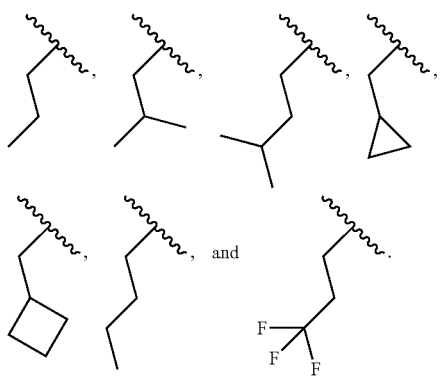

In some embodiments of a compound of Formula (III), (IIIa), (IIIb), or (IIIc), Y is a bond. In some embodiments of a compound of Formula (III), (IIIa), (IIIb), or (IIIc), Y is optionally substituted $C_1$-$C_6$ alkylene. In some embodiments of a compound of Formula (III), (IIIa), (IIIb), or (IIIc), Y is optionally substituted $C_1$-$C_2$ alkylene. In some embodiments of a compound of Formula (III), (IIIa), (IIIb), or (IIIc), Y is optionally substituted $C_1$ alkylene. In some embodiments of a compound of Formula (III), (IIIa), (IIIb), or (IIIc), Y is $C_1$-$C_6$ alkylene. In some embodiments of a compound of Formula (III), (IIIa), (IIIb), or (IIIc), Y is $C_1$-$C_2$ alkylene. In some embodiments of a compound of Formula (III), (IIIa), (IIIb), or (IIIc), Y is $C_1$ alkylene.

In some embodiments of a compound of Formula (III), (IIIa), (IIIb), or (IIIc), $R^{21}$ is $C_3$-$C_7$ cycloalkyl optionally substituted with one, two, or three halogen or $C_1$-$C_6$ alkyl. In some embodiments of a compound of Formula (III), (IIIa), (IIIb), or (IIIc), $R^{21}$ is $C_3$-$C_7$ cycloalkyl optionally substituted with one, two, or three halogen. In some embodiments of a compound of Formula (III), (IIIa), (IIIb), or (IIIc), $R^{21}$ is $C_3$-$C_7$ cycloalkyl. In some embodiments of a compound of Formula (III), (IIIa), (IIIb), or (IIIc), $R^{21}$ is cyclobutyl, cyclopentyl, cyclohexyl, or cycloheptyl. In some embodiments of a compound of Formula (III), (IIIa), (IIIb), or (IIIc), $R^{16}$ is cyclohexyl. In some embodiments of a compound of Formula (III), (IIIa), (IIIb), or (IIIc), $R^{16}$ is cycloheptyl.

In some embodiments of a compound of Formula (III), (IIIa), (IIIb), or (IIIc), $R^{20}$ is —OH.

In some embodiments of a compound of Formula (III), (IIIa), (IIIb), or (IIIc), $R^{20}$ is —NR$^1$R$^2$.

In some embodiments of a compound of Formula (III), (IIIa), (IIIb), or (IIIc), $R^1$ and $R^2$ are each independently hydrogen, optionally substituted $C_1$-$C_6$ alkyl, optionally substituted $C_2$-$C_6$ alkynyl, optionally substituted cycloalkyl, optionally substituted heterocycloalkyl, optionally substituted aryl, optionally substituted heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$. In some embodiments of a compound of Formula (III), (IIIa), (IIIb), or (IIIc), $R^1$ and $R^2$ are each independently hydrogen, optionally substituted $C_1$-$C_6$ alkyl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$. In some embodiments of a compound of Formula (III), (IIIa), (IIIb), or (IIIc), $R^1$ and $R^2$ are each independently hydrogen, optionally substituted $C_1$-$C_6$ alkyl, or —(C=NR$^b$)NR$^b$R$^c$. In some embodiments of a compound of Formula (III), (IIIa), (IIIb), or (IIIc), $R^1$ and $R^2$ are each independently hydrogen or optionally substituted $C_1$-$C_6$ alkyl. In some embodiments of a compound of Formula (III), (IIIa), (IIIb), or (IIIc), $R^1$ and $R^2$ are each independently hydrogen or $C_1$-$C_6$ alkyl. In some embodiments of a compound of Formula (III), (IIIa), (IIIb), or (IIIc), $R^1$ is hydrogen. In some embodiments of a compound of Formula (III), (IIIa), (IIIb), or (IIIc), $R^2$ is hydrogen.

In some embodiments of a compound of Formula (III), (IIIa), (IIIb), or (IIIc), each $R^a$ is independently $C_1$-$C_6$ alkyl. In some embodiments of a compound of Formula (III), (IIIa), (IIIb), or (IIIc), each $R^b$ and $R^c$ is independently hydrogen or $C_1$-$C_6$ alkyl. In some embodiments of a compound of Formula (III), (IIIa), (IIIb), or (IIIc), each $R^b$ and $R^c$ is hydrogen.

Also disclosed herein are compounds of Formula (IV):

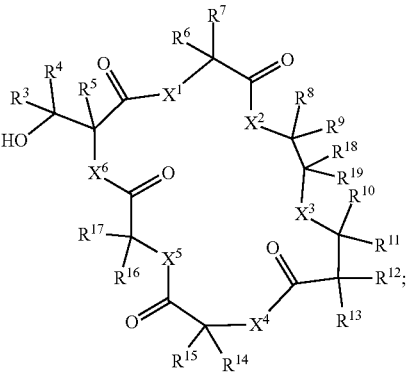

Formula (IV)

wherein:

$X^1$ is —O— or —NR$^{1a}$—;
$X^2$ is —O— or —NR$^{2a}$—;
$X^3$ is —O— or —NR$^{3a}$—;
$X^4$ is —O— or —NR$^{4a}$—;
$X^5$ is —O— or —NR$^{5a}$—;
$X^6$ is —O— or —NR$^{6a}$—;

$R^{1a}$, $R^{2a}$, $R^{3a}$, $R^{4a}$, $R^{5a}$, and $R^{6a}$ are each independently hydrogen or optionally substituted $C_1$-$C_6$ alkyl;

$R^3$ and $R^4$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ is optionally substituted branched $C_3$-$C_{20}$ alkyl or optionally substituted $C_{10}$-$C_{20}$ alkyl;

$R^{11}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{12}$ is optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{13}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof;

provided that the compound of Formula (IV) is not:

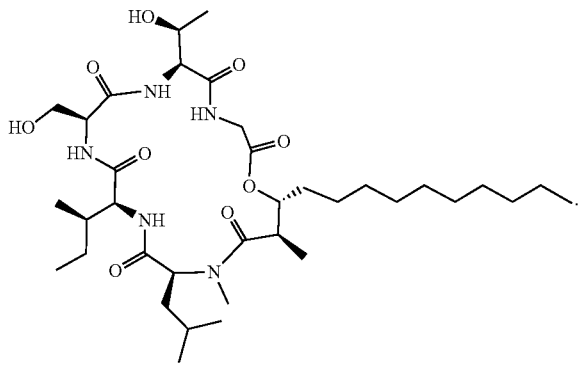 [SMILES: CCCCCCCCCC[C@H]1OC(=O)CNC(=O)[C@H]([C@H](C)O)NC(=O)[C@H](CO)NC(=O)[C@H]([C@H](C)CC)NC(=O)[C@H](CC(C)C)N(C)C(=O)[C@@H]1C]

In some embodiments of a compound of Formula (IV), $R^{18}$ and $R^{19}$ are taken together with the carbon atom to which they are attached to form an oxo.

In some embodiments of a compound of Formula (IV), $R^{18}$ and $R^{19}$ are each independently hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (IV), $R^{18}$ and $R^{19}$ are each independently hydrogen, halogen, or optionally substituted $C_1$-$C_6$ alkyl. In some embodiments of a compound of Formula (IV), $R^{18}$ and $R^{19}$ are each independently hydrogen or $C_1$-$C_6$ alkyl. In some embodiments of a compound of Formula (IV), $R^{18}$ and $R^{19}$ are hydrogen.

In some embodiments the compound of Formula (IV) has the structure of Formula (IVa):

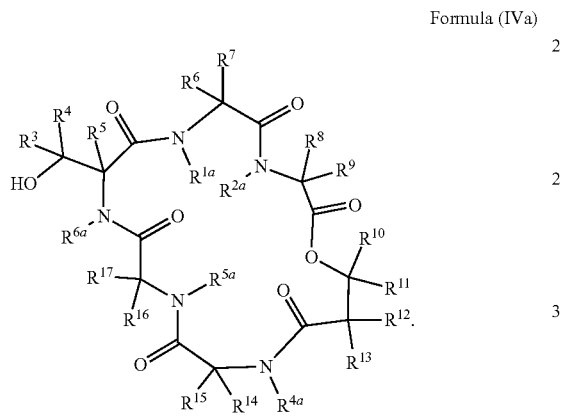

Formula (IVa)

In some embodiments of a compound of Formula (IV) or (IVa), $R^5$ is hydrogen or optionally substituted $C_1$-$C_6$ alkyl. In some embodiments of a compound of Formula (IV) or (IVa), $R^5$ is hydrogen or $C_1$-$C_6$ alkyl. In some embodiments of a compound of Formula (IV) or (IVa), $R^5$ is hydrogen.

In some embodiments of a compound of Formula (IV) or (IVa), $R^7$ is hydrogen or optionally substituted $C_1$-$C_6$ alkyl. In some embodiments of a compound of Formula (IV) or (IVa), $R^7$ is hydrogen or $C_1$-$C_6$ alkyl. In some embodiments of a compound of Formula (IV) or (IVa), $R^7$ is hydrogen.

In some embodiments of a compound of Formula (IV) or (IVa), $R^9$ is hydrogen or optionally substituted $C_1$-$C_6$ alkyl. In some embodiments of a compound of Formula (IV) or (IVa), $R^9$ is hydrogen or $C_1$-$C_6$ alkyl. In some embodiments of a compound of Formula (IV) or (IVa), $R^9$ is hydrogen.

In some embodiments of a compound of Formula (IV) or (IVa), $R^{11}$ is hydrogen or optionally substituted $C_1$-$C_6$ alkyl. In some embodiments of a compound of Formula (IV) or (IVa), $R^{11}$ is hydrogen or $C_1$-$C_6$ alkyl. In some embodiments of a compound of Formula (IV) or (IVa), $R^{11}$ is hydrogen.

In some embodiments of a compound of Formula (IV) or (IVa), $R^{13}$ is hydrogen or optionally substituted $C_1$-$C_6$ alkyl. In some embodiments of a compound of Formula (IV) or (IVa), $R^{13}$ is hydrogen or $C_1$-$C_6$ alkyl. In some embodiments of a compound of Formula (IV) or (IVa), $R^{13}$ is hydrogen.

In some embodiments of a compound of Formula (IV) or (IVa), $R^{15}$ is hydrogen or optionally substituted $C_1$-$C_6$ alkyl. In some embodiments of a compound of Formula (IV) or (IVa), $R^{15}$ is hydrogen or $C_1$-$C_6$ alkyl. In some embodiments of a compound of Formula (IV) or (IVa), $R^{15}$ is hydrogen.

In some embodiments of a compound of Formula (IV) or (IVa), $R^{17}$ is hydrogen or optionally substituted $C_1$-$C_6$ alkyl.

In some embodiments of a compound of Formula (IV) or (IVa), $R^{17}$ is hydrogen or $C_1$-$C_6$ alkyl. In some embodiments of a compound of Formula (IV) or (IVa), $R^{17}$ is hydrogen.

In some embodiments the compound of Formula (IV) or (IVa) has the structure of Formula (IVb):

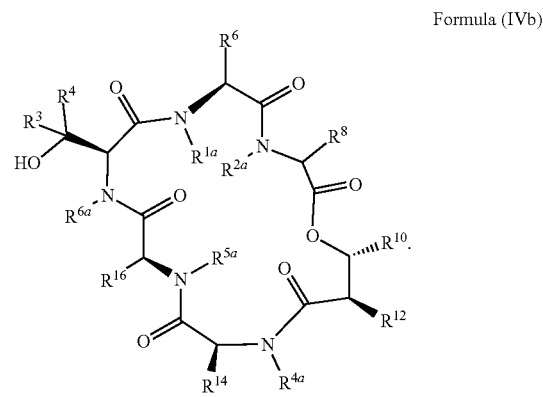

Formula (IVb)

In some embodiments of a compound of Formula (IV), (IVa), or (IVb), $R^{1a}$ is hydrogen or $C_1$-$C_6$ alkyl. In some embodiments of a compound of Formula (IV), (IVa), or (IVb), $R^{1a}$ is hydrogen. In some embodiments of a compound of Formula (IV), (IVa), or (IVb), $R^{1a}$ is $C_1$-$C_6$ alkyl.

In some embodiments of a compound of Formula (IV), (IVa), or (IVb), $R^{2a}$ is hydrogen or $C_1$-$C_6$ alkyl. In some embodiments of a compound of Formula (IV), (IVa), or (IVb), $R^{2a}$ is hydrogen. In some embodiments of a compound of Formula (IV), (IVa), or (IVb), $R^{2a}$ is $C_1$-$C_6$ alkyl.

In some embodiments of a compound of Formula (IV), (IVa), or (IVb), $R^{5a}$ is hydrogen or $C_1$-$C_6$ alkyl. In some embodiments of a compound of Formula (IV), (IVa), or (IVb), $R^{5a}$ is hydrogen. In some embodiments of a compound of Formula (IV), (IVa), or (IVb), $R^{5a}$ is $C_1$-$C_6$ alkyl.

In some embodiments of a compound of Formula (IV), (IVa), or (IVb), $R^{6a}$ is hydrogen or $C_1$-$C_6$ alkyl. In some embodiments of a compound of Formula (IV), (IVa), or (IVb), $R^{6a}$ is hydrogen. In some embodiments of a compound of Formula (IV), (IVa), or (IVb), $R^{6a}$ is $C_1$-$C_6$ alkyl.

In some embodiments the compound of Formula (IV), (IVa), or (IVb) has the structure of Formula (IVc):

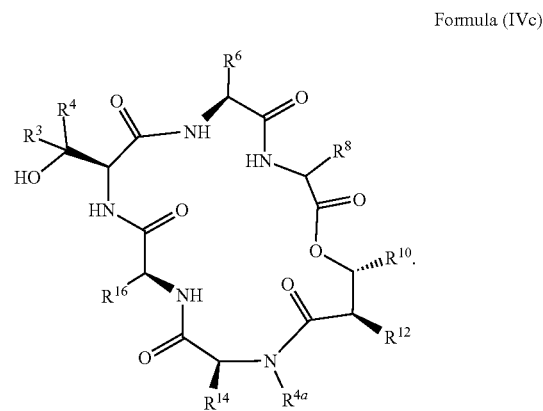

Formula (IVc)

In some embodiments of a compound of Formula (IV), (IVa), (IVb), or (IVc), $R^{4a}$ is hydrogen or $C_1$-$C_6$ alkyl. In some embodiments of a compound of Formula (IV), (IVa), (IVb), or (IVc), $R^{4a}$ is hydrogen. In some embodiments of a compound of Formula (IV), (IVa), (IVb), or (IVc), $R^{4a}$ is $C_1$-$C_6$ alkyl.

In some embodiments of a compound of Formula (IV), (IVa), (IVb), or (IVc), $R^{14}$ and $R^{4a}$ are taken together with the atoms to which they are attached to form an optionally substituted 5- or 6-membered heterocycloalkyl. In some embodiments of a compound of Formula (IV), (IVa), (IVb), or (IVc), $R^{14}$ and $R^{4a}$ are taken together with the atoms to which they are attached to form an optionally substituted 5-membered heterocycloalkyl. In some embodiments of a compound of Formula (IV), (IVa), (IVb), or (IVc), $R^{14}$ and $R^{4a}$ are taken together with the atoms to which they are attached to form an optionally substituted 6-membered heterocycloalkyl.

In some embodiments of a compound of Formula (IV), (IVa), (IVb), or (IVc), each $R^3$ and $R^4$ are independently hydrogen or optionally substituted $C_1$-$C_6$ alkyl. In some embodiments of a compound of Formula (IV), (IVa), (IVb), or (IVc), each $R^3$ and $R^4$ are independently hydrogen or $C_1$-$C_6$ alkyl. In some embodiments of a compound of Formula (IV), (IVa), (IVb), or (IVc), each $R^3$ and $R^4$ are hydrogen. In some embodiments of a compound of Formula (IV), (IVa), (IVb), or (IVc), $R^3$ is hydrogen and $R^4$ is $C_1$-$C_6$ alkyl.

In some embodiments of a compound of Formula (IV), (IVa), (IVb), or (IVc), $R^6$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (IV), (IVa), (IVb), or (IVc), $R^6$ is hydrogen, optionally substituted $C_1$-$C_6$ alkyl, or optionally substituted heterocycloalkyl. In some embodiments of a compound of Formula (IV), (IVa), (IVb), or (IVc), $R^6$ is optionally substituted $C_1$-$C_6$ alkyl or optionally substituted heterocycloalkyl. In some embodiments of a compound of Formula (IV), (IVa), (IVb), or (IVc), $R^6$ is optionally substituted heterocycloalkyl selected from aziridinyl, azetidinyl, pyrrolidinyl, piperidinyl, or piperazinyl. In some embodiments of a compound of Formula (IV), (IVa), (IVb), or (IVc), $R^6$ is $C_1$-$C_6$ alkyl optionally substituted with one, two, or three halogen, —$OR^b$, —$NR^bR^c$, —NC(=$NR^b$)$NR^bR^c$, —S(=O)$_2R^a$, —$NR^bS$(=O)$_2R^a$, —S(=O)$_2NR^bR^c$, —C(=O)$R^a$, —OC(=O)$R^a$, —C(=O)$OR^a$, —OC(=O)$OR^b$, —C(=O)$NR^bR^c$, —$NR^bC$(=O) $[(R^d)_2]_{1-4}NR^bR^c$, —OC$[(R^d)_2]_{2-4}OR^b$, —OC$[(R^d)_2]_{2-4}$ $NR^bR^c$, —OC$[(R^d)_2]_{2-4}$OC$[(R^d)_2]_{2-4}NR^bR^c$, —OC$[(R^d)_2]_{2-4}$NC(=$NR^b$)$NR^bR^c$, —OC(=O)$NR^bR^c$, —$NR^bC$(=O)$NR^bR^c$, —$NR^bC$(=O)$R^a$, —$NR^bC$(=O) $OR^b$, —O-(optionally substituted heterocycloalkyl), —O-(optionally substituted aryl), or heteroaryl; and each $R^d$ is independently hydrogen, halogen, —OH, —$OCH_3$, or $C_1$-$C_6$ alkyl. In some embodiments of a compound of Formula (IV), (IVa), (IVb), or (IVc), $R^6$ is $C_1$-$C_6$ alkyl optionally substituted with one, two, or three halogen, —$OR^b$, —$NR^bR^c$, —S(=O)$_2R^a$, —$NR^bS$(=O)$_2R^a$, —S(=O)$_2NR^bR^c$, —C(=O)$R^a$, —OC(=O)$R^a$, —C(=O) $OR^a$, —OC(=O)$OR^b$, —C(=O)$NR^bR^c$, —OC(=O) $NR^bR^c$, —$NR^bC$(=O)$NR^bR^c$, —$NR^bC$(=O)$R^a$, —$NR^bC$ (=O)$OR^b$, or heteroaryl. In some embodiments of a compound of Formula (IV), (IVa), (IVb), or (IVc), $R^6$ is $C_1$-$C_6$ alkyl optionally substituted —$OR^b$. In some embodiments of a compound of Formula (IV), (IVa), (IVb), or (IVc), $R^6$ is selected from:

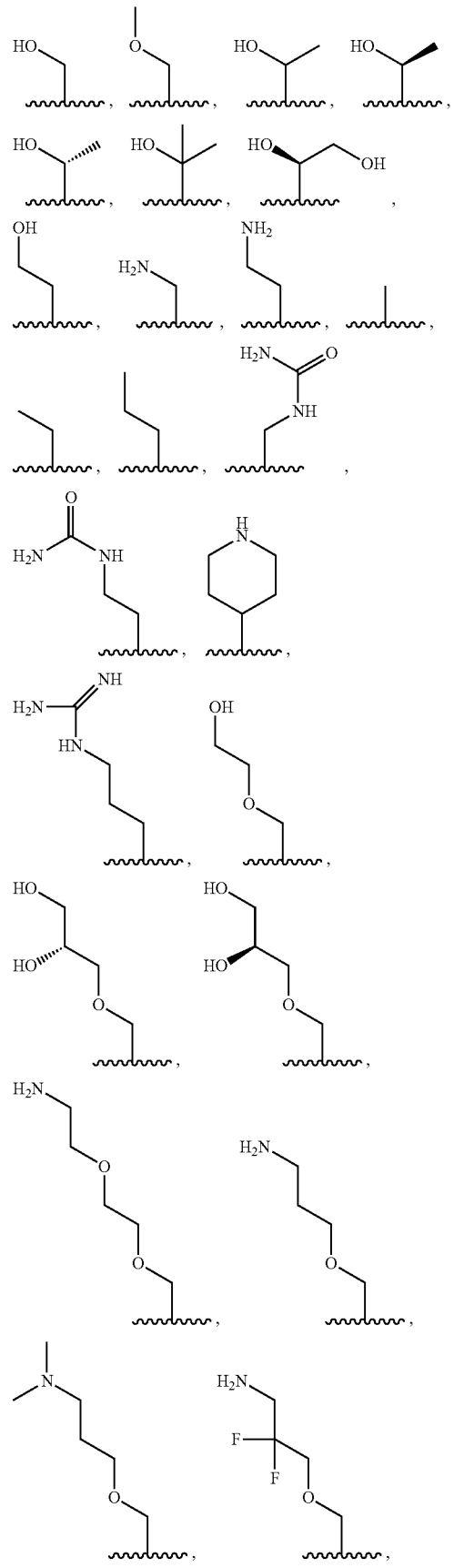

-continued

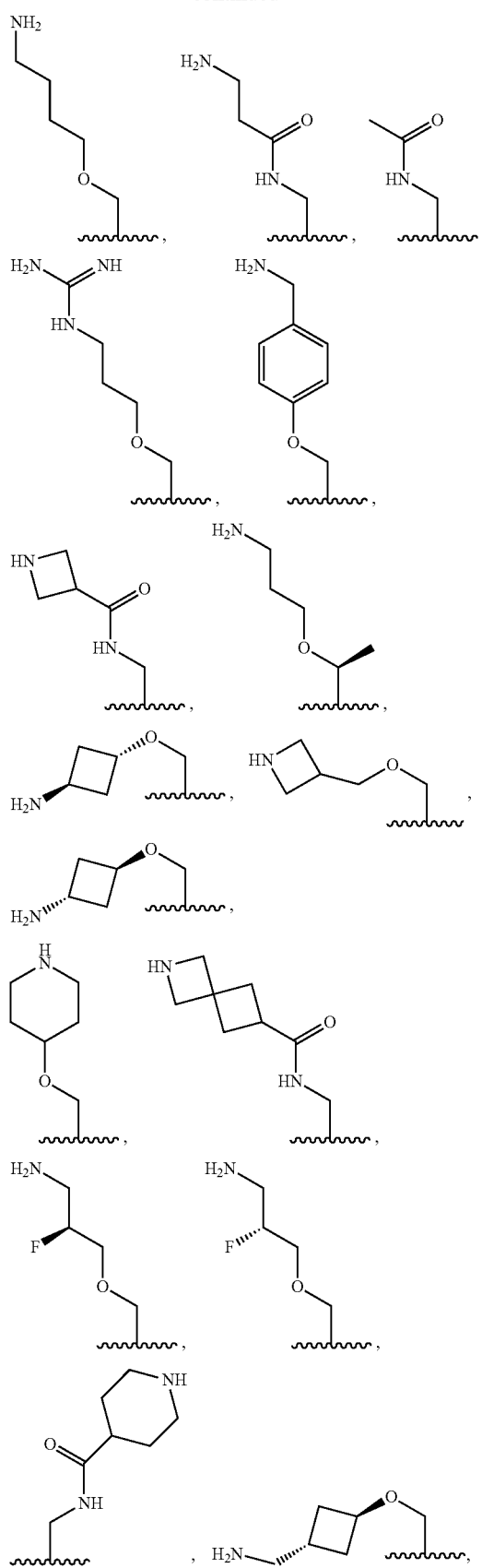

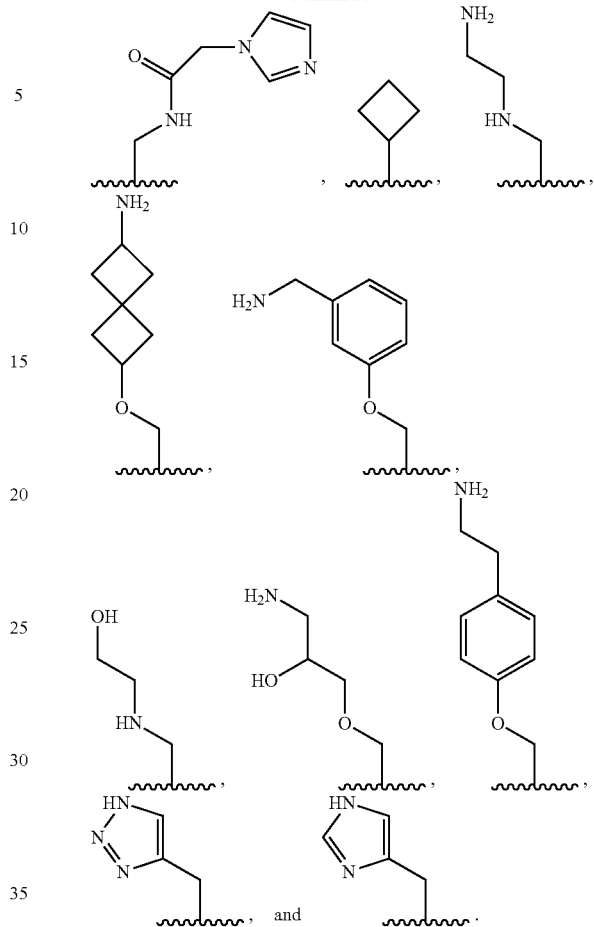

In some embodiments of a compound of Formula (IV), (IVa), (IVb), or (IVc), $R^8$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (IV), (IVa), (IVb), or (IVc), $R^8$ is hydrogen or $C_1$-$C_6$ alkyl. In some embodiments of a compound of Formula (IV), (IVa), (IVb), or (IVc), $R^8$ is hydrogen. In some embodiments of a compound of Formula (IV), (IVa), (IVb), or (IVc), $R^8$ is $C_1$-$C_6$ alkyl.

In some embodiments of a compound of Formula (IV), (IVa), (IVb), or (IVc), $R^{10}$ is optionally substituted branched $C_3$-$C_{20}$ alkyl. In some embodiments of a compound of Formula (IV), (IVa), (IVb), or (IVc), $R^{10}$ is optionally substituted branched $C_3$-$C_{10}$ alkyl. In some embodiments of a compound of Formula (IV), (IVa), (IVb), or (IVc), $R^{10}$ is optionally substituted branched $C_3$-$C_9$ alkyl. In some embodiments of a compound of Formula (IV), (IVa), (IVb), or (IVc), $R^{10}$ is branched $C_3$-$C_{20}$ alkyl. In some embodiments of a compound of Formula (IV), (IVa), (IVb), or (IVc), $R^{10}$ is branched $C_3$-$C_{10}$ alkyl. In some embodiments of a compound of Formula (IV), (IVa), (IVb), or (IVc), $R^{10}$ is branched $C_3$-$C_9$ alkyl. In some embodiments of a compound of Formula (IV), (IVa), (IVb), or (IVc), $R^{10}$ is optionally substituted linear $C_{10}$-$C_{20}$ alkyl. In some embodiments of a compound of Formula (IV), (IVa), (IVb), or (IVc), $R^{10}$ is optionally substituted linear $C_{10}$-$C_{15}$ alkyl. In some embodiments of a compound of Formula (IV), (IVa), (IVb), or (IVc), $R^{10}$ is optionally substituted linear $C_{11}$-$C_{15}$ alkyl. In some embodiments of a compound of Formula (IV), (IVa), (IVb), or (IVc), $R^{10}$ is optionally substituted linear $C_{10}$-$C_{12}$ alkyl. In some embodiments of a compound of Formula (IV), (IVa), (IVb), or (IVc), $R^{10}$ is optionally substituted linear $C_{10}$ alkyl. In some embodiments of a compound of Formula (IV), (IVa), (IVb), or (IVc), $R^{10}$ is linear $C_{10}$-$C_{15}$ alkyl. In some embodiments of a compound of Formula (IV), (IVa), (IVb), or (IVc), $R^{10}$ is linear $C_{11}$-$C_{15}$ alkyl. In some embodiments of a compound of Formula (IV), (IVa), (IVb), or (IVc), $R^{10}$ is linear $C_{10}$-$C_{12}$ alkyl. In some embodiments of a compound of Formula (IV), (IVa), (IVb), or (IVc), $R^{10}$ is linear $C_{10}$ alkyl.

In some embodiments of a compound of Formula (IV), (IVa), (IVb), or (IVc), $R^{10}$ is optionally substituted $C_{10}$-$C_{15}$ alkyl. In some embodiments of a compound of Formula (IV), (IVa), (IVb), or (IVc), $R^{10}$ is optionally substituted $C_{11}$-$C_{15}$ alkyl. In some embodiments of a compound of Formula (IV), (IVa), (IVb), or (IVc), $R^{10}$ is optionally substituted $C_{10}$-$C_{12}$ alkyl. In some embodiments of a compound of Formula (IV), (IVa), (IVb), or (IVc), $R^{10}$ is $C_{10}$-$C_{15}$ alkyl. In some embodiments of a compound of Formula (IV), (IVa), (IVb), or (IVc), $R^{10}$ is $C_{11}$-$C_{15}$ alkyl. In some embodiments of a compound of Formula (IV), (IVa), (IVb), or (IVc), $R^{10}$ is $C_{10}$-$C_{12}$ alkyl.

In some embodiments of a compound of Formula (IV), (IVa), (IVb), or (IVc), $R^{10}$ is

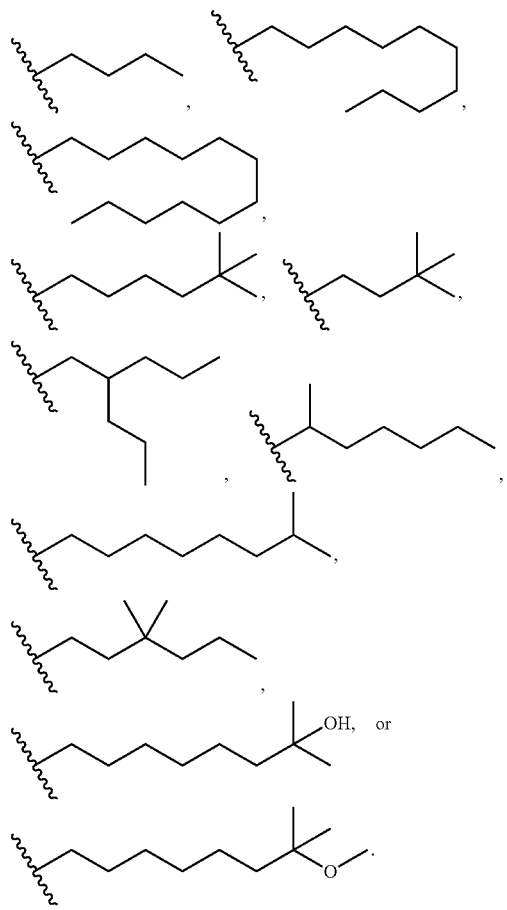

In some embodiments of a compound of Formula (IV), (IVa), (IVb), or (IVc), $R^{12}$ is halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (IV), (IVa), (IVb), or (IVc), $R^{12}$ is optionally substituted $C_1$-$C_6$ alkyl. In some embodiments of a compound of Formula (IV), (IVa), (IVb), or (IVc), $R^{12}$ is $C_1$-$C_6$ alkyl. In some embodiments of a compound of Formula (IV), (IVa), (IVb), or (IVc), $R^{12}$ is ethyl or methyl. In some embodiments of a compound of Formula (IV), (IVa), (IVb), or (IVc), $R^{12}$ is methyl.

In some embodiments of a compound of Formula (IV), (IVa), (IVb), or (IVc), $R^{12}$ is halogen, optionally substituted $C_2$-$C_6$ alkyl, optionally substituted cycloalkyl, optionally substituted heterocycloalkyl, optionally substituted aryl, or optionally substituted heteroaryl. In some embodiments of a compound of Formula (IV), (IVa), (IVb), or (IVc), $R^{12}$ is halogen, optionally substituted $C_1$-$C_6$ alkyl, optionally substituted ($C_1$-$C_6$ alkyl)aryl, or optionally substituted ($C_1$-$C_6$ alkyl)cycloalkyl. In some embodiments of a compound of Formula (IV), (IVa), (IVb), or (IVc), $R^{12}$ is $C_1$-$C_6$ alkyl, $C_1$-$C_6$ haloalkyl, ($C_1$-$C_6$ alkyl)aryl, or ($C_1$-$C_6$ alkyl)cycloalkyl; wherein the aryl is optionally substituted with one, two, or three halogen, $C_1$-$C_6$ alkyl, $C_1$-$C_6$ haloalkyl, —OH, —OCH$_3$, or aryl. In some embodiments of a compound of Formula (IV), (IVa), (IVb), or (IVc), $R^{12}$ is $C_2$-$C_6$ alkyl. In some embodiments of a compound of Formula (IV), (IVa), (IVb), or (IVc), $R^{12}$ is optionally substituted ($C_1$-$C_6$ alkyl)aryl. In some embodiments of a compound of Formula (IV), (IVa), (IVb), or (IVc), $R^{12}$ is optionally substituted ($C_1$-$C_6$ alkyl)aryl wherein the aryl is optionally substituted phenyl.

In some embodiments of a compound of Formula (IV), (IVa), (IVb), or (IVc), $R^{12}$ is

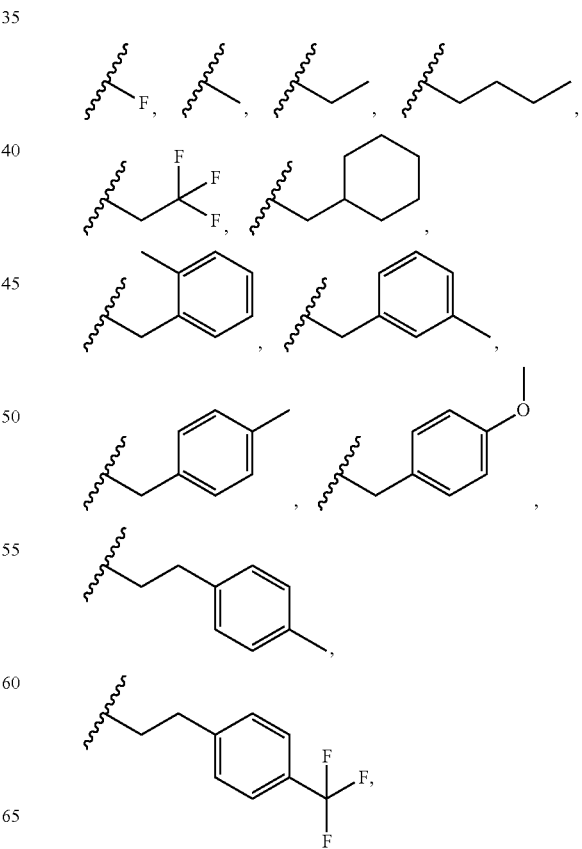

-continued

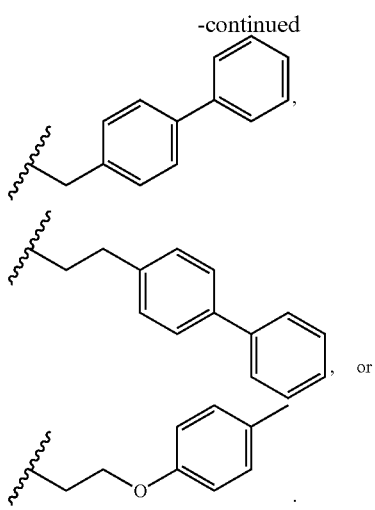

In some embodiments of a compound of Formula (IV), (IVa), (IVb), or (IVc), $R^{14}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, or optionally substituted heteroaryl. In some embodiments of a compound of Formula (IV), (IVa), (IVb), or (IVc), $R^{14}$ is hydrogen, optionally substituted $C_1$-$C_6$ alkyl, optionally substituted cycloalkyl, or optionally substituted ($C_1$-$C_6$ alkyl)cycloalkyl. In some embodiments of a compound of Formula (IV), (IVa), (IVb), or (IVc), $R^{14}$ is optionally substituted $C_1$-$C_6$ alkyl or optionally substituted ($C_1$-$C_6$ alkyl)cycloalkyl. In some embodiments of a compound of Formula (IV), (IVa), (IVb), or (IVc), $R^{14}$ is $C_1$-$C_6$ alkyl, $C_1$-$C_6$ haloalkyl, or ($C_1$-$C_6$ alkyl)cycloalkyl. In some embodiments of a compound of Formula (IV). (IVa), (IVb), or (IVc), $R^{14}$ is selected from:

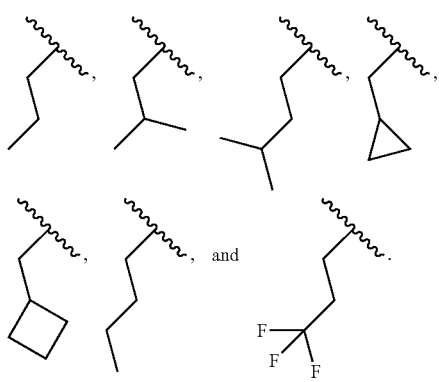

In some embodiments of a compound of Formula (IV), (IVa), (IVb), or (IVc), $R^{16}$ is hydrogen, halogen, optionally substituted $C_1$-$C_6$ alkyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, or optionally substituted heteroaryl. In some embodiments of a compound of Formula (IV), (IVa), (IVb), or (IVc), $R^{16}$ is optionally substituted $C_1$-$C_6$ alkyl, optionally substituted ($C_1$-$C_6$ alkyl)cycloalkyl, optionally substituted cycloalkyl, optionally substituted ($C_1$-$C_6$ alkyl)aryl, or optionally substituted aryl. In some embodiments of a compound of Formula (IV), (IVa), (IVb), or (IVc), $R^{16}$ is optionally substituted $C_1$-$C_6$ alkyl, optionally substituted ($C_1$-$C_6$ alkyl)cycloalkyl, or optionally substituted cycloalkyl. In some embodiments of a compound of Formula (IV), (IVa), (IVb), or (IVc), $R^{16}$ is optionally substituted $C_1$-$C_6$ alkyl, optionally substituted ($C_1$-$C_6$ alkyl)cycloalkyl, or optionally substituted cycloalkyl. In some embodiments of a compound of Formula (IV), (IVa), (IVb), or (IVc), $R^{16}$ is $C_1$-$C_6$ alkyl, ($C_1$-$C_6$ alkyl)cycloalkyl, cycloalkyl, ($C_1$-$C_6$ alkyl)aryl, or aryl, each optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl. In some embodiments of a compound of Formula (IV), (IVa), (IVb), or (IVc), $R^{16}$ is $C_1$-$C_6$ alkyl, ($C_1$-$C_6$ alkyl)cycloalkyl, or cycloalkyl, each optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl. In some embodiments of a compound of Formula (IV), (IVa), (IVb), or (IVc), $R^{16}$ is $C_3$-$C_7$ cycloalkyl. In some embodiments of a compound of Formula (IV), (IVa), (IVb), or (IVc), $R^{16}$ is cyclobutyl, cyclopentyl, cyclohexyl, or cycloheptyl. In some embodiments of a compound of Formula (IV), (IVa), (IVb), or (IVc), $R^{16}$ is cyclohexyl. In some embodiments of a compound of Formula (IV), (IVa), (IVb), or (IVc), $R^{16}$ is cycloheptyl. In some embodiments of a compound of Formula (IV), (IVa), (IVb), or (IVc), $R^{16}$ is selected from:

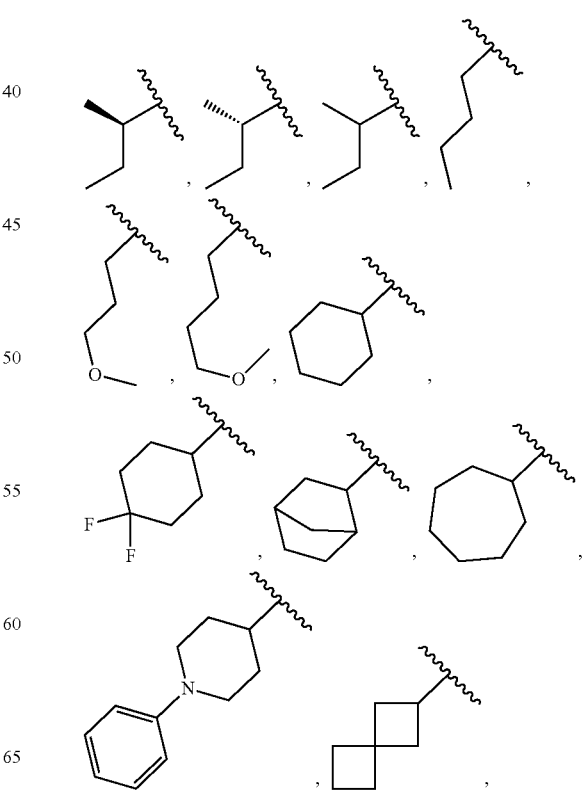

-continued

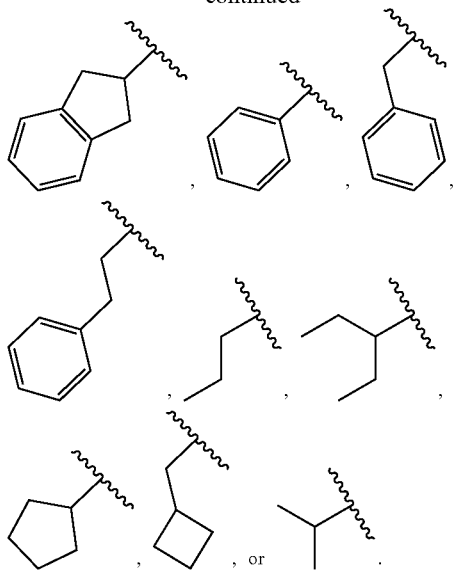

In some embodiments of a compound of Formula (IV), (IVa), (IVb), or (IVc), each $R^a$ is independently $C_1$-$C_6$ alkyl. In some embodiments of a compound of Formula (IV), (IVa), (IVb), or (IVc), each $R^b$ and $R^c$ is independently hydrogen or $C_1$-$C_6$ alkyl. In some embodiments of a compound of Formula (IV), (IVa), (IVb), or (IVc), each $R^b$ and $R^c$ is hydrogen.

Also disclosed herein is a compound of Formula (V):

Formula (V)

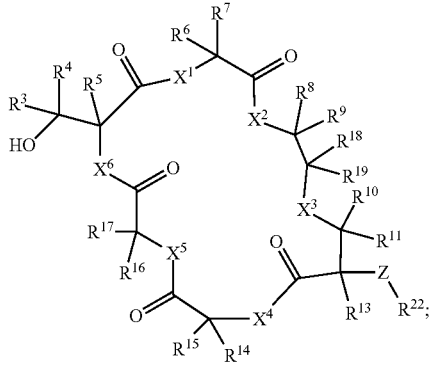

wherein:
$X^1$ is —O— or —NR$^{1a}$—;
$X^2$ is —O— or —NR$^{2a}$—;
$X^3$ is —O— or —NR$^{3a}$—;
$X^4$ is —O— or —NR$^{4a}$—;
$X^5$ is —O— or —NR$^{5a}$—;
$X^6$ is —O— or —NR$^{6a}$—;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^3$ and $R^4$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;
or $R^3$ and $R^4$ are taken together with the carbon atom to which they are attached to form an oxo; $R^5$ is hydrogen, halogen, optionally substituted $C_1$-$C_6$ alkyl, optionally substituted $C_2$-$C_6$ alkenyl, or optionally substituted $C_2$-$C_6$ alkynyl;
$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{10}$ is optionally substituted $C_2$-$C_{20}$ alkyl;
$R^{11}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
Z is —CR$^{23}$R$^{24}$—, —O—, or —NR$^{25}$—;
$R^{22}$ is optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{23}$, $R^{24}$, and $R^{25}$ are each independently hydrogen or optionally substituted $C_1$-$C_6$ alkyl;
$R^{13}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;
or $R^{14}$ and $R^{4a}$ are taken together with the atoms to which they are attached to form an optionally substituted heterocycloalkyl;
$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

In some embodiments of a compound of Formula (V), $R^{18}$ and $R^{19}$ are taken together with the carbon atom to which they are attached to form an oxo.

In some embodiments of a compound of Formula (V), $R^{18}$ and $R^{19}$ are each independently hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (V), $R^{18}$ and $R^{19}$ are each independently hydrogen, halogen, or optionally substituted $C_1$-$C_6$ alkyl. In some embodiments of a compound of Formula (V), $R^{18}$ and $R^{19}$ are each independently hydrogen or $C_1$-$C_6$ alkyl. In some embodiments of a compound of Formula (V), $R^{18}$ and $R^{19}$ are hydrogen.

In some embodiments the compound of Formula (V) has the structure of Formula (Va):

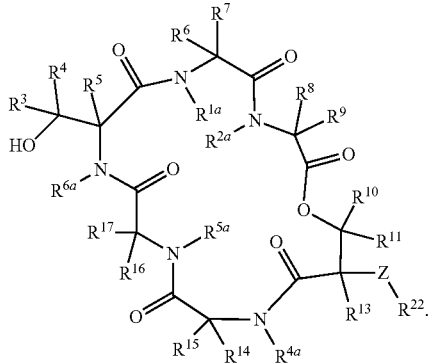

Formula (Va)

In some embodiments of a compound of Formula (V) or (Va), $R^5$ is hydrogen or optionally substituted $C_1$-$C_6$ alkyl. In some embodiments of a compound of Formula (V) or (Va), $R^5$ is hydrogen or $C_1$-$C_6$ alkyl. In some embodiments of a compound of Formula (V) or (Va), $R^5$ is hydrogen.

In some embodiments of a compound of Formula (V) or (Va), $R^7$ is hydrogen or optionally substituted $C_1$-$C_6$ alkyl. In some embodiments of a compound of Formula (V) or (Va), $R^7$ is hydrogen or $C_1$-$C_6$ alkyl. In some embodiments of a compound of Formula (V) or (Va), $R^7$ is hydrogen.

In some embodiments of a compound of Formula (V) or (Va), $R^9$ is hydrogen or optionally substituted $C_1$-$C_6$ alkyl. In some embodiments of a compound of Formula (V) or (Va), $R^9$ is hydrogen or $C_1$-$C_6$ alkyl. In some embodiments of a compound of Formula (V) or (Va), $R^9$ is hydrogen.

In some embodiments of a compound of Formula (V) or (Va), $R^{11}$ is hydrogen or optionally substituted $C_1$-$C_6$ alkyl. In some embodiments of a compound of Formula (V) or (Va), $R^{11}$ is hydrogen or $C_1$-$C_6$ alkyl. In some embodiments of a compound of Formula (V) or (Va), $R^{11}$ is hydrogen.

In some embodiments of a compound of Formula (V) or (Va), $R^{13}$ is hydrogen or optionally substituted $C_1$-$C_6$ alkyl. In some embodiments of a compound of Formula (V) or (Va), $R^{13}$ is hydrogen or $C_1$-$C_6$ alkyl. In some embodiments of a compound of Formula (V) or (Va), $R^{13}$ is hydrogen.

In some embodiments of a compound of Formula (V) or (Va), $R^{15}$ is hydrogen or optionally substituted $C_1$-$C_6$ alkyl. In some embodiments of a compound of Formula (V) or (Va), $R^{15}$ is hydrogen or $C_1$-$C_6$ alkyl. In some embodiments of a compound of Formula (V) or (Va), $R^{15}$ is hydrogen.

In some embodiments of a compound of Formula (V) or (Va), $R^{17}$ is hydrogen or optionally substituted $C_1$-$C_6$ alkyl. In some embodiments of a compound of Formula (V) or (Va), $R^{17}$ is hydrogen or $C_1$-$C_6$ alkyl. In some embodiments of a compound of Formula (V) or (Va), $R^{17}$ is hydrogen.

In some embodiments the compound of Formula (V) or (Va) has the structure of Formula (Vb):

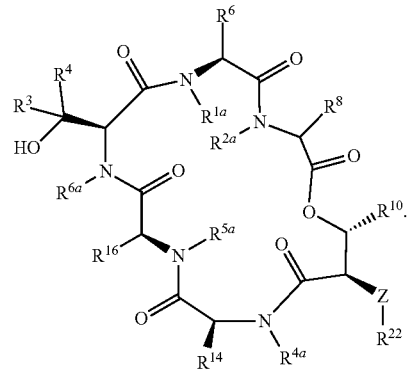

Formula (Vb)

In some embodiments of a compound of Formula (V), (Va), or (Vb), $R^{1a}$ is hydrogen or $C_1$-$C_6$ alkyl. In some embodiments of a compound of Formula (V), (Va), or (Vb), $R^{1a}$ is hydrogen. In some embodiments of a compound of Formula (V), (Va), or (Vb), $R^{1a}$ is $C_1$-$C_6$ alkyl.

In some embodiments of a compound of Formula (V), (Va), or (Vb), $R^{2a}$ is hydrogen or $C_1$-$C_6$ alkyl. In some embodiments of a compound of Formula (V), (Va), or (Vb), $R^{2a}$ is hydrogen. In some embodiments of a compound of Formula (V), (Va), or (Vb), $R^{2a}$ is $C_1$-$C_6$ alkyl.

In some embodiments of a compound of Formula (V), (Va), or (Vb), $R^{5a}$ is hydrogen or $C_1$-$C_6$ alkyl. In some embodiments of a compound of Formula (V), (Va), or (Vb), $R^{5a}$ is hydrogen. In some embodiments of a compound of Formula (V), (Va), or (Vb), $R^{5a}$ is $C_1$-$C_6$ alkyl.

In some embodiments of a compound of Formula (V), (Va), or (Vb), $R^{6a}$ is hydrogen or $C_1$-$C_6$ alkyl. In some embodiments of a compound of Formula (V), (Va), or (Vb), $R^{6a}$ is hydrogen. In some embodiments of a compound of Formula (V), (Va), or (Vb), $R^{6a}$ is $C_1$-$C_6$ alkyl.

In some embodiments the compound of Formula (V), (Va), or (Vb) has the structure of Formula (Vc):

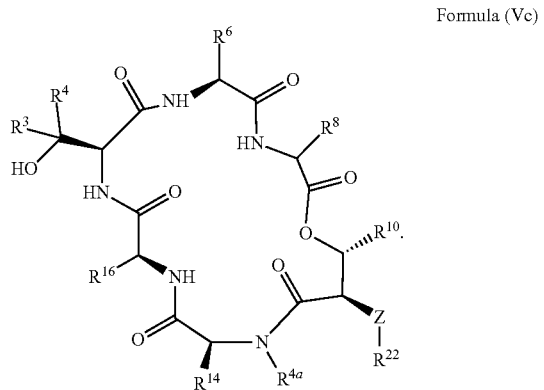

Formula (Vc)

In some embodiments of a compound of Formula (V), (Va), (Vb), or (Vc), $R^{4a}$ is hydrogen or $C_1$-$C_6$ alkyl. In some embodiments of a compound of Formula (V), (Va), (Vb), or (Vc), $R^{4a}$ is hydrogen. In some embodiments of a compound of Formula (V), (Va), (Vb), or (Vc), $R^{4a}$ is $C_1$-$C_6$ alkyl.

In some embodiments of a compound of Formula (V), (Va), (Vb), or (Vc), $R^{14}$ and $R^{4a}$ are taken together with the atoms to which they are attached to form an optionally substituted 5- or 6-membered heterocycloalkyl. In some embodiments of a compound of Formula (V), (Va), (Vb), or (Vc), $R^{14}$ and $R^{4a}$ are taken together with the atoms to which they are attached to form an optionally substituted 5-membered heterocycloalkyl. In some embodiments of a compound of Formula (V), (Va), (Vb), or (Vc), $R^{14}$ and $R^{4a}$ are taken together with the atoms to which they are attached to form an optionally substituted 6-membered heterocycloalkyl.

In some embodiments of a compound of Formula (V), (Va), (Vb), or (Vc), each $R^3$ and $R^4$ are independently hydrogen or optionally substituted $C_1$-$C_6$ alkyl. In some embodiments of a compound of Formula (V), (Va), (Vb), or (Vc), each $R^3$ and $R^4$ are independently hydrogen or $C_1$-$C_6$ alkyl. In some embodiments of a compound of Formula (V), (Va), (Vb), or (Vc), each $R^3$ and $R^4$ are hydrogen. In some embodiments of a compound of Formula (V), (Va), (Vb), or (Vc), $R^3$ is hydrogen and $R^4$ is $C_1$-$C_6$ alkyl.

In some embodiments of a compound of Formula (V), (Va), (Vb), or (Vc), $R^6$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (V), (Va), (Vb), or (Vc), $R^6$ is hydrogen, optionally substituted $C_1$-$C_6$ alkyl, or optionally substituted heterocycloalkyl. In some embodiments of a compound of Formula (V), (Va), (Vb), or (Vc), $R^6$ is optionally substituted $C_1$-$C_6$ alkyl or optionally substituted heterocycloalkyl. In some embodiments of a compound of Formula (V), (Va), (Vb), or (Vc), $R^6$ is optionally substituted heterocycloalkyl selected from aziridinyl, azetidinyl, pyrrolidinyl, piperidinyl, or piperazinyl. In some embodiments of a compound of Formula (V), (Va), (Vb), or (Vc), $R^6$ is $C_1$-$C_6$ alkyl optionally substituted with one, two, or three halogen, —$OR^b$, —$NR^bR^c$, —$NC(=NR^b)NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$NR^bC(=O)[(R^d)_2]_{1-4}NR^bR^c$, —$OC[(R^d)_2]_{2-4}OR^b$, —$OC[(R^d)_2]_{2-4}NR^bR^c$, —$OC[(R^d)_2]_{2-4}OC[(R^d)_2]_{2-4}NR^bR^c$, —$OC[(R^d)_2]_{2-4}NC(=NR^b)NR^bR^c$, —$OC(=O)NR^bR^c$, —$NR^bC(=O)NR^bR^c$, —$NR^bC(=O)R^a$, —$NR^bC(=O)OR^b$, —O-(optionally substituted heterocycloalkyl), —O-(optionally substituted aryl), or heteroaryl; and each $R^d$ is independently hydrogen, halogen, —OH, —$OCH_3$, or $C_1$-$C_6$ alkyl. In some embodiments of a compound of Formula (V), (Va), (Vb), or (Vc), $R^6$ is $C_1$-$C_6$ alkyl optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or heteroaryl. In some embodiments of a compound of Formula (V), (Va), (Vb), or (Vc), $R^6$ is $C_1$-$C_6$ alkyl optionally substituted with one, two, or three —$OR^b$. In some embodiments of a compound of Formula (V), (Va), (Vb), or (Vc), $R^6$ is selected from:

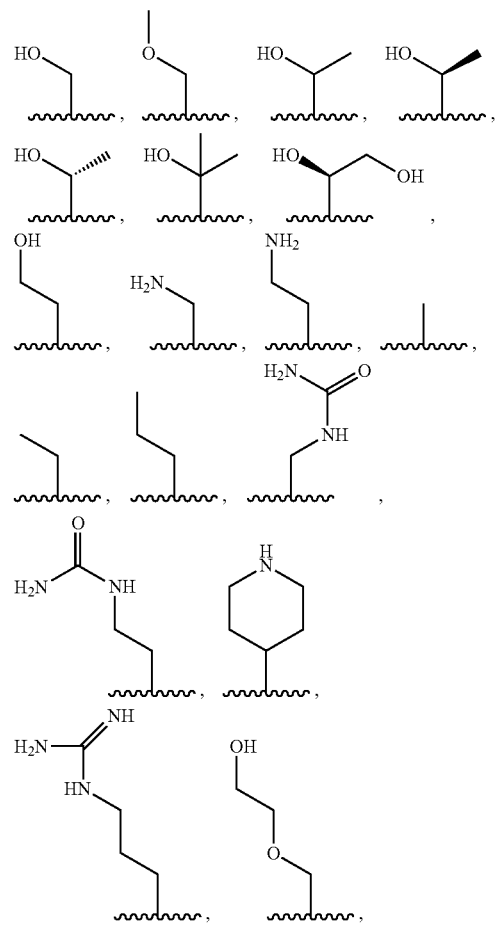

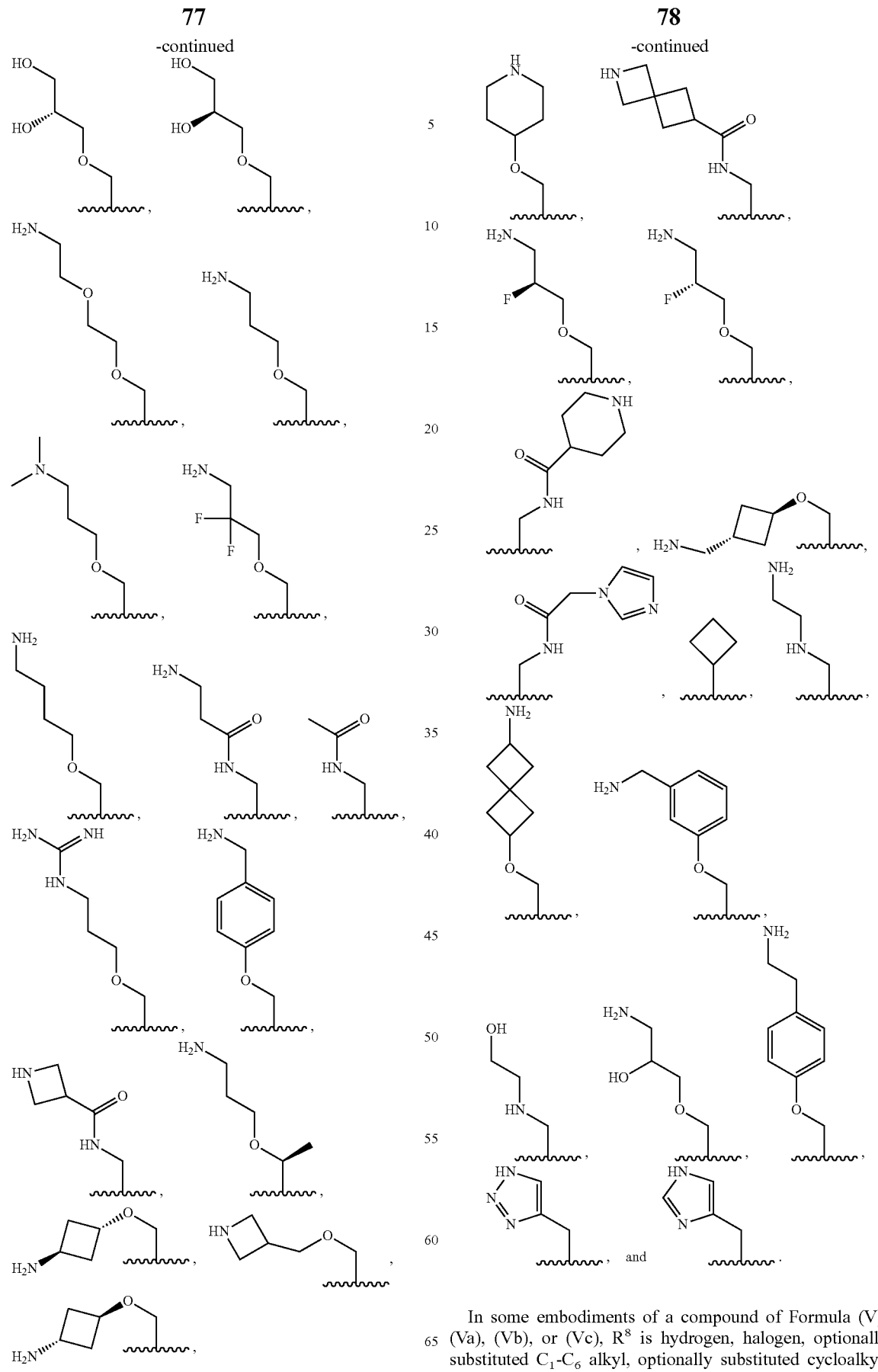
In some embodiments of a compound of Formula (V), (Va), (Vb), or (Vc), $R^8$ is hydrogen, halogen, optionally substituted $C_1$-$C_6$ alkyl, optionally substituted cycloalkyl, optionally substituted heterocycloalkyl, optionally substituted aryl, or optionally substituted heteroaryl. In some embodiments of a compound of Formula (V), (Va), (Vb), or (Vc), $R^8$ is hydrogen or $C_1$-$C_6$ alkyl. In some embodiments of a compound of Formula (V), (Va), (Vb), or (Vc), $R^8$ is hydrogen. In some embodiments of a compound of Formula (V), (Va), (Vb), or (Vc), $R^8$ is $C_1$-$C_6$ alkyl.

In some embodiments of a compound of Formula (V), (Va), (Vb), or (Vc), $R^{10}$ is optionally substituted $C_5$-$C_{12}$ alkyl. In some embodiments of a compound of Formula (V), (Va), (Vb), or (Vc), $R^{10}$ is optionally substituted $C_5$-$C_{10}$ alkyl. In some embodiments of a compound of Formula (V), (Va), (Vb), or (Vc), $R^{10}$ is optionally substituted $C_{10}$-$C_{15}$ alkyl.

In some embodiments of a compound of Formula (V), (Va), (Vb), or (Vc), $R^{10}$ is $C_2$-$C_{20}$ alkyl. In some embodiments of a compound of Formula (V), (Va), (Vb), or (Vc), $R^{10}$ is $C_5$-$C_{12}$ alkyl. In some embodiments of a compound of Formula (V), (Va), (Vb), or (Vc), $R^{10}$ is $C_5$-$C_{10}$ alkyl. In some embodiments of a compound of Formula (V), (Va), (Vb), or (Vc), R is $C_{10}$-$C_{15}$ alkyl.

In some embodiments of a compound of Formula (I), (Ia), (Ib), or (Ic), $R^{10}$ is

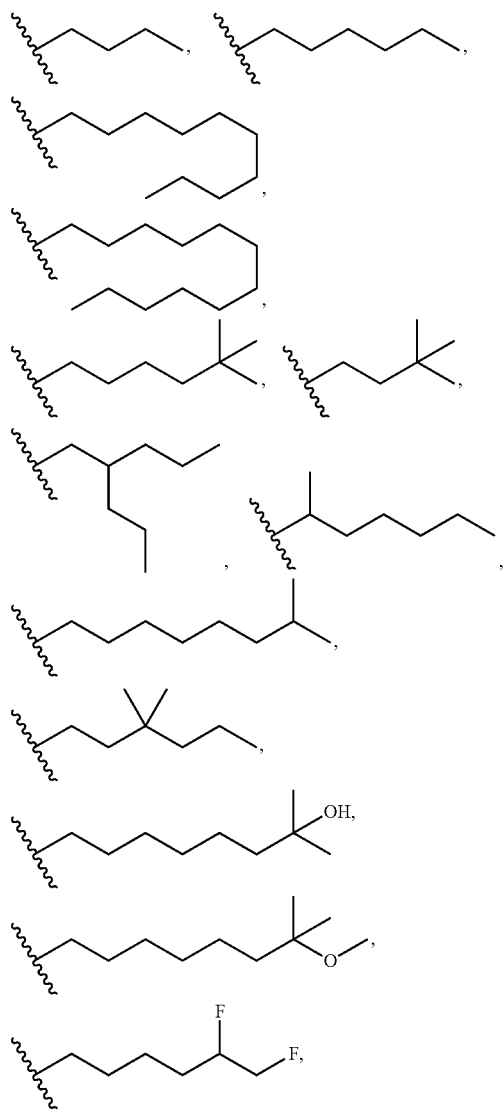

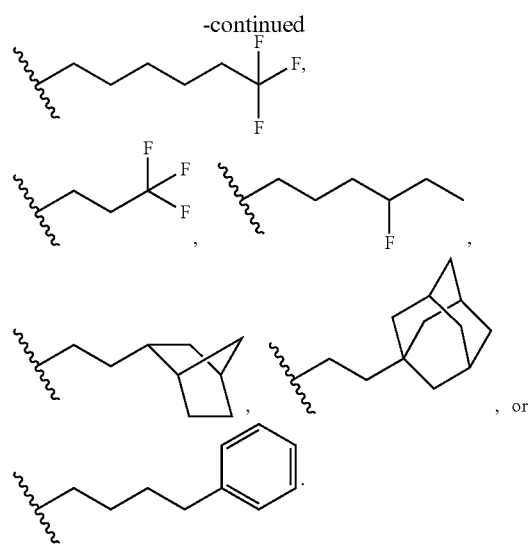

In some embodiments of a compound of Formula (V), (Va), (Vb), or (Vc), $R^{22}$ is optionally substituted $C_1$-$C_6$ alkyl or optionally substituted ($C_1$-$C_6$ alkyl)aryl. In some embodiments of a compound of Formula (V), (Va), (Vb), or (Vc), $R^{22}$ is optionally substituted $C_1$-$C_6$ alkyl. In some embodiments of a compound of Formula (V), (Va), (Vb), or (Vc), $R^{22}$ is optionally substituted $C_1$ alkyl. In some embodiments of a compound of Formula (V), (Va), (Vb), or (Vc), $R^{22}$ is $C_1$-$C_6$ alkyl. In some embodiments of a compound of Formula (V), (Va), (Vb), or (Vc), $R^{22}$ is $C_1$ alkyl. In some embodiments of a compound of Formula (V), (Va), (Vb), or (Vc), $R^{22}$ is optionally substituted ($C_1$-$C_6$ alkyl)aryl. In some embodiments of a compound of Formula (V), (Va), (Vb), or (Vc), $R^{22}$ is optionally substituted ($C_1$-$C_6$ alkyl)phenyl. In some embodiments of a compound of Formula (V), (Va), (Vb), or (Vc), $R^{22}$ is ($C_1$-$C_6$ alkyl)aryl. In some embodiments of a compound of Formula (V), (Va), (Vb), or (Vc), $R^{22}$ is ($C_1$-$C_6$ alkyl)phenyl.

In some embodiments of a compound of Formula (V), (Va), (Vb), or (Vc), each $R^{22}$ is optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or $C_1$-$C_6$ alkyl. In some embodiments of a compound of Formula (V), (Va), (Vb), or (Vc), each $R^{22}$ is optionally substituted with one, two, or three halogen, —$OR^b$, —$NR^bR^c$, —$C(=O)OR^a$, —$C(=O)NR^bR^c$, or $C_1$-$C_6$ alkyl. In some embodiments of a compound of Formula (V), (Va), (Vb), or (Vc), each $R^{22}$ is optionally substituted with one, two, or three halogen, —$OR^b$, —$NR^bR^c$, —$C(=O)OR^a$, —$C(=O)NR^bR^c$, $C_1$-$C_6$ alkyl, $C_1$-$C_6$ haloalkyl, or aryl. In some embodiments of a compound of Formula (V), (Va), (Vb), or (Vc), each $R^{22}$ is optionally substituted with one, two, or three halogen, —$OR^b$, $C_1$-$C_6$ alkyl, $C_1$-$C_6$ haloalkyl, or aryl. In some embodiments of a compound of Formula (V), (Va), (Vb), or (Vc), each $R^{22}$ is optionally substituted with one, two, or three halogen or $C_1$-$C_6$ alkyl. In some embodiments of a compound of Formula (V), (Va), (Vb), or (Vc), each $R^{22}$ is optionally substituted with one, two, or three $C_1$-$C_6$ alkyl.

In some embodiments of a compound of Formula (V), (Va), (Vb), or (Vc), Z is —O—. In some embodiments of a compound of Formula (V), (Va), (Vb), or (Vc), Z is —$NR^{25}$—; and $R^{25}$ is hydrogen or $C_1$-$C_6$ alkyl. In some embodiments of a compound of Formula (V), (Va), (Vb), or (Vc), Z is —NR$^{25}$—; and R$^{25}$ is hydrogen. In some embodiments of a compound of Formula (V), (Va), (Vb), or (Vc), Z is —NR$^{25}$—; and R$^{25}$ is C$_1$-C$_6$ alkyl. In some embodiments of a compound of Formula (V), (Va), (Vb), or (Vc), Z is —CR$^{23}$R$^{24}$—; and R$^{23}$ and R$^{24}$ are each independently hydrogen or C$_1$-C$_6$ alkyl. In some embodiments of a compound of Formula (V), (Va), (Vb), or (Vc), Z is —CR$^{23}$R$^{24}$—; and R$^{23}$ and R$^{24}$ are hydrogen.

In some embodiments of a compound of Formula (V), (Va), (Vb), or (Vc), —Z—R$^{22}$ is selected from

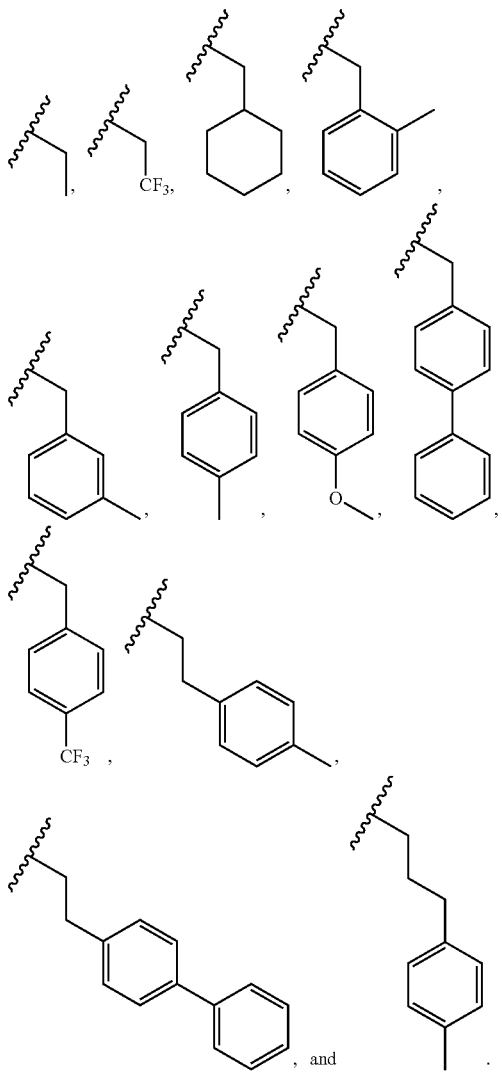

In some embodiments of a compound of Formula (V), (Va), (Vb), or (Vc), R$^{14}$ is hydrogen, halogen, optionally substituted C$_1$-C$_6$ alkyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, or optionally substituted heteroaryl. In some embodiments of a compound of Formula (V), (Va), (Vb), or (Vc), R$^{14}$ is hydrogen, optionally substituted C$_1$-C$_6$ alkyl, optionally substituted cycloalkyl, or optionally substituted (C$_1$-C$_6$ alkyl)cycloalkyl. In some embodiments of a compound of Formula (V), (Va), (Vb), or (Vc), R$^{14}$ is optionally substituted C$_1$-C$_6$ alkyl or optionally substituted (C$_1$-C$_6$ alkyl)cycloalkyl. In some embodiments of a compound of Formula (V), (Va), (Vb), or (Vc), R$^{14}$ is C$_1$-C$_6$ alkyl, C$_1$-C$_6$ haloalkyl, or (C$_1$-C$_6$ alkyl)cycloalkyl. In some embodiments of a compound of Formula (V), (Va), (Vb), or (Vc), R$^{14}$ is selected from:

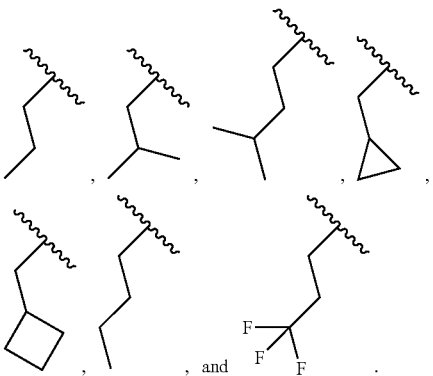

In some embodiments of a compound of Formula (V), (Va), (Vb), or (Vc), R$^{16}$ is hydrogen, halogen, optionally substituted C$_1$-C$_6$ alkyl, optionally substituted cycloalkyl, optionally substituted (C$_1$-C$_6$ alkyl)cycloalkyl, optionally substituted heterocycloalkyl, optionally substituted (C$_1$-C$_6$ alkyl)heterocycloalkyl, optionally substituted aryl, optionally substituted (C$_1$-C$_6$ alkyl)aryl, or optionally substituted heteroaryl. In some embodiments of a compound of Formula (V), (Va), (Vb), or (Vc), R$^{16}$ is optionally substituted C$_1$-C$_6$ alkyl, optionally substituted (C$_1$-C$_6$ alkyl)cycloalkyl, optionally substituted cycloalkyl, optionally substituted (C$_1$-C$_6$ alkyl)aryl, or optionally substituted aryl. In some embodiments of a compound of Formula (V), (Va), (Vb), or (Vc), R$^{16}$ is optionally substituted C$_1$-C$_6$ alkyl, optionally substituted (C$_1$-C$_6$ alkyl)cycloalkyl, or optionally substituted cycloalkyl. In some embodiments of a compound of Formula (V), (Va), (Vb), or (Vc), R$^{16}$ is optionally substituted C$_1$-C$_6$ alkyl, optionally substituted (C$_1$-C$_6$ alkyl)cycloalkyl, or optionally substituted cycloalkyl. In some embodiments of a compound of Formula (V), (Va), (Vb), or (Vc), R$^{16}$ is C$_1$-C$_6$ alkyl, (C$_1$-C$_6$ alkyl)cycloalkyl, cycloalkyl, (CV C$_6$ alkyl)aryl, or aryl, each optionally substituted with one, two, or three halogen, —OR$^b$, —NR$^b$R$^c$, —S(=O)$_2$R$^a$, —NR$^b$S(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, or aryl. In some embodiments of a compound of Formula (V), (Va), (Vb), or (Vc), R$^{16}$ is C$_1$-C$_6$ alkyl, (C$_1$-C$_6$ alkyl)cycloalkyl, or cycloalkyl, each optionally substituted with one, two, or three halogen, —OR$^b$, —NR$^b$R$^c$, —S(=O)$_2$R$^a$, —NR$^b$S(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, or aryl. In some embodiments of a compound of Formula (V), (Va), (Vb), or (Vc), R$^{16}$ is C$_3$-C$_7$ cycloalkyl. In some embodiments of a compound of Formula (V), (Va), (Vb), or (Vc), R$^{16}$ is cyclobutyl, cyclopentyl, cyclohexyl, or cycloheptyl. In some embodiments of a compound of Formula (V), (Va), (Vb), or (Vc), R$^{16}$ is cyclohexyl. In some embodiments of a compound of Formula (V), (Va), (Vb), or (Vc), R$^{16}$ is cycloheptyl. In some embodiments of a compound of Formula (V), (Va), (Vb), or (Vc), R$^{16}$ is selected from:

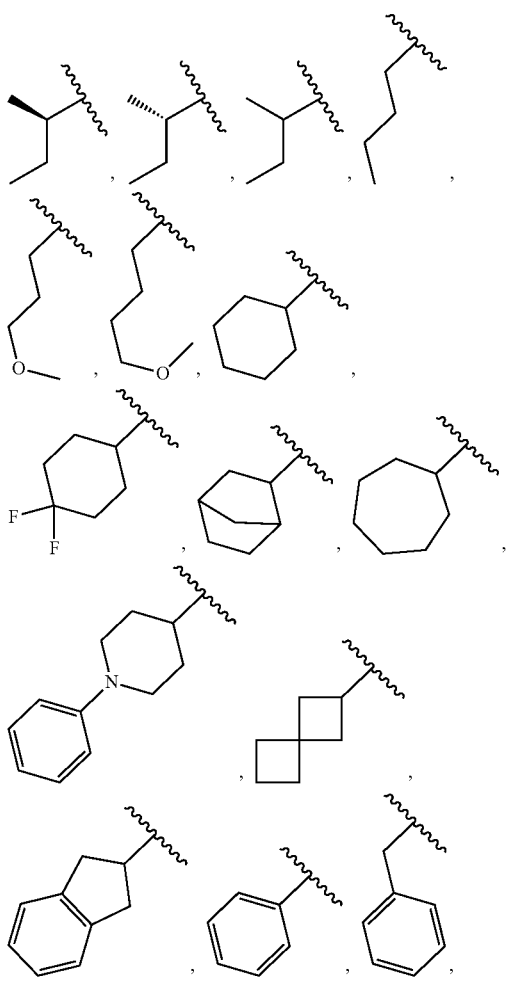

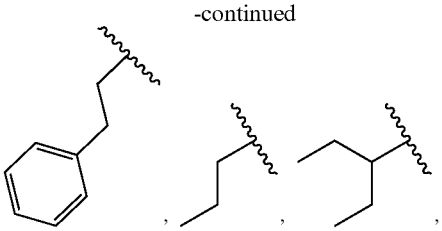

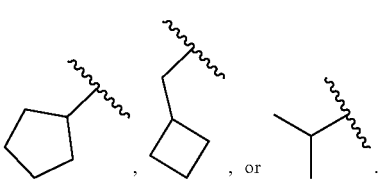

In some embodiments of a compound of Formula (V), (Va), (Vb), or (Vc), each $R^a$ is independently $C_1$-$C_6$ alkyl. In some embodiments of a compound of Formula (V), (Va), (Vb), or (Vc), each $R^b$ and $R^c$ is independently hydrogen or $C_1$-$C_6$ alkyl. In some embodiments of a compound of Formula (V), (Va), (Vb), or (Vc), each $R^b$ and $R^c$ is hydrogen.

In some embodiments, the compound of Formula (I), (Ia)-(Ic), (II), (IIa)-(IIc), (III), (IIIa)-(IIIc), (IV), (IVa)-(IVc), (V), and (Va)-(Vc) is selected from a compound in table 1 or a pharmaceutically acceptable salt, solvate, or stereoisomer thereof.

TABLE 1

| Ex. | Structure | Name |
|---|---|---|
| 1 | 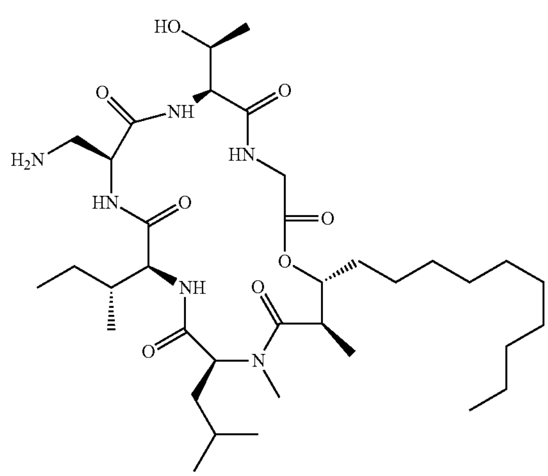 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-decyl-6-[(1S)-1-hydroxyethyl]-15-isobutyl-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
| --- | --- | --- |
| 2 | 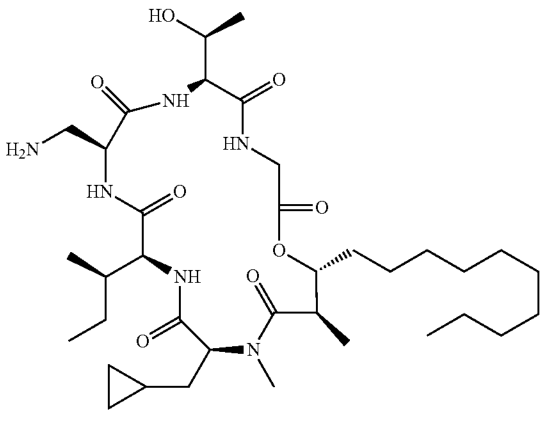 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CC2CC2)N(C)C(=O)[C@@H]1C] | (6S,9S,12S,15S,18R,19R)-9-(aminomethyl)-15-(cyclopropylmethyl)-19-decyl-6-[(1S)-1-hydroxyethyl]-16,18-dimethyl-12-[(1R)-1-methylpropyl]-1-oxa-4,7,10,13,16-pentazacyclononadecane-2,5,8,11,14,17-hexone |
| 3 | 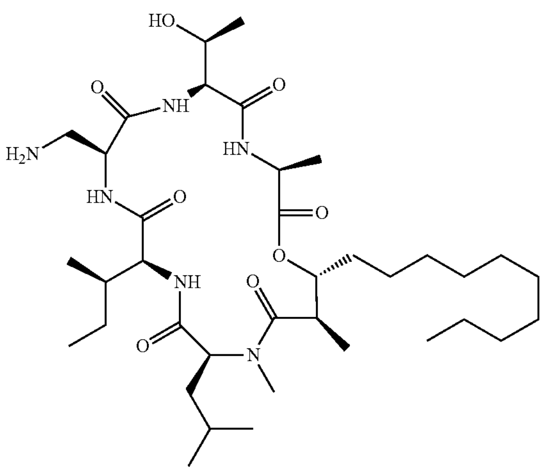 [SMILES: CCCCCCCCCC[C@H]1OC(=O)[C@H](C)NC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (3S,6S,9S,12S,15S,18R,19R)-9-(aminomethyl)-19-decyl-6-[(1S)-1-hydroxyethyl]-15-isobutyl-3,16,18-trimethyl-12-[(1R)-1-methylpropyl]-1-oxa-4,7,10,13,16-pentazacyclononadecane-2,5,8,11,14,17-hexone |
| 4 | 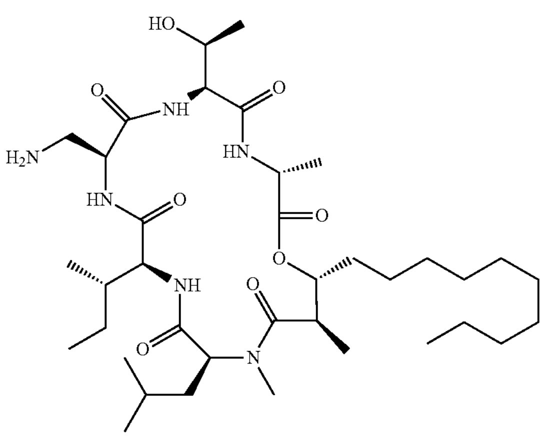 [SMILES: CCCCCCCCCC[C@H]1OC(=O)[C@@H](C)NC(=O)[C@H]([C@H](C)O)NC(=O)[C@H](CN)NC(=O)[C@H]([C@@H](C)CC)NC(=O)[C@H](CC(C)C)N(C)C(=O)[C@@H]1C] | (3R,6S,9S,12S,15S,18R,19R)-19-decyl-6-[(1S)-1-hydroxyethyl]-9-(hydroxymethyl)-15-isobutyl-3,16,18-trimethyl-12-[(1S)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 5 | 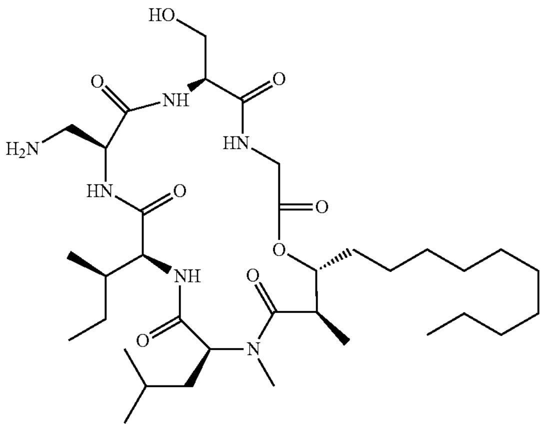 [SMILES: CCCCCCCCCC[C@H]1OC(=O)CNC(=O)[C@H](CO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-19-decyl-6,9-bis(hydroxymethyl)-15-isobutyl-16,18-dimethyl-12-[(1R)-1-methylpropyl]-1-oxa-4,7,10,13,16-pentazacyclononadecane-2,5,8,11,14,17-hexone |
| 6 | 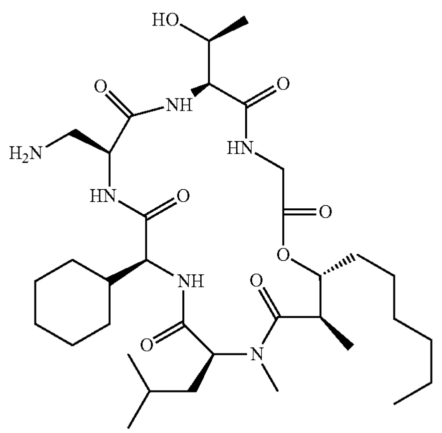 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-19-hexyl-6-[(1S)-1-hydroxyethyl]-15-isobutyl-16,18-dimethyl-1-oxa-4,7,10,13,16-pentazacyclononadecane-2,5,8,11,14,17-hexone |
| 7 | 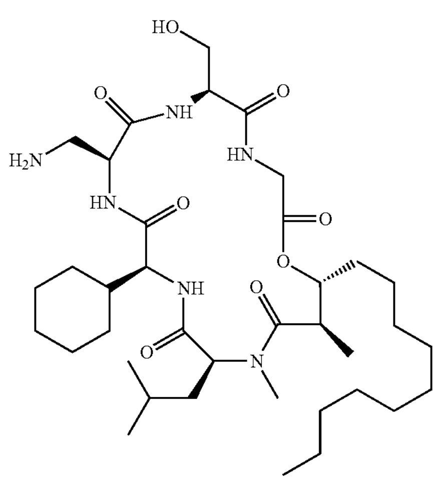 [SMILES: CCCCCCCCCC[C@H]1OC(=O)CNC(=O)[C@H](CO)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-12-cyclohexyl-19-decyl-6,9-bis(hydroxymethyl)-15-isobutyl-16,18-dimethyl-1-oxa-4,7,10,13,16-pentazacyclononadecane-2,5,8,11,14,17-hexone |

TABLE 1-continued

| Ex. | Structure | Name |
|---|---|---|
| 8 | 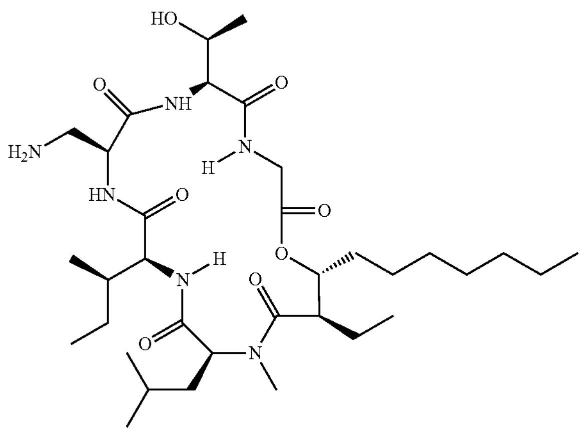 [SMILES: CCCCCCC[C@H]1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)[C@@H]1CC] | (6S,9S,12S,15S,18R,19R)-18-ethyl-19-heptyl-6-[(1S)-1-hydroxyethyl]-9-(hydroxymethyl)-15-isobutyl-16-methyl-12-[(1R)-1-methylpropyl]-1-oxa-4,7,10,13,16-pentazacyclononadecane-2,5,8,11,14,17-hexone |
| 9 | 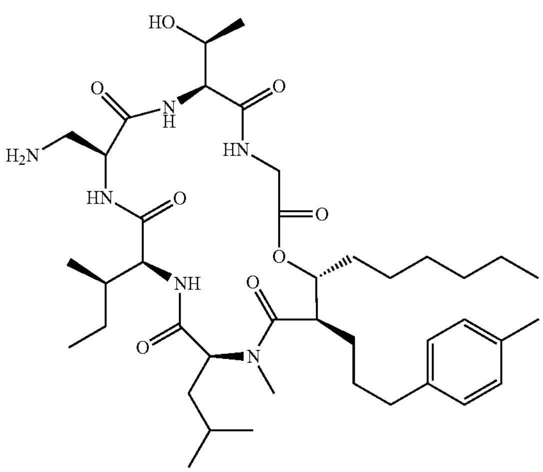 [SMILES: CCCCCC[C@H]1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)[C@@H]1CCCc1ccc(C)cc1] | (6S,9S,12S,15S,18R,19R)-19-hexyl-9-(hydroxymethyl)-15-isobutyl-16-methyl-18-[3-(p-tolyl)propyl]-6-[rac-(1S)-1-hydroxyethyl]-12-[rac-(1R)-1-methylpropyl]-1-oxa-4,7,10,13,16-pentazacyclononadecane-2,5,8,11,14,17-hexone |
| 10 | 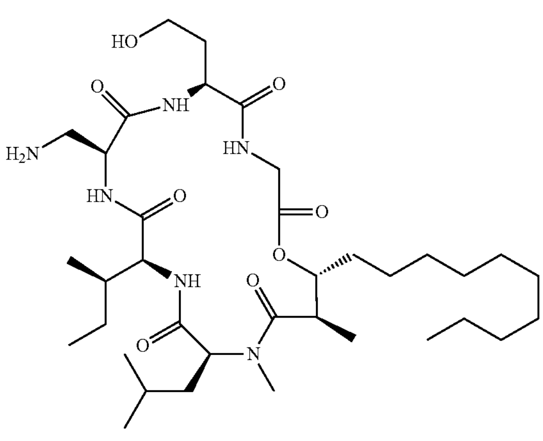 [SMILES: CCCCCCCCCC[C@H]1OC(=O)CNC(=O)[C@H](CCO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-decyl-6-(2-hydroxyethyl)-15-isobutyl-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 11 | 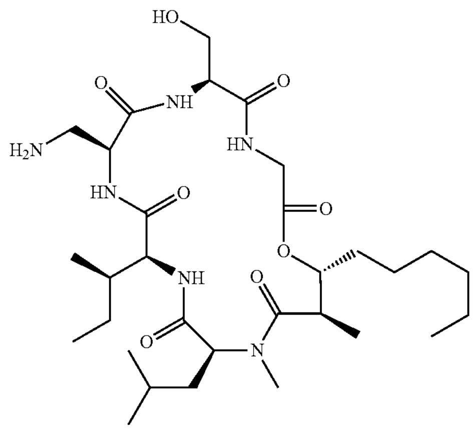 [SMILES: CCCCCC[C@H]1OC(=O)CNC(=O)[C@H](CO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-hexyl-6-(hydroxymethyl)-15-isobutyl-16,18-dimethyl-12-[(1R)-1-methylpropyl]-1-oxa-4,7,10,13,16-pentazacyclononadecane-2,5,8,11,14,17-hexone |
| 12 | 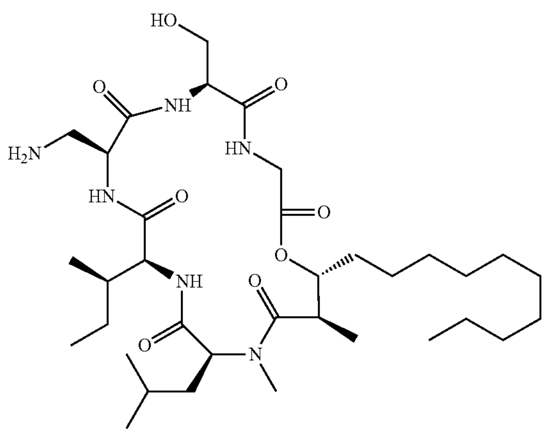 [SMILES: CCCCCCCCCC[C@H]1OC(=O)CNC(=O)[C@H](CO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-decyl-6-(hydroxymethyl)-15-isobutyl-16,18-dimethyl-12-[(1R)-1-methylpropyl]-1-oxa-4,7,10,13,16-pentazacyclononadecane-2,5,8,11,14,17-hexone |
| 13 | 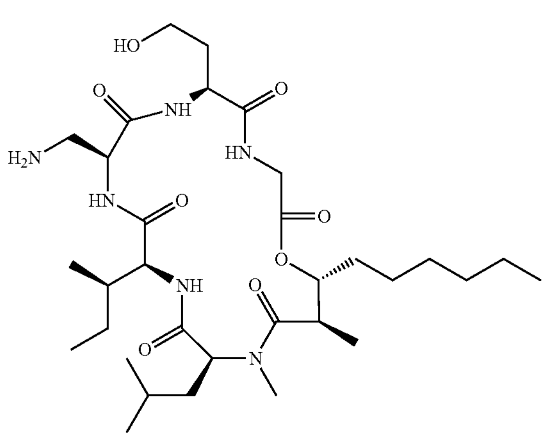 [SMILES: CCCCCC[C@H]1OC(=O)CNC(=O)[C@H](CCO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-hexyl-6-(2-hydroxyethyl)-15-isobutyl-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 14 | 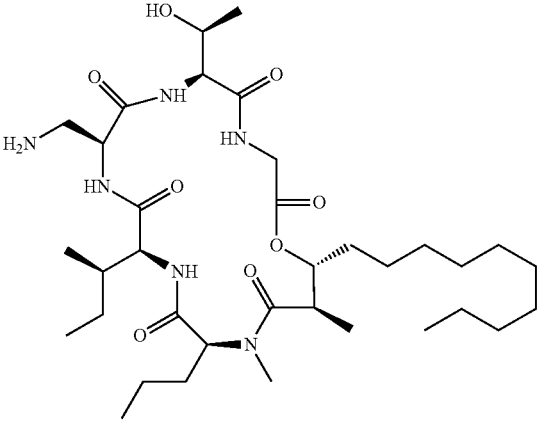 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CCC)N(C)C(=O)[C@@H]1C] | (6S,9S,12S,15S,18R,19R)-9-(aminomethyl)-19-decyl-6-[(1S)-1-hydroxyethyl]-16,18-dimethyl-12-[(1R)-1-methylpropyl]-15-propyl-1-oxa-4,7,10,13,16-pentazacyclononadecane-2,5,8,11,14,17-hexone |
| 15 | 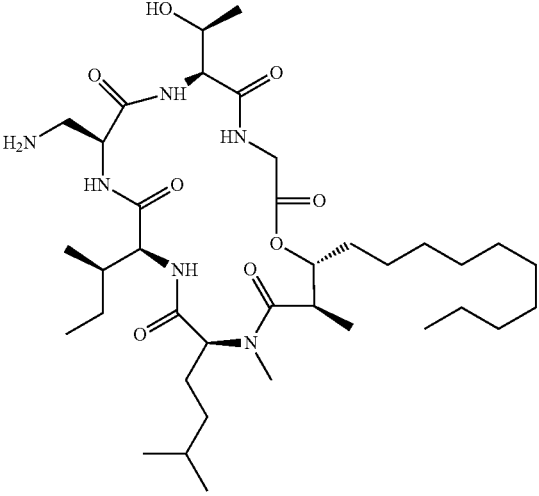 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CCC(C)C)N(C)C(=O)[C@@H]1C] | (6S,9S,12S,15S,18R,19R)-9-(aminomethyl)-19-decyl-6-[(1S)-1-hydroxyethyl]-15-isopentyl-16,18-dimethyl-12-[(1R)-1-methylpropyl]-1-oxa-4,7,10,13,16-pentazacyclononadecane-2,5,8,11,14,17-hexone |
| 16 | 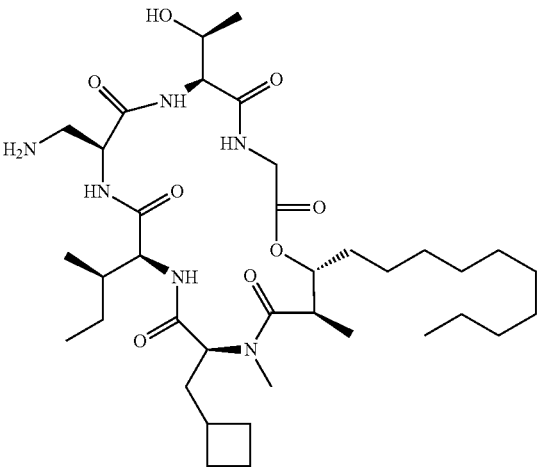 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CC2CCC2)N(C)C(=O)[C@@H]1C] | (6S,9S,12S,15S,18R,19R)-9-(aminomethyl)-15-(cyclobutylmethyl)-19-decyl-6-[(1S)-1-hydroxyethyl]-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 17 | 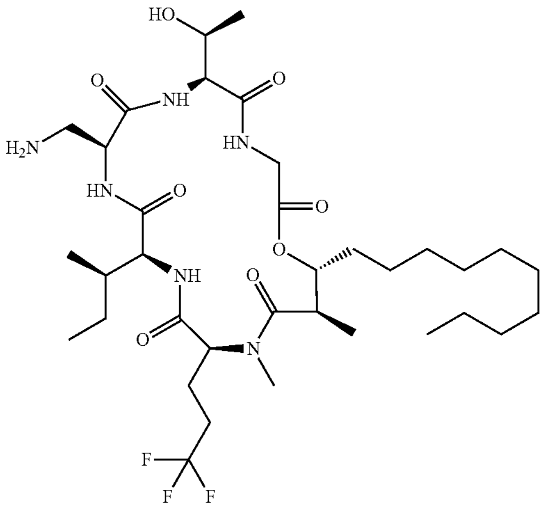 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CCC(F)(F)F)N(C)C(=O)[C@@H]1C] | 9-(aminomethyl)-19-decyl-6-(1-hydroxyethyl)-16,18-dimethyl-12-sec-butyl-15-(3,3,3-trifluoropropyl)-1-oxa-4,7,10,13,16-pentazacyclononadecane-2,5,8,11,14,17-hexone |
| 18 | 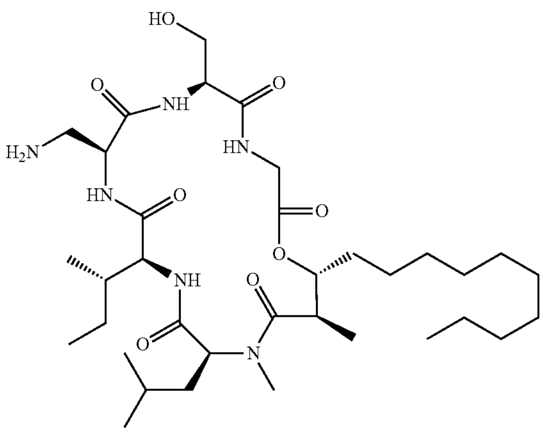 [SMILES: CCCCCCCCCC[C@H]1OC(=O)CNC(=O)[C@H](CO)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-19-decyl-6,9-bis(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 19 | 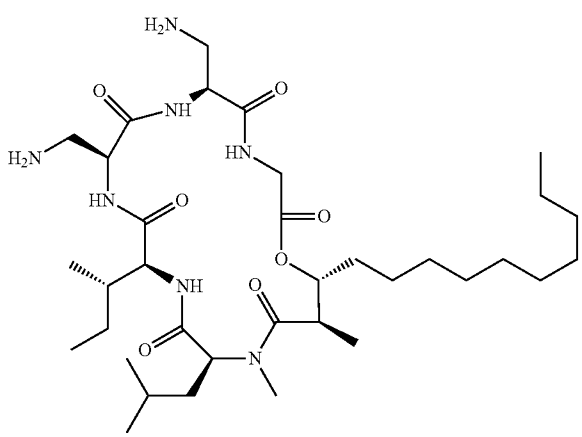 [SMILES: CCCCCCCCCC[C@H]1OC(=O)CNC(=O)[C@H](CN)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-6-(aminomethyl)-19-decyl-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 20 | 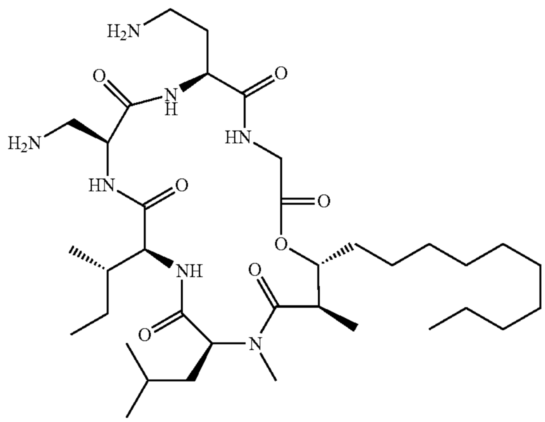 [SMILES: CCCCCCCCCC[C@H]1OC(=O)CNC(=O)[C@H](CCN)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-6-(2-aminoethyl)-19-decyl-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 21 | 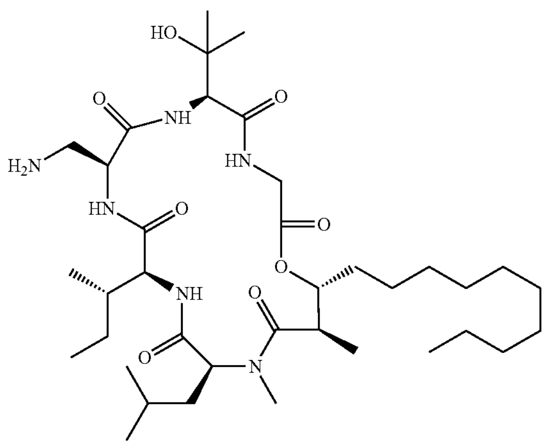 [SMILES: CCCCCCCCCC[C@H]1OC(=O)CNC(=O)[C@H](C(C)(C)O)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-19-decyl-9-(hydroxymethyl)-6-(1-hydroxy-1-methyl-ethyl)-15-isobutyl-16,18-dimethyl-12-[(1S)-1-methylpropyl]-1-oxa-4,7,10,13,16-pentazacyclononadecane-2,5,8,11,14,17-hexone |
| 22 | 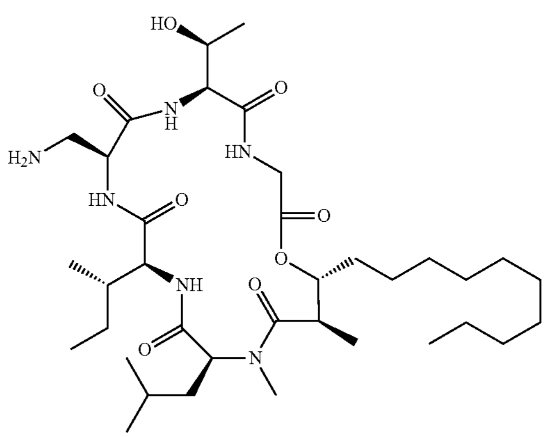 [SMILES: CCCCCCCCCC[C@H]1OC(=O)CNC(=O)[C@H]([C@H](C)O)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-19-decyl-6-[(1S)-1-hydroxyethyl]-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 23 | 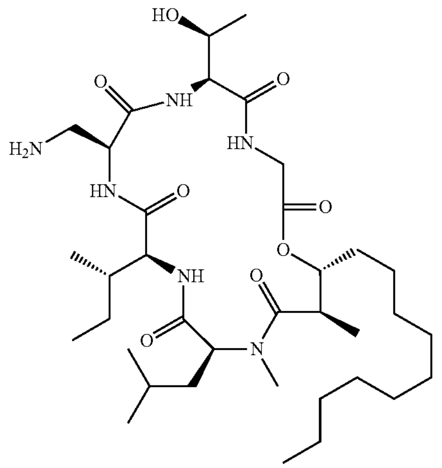 [SMILES: CCCCCCCCCC[C@H]1OC(=O)CNC(=O)[C@H]([C@H](C)O)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-9-(aminomethyl)-19-decyl-6-[(1S)-1-hydroxyethyl]-15-isobutyl-16,18-dimethyl-12-[(1S)-1-methylpropyl]-1-oxa-4,7,10,13,16-pentazacyclononadecane-2,5,8,11,14,17-hexone |
| 24 | 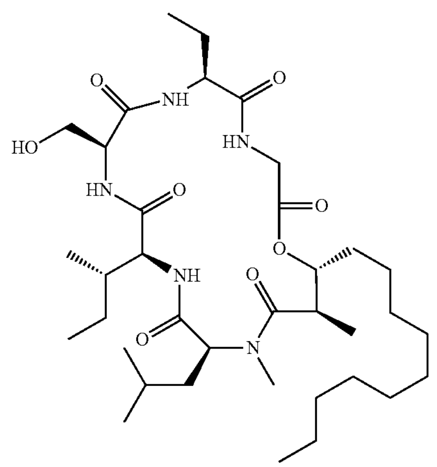 [SMILES: CCCCCCCCCC[C@H]1OC(=O)CNC(=O)[C@H](CC)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-decyl-16-ethyl-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 25 | 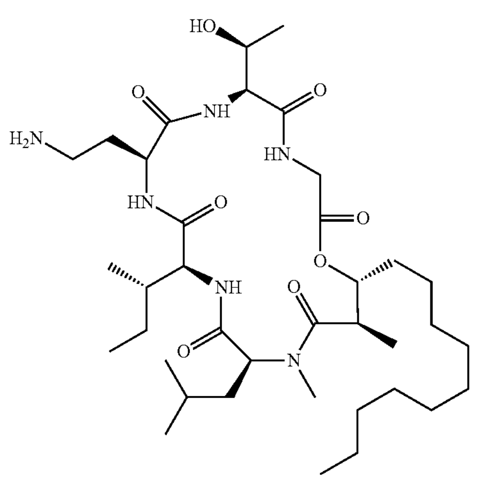 [SMILES: CCCCCCCCCC[C@H]1OC(=O)CNC(=O)[C@H]([C@H](C)O)NC(=O)[C@H](CCN)NC(=O)[C@H]([C@@H](C)CC)NC(=O)[C@H](CC(C)C)N(C)C(=O)[C@@H]1C] | (6S,9S,12S,15S,18R,19R)-9-(2-aminoethyl)-19-decyl-6-[(1S)-1-hydroxyethyl]-15-isobutyl-16,18-dimethyl-12-[(1S)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 26 | 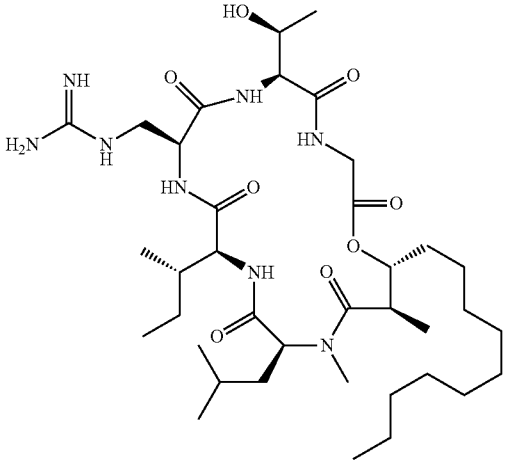 [SMILES: CCCCCCCCCC[C@H]1OC(=O)CNC(=O)[C@H]([C@H](C)O)NC(=O)[C@H](CNC(=N)N)NC(=O)[C@H]([C@@H](C)CC)NC(=O)[C@H](CC(C)C)N(C)C(=O)[C@@H]1C] | 1-[[(6S,9S,12S,15S,18R,19R)-19-decyl-6-[(1S)-1-hydroxyethyl]-15-isobutyl-16,18-dimethyl-12-[(1S)-1-methylpropyl]-2,5,8,11,14,17-hexaoxo-1-oxa-4,7,10,13,16-pentazacyclononadec-9-yl]methyl]guanidine |
| 27 | 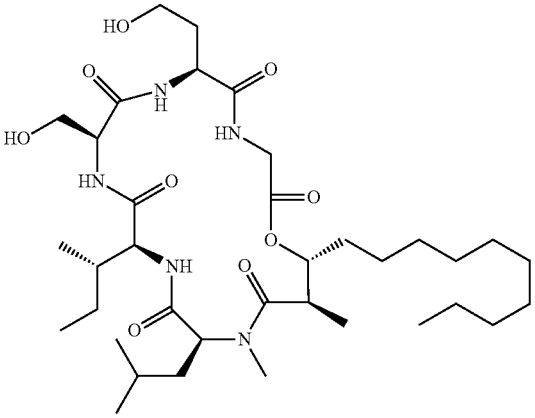 [SMILES: CCCCCCCCCC[C@H]1OC(=O)CNC(=O)[C@H](CCO)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-decyl-6-(2-hydroxyethyl)-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 28 | 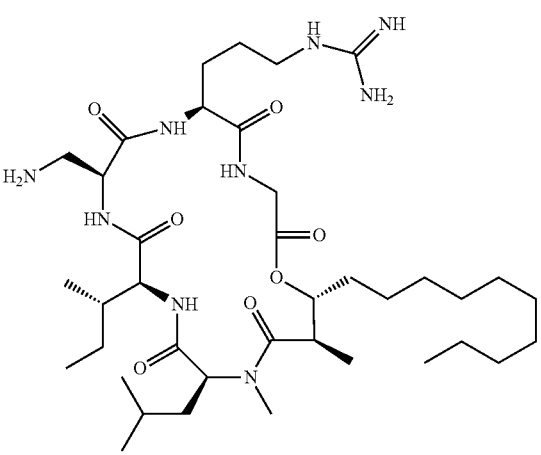 [SMILES: CCCCCCCCCC[C@H]1OC(=O)CNC(=O)[C@H](CCCNC(=N)N)NC(=O)[C@H](CN)NC(=O)[C@H]([C@@H](C)CC)NC(=O)[C@H](CC(C)C)N(C)C(=O)[C@@H]1C] | 1-[3-[(6S,9S,12S,15S,18R,19R)-19-decyl-9-(hydroxymethyl)-15-isobutyl-16,18-dimethyl-12-[(1S)-1-methylpropyl]-2,5,8,11,14,17-hexaoxo-1-oxa-4,7,10,13,16-pentazacyclononadec-6-yl]propyl]guanidine |

TABLE 1-continued

| Ex. | Structure | Name |
|---|---|---|
| 29 | 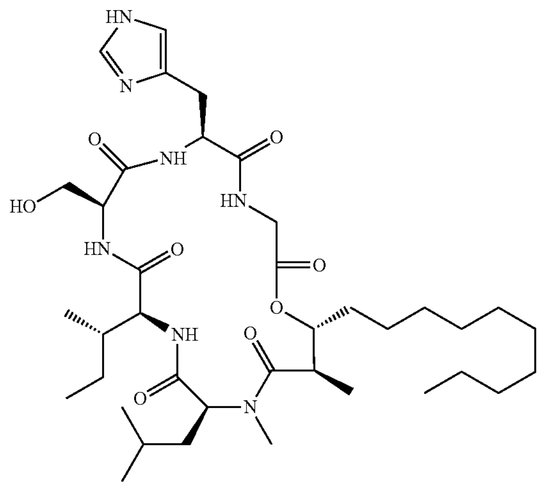 [SMILES: CCCCCCCCCC[C@H]1OC(=O)CNC(=O)[C@H](Cc2c[nH]cn2)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-decyl-9-(hydroxymethyl)-6-(1H-imidazol-4-ylmethyl)-15-isobutyl-16,18-dimethyl-12-[(1S)-1-methylpropyl]-1-oxa-4,7,10,13,16-pentazacyclononadecane-2,5,8,11,14,17-hexone |
| 30 | 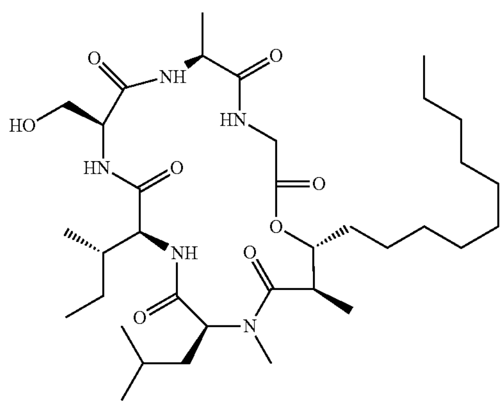 [SMILES: CCCCCCCCCC[C@H]1OC(=O)CNC(=O)[C@H](C)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-decyl-9-(hydroxymethyl)-15-isobutyl-6,16,18-trimethyl-12-[(1S)-1-methylpropyl]-1-oxa-4,7,10,13,16-pentazacyclononadecane-2,5,8,11,14,17-hexone |
| 31 | 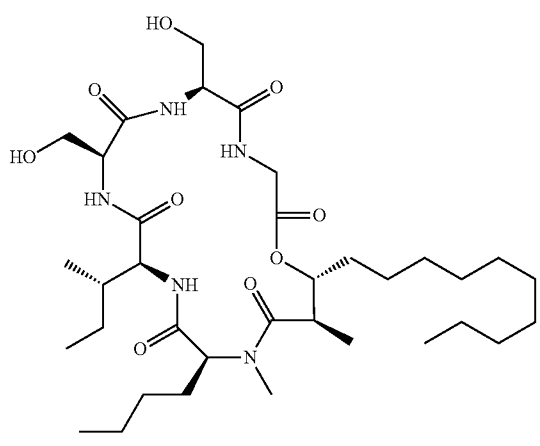 [SMILES: CCCCCCCCCC[C@H]1OC(=O)CNC(=O)[C@H](CO)NC(=O)[C@H](CO)NC(=O)[C@H]([C@@H](C)CC)NC(=O)[C@H](CCCC)N(C)C(=O)[C@@H]1C] | (6S,9S,12S,15S,18R,19R)-15-butyl-19-decyl-6,9-bis(hydroxymethyl)-16,18-dimethyl-12-[(1S)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 32 | 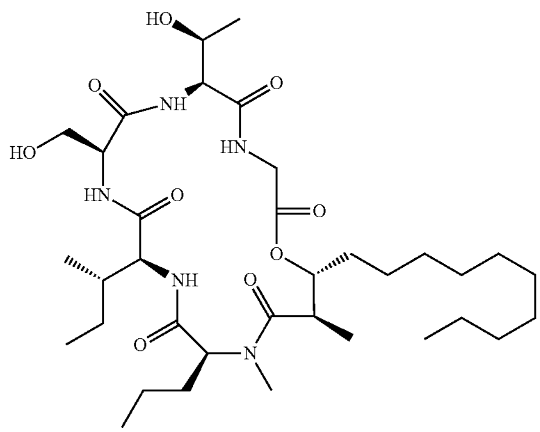 [SMILES: CCCCCCCCCC[C@H]1OC(=O)CNC(=O)[C@H]([C@H](C)O)NC(=O)[C@H](CO)NC(=O)[C@H]([C@@H](C)CC)NC(=O)[C@H](CCC)N(C)C(=O)[C@@H]1C] | (6S,9S,12S,15S,18R,19R)-19-decyl-6-[(1S)-1-hydroxyethyl]-9-(hydroxymethyl)-16,18-dimethyl-12-[(1S)-1-methylpropyl]-15-propyl-1-oxa-4,7,10,13,16-pentazacyclononadecane-2,5,8,11,14,17-hexone |
| 33 | 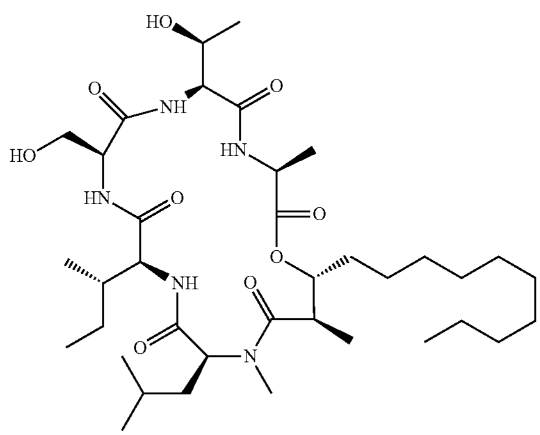 [SMILES: CCCCCCCCCC[C@H]1OC(=O)[C@H](C)NC(=O)[C@H]([C@H](C)O)NC(=O)[C@H](CO)NC(=O)[C@H]([C@@H](C)CC)NC(=O)[C@H](CC(C)C)N(C)C(=O)[C@@H]1C] | (3S,6S,9S,12S,15S,18R,19R)-19-decyl-6-[(1S)-1-hydroxyethyl]-9-(hydroxymethyl)-15-isobutyl-3,16,18-trimethyl-12-[(1S)-1-methylpropyl]-1-oxa-4,7,10,13,16-pentazacyclononadecane-2,5,8,11,14,17-hexone |
| 34 | 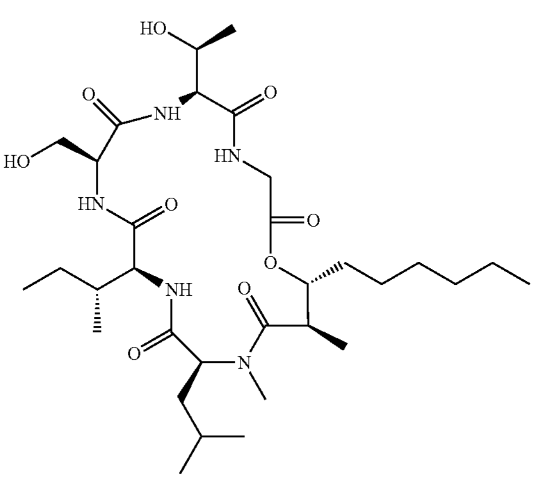 [SMILES: CCCCCC[C@H]1OC(=O)CNC(=O)[C@H]([C@H](C)O)NC(=O)[C@H](CO)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-hexyl-6-[(1S)-1-hydroxyethyl]-15-isobutyl-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 35 | 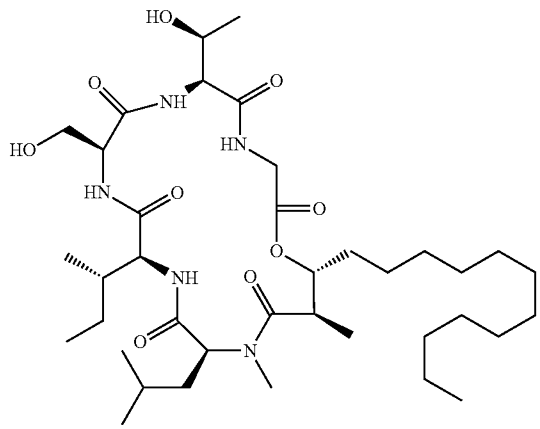 [SMILES: CCCCCCCCCCCC[C@H]1OC(=O)CNC(=O)[C@H]([C@H](C)O)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-dodecyl-6-[(1S)-1-hydroxyethyl]-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 36 | 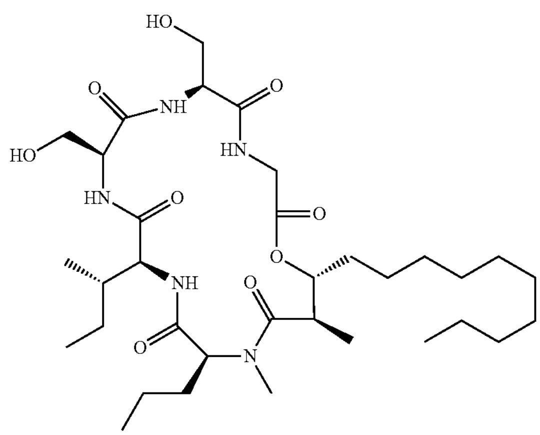 [SMILES: CCCCCCCCCC[C@H]1OC(=O)CNC(=O)[C@H](CO)NC(=O)[C@H](CO)NC(=O)[C@H]([C@@H](C)CC)NC(=O)[C@H](CCC)N(C)C(=O)[C@@H]1C] | (6S,9S,12S,15S,18R,19R)-19-decyl-6,9-bis(hydroxymethyl)-16,18-dimethyl-12-[(1S)-1-methylpropyl]-15-propyl-1-oxa-4,7,10,13,16-pentazacyclononadecane-2,5,8,11,14,17-hexone |
| 37 | 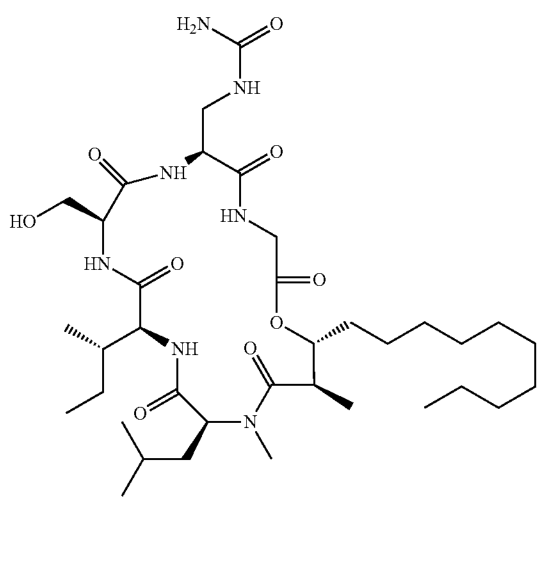 [SMILES: CCCCCCCCCC[C@H]1OC(=O)CNC(=O)[C@H](CNC(N)=O)NC(=O)[C@H](CO)NC(=O)[C@H]([C@@H](C)CC)NC(=O)[C@H](CC(C)C)N(C)C(=O)[C@@H]1C] | [(6S,9S,12S,15S,18R,19R)-19-decyl-9-(hydroxymethyl)-15-isobutyl-16,18-dimethyl-12-[(1S)-1-methylpropyl]-2,5,8,11,14,17-hexaoxo-1-oxa-4,7,10,13,16-pentazacyclononadec-6-yl]methylurea |

TABLE 1-continued

| Ex. | Structure | Name |
|---|---|---|
| 38 | 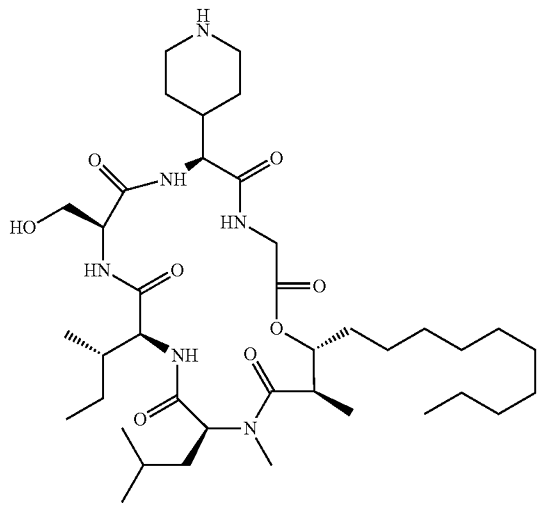 [SMILES: CCCCCCCCCC[C@H]1OC(=O)CNC(=O)[C@H](C2CCNCC2)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-decyl-9-(hydroxymethyl)-15-isobutyl-16,18-dimethyl-12-[(1S)-1-methylpropyl]-6-(4-piperidyl)-1-oxa-4,7,10,13,16-pentazacyclononadecane-2,5,8,11,14,17-hexone |
| 39 | 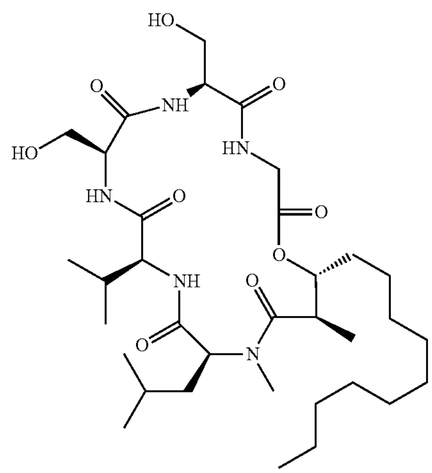 [SMILES: CCCCCCCCCC[C@H]1OC(=O)CNC(=O)[C@H](CO)NC(=O)[C@H](CO)NC(=O)[C@H](C(C)C)NC(=O)[C@H](CC(C)C)N(C)C(=O)[C@@H]1C] | (6S,9S,12S,15S,18R,19R)-19-decyl-6,9-bis(hydroxymethyl)-15-isobutyl-12-isopropyl-16,18-dimethyl-1-oxa-4,7,10,13,16-pentazacyclononadecane-2,5,8,11,14,17-hexone |
| 40 | 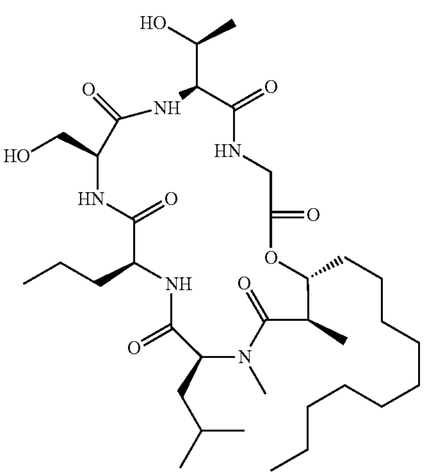 [SMILES: CCCCCCCCCC[C@H]1OC(=O)CNC(=O)[C@H]([C@H](C)O)NC(=O)[C@H](CO)NC(=O)[C@H](CCC)NC(=O)[C@H](CC(C)C)N(C)C(=O)[C@@H]1C] | (6S,9S,12S,15S,18R,19R)-19-decyl-6-[(1S)-1-hydroxyethyl]-9-(hydroxymethyl)-15-isobutyl-16,18-dimethyl-12-propyl-1-oxa-4,7,10,13,16-pentazacyclononadecane-2,5,8,11,14,17-hexone |

TABLE 1-continued

| Ex. | Structure | Name |
| --- | --- | --- |
| 41 | 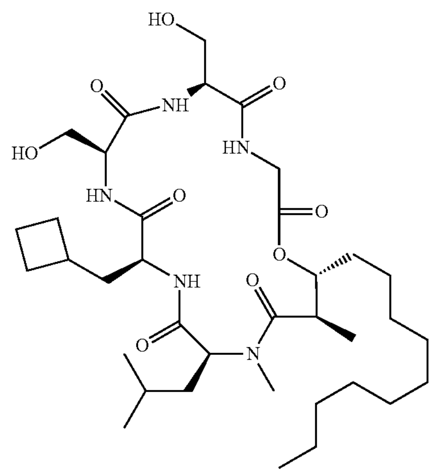 [SMILES: CCCCCCCCCC[C@H]1OC(=O)CNC(=O)[C@H](CO)NC(=O)[C@H](CO)NC(=O)[C@H](CC2CCC2)NC(=O)[C@H](CC(C)C)N(C)C(=O)[C@@H]1C] | (6S,9S,12S,15S,18R,19R)-12-(cyclobutylmethyl)-19-decyl-6,9-bis(hydroxymethyl)-15-isobutyl-16,18-dimethyl-1-oxa-4,7,10,13,16-pentazacyclononadecane-2,5,8,11,14,17-hexone |
| 42 | 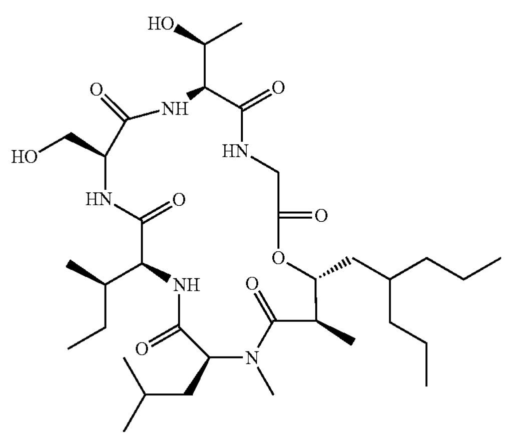 [SMILES: CCCC(CCC)C[C@H]1OC(=O)CNC(=O)[C@H]([C@H](C)O)NC(=O)[C@H](CO)NC(=O)[C@H]([C@H](C)CC)NC(=O)[C@H](CC(C)C)N(C)C(=O)[C@@H]1C] | (6S,9S,12S,15S,18R,19R)-6-[(1S)-1-hydroxyethyl]-9-(hydroxymethyl)-15-isobutyl-16,18-dimethyl-12-[(1R)-1-methylpropyl]-19-(2-propylpentyl)-1-oxa-4,7,10,13,16-pentazacyclononadecane-2,5,8,11,14,17-hexone |
| 43 | 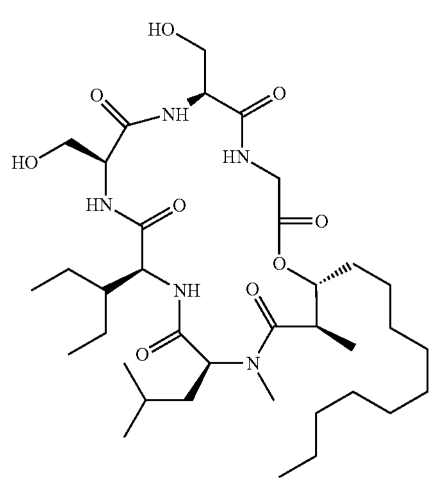 [SMILES: CCCCCCCCCC[C@H]1OC(=O)CNC(=O)[C@H](CO)NC(=O)[C@H](CO)NC(=O)[C@H](C(CC)CC)NC(=O)[C@H](CC(C)C)N(C)C(=O)[C@@H]1C] | (6S,9S,12S,15S,18R,19R)-19-decyl-12-(1-ethylpropyl)-6,9-bis(hydroxymethyl)-15-isobutyl-16,18-dimethyl-1-oxa-4,7,10,13,16-pentazacyclononadecane-2,5,8,11,14,17-hexone |

TABLE 1-continued

| Ex. | Structure | Name |
|---|---|---|
| 44 | 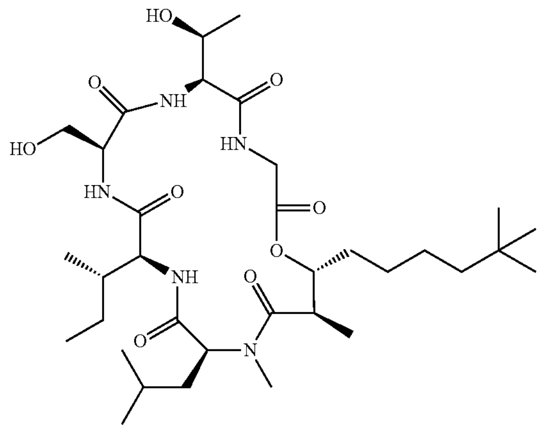 [SMILES: CC[C@H](C)[C@@H]1NC(=O)[C@H](CC(C)C)N(C)C(=O)[C@H](C)[C@@H](CCCCC(C)(C)C)OC(=O)CNC(=O)[C@H]([C@H](C)O)NC(=O)[C@H](CO)NC1=O] | (6S,9S,12S,15S,18R,19R)-19-(5,5-dimethylhexyl)-6-[(1S)-1-hydroxyethyl]-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 45 | 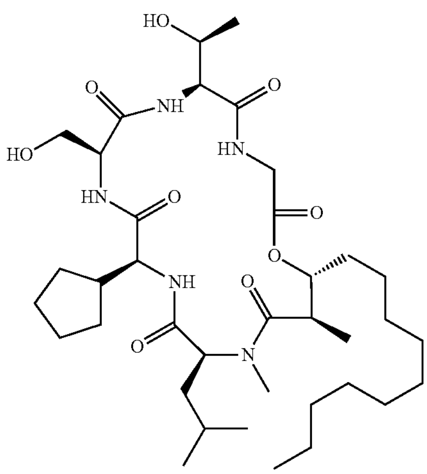 [SMILES: CCCCCCCCCC[C@H]1OC(=O)CNC(=O)[C@H]([C@H](C)O)NC(=O)[C@H](CO)NC(=O)[C@H](C2CCCC2)NC(=O)[C@H](CC(C)C)N(C)C(=O)[C@@H]1C] | (6S,9S,12S,15S,18R,19R)-9-(aminomethyl)-12-cyclopentyl-19-decyl-6-[(1S)-1-hydroxyethyl]-15-isobutyl-16,18-dimethyl-1-oxa-4,7,10,13,16-pentazacyclononadecane-2,5,8,11,14,17-hexone |
| 46 | 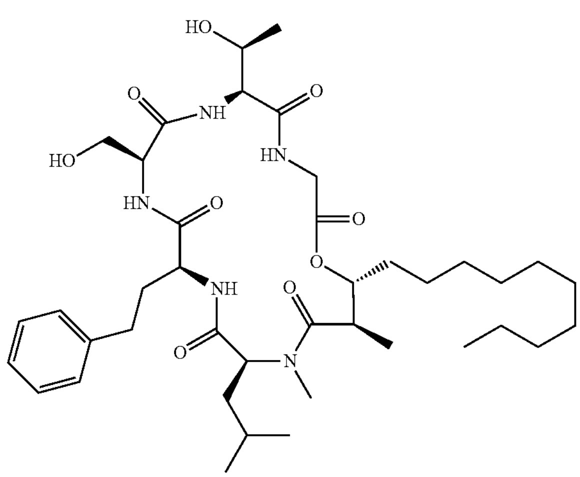 [SMILES: CCCCCCCCCC[C@H]1OC(=O)CNC(=O)[C@H]([C@H](C)O)NC(=O)[C@H](CO)NC(=O)[C@H](CCc2ccccc2)NC(=O)[C@H](CC(C)C)N(C)C(=O)[C@@H]1C] | (6S,9S,12S,15S,18R,19R)-9-(aminomethyl)-19-decyl-6-[(1S)-1-hydroxyethyl]-15-isobutyl-16,18-dimethyl-12-(2-phenylethyl)-1-oxa-4,7,10,13,16-pentazacyclononadecane-2,5,8,11,14,17-hexone |

TABLE 1-continued

| Ex. | Structure | Name |
|---|---|---|
| 47 | 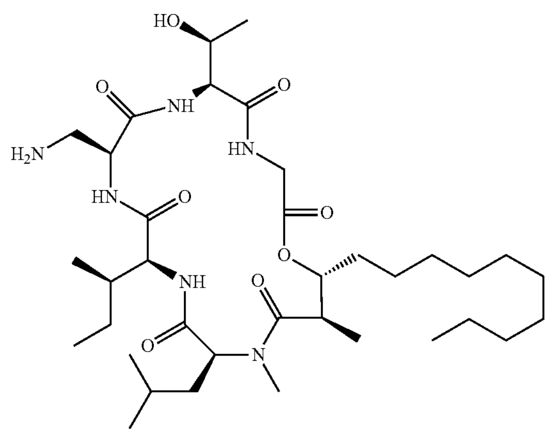 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-decyl-6-[(1S)-1-hydroxyethyl]-15-isobutyl-16,18-dimethyl-12-[(1R)-1-methylpropyl]-1-oxa-4,7,10,13,16-pentazacyclononadecane-5,8,11,14,17-pentone |
| 48 | 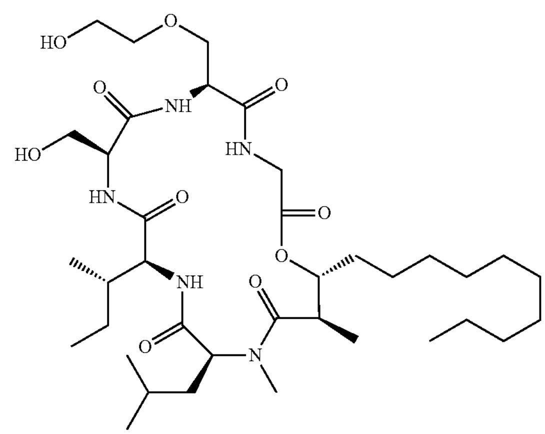 [SMILES: CCCCCCCCCC[C@H]1OC(=O)CNC(=O)[C@H](COCCO)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-19-decyl-6-(2-hydroxyethoxymethyl)-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 49 | 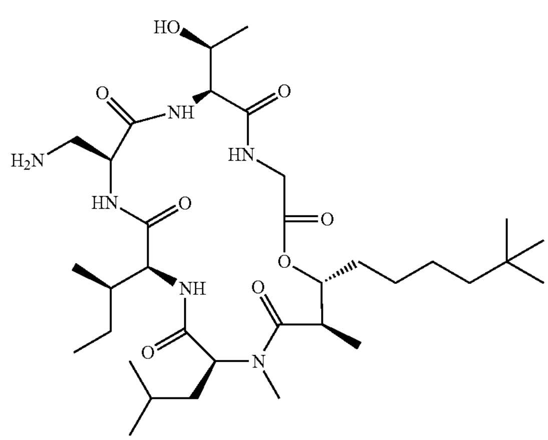 [SMILES: CC[C@@H](C)[C@@H]1NC(=O)[C@H](CC(C)C)N(C)C(=O)[C@H](C)[C@@H](CCCCC(C)(C)C)OC(=O)CNC(=O)[C@H]([C@H](C)O)NC(=O)[C@H](CN)NC1=O] | (6S,9S,12S,15S,18R,19R)-9-(aminomethyl)-19-(5,5-dimethylhexyl)-6-[(1S)-1-hydroxyethyl]-15-isobutyl-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 50 | 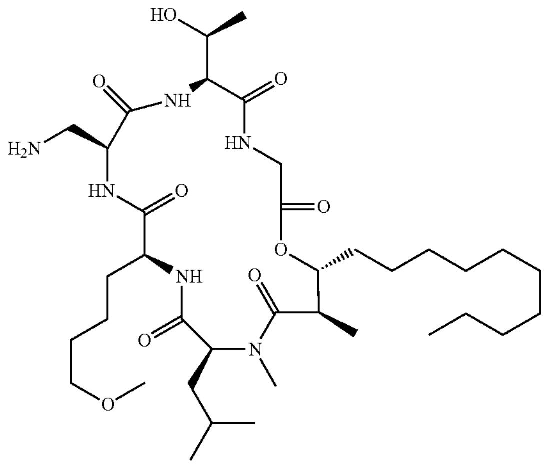 [SMILES: CCCCCCCCCC[C@H]1OC(=O)CNC(=O)[C@H]([C@H](C)O)NC(=O)[C@H](CN)NC(=O)[C@H](CCCCOC)NC(=O)[C@H](CC(C)C)N(C)C(=O)[C@@H]1C] | (6S,9S,12S,15S,18R,19R)-9-(aminomethyl)-19-decyl-6-[(1S)-1-hydroxyethyl]-15-isobutyl-12-(4-methoxybutyl)-16,18-dimethyl-1-oxa-4,7,10,13,16-pentazacyclononadecane-2,5,8,11,14,17-hexone |
| 51 | 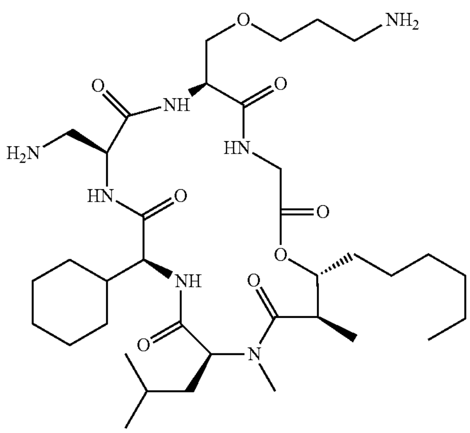 [SMILES: CCCCCC[C@H]1OC(=O)CNC(=O)[C@H](COCCCN)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-6-(3-aminopropoxymethyl)-12-cyclohexyl-19-hexyl-15-isobutyl-16,18-dimethyl-1-oxa-4,7,10,13,16-pentazacyclononadecane-2,5,8,11,14,17-hexone |
| 52 | 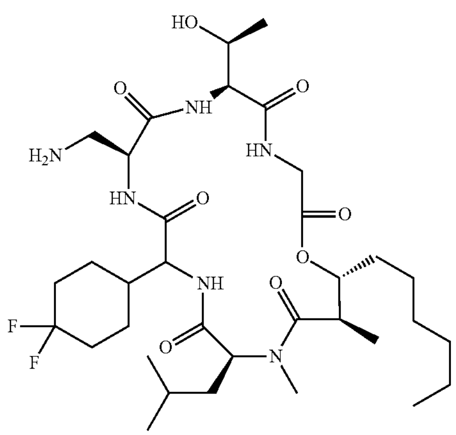 [SMILES: CCCCCC[C@H]1OC(=O)CNC(=O)[C@H]([C@H](C)O)NC(=O)[C@H](CN)NC(=O)C(C2CCC(F)(F)CC2)NC(=O)[C@H](CC(C)C)N(C)C(=O)[C@@H]1C] | (6S,9S,15S,18R,19R)-9-(aminomethyl)-12-(4,4-difluorocyclohexyl)-19-hexyl-15-isobutyl-16,18-dimethyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 53 | 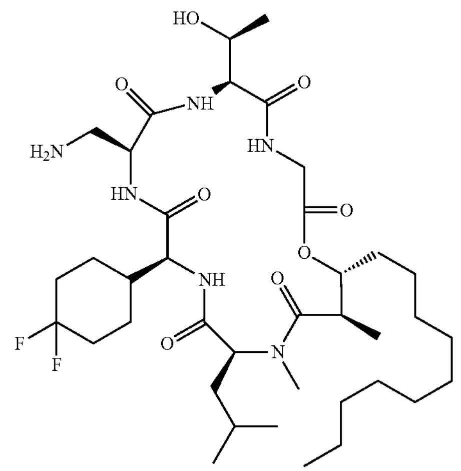 [SMILES: CCCCCCCCCC[C@H]1OC(=O)CNC(=O)[C@H]([C@H](C)O)NC(=O)[C@H](CN)NC(=O)[C@H](C2CCC(F)(F)CC2)NC(=O)[C@H](CC(C)C)N(C)C(=O)[C@@H]1C] | (6S,9S,12S,15S,18R,19R)-9-(aminomethyl)-19-decyl-12-(4,4-difluorocyclohexyl)-15-isobutyl-16,18-dimethyl-6-[(1S)-1-hydroxyethyl]-1-oxa-4,7,10,13,16-pentazacyclononadecane-2,5,8,11,14,17-hexone |
| 54 | 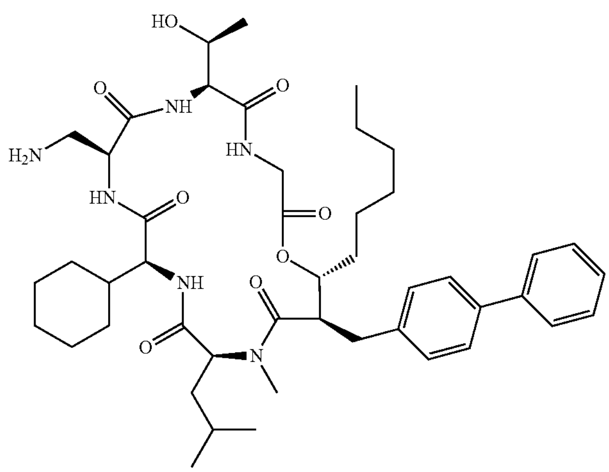 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1ccc(-c2ccccc2)cc1] | (6S,9S,12S,15S,18R,19R)-9-(aminomethyl)-12-cyclohexyl-19-hexyl-15-isobutyl-16-methyl-18-[(4-phenylphenyl)methyl]-6-[(1S)-1-hydroxyethyl]-1-oxa-4,7,10,13,16-pentazacyclononadecane-2,5,8,11,14,17-hexone |
| 55 | 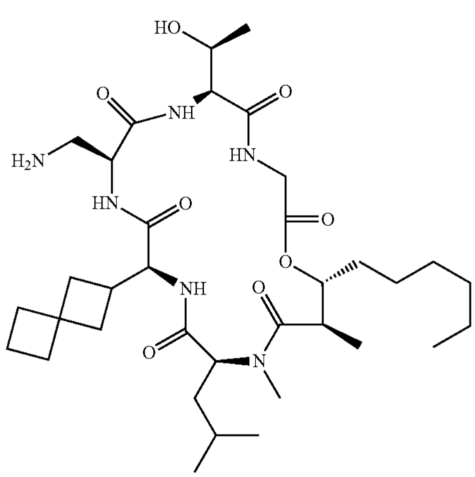 [SMILES: CCCCCC[C@H]1OC(=O)CNC(=O)[C@H]([C@H](C)O)NC(=O)[C@H](CN)NC(=O)[C@H](C2CC3(CCC3)C2)NC(=O)[C@H](CC(C)C)N(C)C(=O)[C@@H]1C] | (6S,9S,12S,15S,18R,19R)-9-(aminomethyl)-19-hexyl-15-isobutyl-16,18-dimethyl-6-[(1S)-1-hydroxyethyl]-12-spiro[3.3]heptan-2-yl-1-oxa-4,7,10,13,16-pentazacyclononadecane-2,5,8,11,14,17-hexone |

TABLE 1-continued

| Ex. | Structure | Name |
|---|---|---|
| 56 | 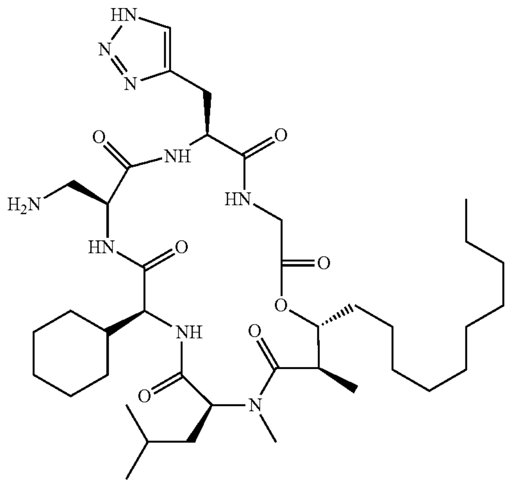 [SMILES: CCCCCCCCCC[C@H]1OC(=O)CNC(=O)[C@H](Cc2c[nH]nn2)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-19-decyl-15-isobutyl-16,18-dimethyl-6-(1H-triazol-4-ylmethyl)-1-oxa-4,7,10,13,16-pentazacyclononadecane-2,5,8,11,14,17-hexone |
| 57 | 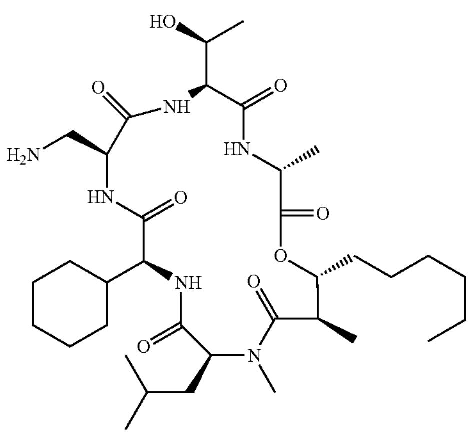 [SMILES: CCCCCC[C@H]1OC(=O)[C@@H](C)NC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-3,16,18-trimethyl-6-[(1S)-1-hydroxyethyl]-1-oxa-4,7,10,13,16-pentazacyclononadecane-5,8,11,14,17-pentone |
| 58 | 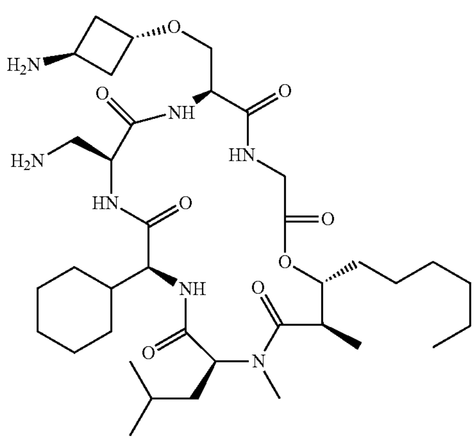 [SMILES: CCCCCC[C@H]1OC(=O)CNC(=O)[C@H](CO[C@H]2C[C@H](N)C2)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-6-[(3-aminocyclobutoxy)methyl]-9-(aminomethyl)-12-cyclohexyl-19-hexyl-15-isobutyl-16,18-dimethyl-1-oxa-4,7,10,13,16-pentazacyclononadecane-2,5,8,11,14,17-hexone |

TABLE 1-continued

| Ex. | Structure | Name |
|---|---|---|
| 59 | 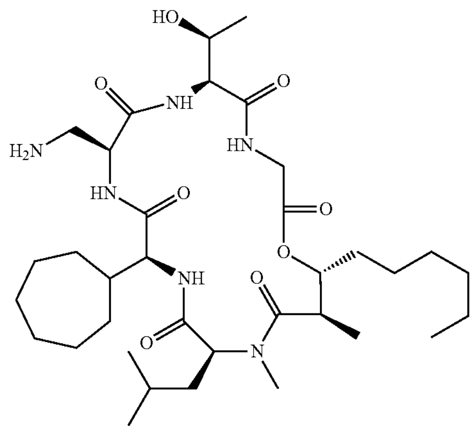 [SMILES: CCCCCC[C@H]1OC(=O)CNC(=O)[C@H]([C@H](C)O)NC(=O)[C@H](CN)NC(=O)[C@H](C2CCCCCC2)NC(=O)[C@H](CC(C)C)N(C)C(=O)[C@@H]1C] | (6S,9S,12S,15S,18R,19R)-9-(aminomethyl)-12-cycloheptyl-19-hexyl-15-isobutyl-16,18-dimethyl-6-[(1S)-1-hydroxyethyl]-1-oxa-4,7,10,13,16-pentazacyclononadecane-2,5,8,11,14,17-hexane |
| 60 | 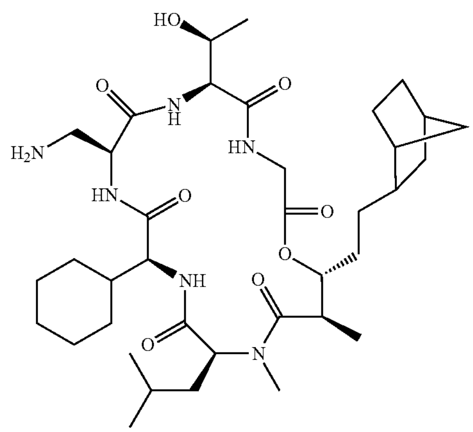 [SMILES: CC(C)C[C@H]1C(=O)N[C@@H](C2CCCCC2)C(=O)N[C@@H](CN)C(=O)N[C@@H]([C@H](C)O)C(=O)NCC(=O)O[C@H](CCC2CC3CCC2C3)[C@@H](C)C(=O)N1C] | (6S,9S,12S,15S,18R,19R)-9-(aminomethyl)-12-cyclohexyl-15-isobutyl-16,18-dimethyl-19-(2-norbornan-2-ylethyl)-6-[(1S)-1-hydroxyethyl]-1-oxa-4,7,10,13,16-pentazacyclononadecane-2,5,8,11,14,17-hexone |
| 61 | 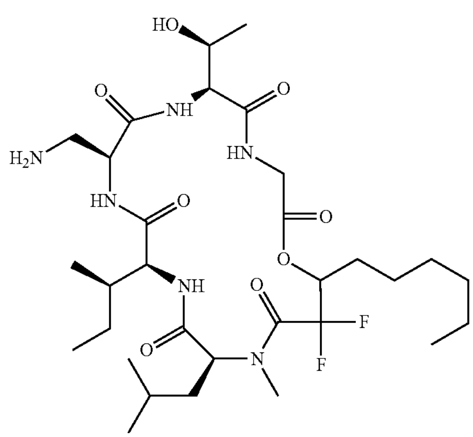 [SMILES: CCCCCCC1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)C1(F)F] | (6S,9S,12S,15S)-9-(aminomethyl)-18,18-difluoro-19-hexyl-15-isobutyl-16-methyl-6-[(1S)-1-hydroxyethyl]-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 62 | 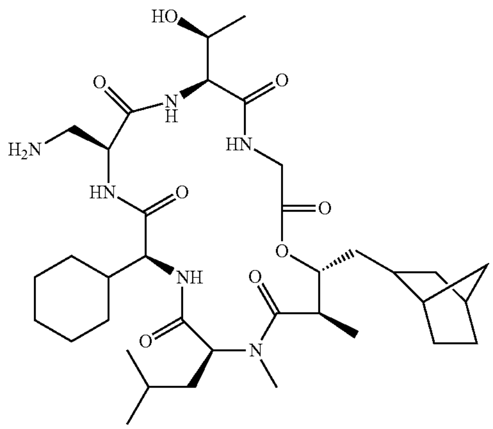 [SMILES: CC(C)C[C@H]1C(=O)N[C@@H](C2CCCCC2)C(=O)N[C@@H](CN)C(=O)N[C@@H]([C@H](C)O)C(=O)NCC(=O)O[C@H](CC2CC3CCC2C3)[C@@H](C)C(=O)N1C] | (6S,9S,12S,15S,18R,19R)-9-(aminomethyl)-12-cyclohexyl-15-isobutyl-16,18-dimethyl-19-(norbornan-2-ylmethyl)-6-[(1S)-1-hydroxyethyl]-1-oxa-4,7,10,13,16-pentazacyclononadecane-2,5,8,11,14,17-hexone |
| 63 | 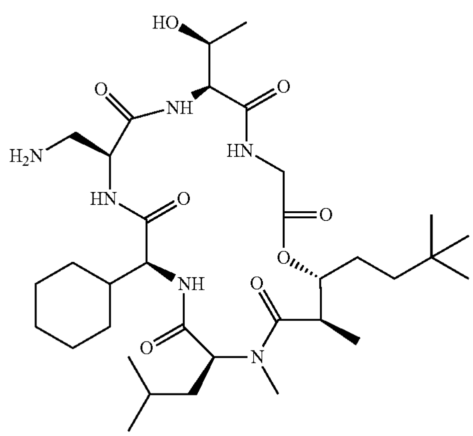 [SMILES: CC(C)C[C@H]1C(=O)N[C@@H](C2CCCCC2)C(=O)N[C@@H](CN)C(=O)N[C@@H]([C@H](C)O)C(=O)NCC(=O)O[C@H](CCC(C)(C)C)[C@@H](C)C(=O)N1C] | (6S,9S,12S,15S,18R,19R)-9-(aminomethyl)-12-cyclohexyl-19-(3,3-dimethylbutyl)-15-isobutyl-16,18-dimethyl-6-[(1S)-1-hydroxyethyl]-1-oxa-4,7,10,13,16-pentazacyclononadecane-2,5,8,11,14,17-hexone |
| 64 | 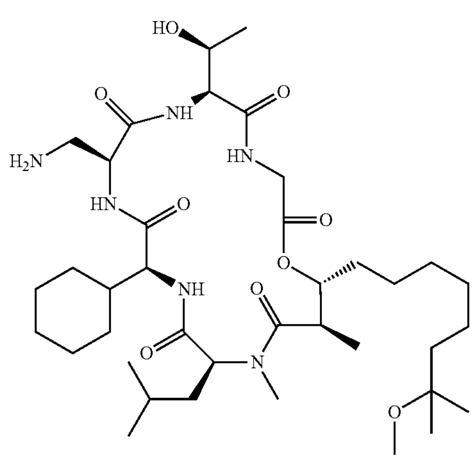 [SMILES: COC(C)(C)CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-15-isobutyl-19-(7-methoxy-7-methyl-octyl)-16,18-dimethyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
| --- | --- | --- |
| 65 | 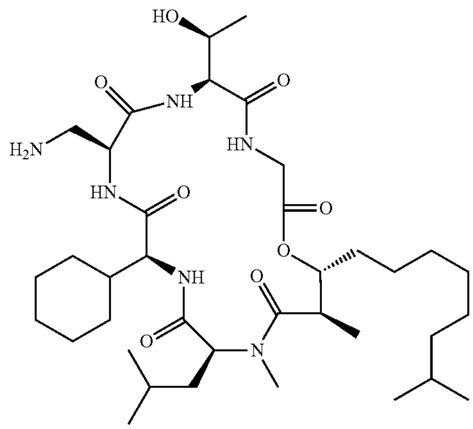 [SMILES: CC(C)CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-15-isobutyl-16,18-dimethyl-19-(7-methyloctyl)-6-[(1S)-1-hydroxyethyl]-1-oxa-4,7,10,13,16-pentazacyclononadecane-2,5,8,11,14,17-hexone |
| 66 | 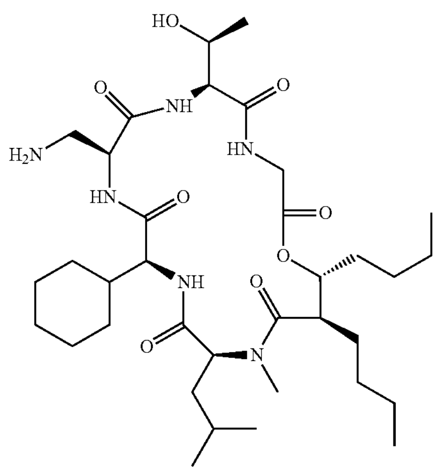 [SMILES: CCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1CCCC] | (6S,9S,12S,15S,18R,19R)-9-(aminomethyl)-18,19-dibutyl-12-cyclohexyl-15-isobutyl-16-methyl-6-[(1S)-1-hydroxyethyl]-1-oxa-4,7,10,13,16-pentazacyclononadecane-2,5,8,11,14,17-hexone |
| 67 | 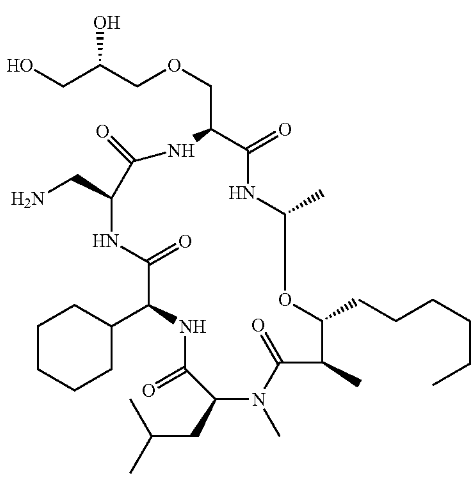 [SMILES: CCCCCC[C@H]1OC[C@@H](C)NC(=O)[C@H](COC[C@@H](O)CO)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-3,16,18-trimethyl-6-[[(2S)-2,3-dihydroxypropoxy]methyl]-1-oxa-4,7,10,13,16-pentazacyclononadecane-5,8,11,14,17-pentone |

TABLE 1-continued

| Ex. | Structure | Name |
|---|---|---|
| 68 | 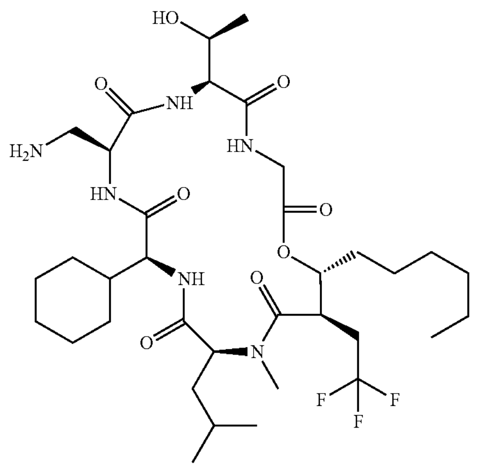 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1CC(F)(F)F] | (6S,9S,12S,15S,18R,19R)-9-(aminomethyl)-12-cyclohexyl-19-hexyl-15-isobutyl-16-methyl-6-[(1S)-1-hydroxyethyl]-18-(2,2,2-trifluoroethyl)-1-oxa-4,7,10,13,16-pentazacyclononadecane-2,5,8,11,14,17-hexone |
| 69 | 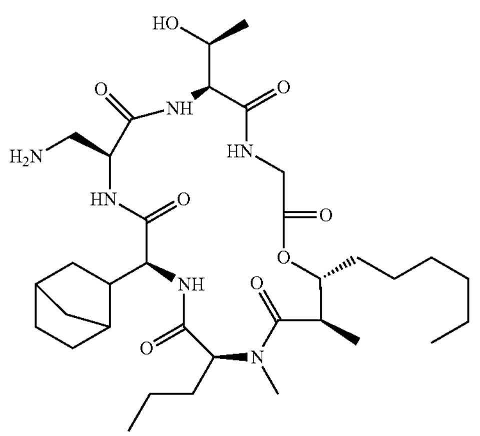 [SMILES: CCCCCC[C@H]1OC(=O)CNC(=O)[C@H]([C@H](C)O)NC(=O)[C@H](CN)NC(=O)[C@H](C2CC3CCC2C3)NC(=O)[C@H](CCC)N(C)C(=O)[C@@H]1C] | (6S,9S,12S,15S,18R,19R)-9-(aminomethyl)-19-hexyl-16,18-dimethyl-12-norbornan-2-yl-15-propyl-6-[(1S)-1-hydroxyethyl]-1-oxa-4,7,10,13,16-pentazacyclononadecane-2,5,8,11,14,17-hexone |
| 70 | 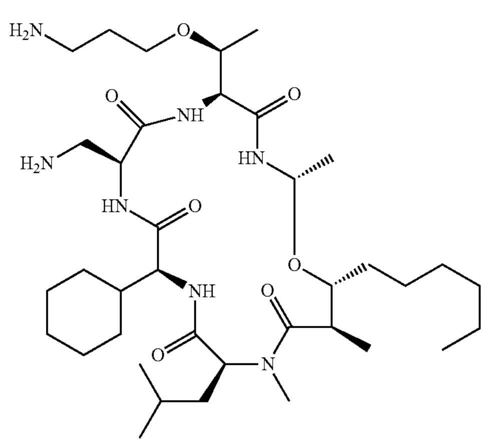 [SMILES: CCCCCC[C@H]1OC[C@@H](C)NC(=O)[C@H]([C@H](C)OCCCN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-3,16,18-trimethyl-6-[(1S)-1-(3-aminopropoxy)ethyl]-1-oxa-4,7,10,13,16-pentazacyclononadecane-5,8,11,14,17-pentone |

TABLE 1-continued

| Ex. | Structure | Name |
|---|---|---|
| 71 | 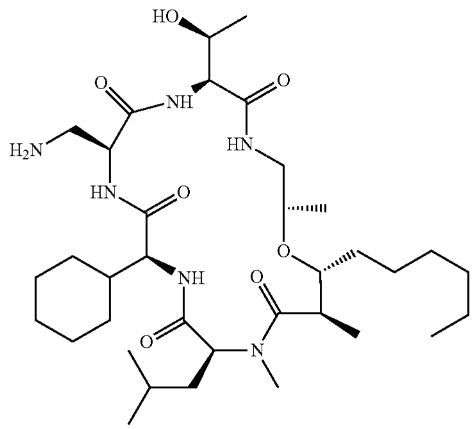 [SMILES: CCCCCC[C@H]1O[C@H](C)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (2S,6S,9S,12S,15S,18R,19R)-9-(aminomethyl)-12-cyclohexyl-19-hexyl-15-isobutyl-2,16,18-trimethyl-6-[(1S)-1-hydroxyethyl]-1-oxa-4,7,10,13,16-pentazacyclononadecane-5,8,11,14,17-pentone |
| 72 | 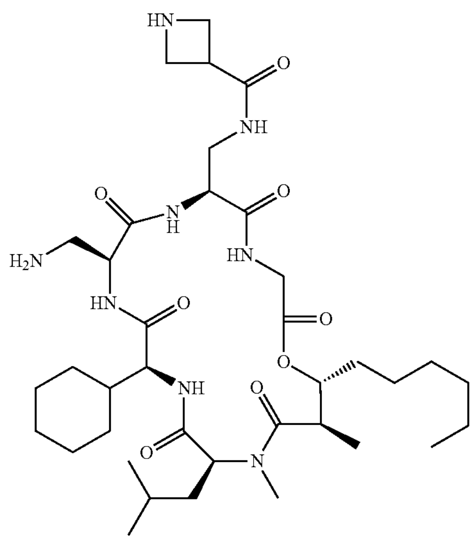 [SMILES: CCCCCC[C@H]1OC(=O)CNC(=O)[C@H](CNC(=O)C2CNC2)NC(=O)[C@H](CN)NC(=O)[C@H](C2CCCCC2)NC(=O)[C@H](CC(C)C)N(C)C(=O)[C@@H]1C] | N-[[(6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentaxacyclononadec-6-yl]methyl]azetidine-3-carboxamide |
| 73 | 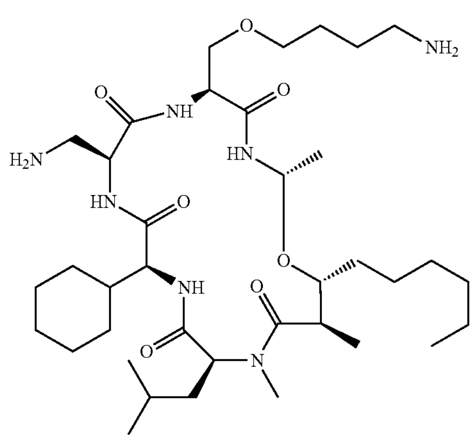 [SMILES: CCCCCC[C@H]1OC[C@@H](C)NC(=O)[C@H](COCCCCN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-(4-aminobutoxymethyl)-9-(aminomethyl)-12-cyclohexyl-19-hexyl-15-isobutyl-3,16,18-trimethyl-1-oxa-4,7,10,13,16-pentazacyclononadecane-5,8,11,14,17-pentone |

TABLE 1-continued

| Ex. | Structure | Name |
|---|---|---|
| 74 | 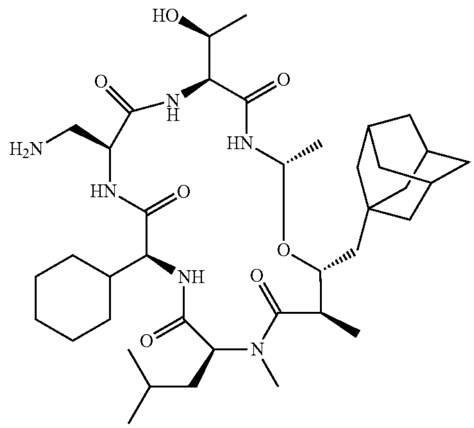 [SMILES: CC(C)C[C@H]1C(=O)N[C@@H](C2CCCCC2)C(=O)N[C@@H](CN)C(=O)N[C@@H]([C@H](C)O)C(=O)N[C@H](C)CO[C@H](CC23CC4CC(CC(C4)C2)C3)[C@@H](C)C(=O)N1C] | (3R,6S,9S,12S,15S,18R,19R)-19-(1-adamantylmethyl)-9-(aminomethyl)-12-cyclohexyl-15-isobutyl-3,16,18-trimethyl-6-[(1S)-1-hydroxyethyl]-1-oxa-4,7,10,13,16-pentazacyclononadecane-5,8,11,14,17-pentone |
| 75 | 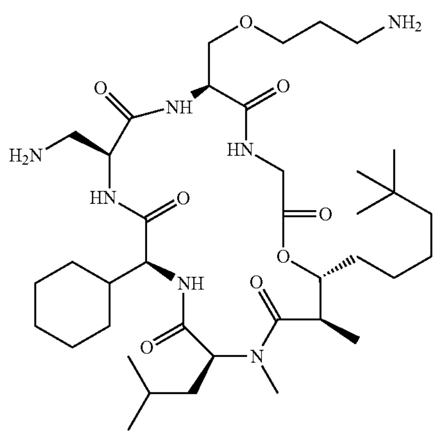 [SMILES: CC(C)C[C@H]1C(=O)N[C@@H](C2CCCCC2)C(=O)N[C@@H](CN)C(=O)N[C@@H](COCCCN)C(=O)NCC(=O)O[C@H](CCCCC(C)(C)C)[C@@H](C)C(=O)N1C] | (6S,9S,12S,15S,18R,19R)-9-(aminomethyl)-6-(3-aminopropoxymethyl)-12-cyclohexyl-19-(5,5-dimethylhexyl)-15-isobutyl-16,18-dimethyl-1-oxa-4,7,10,13,16-pentazacyclononadecane-2,5,8,11,14,17-hexone |
| 76 | 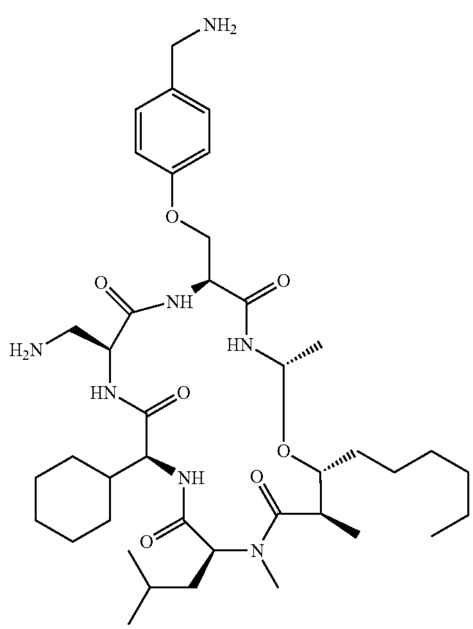 [SMILES: CCCCCC[C@H]1OC[C@@H](C)NC(=O)[C@H](COc2ccc(CN)cc2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-6-[[4-(aminomethyl)phenoxy]methyl]-12-cyclohexyl-19-hexyl-15-isobutyl-3,16,18-trimethyl-1-oxa-4,7,10,13,16-pentazacyclononadecane-5,8,11,14,17-pentone |

TABLE 1-continued

| Ex. | Structure | Name |
| --- | --- | --- |
| 77 | 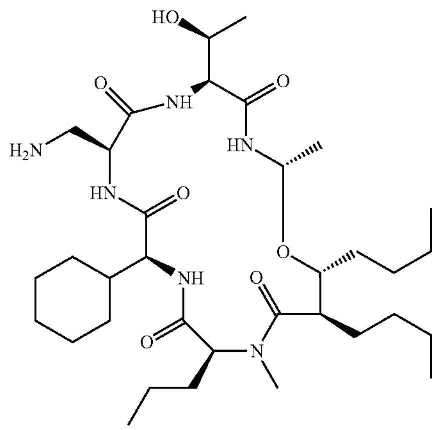 [SMILES: CCCC[C@H]1OC[C@@H](C)NC(=O)[C@H]([C@H](C)O)NC(=O)[C@H](CN)NC(=O)[C@H](C2CCCCC2)NC(=O)[C@H](CCC)N(C)C(=O)[C@@H]1CCCC] | (3R,6S,9S,12S,15S,18R,19R)-9-(aminomethyl)-18,19-dibutyl-12-cyclohexyl-3,16-dimethyl-15-propyl-6-[(1S)-1-hydroxyethyl]-1-oxa-4,7,10,13,16-pentazacyclononadecane-5,8,11,14,17-pentone |
| 78 | 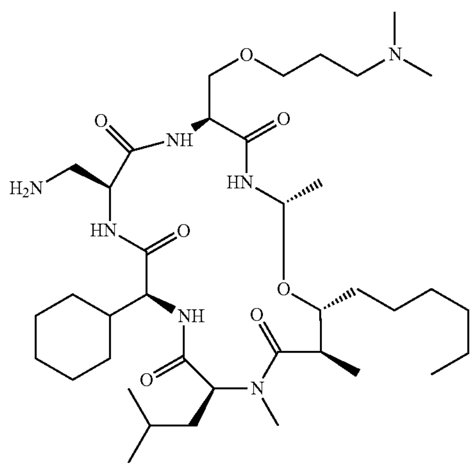 [SMILES: CCCCCC[C@H]1OC[C@@H](C)NC(=O)[C@H](COCCCN(C)C)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-6-[3-(dimethylamino)propoxymethyl]-19-hexyl-15-isobutyl-3,16,18-trimethyl-1-oxa-4,7,10,13,16-pentazacyclononadecane-5,8,11,14,17-pentone |
| 79 | 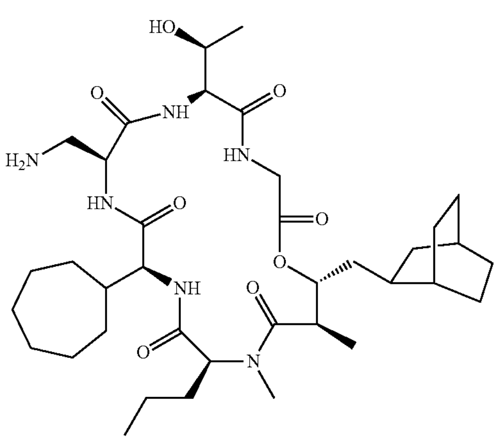 [SMILES: CCC[C@H]1C(=O)N[C@@H](C2CCCCCC2)C(=O)N[C@@H](CN)C(=O)N[C@@H]([C@H](C)O)C(=O)NCC(=O)O[C@H](CC2CC3CCC2CC3)[C@@H](C)C(=O)N1C] | (6S,9S,12S,15S,18R,19R)-9-(aminomethyl)-19-(2-bicyclo[2.2.2]octanylmethyl)-12-cycloheptyl-16,18-dimethyl-15-propyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 80 | 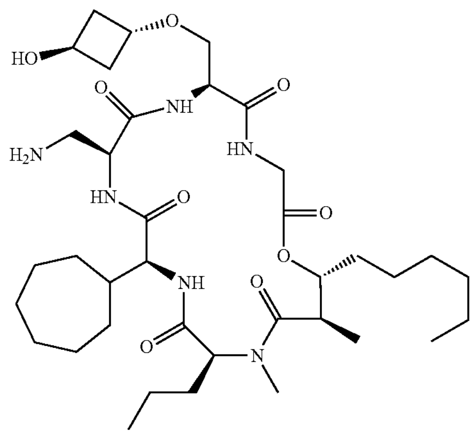 [SMILES: CCCCCC[C@H]1OC(=O)CNC(=O)[C@H](CO[C@H]2C[C@H](O)C2)NC(=O)[C@H](CN)NC(=O)[C@H](C2CCCCCC2)NC(=O)[C@H](CCC)N(C)C(=O)[C@@H]1C] | (6S,9S,12S,15S,18R,19R)-6-[(3-aminocyclobutoxy)methyl]-9-(aminomethyl)-12-cycloheptyl-19-hexyl-16,18-dimethyl-15-propyl-1-oxa-4,7,10,13,16-pentazacyclononadecane-5,8,11,14,17-pentone |
| 81 | 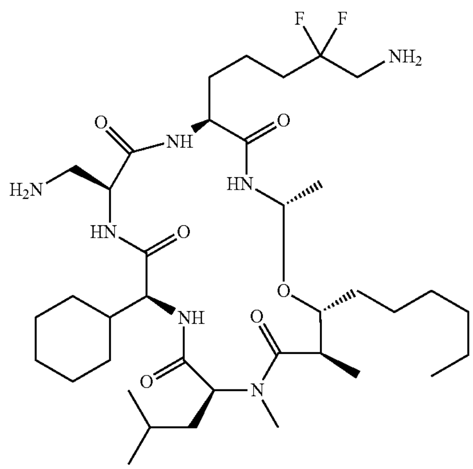 [SMILES: CCCCCC[C@H]1OC[C@@H](C)NC(=O)[C@H](CCCC(F)(F)CN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-[(3-amino-2,2-difluoro-propoxy)methyl]-9-(aminomethyl)-12-cyclohexyl-19-hexyl-15-isobutyl-3,16,18-trimethyl-1-oxa-4,7,10,13,16-pentazacyclononadecane-5,8,11,14,17-pentone |
| 82 | 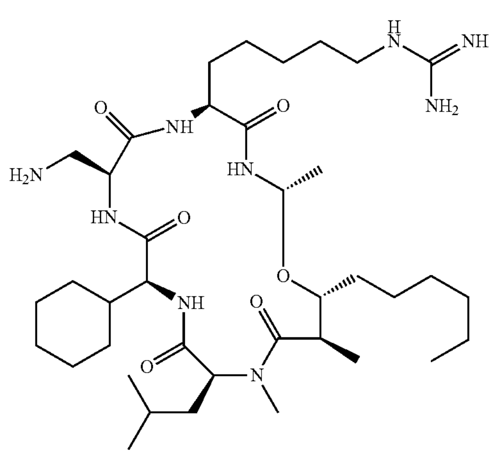 [SMILES: CCCCCC[C@H]1OC[C@@H](C)NC(=O)[C@H](CCCCCNC(=N)N)NC(=O)[C@H](CN)NC(=O)[C@H](C2CCCCC2)NC(=O)[C@H](CC(C)C)N(C)C(=O)[C@@H]1C] | 1-[3-[[(3R,6S,9S,12S,15S,18R,19R)-9-(aminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methoxy]propyl]guanidine |

TABLE 1-continued

| Ex. | Structure | Name |
|---|---|---|
| 83 | 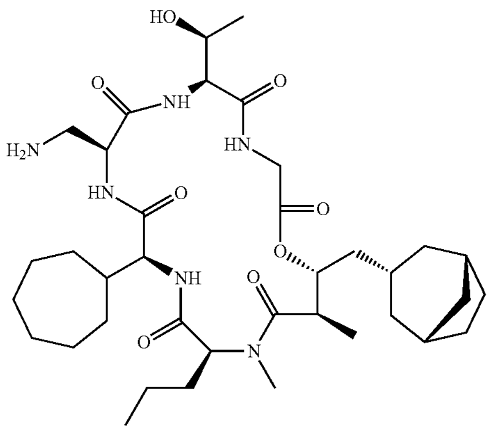 [SMILES: CCC[C@H]1C(=O)N[C@@H](C2CCCCCC2)C(=O)N[C@@H](CN)C(=O)N[C@@H]([C@H](C)O)C(=O)NCC(=O)O[C@H](C[C@@H]2C[C@@H]3CC[C@@H](C3)C2)[C@@H](C)C(=O)N1C] | (6S,9S,12S,15S,18R,19R)-9-(aminomethyl)-12-cycloheptyl-16,18-dimethyl-15-propyl-19-[[(1S,5R)-3-bicyclo[3.2.1]octanyl]methyl]-6-[(1S)-1-hydroxyethyl]-1-oxa-4,7,10,13,16-pentazacyclononadecane-2,5,8,11,14,17-hexone |
| 84 | 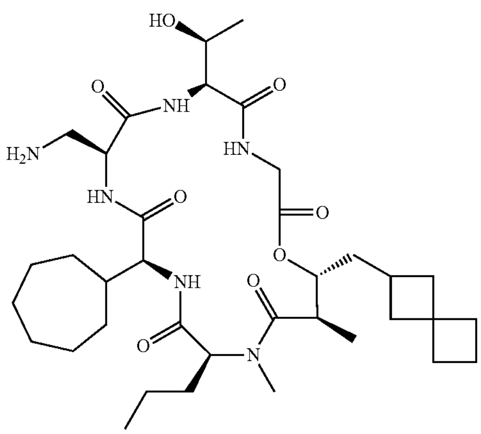 [SMILES: CCC[C@H]1C(=O)N[C@@H](C2CCCCCC2)C(=O)N[C@@H](CN)C(=O)N[C@@H]([C@H](C)O)C(=O)NCC(=O)O[C@H](CC2CC3(CCC3)C2)[C@@H](C)C(=O)N1C] | (6S,9S,12S,15S,18R,19R)-9-(aminomethyl)-12-cycloheptyl-16,18-dimethyl-15-propyl-6-[(1S)-1-hydroxyethyl]-19-(spiro[3.3]heptan-2-ylmethyl)-1-oxa-4,7,10,13,16-pentazacyclononadecane-2,5,8,11,14,17-hexone |
| 85 | 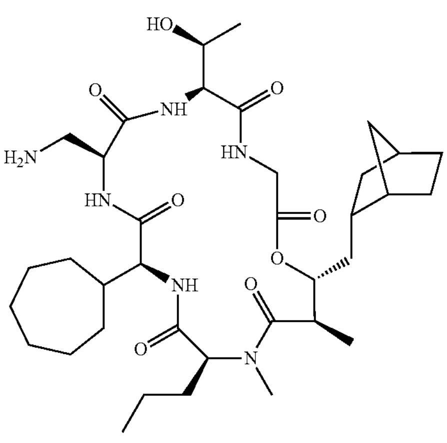 [SMILES: CCC[C@H]1C(=O)N[C@@H](C2CCCCCC2)C(=O)N[C@@H](CN)C(=O)N[C@@H]([C@H](C)O)C(=O)NCC(=O)O[C@H](CC2CC3CCC2C3)[C@@H](C)C(=O)N1C] | (6S,9S,12S,15S,18R,19R)-9-(aminomethyl)-12-cycloheptyl-16,18-dimethyl-19-(norbornan-2-ylmethyl)-15-propyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 86 | 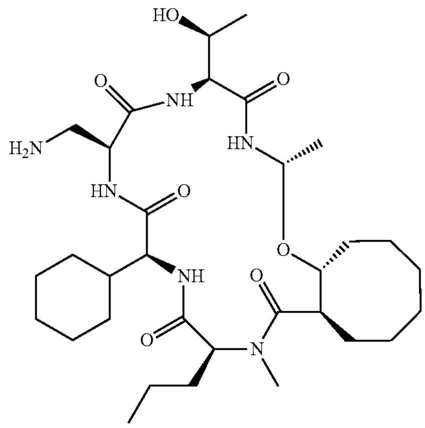 [SMILES: CCC[C@H]1C(=O)N[C@@H](C2CCCCC2)C(=O)N[C@@H](CN)C(=O)N[C@@H]([C@H](C)O)C(=O)N[C@H](C)CO[C@@H]2CCCCCC[C@H]2C(=O)N1C] | (1R,4R,7S,10S,13S,16S,19R)-10-(aminomethyl)-13-cyclohexyl-4,17-dimethyl-16-propyl-7-[(1S)-1-hydroxyethyl]-2-oxa-5,8,11,14,17-pentazabicyclo[17.6.0]pentacosane-6,9,12,15,18-pentone |
| 87 | 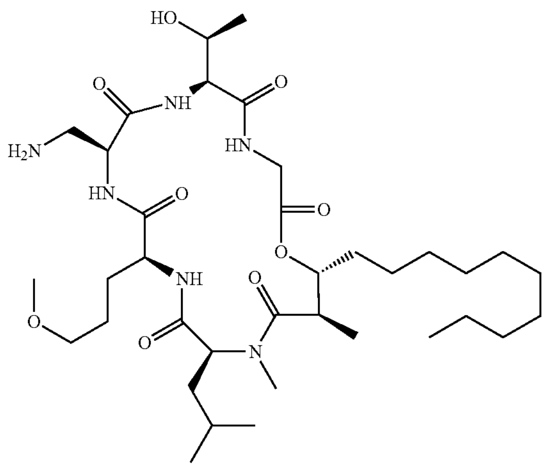 [SMILES: CCCCCCCCCC[C@H]1OC(=O)CNC(=O)[C@H]([C@H](C)O)NC(=O)[C@H](CN)NC(=O)[C@H](CCCOC)NC(=O)[C@H](CC(C)C)N(C)C(=O)[C@@H]1C] | (6S,9S,12S,15S,18R,19R)-9-(aminomethyl)-19-decyl-15-isobutyl-12-(3-methoxypropyl)-16,18-dimethyl-6-[(1S)-1-hydroxyethyl]-1-oxa-4,7,10,13,16-pentazacyclononadecane-2,5,8,11,14,17-hexone |
| 88 | 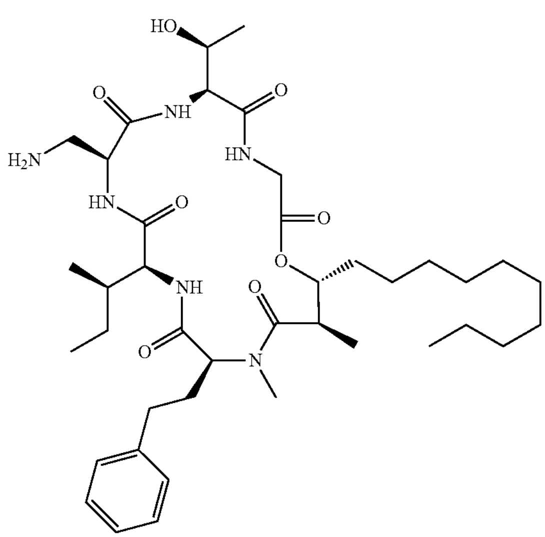 [SMILES: CCCCCCCCCC[C@H]1OC(=O)CNC(=O)[C@H]([C@H](C)O)NC(=O)[C@H](CN)NC(=O)[C@H]([C@H](C)CC)NC(=O)[C@H](CCc2ccccc2)N(C)C(=O)[C@@H]1C] | (6S,9S,12S,15S,18R,19R)-9-(aminomethyl)-19-decyl-16,18-dimethyl-15-(2-phenylethyl)-6-[(1S)-1-hydroxyethyl]-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 89 | 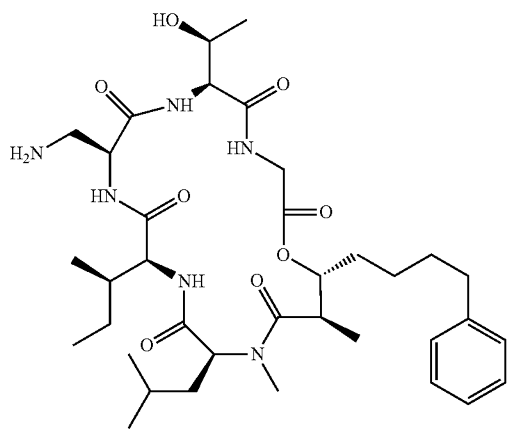 [SMILES: CC[C@@H](C)[C@@H]1NC(=O)[C@H](CC(C)C)N(C)C(=O)[C@H](C)[C@@H](CCCCc2ccccc2)OC(=O)CNC(=O)[C@H]([C@H](C)O)NC(=O)[C@H](CN)NC1=O] | (6S,9S,12S,15S,18R,19R)-9-(aminomethyl)-15-isobutyl-16,18-dimethyl-19-(4-phenylbutyl)-6-[(1S)-1-hydroxyethyl]-12-[(1R)-1-methylpropyl]-1-oxa-4,7,10,13,16-pentazacyclononadecane-2,5,8,11,14,17-hexone |
| 90 | 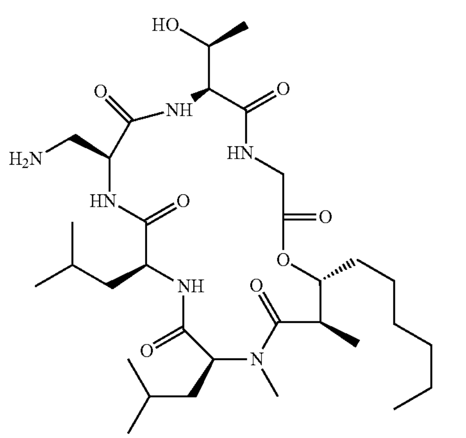 [SMILES: CCCCCC[C@H]1OC(=O)CNC(=O)[C@H]([C@H](C)O)NC(=O)[C@H](CN)NC(=O)[C@H](CC(C)C)NC(=O)[C@H](CC(C)C)N(C)C(=O)[C@@H]1C] | (6S,9S,12S,15S,18R,19R)-9-(aminomethyl)-19-hexyl-12,15-diisobutyl-16,18-dimethyl-6-[(1S)-1-hydroxyethyl]-1-oxa-4,7,10,13,16-pentazacyclononadecane-2,5,8,11,14,17-hexone |
| 91 | 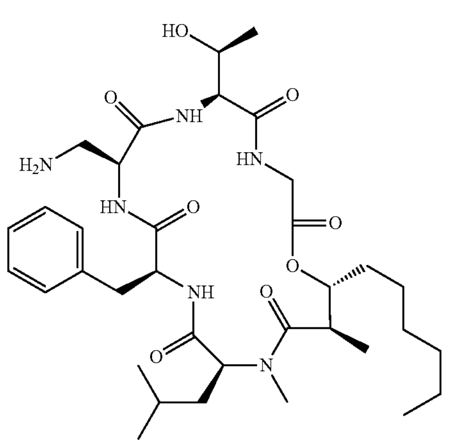 [SMILES: CCCCCC[C@H]1OC(=O)CNC(=O)[C@H]([C@H](C)O)NC(=O)[C@H](CN)NC(=O)[C@H](Cc2ccccc2)NC(=O)[C@H](CC(C)C)N(C)C(=O)[C@@H]1C] | (6S,9S,12S,15S,18R,19R)-9-(aminomethyl)-12-benzyl-19-hexyl-15-isobutyl-16,18-dimethyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 92 | 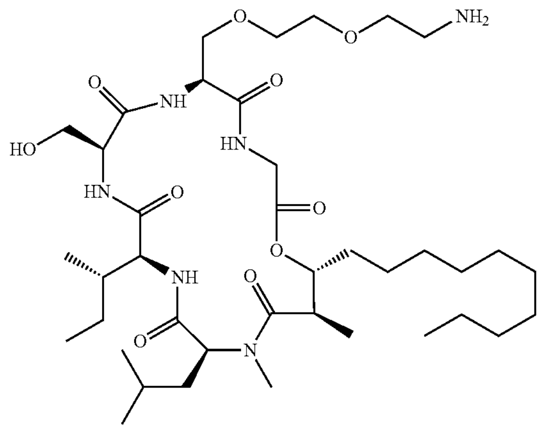 [SMILES: CCCCCCCCCC[C@H]1OC(=O)CNC(=O)[C@H](COCCOCCN)NC(=O)[C@H](CO)NC(=O)[C@H]([C@@H](C)CC)NC(=O)[C@H](CC(C)C)N(C)C(=O)[C@@H]1C] | (6S,9S,12S,15S,18R,19R)-6-[2-(2-aminoethoxy)ethoxymethyl]-19-decyl-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 93 | 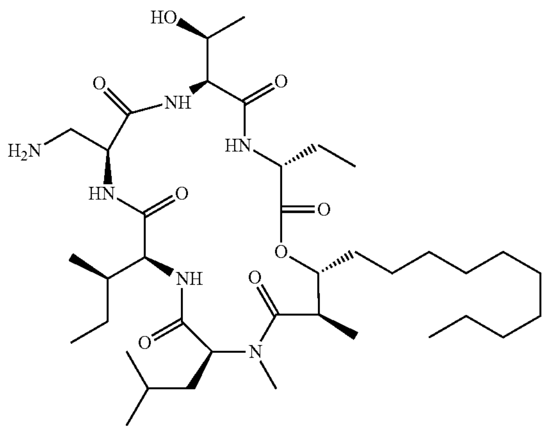 [SMILES: CCCCCCCCCC[C@H]1OC(=O)[C@@H](CC)NC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (3R,6S,9S,12S,15S,18R,19R)-9-(aminomethyl)-19-decyl-3-ethyl-15-isobutyl-16,18-dimethyl-6-[(1S)-1-hydroxyethyl]-12-[(1R)-1-methylpropyl]-1-oxa-4,7,10,13,16-pentazacyclononadecane-2,5,8,11,14,17-hexone |
| 94 | 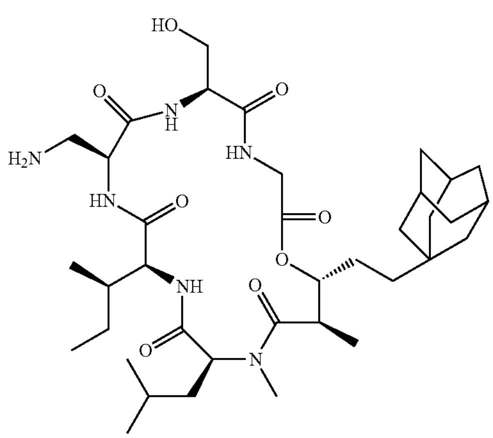 [SMILES: CC[C@@H](C)[C@@H]1NC(=O)[C@H](CC(C)C)N(C)C(=O)[C@H](C)[C@@H](CCC23CC4CC(CC(C4)C2)C3)OC(=O)CNC(=O)[C@H](CO)NC(=O)[C@H](CN)NC1=O] | (6S,9S,12S,15S,18R,19R)-19-[2-(1-adamantyl)ethyl]-9-(aminomethyl)-6-(hydroxymethyl)-15-isobutyl-16,18-dimethyl-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 95 | 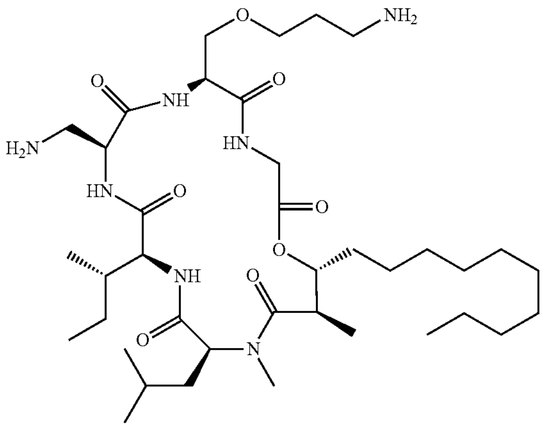 [SMILES: CCCCCCCCCC[C@H]1OC(=O)CNC(=O)[C@H](COCCCN)NC(=O)[C@H](CN)NC(=O)[C@H]([C@@H](C)CC)NC(=O)[C@H](CC(C)C)N(C)C(=O)[C@@H]1C] | (6S,9S,12S,15S,18R,19R)-6-(3-aminopropoxymethyl)-19-decyl-9-(hydroxymethyl)-15-isobutyl-16,18-dimethyl-12-[(1S)-1-methylpropyl]-1-oxa-4,7,10,13,16-pentazacyclononadecane-2,5,8,11,14,17-hexone |
| 96 | 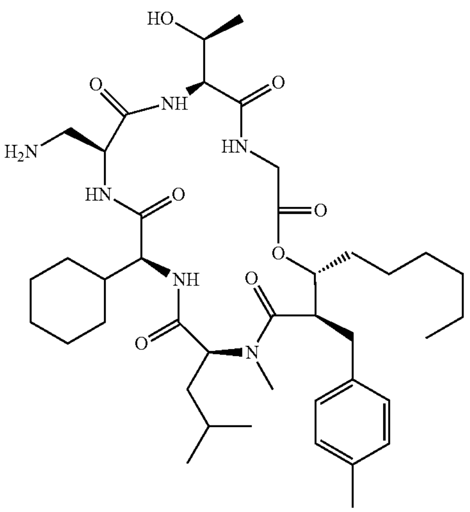 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1ccc(C)cc1] | (6S,9S,12S,15S,18R,19R)-9-(aminomethyl)-12-cyclohexyl-19-hexyl-15-isobutyl-16-methyl-18-(p-tolylmethyl)-6-[(1S)-1-hydroxyethyl]-1-oxa-4,7,10,13,16-pentazacyclononadecane-2,5,8,11,14,17-hexone |
| 97 | 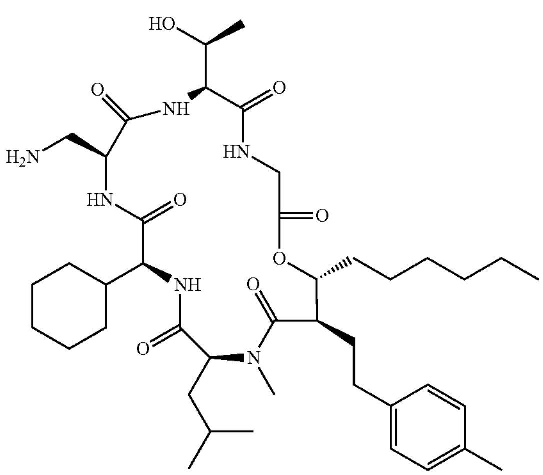 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1CCc1ccc(C)cc1] | (6S,9S,12S,15S,18R,19R)-9-(aminomethyl)-12-cyclohexyl-19-hexyl-15-isobutyl-16-methyl-18-[2-(p-tolyl)ethyl]-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 98 | 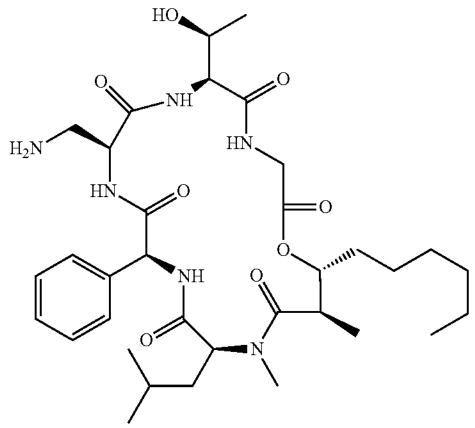 [SMILES: CCCCCC[C@H]1OC(=O)CNC(=O)[C@H]([C@H](C)O)NC(=O)[C@H](CN)NC(=O)[C@H](c2ccccc2)NC(=O)[C@H](CC(C)C)N(C)C(=O)[C@@H]1C] | (6S,9S,12S,15S,18R,19R)-9-(aminomethyl)-19-hexyl-15-isobutyl-16,18-dimethyl-12-phenyl-6-[(1S)-1-hydroxyethyl]-1-oxa-4,7,10,13,16-pentazacyclononadecane-2,5,8,11,14,17-hexone |
| 99 | 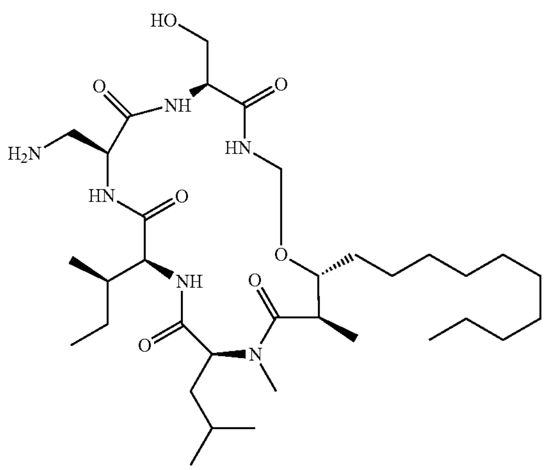 [SMILES: CCCCCCCCCC[C@H]1OCCNC(=O)[C@H](CO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-decyl-6-(hydroxymethyl)-15-isobutyl-16,18-dimethyl-12-[(1R)-1-methylpropyl]-1-oxa-4,7,10,13,16-pentazacyclononadecane-5,8,11,14,17-pentone |
| 100 | 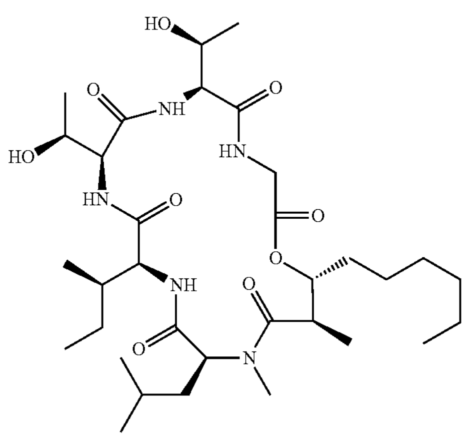 [SMILES: CCCCCC[C@H]1OC(=O)CNC(=O)[C@H]([C@H](C)O)NC(=O)[C@H]([C@H](C)O)NC(=O)[C@H]([C@H](C)CC)NC(=O)[C@H](CC(C)C)N(C)C(=O)[C@@H]1C] | (6S,9S,12S,15S,18R,19R)-19-hexyl-15-isobutyl-16,18-dimethyl-6,9-bis[(1S)-1-hydroxyethyl]-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 101 | 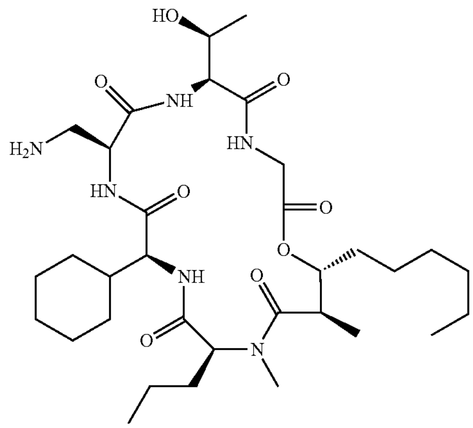 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CCC)N(C)C(=O)[C@@H]1C] | (6S,9S,12S,15S,18R,19R)-9-(aminomethyl)-12-cyclohexyl-19-hexyl-16,18-dimethyl-15-propyl-6-[(1S)-1-hydroxyethyl]-1-oxa-4,7,10,13,16-pentazacyclononadecane-2,5,8,11,14,17-hexone |
| 102 | 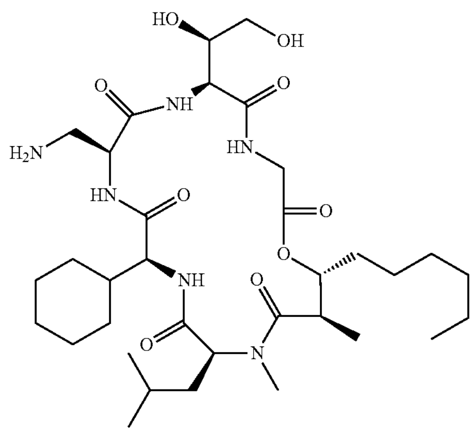 [SMILES: CCCCCC[C@H]1OC(=O)CNC(=O)[C@H]([C@@H](O)CO)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-19-hexyl-15-isobutyl-16,18-dimethyl-6-[(1R)-1,2-dihydroxyethyl]-1-oxa-4,7,10,13,16-pentazacyclononadecane-2,5,8,11,14,17-hexone |
| 103 | 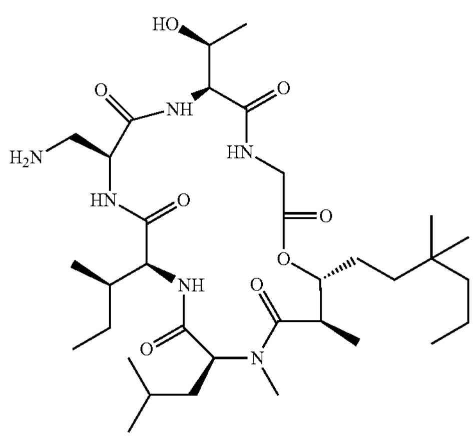 [SMILES: CCCC(C)(C)CC[C@H]1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-(3,3-dimethylhexyl)-15-isobutyl-16,18-dimethyl-6-[(1S)-1-hydroxyethyl]-12-[(1R)-1-methylpropyl]-1-oxa-4,7,10,13,16-pentazacyclononadecane-2,5,8,11,14,17-hexone |

TABLE 1-continued

| Ex. | Structure | Name |
|---|---|---|
| 104 | 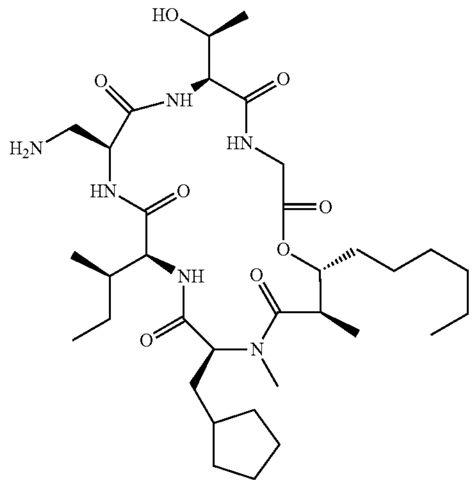 [SMILES: CCCCCC[C@H]1OC(=O)CNC(=O)[C@H]([C@H](C)O)NC(=O)[C@H](CN)NC(=O)[C@H]([C@H](C)CC)NC(=O)[C@H](CC2CCCC2)N(C)C(=O)[C@@H]1C] | (6S,9S,12S,15S,18R,19R)-9-(aminomethyl)-15-(cyclopentylmethyl)-19-hexyl-16,18-dimethyl-6-[(1S)-1-hydroxyethyl]-12-[(1R)-1-methylpropyl]-1-oxa-4,7,10,13,16-pentazacyclononadecane-2,5,8,11,14,17-hexone |
| 105 | 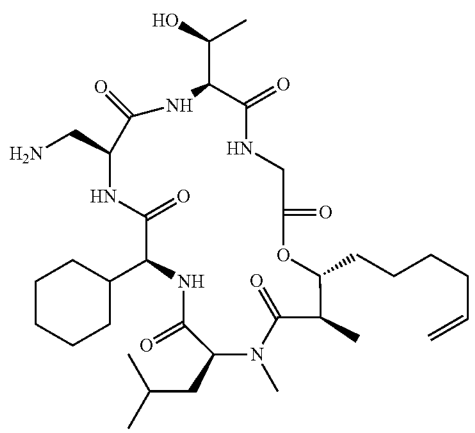 [SMILES: C=CCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-19-hex-5-enyl-15-isobutyl-16,18-dimethyl-6-[(1S)-1-hydroxyethyl]-1-oxa-4,7,10,13,16-pentazacyclononadecane-2,5,8,11,14,17-hexone |
| 106 | 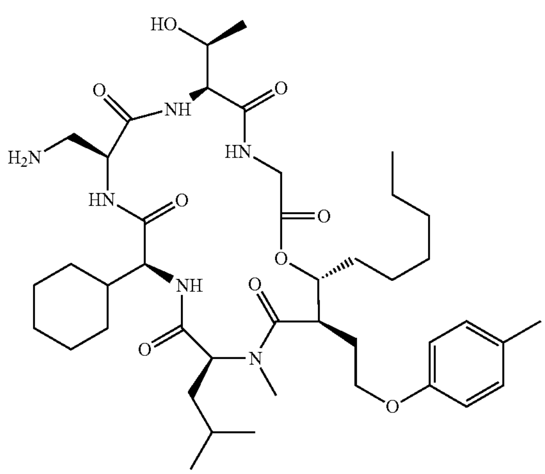 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1CCOc1ccc(C)cc1] | (6S,9S,12S,15S,18R,19R)-9-(aminomethyl)-12-cyclohexyl-19-hexyl-15-isobutyl-16-methyl-18-[2-(4-methylphenoxy)ethyl]-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 107 | 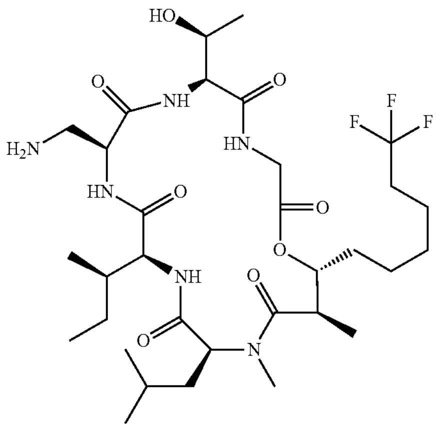 [SMILES: CC[C@@H](C)[C@@H]1NC(=O)[C@H](CC(C)C)N(C)C(=O)[C@H](C)[C@@H](CCCCCC(F)(F)F)OC(=O)CNC(=O)[C@H]([C@H](C)O)NC(=O)[C@H](CN)NC1=O] | (6S,9S,12S,15S,18R,19R)-9-(aminomethyl)-15-isobutyl-16,18-dimethyl-6-[(1S)-1-hydroxyethyl]-12-[(1R)-1-methylpropyl]-19-(6,6,6-trifluorohexyl)-1-oxa-4,7,10,13,16-pentazacyclononadecane-2,5,8,11,14,17-hexone |
| 108 | 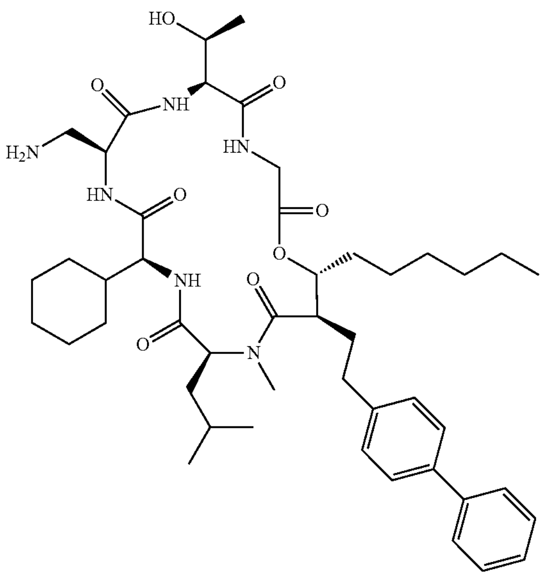 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1CCc1ccc(-c2ccccc2)cc1] | (6S,9S,12S,15S,18R,19R)-9-(aminomethyl)-12-cyclohexyl-19-hexyl-15-isobutyl-16-methyl-18-[2-(4-phenylphenyl)ethyl]-6-[(1S)-1-hydroxyethyl]-1-oxa-4,7,10,13,16-pentazacyclononadecane-2,5,8,11,14,17-hexone |
| 109 | 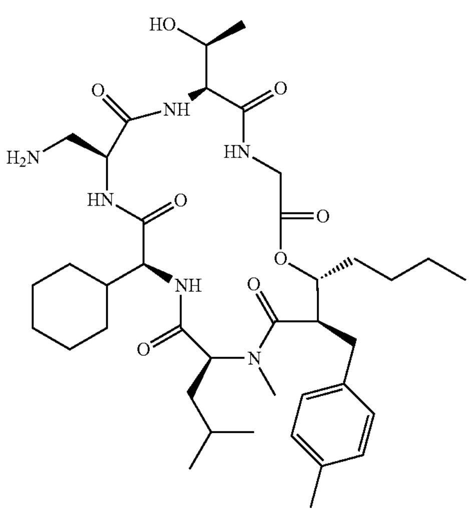 [SMILES: CCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1ccc(C)cc1] | (6S,9S,12S,15S,18R,19R)-9-(aminomethyl)-19-butyl-12-cyclohexyl-15-isobutyl-16-methyl-18-(p-tolylmethyl)-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 110 | 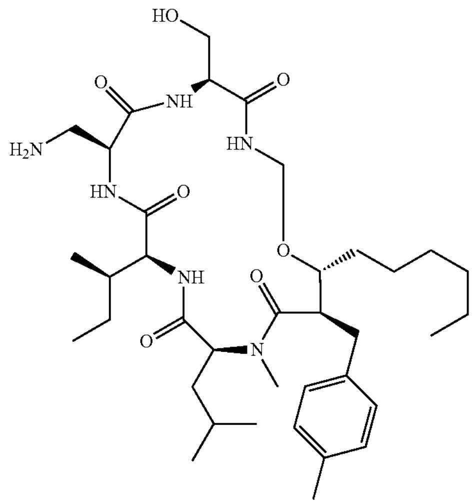 [SMILES: CCCCCC[C@H]1OCCNC(=O)[C@H](CO)NC(=O)[C@H](CN)NC(=O)[C@H]([C@H](C)CC)NC(=O)[C@H](CC(C)C)N(C)C(=O)[C@@H]1Cc1ccc(C)cc1] | (6S,9S,12S,15S,18R,19R)-9-(aminomethyl)-19-hexyl-6-(hydroxymethyl)-15-isobutyl-16-methyl-18-(p-tolylmethyl)-12-[(1R)-1-methylpropyl]-1-oxa-4,7,10,13,16-pentazacyclononadecane-5,8,11,14,17-pentone |
| 111 | 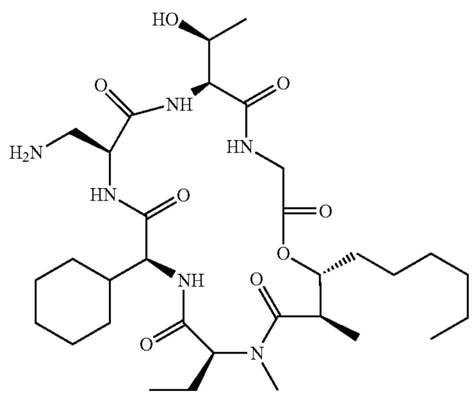 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC)N(C)C(=O)[C@@H]1C] | (6S,9S,12S,15S,18R,19R)-9-(aminomethyl)-12-cyclohexyl-15-ethyl-19-hexyl-16,18-dimethyl-6-[(1S)-1-hydroxyethyl]-1-oxa-4,7,10,13,16-pentazacyclononadecane-2,5,8,11,14,17-hexone |
| 112 | 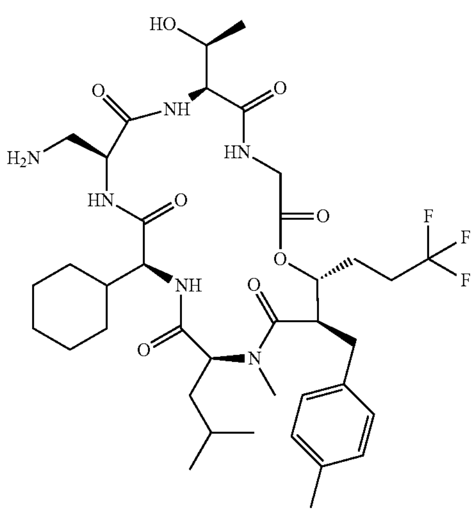 [SMILES: Cc1ccc(C[C@H]2C(=O)N(C)[C@@H](CC(C)C)C(=O)N[C@@H](C3CCCCC3)C(=O)N[C@@H](CN)C(=O)N[C@@H]([C@H](C)O)C(=O)NCC(=O)O[C@@H]2CCC(F)(F)F)cc1] | (6S,9S,12S,15S,18R,19R)-9-(aminomethyl)-12-cyclohexyl-15-isobutyl-16-methyl-18-(p-tolylmethyl)-6-[(1S)-1-hydroxyethyl]-19-(3,3,3-trifluoropropyl)-1-oxa-4,7,10,13,16-pentazacyclononadecane-2,5,8,11,14,17-hexone |

TABLE 1-continued

| Ex. | Structure | Name |
|---|---|---|
| 113 | 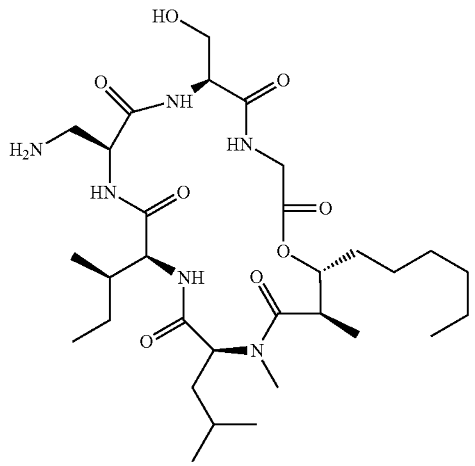 [SMILES: CCCCCC[C@H]1OC(=O)CNC(=O)[C@H](CO)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-hexyl-6-(hydroxymethyl)-15-isobutyl-16,18-dimethyl-12-[(1R)-1-methylpropyl]-1-oxa-4,7,10,13,16-pentazacyclononadecane-5,8,11,14,17-pentone |
| 114 | 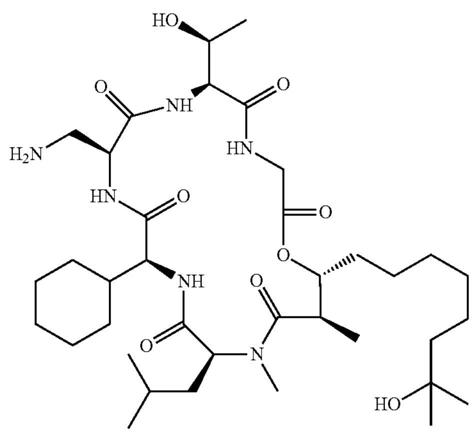 [SMILES: CC(C)C[C@H]1C(=O)N[C@@H](C2CCCCC2)C(=O)N[C@@H](CN)C(=O)N[C@@H]([C@H](C)O)C(=O)NCC(=O)O[C@H](CCCCCCC(C)(C)O)[C@@H](C)C(=O)N1C] | (6S,9S,12S,15S,18R,19R)-9-(aminomethyl)-12-cyclohexyl-19-(7-hydroxy-7-methyl-octyl)-15-isobutyl-16,18-dimethyl-6-[(1S)-1-hydroxyethyl]-1-oxa-4,7,10,13,16-pentazacyclononadecane-2,5,8,11,14,17-hexone |
| 115 | 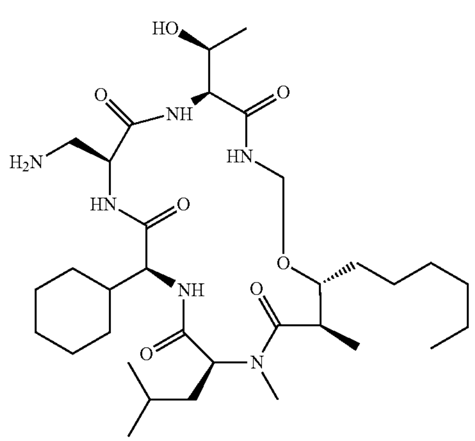 [SMILES: CCCCCC[C@H]1OCCNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-19-hexyl-15-isobutyl-16,18-dimethyl-6-[(1S)-1-hydroxyethyl]-1-oxa-4,7,10,13,16-pentazacyclononadecane-5,8,11,14,17-pentone |

TABLE 1-continued

| Ex. | Structure | Name |
|---|---|---|
| 116 | 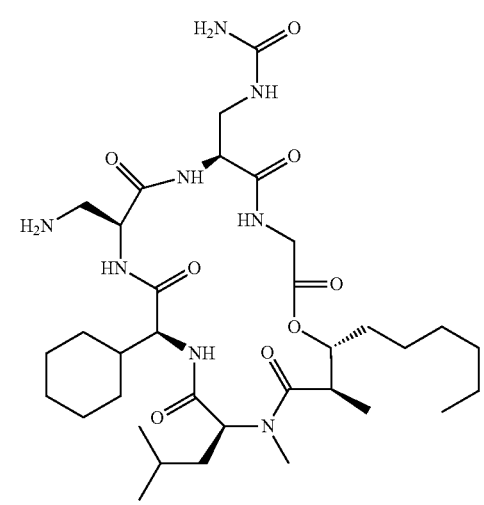 [SMILES: CCCCCC[C@H]1OC(=O)CNC(=O)[C@H](CNC(N)=O)NC(=O)[C@H](CN)NC(=O)[C@H](C2CCCCC2)NC(=O)[C@H](CC(C)C)N(C)C(=O)[C@@H]1C] | [(6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methylurea |
| 117 | 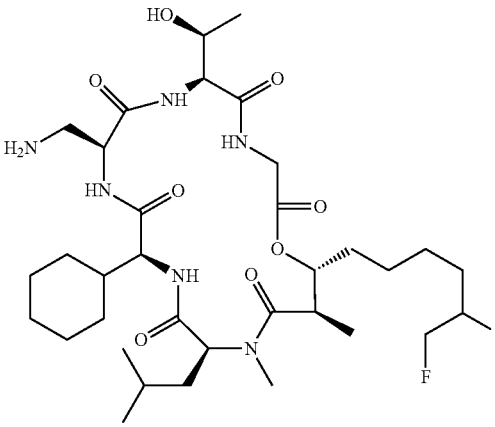 | (6S,9S,12S,15S,18R,19R)-9-(aminomethyl)-12-cyclohexyl-19-(5,6-difluorohexyl)-15-isobutyl-16,18-dimethyl-6-[(1S)-1-hydroxyethyl]-1-oxa-4,7,10,13,16-pentazacyclononadecane-2,5,8,11,14,17-hexone |
| 118 | 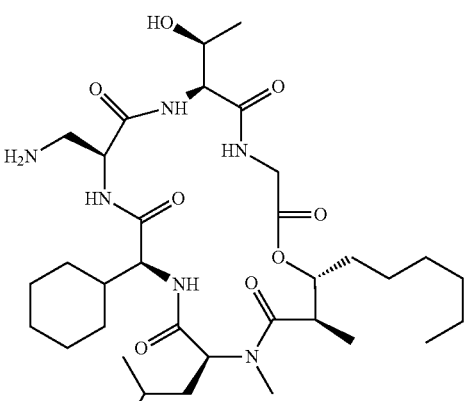 | (6S,9S,12S,15S,18R,19R)-12-cyclohexyl-19-hexyl-9-(hydroxymethyl)-15-isobutyl-16,18-dimethyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 119 | 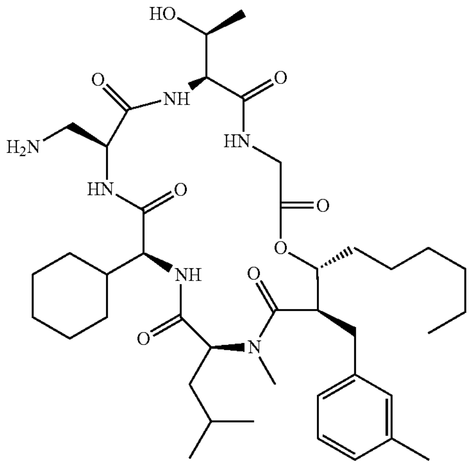 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1cccc(C)c1] | (6S,9S,12S,15S,18R,19R)-9-(aminomethyl)-12-cyclohexyl-19-hexyl-15-isobutyl-16-methyl-18-(m-tolylmethyl)-6-[(1S)-1-hydroxyethyl]-1-oxa-4,7,10,13,16-pentazacyclononadecane-2,5,8,11,14,17-hexone |
| 120 | 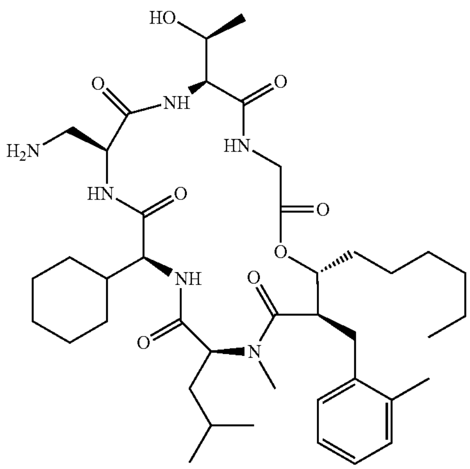 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1ccccc1C] | (6S,9S,12S,15S,18R,19R)-9-(aminomethyl)-12-cyclohexyl-19-hexyl-15-isobutyl-16-methyl-18-(o-tolylinethyl)-6-[(1S)-1-hydroxyethyl]-1-oxa-4,7,10,13,16-pentazacyclononadecane-2,5,8,11,14,17-hexone |
| 121 | 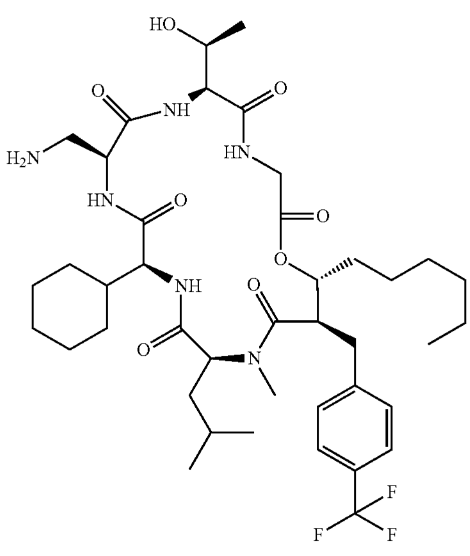 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1ccc(C(F)(F)F)cc1] | (6S,9S,12S,15S,18R,19R)-9-(aminomethyl)-12-cyclohexyl-19-hexyl-15-isobutyl-16-methyl-6-[(1S)-1-hydroxyethyl]-18-[[4-(trifluoromethyl)phenyl]methyl]-1-oxa-4,7,10,13,16-pentazacyclononadecane-2,5,8,11,14,17-hexone |

TABLE 1-continued

| Ex. | Structure | Name |
|---|---|---|
| 122 | 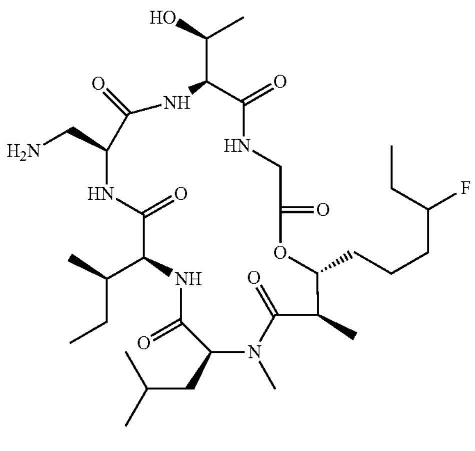 [SMILES: CCC(F)CCC[C@H]1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)[C@@H]1C] | (6S,9S,12S,15S,18R,19R)-9-(aminomethyl)-19-(4-fluorohexyl)-15-isobutyl-16,18-dimethyl-6-[(1S)-1-hydroxyethyl]-12-[(1R)-1-methylpropyl]-1-oxa-4,7,10,13,16-pentazacyclononadecane-2,5,8,11,14,17-hexone |
| 123 | 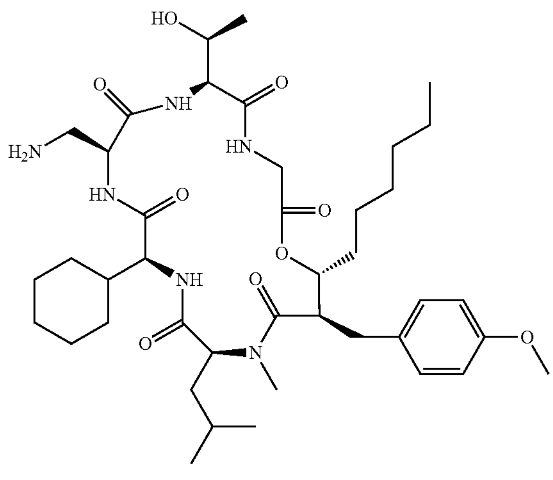 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1Cc1ccc(OC)cc1] | (6S,9S,12S,15S,18R,19R)-9-(aminomethyl)-12-cyclohexyl-19-hexyl-6-[(1S)-1-hydroxyethyl]-15-isobutyl-18-[(4-methoxyphenyl)methyl]-16-methyl-1-oxa-4,7,10,13,16-pentazacyclononadecane-2,5,8,11,14,17-hexone |
| 124 | 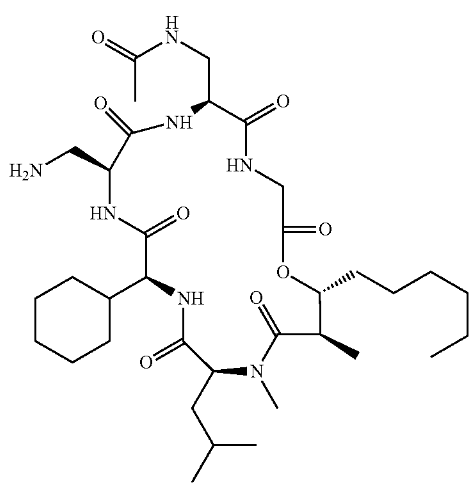 [SMILES: CCCCCC[C@H]1OC(=O)CNC(=O)[C@H](CNC(C)=O)NC(=O)[C@H](CN)NC(=O)[C@H](C2CCCCC2)NC(=O)[C@H](CC(C)C)N(C)C(=O)[C@@H]1C] | N-[[(6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]acetamide |

TABLE 1-continued

| Ex. | Structure | Name |
|---|---|---|
| 125 | 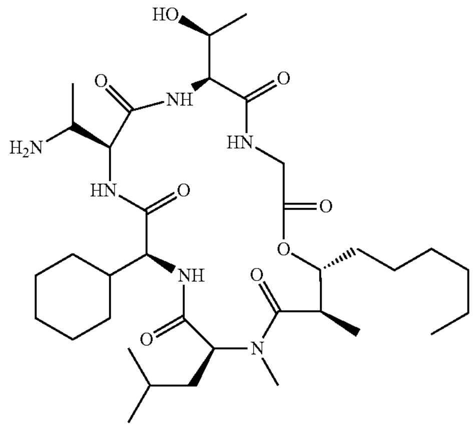 [SMILES: CCCCCC[C@H]1OC(=O)CNC(=O)[C@H]([C@H](C)O)NC(=O)[C@H](C(C)N)NC(=O)[C@H](C2CCCCC2)NC(=O)[C@H](CC(C)C)N(C)C(=O)[C@@H]1C] | (6S,9S,12S,15S,18R,19R)-12-cyclohexyl-19-hexyl-15-isobutyl-16,18-dimethyl-9-[(1S)-1-aminoethyl]-6-[(1S)-1-hydroxyetltyl]-1-oxa-4,7,10,13,16-pentazacyclononadecane-2,5,8,11,14,17-hexone |
| 126 | 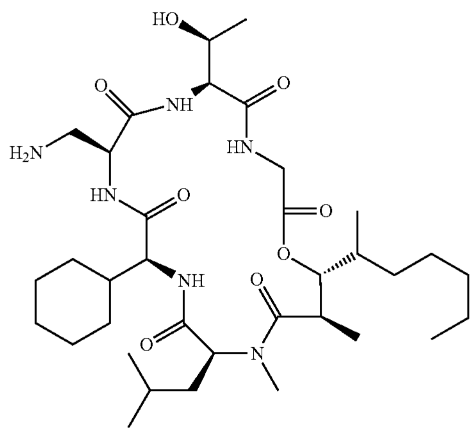 [SMILES: CCCCCC(C)[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(aminomethyl)-12-cyclohexyl-15-isobutyl-16,18-dimethyl-19-(1-methylhexyl)-6-[(1S)-1-hydroxyethyl]-1-oxa-4,7,10,13,16-pentazacyclononadecane-2,5,8,11,14,17-hexone |
| 127 | 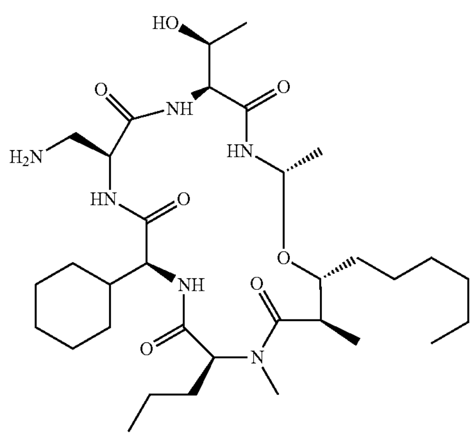 [SMILES: CCCCCC[C@H]1OC[C@@H](C)NC(=O)[C@H]([C@H](C)O)NC(=O)[C@H](CN)NC(=O)[C@H](C2CCCCC2)NC(=O)[C@H](CCC)N(C)C(=O)[C@@H]1C] | (3R,6S,9S,12S,15S,18R,19R)-9-(aminomethyl)-12-cyclohexyl-19-hexyl-3,16,18-trimethyl-15-propyl-6-[(1S)-1-hydroxyethyl]-1-oxa-4,7,10,13,16-pentazacyclononadecane-5,8,11,14,17-pentone |

TABLE 1-continued

| Ex. | Structure | Name |
|---|---|---|
| 128 | 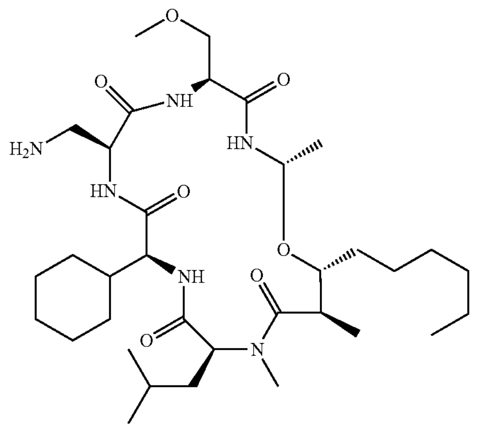 [SMILES: CCCCCC[C@H]1OC[C@@H](C)NC(=O)[C@H](COC)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-6-(methoxymethyl)-3,16,18-trimethyl-1-oxa-4,7,10,13,16-pentazacyclononadecane-5,8,11,14,17-pentone |
| 129 | 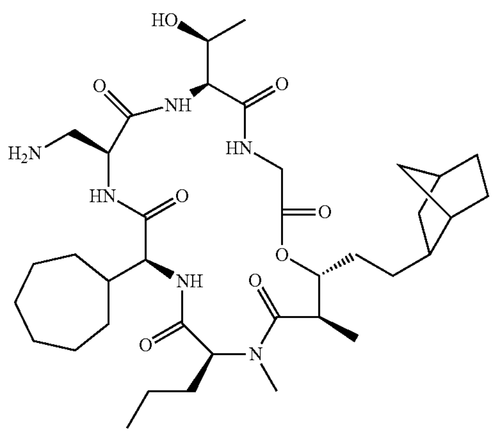 [SMILES: CCC[C@H]1C(=O)N[C@@H](C2CCCCCC2)C(=O)N[C@@H](CN)C(=O)N[C@@H]([C@H](C)O)C(=O)NCC(=O)O[C@H](CCC2CC3CCC2C3)[C@@H](C)C(=O)N1C] | (6S,9S,12S,15S,18R,19R)-9-(aminomethyl)-12-cycloheptyl-16,18-dimethyl-19-(2-norbornan-2-ylethyl)-15-propyl-6-[(1S)-1-hydroxyethyl]-1-oxa-4,7,10,13,16-pentazacyclononadecane-2,5,8,11,14,17-hexone |
| 130 | 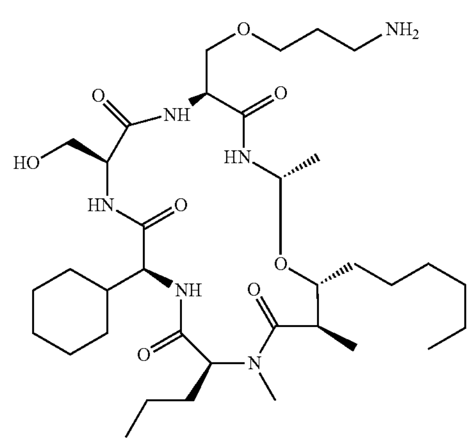 [SMILES: CCCCCC[C@H]1OC[C@@H](C)NC(=O)[C@H](COCCCN)NC(=O)[C@H](CO)NC(=O)[C@H](C2CCCCC2)NC(=O)[C@H](CCC)N(C)C(=O)[C@@H]1C] | (3R,6S,9S,12S,15S,18R,19R)-6-(3-aminopropoxymethyl)-12-cyclohexyl-19-hexyl-9-(hydroxymethyl)-3,16,18-trimethyl-15-propyl-1-oxa-4,7,10,13,16-pentazacyclononadecane-5,8,11,14,17-pentone |

TABLE 1-continued

| Ex. | Structure | Name |
|---|---|---|
| 131 | 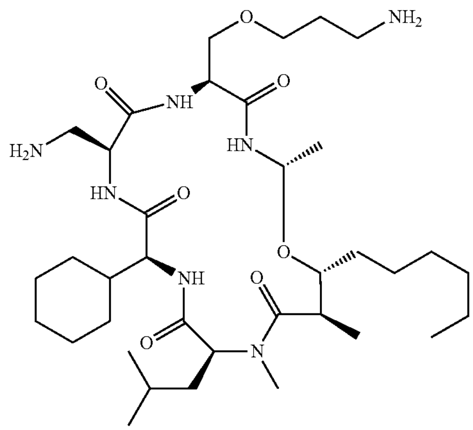 [SMILES: CCCCCC[C@H]1OC[C@@H](C)NC(=O)[C@H](COCCCN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-6-(3-aminopropoxymethyl)-12-cyclohexyl-19-hexyl-15-isobutyl-3,16,18-trimethyl-1-oxa-4,7,10,13,16-pentazacyclononadecane-5,8,11,14,17-pentone |
| 132 | 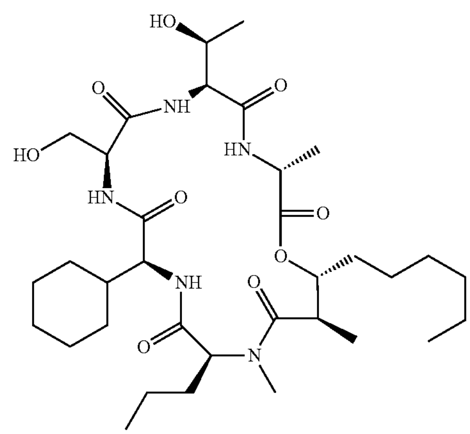 [SMILES: CCCCCC[C@H]1OC(=O)[C@@H](C)NC(=O)[C@H]([C@H](C)O)NC(=O)[C@H](CO)NC(=O)[C@H](C2CCCCC2)NC(=O)[C@H](CCC)N(C)C(=O)[C@@H]1C] | (6S,9S,12S,15S,18R,19R)-12-cyclohexyl-19-hexyl-9-(hydroxymethyl)-16,18-dimethyl-15-propyl-6-[(1S)-1-hydroxyethyl]-1-oxa-4,7,10,13,16-pentazacyclononadecane-2,5,8,11,14,17-hexone |
| 133 | 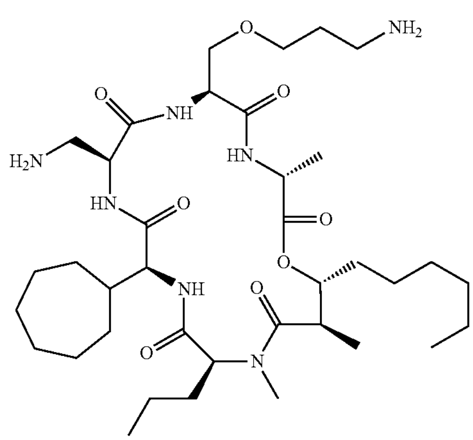 [SMILES: CCCCCC[C@H]1OC(=O)[C@@H](C)NC(=O)[C@H](COCCCN)NC(=O)[C@H](CN)NC(=O)[C@H](C2CCCCCC2)NC(=O)[C@H](CCC)N(C)C(=O)[C@@H]1C] | (6S,9S,12S,15S,18R,19R)-9-(aminomethyl)-6-(3-aminopropoxymethyl)-12-cycloheptyl-19-hexyl-16,18-dimethyl-15-propyl-1-oxa-4,7,10,13,16-pentazacyclononadecane-2,5,8,11,14,17-hexone |

TABLE 1-continued

| Ex. | Structure | Name |
|---|---|---|
| 134 | 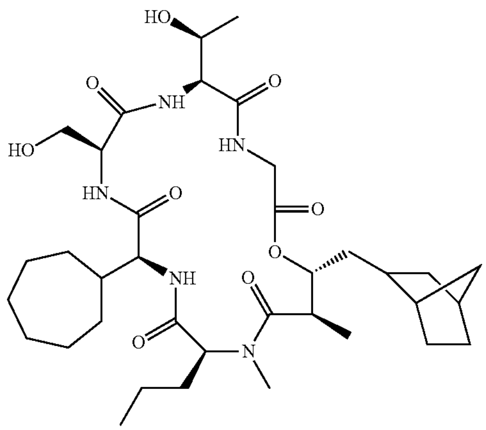 [SMILES: CCC[C@H]1C(=O)N[C@@H](C2CCCCCC2)C(=O)N[C@@H](CO)C(=O)N[C@@H]([C@H](C)O)C(=O)NCC(=O)O[C@H](CC2CC3CCC2C3)[C@@H](C)C(=O)N1C] | (6S,9S,12S,15S,18R,19R)-9-(aminomethyl)-12-cycloheptyl-16,18-dimethyl-19-(norbornan-2-ylmethyl)-15-propyl-6-[(1S)-1-hydroxyethyl]-1-oxa-4,7,10,13,16-pentazacyclononadecane-2,5,8,11,14,17-hexone |
| 135 | 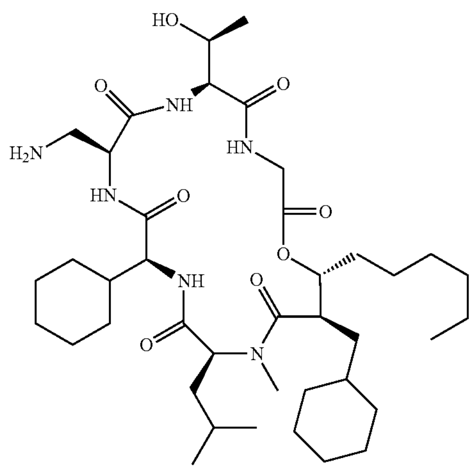 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1CC1CCCCC1] | (6S,9S,12S,15S,18R,19R)-9-(aminomethyl)-12-cyclohexyl-18-(cyclohexylmethyl)-19-hexyl-15-isobutyl-16-methyl-6-[(1S)-1-hydroxyethyl]-1-oxa-4,7,10,13,16-pentazacyclononadecane-2,5,8,11,14,17-hexone |
| 136 | 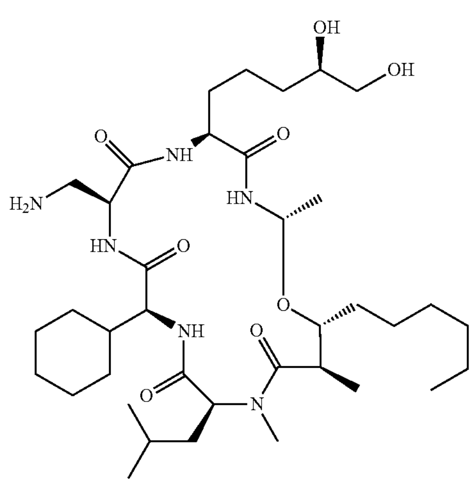 [SMILES: CCCCCC[C@H]1OC[C@@H](C)NC(=O)[C@H](CCC[C@@H](O)CO)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-19-hexyl-15-isobutyl-3,16,18-trimethyl-6-[[(2R)-2,3-dihydroxypropoxy]methyl]-1-oxa-4,7,10,13,16-pentazacyclononadecane-5,8,11,14,17-pentone |

TABLE 1-continued

| Ex. | Structure | Name |
|---|---|---|
| 137 | 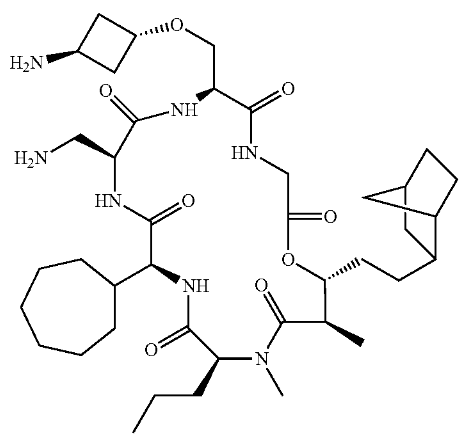 [SMILES: CCC[C@H]1C(=O)N[C@@H](C2CCCCCC2)C(=O)N[C@@H](CN)C(=O)N[C@@H](CO[C@H]2C[C@H](N)C2)C(=O)NCC(=O)O[C@H](CCC2CC3CCC2C3)[C@@H](C)C(=O)N1C] | (6S,9S,12S,15S,18R,19R)-6-[(3-aminocyclobutoxy)methyl]-9-(aminomethyl)-12-cycloheptyl-16,18-dimethyl-19-(2-norbornan-2-ylethyl)-15-propyl-1-oxa-4,7,10,13,16-pentazacyclononadecane-2,5,8,11,14,17-hexone |
| 138 | 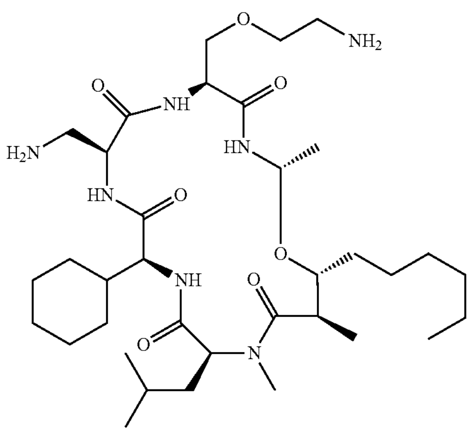 [SMILES: CCCCCC[C@H]1OC[C@@H](C)NC(=O)[C@H](COCCN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-(2-aminoethoxymethyl)-9-(aminomethyl)-12-cyclohexyl-19-hexyl-15-isobutx1-3,16,18-trimethyl-1-oxa-4,7,10,13,16-pentazacyclononadecane-5,8,11,14,17-pentone |
| 139 | 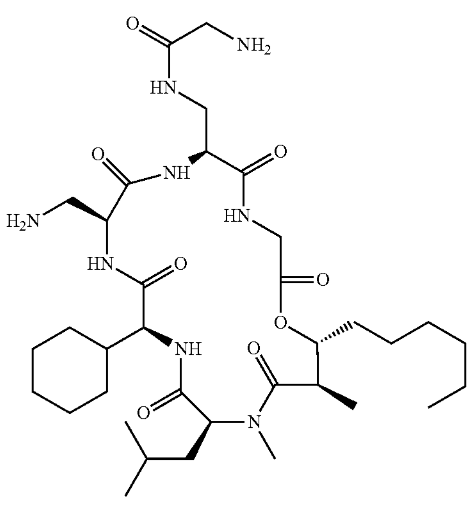 [SMILES: CCCCCC[C@H]1OC(=O)CNC(=O)[C@H](CNC(=O)CN)NC(=O)[C@H](CN)NC(=O)[C@H](C2CCCCC2)NC(=O)[C@H](CC(C)C)N(C)C(=O)[C@@H]1C] | 2-amino-N-[[(6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]acetamide |

TABLE 1-continued

| Ex. | Structure | Name |
|---|---|---|
| 140 | 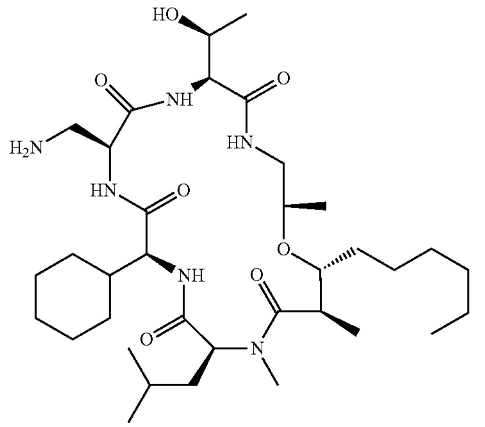 [SMILES: CCCCCC[C@H]1O[C@@H](C)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (2R,6S,9S,12S,15S,18R,19R)-9-(aminomethyl)-12-cyclohexyl-19-hexyl-15-isobutyl-2,16,18-trimethyl-6-[(1S)-1-hydroxyethyl]-1-oxa-4,7,10,13,16-pentazacyclononadecane-5,8,11,14,17-pentone |
| 141 | 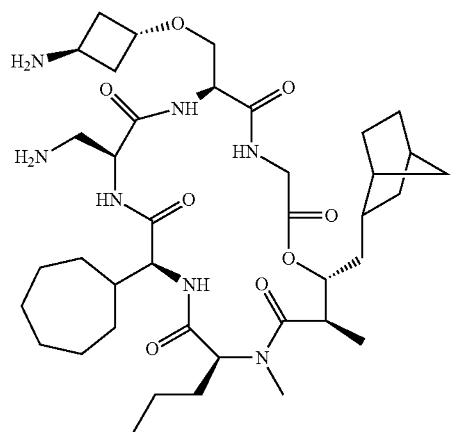 [SMILES: CCC[C@H]1C(=O)N[C@@H](C2CCCCCC2)C(=O)N[C@@H](CN)C(=O)N[C@@H](CO[C@H]2C[C@H](N)C2)C(=O)NCC(=O)O[C@H](CC2CC3CCC2C3)[C@@H](C)C(=O)N1C] | (6S,9S,12S,15S,18R,19R)-6-[(3-aminocyclobutoxy)methyl]-9-(aminomethyl)-12-cycloheptyl-16,18-dimethyl-19-(norbornan-2-ylmethyl)-15-propyl-1-oxa-4,7,10,13,16-pentazacyclononadecane-2,5,8,11,14,17-hexone |
| 142 | 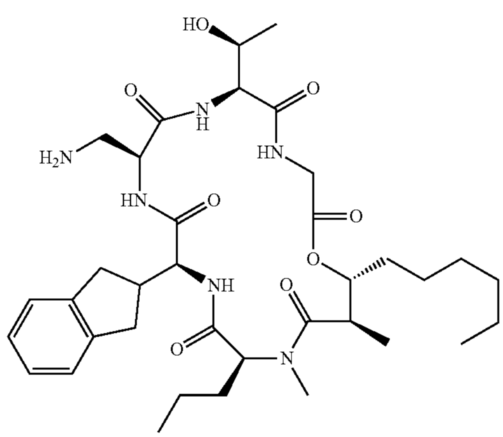 [SMILES: CCCCCC[C@H]1OC(=O)CNC(=O)[C@H]([C@H](C)O)NC(=O)[C@H](CN)NC(=O)[C@H](C2Cc3ccccc3C2)NC(=O)[C@H](CCC)N(C)C(=O)[C@@H]1C] | (6S,9S,12S,15S,18R,19R)-9-(aminomethyl)-19-hexyl-12-indan-2-yl-16,18-dimethyl-15-propyl-6-[(1S)-1-hydroxyethyl]-1-oxa-4,7,10,13,16-pentazacyclononadecane-2,5,8,11,14,17-hexone |

TABLE 1-continued

| Ex. | Structure | Name |
|---|---|---|
| 143 | 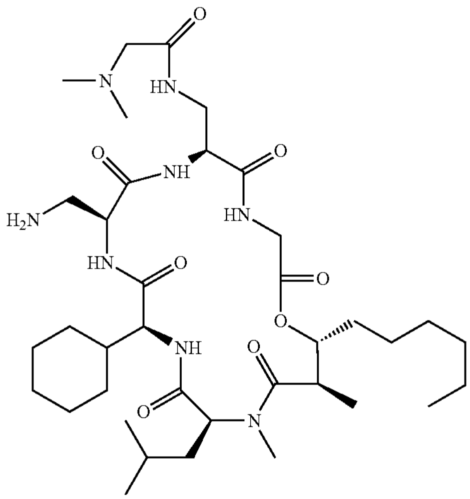 [SMILES: CCCCCC[C@H]1OC(=O)CNC(=O)[C@H](CNC(=O)CN(C)C)NC(=O)[C@H](CN)NC(=O)[C@H](C2CCCCC2)NC(=O)[C@H](CC(C)C)N(C)C(=O)[C@@H]1C] | 2-(dimethylamino)-N-[[(6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]acetamide |
| 144 | 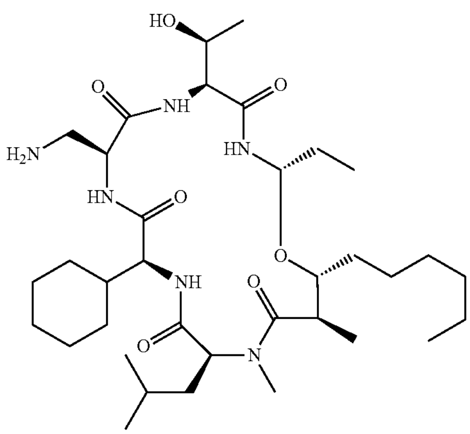 [SMILES: CCCCCC[C@H]1OC[C@@H](CC)NC(=O)[C@H]([C@H](C)O)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(aminomethyl)-12-cyclohexyl-3-ethyl-19-hexyl-15-isobutyl-16,18-dimethyl-6-[(1S)-1-hydroxyethyl]-1-oxa-4,7,10,13,16-pentazacyclononadecane-5,8,11,14,17-pentone |
| 145 | 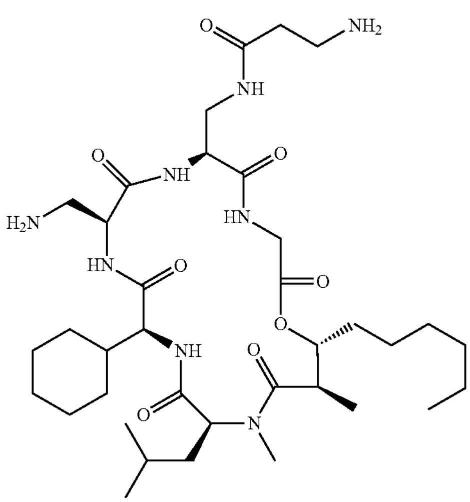 [SMILES: CCCCCC[C@H]1OC(=O)CNC(=O)[C@H](CNC(=O)CCN)NC(=O)[C@H](CN)NC(=O)[C@H](C2CCCCC2)NC(=O)[C@H](CC(C)C)N(C)C(=O)[C@@H]1C] | 3-amino-N-[[(6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]propanamide |

TABLE 1-continued

| Ex. | Structure | Name |
| --- | --- | --- |
| 146 | 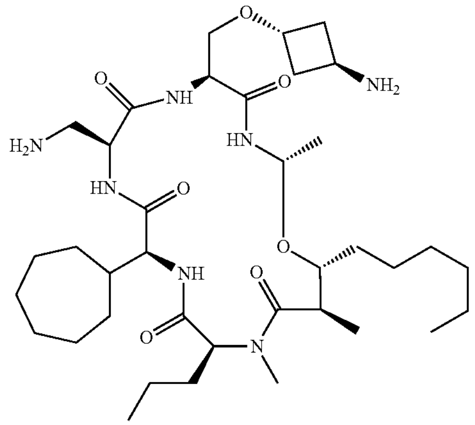 [SMILES: CCCCCC[C@H]1OC[C@@H](C)NC(=O)[C@H](CO[C@H]2C[C@H](N)C2)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-6-[(3-aminocyclobutoxy)methyl]-9-(aminomethyl)-12-cycloheptyl-19-hexyl-3,16,18-trimethyl-15-propyl-1-oxa-4,7,10,13,16-pentazacyclononadecane-5,8,11,14,17-pentone |
| 147 | 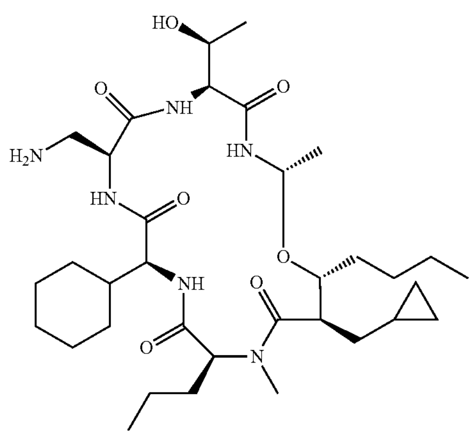 [SMILES: CCCC[C@H]1OC[C@@H](C)NC(=O)[C@H]([C@H](C)O)NC(=O)[C@H](CN)NC(=O)[C@H](C2CCCCC2)NC(=O)[C@H](CCC)N(C)C(=O)[C@@H]1CC1CC1] | (3R,6S,9S,12S,15S,18R,19R)-9-(Aminomethyl)-19-butyl-12-cyclohexyl-18-(cyclopropylmethyl)-6-((S)-1-hydroxyethyl)-3,16-dimethyl-15-propyl-1-oxa-4,7,10,13,16-pentaazacyclononadecane-5,8,11,14,17-pentaone |
| 148 | 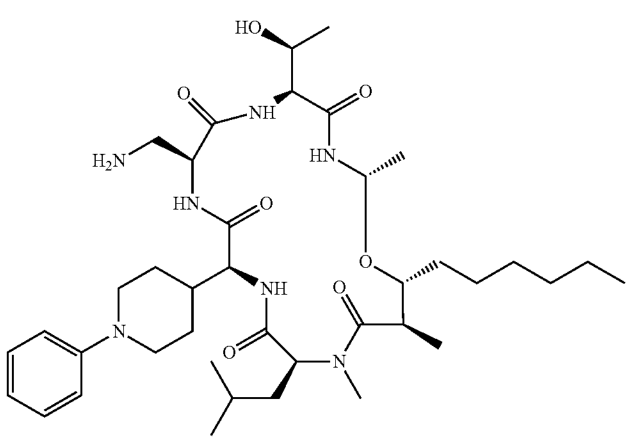 [SMILES: CCCCCC[C@H]1OC[C@@H](C)NC(=O)[C@H]([C@H](C)O)NC(=O)[C@H](CN)NC(=O)[C@H](C2CCN(c3ccccc3)CC2)NC(=O)[C@H](CC(C)C)N(C)C(=O)[C@@H]1C] | (3R,6S,9S,12S,15S,18R,19R)-9-(Aminomethyl)-19-hexyl-6-((S)-1-hydroxyethyl)-15-isobutyl-3,16,18-trimethyl-12-(1-phenylpiperidin-4-yl)-1-oxa-4,7,10,13,16-pentaazacyclononadecane-5,8,11,14,17-pentaone |

TABLE 1-continued

| Ex. | Structure | Name |
|---|---|---|
| 149 | 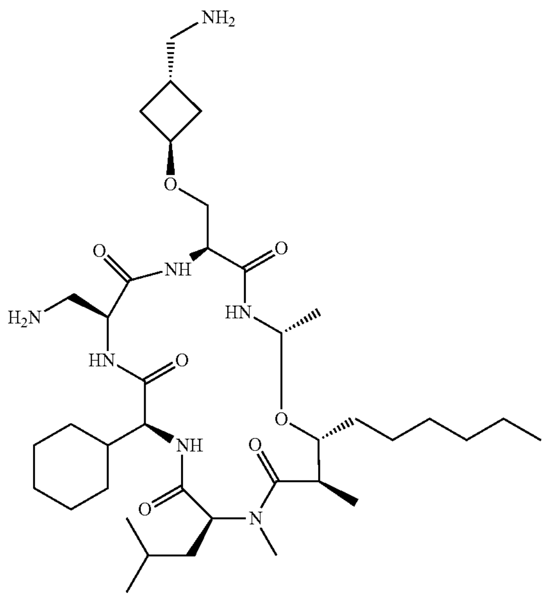 [SMILES: CCCCCC[C@H]1OC[C@@H](C)NC(=O)[C@H](CO[C@H]2C[C@H](CN)C2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(Aminomethyl)-6-(((1r,3,S)-3-(aminomethyl)cyclobutoxy)methyl)-12-cyclohexyl-19-hexyl-15-isobutyl-3,16,18-trimethyl-1-oxa-4,7,10,13,16-pentaazacyclononadecane-5,8,11,14,17-pentaone |
| 150 | 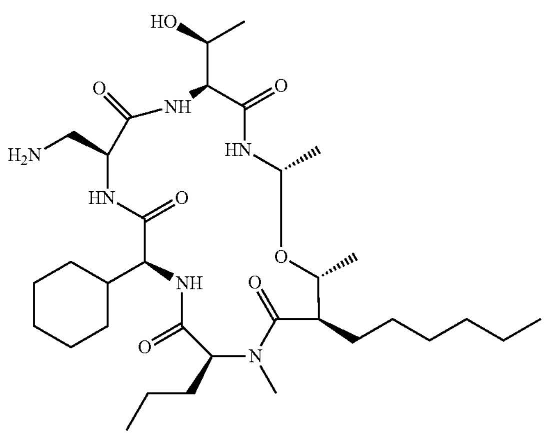 [SMILES: CCCCCC[C@H]1C(=O)N(C)[C@@H](CCC)C(=O)N[C@@H](C2CCCCC2)C(=O)N[C@@H](CN)C(=O)N[C@@H]([C@H](C)O)C(=O)N[C@H](C)CO[C@@H]1C] | (3R,6S,9S,12S,15S,18R,19R)-9-(Aminomethyl)-12-cyclohexyl-18-hexyl-6-((S)-1-hydroxyethyl)-3,16,19-trimethyl-15-propyl-1-oxa-4,7,10,13,16-pentaazacyclononadecane-5,8,11,14,17-pentaone |
| 151 | 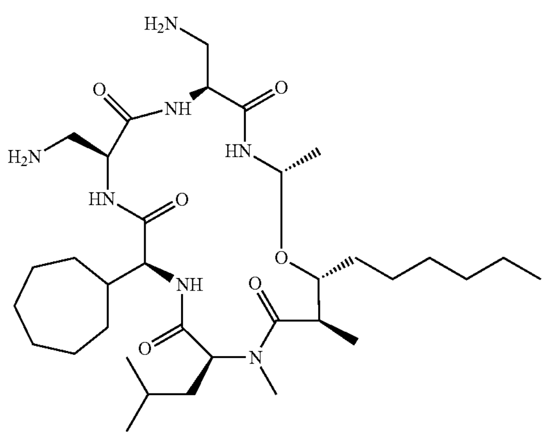 [SMILES: CCCCCC[C@H]1OC[C@@H](C)NC(=O)[C@H](CN)NC(=O)[C@H](CN)NC(=O)[C@H](C2CCCCCC2)NC(=O)[C@H](CC(C)C)N(C)C(=O)[C@@H]1C] | (3R,6S,9S,12S,15S,18R,19R)-6,9-Bis(aminomethyl)-12-cycloheptyl-19-hexyl-15-isobutyl-3,16,18-trimethyl-1-oxa-4,7,10,13,16-pentazacyclononadecane-5,8,11,14,17-pentone |

TABLE 1-continued

| Ex. | Structure | Name |
|---|---|---|
| 152 | 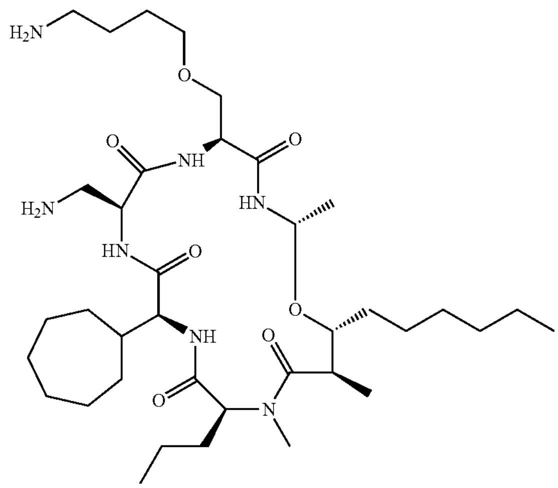 [SMILES: CCCCCC[C@H]1OC[C@@H](C)NC(=O)[C@H](COCCCCN)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-6-((4-Aminobutoxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone |
| 153 | 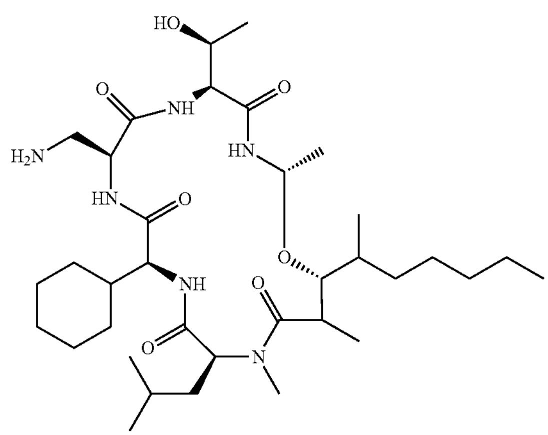 [SMILES: CCCCCC(C)[C@H]1OC[C@@H](C)NC(=O)[C@H]([C@H](C)O)NC(=O)[C@H](CN)NC(=O)[C@H](C2CCCCC2)NC(=O)[C@H](CC(C)C)N(C)C(=O)C1C] | (3R,6S,9S,12S,15S,18R,19R)-9-(Aminomethyl)-12-cyclohexyl-19-(heptan-2-yl)-6-((S)-1-hydroxyethyl)-15-isobutyl-3,16,18-trimethyl-1-oxa-4,7,10,13,16-pentaazacyclononadecane-5,8,11,14,17-pentaone |
| 154 | 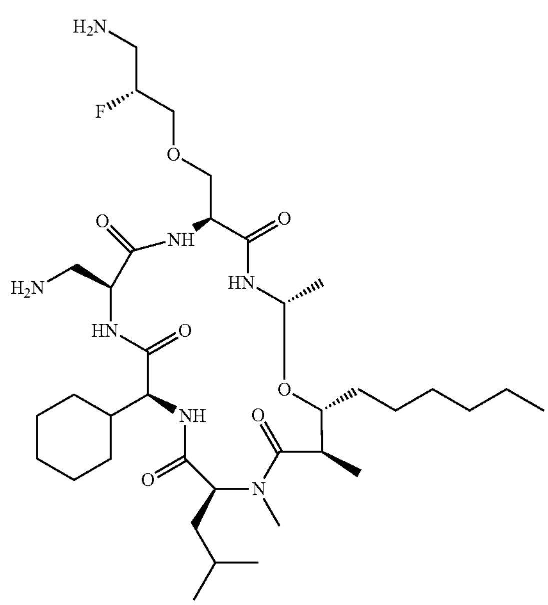 [SMILES: CCCCCC[C@H]1OC[C@@H](C)NC(=O)[C@H](COC[C@H](F)CN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-(((R)-3-Amino-2-fluoropropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone |

TABLE 1-continued

| Ex. | Structure | Name |
|---|---|---|
| 155 | 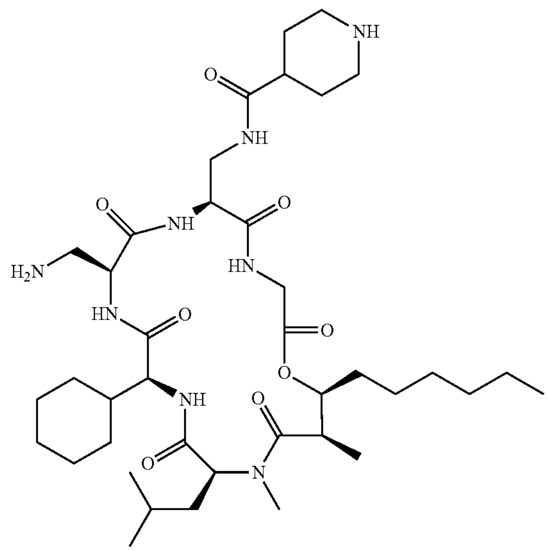 [SMILES: CCCCCC[C@@H]1OC(=O)CNC(=O)[C@H](CNC(=O)C2CCNCC2)NC(=O)[C@H](CN)NC(=O)[C@H](C2CCCCC2)NC(=O)[C@H](CC(C)C)N(C)C(=O)[C@@H]1C] | 5-[[(3R,6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]piperidine-4-carboxamide |
| 156 | 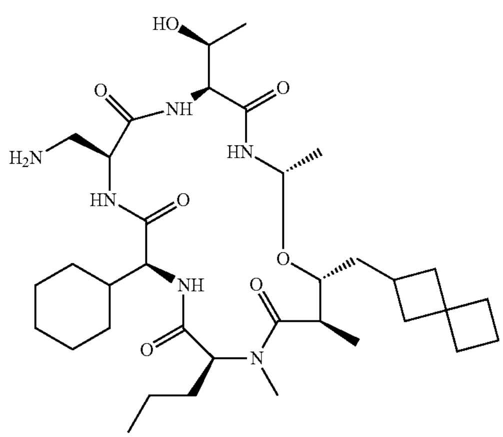 [SMILES: CCC[C@H]1C(=O)N[C@@H](C2CCCCC2)C(=O)N[C@@H](CN)C(=O)N[C@@H]([C@H](C)O)C(=O)N[C@H](C)CO[C@H](CC2CC3(CCC3)C2)[C@@H](C)C(=O)N1C] | (3R,6S,9S,12S,15S,18R,19R)-9-(Aminomethyl)-12-cyclohexyl-6-((S)-1-hydroxyethyl)-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 157 | 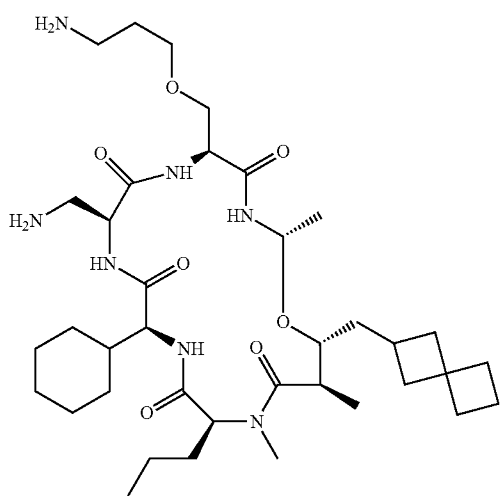 [SMILES: CCC[C@H]1C(=O)N[C@@H](C2CCCCC2)C(=O)N[C@@H](CN)C(=O)N[C@@H](COCCCN)C(=O)N[C@H](C)CO[C@H](CC2CC3(CCC3)C2)[C@@H](C)C(=O)N1C] | (3R,6S,9S,12S,15S,18R,19R)-9-(Aminomethyl)-6-((3-aminopropoxy)methyl)-12-cyclohexyl-3,16,18-trimethyl-15-propyl-19-(spiro[3.3]heptan-2-ylmethyl)-1-oxa-4,7,10,13,16-pentaazacyclononadecane-5,8,11,14,17-pentaone |

TABLE 1-continued

| Ex. | Structure | Name |
|---|---|---|
| 158 | 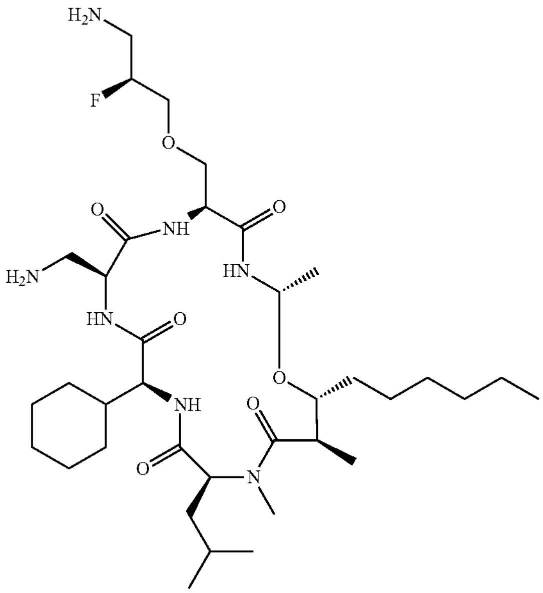 [SMILES: CCCCCC[C@H]1OC[C@@H](C)NC(=O)[C@H](COC[C@@H](F)CN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-(((S)-3-Amino-2-fluoropropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone |
| 159 | 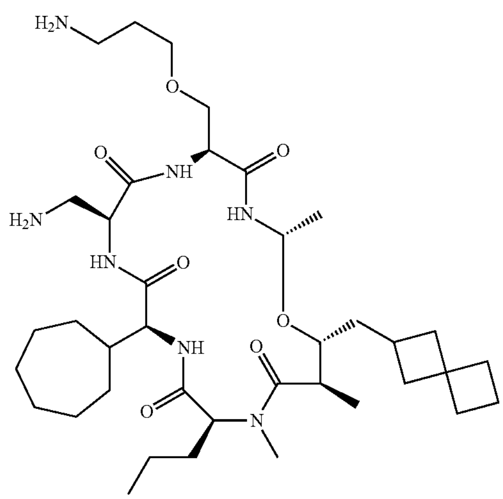 [SMILES: CCC[C@H]1C(=O)N[C@@H](C2CCCCCC2)C(=O)N[C@@H](CN)C(=O)N[C@@H](COCCCN)C(=O)N[C@H](C)CO[C@H](CC2CC3(CCC3)C2)[C@@H](C)C(=O)N1C] | (3R,6S,9S,12S,15S,18R,19R)-9-(Aminomethyl)-6-((3-aminopropoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 160 | 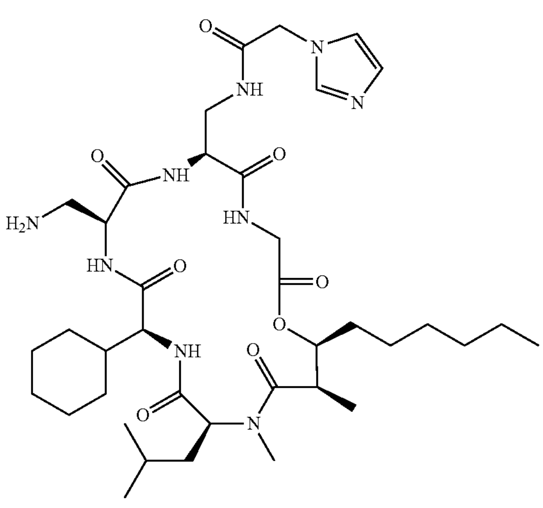 [SMILES: CCCCCC[C@@H]1OC(=O)CNC(=O)[C@H](CNC(=O)Cn2ccnc2)NC(=O)[C@H](CN)NC(=O)[C@H](C2CCCCC2)NC(=O)[C@H](CC(C)C)N(C)C(=O)[C@@H]1C] | N-[[(6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentaazacyclononadec-6-yl]methyl]-2-imidazol-1-yl-acetamide |

TABLE 1-continued

| Ex. | Structure | Name |
|---|---|---|
| 161 | 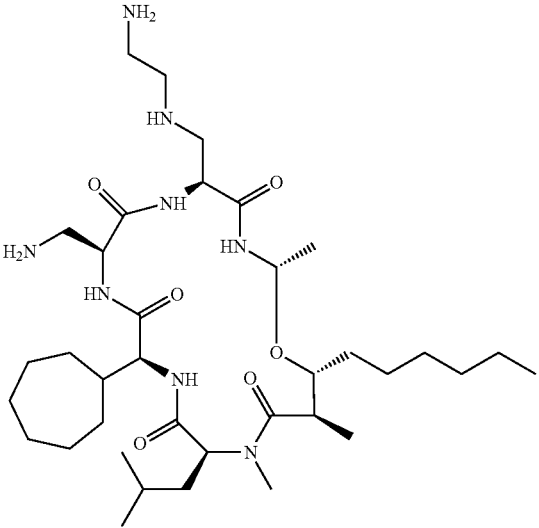 [SMILES: CCCCCC[C@H]1OC[C@@H](C)NC(=O)[C@H](CNCCN)NC(=O)[C@H](CN)NC(=O)[C@H](C2CCCCCC2)NC(=O)[C@H](CC(C)C)N(C)C(=O)[C@@H]1C] | (3R,6S,9S,12S,15S,18R,19R)-6-[(2-Aminoethylamino)methyl]-9-(aminomethyl)-12-cycloheptyl-19-hexyl-15-isobutyl-3,16,18-trimethyl-1-oxa-4,7,10,13,16-pentazacyclononadecane-5,8,11,14,17-pentone |
| 162 | 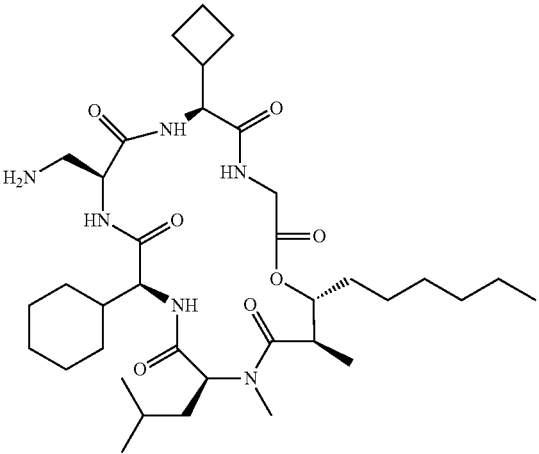 [SMILES: CCCCCC[C@H]1OC(=O)CNC(=O)[C@H](C2CCC2)NC(=O)[C@H](CN)NC(=O)[C@H](C2CCCCC2)NC(=O)[C@H](CC(C)C)N(C)C(=O)[C@@H]1C] | (6S,9S,12S,15S,18R,19R)-9-(Aminomethyl)-6-cyclobutyl-12-cyclohexyl-19-hexyl-15-isobutyl-16,18-dimethyl-1-oxa-4,7,10,13,16-pentaazacyclononadecane-2,5,8,11,14,17-hexaone |
| 163 | 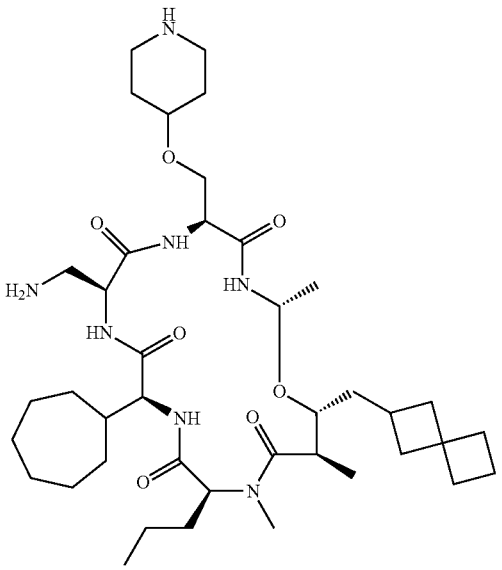 [SMILES: CCC[C@H]1C(=O)N[C@@H](C2CCCCCC2)C(=O)N[C@@H](CN)C(=O)N[C@@H](COC2CCNCC2)C(=O)N[C@H](C)CO[C@H](CC2CC3(CCC3)C2)[C@@H](C)C(=O)N1C] | (3R,6S,9S,12S,15S,18R,19R)-9-(Aminomethyl)-12-cycloheptyl-3,16,18-trimethyl-6-((piperidin-4-yloxy)methyl)-15-propyl-19-(spiro[3.3]heptan-2-ylmethyl)-1-oxa-4,7,10,13,16-pentaazacyclononadecane-5,8,11,14,17-pentaone |

TABLE 1-continued
| Ex. | Structure | Name |
|---|---|---|
| 164 | 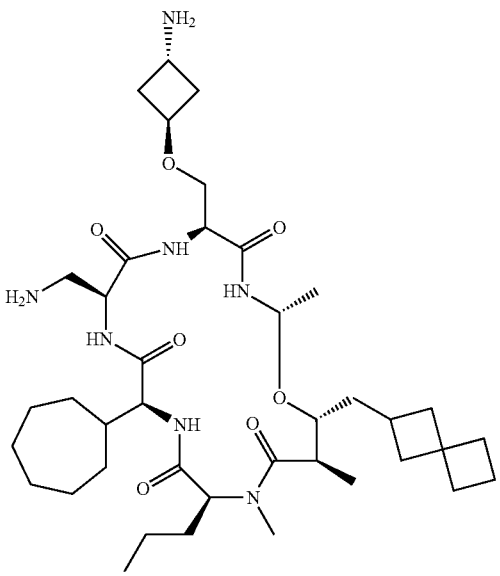 [SMILES: CCC[C@H]1C(=O)N[C@@H](C2CCCCCC2)C(=O)N[C@@H](CN)C(=O)N[C@@H](CO[C@H]2C[C@H](N)C2)C(=O)N[C@H](C)CO[C@H](CC2CC3(CCC3)C2)[C@@H](C)C(=O)N1C] | (3R,6S,9S,12S,15S,18R,19R)-6-(((1r,3S)-3-Aminocyclobutoxy)methyl)-9-(aminomethyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 165 | 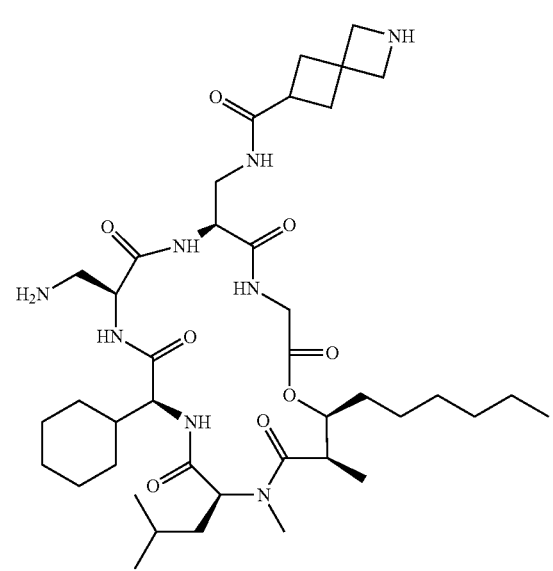 [SMILES: CCCCCC[C@@H]1OC(=O)CNC(=O)[C@H](CNC(=O)C2CC3(CNC3)C2)NC(=O)[C@H](CN)NC(=O)[C@H](C2CCCCC2)NC(=O)[C@H](CC(C)C)N(C)C(=O)[C@@H]1C] | N-[[(6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]-2-azaspiro[3.3]heptane-6-carboxamide |

TABLE 1-continued
| Ex. | Structure | Name |
|---|---|---|
| 166 | 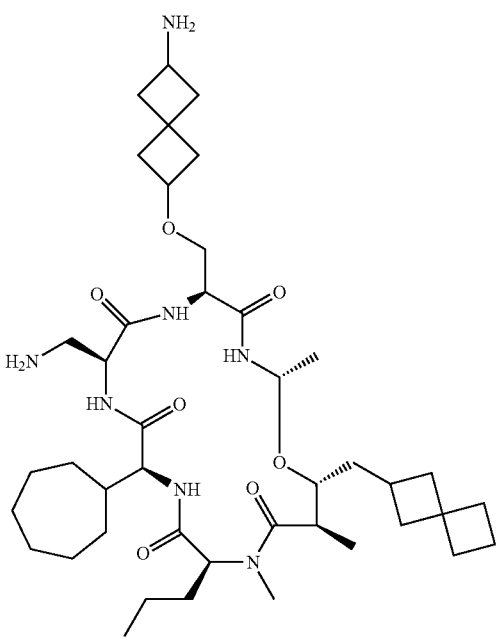 [SMILES: CCC[C@H]1C(=O)N[C@@H](C2CCCCCC2)C(=O)N[C@@H](CN)C(=O)N[C@@H](COC2CC3(CC(N)C3)C2)C(=O)N[C@H](C)CO[C@H](CC2CC3(CCC3)C2)[C@@H](C)C(=O)N1C] | (3R,6S,9S,12S,15S,18R,19R)-9-(Aminomethyl)-6-(((6-aminospiro[3.3]heptan-2-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 167 | 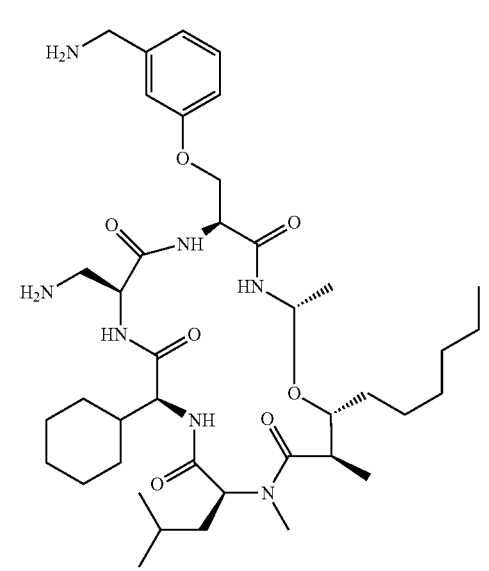 [SMILES: CCCCCC[C@H]1OC[C@@H](C)NC(=O)[C@H](COc2cccc(CN)c2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-9-(Aminomethyl)-6-((3-(aminomethyl)phenoxy)methyl)-12-cyclohexyl-19-hexyl-15-isobutyl-3,16,18-trimethyl-1-oxa-4,7,10,13,16-pentaazacyclononadecane-5,8,11,14,17-pentaone |

TABLE 1-continued

| Ex. | Structure | Name |
|---|---|---|
| 168 | 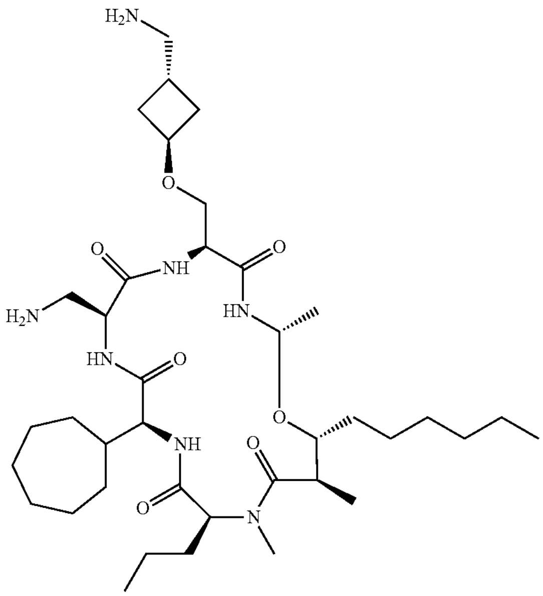 [SMILES: CCCCCC[C@H]1OC[C@@H](C)NC(=O)[C@H](CO[C@H]2C[C@H](CN)C2)NC(=O)[C@H](CN)NC(=O)[C@H](C2CCCCCC2)NC(=O)[C@H](CCC)N(C)C(=O)[C@@H]1C] | (3R,6S,9S,12S,15S,18R,19R)-9-(Aminomethyl)-6-(((1r,3S)-3-(aminomethyl)cyclobutoxy)methyl)-12-cycloheptyl-19-hexyl-3,16,18-trimethyl-15-propyl-1-oxa-4,7,10,13,16-pentaazacyclononadecane-5,8,11,14,17-pentaone |
| 169 | 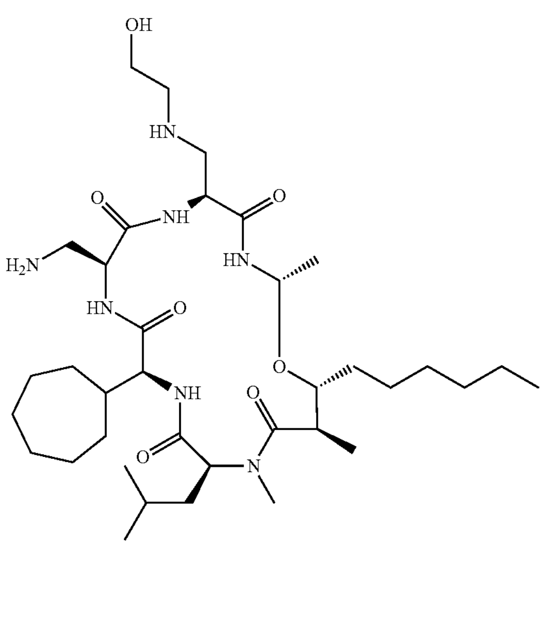 [SMILES: CCCCCC[C@H]1OC[C@@H](C)NC(=O)[C@H](CNCCO)NC(=O)[C@H](CN)NC(=O)[C@H](C2CCCCCC2)NC(=O)[C@H](CC(C)C)N(C)C(=O)[C@@H]1C] | (3R,6S,9S,12S,15S,18R,19R)-9-(Aminomethyl)-12-cycloheptyl-19-hexyl-6-(((2-hydroxyethyl)amino)methyl)-15-isobutyl-3,16,18-trimethyl-1-oxa-4,7,10,13,16-pentaazacyclononadecane-5,8,11,14,17-pentaone |

TABLE 1-continued
| Ex. | Structure | Name |
|---|---|---|
| 170 | 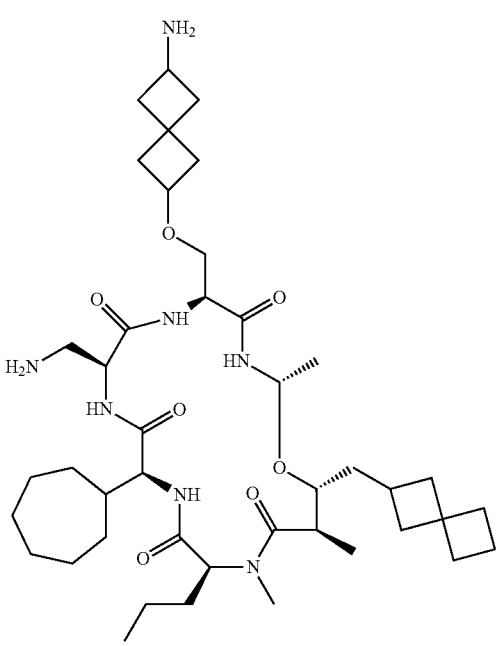 [SMILES: CCC[C@H]1C(=O)N[C@@H](C2CCCCCC2)C(=O)N[C@@H](CN)C(=O)N[C@@H](COC2CC3(CC(N)C3)C2)C(=O)N[C@H](C)CO[C@H](CC2CC3(CCC3)C2)[C@@H](C)C(=O)N1C] | (3R,6S,9S,12S,15S,18R,19R)-9-(Aminomethyl)-6-(((6-aminospiro[3.3]heptan-2-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 171 | 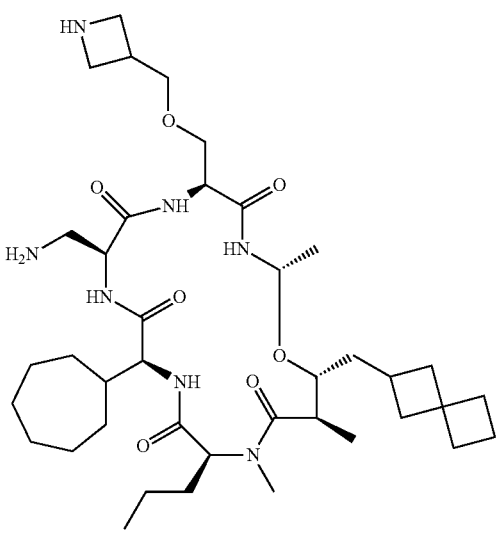 [SMILES: CCC[C@H]1C(=O)N[C@@H](C2CCCCCC2)C(=O)N[C@@H](CN)C(=O)N[C@@H](COCC2CNC2)C(=O)N[C@H](C)CO[C@H](CC2CC3(CCC3)C2)[C@@H](C)C(=O)N1C] | (3R,6S,9S,12S,15S,18R,19R)-9-(Aminomethyl)-6-((azetidin-3-ylmethoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone |

TABLE 1-continued
| Ex. | Structure | Name |
|---|---|---|
| 172 | 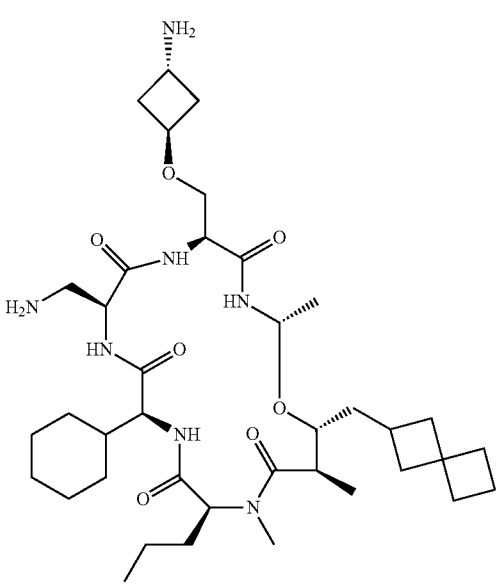 [SMILES: CCC[C@H]1C(=O)N[C@@H](C2CCCCC2)C(=O)N[C@@H](CN)C(=O)N[C@@H](CO[C@H]2C[C@H](N)C2)C(=O)N[C@H](C)CO[C@H](CC2CC3(CCC3)C2)[C@@H](C)C(=O)N1C] | (3R,6S,9S,12S,15S,18R,19R)-6-(((1r,3S)-3-Aminocyclobutoxy)methyl)-9-(aminomethyl)-12-cyclohexyl-3,16,18-trimethyl-15-propyl-19-(spiro[3.3]heptan-2-ylmethyl)-1-oxa-4,7,10,13,16-pentaazacyclononadecane-5,8,11,14,17-pentaone |
| 173 | 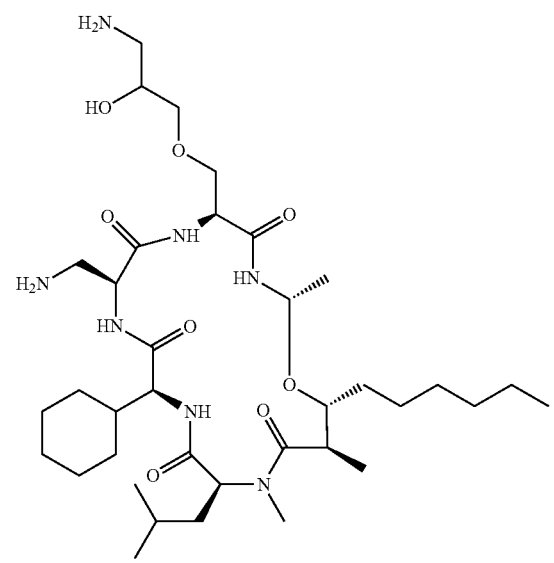 [SMILES: CCCCCC[C@H]1OC[C@@H](C)NC(=O)[C@H](COCC(O)CN)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-((3-Amino-2-hydroxypropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone |

TABLE 1-continued

| Ex. | Structure | Name |
|---|---|---|
| 174 | 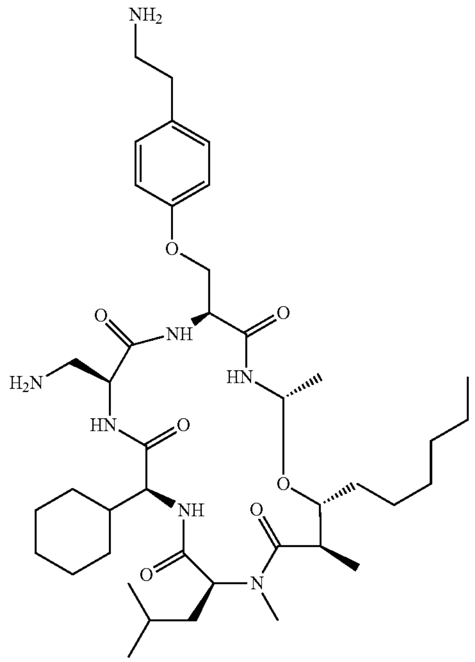 [SMILES: CCCCCC[C@H]1OC[C@@H](C)NC(=O)[C@H](COc2ccc(CCN)cc2)NC(=O)[C@H](CN)NC(=O)[C@H](C2CCCCC2)NC(=O)[C@H](CC(C)C)N(C)C(=O)[C@@H]1C] | (3R,6S,9S,12S,15S,18R,19R)-6-((4-(2-Aminoethyl)phenoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methane sulfonic acid, ethane sulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4} \text{ alkyl})_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions. Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Also disclosed herein are methods of treating a mammal in need of such treatment comprising administering to the mammal an antibacterial effective amount of any of the aforementioned compounds at a frequency and for a duration sufficient to provide a beneficial effect to the mammal. In one embodiment, the mammal has a bacteria-related infection that is resistant to treatment with one or more clinically used antibiotics. In a further embodiment, the causative bacterial species of the bacterial infection is an infection involving *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter* baumannii, *Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* or *Bacteroides splanchnicus*. In this embodiment the bacterial infection is an infection involving a Gram-negative bacteria.

In one embodiment, is a compound described herein which displays antibiotic activity useful in the treatment of bacterial infections, such as by way of example only, various strains of *E. coli, E. cloaceae, K. pneumoniae, A. baumannii* or *P. aeruginosa*.

Combination Therapy

Also disclosed herein are methods of treating a mammal in need of such treatment comprising administering to the mammal a second therapeutic agent to any of the aforementioned methods of treatment. In another embodiment, the second therapeutic agent is a not an LspA inhibitor. In another embodiment, the second therapeutic agent is an aminoglycoside antibiotic, fluoroquinolone antibiotic, (1-lactam antibiotic, macrolide antibiotic, glycopeptide antibiotic, rifampicin, chloramphenicol, fluoramphenicol, colistin, mupirocin, bacitracin, daptomycin, or linezolid.

In some embodiments is a method for treating a bacterial infection in a patient, preferably a human, where the treatment includes administering a therapeutically or pharmacologically effective amount of a combination of 1) a β-lactam antibiotic; and 2) a compound of Formula (I), (Ia)-(Ic), (II), (IIa)-(IIc), (III), (IIIa)-(IIIc), or (IV), (IVa)-(IVc), or a pharmaceutically acceptable salt, solvate, or stereoisomer thereof; and 3) a pharmaceutically acceptable carrier. In some embodiments, the β-lactam antibiotic is a carbapenem, cephalosporin, cephamycin, monobactam, or penicillin. Exemplary carbapenem antibiotics include, but are not limited to, ertapenem, imipenem, biapenem, and meropenem. Exemplary cephalosporin antibiotics include but are not limited to, ceftobiprole, ceftaroline, cefiprome, cefozopran, cefepime, cefotaxime, and ceftriaxone. Exemplary penicillin antibiotics include, but are not limited to, ampicillin, amoxacillin, piperacillin, oxacillin, cloxacillin, methicillin, and nafcillin. In some embodiments, the β-lactam is administered with a β-lactamase inhibitor. In some embodiments, the carbapenem is administered with a DHP inhibitor, e.g., cilastatin.

In some embodiments, the β-lactam antibiotic and compound of Formula (I), (Ia)-(Ic), (II), (IIa)-(IIc), (III), (IIIa)-(IIIc), (IV), (IVa)-(IVc), (V), or (Va)-(Vc) are administered sequentially or concurrently. In some embodiments, the β-lactam antibiotic and compound of Formula (I), (Ia)-(Ic), (II), (IIa)-(IIc), (III), (IIIa)-(IIIc), (IV), (IVa)-(IVc), (V), or (Va)-(Vc) are administered together. In some embodiments, the β-lactam antibiotic and compound of Formula (I), (Ia)-(Ic), (II), (IIa)-(IIc), (III), (IIIa)-(IIIc), (IV), (IVa)-(IVc), (V), or (Va)-(Vc) are administered in the same formulation or in separate formulations. In some embodiments, either the β-lactam or compound of Formula (I), (Ia)-(Ic), (II), (IIa)-(IIc), (III), (IIIa)-(IIIc), (IV), (IVa)-(IVc), (V), or (Va)-(Vc) is administered first. After administration of the first compound, the other compound is administered, for example, within from 1 to 60 minutes, e.g., within 1, 2, 3, 4, 5, 10, 15, 30, or 60 minutes. In one aspect, when a β-lactamase inhibitor is used, it is administered separately, or in a formulation with the compound of Formula (I), (Ia)-(Ic), (II), (IIa)-(IIc), (III), (IIIa)-(IIIc), (IV), (IVa)-(IVc), (V), or (Va)-(Vc) and/or β-lactam antibiotic. In one aspect, when a DHP inhibitor is used to improve the stability of a carbapenem, it is administered separately, or in a formulation with the compound of Formula (I), (Ia)-(Ic), (II), (IIa)-(IIc), (III), (IIIa)-(IIIc), (IV), (IVa)-(IVc), (V), or (Va)-(Vc) and/or carbapenem.

Further described herein are pharmaceutical compositions comprising a compound of Formula (I), (Ia)-(Ic), (II), (IIa)-(IIc), (III), (IIIa)-(IIIc), (IV), (IVa)-(IVc), (V), or (Va)-(Vc), a pharmaceutically acceptable carrier, and optionally a β-lactam antibiotic. In embodiments where a combination is used, the β-lactam antibiotic and the compound of Formula (I), (Ia)-(Ic), (II), (IIa)-(IIc), (III), (IIIa)-(IIIc), (IV), (IVa)-(IVc), (V), or (Va)-(Vc), are present in such amounts that their combination constitutes a therapeutically effective amount. Due to the potentiating effects of the compound of Formula (I), (Ia)-(Ic), (II), (IIa)-(IIc), (III), (IIIa)-(IIIc), (IV), (IVa)-(IVc), (V), or (Va)-(Vc), the amount of β-lactam antibiotic present in a combination may be less that of a β-lactam antibiotic used alone. In certain embodiments, the composition further comprises a β-lactamase antibiotic.

In further embodiments where the β-lactam antibiotic is a carbapenem, is provided a pharmaceutical composition comprising a carbapenem antibiotic, a DHP inhibitor, a compound of Formula (I), (Ia)-(Ic), (II), (IIa)-(IIc), (III), (IIIa)-(IIIc), (IV), (IVa)-(IVc), (V), or (Va)-(Vc), and a pharmaceutically acceptable carrier. In some embodiments where the β-lactam antibiotic is a carbepenem, the carbapenem antibiotic is preferably selected from the group consisting of ertapenem, imipenem, and meropenem.

In some embodiments is a compound of Formula (I), (Ia)-(Ic), (II), (IIa)-(IIc), (III), (IIIa)-(IIIc), (IV), (IVa)-(IVc), (V), or (Va)-(Vc) for use in treating a bacterial infection. In some embodiments is a compound of Formula (I), (Ia)-(Ic), (II), (IIa)-(IIc), (III), (IIIa)-(IIIc), (IV), (IVa)-(IVc), (V), or (Va)-(Vc), in combination with one or more additional therapeutic agents including a β-lactam antibiotic, for use in treating a bacterial infection. In some embodiments is a compound of Formula (I), (Ia)-(Ic), (II), (IIa)-(IIc), (III), (IIIa)-(IIIc), (IV), (IVa)-(IVc), (V), or (Va)-(Vc) for use as a medicament for treating a bacterial infection. In some embodiments is a compound of Formula (I), (Ia)-(Ic), (II), (IIa)-(IIc), (III), (IIIa)-(IIIc), (IV), (IVa)-(IVc), (V), or (Va)-(Vc), in combination with one or more additional therapeutic agents including a β-lactam antibiotic, for use as a medicament for treating a bacterial infection. In some embodiments is a compound of Formula (I), (Ia)-(Ic), (II), (IIa)-(IIc), (III), (IIIa)-(IIIc), (IV), (IVa)-(IVc), (V), or (Va)-(Vc) for use in the preparation of a medicament for treating a bacterial infection. In some embodiments is a compound of Formula (I), (Ia)-(Ic), (II), (IIa)-(IIc), (III), (IIIa)-(IIIc), (IV), (IVa)-(IVc), (V), or (Va)-(Vc), in combination with one or more additional therapeutic agents including a β-lactam antibiotic, for use in the preparation of a medicament for treating a bacterial infection.

In some embodiments described herein, a compound of Formula (I), (Ia)-(Ic), (II), (IIa)-(IIc), (III), (IIIa)-(IIIc), (IV), (IVa)-(IVc), (V), or (Va)-(Vc) can enhance the activity of a β-lactam antibacterial agent by inducing susceptibility to the antibacterial agent in a drug-resistant strain such as MRSA. In some embodiments, a compound of Formula (I), (Ia)-(Ic), (II), (IIa)-(IIc), (III), (IIIa)-(IIIc), (IV), (IVa)-(IVc), (V), or (Va)-(Vc) can enhance the activity of a β-lactam antibacterial agent by reducing the dosage of the antibacterial agent need for a therapeutic effect in a drug-sensitive strain. For example, if a compound of Formula (I), (Ia)-(Ic), (II), (IIa)-(IIc), (III), (IIIa)-(IIIc), (IV), (IVa)-(IVc), (V), or (Va)-(Vc) reduces the Minimum Inhibitory Concentration (MIC) of an antibacterial agent (where the MIC is the minimum concentration of antibacterial agent which will completely inhibit growth) in a susceptible strain, then such treatment may be advantageous to enable a reduction in the amount of antibacterial agent administered (could reduce side effects of an antibiotic), or to decrease the frequency of administration. In some embodiments, compounds of Formula (I), (Ia)-(Ic), (II), (IIa)-(IIc), (III), (IIIa)-(IIIc), (IV), (IVa)-(IVc), (V), or (Va)-(Vc) can enhance the activity of an antibacterial agent such as a carbapenem to prevent the emergence of a resistant sub-population in a heterogeneous bacterial population with a resistant sub-population.

In some embodiments, potentiators are used to enhance the activity of antibacterial agents whose clinical efficacy has been limited by the increasing prevalence of resistant strains. In some embodiments described herein, a compound of Formula (I), (Ia)-(Ic), (II), (IIa)-(IIc), (III), (IIIa)-(IIIc), (IV), (IVa)-(IVc), (V), or (Va)-(Vc) is used as a potentiator wherein a compound of Formula (I), (Ia)-(Ic), (II), (IIa)-(IIc), (III), (IIIa)-(IIIc), (IV), (IVa)-(IVc), (V), or (Va)-(Vc) can be administered together with a β-lactam antibiotic (either concurrently or sequentially) to allow effective treatment of an infection involving a resistant bacterium, or to reduce the amount of antibacterial agent necessary to treat an infection.

Administration and Pharmaceutical Composition

Pharmaceutical compositions described herein comprise a therapeutically effective amount of a compound described herein (i.e., a compound of any of Formula (I), (Ia)-(Ic), (II), (IIa)-(IIc), (III), (IIIa)-(IIIc), (IV), (IVa)-(IVc), (V), or (Va)-(Vc)) formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions described herein can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are optionally formulated according to the known art using suitable dispersing or wetting agents and suspending agents. The sterile injectable preparation is optionally a sterile injectable solution, suspension or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This is optionally accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is optionally accomplished by dissolving or suspending the drug in an oil vehicle. Injectable depot forms are made by forming microencapsuled matrices of the drug in biodegradable polymers such as poly lactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are optionally prepared by entrapping the drug in liposomes or microemulsions which are compatible with body tissues.

Compositions for rectal or vaginal administration are preferably suppositories which can be prepared by mixing the compound described herein (i.e., a compound of any of Formula (I), (Ia)-(Ic), (II), (IIa)-(IIc), (III), (IIIa)-(IIIc), (IV), (IVa)-(IVc), (V), or (Va)-(Vc)) with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form optionally comprise buffering agents.

Solid compositions of a similar type are optionally employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type are optionally employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings known in the pharmaceutical formulating art. In such solid dosage forms the active compound is optionally admixed with at least one inert diluent such as sucrose, lactose or starch. Such dosage forms optionally comprise, as is normal practice, additional substances other than inert diluents, e.g., tableting lubricants and other tableting aids such a magnesium stearate and microcrystalline cellulose. In the case of capsules, tablets and pills, the dosage forms optionally comprise buffering agents. They optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as are optionally required. Ophthalmic formulations, ear drops, and the like are also contemplated.

The ointments, pastes, creams and gels may contain, in addition to an active compound described herein, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions described herein are optionally formulated for delivery as a liquid aerosol or inhalable dry powder. Liquid aerosol formulations are optionally nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of an aerosol particles having with a mass medium average diameter predominantly between 1 to 5 µm. Further, the formulation preferably has balanced osmolarity ionic strength and chloride concentration, and the smallest aerosolizable volume able to deliver effective dose of the compounds described herein compound described herein (i.e., a compound of any of Formula (I), (Ia)-(Ic), (II), (IIa)-(IIc), (III), (IIIa)-(IIIc), (IV), (IVa)-(IVc), (V), or (Va)-(Vc)) to the site of the infection. Additionally, the aerosolized formulation preferably does not impair negatively the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, compounds described herein compound described herein (i.e., a compound of any of Formula (I), (Ia)-(Ic), (II), (IIa)-(IIc), (III), (IIIa)-(IIIc), (IV), (IVa)-(IVc), (V), or (Va)-(Vc)) are formulated for use as topical powders and sprays that contain, in addition to the compounds described herein, excipients such as lactose, talc, silicic acid, aluminum hydroxide, calcium silicates and polyamide powder, or mixtures of these substances. Sprays optionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment described herein, bacterial infections are treated or prevented in a patient such as a human or lower mammal by administering to the patient a therapeutically effective amount of a compound described herein, in such amounts and for such time as is necessary to achieve the desired result. By a "therapeutically effective amount" of a compound described herein is meant a sufficient amount of the compound to treat bacterial infections, at a reasonable benefit/risk ratio applicable to any medical treatment. It will be understood, however, that the total daily usage of the compounds and compositions described herein will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors known in the medical arts.

The total daily dose of the compounds described herein compound described herein (i.e., a compound of any of Formula (I), (Ia)-(Ic), (II), (IIa)-(IIc), (III), (IIIa)-(IIIc), (IV), (IVa)-(IVc), (V), or (Va)-(Vc)) administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens described herein comprise administration to a patient in need of such treatment from about 10 mg to about 2000 mg of the compound(s) described herein per day in single or multiple doses.

EXAMPLES

Compounds disclosed herein are made by the methods depicted in the reaction schemes shown below. Procedures are provided herein that, in combination with the knowledge of the synthetic organic chemist of ordinary skill in the art, are in some embodiments used to prepare the full range of compounds as disclosed and claimed herein.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds disclosed herein are in some embodiments synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data. Compounds are typically isolated as trifluoroacetic acid salts by reverse phase HPLC using $CH_3CN/H_2O$ with trifluoroacetic acid as an additive. In some instances, purifications are conducted without trifluoroacetic acid, and the compounds are isolated as the free base.

Abbreviations

AcOH acetic acid

DCM dichloromethane

DIPEA N,N-diisopropylethylamine

DMA N,N-dimethylacetamide

DMAP 4-dimethylaminopyridine

DMF N,N-dimethylformamide

DMSO dimethyl sulfoxide

ESI electrospray ionization

EtOAc ethyl acetate h hour

HATU 1-[Bis(dimethylamino)methylene]-1H,2,3-triazolo[4,5-b]pyridinium 3-oxid hexafluorophosphate HOBt hydroxybenzotriazole HPLC high pressure liquid chromatography LCMS liquid chromatography mass spectrometry EDA lithium diisopropyl amide M molar min minute N normal NMR nuclear magnetic resonance $R_T$ retention time SEC super critical fluid chromatography THF tetrahydrofuran TEA trifluoroacetic acid TEE 2,2,2-trifluoroethanol TfOH trifluorome thane sulfonic acid Compounds disclosed herein were prepared as illustrated in general Schemes 1-2.

Scheme 1.

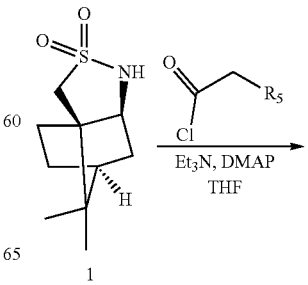

215

-continued

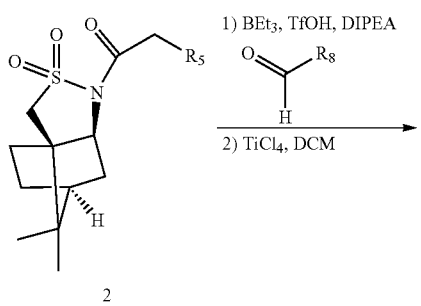

2

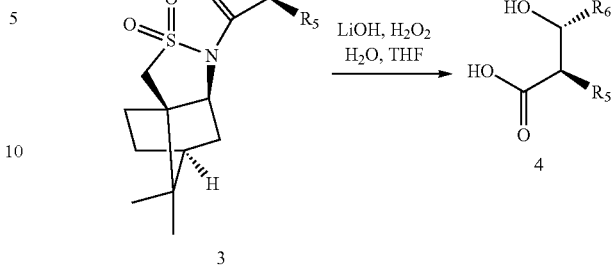

As described in Scheme 1, beta-hydroxy acids 4 may be prepared starting with Oppolzer's sultam 1, which may be acylated with acid chlorides to generate intermediate 2. Intermediate 2 may be subjected to Lewis-acid mediated aldol alkylation to generate the anti-aldol product 3. Compound 3 may be hydrolyzed with aqueous lithium hydroxide and hydrogen peroxide to yield the desired beta-hydroxy acid compounds 4.

Scheme 2.

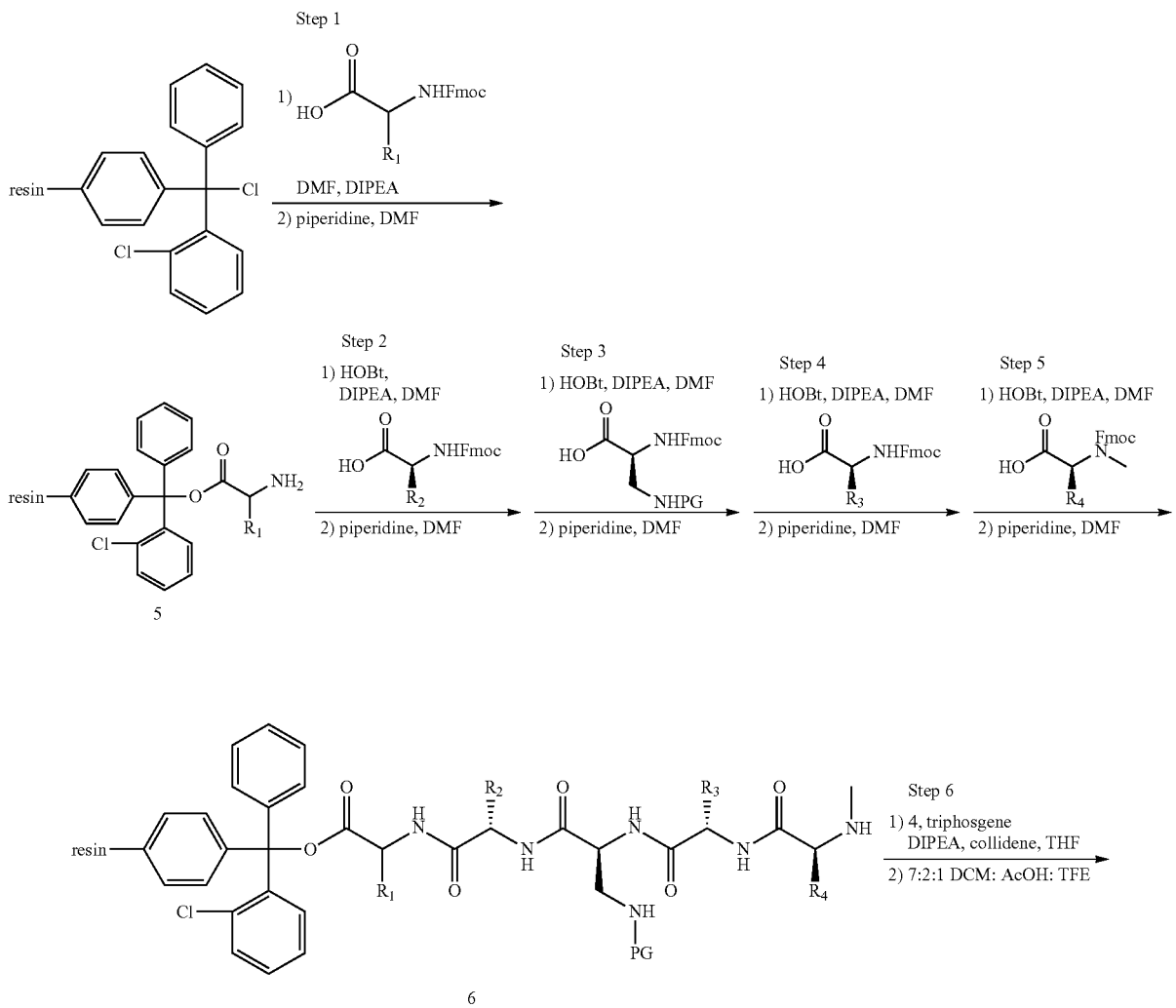

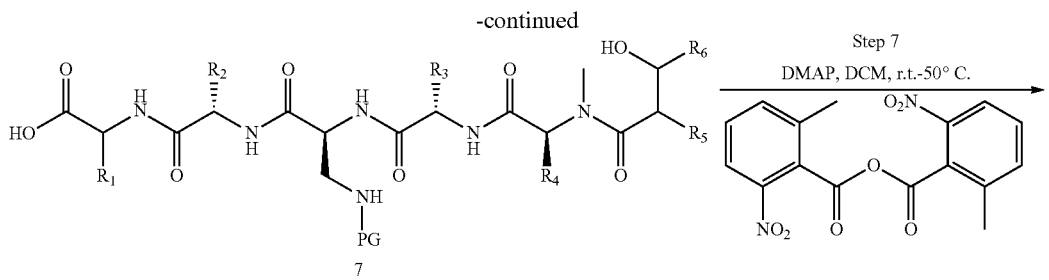

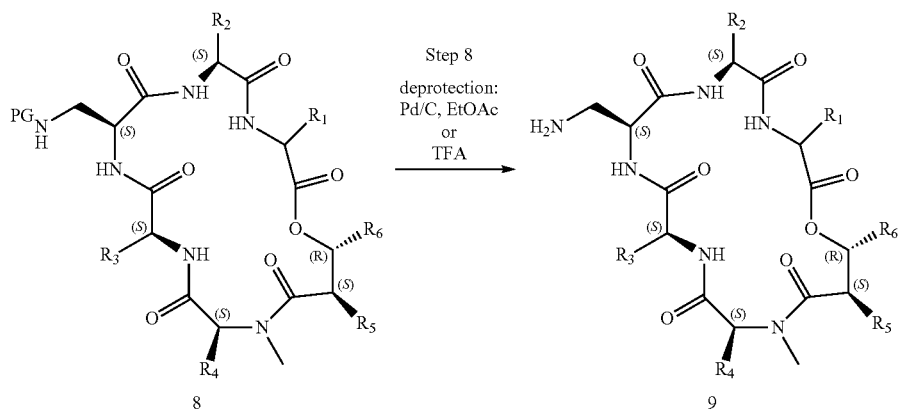

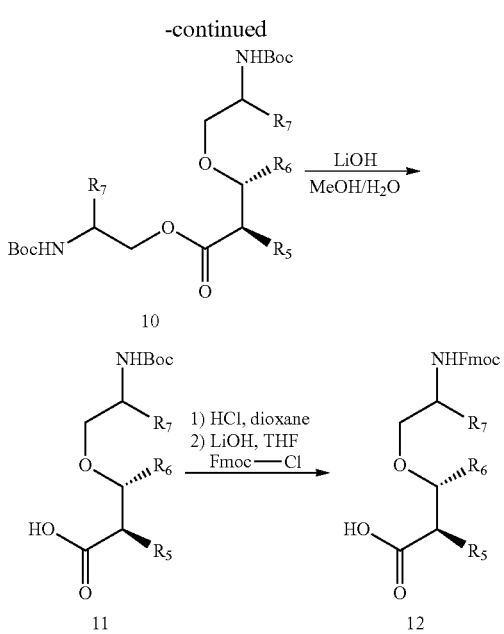

As shown in Scheme 2, chloro-(2-chlorotrityl)-resin may be loaded with an Fmoc-protected amino acid, and the Fmoc group removed with piperidine in DMF, to yield intermediate 5. Intermediate 5 may be elaborated through steps 2-5 using standard solid-phase chemistry techniques utilizing HOBt couplings with Fmoc-protected amino acids and standard side-chain protecting groups, to yield elaborated peptide 6. Triphosgene mediated coupling with beta-hydroxy carboxylic acid 4, followed by cleavage from resin using DCM:AcOH:TFE to yield the depsipeptide 7. Depsipeptide 7 may be cyclized to yield the macrolactone 8 using Yamaguchi esterification conditions. Macrolactone 8 may be globally deprotected using appropriate conditions (Pd hydrogenation or acidic conditions) to yield compounds 9.

Scheme 3.

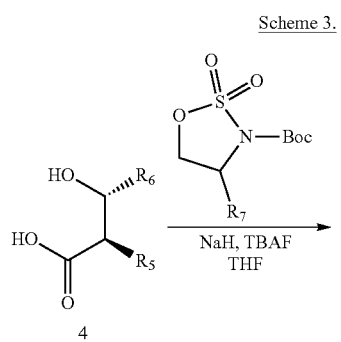

As shown in Scheme 3, beta-hydroxy acid compounds 4 may be alkylated with an appropriately substituted tert-butyl 2,2-dioxo-oxathiazolidine-3-carboxylate to yield esters 10. These esters may be saponified to yield carboxylic acids 11. The amino protecting group may be converted from Boc to Fmoc by acidic deprotection followed by reprotection with 9-fluorenylmethylchloroformate to yield intermediates 12.

Scheme 4.

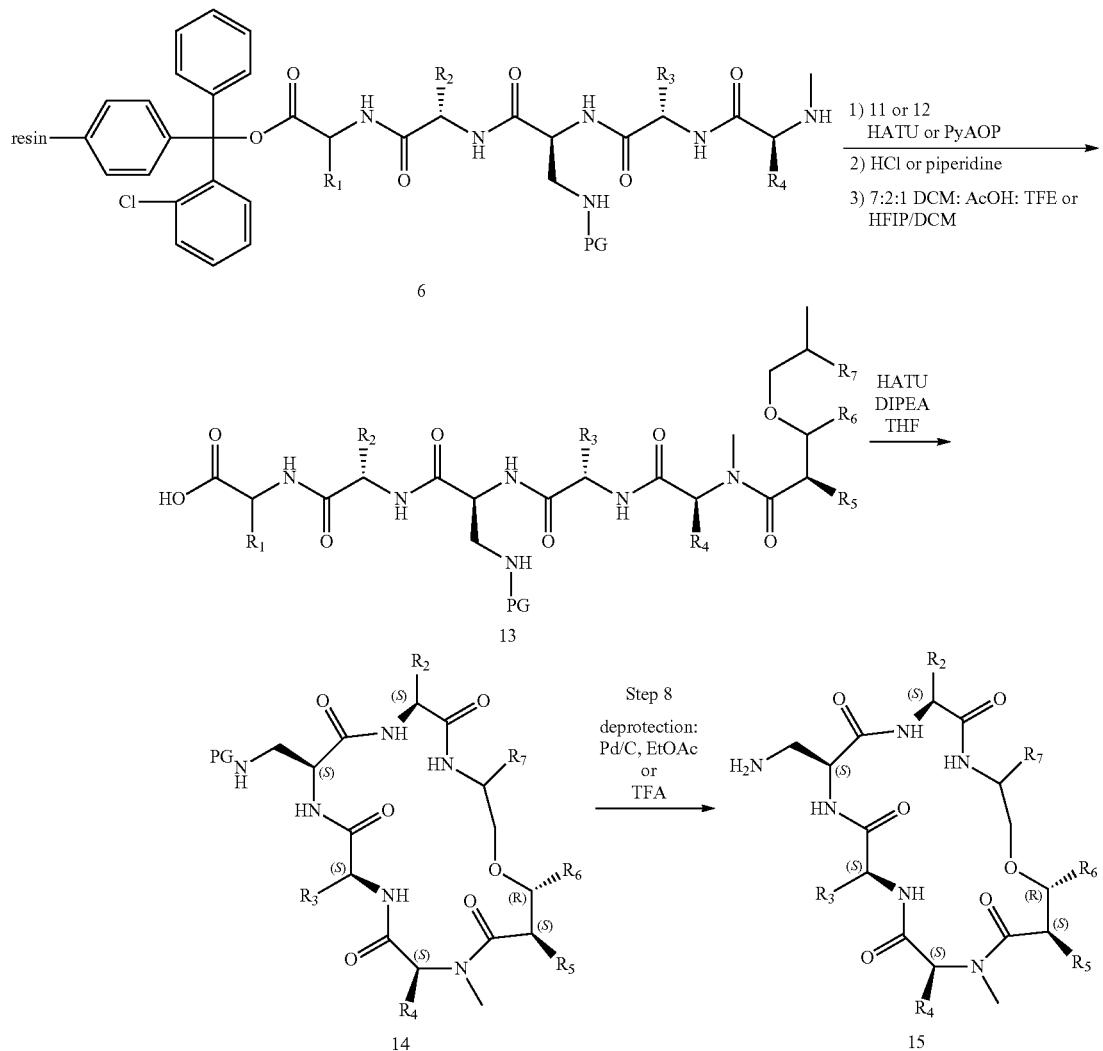

As shown in Scheme 4, resin-bound peptides 6 may be coupled to carboxylic acids 11 or 12 using standard coupling reagents such as HATU or PyAOP, followed by Boc or Fmoc deprotection and resin cleavage to yield protected peptides 13. The linear peptides may be cyclized using macrolactamization conditions such as HATU/DIPEA to yield macrocycles 14. The side chains of macrocyclic depsipeptides 14 may be globally deprotected using palladium/hydrogenation and/or acidic conditions to yield compounds 15.

General Experimental Conditions $^1$H NMR spectra were recorded at ambient temperature using either a Varian Unity Inova (400 MHz) spectrometer with a triple resonance 5 mm probe, an Avance III (300 MHz) spectrometer or a Bruker Ultrashield (400 MHz or 500 MHz) spectrometer. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a CEM Discover, Smith Synthesiser or a Biotage Initiator 60™, which uses a single-mode resonator and dynamic field tuning, both of which give reproducibility and control. Temperatures from 40-250° C. can be achieved and pressures of up to 30 bar can be reached.

High Pressure Liquid Chromatography—Mass Spectrometry (LCMS) experiments to determine retention times ($R_T$) and associated mass ions were performed using one of the following methods. The spectrometers have an electrospray source operating in positive and negative ion mode. UV absorbance was collected at 220 nm and 254 nm and mass spec full scan was applied to all experiments. Additional detection was achieved using a Sedex 85 evaporative light scattering detector. A Thermo Scientific charged aerosol detector (model: Corona) was used to measure the purity of the UV-insensitive analytes. The CAD parameters are set up as follows:

Gas pressure: 35-40 psi
Flow ratio: 0.51
Ion Trap: 20.3 v
Charger voltage: 2.91 kv
Charger current: 1.01 uA
LCMS Method A:
Experiments performed on an Agilent 1290 HPLC coupled with Agilent MSD mass spectrometer using ESI as ionization source. The EC separation was using a Phenomenex XB-C18, 1.7 mm, 50*2.1 mm column with a 0.4 mL/minute flow rate. Solvent A is water with 0.1% formic acid and solvent B is acetonitrile with 0.1% formic acid. The gradient consisted with 2-98% solvent B over 7 minutes and hold 97% B for 1.5 minutes following equilibration for 1.5 minutes. EC column temperature is 40° C.

LCMS Method B:

Experiments performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 um 100×2.1 mm column, maintained at 40° C. or an Acquity BEH Shield RP18 1.7 μm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95% solvent A and 5% solvent B over the next 0.2 minutes.

LCMS Method C:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 5% solvent A and 95% solvent B over the next 2.0 minutes. This was maintained for 0.7 minutes before returning to 95% solvent A and 5% solvent B over the next 0.3 minutes.

LCMS Method D:

Experiments performed on Shimadzu UFLC coupled with DAD detector, ELSD detector and 2020EV MS. The spectrometer has an electrospray source operating in positive ion mode. This system uses a Shim-Pack XR-ODS CIS 2.2 μm 50*3.0 mm column, maintained at 40° C. and a 1.2 mL/minute flow rate. The initial solvent system was 60% water containing 0.05% trifluoroacetic acid (solvent A) and 40% acetonitrile containing 0.05% trifluoroacetic acid (solvent B) for the first 0.01 minute followed by a gradient up to 5% solvent A and 95% solvent B over the next 3.5 minutes. This was maintained for 0.6 minutes before returning to 95% solvent A and 5% solvent B over the next 0.2 minutes.

LCMS Method E:

Experiments performed on Dionex EC Ultimate3000 coupled with ThermoScientific Q Exactive orbitrap mass spectrometer using ESI as the ionization source. The EC separation was using a Phenomenex XB-C18, 1.7·m, 50×2.1 mm column with a 0.5 ml/minute flow rate. Mobile phase A was water with 0.1% FA and mobile phase B was acetonitrile with 0.1% FA. The gradient consisted with 2-98% B over 7 min and held 98% B for 1.5 min following equilibration for 1.0 min. EC column temperature was 40 C. UV absorbance was collected at 220 nm and 254 nm. Mass spectrometer full scan 100-2000 amu with 17,500 resolution was applied to all experiments.

LCMS Method F:

Experiments were performed on an Agilent 1290 HPLC coupled with Agilent MSD mass spectrometer using ESI as ionization source. The LC separation was done on an Agilent Zorbax Eclipse XDB-C18, 3.5 mm, 100×3.0 mm column at a flow rate of 0.7 ml/minute. MPA (mobile phase A) was water with 0.1% FA and MPB (mobile phase B) was acetonitrile with 0.1% FA. The gradient started at 2% MPB and ended at 98% MPB over 25.5 min and held at 98% B for 2.5 min following equilibration for 1.5 min. LC column temperature was 40° C. UV absorbance were collected at 220 nm and 254 nm and mass spec full scan was applied to all experiments.

LCMS Method G:

Experiments performed on Shimadzu UFLC coupled with DAD detector, ELSD detector and 2020EV MS. The spectrometer has an electrospray source operating in positive ion mode. This system uses a Poroshell HPH-C18 2.7 μm 50*3.0 mm column, maintained at 40° C. and a 1.2 mL/minute flow rate. The initial solvent system was 90% water containing 5 mM $NH_4HCO_3$ (solvent A) and 10% acetonitrile (solvent B) for the first 0.01 minute followed by a gradient up to 5% solvent A and 95% solvent B over the next 2.0 minutes. This was maintained for 0.7 minutes before returning to 90% solvent A and 10% solvent B over the next 0.3 minutes.

LCMS Method H:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 30% solvent A and 70% solvent B over the next 3.2 minutes. And then followed by a gradient up 100% solvent B over the next 0.5 minutes. This was maintained for 0.8 minutes before returning to 95% solvent A and 5% solvent B over the next 0.3 minutes.

LCMS Method I:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 50% water containing 0.05% trifluoroacetic acid (solvent A) and 50% acetonitrile containing 0.05% trifluoroacetic acid (solvent B) for the first 0.01 minute followed by a gradient up to 100% solvent B over the next 4.0 minutes. This was maintained for 0.7 minutes before returning to 95% solvent A and 5% solvent B over the next 0.3 minutes.

LCMS Method J:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 60% water containing 0.05% trifluoroacetic acid (solvent A) and 40% acetonitrile containing 0.05% trifluoroacetic acid (solvent B) for the first 0.01 minute followed by a gradient up to 5% solvent A and 95% solvent B over the next 3.5 minutes. This was maintained for 0.6 minutes before returning to 95% solvent A and 5% solvent B over the next 0.3 minutes.

LCMS Method K:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 70% water containing 0.05% trifluoroacetic acid (solvent A) and 30% acetonitrile containing 0.05% trifluoroacetic acid (solvent B) for the first 0.01 minute followed by a gradient up to 5% solvent A and 95% solvent B over the next 3.5 minutes. This was maintained for 0.6 minutes before returning to 95% solvent A and 5% solvent B over the next 0.2 minutes.

LCMS Method L:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 95% water containing 0.05% trifluoroacetic acid (solvent A) and 5% acetonitrile containing 0.05% trifluoroacetic acid (solvent B) for the first 0.01 minute followed by a gradient up to 100% solvent B over the next 2.0 minutes. This was maintained for 0.7 minutes before returning to 95% solvent A and 5% solvent B over the next 0.3 minutes.

LCMS Method M:

Experiments performed on Shimadzu UFLC coupled with DAD detector, ELSD detector and 2020EV MS. The spectrometer has an electrospray source operating in positive ion mode. This system uses a Shim-Pack XR-ODS C18 2.2 μm 50*3.0 mm column, maintained at 40° C. and a 1.2 mL/minute flow rate. The initial solvent system was 70% water containing 0.05% trifluoroacetic acid (solvent A) and 30% acetonitrile containing 0.05% trifluoroacetic acid (solvent B) for the first 0.01 minute followed by a gradient up to 30% solvent A and 70% solvent B over the next 3.6 minutes. And then followed by a gradient up 100% solvent B over the next 0.4 minutes. This was maintained for 0.5 minutes before returning to 95% solvent A and 5% solvent B over the next 0.3 minutes.

LCMS Method N

Experiments performed on Shimadzu UFLC coupled with DAD detector, ELSD detector and 2020EV MS. The spectrometer has an electrospray source operating in positive ion mode. This system uses a Shim-Pack XR-ODS CIS 2.2 μm 50*3.0 mm column, maintained at 40° C. and a 1.2 mL/minute flow rate. The initial solvent system was 70% water containing 0.05% trifluoroacetic acid (solvent A) and 30% acetonitrile containing 0.05% trifluoroacetic acid (solvent B) for the first 0.01 minute followed by a gradient up to 100% solvent B over the next 3.2 minutes. This was maintained for 0.9 minutes before returning to 95% solvent A and 5% solvent B over the next 0.2 minutes.

Intermediate 1.
(2R,3R)-3-hydroxy-2-methylnonanoic acid

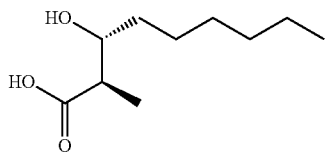

Step 1. 1-((3aR,6S,7aS)-8,8-dimethyl-2,2-dioxido-tetrahydro-3H-3a,6-methanobenzo[c]isothiazol-1 (4H)-yl)propan-1-one

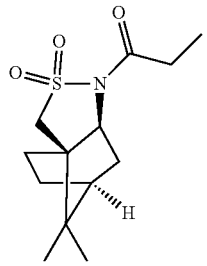 [SMILES: CCC(=O)N1[C@H]2C[C@@H]3CC[C@@]2(CS1(=O)=O)C3(C)C]

Propionyl chloride (844 g, 894 mmol) was added to a solution of (3aR,6S,7aS)-8,8-dimethylhexahydro-3H-3a,6-methanobenzo[c]isothiazole 2,2-dioxide (175 g, 813 mmol), DMAP (10.5 g, 81.3 mmol), and triethylamine (172 mL, 1220 mmol) in THE (1.4 L) at 0° C. After 30 min, the reaction was warmed to room temperature and was allowed to stir for an additional 3 h. The reaction was evaporated under reduced pressure. The resulting residue was diluted with water and isopropyl acetate. The aqueous layer was extracted with isopropyl acetate (2×). The combined organic layers were washed with 1 M NaOH (×2), 1 M HCl (×2), brine, dried with magnesium sulfate, and evaporated in vacuo. The crude solid was recrystallized from DCM and heptane to give the title compound (213.3 g, 97% yield).

Step 2. (2R,3R)-1-((3aR,6S,7aS)-8,8-dimethyl-2,2-dioxidotetrahydro-3H-3a,6-methanobenzo[c]isothi-azol-1 (4H)-yl)-3-hydroxy-2-methylnonan-1-one

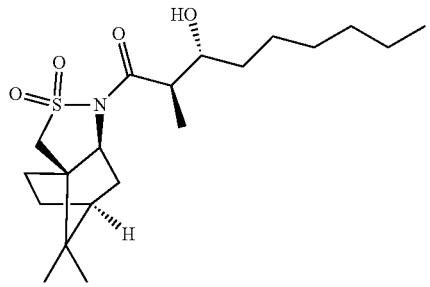 [SMILES: CCCCCC[C@@H](O)[C@@H](C)C(=O)N1[C@H]2C[C@@H]3CC[C@@]2(CS1(=O)=O)C3(C)C]

To a solution of triethylborante (91 mL, 1 mol/L in hexane) in DCM (50 mL) in a 500 mL 3-neck round-bottom flask was added TfOH (13.825 g, 92.122 mmol) dropwise at 0° C. under nitrogen. The mixture was then stirred for 30 min at 0° C., and then cooled to −15° C. To this was added a solution of 1-((3aR,6S,7aS)-8,8-dimethyl-2,2-dioxidotetrahydro-3H-3a,6-methanobenzo[c]isothiazol-1(4H)-yl)propan-1-one (10.00 g, 36.8 mmol) and DIPEA (12.3 g) in DCM (50 mL) dropwise at −15° C. The resulting solution was stirred for 1 h at −10° C. in a water/brine bath (mixture A).

Into a 250 mL 3-necked round-bottom flask, was placed titanium tetrachloride (110 mL, 1 mol/L in DCM, 3.0 equiv) under nitrogen. To this solution was added heptaldehyde (6.3 g, 55.3 mmol, 1.5 equiv) dropwise at −78° C., and the mixture was stirred for 30 min at −50° C. The resulting solution was then transferred to an additional funnel (mixture B).

The mixture B was added to mixture A dropwise at −78° C., and stirred for 4 h at −50° C. The reaction was quenched with 300 mL of saturated aqueous ammonium chloride, and extracted with 2×500 mL of ethyl acetate. The organic layers were combined and washed with 1×300 mL brine, dried over anhydrous sodium sulfate, filtered and evaporated in vacuo. The residue was applied onto a silica gel column eluting with ethyl acetate/petroleum ether (1:4). The appropriate fractions were combined and concentrated under vacuum to afford the title compound (12 g) as a light yellow oil of 85% purity (containing ~15% starting material), and was carried forward to the next step without purification. LCMS (ESI): [M+H]$^+$=386.

Step 3. (2R,3R)-3-hydroxy-2-methylnonanoic acid

Into a 250 mL round-bottom flask, was placed THF (60 mL), 30% $H_2O_2$ (6.3 mL), LiOH (1.96 g, 81.844 mmol), water (30 mL, 1.665 mol), (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-methylnonan-1-one (6.30 g, 16.340 mmol). The resulting solution was stirred overnight at 25° C. The reaction was then quenched by the addition of 100 mL of saturated aqueous $Na_2SO_3$ solution. The pH value of the solution was adjusted to 3 with 1 N HCl solution. The resulting solution was extracted with 3×200 mL of ethyl acetate and the organic layers combined and dried over anhydrous sodium sulfate, filtered and concentrated under vacuum. The residue was applied onto a silica gel column eluting with ethyl acetate/petroleum ether (1:2). The appropriate fractions were combined and concentrated under vacuum. This resulted in 2.2 g (70% yield) of the title compound as a light yellow oil. LCMS (ESI): [M−H]$^-$=187; $^1$H NMR (400 MHz, DMSO-d$_6$) δ 11.95 (s, 1H), 4.60 (d, J=52 Hz, 1H), 3.59 (s, 1H), 2.43-2.31 (m, 1H), 1.48-1.15 (m, 10H), 0.98 (d, J=7.0 Hz, 3H), 0.92-0.82 (m, 3H).

Intermediate 2.
(2R,3R)-3-hydroxy-2-methyltridecanoic acid

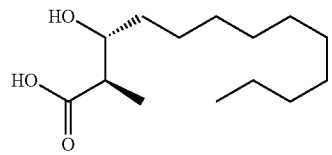 [SMILES: CCCCCCCCCC[C@@H](O)[C@@H](C)C(=O)O]

The title compound was prepared following procedures analogous to those described for Intermediate 1, using undecanal instead of heptanal. LCMS(ESI): [M−H]$^-$=243; $^1$H NMR (400 MHz. DMSO-d$_6$) δ 11.95 (s, 1H), 4.60 (d, J=4.4 Hz, 1H), 3.65-3.55 (m, 1H), 2.39-2.32 (m, 1H), 1.41-1.19 (m, 18H), 0.97 (d, J=6.8 Hz, 3H), 0.86 (t, J=6.8 Hz, 3H).

TABLE 2

The intermediates depicted in the table below were prepared using methods analogous to those described for Intermediate 1 from alkyl aldehydes which are commerically available or readily prepared from the corresponding alcohol with conventional methods.

| Intermediate No. | Structure | LCMS (ESI): [M − H]$^-$ |
|---|---|---|
| T1 | 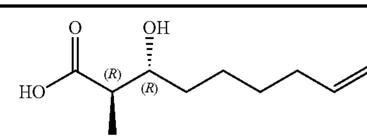 | 185.1 |
| T2 | 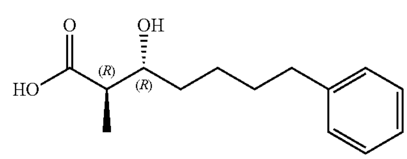 | 235.1 |
| T3 | 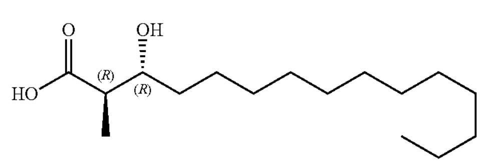 | 271.2 |

TABLE 2-continued
The intermediates depicted in the table below were prepared using methods analogous to those described for Intermediate 1 from alkyl aldehydes which are commerically available or readily prepared from the corresponding alcohol with conventional methods.
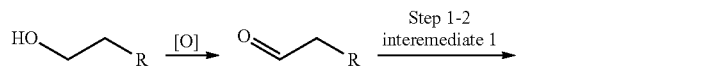
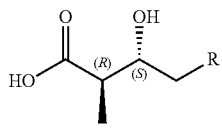
| Intermediate No. | Structure | LCMS (ESI): [M − H]− |
|---|---|---|
| T4 | 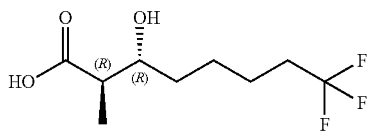 | 241.0 |
| T5 | 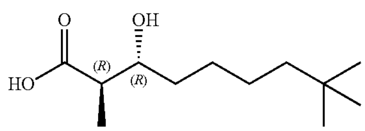 | 215.1 |
| T6 | 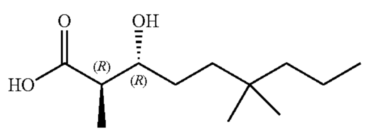 | 215.1 |
| T7 | 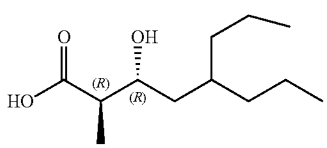 | 215.2 |
| T8 | 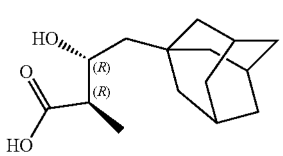 | 251.1 |
| T9 | 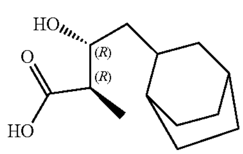 | 225.1 |

Intermediate T10: (2R,3R)-8,9-Difluoro-3-hydroxy-2-methylnonanoic acid

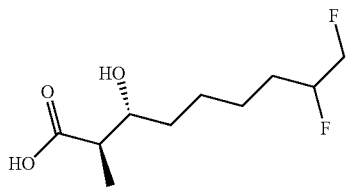

Step 1: Hept-6-enal

To a solution of hept-6-en-1-ol (15.0 g, 131.3 mmol) in DCM (2000 mL) was added pyridinium chlorochromate (42.87 g, 197.04 mmol) in several portions. The reaction mixture was stirred at room temperature for 2 h. The solid was removed via filtration and the filtrate was evaporated under reduced pressure. The residue was purified by flash chromatography on silica gel eluting with ethyl acetate/petroleum ether (1/5) to afford hept-6-enal (13 g, 88% yield) as colorless oil. TLC $R_f$=0.4, PE/EA=4/1.

Step 2: (2R,3R)-1-((3aR,6S,7aS)-8,8-Dimethyl-2,2-dioxidotetrahydro-3H-3a,6-methanobenzo[c]isothiazol-1(4H)-yl)-3-hydroxy-2-methylnon-8-en-1-one

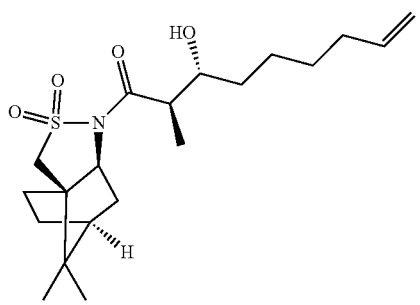 [SMILES: C=CCCCC[C@@H](O)[C@@H](C)C(=O)N1[C@H]2C[C@@H]3CC[C@@]2(CS1(=O)=O)C3(C)C]

The title compound was prepared using hept-6-enal instead of heptaldehyde and following procedures analogous to those described for Intermediate 1 (steps 1-2). LCMS (ESI): [M+H]$^+$=384.2.

Step 3: (2R,3R)-1-((3aR,6S,7aS)-8,8-Dimethyl-2,2-dioxidotetrahydro-3H-3a,6-methanobenzo[c]isothiazol-1(4H)-yl)-8,9-difluoro-3-hydroxy-2-methylnonan-1-one

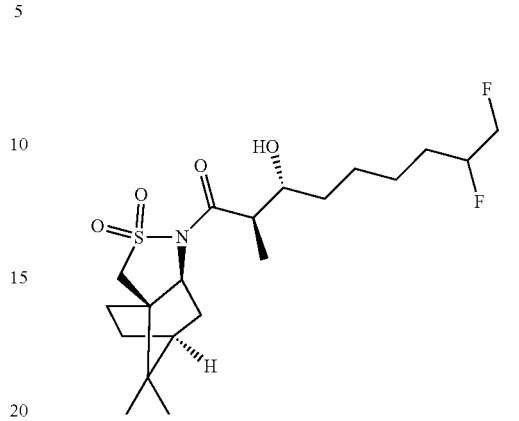

To a solution of 4-iodotoluene (341.1 mg, 1.56 mmol) and (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-methylnon-8-en-1-one (3.12 g, 7.82 mmol) in 1,2-dichloroethane (30 mL) was added a mixture of Et$_3$N.3HF (amine:HF=1:3, 2 ml) and Pyr.(HF)x (Olah's reagent) (amine:HF=1:9.23, 1 mL) dropwise at 0° C. Then into the resulting mixture was added 1-chloromethyl-4-fluoro-1,4-diazoniabicyclo[2.2.2]octane bis(tetrafluoroborate) (4.16 g, 11.73 mmol) at 0-10° C. The resulting mixture was stirred overnight at room temperature and quenched with saturated sodium bicarbonate solution to pH 9. The resulting solution was extracted with ethyl acetate (3×200 mL). The organic layers were combined, dried over anhydrous sodium sulfate, filtered and concentrated under reduced pressure. The residue was purified on silica gel column with 30% ethyl acetate in petroleum ether to afford the title compound (2.13 g, 60% yield) as a yellow oil. LCMS (ESI): [M+H]$^+$=422.2.

Step 4: (2R,3R)-8,9-Difluoro-3-hydroxy-2-methylnonanoic acid

To a solution of (2R,3R)-1-((3aR,6S,7aS)-8,8-dimethyl-2,2-dioxidotetrahydro-3H-3a,6-methanobenzo[c]isothiazol-1(4H)-yl)-8,9-difluoro-3-hydroxy-2-methylnonan-1-one (1.01 g, 2.40 mmol) in THF (100 mL) and water (100 mL) was added LiOH (569.3 mg, 23.7 mmol) and H$_2$O$_2$ (10 mL) at 0° C. The reaction mixture was stirred for 3 h at room temperature and acidified with diluted hydrochloric acid (1 mol/L) to pH 4. The resulting solution was extracted with ethyl acetate (3×200 mL). The organic layers were combined, dried over anhydrous sodium sulfate, filtered and evaporated under reduced pressure. The residue was purified on silica gel column eluting with 30% ethyl acetate in petroleum ether to afford the title compound (200 mg, 37% yield) as a light yellow oil. LCMS (ESI): [M+H]$^+$=225.1; $^1$H NMR (400 MHz, DMSO-d$_6$) δ 11.97 (s, 1H), 4.70-4.40 (m, 4H), 3.61-3.57 (m, 1H), 2.39-2.32 (m, 1H), 1.60-1.27 (m, 8H), 0.98 (d, J=7.2 Hz, 3H).

Intermediate T1: (2R,3R,E)-3,10-Dihydroxy-2,10-dimethylundec-8-enoic acid

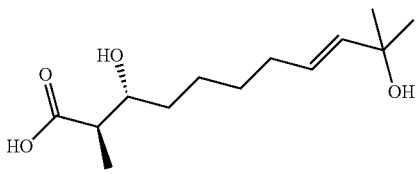 [SMILES: C[C@@H](C(=O)O)[C@H](O)CCCC/C=C/C(C)(C)O]

To a solution of (2R,3R)-3-hydroxy-2-methylnon-8-enoic acid (Intermediate T1) (1.03 g, 5.38 mmol) and 3-methoxy-3-methyl-but-1-ene (1.07 g, 10.76 mmol) in DCM (4 mL) was added benzylidene-bis(tricyclohexylphosphine)dichlororuthenium (1.80 g, 2.15 mmol) under nitrogen. The reaction mixture was stirred at 40° C. for 2 h and evaporated under reduced pressure. The residue was purified by flash chromatography on silica gel eluting with MeOH/DCM (1/9) to afford the title compound (500.6 mg) as a light yellow oil. LCMS (ESI): [M+H]$^+$=245.2; $^1$H NMR (400 MHz, DMSO-d$_6$) δ 11.89 (s, 1H), 5.50-4.05 (m, 4H), 3.60-3.55 (m, 1H), 2.38-2.31 (m, 1H), 1.41-1.21 (m, 8H), 1.05 (s, 6H), 0.97 (d, J=7.2 Hz, 3H).

Intermediate T12: (2R,3R)-7-Fluoro-3-hydroxy-2-methylnonanoic acid

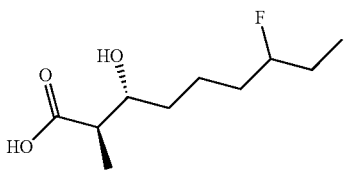

Step 1: 7-(Benzyloxy)heptan-3-ol

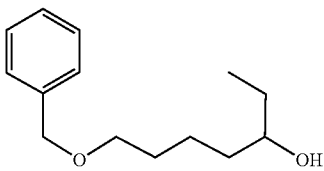 [SMILES: CCC(O)CCCCOCc1ccccc1]

To a solution of 5-benzyloxy-1-pentanol (9.6 g, 49.42 mmol) in DCM (500 mL) was added pyridinium chlorochromate (16.37 g, 75.04 mmol) in several portions. The reaction mixture was stirred at room temperature for 2 h. The solid was removed via filtration and the filtrate was evaporated under reduced pressure. The residue was purified by flash chromatography on silica gel eluting with ethyl acetate/petroleum ether (1/5) to afford 5-benzyloxypentanal (6.9 g, 72% yield) as a colorless oil.

To a solution of 5-benzyloxypentanal (6.9 g, 35.89 mmol) in THF (200 ml) at 0° C. was added ethylmagnesiumbromide (36 mL, 1 M solution in THF). The resulting solution was stirred for 1.5 h at 0° C. The reaction mixture was quenched with 30 mL of water and extracted with ethyl acetate (3×50 mL). The organic layers were combined, dried over anhydrous sodium sulfate, filtered and evaporated under reduced pressure. The residue was purified by flash chromatography on silica gel eluting with ethyl acetate/petroleum ether (1/9) to afford the title compound (5.3 g, 66% yield) as a colorless oil. TLC R$_f$=0.4, PE/EA=2/1.

Step 2: 5-Fluoroheptan-1-ol

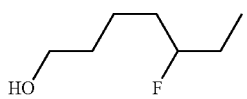

To a solution of 7-benzyloxyheptan-3-ol (5.3 g, 24.2 mmol) in DCM (150 mL) was added diethylaminosulfur trifluoride (8.12 g, 50.37 mmol) at 0° C. The mixture was stirred at room temperature for 3 h and quenched by the addition of saturated sodium bicarbonate solution (30 mL). The resulting solution was extracted with DCM (3×100 mL). The organic layers were combined, dried over anhydrous sodium sulfate, filtered and evaporated under reduced pressure. The residue was purified by flash chromatography on silica gel eluting with ethyl acetate/petroleum ether (1/50) to afford 5-fluoroheptoxymethylbenzene (2.5 g, 44% yield) as a yellow oil.

A mixture of 5-fluoroheptoxymethylbenzene (2.5 g, 11.14 mmol) and palladium (5.26 g, 10% loading on carbon) in methanol (300 mL) was stirred under a hydrogen balloon at room temperature for 24 h. The solid was removed via filtration and the filtrate was evaporated under reduced pressure. The residue was purified by flash chromatography on silica gel eluting with ethyl acetate/petroleum ether (1/4) to afford the title compound (790 mg, 52% yield) as a colorless oil. TLC R$_f$=0.2, PE/EA=2/1.

Step 3: 5-Fluoroheptanal

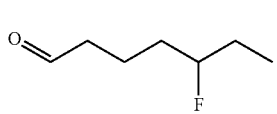

To a solution oxalyl dichloride (2.77 g, 21.81 mmol) in DCM (20 mL) was added dropwise a solution of DMSO (3.41 g, 43.62 mmol) in DCM (10 mL) at −78° C. under nitrogen. The reaction mixture was stirred at −78° C. for 10 min. Then a solution of 5-fluoroheptan-1-ol (1.46 g, 10.9 mmol) in 20 mL DCM was added dropwise at −78° C. The reaction mixture was stirred at −78° C. for 2 h and then DIPEA (7.03 g, 54.51 mmol) was added. The resulting mixture was stirred at 0° C. for 1 h and poured into 50 mL of saturated aqueous ammonium chloride, then extracted with DCM (3×). The combined organic phases were dried with anhydrous sodium sulfate, filtered and evaporated under reduced pressure to afford 5-fluoroheptanal (1.2 g, crude). The crude product was used directly for the next step. TLC R$_f$=0.4, PE/EA=4/1.

Step 4: (2R,3R)-7-Fluoro-3-hydroxy-2-methylnonanoic acid

The title compound was prepared using 5-fluoroheptanal instead of heptaldehyde and following procedures analogous to those described for Intermediate 1 (steps 1-2). LCMS (ESI): [M+H]⁺=207.1; ¹H NMR (400 MHz, DMSO-d₆) δ 11.96 (s, 1H), 4.66 (d, J=5.6 Hz, 1H), 4.48-4.33 (m, 1H), 3.66-3.58 (m, 1H), 2.40-2.33 (m, 1H), 1.62-1.28 (m, 8H), 0.98 (d, J=7.2 Hz, 3H), 0.90 (t, J=7.6 Hz, 3H).

Intermediate T13:
(2R,3R)-3-Hydroxy-2,4-dimethylnonanoic acid (single unknown stereoisomer)

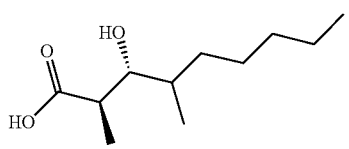

Step 1: (4S)-4-Benzyl-3-(2-methylheptanoyl)oxazolidin-2-one

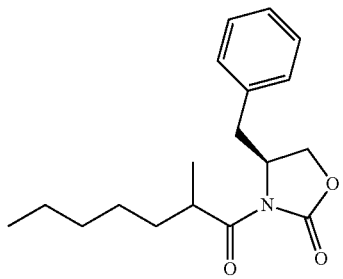 [SMILES: CCCCCC(C)C(=O)N1C(=O)OC[C@@H]1Cc1ccccc1]

To a solution of 2-methylheptanoic acid (18.14 g, 124.8 mmol) in DCM (100 mL) was added oxalyl dichloride (20.25 g) dropwise at 0° C. under nitrogen. The reaction mixture was stirred at room temperature for 3 h and concentrated under reduced pressure to afford crude 2-methylheptanoyl chloride (20.31 g) as light yellow oil. This material was dissolved in DCM (150 mL) and added dropwise to a solution of (4S)-4-benzyl-1,3-oxazolidin-2-one (20.3 g, 112.8 mmol), 4-dimethylaminopyridine (1.38 g, 11.3 mmol), and triethylamine (45.68 g, 451.4 mmol) in DCM (150 mL) at 0° C. The resulting mixture was stirred for 3 h at 0° C. Water (200 mL) was added and phases were separated. The aqueous phase was extracted with DCM (3×). The organic layers were combined, dried over anhydrous sodium sulfate and evaporated under reduced pressure. The residue was purified on silica gel column eluting with 10% ethyl acetate in petroleum ether to afford (4S)-4-benzyl-3-[(2R)-2-methylheptanoyl]oxazolidin-2-one (35 g), which was subjected to SFC separation (Column: Phenomenex Lux 5u Cellulose-35*25 cm, 5 um Chiral-P (Lux-3); Flow Rate (g/min): 150; % Solvent A: CO2:85; % Solvent B: EtOH:15) to afford two fractions as single unknown stereoisomers (first peak: 13 g and second peak: 14.2 g). LCMS (ESI): [M+H]⁺=304.2.

Step 2: 2-Methylheptan-1-ol

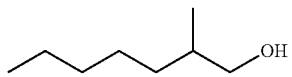

To a solution of (4S)-4-benzyl-3-[(2S)-2-methylheptanoyl]oxazolidin-2-one (14.2 g, 46.86 mmol) (second peak from SFC separation in Step 1) in THF (200 mL) was added LiAlH₄ (8.52 g, 224.1 mmol) in several portions at 0° C. The reaction mixture was stirred for 3 h at 0° C. and quenched by the sequential addition of water (9 mL), NaOH solution (25% W, 9 mL) and 9 mL of water. The resulting precipitate was removed via filtration. The filtrate was evaporated under reduced pressure and the resulting residue was purified on silica gel column with 30% ethyl acetate in petroleum ether to afford 2-methylheptan-1-ol, single unknown stereoisomer, (6.15 g, 82% yield) as a colorless oil. TLC R_f=0.3, PE/EA=1/1.

Step 3: 2-Methylheptanal

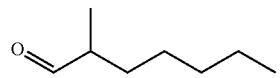

To a solution of 2-methylheptan-1-ol (single unknown stereoisomer from Step 2) (6.15 g, 46.07 mmol) in DCM (50 mL) was added pyridinium chlorochromate (14.89 g, 69.11 mmol) at 0° C. The reaction mixture was stirred for 3 h at room temperature. The solids were removed via filtration and the filtrate was evaporated under reduced pressure to afford 2-methylheptanal, single unknown stereoisomer, (3.5 g, crude) as light yellow oil, which was used in the next step without purification. TLC R_f=0.4, PE/EA=4/1.

Step 4: (2R,3R)-3-Hydroxy-2,4-dimethylnonanoic acid (single unknown stereoisomer)

The title compound was prepared using 2-methylheptanal (single unknown stereoisomer from Step 3) instead of heptaldehyde and following procedures analogous to those described for Intermediate 1 (steps 1-2). LCMS (ESI): [M+H]⁺=203.2; ¹H NMR (300 MHz, DMSO-d₆) δ11.90 (s, 1H), 4.65-4.45 (m, 1H), 3.39-3.35 (m, 1H), 2.47-2.40 (m, 1H), 1.56-1.11 (m, 9H), 0.99 (d, J=7.2 Hz, 3H), 0.87 (t, J=6.6 Hz, 3H), 0.86 (d, J=6.9 Hz, 3H).

Intermediate 3. (2R,3R)-3-((R)-2-((tert-Butoxycarbonyl)amino)propoxy)-2-methylnonanoic acid

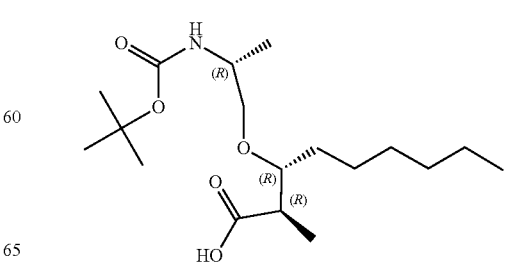

Step 1: (R)-2-((tert-Butoxycarbonyl)amino)propyl (2S,3R)-3-((R)-2-((tert-butoxy carbonyl)amino) propoxy)-2-methylnonanoate

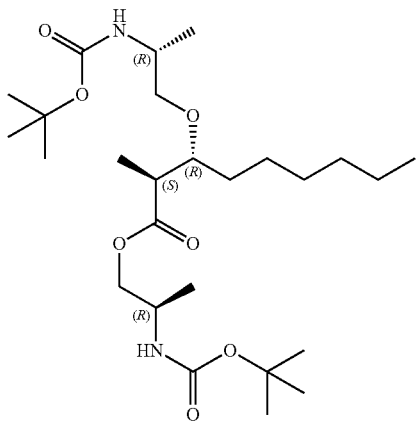

To a solution of (2R,3R)-3-hydroxy-2-methyl-nonanoic acid (10.13 g, 53.81 mmol, Intermediate 1) in anhydrous THF (100 mL) was added tert-butyl (4R)-4-methyl-2,2-dioxo-oxathiazolidine-3-carboxylate (38.31 g, 161.46 mmol) and tetrabutylammonium fluoride (1 mol/L solution in THF, 80 mL, 53.81 mmol) at room temperature. Sodium hydride (60% in mineral oil, 8.61 g, 215.2 mmol) was added portionwise at 0° C. After the completion of sodium hydride addition and hydrogen evolution ceased, the reaction mixture was allowed to warm to room temperature and stirred at room temperature for 16 h. Aqueous HCl solution (1 mol/L) was carefully added with stirring until pH6-7. The resulting solution was extracted with ethyl acetate (3×100 mL) and the organic layers were combined. The combined organic phases were dried over anhydrous sodium sulfate, filtered and concentrated under reduced pressure. The residue was purified by flash chromatography on silica gel eluting with ethyl acetate/petroleum ether (1/9) to afford the title compound (23.01 g, 85% yield) as a colorless oil. LCMS (ESI): [M+H]$^+$=503.4.

Step 3: (2R,3R)-3-((R)-2-((tert-Butoxycarbonyl) amino)propoxy)-2-methylnonanoic acid To a solution of (R)-2-((tert-butoxycarbonyl)amino)propyl (2S,3R)-3-((R)-2-((tert-butoxy carbonyl)amino) propoxy)-2-methylnonanoate (5.02 g, 9.98 mmol) in methanol (50 mL) was added a solution of lithium hydroxide (2.3 g, 99.87 mmol) in water (23 mL) at 25° C. The resulting solution was stirred at 30° C. for 16 h. The resulting solution was concentrated under reduced pressure to approximately ⅓ of volume (evaporating methanol). Aqueous HCl (1 mol/L) was carefully added until pH-6. The resulting solution was extracted with ethyl acetate (3×100 mL). The combined organic layers were dried over anhydrous sodium sulfate and concentrated under reduced pressure. The residue was purified by flash chromatography on silica gel eluting with ethyl acetate/petroleum ether (1/6) to afford (2R,3R)-3-((R)-2-((tert-butoxycarbonyl)amino)propoxy)-2-methylnonanoic acid (3.03 g, 87% yield) as a colorless oil. LCMS (ESI): [M+H]$^+$=346.2; $^1$H NMR (300 MHz, DMSO-$d_6$) δ 12.11 (s, 1H), 6.56 (d, J=8.1 Hz, 1H), 3.53-3.15 (m, 4H), 2.64-2.60 (m, 1H), 1.37 (s, 9H), 1.35-1.25 (m, 10H), 0.99 (d, J=6.9 Hz, 3H), 0.95 (d, J=7.2 Hz, 3H), 0.86 (t, J=6.6 Hz, 3H).

Intermediate 4. (2R,3R)-3-((R)-2-(((((9H-Fluoren-9-yl)methoxy)carbonyl)amino)propoxy)-2-methyl-nonanoic acid

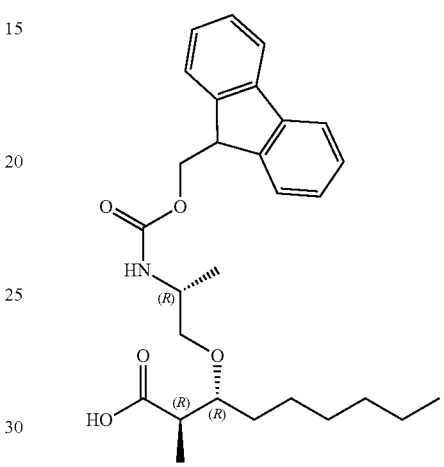

To a solution of (2S,3R)-3-[(2R)-2-(tert-butoxycarbonylamino)propoxy]-2-methyl-nonanoic acid (1.15 g, 3.33 mmol, Intermediate 3) in dioxane (10 mL) was added a solution of HCl/dioxane (40 mL, 4 mol/L). The mixture was stirred at 25° C. for 1 h, and concentrated under reduced pressure. The residue was dissolved with water (10 mL) and THF (30 mL) and a solution of lithium hydroxide (320.0 mg, 13.33 mmol) in water (5 mL) was added at 0° C., followed by a solution of 9-fluorenylmethylchloroformate (1.03 g, 3.99 mmol) in THF (5 mL) at 0° C. The reaction mixture was stirred at 25° C. for 4 h, and concentrated under reduced pressure. The residue was diluted with water (10 mL), and aqueous HCl solution (1 M) was carefully added until pH6. The resulting solution was concentrated under reduced pressure. The residue was purified by flash chromatography on silica gel eluting with petroleum ether/ethyl acetate (2/1) to afford the title compound (1.12 g, 72% yield) as a colorless oil. LCMS (ESI): [M+H]$^+$=468.2; $^1$H NMR (400 MHz, DMSO-$d_6$) δ 12.16 (s, 1H), 7.88 (d, J=7.6 Hz, 2H), 7.69 (d, J=7.6 Hz, 2H), 7.43-7.39 (m, 2H), 7.34-7.30 (m, 2H), 7.14 (d, J=8.4 Hz, 1H), 4.28-4.18 (m, 3H), 3.64-3.47 (m, 2H), 3.36-3.21 (m, 2H), 2.67-2.60 (m, 1H), 1.34-1.18 (m, 10H), 1.04 (d, J=6.4 Hz, 3H), 0.96 (d, J=7.2 Hz, 3H), 0.80 (t, J=6.4 Hz, 3H).

237

Intermediate 5. N-(((9H-Fluoren-9-yl)methoxy)carbonyl)-O-(3-((tert-butoxycarbonyl)amino)propyl)-L-serine

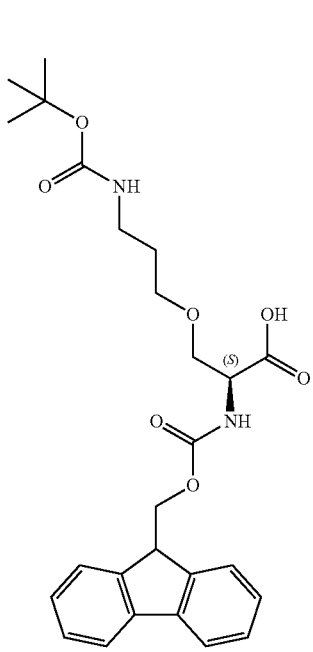

Step 1. Methyl N-((benzyloxy)carbonyl)-O-(3-nitropropyl)-L-serinate

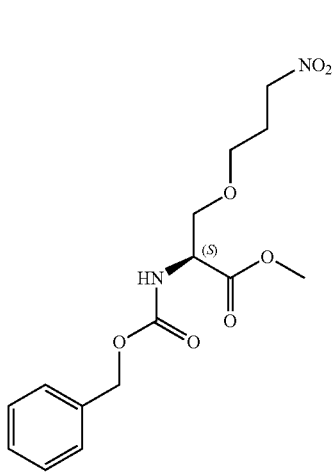

To a solution of 1-benzyl 2-methyl (S)-aziridine-1,2-dicarboxylate (11.32 g, 48.14 mmol) and 3-nitropropan-1-ol (5.06 g, 48.12 mmol) in chloroform (150 mL) at 0° C. was added $BF_3·Et_2O$ (0.1 mL) under nitrogen. The reaction mixture was allowed to warm to room temperature and stirred at room temperature for 16 h. The solvent was removed under reduced pressure. The residue was purified by flash chromatography on silica gel eluting with petroleum ether/ethyl acetate (5/1) to afford the title compound (11.02 g, 67% yield) as a colorless oil. LCMS (ESI): $[M+H]^+=341.1$.

238

Step 2. Methyl N-((benzyloxy)carbonyl)-O-(3-((tert-butoxycarbonyl)amino)propyl)-L-serinate

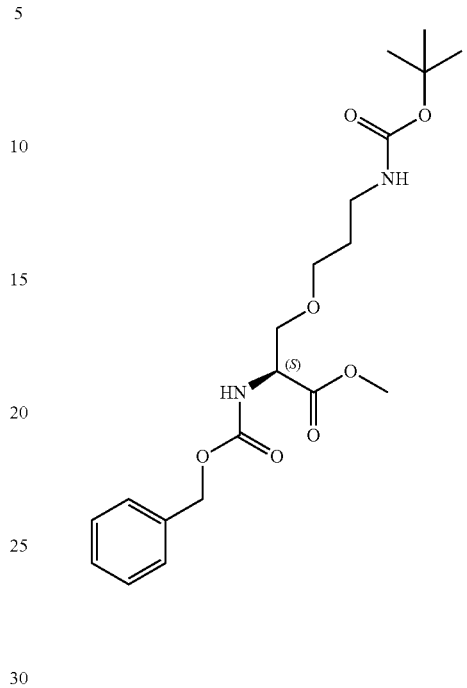

To a solution of methyl N-((benzyloxy)carbonyl)-O-(3-nitropropyl)-L-serinate (11.02 g, 32.4 mmol) in ethanol (80 mL) and water (80 mL) was added $NH_4Cl$ (8.75 g, 162 mmol), followed by the addition of iron powder (9.07 g, 162 mmol). The reaction mixture was stirred at reflux for 4 h. The solid was filtered off and washed with ethanol. The filtrate was concentrated under reduced pressure to remove approximately half of the volume. The residue was partitioned between water and ethyl acetate. The aqueous phase was extracted with ethyl acetate (2×). The combined organic phases were dried over sodium sulfate and concentrated under reduced pressure to afford a residue (8.89 g), which was re-dissolved in DCM (100 mL), then di-tert-butyl dicarbonate (9.36 g, 42.95 mmol) was added, followed by triethylamine (8.68 g, 85.89 mmol). The reaction mixture was stirred at ambient temperature for 2 h. The solvent was evaporated under reduced pressure. The residue was purified by flash chromatography on silica gel eluting with ethyl acetate/petroleum ether (0-50%) to afford the title compound (9.22 g, 78% yield) as a yellow oil. LCMS (ESI): $[M+H]^+=411.2$.

Step 3. Methyl O-(3-((tert-butoxycarbonyl)amino)propyl)-L-serinate

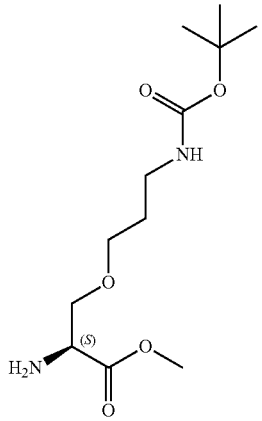

To a solution of methyl N-((benzyloxy)carbonyl)-O-(3-((tert-butoxycarbonyl)amino)propyl)-L-serinate (9.22 g, 22.48 mmol) in ethyl acetate (100 mL) under nitrogen was added palladium (10 wt. % on carbon, 0.93 g) at 0° C. The flask was evacuated and backfilled with hydrogen, and then stirred at 25° C. under a hydrogen balloon for 3 h. The reaction mixture was filtered through celite, and the filtrate was concentrated under reduced pressure to give the title compound. LCMS (ESI) [M+H]$^+$=277.2.

Step 4. N-(((9H-Fluoren-9-yl)methoxy)carbonyl)-O-(3-((tert-butoxycarbonyl)amino)propyl)-L-serine To a solution of methyl O-(3-((tert-butoxycarbonyl)amino)propyl)-L-serinate (5.90 g, 21.35 mmol) in THF (150 mL) and water (150 mL) was added lithium hydroxide (2.05 g, 85.41 mmol) at ambient temperature. The resulting mixture was stirred at 25° C. for 3 h, cooled to 0° C., and then a solution of 9-fluorenylmethylchloroformate (8.71 g, 33.74 mmol) in THF (10 mL) was added dropwise. The reaction mixture was stirred at 0° C. for 2 h. The reaction mixture was acidified by the addition of 1M HCl to pH6 and extracted with ethyl acetate (3×100 mL). The combined organic phases were dried with Na$_2$SO$_4$, filtered and concentrated under reduced pressure. The residue was purified by flash chromatography on silica gel eluting with petroleum ether/ethyl acetate (5/1) to afford the title compound (6.12 g, 56% yield) as a white solid. LCMS (ESI): [M+H]$^+$=485.1. $^1$H NMR (300 MHz, DMSO-d$_6$) δ 12.78 (s, 1H), 7.90 (d, J=7.5 Hz, 2H), 7.75 (d, J=7.5 Hz, 2H), 7.64 (d, J=8.1 Hz, 1H), 7.45-7.37 (m, 2H), 7.32-7.30 (m, 2H), 6.79 (t, J=5.7 Hz, 1H), 4.30-4.09 (m, 4H), 3.67-3.61 (m, 2H), 3.46-3.39 (m, 2H), 3.00-2.94 (m, 2H), 1.63-1.56 (m, 2H), 1.37 (s, 9H).

Intermediate 6. N-(((9H-Fluoren-9-yl)methoxy)carbonyl)-O-((1r,3S)-3-((tert-butoxy carbonyl)amino) cyclobutyl)-L-serine

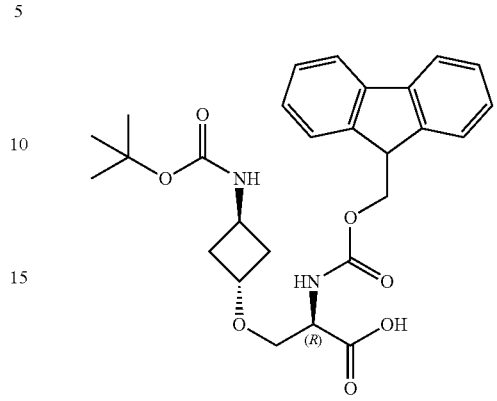

Step 1: Methyl N-((benzyloxy)carbonyl)-O-((1r,3S)-3-((tert-butoxycarbonyl)amino) cyclobutyl)-L-serinate

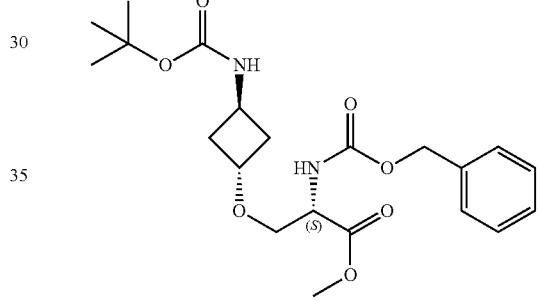

A solution of trans-tert-butyl N-(3-hydroxycyclobutyl)carbamate (7.95 g, 42.46 mmol) and BF$_3$.Et$_2$O (1.23 g, 8.54 mmol) in chloroform (100 mL) was stirred at 0° C. Then a solution of 1-benzyl 2-methyl (S)-aziridine-1,2-dicarboxylate (10.0 g, 42.51 mmol) in chloroform (10 mL) was added dropwise at 0° C. The reaction mixture was then stirred at 25° C. for 20 h and concentrated under reduced pressure. The residue was purified by flash chromatography on silica gel eluting with petroleum ether/ethyl acetate (2/1) to afford the title compound (2.5 g, 13% yield) as a white solid. LCMS (ESI): [M+H]$^+$=423.2.

Step 2: N-(((9H-Fluoren-9-yl)methoxy)carbonyl)-O-((1r,3S)-3-((tert-butoxy carbonyl)amino)cyclobutyl)-L-serine To a solution of methyl (2S)-2-(benzyloxycarbonylamino)-3-[3-(tert-butoxycarbonylamino) cyclobutoxy]propanoate (2.5 g, 5.92 mmol) in ethyl acetate (30 mL) was added palladium (10 wt. % on carbon, 1.0 g) under nitrogen. The reaction mixture was evacuated and backfilled with hydrogen and stirred at 25° C. for 1 h under a hydrogen balloon. The catalyst was filtered off and rinsed with ethyl acetate. The filtrate was concentrated under reduced pressure to afford methyl (2S)-2-amino-3-[3-(tert-butoxycarbonylamino)cyclobutoxy]propanoate (1.7 g, crude) as a yellow oil. To 1.5 g of this material was added a solution of lithium hydroxide (250.0 mg, 10.42 mmol) in water (5 mL) and dioxane (15 mL). The resulting solution was stirred for 1 h at 25° C. Then 9-fluorenylmethylchloroformate (1.61 g, 6.24 mmol) was added. The mixture was stirred at 25° C. for 1 h, diluted with water (20 ml) and acidified to pH 6 with 1 N HCl. The resulting solution was extracted with ethyl acetate (3×100 mL). The organic combined layers were dried over anhydrous sodium sulfate, filtered and concentrated under reduced pressure. The residue was purified by flash chromatography on silica gel eluting with petroleum ether/ethyl acetate (4/1) to afford the title compound (1.85 g, 71% yield) as a white solid. LCMS (ESI): [M+H]$^+$=497.2; $^1$H NMR (400 MHz, DMSO-d$_6$) δ 12.76 (s, 1H), 7.89 (d, J=7.6 Hz, 2H), 7.76 (d, J=7.6 Hz, 2H), 7.64 (d, J=8.4 Hz, 1H), 7.44-7.40 (m, 2H), 7.35-7.31 (m, 2H), 7.16 (d, J=7.2 Hz, 1H), 4.29-4.17 (m, 4H), 4.04-3.98 (m, 2H), 3.58-3.49 (m, 2H), 2.17-2.01 (m, 4H), 1.37 (s, 9H).

TABLE 3

Intermediates depicted in the following table were prepared using methods analogous to those described for Intermediate 6.

| Intermediate No. | Structure | LCMS (ESI): [M + H]+ |
|---|---|---|
| P2A | 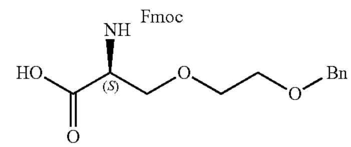 | 462.2 |
| P2B | 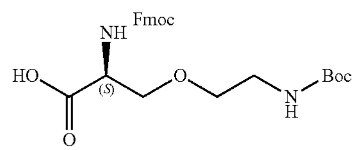 | 471.2 |
| P2C | 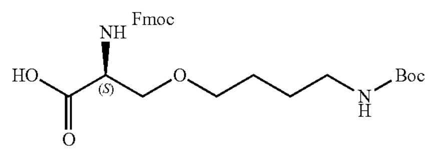 | 499.2 |
| P2D | 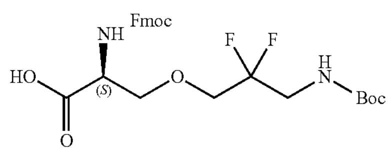 | 521.2 |
| P2E | 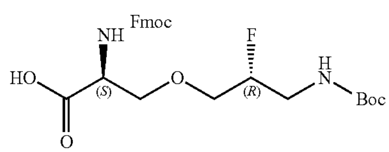 | 503.2 |
| P2F | 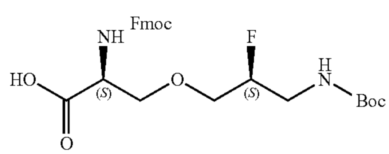 | 503.2 |
| P2G | 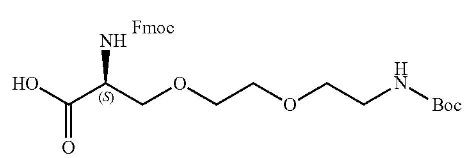 | 515.2 |
| P2H | 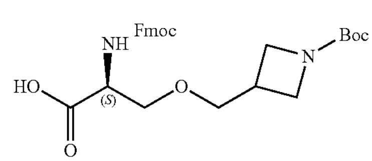 | 497.2 |

TABLE 3-continued

Intermediates depicted in the following table were prepared using methods analogous to those described for Intermediate 6.

| Intermediate No. | Structure | LCMS (ESI): [M + H]+ |
|---|---|---|
| P2I | 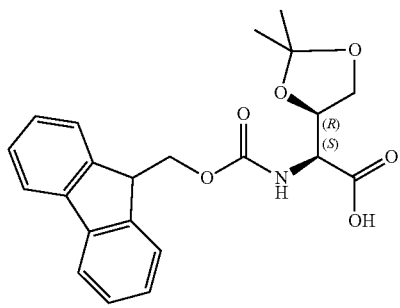 | 511.3 |
| P2L | 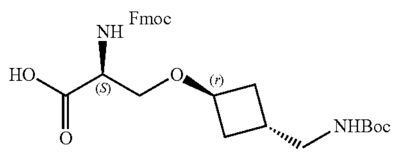 | 511.2 |

Intermediate P2J: (S)-2-((((9H-Fluoren-9-yl)methoxy)carbonyl)amino)-2-((R)-2,2-dimethyl-1,3-dioxolan-4-yl)acetic acid Step 1: Methyl (S)-2-azido-2-((R)-2,2-dimethyl-1,3-dioxolan-4-yl)acetate

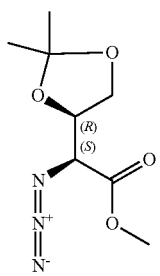

To a solution of methyl (R)-2-((S)-2,2-dimethyl-1,3-dioxolan-4-yl)-2-hydroxyacetate (3.7 g, 19.45 mmol) in DCM (20 mL) was added dropwise trifluoromethanesulfonic anhydride (4.5 mL, 26.3 mmol) at −20° C., followed by 2,6-lutidine (2.6 mL, 22.8 mmol) at −20° C. under nitrogen. The reaction mixture was stirred at −20° C. for 2 h. The reaction was quenched by the addition of 10 mL water. The resulting solution was extracted with DCM (3×50 mL). The organic layers were combined, dried over sodium sulfate and evaporated under reduced pressure.

The resulting material was dissolved in DMF (50 mL), then lithium azide (12 mL, 20% in water) was added dropwise into the solution at 0° C. The reaction mixture was stirred at room temperature for 3 h and then partitioned between DCM (100 mL) and water (60 mL). The aqueous phase was extracted with DCM (2×). The organic layers were combined, dried over anhydrous sodium sulfate and evaporated under reduced pressure. The residue was purified by flash chromatography on silica gel eluting with 20% ethyl acetate in petroleum ether to afford the title compound (2.49 g, 59% yield) as a colorless oil. TLC $R_f$=0.3, PE/EA=4/1.

Step 2: (S)-2-((((9H-Fluoren-9-yl)methoxy)carbonyl)amino)-2-((R)-2,2-dimethyl-1,3-dioxolan-4-yl)acetic acid A solution of methyl (S)-2-azido-2-((R)-2,2-dimethyl-1,3-dioxolan-4-yl)acetate (2.49 g, 11.62 mmol) in methanol (150 mL) was treated with palladium (680 mg, 10% loading on carbon) and stirred under a hydrogen balloon at room temperature for 2 h. The solid was removed via filtration, and the filtrate was evaporated under reduced pressure. The resulting residue was dissolved in THF (150 mL). Then a solution of LiOH (557.0 mg, 23.21 mmol) in water (50 mL) was added. The resulting mixture was stirred for 2 h at room temperature. Then 9-fluorenylmethylchloroformate (3.61 g, 13.95 mmol) was added. The mixture was stirred for 30 min and acidified with aqueous hydrochloric acid (1 M). The majority of the solvent was removed via filtration and the remaining solution was extracted with ethyl acetate (3×50 mL). The organic layers were combined, dried over anhydrous sodium sulfate and evaporated under reduced pressure. The residue was purified by flash chromatography on silica gel eluting with 5-10% ethyl acetate in petroleum ether for 20 min, then 9% methanol in DCM, to afford the title compound (4.05 g, 87% yield) as a white solid. LCMS (ESI): [M+H]$^+$=398.2; $^1$H NMR (400 MHz, DMSO-$d_6$) δ 12.75 (s, 1H), 7.90 (d, J=7.6 Hz, 2H), 7.81 (d, J=8.8 Hz, 1H), 7.72 (d, J=7.2 Hz, 2H), 7.44-7.41 (m, 2H), 7.34-7.31 (m, 2H), 4.35-4.21 (m, 4H), 4.13-4.09 (m, 1H), 3.98-3.93 (m, 1H), 3.81-3.75 (m, 1H), 1.31 (s, 3H), 1.26 (s, 3H).

Intermediate P2K: (S)-2-((((9H-Fluoren-9-yl)methoxy)carbonyl)amino)-3-acetamidopropanoic acid

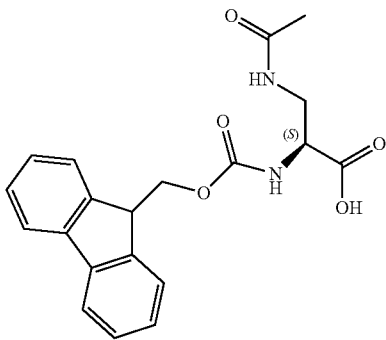

To a solution of (S)-2-((((9H-fluoren-9-yl)methoxy)carbonyl)amino)-3-aminopropanoic acid (4.0 g, 12 mmol) and DIPEA (3.2 mL, 18 mmol) in DCM (40 mL) was added acetic anhydride (1376 mg, 13.48 mmol) at 0° C. The resulting solution was stirred for 2 h at room temperature. The reaction was quenched with 50 mL of water. The resulting solution was extracted with ethyl acetate (3×100 mL) and the organic layers were combined. The organic layer was dried over anhydrous sodium sulfate, filtered and evaporated under reduced pressure. The residue was purified by flash chromatography on silica gel eluting with ethyl acetate/petroleum ether (1/5) to afford the title compound (3.8 g, 84% yield) as a white solid. LCMS (ESI): [M+H]⁺=369.1; ¹H NMR (300 MHz, DMSO-$d_6$) δ 12.73 (s, 1H), 7.94 (t, J=5.7 Hz, 1H), 7.88 (d, J=7.5 Hz, 2H), 7.70 (d, J=7.5 Hz, 2H), 7.54 (d, J=8.1 Hz, 1H), 7.43-7.38 (m, 2H), 7.34-7.29 (m, 2H), 4.30-4.19 (m, 3H), 4.11-4.02 (m, 1H), 3.49-3.41 (m, 1H), 3.30-3.15 (m, 1H), 1.78 (s, 3H).

Intermediate 7: (2S,3S)-3-Amino-2-((tert-butoxycarbonyl)amino)butanoic acid

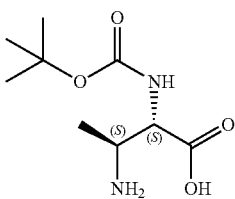

Step 1: Benzyl (tert-butoxycarbonyl)-L-threoninate

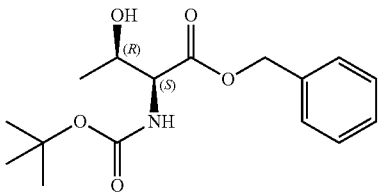

To a mixture of benzyl L-threoninate (400 g, 1.5 mol, 0.5 oxalic acid salt) and di-tert-butyl-dicarbonate (514 g, 2.3 mol) in methanol (3 L) and H₂O (3 L) was added NaHCO₃ (395 g, 4.7 mol) in one portion at 0° C. under N₂. The mixture was stirred at 20° C. for 12 hours. TLC (Petroleum ether:Ethyl acetate=10:1, $R_f$ 0.2) showed the reaction was complete. The mixture was concentrated under vacuum, then treated with 1000 mL 1M HCl to pH=7, the aqueous phase was extracted with ethyl acetate (600 mL×3). The combined organic phases were washed with brine (200 mL×2), dried over anhydrous Na₂SO₄, filtered and concentrated in vacuum. This step was repeated in parallel, to give the title compound (combined yield 880 g, 90%) as a yellow oil.

Step 2: 4-Benzyl 3-(tert-butyl) (4S,5R)-5-methyl-1,2,3-oxathiazolidine-3,4-dicarboxylate 2-oxide

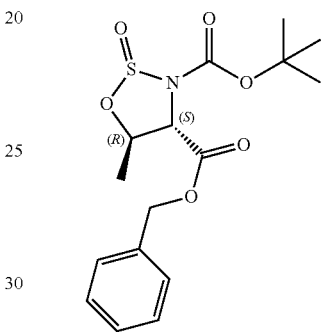

To a mixture of SOCl₂ (361 g, 3 mol, 220 mL) in acetonitrile (4.5 L) was added benzyl (tert-butoxycarbonyl)-L-threoninate (470 g, 1.5 mol, 1 eq) in one portion at −5° C. under N₂. The mixture was stirred at −5° C. for 30 min, then added pyridine (613 mL) at 0° C., and the resulting mixture was stirred for 3 hours. TLC (Petroleum ether:Ethyl acetate=10:1, $R_f$ 0.5) showed the reaction was complete. The mixture was evaporated in vacuo. The resulting residue was dissolved in ethyl acetate (500 mL), washed with H₂O (200 mL×3) and brine (200 mL), dried over anhydrous Na₂SO₄, filtered and evaporated under vacuum. This step was repeated in parallel to afford the title compound (combined 890 g, crude) as a yellow oil. The crude product was used to the next step directly.

Step 3: 4-Benzyl 3-(tert-butyl) (4S,5R)-5-methyl-1,2,3-oxathiazolidine-3,4-dicarboxylate 2,2-dioxide

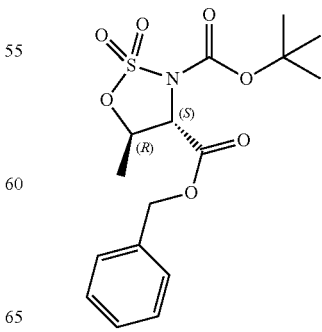

To a mixture of 4-benzyl 3-(tert-butyl) (4S,5R)-5-methyl-1,2,3-oxathiazolidine-3,4-dicarboxylate 2-oxide (445 g, 1.2 mol) in acetonitrile (2.5 L) was added RuCl$_3$ (25.9 g, 125 mmol) and NaIO$_4$ (535 g, 2.5 mol) in one portion at 0° C. under N$_2$. The resulting mixture was stirred for 30 min, then added H$_2$O (2.1 L) slowly at 0° C. The mixture was stirred at 20° C. for 1.5 hours TLC (Petroleum ether:Ethyl acetate=5:1, R$_f$ 0.5) showed the reaction was complete. The reaction mixture was filtered and the filtrate was extracted with ethyl acetate (500 mL×3). The combined organic phase was washed with brine (100 mL×2), dried with anhydrous Na$_2$SO$_4$, filtered and evaporated under vacuum. This step was repeated in parallel to afford the title compound (combined 860 g, crude) as a red oil. The crude product was used to the next step directly.

Step 4: Benzyl (2S,3S)-3-azido-2-((tert-butoxycarbonyl)amino)butanoate

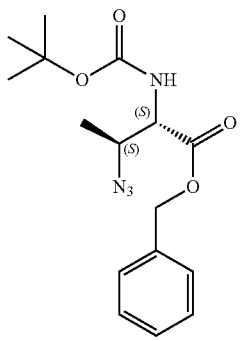

To a mixture of 4-benzyl 3-(tert-butyl) (4S,5R)-5-methyl-1,2,3-oxathiazolidine-3,4-dicarboxylate 2,2-dioxide (300 g, 807 mmol) in DMF (1.5 L) was added NaN$_3$ (73 g, 1.1 mol) in one portion at −40° C. under N$_2$. The mixture was warmed to 20° C. and stirred at 20° C. for 3 h, then cooled to 0° C. and brine (2 L) and H$_2$SO$_4$ (2 M, 100 mL, 0.2 eq) were added sequentially. The mixture was warmed to 20° C. and stirred for 8 hours. TLC (Petroleum ether:Ethyl acetate=5:1, R$_f$ 0.5) showed the reaction was complete. The mixture cooled to 0° C. and saturated aqueous Na$_2$CO$_3$ (500 mL) was added to adjust to pH=8, then the aqueous phase was extracted with methyl-tert-butyl ether (400 mL×3). The combined organic phases were washed with brine (100 mL×2), dried with anhydrous Na$_2$SO$_4$, filtered and evaporated under vacuum. This step was repeated in parallel to afford the title compound (combined 460.00 g, crude) as a yellow oil. The crude product was used to the next step directly.

Step 5: (2S,3S)-3-Amino-2-((tert-butoxycarbonyl)amino)butanoic acid

To a solution of benzyl (2S,3S)-3-azido-2-((tert-butoxycarbonyl)amino)butanoate (30 g, 89 mmol) in MeOH (500 mL) was added palladium (10 g, 10% on carbon) under N$_2$. The suspension was degassed under vacuum and purged with H$_2$ (50 psi) several times. The mixture was stirred under H$_2$ (50 psi) at 20° C. for 12 h. The reaction mixture was filtered and the filtrate was evaporated in vacuo. This step was repeated in parallel to afford the title compound (combined 10 g, yield: 51%) as a white solid. LCMS (ESI):

[M+H]$^+$=219.2; $^1$H NMR (400 MHz, methanol-d$_4$) δ 4.11 (1H, d, J=4.02 Hz), 3.59-3.76 (1H, m), 1.47 (9H, s) 1.22 (3H, d, J=6.53 Hz).

Intermediate 8: O-Benzyl-N—((S)-3-(((benzyloxy)carbonyl)amino)-2-((S)-2-cyclohexyl-2-((S)-4-methyl-2-(methylamino)pentanamido)acetamido)propanoyl)-L-allothreonine-(2-chlorotrityl resin)

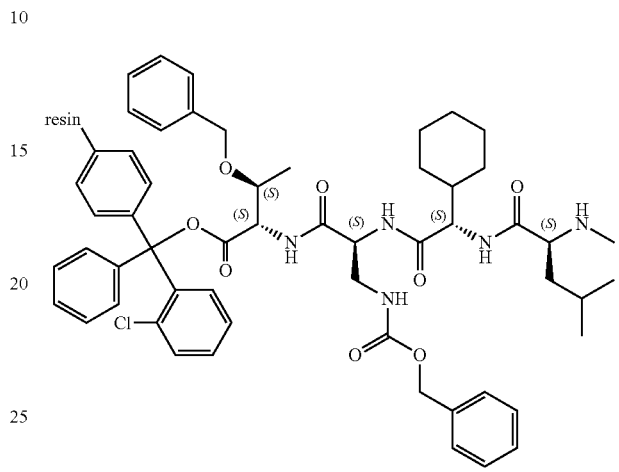

2-Chlorotrityl chloride resin (loading 0.956 mmol/g, 5 g) was swelled with the mixture of DMF:DCM (1:1, 20 mL) for 40 min. The resin was drained and then a solution of (2S,3S)-3-benzyloxy-2-(9H-fluoren-9-ylmethoxycarbonylamino)butanoic acid (Example 1, step 2) (2.461 g, 5.70 mmol), DMF (10 mL) and DIPEA (495.6 mg, 3.84 mmol) was added. The resin was agitated with nitrogen bubbling for 4 h, drained, and rinsed sequentially with 10 mL DCM/MeOH/DIPEA (10/10/1=V/V/V), 10 mL DMF, 10 mL DCM, 10 mL DMF.

The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2S)-3-(benzyloxycarbonylamino)-2-(9H-fluoren-9-ylmethoxycarbonylamino)propanoic acid (4.372 g, 9.494 mmol), a pre-prepared stock solution of HOBt/HATU (1:1) in DMF (0.4 mmol/mL, 25 mL) and DIPEA (2.4 g, 19 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (S)-2-((((9H-fluoren-9-yl)methoxy)carbonyl)amino)-2-cyclohexylacetic acid (3.61 g, 9.52 mmol), a pre-prepared stock solution of HOBt/HATU (1:1) in DMF (0.4 mmol/mL, 25 mL) and DIPEA (2.4 g, 19 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2S)-2-{[(9H-fluoren-9-yl-methoxy)carbonyl](methyl)amino}-4-methylpentanoic acid (3.492 g, 9.50 mmol), a pre-prepared stock solution of HOBt/HATU (1:1) in DMF (0.4 mmol/mL, 25 mL) and DIPEA (2.4 g, 19 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed with DMF (3×25 mL) and DCM (3×25 mL) to afford a resin-bound tetrapeptide with a loading of 0.44 mmol/g.

Example 1: (6S,9S,12S,15S,18R,19R)-9-(aminomethyl)-12-((R)-sec-butyl)-19-decyl-6-((S)-1-hydroxyethyl)-15-isobutyl-16,18-dimethyl-1-oxa-4,7,10,13,16-pentaazacyclononadecane-2,5,8,11,14,17-hexaone

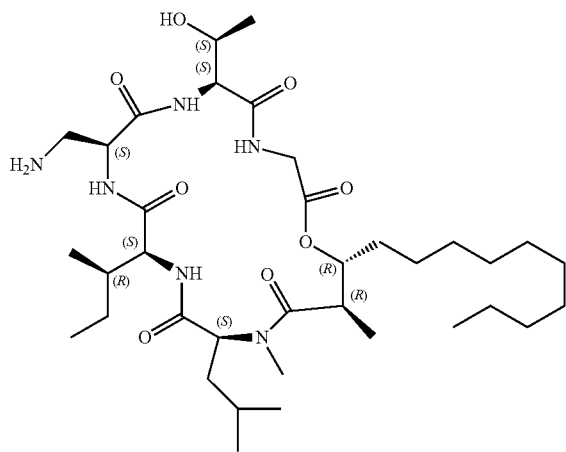

Step 1.
O-benzyl-N-(tert-butxycarbony)-L-alothreonine

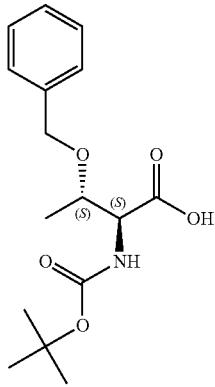

Into a 2000 mL 3-necked round-bottom flask purged and maintained with an inert atmosphere of nitrogen, was placed (2S,3S)-2-amino-3-hydroxybutanoic acid (85 g, 714 mmol), methanol (450 mL), water (450 mL), and sodium bicarbonate (150 g, 1.79 mol). This was followed by the addition of Boc$_2$O (187 g, 856.82 mmol, 1.20 equiv), in portions at 0° C. over 60 min. The resulting solution was stirred for 12 h at 25° C. The resulting mixture was concentrated under reduced pressure. The resulting solution was diluted with 500 mL of water. The resulting solution was extracted with 3×500 mL of ether and the aqueous layers combined. The pH value of the aqueous was adjusted to 3 with hydrogen chloride (1 mol/L). The resulting solution was extracted with 3×500 mL of ethyl acetate and the organic layers combined and dried over anhydrous sodium sulfate and concentrated under reduced pressure. This resulted in 110 g (67%) of (2S,3S)-2-[[(tert-butoxy)carbonyl]amino]-3-hydroxybutanoic acid Into a 2000 mL 3-necked round-bottom flask purged and maintained with an inert atmosphere of nitrogen, was placed (2S,3S)-2-[[(tert-butoxy)carbonyl]amino]-3-hydroxybutanoic acid (110 g, 501.74 mmol) and DMF (1100 mL). This was followed by the addition of sodium hydride (84.4 g, 3.52 mol), in portions at 0° C. over 60 min. The resulting solution was stirred for 2 h at 0° C. To this was added benzyl bromide (85.4 g, 499.33 mmol) dropwise with stirring at 0° C. over 30 min. The resulting solution was stirred for 5 h at 0° C. The reaction was then quenched by the addition of 1000 mL of water/ice. The resulting solution was extracted with 3×2000 mL of ethyl acetate and the aqueous layers combined. The pH value of the solution was adjusted to 3 with aqueous hydrogen chloride (1 mol/L). The resulting solution was extracted with 3×2000 mL of ethyl acetate and the organic layers combined and dried over anhydrous sodium sulfate and concentrated under vacuum. The crude product was re-crystallized from petroleum ether:ethyl acetate in the ratio of 10:1. This resulted in 60 g (37%) of O-benzyl-N-(tert-butoxycarbonyl)-L-allothreonine.

Step 2. Fmoc-allothreonine(Bzl)-OH

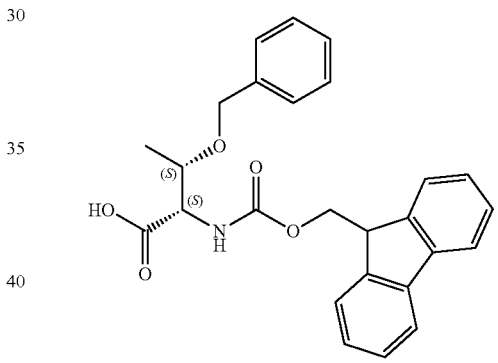

Into a 2000 mL 3-necked round-bottom flask, was placed O-benzyl-N-(tert-butoxycarbonyl)-L-allothreonine (60 g, 193.95 mmol), dioxane (600 mL), hydrogen chloride (4N solution in dioxane, 600 mL). The resulting solution was stirred for 12 h at 25° C. The resulting mixture was concentrated under vacuum. This resulted in 50 g (crude) O-benzyl-L-allothreonine hydrochloride as a white solid.

Into a 2000 mL 3-necked round-bottom flask purged and maintained with an inert atmosphere of nitrogen, was placed O-benzyl-L-allothreonine hydrochloride (50 g, 203.50 mmol), dioxane (500 mL), water (500 mL), sodium carbonate (43.3 g, 408.53 mmol), and FmocONSu (69 g, 1.00 equiv). The resulting solution was stirred for 12 h at 25° C. The pH value of the solution was adjusted to 3 with hydrogen chloride (1 mol/L). The resulting solution was extracted with 3×500 mL of ethyl acetate and the organic layers combined and concentrated under vacuum. The residue was purified via silica gel chromatography with ethyl acetate/petroleum ether (1:1). This resulted in 53.4 g (58% yield over two steps) of Fmoc-allothreonine(Bzl)-OH as a white solid. LCMS (ESI): [M+H]$^+$=432; $^1$H NMR (300 MHz, CDCl$_3$) δ 12.85 (1H, s), 7.88-7.90 (2H, m), 7.74-7.77 (2H, m), 7.64-7.67 (1H, m), 7.41-7.44 (2H, m), 7.22-7.39 (7H, m), 4.46-4.50 (2H, m), 4.34-4.38 (1H, m), 4.20-4.30 (3H, m), 3.89-3.93 (1H, m), 1.16 (3H, s).

Step 3. N-Me-leucine-alloisoleucine-Dap(Cbz)-allo-threonine(Bzl)-glycine-(2-chlorotrityl resin)

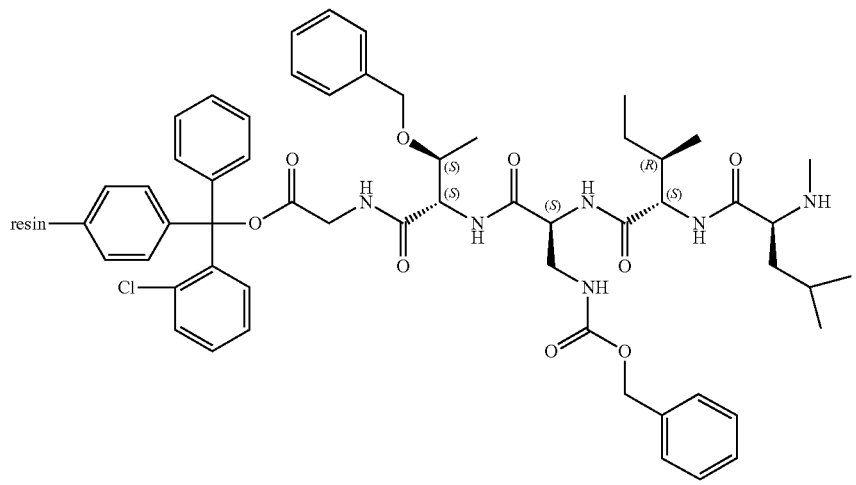

Commercially available 2-chlorotrityl resin preloaded with glycine (resin loading 0.536 mmol/g, 5.60 g) was swelled with 30 mL DMA for 2 h. The resin was drained, and treated with a solution (premixed at room temperature for 15 min) of Fmoc-allothreonine(Bzl)-OH (3.267 g, 7.571 mmol), HBTU (2.904 g, 7.657 mmol), DIPEA (1.9 mL, 11 mmol) and DMA (25 mL). The resin was agitated with nitrogen bubbling for 2.5 hr, and then drained and rinsed with DMA. Unreacted starting material was capped by treating the resin with 25 mL DMA, 1 mL DIPEA and 1 mL acetic anhydride. The resin was agitated with nitrogen bubbling for 5 min, and then drained and rinsed with DMA (2×25 mL) and DCM (3×25 mL).

The resin was treated with 25 mL of 20% piperidine in DMF, and agitated with nitrogen bubbling for 30 min. The resin was drained and rinsed with DMA (3×25 mL) and DCM (3×25 mL). The resin was treated with a solution (premixed at room temperature for 15 min) of (S)-2-(Fmoc-amino)-3-(((benzyloxy)carbonyl)amino)propanoic acid (3.48 g, 7.56 mmol), HBTU (2.88 g, 7.59 mmol), and DIPEA (1.9 mL, 11 mmol) in DMA (25 mL). The resin was agitated with nitrogen bubbling for 2 hr, and then drained and rinsed with DMA (2×25 mL) and DCM (3×25 mL).

The resin was treated with 25 mL of 20% piperidine in DMF, and agitated with nitrogen bubbling for 60 min. The resin was drained and rinsed with DMA (3×25 mL) and DCM (3×25 mL). The resin was treated with a solution (premixed at room temperature for 15 min) of Fmoc-L-alloisoleucine (2.65 g, 7.50 mmol), HBTU (2.87 g, 7.57 mmol) and DIPEA (2.0 mL, 11 mmol) in DMA (25 mL). The resin was agitated with nitrogen bubbling for 2 hr, and then drained and rinsed with DMA (2×25 mL) and DCM (3×25 mL).

The resin was treated with 25 mL of 20% piperidine in DMF, and agitated with nitrogen bubbling for 60 min. The resin was drained and rinsed with DMA (3×25 mL) and DCM (3×25 mL) and dried under vacuum to afford 6.06 g of peptide on resin. Of this material, 1 g was placed in a vial and treated with a solution (premixed at room temperature for 20 min) of Fmoc-N-Me-leucine-OH (286 mg, 0.7784 mmol), HBTU (298 mg, 0.78578 mmol) and DIPEA (0.20 mL, 1.1 mmol) in DMA (5 mL). The vial was placed on a rotator at room temperature for 2.5 h, and then drained and rinsed with DMA (4×5 mL) and DCM (4×5 mL).

The resin was treated with 8 mL of 20% piperidine in DMF, and the vial was placed on a rotator at room temperature for 3 h, and then filtered and rinsed with DMA (4×5 mL) and DCM (4×5 mL) to afford the resin-bound peptide.

Step 4. O-benzyl-N—((S)-3-(((benzyloxy)carbonyl)amino)-2-((2S,3R)-2-((S)-2-((2R,3R)-3-hydroxy-N,2-dimethyltridecanamido)-4-methylpentanamido)-3-methylpentanamido)propanoyl)-L-allothreonylglycine

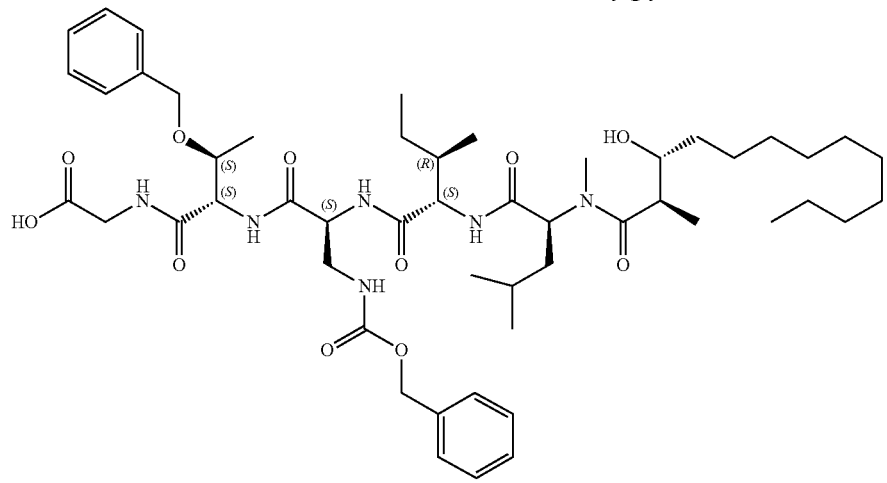

The resin-bound peptide from Step 2 was treated with THF (2 mL) and DIPEA (0.40 mL, 2.3 mmol), and allowed to swell for 50 min. Separately a solution of (2R,3R)-3-hydroxy-2-methyl-tridecanoic acid (Intermediate 2) (150.6 mg, 0.6162 mmol) in 3 mL THF was added to a solution of triphosgene (74 mg, 0.249 mmol) in 1 mL THF. 2,4,6-Trimethylpyridine (0.70 mL, 5.3 mmol) was added dropwise, upon which the mixture evolves heat and a colorless precipitate formed. This suspension was gently shaken for about 1 minute, after which it was added to the pretreated resin. The mixture was placed on a rotator at room temperature for 2 h, and then rinsed with DMA (4×5 mL) and DCM (4×5 mL).

The resin-bound depsipeptide was treated with 8 mL of 7:2:1 DCM:AcOH:TFE. The mixture was placed on a rotator at room temperature for 3 h, and then filtered, rinsing with 8 mL DCM. The combined filtrates were evaporated in vacuo, azeotroping with toluene (2×2 mL) and diethyl ether (1×2 mL) to afford 160.7 mg (0.1685 mmol, 37% yield over two steps) of the title compound, which was carried forward without purification. LCMS (ESI): [M+H]$^+$=953.5.

Step 5. Benzyl ((((6S,9S,12S,15S,18R,19R)-6-((S)-1-(benzyloxy)ethyl)-12-((R)-sec-butyl)-19-decyl-15-isobutyl-16,18-dimethyl-2,5,8,11,14,17-hexaoxo-1-oxa-4,7,10,13,16-pentaazacyclononadecan-9-yl)methyl)carbamate

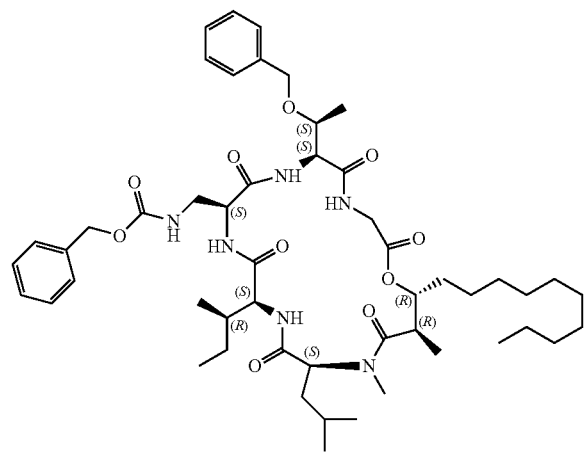

A solution of O-benzyl-N—((S)-3-(((benzyloxy)carbonyl)amino)-2-((2S,3R)-2-((S)-2-((2R,3R)-3-hydroxy-N,2-dimethyltridecanamido)-4-methylpentanamido)-3-methylpentanamido)propanoyl)-L-allothreonylglycine (160.7 mg, 0.1686 mmol) in THF (150 mL, 1850 mmol) was added dropwise via addition funnel over approximately 6 h to a stirring mixture of 2-methyl-6-nitrobenzoic anhydride (144 mg, 0.410 mmol) and DMAP (111 mg, 0.909 mmol) in DCM (50 mL, 780.1 mmol) at 35° C. After an additional 2 h, 2-methyl-6-nitrobenzoic anhydride (72 mg, 0.21 mmol) and DMAP (55 mg, 0.45 mmol) were added and the reaction mixture stirred overnight at room temperature. The reaction mixture was evaporated in vacuo and the resulting residue was dissolved in 120 mL ethyl acetate and washed sequentially with 2×20 mL 10% aqueous citric acid and 2×20 mL 2M aqueous Na$_2$CO$_3$. The organic layer was dried over magnesium sulfate and filtered, and evaporated in vacuo. The crude product was purified via flash chromatography on silica gel (12 g silica, solvent gradient: 0-10% methanol in dichloromethane) to yield 55.8 mg (35% yield) of the title compound. LCMS (ESI): [M+H]$^+$=935.45.

Step 6. (6S,9S,12S,15S,18R,19R)-9-(aminomethyl)-12-((R)-sec-butyl)-19-decyl-6-((S)-1-hydroxyethyl)-15-isobutyl-16,18-dimethyl-1-oxa-4,7,10,13,16-pentaazacyclononadecane-2,5,8,11,14,17-hexaone To a solution of benzyl ((((6S,9S,12S,15S,18R,19R)-6-((S)-1-(benzyloxy)ethyl)-12-((R)-sec-butyl)-19-decyl-15-isobutyl-16,18-dimethyl-2,5,8,11,14,17-hexaoxo-1-oxa-4,7,10,13,16-pentaazacyclononadecan-9-yl)methyl)carbamate (55.8 mg, 0.0597 mmol) in ethyl acetate (8 mL, 80 mmol), was added palladium (10 wt. % on carbon) (152 mg, 0.1429 mmol). The flask was evacuated and backfilled with hydrogen, and then stirred at 40° C. under a hydrogen balloon for 15 h. The reaction mixture was filtered through celite, rinsing with 100 mL 5% AcOH in methanol. The combined filtrates were evaporated in vacuo, and the crude product purified via reverse-phase HPLC and lyophilized to yield the title compound (5.68 mg, 13% yield) as the TFA salt. LCMS (ESI): R$_T$ (min)=5.489, [M+H]$^+$=711.5, method=A; $^1$H NMR (400 MHz, DMSO-d$_6$) δ 8.49-7.33 (m, 4H), 6.51 (br s, 2H), 5.08-4.00 (m, 3H), 3.91-3.69 (m, 1H), 3.11 (s, 3H), 2.73 (s, 1H), 2.26-1.95 (m, 1H), 1.72-1.30 (m, 6H), 1.29-1.19 (m, 19H), 1.11-0.97 (m, 7H), 0.96-0.82 (m, 15H), 0.82-0.72 (m, 3H).

Example 2: (6S,9S,12S,15S,18R,19R)-9-(aminomethyl)-12-((R)-sec-butyl)-15-(cyclopropylmethyl)-19-decyl-6-((S)-1-hydroxyethyl)-16,18-dimethyl-1-oxa-4,7,10,13,16-pentaazacyclononadecane-2,5,8,11,14,17-hexaone

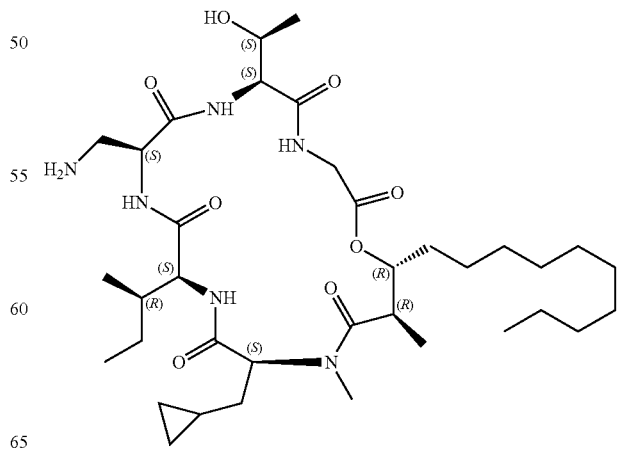

Step 1: (S)-2-((Fmoc)(methyl)amino)-3-cyclopropylpropanoic acid

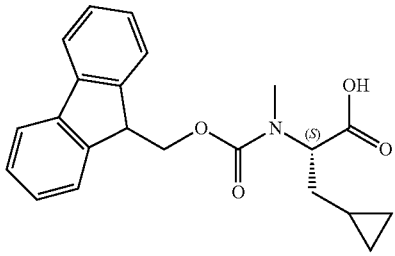

A mixture of (2S)-3-cyclopropyl-2-(Fmoc-amino)propanoic acid (0.989 g, 2.81 mmol), paraformaldehyde (816 mg, 8.60593 mmol), p-toluenesulfonic acid monohydrate (58 mg, 0.300 mmol), and toluene (10 mL, 93.4 mmol) was heated at 100° C., for 24 h. To the reaction was added paraformaldehyde (542 mg) and heating was continued for 6 h. The reaction mixture partitioned between ethyl acetate and saturated aqueous sodium bicarbonate, and the organic portion was washed with brine, dried over magnesium sulfate, filtered, and evaporated in vacuo. The crude product was purified via flash chromatography on silica gel (40 g silica, solvent gradient: 0-50% ethyl acetate in heptanes) to yield 0.953 g (93%) of (9H-fluoren-9-yl)methyl (S)-4-(cyclopropylmethyl)-5-oxooxazolidine-3-carboxylate. LCMS (ESI): $[M+H]^+=364.15$.

This material was dissolved in chloroform (3.5 mL, 43 mmol) and treated with triethylsilane (1.0 mL, 6.2 mmol) and TFA (3.5 mL, 45 mmol). The resulting mixture was stirred at room temperature for 7 h, and then evaporated in vacuo, azeotroping 2× with toluene. The crude product was purified via flash chromatography on silica gel (40 g silica, solvent gradient: 0-100% ethyl acetate in dichloromethane) to yield 0.7965 g (83%) of the title compound. LCMS (ESI): $[M+H]^+=366.15$; $^1$H NMR (400 MHz, DMSO-$d_6$) δ 7.89 (t, J=6.1 Hz, 2H), 7.65 (dd, J=7.5, 4.1 Hz, 2H), 7.41 (ddd, J=7.6, 5.4, 2.4 Hz, 2H), 7.33 (td, J=7.4, 6.9, 4.0 Hz, 2H), 4.58-4.22 (m, 4H), 2.76 (s, 3H), 1.83-1.41 (m, 2H), 0.59-0.25 (m, 3H), 0.11-0.04 (m, 2H).

Step 2. (6S,9S,12S,15S,18R,19R)-9-(aminomethyl)-12-((R)-sec-butyl)-15-(cyclopropylmethyl)-19-decyl-6-((S)-1-hydroxyethyl)-16,18-dimethyl-1-oxa-4,7,10,13,16-pentaazacyclononadecane-2,5,8,11,14,17-hexaone The title compound was prepared using (S)-2-((Fmoc)(methyl)amino)-3-cyclopropylpropanoic acid and following procedures analogous to those described for Example 1. LCMS (ESI): $R_T$ (mm) 5.196, $[M+H]^+=709.49$, method=A.

Example 3: (3S,6S,9S,12S,15S,18R,19R)-9-(aminomethyl)-12-((R)-sec-butyl)-19-decyl-6-((S)-1-hydroxyethyl)-15-isobutyl-3,16,18-trimethyl-1-oxa-4,7,10,13,16-pentaazacyclononadecane-2,5,8,11,14,17-hexaone

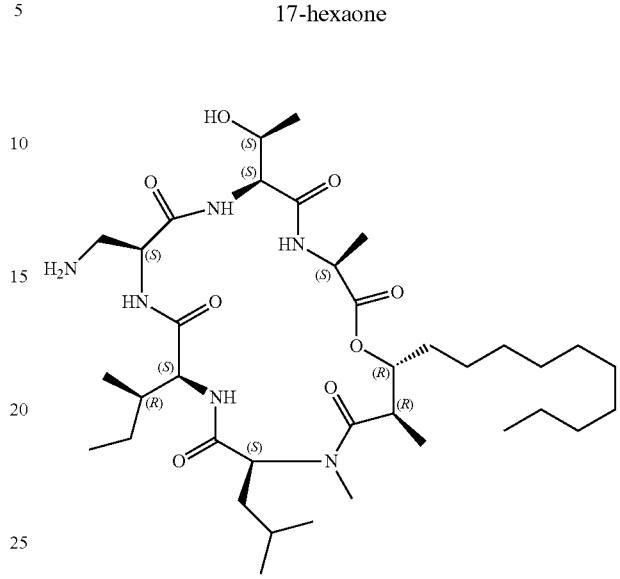

Step 1. 2-chlorotrityl resin loaded with alanine

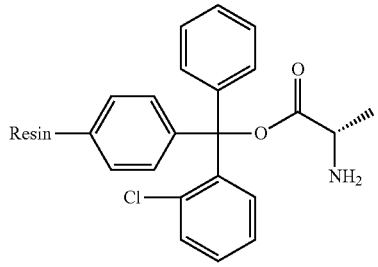

2-Chlorotrityl chloride resin (loading 0.956 mmol/g, 800 mg) was swelled with the mixture of DMF:DCM (1:1, 20 mL) for 40 min. The resin was drained and then a solution of Fmoc-Alanine-OH (473 mg, 1.52 mmol) and DIPEA (0.530 mL, 3.04 mmol) in DMF (8.00 mL) was added. The mixture was agitated with nitrogen bubbling for 3 h. The resin was drained and then a solution of MeOH:DCM (1:1, 20 mL) with DIPEA (1.00 mL) was added, and the mixture was agitated with nitrogen bubbling for 10 min. The resin was drained, rinsed with 10 mL DMF, 10 mL DCM, 10 mL DMF and drained. Then, to the resin was added 2 mL piperidine and 8 mL DMF, and the mixture agitated with nitrogen bubbling for 1 h. The resin was drained, and rinsed sequentially with 10 mL DMF, 10 mL DCM, 10 mL DMF, and 10 mL DMF.

Step 2. tert-Butyl ((3S,6S,9S,12S,15S,18R,19R)-6-((S)-1-tert-butoxyethyl)-12-((R)-sec-butyl)-19-decyl-15-isobutyl-3,16,18-trimethyl-2,5,8,11,14,17-hexaoxo-1-oxa-4,7,10,13,16-pentaazacyclononadecan-9-yl)methylcarbamate

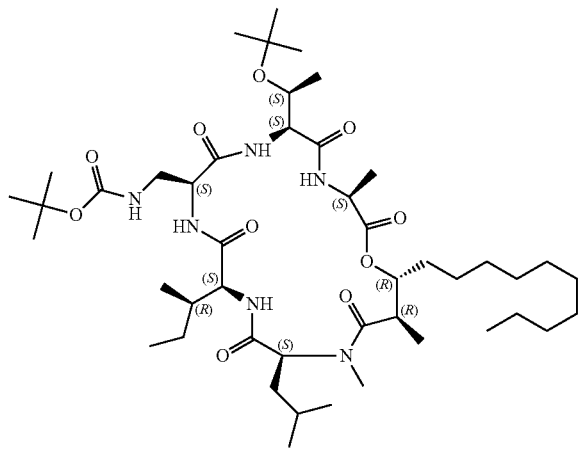

The title compound was prepared using the 2-chlorotrityl resin loaded with alanine from previous step, Fmoc-allothreonine(tBu)-OH, and (S)-2-(Fmoc-amino)-3-((tert-butoxycarbonyl)amino)propanoic acid following procedures analogous to those described for Example 1, Steps 3-5. LCMS (ESI): [M+H]$^+$=881.65.

Step 3. (3S,6S,9S,12S,15S,18R,19R)-9-(aminomethyl)-12-((R)-sec-butyl)-19-decyl-6-((S)-1-hydroxyethyl)-15-isobutyl-3,16,18-trimethyl-1-oxa-4,7,10,13,16-pentaazacyclononadecane-2,5,8,11,14,17-hexaone tert-Butyl ((3S,6S,9S,12S,15S,18R,19R)-6-((S)-1-tert-butoxyethyl)-12-((R)-sec-butyl)-19-decyl-15-isobutyl-3,16,18-trimethyl-2,5,8,11,14,17-hexaoxo-1-oxa-4,7,10,13,16-pentaazacyclononadecan-9-yl)methylcarbamate (200 mg, 0.227 mmol) was dissolved in neat TFA (14.0 mL, 180 mmol) at 0° C. The mixture was stirred for 4 h at 0 C. The mixture was diluted with toluene (20.0 mL) and the resulting mixture was evaporated in vacuo at room temperature. The residue was purified via Prep-LCMS and lyophilized to yield the title compound (56.8 mg, 34% yield) as the TFA salt. LCMS (ESI): R$_T$ (min)=2.089, [M+H]$^+$=725.5, method=C; $^1$H NMR (400 MHz, DMSO-d$_6$) δ 8.33-7.99 (m, 5H), 7.80-7.15 (m, 2H), 5.15-4.55 (m, 3H), 4.50-3.70 (m, 5H), 3.35-3.05 (m, 4H), 2.90-2.75 (m, 2H), 2.25-1.75 (m, 2H), 1.70-1.40 (m, 4H), 1.40-1.10 (m, 21H), 1.10-1.01 (m, 5H), 0.98-0.50 (m, 16H).

Example 4: (3R,6S,9S,12S,15S,18R,19R)-12-((S)-sec-butyl)-19-decyl-6-((S)-1-hydroxyethyl)-9-(hydroxymethyl)-15-isobutyl-3,16,18-trimethyl-1-oxa-4,7,10,13,16-pentaazacyclononadecane-2,5,8,11,14,17-hexaone

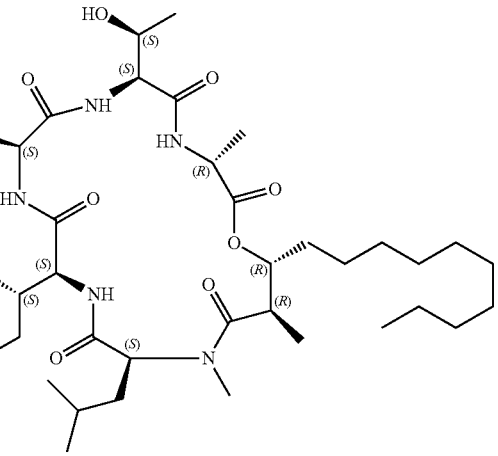

The title compound was prepared following procedures analogous to those described for Example 1. LCMS (ESI): R$_T$ (min)=2.369, [M+H]$^+$=726.5, method=C; H NMR (400 MHz, DMSO-d$_6$) δ 8.60-7.95 (m, 2H), 7.70-7.50 (m, 1H), 7.35-7.15 (m, 1H), 5.30-4.70 (m, 3H), 4.60-4.45 (m, 1H), 4.25-3.95 (m, 4H), 3.90-3.55 (m, 3H), 3.10-2.90 (m, 1H), 2.85-2.65 (m, 3H), 2.05-1.70 (m, 2H), 1.65-1.15 (m, 24H), 1.10-0.85 (m, 22H).

Example 5: (6S,9S,12S,15S,18R,19R)-12-((R)-sec-butyl)-19-decyl-6,9-bis(hydroxymethyl)-15-isobutyl-16,18-dimethyl-1-oxa-4,7,10,13,16-pentaazacyclononadecane-2,5,8,11,14,17-hexaone

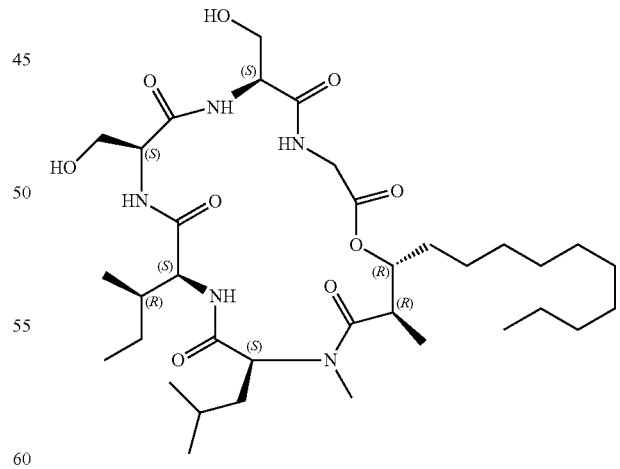

The title compound was prepared following procedures analogous to those described for Example 1. LCMS (ESI): R$_T$ (min)=2.729, [M+H]$^+$=698.5, method=D; H NMR (400 MHz, DMSO-d$_6$) δ 8.70-8.60 (m, 1H), 8.05-7.90 (m, 1H), 7.80-7.55 (m, 1H), 7.35-6.90 (m, 1H), 5.20-4.85 (m, 3H), 4.55-4.25 (m, 2H), 4.10-4.00 (m, 1H), 3.92-3.52 (m, 6H), 3.45-3.40 (m, 1H), 3.15-2.70 (m, 3H), 2.18-1.88 (m, 2H), 1.70-1.31 (m, 6H), 1.30-1.18 (m, 16H), 1.05-0.95 (m, 3H), 0.94-0.79 (m, 13H), 0.78-0.67 (m, 3H).

Example 6: (6S,9S,12S,15S,18R,19R)-9-(aminomethyl)-12-cyclohexyl-19-hexyl-6-[(1S)-1-hydroxyethyl]-15-isobutyl-16,18-dimethyl-1-oxa-4,7,10,13,16-pentazacyclononadecane-2,5,8,11,14,17-hexone

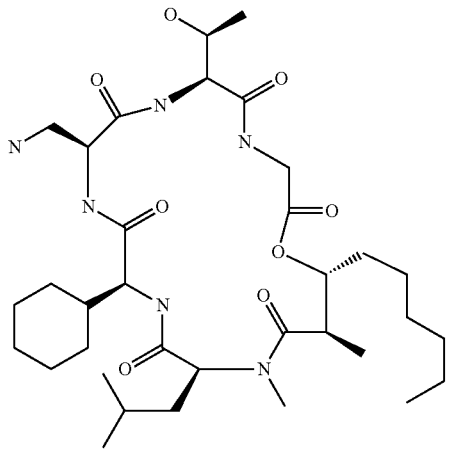 [SMILES: CCCCCC[C@H]1OC(=O)CNC(=O)[C@H]([C@H](C)O)NC(=O)[C@H](CN)NC(=O)[C@H](C2CCCCC2)NC(=O)[C@H](CC(C)C)N(C)C(=O)[C@@H]1C]

The title compound was prepared following procedures analogous to those described for Example 1 but substituting Fmoc-cyclohexylglycine-OH for Fmoc-allothreonine-OH in Step 3 and (2R,3R)-3-hydroxy-2-methylnonanoic acid for (2R,3R)-3-hydroxy-2-methyl-tridecanoic acid in step 4. The residue was purified via Prep-LCMS and lyophilized to yield 7.3 mg of the title compound as the TFA salt. LCMS (ESI): $R_T$ (min)=4.66, [M+H]$^+$=681.45, method=A. $^1$H NMR (400 MHz, DMSO-d$_6$) δ 8.60-8.46 (m, 1H), 7.97-7.58 (m, 8H), 5.08-4.79 (m, 3H), 4.79-4.47 (m, 1H), 4.34-3.79 (m, 4H), 3.23-3.05 (m, 2H), 2.74 (s, 2H), 2.70-2.65 (m, 1H), 2.35-2.28 (m, 1H), 1.80-1.36 (m, 6H), 1.31-1.15 (m, 14H), 1.08-0.97 (m, 6H), 0.95-0.81 (m, 11H).

Example 7: (6S,9S,12S,15S,18R,19R)-12-cyclohexyl-19-decyl-6,9-bis(hydroxymethyl)-15-isobutyl-16,18 dimethyl-1-oxa-4,7,10,13,16-pentazacyclononadecane-2,5,8,11,14,17-hexone

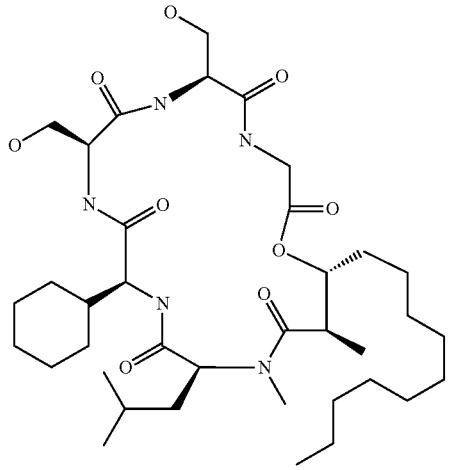 [SMILES: CCCCCCCCCC[C@H]1OC(=O)CNC(=O)[C@H](CO)NC(=O)[C@H](CO)NC(=O)[C@H](C2CCCCC2)NC(=O)[C@H](CC(C)C)N(C)C(=O)[C@@H]1C]

The title compound was prepared following procedures analogous to those described for Example 1 but substituting Fmoc-Ser(OBzl)-OH for Fmoc-allothreonine(Bzl)-OH and Fmoc-cyclohexylglycine-OH for Fmoc-allothreonine-OH in step 3. The residue was purified via Prep-LCMS and lyophilized to yield 36.3 mg of the title compound. LCMS (ESI): $R_T$ (min)=6.65, [M+H]$^+$=724.49, method=E. $^1$H NMR (400 MHz, DMSO-d$_6$) δ 8.71-8.59 (m, 1H), 8.10-7.93 (m, 1H), 7.69-7.40 (m, 1H), 7.31-6.93 (m, 1H), 5.24-4.88 (m, 3H), 4.52-4.07 (m, 3H), 3.94-3.51 (m, 4H), 3.22-3.08 (m, 1H), 3.04 (s, 2H), 2.67 (s, 1H), 2.05-1.84 (m, 2H), 1.72-1.55 (m, 7H), 1.53-1.36 (m, 1H), 1.28-1.19 (m, 17H), 1.11-0.95 (m, 10H), 0.93-0.83 (m, 10H).

Example 8: (6S,9S,12S,15S,18R,19R)-12-((R)-sec-Butyl)-18-ethyl-9-heptyl-6-((S)-1-hydroxyethyl)-9-(hydroxymethyl)-15-isobutyl-16-methyl-1-oxa-4,7,10,13,16-pentaazacyclononadecane-2,5,8,11,14,17-hexaone

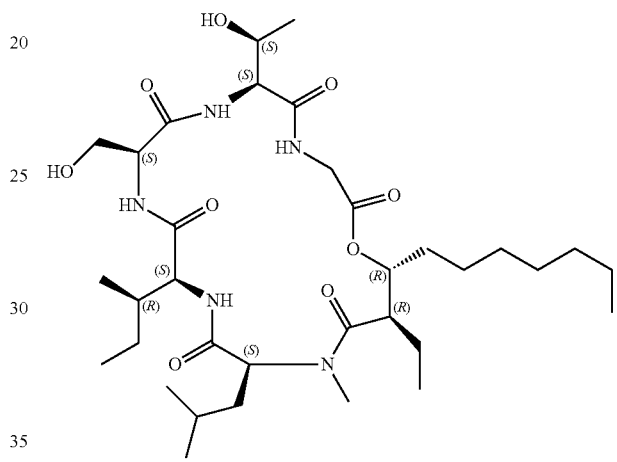

Step 1. Methyl (2R,3R)-2-ethyl-3-hydroxy-decanoate

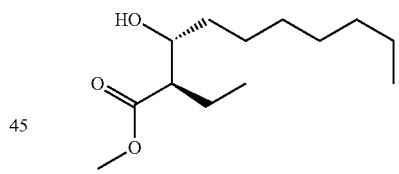

To a solution of diisopropylamine (7.71 mmol, 1.09 mL) in THF (12 mL) at −78° C. was added dropwise, n-butyllithium (2.5 mol/L in hexanes, 2.2 equiv, 2.8 mL). The mixture was stirred at −78° C. for 30 min and then warmed to 0° C. for another 30 min. The resulting solution was cooled to −78° C. and methyl (3R)-3-hydroxydecanoate (1.0 equiv, 600 mg) in THF (3 mL) was added dropwise. After complete addition, iodoethane (4.45 mmol, 0.356 mL) and hexamethylphosphoramide (14.8 mmol, 2.6 mL) were introduced at −78° C. and the solution was then stirred for 1 h and −40° C. for a further period of 3 h. The reaction was quenched by the addition of a saturated solution of ammonium chloride and the aqueous phase was extracted with ethyl acetate. The combined organic extracts were dried over Na$_2$SO$_4$ and concentrated in vacuo. The residue was purified on a silica column (solvent gradient 0 to 20% isopropylacetate:heptanes) to provide the title compound (1.607 mmol, 370 mg). $^1$H NMR (400 MHz, CDCl$_3$) δ 3.71 (s, 3H), 3.72-3.64 (m, 1H), 2.43-2.35 (m, 2H), 1.81-1.21 (m, 14H), 0.93 (t, J=7.5 Hz, 3H), 0.88 (t, J=6.6 Hz, 3H).

Step 2. (2R,3R)-2-Ethyl-3-hydroxydecanoic acid

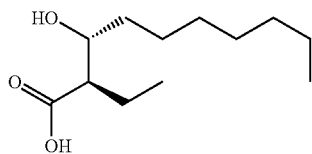

To a solution of methyl (2R,3R)-2-ethyl-3-hydroxy-decanoate (1.39 mmol, 320 mg) in THF (7 mL) and water (3 mL) was added lithium hydroxide hydrate (3.47 mmol, 146 mg). The reaction mixture was heated overnight at 50° C. 1 M HCl solution was then added to reach pH=3, and the mixture extracted with DCM 3 times. The combined DCM extracts were evaporated in vacuo, and the residue was purified on a silica column (solvent gradient 0 to 60% isopropylacetate:heptanes) to provide the title compound (280 mg, 93% yield).

Step 3. N-Me-leucine-alloisoleucine-serine(tBu)-allothreonine(tBu)-glycine-(2-chlorotrityl resin)

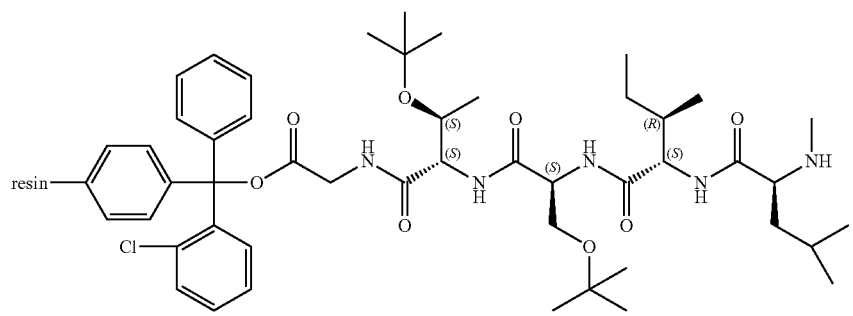

The resin-bound peptide N-Me-leucine-alloisoleucine-serine(tBu)-allothreonine(tBu)-glycine-(2-chlorotrityl resin) was prepared following methods analogous to those described for Example 1, Step 3.

Step 4. (6S,9S,12S,15S,18R,19R)-6-((S)-1-(tert-Butoxy)ethyl)-9-(tert-butoxymethyl)-12-((R)-sec-butyl)-18-ethyl-19-heptyl-15-isobutyl-16-methyl-1-oxa-4,7,10,13,16-pentaazacyclononadecane-2,5,8,11,14,17-hexaone

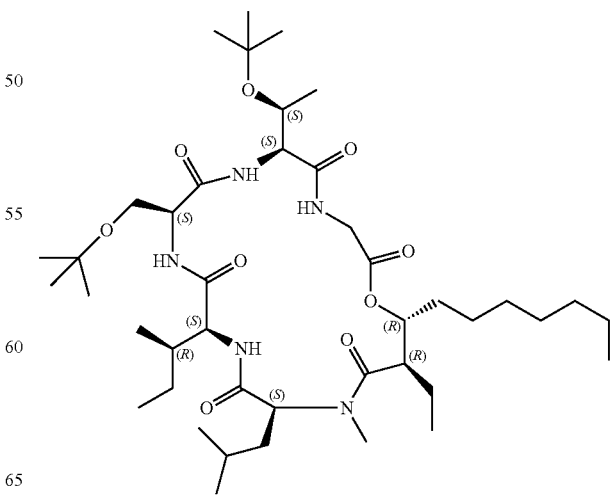

The title compound was prepared using the 2-chlorotrityl resin-bound peptide from Step 3 and (2R,3R)-2-ethyl-3-hydroxydecanoic acid and following procedures analogous to those described for Example 1, Steps 4-5. LCMS (ESI): [M+H]+=797.1.

Step 5. (6S,9S,12S,15S,18R,19R)-12-((R)-sec-butyl)-18-ethyl-9-heptyl-6-((S)-1-hydroxyethyl)-9-(hydroxymethyl)-15-isobutyl-16-methyl-1-oxa-4,7,10,13,16-pentaazacyclononadecane-2,5,8,11,14,17-hexaone (6S,9S,12S,15S,18R,19R)-6-((S)-1-(tert-Butoxy)ethyl)-9-(tert-butoxymethyl)-12-((R)-sec-butyl)-18-ethyl-19-heptyl-15-isobutyl-16-methyl-1-oxa-4,7,10,13,16-pentaazacyclononadecane-2,5,8,11,14,17-hexaone (150 mg, 0.184 mmol) was dissolved in neat TFA (7.0 mL, 50 mmol) at 0° C. The mixture was stirred for 4 h at 0° C. The mixture was diluted with toluene (10.0 mL) and the resulting mixture was evaporated in vacuo at room temperature. The residue was purified via Prep-LCMS and lyophilized to yield the title compound (6.5 mg, 5.2% yield) as the TFA salt. LCMS (ESI): $R_T$ (min)=6.054, [M+H]f=725.5, method=E; $^1$H NMR (400 MHz, DMSO-$d_6$) δ 8.54-7.98 (m, 2H), 7.80-7.47 (m, 1H), 7.37-7.02 (m, 1H), 5.30-4.85 (m, 4H), 4.70-4.55 (m, 1H), 4.25-3.95 (m, 5H), 3.90-3.55 (m, 3H), 3.12-2.90 (m, 1H), 2.87-2.65 (m, 3H), 2.15-1.00 (m, 21H), 1.11-0.68 (m, 19H).

Example 9: (6S,9S,12S,15S,18R,19R)-12-((R)-sec-butyl)-19-hexyl-6-((S)-1-hydroxyethyl)-9-(hydroxymethyl)-15-isobutyl-16-methyl-18-(3-(p-tolyl)propyl)-1-oxa-4,7,10,13,16-pentaazacyclononadecane-2,5,8,11,14,17-hexaone

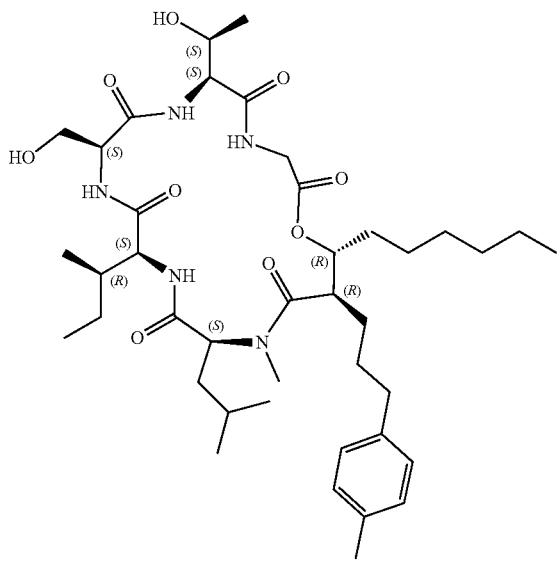

Step 1: 1-((3aR,6S,7aS)-8,8-dimethyl-2,2-dioxido-tetrahydro-3H-3a,6-methanobenzo[c]isothiazol-1(4H)-yl)pent-4-en-1-one

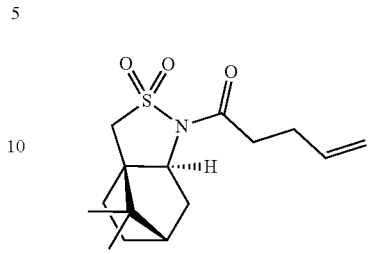

To a mixture of (3aR,6S,7aS)-8,8-dimethylhexahydro-3H-3a,6-methanobenzo[c]isothiazole 2,2-dioxide (3.00 g, 13.9 mmol), triethylamine (4.0 mL, 28 mmol), DMAP (178 mg, 1.46 mmol) and THF (30 mL, 369 mmol) at 0° C. was added pent-4-enoyl chloride (2.0 mL, 18 mmol). The reaction mixture was allowed to warm to room temperature and stirred for 17 h. The reaction mixture was evaporated in vacuo. The resulting residue was partitioned between water (100 mL) and ethyl acetate (150 mL). The aqueous layer was extracted with an additional portion of ethyl acetate (100 mL). The combined organic portions were washed with 1 M NaOH (20 mL), 1 M HCl (20 mL), brine, dried with magnesium sulfate, concentrated and evaporated in vacuo. The crude product was purified via flash chromatography on silica gel (220 g silica, solvent gradient: 0-20% ethyl acetate in heptanes) to yield 3.869 g (93%) of the title compound as a white solid. LCMS (ESI): [M+H]$^+$=298.1; $^1$H NMR (400 MHz, Chloroform-d) δ 5.93-5.77 (m, 1H), 5.15-4.94 (m, 2H), 3.87 (dd, J=7.6, 5.2 Hz, 1H), 3.46 (q, J=13.7 Hz, 2H), 2.93-2.71 (m, 2H), 2.53-2.37 (m, 2H), 2.18-2.03 (m, 2H), 1.96-1.82 (m, 3H), 1.47-1.31 (m, 2H), 1.16 (s, 3H), 0.97 (s, 3H).

Step 2: (2R,3R)-2-allyl-1-((3aR,6S,7aS)-8,8-dimethyl-2,2-dioxidotetrahydro-3H-3a,6-methanobenzo[c]isothiazol-1(4H)-yl)-3-hydroxynonan-1-one

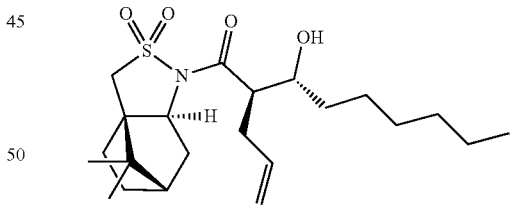

To a 100 mL flask (oven dried) was added DCM (7 mL, 109 mmol) and dibutylboron trifluoromethanesulfonate (1 mol/L in DCM, 13.5 mL, 13.5 mmol) and this mixture was cooled to −10° C. in a brine/ice bath. To this mixture was slowly added a solution of 1-((3aR,6S,7aS)-8,8-dimethyl-2,2-dioxidotetrahydro-3H-3a,6-methanobenzo[c]isothiazol-1(4H)-yl)pent-4-en-1-one (1.59 g, 5.35 mmol) in DCM (3 mL, 46.7 mmol), followed by a dropwise addition of DIPEA (2.4 mL, 14 mmol). The reaction mixture was then allowed to stir at 0° C. for 90 min, and then cooled to −78° C. for 30 min.

Separately, a mixture of titanium(IV) chloride (1.0 mol/L in DCM, 15 mL, 15 mmol) and DCM (5 mL, 77.8 mmol) in an oven-dried flask (50 mL) was cooled to −78° C. To this mixture was slowly added heptaldehyde (2.1 mL, 15 mmol). The resulting mixture was stirred at −78° C. for 30 min.

The heptaldehyde mixture was transferred to the dibutylboron trifluoromethanesulfonate mixture, maintaining both at −78° C., via cannula (18G). The resulting reaction mixture was stirred at −78° C. for 3 h. The reaction mixture was then poured into 100 mL of saturated aqueous ammonium chloride, and stirred at room temperature for 10 min. The layers were separated, the aqueous portion was extracted with DCM (2×75 mL), and the combined organic extracts were dried over magnesium sulfate, filtered, and evaporated in vacuo. The crude product was purified via flash chromatography on silica gel (80 g silica, solvent gradient: 0-50% ethyl acetate in heptanes) to yield 1.9746 g (89%) of the title compound. LCMS (ESI): [M+H]⁺=412.2.

Step 3: (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-((E)-3-(p-tolyl)allyl)nonan-1-one

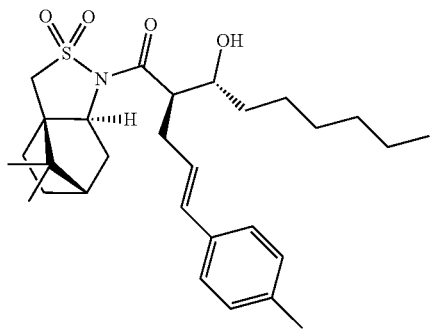 [SMILES: CCCCCC[C@@H](O)[C@@H](C/C=C/c1ccc(C)cc1)C(=O)N1[C@H]2C[C@@H]3CC[C@@]2(CS1(=O)=O)C3(C)C]

To a solution of (2R,3R)-2-allyl-1-((3aR,6S,7aS)-8,8-dimethyl-2,2-dioxidotetrahydro-3H-3a,6-methanobenzo[c]isothiazol-1(4H)-yl)-3-hydroxynonan-1-one (603.5 mg, 1.466 mmol) in DMF (5.0 mL, 64 mmol) was added 1-bromo-4-methyl-benzene (328 mg, 1.9178 mmol) and triethylamine (0.60 mL, 4.3 mmol). Nitrogen was bubbled through this mixture for 5 minutes, and then bis(tri-o-tolylphosphine)palladium(0) (51 mg, 0.069 mmol) was added and the reaction vial was sealed and heated at 100° C. for 4 h. The reaction mixture was cooled to room temperature, diluted with ethyl acetate, washed with water (2×) and brine, dried over magnesium sulfate, filtered, and evaporated in vacuo. The crude product was purified via flash chromatography on silica gel (24 g silica, solvent gradient: 0-20% ethyl acetate in heptanes) to yield 610.1 mg (83%) of the title compound. LCMS (ESI): [M+H]⁺=502.2.

Step 4: (2R,3R)-3-hydroxy-2-((E)-3-(p-tolyl)allyl)nonanoic acid

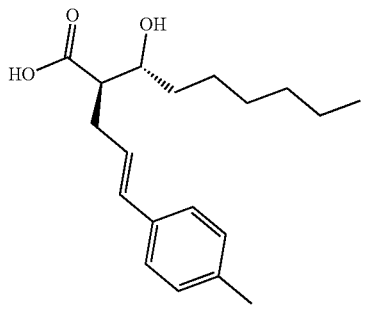 [SMILES: CCCCCC[C@@H](O)[C@@H](C/C=C/c1ccc(C)cc1)C(=O)O]

To a solution of (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-((E)-3-(p-tolyl)allyl)nonan-1-one (610.1 mg, 1.216 mmol) in THF (5 mL, 61.6 mmol) was added lithium hydroxide (1.0 M in water, 5 mL, 5.0 mmol). The reaction mixture was stirred at room temperature for 14 h. The reaction mixture was poured into 10% aqueous citric acid and extracted with DCM (2×100 mL). The combined DCM extracts were dried over magnesium sulfate, filtered, and evaporated in vacuo. The crude product was purified via reverse-phase prep HPLC, eluting with 30-70% ACN in water (0.1% formic acid) to yield 146.6 mg (40%) of the title compound as a white solid. LCMS (ESI): [M+H]⁺=305.2; ¹H NMR (400 MHz, Chloroform-d) δ 7.25-7.20 (m, 2H), 7.10 (d, J=7.7 Hz, 2H), 6.46 (d, J=15.7 Hz, 1H), 6.16-6.06 (m, 1H), 3.84-3.73 (m, 1H), 2.69-2.56 (m, 3H), 2.32 (s, 3H), 1.59-1.47 (m, 4H), 1.34-1.25 (m, 6H), 0.95-0.83 (m, 3H).

Step 5: (6S,9S,12S,15S,18R,19R)-9-((benzyloxy)methyl)-12-((R)-sec-butyl)-6-((S)-1-((tert-butyldimethylsilyl)oxy)ethyl)-19-hexyl-15-isobutyl-16-methyl-18-((E)-3-(p-tolyl)allyl)-1-oxa-4,7,10,13,16-pentaazacyclononadecane-2,5,8,11,14,17-hexaone

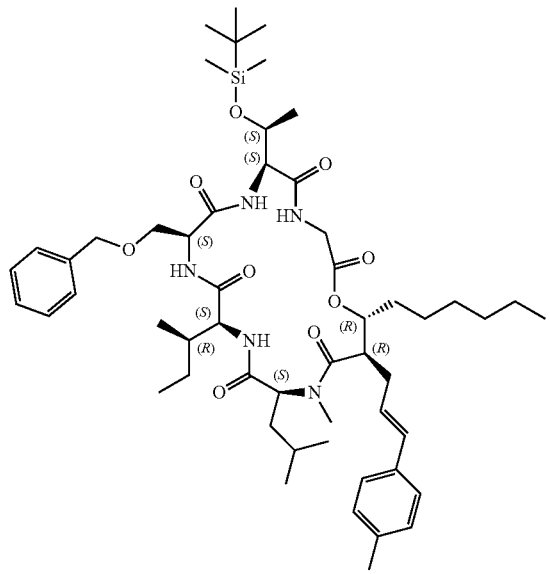

The title compound was prepared following methods analogous to those described for Example 1, substituting the appropriately protected amino acids and using (2R,3R)-3-hydroxy-2-((E)-3-(p-tolyl)allyl)nonanoic acid. LCMS (ESI) [M+H]⁺=976.6.

Step 6: (6S,9S,12S,15S,18R,19R)-12-((R)-sec-butyl)-19-hexyl-6-((S)-1-hydroxyethyl)-9-(hydroxymethyl)-15-isobutyl-16-methyl-18-(3-(p-tolyl)propyl)-1-oxa-4,7,10,13,16-pentaazacyclononadecane-2,5,8,11,14,17-hexaone To a solution of (6S,9S,12S,15S,18R,19R)-9-((benzyloxy)methyl)-12-((R)-sec-butyl)-6-((S)-1-((tert-butyldimethylsilyl)oxy)ethyl)-19-hexyl-15-isobutyl-16-methyl-8-((E)-3-(p-tolyl)allyl)-1-oxa-4,7,10,13,16-pentaazacyclononadecane-2,5,8,11,14,17-hexaone (43.6 mg, 0.0447 mmol) in THF (2 mL, 24.6 mmol) was added acetic acid (0.2 mL, 3 mmol) and tetrabutylammonium fluoride (1 mol/L in THF, 1.5 mL, 1.5 mmol). The resulting mixture was stirred at room temperature for 6 h. The mixture was diluted with ethyl acetate (60 mL), and washed with saturated aqueous sodium bicarbonate (4×20 mL) and brine, dried over magnesium sulfate, filtered, and evaporated in vacuo. The resulting material was dissolved in ethanol (3 mL, 52.5 mmol), and the flask purged with nitrogen. After the addition of palladium hydroxide (20 wt. % on carbon) (96 mg, 0.1368 mmol) the reaction mixture was evacuated and backfilled with hydrogen, and then stirred at 40° C. under a balloon of hydrogen for 16 h. The reaction mixture was filtered through celite, rinsing with methanol, and evaporated in vacuo. The crude product was purified via reverse-phase HPLC and lyophilized to yield 8.9 mg (26%) of the title compound. LCMS (ESI): $R_T$(min)=6.97, [M+H]$^+$=774.5, method=A; $^1$H NMR (400 MHz, DMSO-d$_6$) δ 8.55-8.36 (m, 1H), 8.19-7.95 (m, 1H), 7.76-7.24 (m, 1H), 7.14-6.88 (m, 4H), 5.28-4.70 (m, 2H), 4.68-3.44 (m, 7H), 3.08 (s, 2H), 2.74 (s, 1H), 2.25 (s, 3H), 2.16-2.02 (m, 1H), 1.91-1.33 (m, 10H), 1.32-1.10 (m, 12H), 1.10-0.95 (m, 4H), 0.92-0.80 (m, 11H), 0.80-0.61 (m, 6H).

The Examples listed in Table 4. were prepared following procedures analogous to those described in the above Examples, substituting the appropriate Fmoc-protected amino acids and the carboxylic acid described in either Intermediate 1 or Intermediate 2.

TABLE 4

| Example | Structure/Name | LCMS [M + H]+ | LCMS RT (min), |
|---|---|---|---|
| 10 | 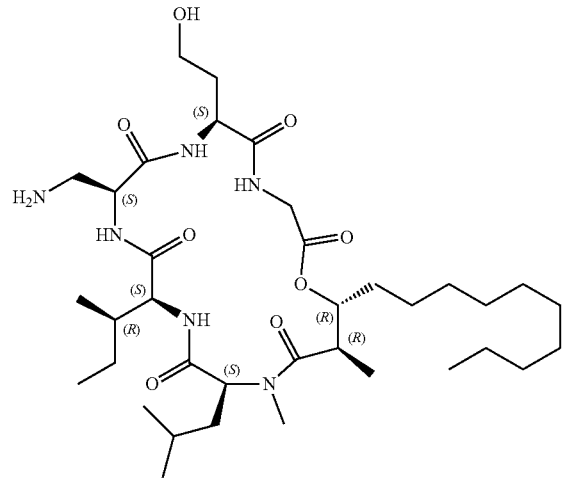<br>(6S,9S,12S,15S,18R,19R)-9-(aminomethyl)-12-((R)-sec-butyl)-19-decyl-6-(2-hydroxyethyl)-15-isobutyl-16,18-dimethyl-1-oxa-4,7,10,13,16-pentaazacyclononadecane-2,5,8,11,14,17-hexaone | 711.5 | 5.347, A |
| 11 | 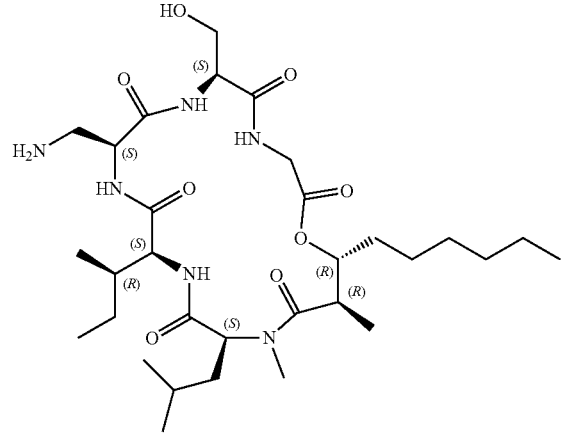<br>(6S,9S,12S,15S,18R,19R)-9-(aminomethyl)-12-((R)-sec-butyl)-19-hexyl-6-(hydroxymethyl)-15-isobutyl-16,18-dimethyl-1-oxa-4,7,10,13,16-pentaazacyclononadecane-2,5,8,11,14,17-hexaone | 641.5 | 4.449, A |

TABLE 4-continued
| Example | Structure/Name | LCMS [M + H]+ | LCMS RT (min), |
|---|---|---|---|
| 12 | 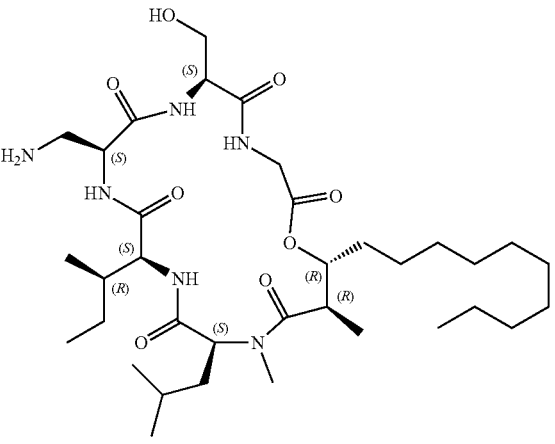<br>(6S,9S,12S,15S,18R,19R)-9-(aminomethyl)-12-((R)-sec-butyl)-19-decyl-6-(hydroxymethyl)-15-isobutyl-16,18-dimethyl-1-oxa-4,7,10,13,16-pentaazacyclononadecane-2,5,8,11,14,17-hexaone | 697.5 | 5.329, A |
| 13 | 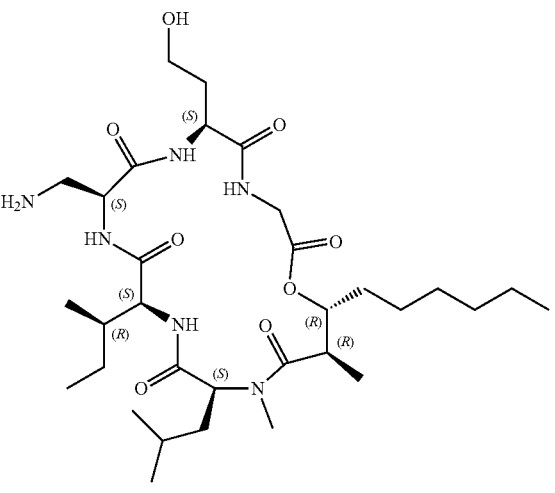<br>(6S,9S,12S,15S,18R,19R)-9-(aminomethyl)-12-((R)-sec-butyl)-19-hexyl-6-(2-hydroxyethyl)-15-isobutyl-16,18-dimethyl-1-oxa-4,7,10,13,16-pentaazacyclononadecane-2,5,8,11,14,17-hexaone | 655.4 | 4.474, A |

TABLE 4-continued

| Example | Structure/Name | LCMS [M + H]+ | LCMS RT (min), |
|---|---|---|---|
| 14 | (6S,9S,12S,15S,18R,19R)-9-(aminomethyl)-12-((R)-sec-butyl)-19-decyl-6-((S)-1-hydroxyethyl)-16,18-dimethyl-15-propyl-1-oxa-4,7,10,13,16-pentaazacyclononadecane-2,5,8,11,14,17-hexaone | 697.5 | 5.226, A |
| 15 | (6S,9S,12S,15S,18R,19R)-9-(aminomethyl)-12-((R)-sec-butyl)-19-decyl-6-((S)-1-hydroxyethyl)-15-isopentyl-16,18-dimethyl-1-oxa-4,7,10,13,16-pentaazacyclononadecane-2,5,8,11,14,17-hexaone | 725.5 | 3.37, B |

TABLE 4-continued
| Example | Structure/Name | LCMS [M + H]+ | LCMS RT (min), |
|---|---|---|---|
| 16 | 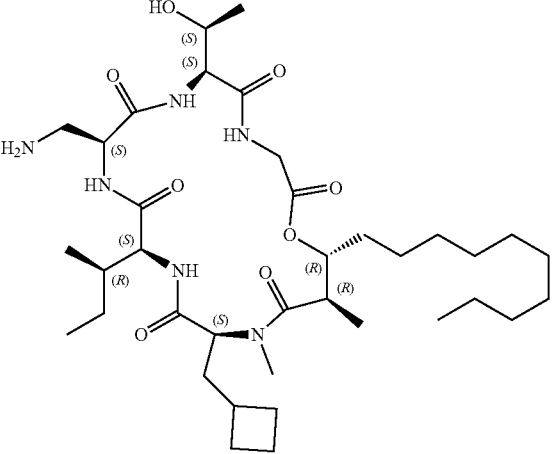<br>(6S,9S,12S,15S,18R,19R)-9-(aminomethyl)-12-((R)-sec-butyl)-15-(cyclobutylmethyl)-19-decyl-6-((S)-1-hydroxyethyl)-16,18-dimethyl-1-oxa-4,7,10,13,16-pentaazacyclononadecane-2,5,8,11,14,17-hexaone | 723.5 | 5.489, A |
| 17 | 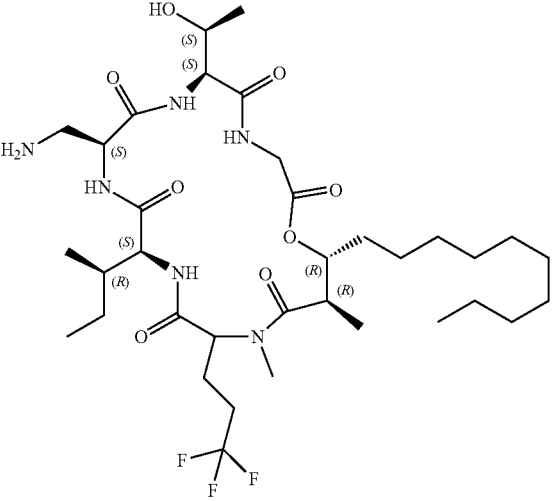<br>(6S,9S,12S,18R,19R)-9-(aminomethyl)-12-((R)-sec-butyl)-19-decyl-6-((S)-1-hydroxyethyl)-16,18-dimethyl-15-(3,3,3-trifluoropropyl)-1-oxa-4,7,10,13,16-pentaazacyclononadecane-2,5,8,11,14,17-hexaone (single unknown stereoisomer) | 751.5 | 5.256, A |

Example 28: 1-(3-(((6S,9S,12S,15S,18R,19R)-12-((S)-sec-butyl)-19-decyl-9-(hydroxymethyl)-15-isobutyl-16,18-dimethyl-2,5,8,11,14,17-hexaoxo-1-oxa-4,7,10,13,16-pentaazacyclononadecan-6-yl)propyl)guanidine

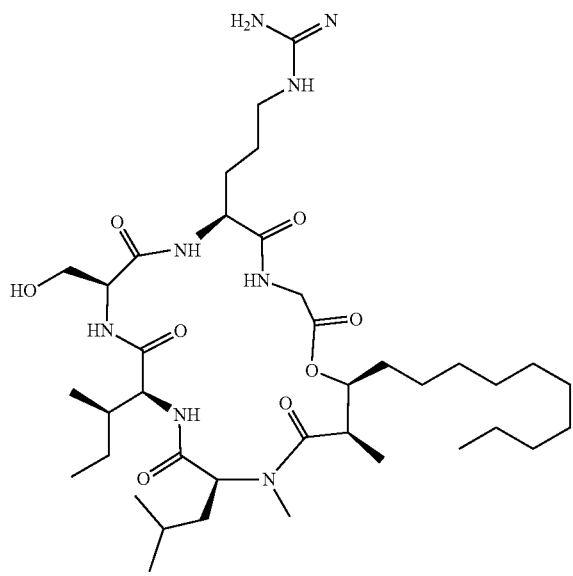

Step 1: 2-Chlorotrityl Resin Loaded with O-Benzyl-L-Serine

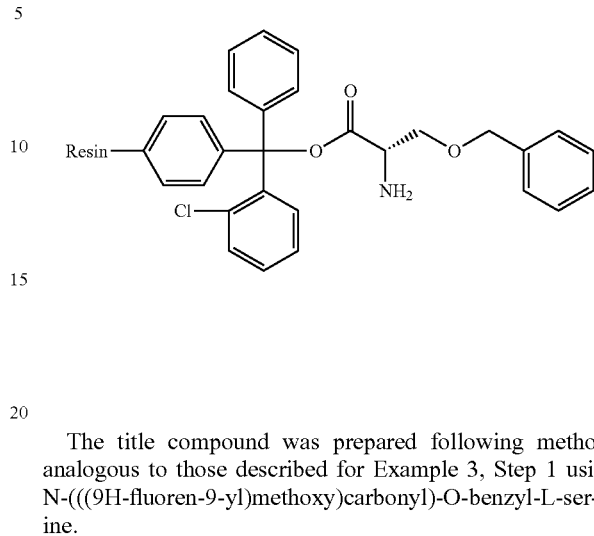

The title compound was prepared following methods analogous to those described for Example 3, Step 1 using N-(((9H-fluoren-9-yl)methoxy)carbonyl)-O-benzyl-L-serine.

Step 2: O-benzyl-N—N-((2R,3R)-3-hydroxy-2-methyltridecanoyl)-N-methyl-L-leucyl-L-isoleucyl-L-serine-(2-chlorotrityl resin)

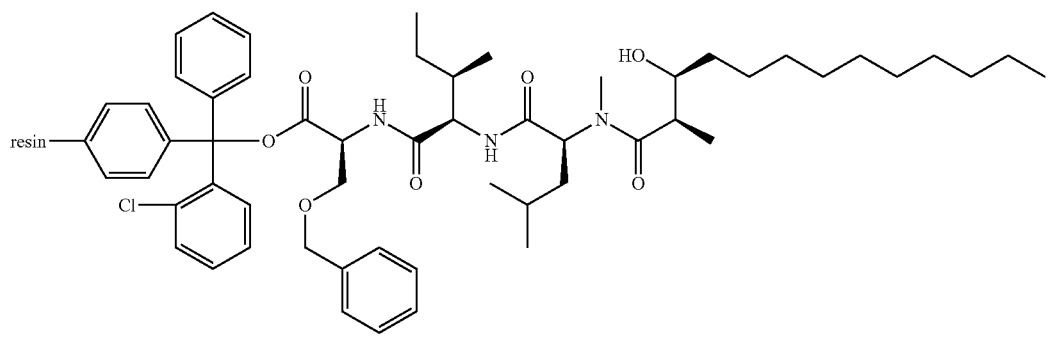

The title compound was prepared using the 2-chlorotrityl resin loaded with serine from previous step, following procedures analogous to those described for Example 1, Steps 3-5, and substituting the appropriate Fmoc-protected amino acids and Intermediate 2.

Step 3:N—N-((2R,3R)-3-(((((9H-fluoren-9-yl)methoxy)carbonyl)glycyl)oxy)-2-methyltridecanoyl)-N-methyl-L-leucyl-L-isoleucyl-O-benzyl-L-serine-(2-chlorotrityl resin)

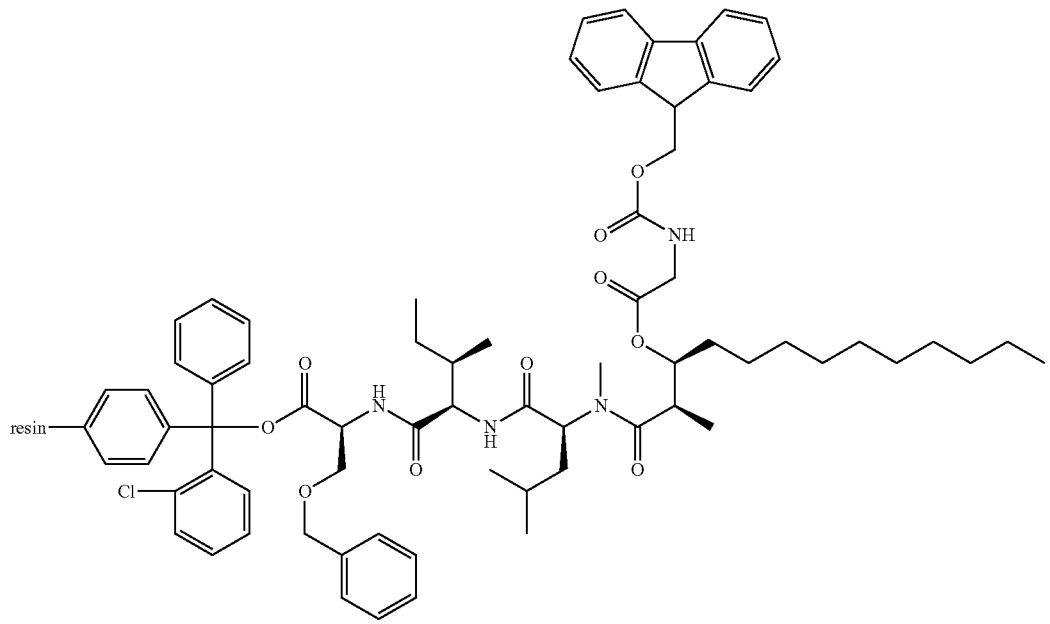

To a vial was added N,N'-Dicyclohexylcarbodiimide (100 mg, 0.8 mmol), DMAP (3 mg, 0.03 mmol), (((9H-fluoren-9-yl)methoxy)carbonyl)glycine (300 mg, 0.8 mmol), DCM (1 mL) and DMF (1 mL). The solution was stirred for a minute then added to the resin (0.55 g, estimated loading 0.50 mmol/g,) from Step 2. After 2 h the reaction solution was drained off the resin, and the resin washed with DMA and DCM. A fresh solution of reagents was prepared and added to the resin. After 2 h the resin was drained and washed with DMA, and DCM. The resin was treated with a solution of acetic anhydride (0.5 mL) and DIPEA (0.5 mL) in DMA (5 mL) and left to agitate. After 30 min the resin was drained and washed with DMA and DCM.

Step 4: N—(N-((2R,3R)-3-(((Z)—N²-(((9H-fluoren-9-yl)methoxy)carbonyl)-N^ω, Nω'-bis((benzyloxy)carbonyl)-D-arginylglycyl)oxy)-2-methyltridecanoyl)-N-methyl-L-leucyl-L-isoleucyl)-O-benzyl-L-serine-(2-chlorotrityl resin)

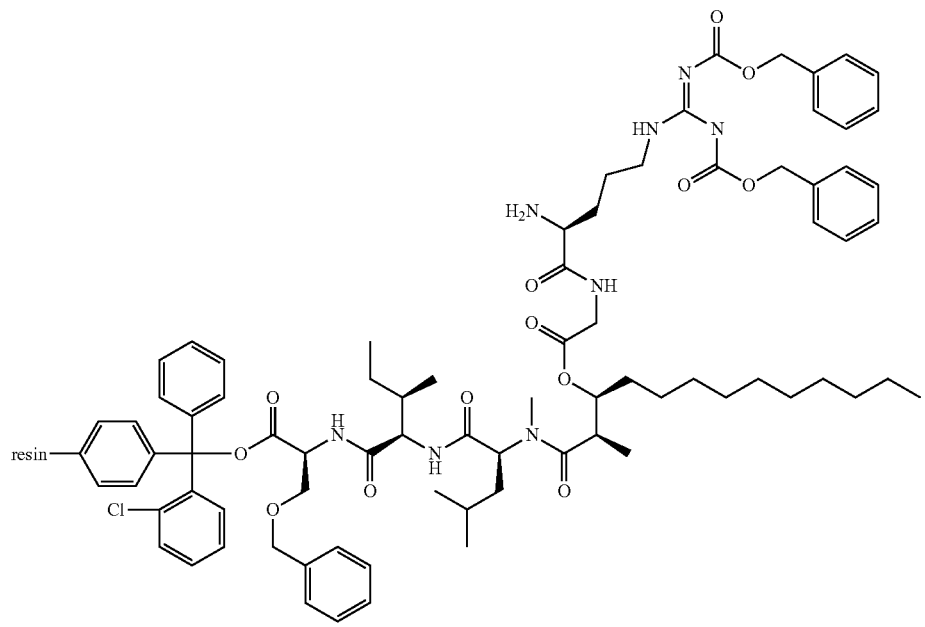

A solution of 20% piperidine in DMF was added to the resin from step 3 and left to agitate for 30 min. The resin was drained and washed with DMA and DCM. Separately, to a vial was added 2-(1H-benzotriazol-1-yl)-1,1,3,3-tetramethyluronium hexafluorophosphate (300 mg, 0.8 mmol), DIPEA (0.3 mL, 2 mmol), DMA (8 mL), and (Z)—N²-(((9H-fluoren-9-yl)methoxy)carbonyl)-N^ω,N^ω'-bis((benzyloxy)carbonyl)-L-arginine (500 mg, 0.8 mmol). This solution was stirred for 30 min then added to the resin. The reaction was placed on a rotator for 1 h, then drained and washed with DMA and DCM. The resin was treated with 8 mL of 20% piperidine in DMF, and the vial was placed on a rotator. After 3 h, the resin was filtered and rinsed with DMA and DCM to afford the desired resin-bound depsipeptide.

Step 5: Benzyl (NE)-N-[benzyloxycarbonylamino-[[(6S,9S,12S,15S,18R,19R)-9-(benzyloxymethyl)-19-decyl-15-isobutyl-16,18-dimethyl-12-[(1S)-1-methylpropyl]-2,5,8,11,14,17-hexaoxo-1-oxa-4,7,10,13,16-pentazacyclononadec-6-yl]methylamino]methylene]carbamate

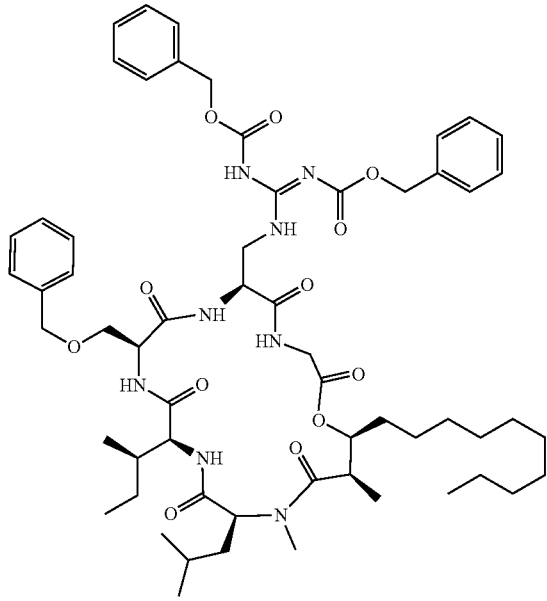 [SMILES: CCCCCCCCCC[C@@H]1OC(=O)CNC(=O)[C@H](CN/C(=N\C(=O)OCc2ccccc2)NC(=O)OCc2ccccc2)NC(=O)[C@H](COCc2ccccc2)NC(=O)[C@H]([C@H](C)CC)NC(=O)[C@H](CC(C)C)N(C)C(=O)[C@@H]1C]

The resin-bound depsipeptide from step 4 was treated with 8 mL of 7:2:1 DCM:AcOH:TFE. The mixture was placed on a rotator at room temperature for 3 h, and then filtered, rinsing with DCM. The combined filtrates were evaporated in vacuo, azeotroping with toluene and diethyl ether. The resulting residue (0.24 g, 0.24 mmol) was dissolved in DCM (250 mL) and slowly added (via dropping funnel) to a flask containing N, N'-Diisopropylcarbodiimide (0.12 g, 0.95 mmol), HOBt (0.036 mg, 0.26 mmol), and DCM (250 mL). After stirring for 8 h, the reaction was concentrated. The resulting residue was treated with water and extracted with ethyl acetate three times. The combined organic layers were washed with brine, dried over magnesium sulfate, filtered, and concentrated to give the title compound (0.30 g) as a yellow oil. LCMS (ESI): [M+H]$^+$=1143.5.

Step 6: 1-(3-((6S,9S,12S,15S,18R,19R)-12-((S)-sec-butyl)-19-decyl-9-(hydroxymethyl)-15-isobutyl-16,18-dimethyl-2,5,8,11,14,17-hexaoxo-1-oxa-4,7,10,13,16-pentaazacyclononadecan-6-yl)propyl)guanidine The title compound was prepared using the product from Step 5, following methods analogous to those described for Example 1, Step 6. LCMS (ESI): R$_T$ (min)=5.271, [M+H]$^+$=767.5, method=A; H NMR (400 MHz, DMSO-d$_6$) δ 8.50-8.00 (m, 2H), 7.42 (t, J=5.8 Hz, 4H), 6.52 (s, 1H), 5.35-4.79 (m, 1H), 4.36-3.95 (m, 3H), 3.95-3.47 (m, 3H), 3.19-2.94 (m, 5H), 2.68 (d, J=5.7 Hz, 1H), 2.19-1.34 (m, 10H), 1.23 (d, J=3.6 Hz, 18H), 1.09-0.66 (m, 21H).

Example 40: (6S,9S,12S,15S,18R,19R)-19-decyl-6-((S)-1-hydroxyethyl)-9-(hydroxymethyl)-15-isobutyl-16,18-dimethyl-12-propyl-1-oxa-4,7,10,13,16-pentaazacyclononadecane-2,5,8,11,14,17-hexaone

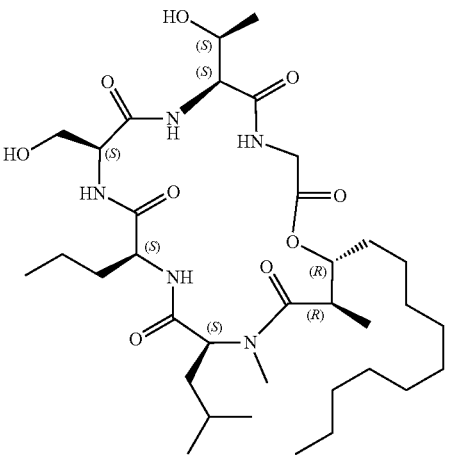

Step 1: (6S,9S,12S,15S,18R,19R)-6-((S)-1-((tert-butyldimethylsilyl)oxy)ethyl)-9-(((tert-butyldimethylsilyl)oxy)methyl)-19-decyl-15-isobutyl-16,18-dimethyl-12-propyl-1-oxa-4,7,10,13,16-pentaazacyclononadecane-2,5,8,11,14,17-hexaone

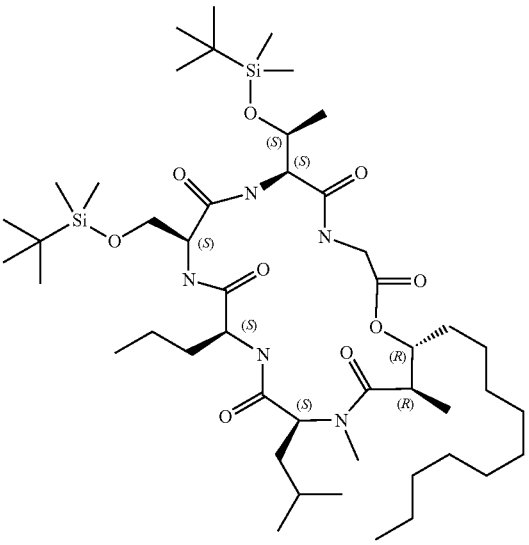

The title compound was synthesized following procedures analogous to those described for Example 53, steps 1-2 and 4 using the appropriately protected amino acids.

Step 2: (6S,9S,12S,15S,18R,19R)-19-Decyl-6-((S)-1-hydroxyethyl)-9-(hydroxymethyl)-15-isobutyl-16,18-dimethyl-12-propyl-1-oxa-4,7,10,13,16-pentaazacyclononadecane-2,5,8,11,14,17-hexaone The title compound was synthesized following procedures analogous to those described for Example 9, step 6 for the global silyl group deprotection. LCMS (ESI): $R_T$ (min)=6.52, [M+H]$^+$=698.47, method=E.

Example 51: (6S,9S,12S,15S,18R,19R)-9-(Aminomethyl)-6-((3-aminopropoxy)methyl)-12-cyclohexyl-19-hexyl-15-isobutyl-16,18-dimethyl-1-oxa-4,7,10,13,16-pentaazacyclononadecane-2,5,8,11,14,17-hexaone

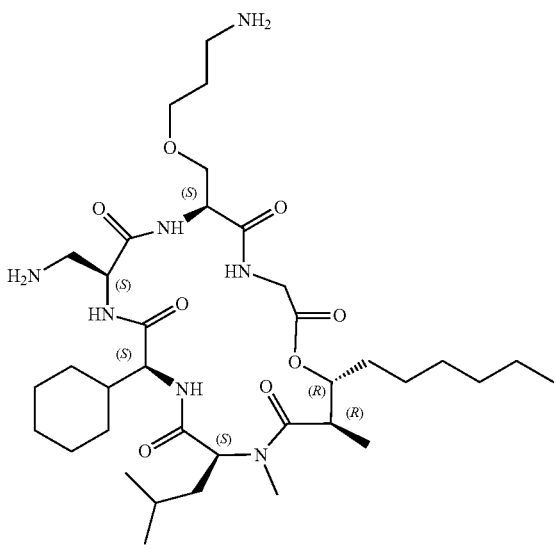

Step 1: N—((S)-3-((tert-Butoxycarbonyl)amino)-2-((S)-2-cyclohexyl-2-((S)-2-((2R,3R)-3-hydroxy-N,2-dimethylnonanamido)-4-methylpentanamido)acetamido)propanoyl)-O-(3-((tert-butoxycarbonyl)amino)propyl)-L-serylglycine

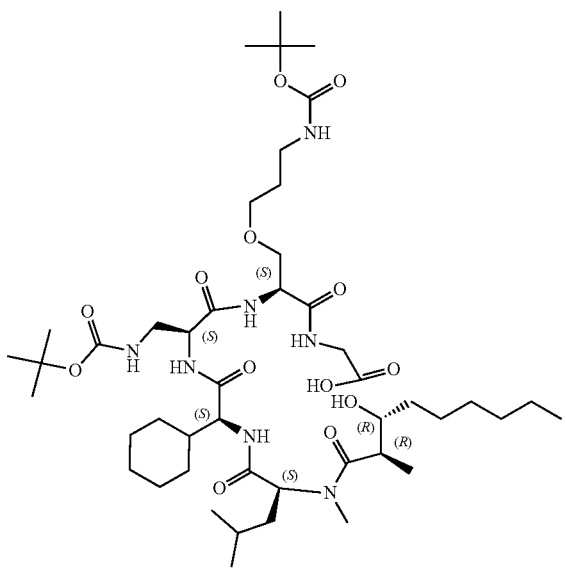

2-Chlorotrityl chloride resin (loading 0.956 mmol/g, 1 g) was swelled with the mixture of DMF:DCM (1:1, 20 mL) for 40 min. The resin was drained and then a solution of {[(9H-fluoren-9-ylmethoxy)carbonyl]amino}acetic acid (580.3 mg, 1.95 mmol), DMF (10 mL) and DIPEA (495.6 mg, 3.84 mmol) was added. The resin was agitated with nitrogen bubbling for 4 h, drained, and rinsed sequentially with 10 mL DCM/MeOH/DIPEA (10/10/1=V/V/V), 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of N-(((9H-fluoren-9-yl)methoxy)carbonyl)-O-(3-((tert-butoxycarbonyl)amino)propyl)-L-serine (Intermediate 5, 920.6 mg, 1.9 mmol), a pre-prepared stock solution of HOBt/HATU (1:1) in DMF (0.4 mmol/mL, 5 mL) and DIPEA (491 mg, 3.81 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (S)-2-((((9H-fluoren-9-yl)methoxy)carbonyl)amino)-3-((tert-butoxycarbonyl)amino)propanoic acid (810.4 mg, 1.9 mmol), a pre-prepared stock solution of HOBt/HATU (1:1) in DMF (0.4 mmol/mL, 5 mL) and DIPEA (498 mg, 3.87 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (S)-2-((((9H-fluoren-9-yl)methoxy)carbonyl)amino)-2-cyclohexylacetic acid (360.5 mg, 0.95 mmol), a pre-prepared stock solution of HOBt/HATU (1:1) in DMF (0.4 mmol/mL, 5 mL) and DIPEA (495 mg, 3.84 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2S)-2-{[(9H-fluoren-9-ylmethoxy) carbonyl](methyl)amino}-4-methylpentanoic acid (701.8 mg, 1.91 mmol), a pre-prepared stock solution of HOBt/HATU (1:1) in DMF (0.4 mmol/mL, 5 mL) and DIPEA (496 mg, 3.84 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2R,3R)-3-hydroxy-2-methylnonanoic acid (579.9 mg, 3.08 mmol), a pre-prepared stock solution of HOBt/HATU (1:1) in DMF (0.4 mmol/mL, 8 mL) and DIPEA (796 mg, 6.16 mmol). The resin was agitated with nitrogen bubbling overnight, drained and rinsed sequentially with 10 mL DMF, 10 mL DCM, 10 mL DMF. The resulting resin-bound depsipeptide was treated with 10 mL of 7:2:1 DCM:AcOH:2,2,2-trifluoroethan-1-ol. The mixture was agitated with nitrogen bubbling for 2 h, and then filtered, rinsed with 8 mL DCM. The cleavage process was repeated twice. The combined filtrates were evaporated in vacuo. The residue was purified by C18 flash chromatography with CH$_3$CN/H$_2$O (40% CH$_3$CN) to afford the title compound (654.1 mg, 0.69 mmol, 45% yield) as oil. LCMS (ESI): [M+H]$^+$=942.6.

Step 2: tert-Butyl (3-(((6S,9S,12S,15S,18R,19R)-9-(((tert-butoxycarbonyl)amino)methyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methoxy)propyl)carbamate

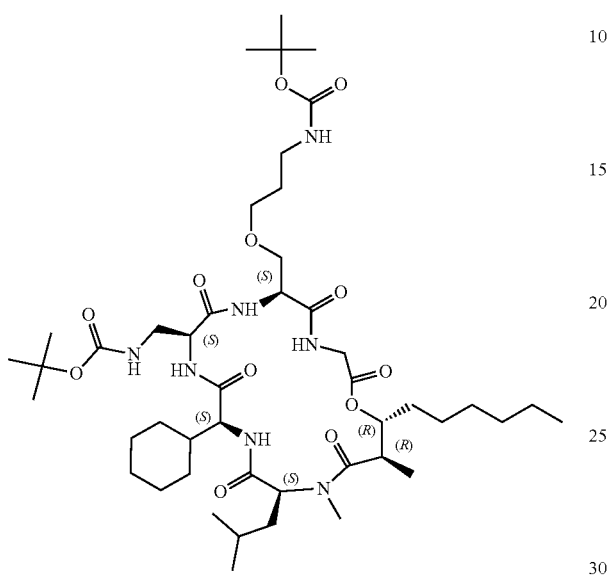

A solution of DMAP (468.6 mg, 3.84 mmol) and 2-methyl-6-nitrobenzoic anhydride (660.3 mg, 1.92 mmol) in DCM (50 mL) was combined at 40° C. Then a solution of N—((S)-3-(((tert-butoxycarbonyl)amino)-2-((S)-2-cyclohexyl-2-((S)-2-((2R,3R)-3-hydroxy-N,2-dimethylnonanamido)-4-methylpentanamido)acetamido)propanoyl)-O-(3-((tert-butoxycarbonyl)amino)propyl)-L-serylglycine (602.3 mg, 0.64 mmol) in THF (200 mL) was added dropwise at 40° C. The reaction mixture was stirred at 40° C. for an additional 4 h, and then the reaction mixture concentrated under vacuum. The residue was purified by C18 flash chromatography eluting with $CH_3CN$/water (96% $CH_3CN$) to afford the title compound (202.3 mg) as a solid. LCMS (ESI): $[M+H]^+$=924.6.

Step 3: (6S,9S,12S,15S,18R,19R)-9-(Aminomethyl)-6-((3-aminopropoxy)methyl)-12-cyclohexyl-19-hexyl-15-isobutyl-16,18-dimethyl-1-oxa-4,7,10,13,16-pentaazacyclononadecane-2,5,8,11,14,17-hexaone tert-Butyl (3-(((6S,9S,12S,15S,18R,19R)-9-(((tert-butoxycarbonyl)amino)methyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methoxy)propyl)carbamate (202 mg, 0.22 mmol) was dissolved in neat TFA (15.0 mL) at 0° C. The mixture was stirred for 1 h at 0° C. The mixture was diluted with toluene (20 mL) and the resulting mixture was evaporated in vacuo at room temperature. The residue was purified via low pH Prep-LCMS and lyophilized to yield the title compound (13.6 mg, 20% yield) as the TFA salt. LCMS (ESI): $R_T$ (min)=1.54, $[M+H]^+$=724.5, method=C; $^1$H NMR (400 MHz, DMSO-$d_6$) δ 9.08-8.68 (m, 1H), 8.50-7.47 (m, 9H), 4.95-4.01 (m, 5H), 4.00-3.38 (m, 5H), 3.25-2.70 (m, 7H), 2.06-1.32 (m, 13H), 1.28-0.79 (m, 25H).

Example 52: (6S,9S,12S,15S,18R,19R)-9-(Aminomethyl)-12-(4,4-difluorocyclohexyl)-19-hexyl-6-((S)-1-hydroxyethyl)-15-isobutyl-16,18-dimethyl-1-oxa-4,7,10,13,16-pentaazacyclononadecane-2,5,8,11,14,17-hexaone

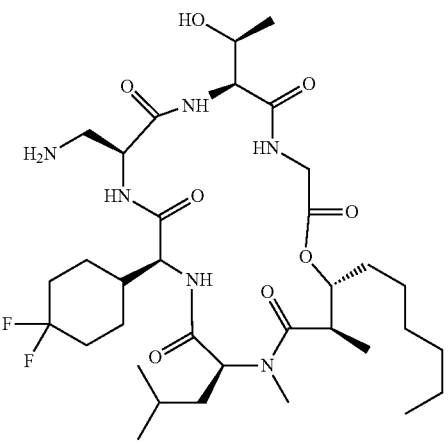 [SMILES: CCCCCC[C@H]1OC(=O)CNC(=O)[C@H]([C@H](C)O)NC(=O)[C@H](CN)NC(=O)[C@H](C2CCC(F)(F)CC2)NC(=O)[C@H](CC(C)C)N(C)C(=O)[C@@H]1C]

Step 1: 2-((((9H-Fluoren-9-yl)methoxy)carbonyl)amino)-2-(4,4-difluorocyclohexyl)acetic acid

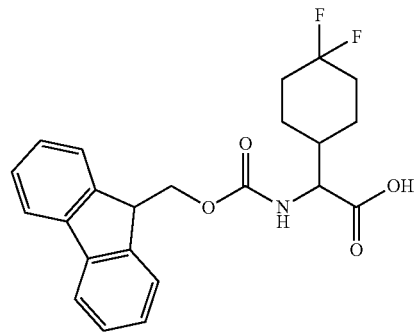 [SMILES: O=C(NC(C(=O)O)C1CCC(F)(F)CC1)OCC1c2ccccc2-c2ccccc21]

Using 2-(tert-butoxycarbonylamino)-2-(4,4-difluorocyclohexyl)acetic acid and following procedures analogous to those described for Example 1, step 2, the title compound was synthesized in 98% over 2 steps. LCMS (ESI) $[M+H]^+$=416.0.

Step 2: (6S,9S,12S,15S,18R,19R)-9-(Aminomethyl)-12-(4,4-difluorocyclohexyl)-19-hexyl-6-((S)-1-hydroxyethyl)-15-isobutyl-16,18-dimethyl-1-oxa-4,7,10,13,16-pentaazacyclononadecane-2,5,8,11,14,17-hexaone The title compound was prepared as a mixture of two diastereomers using 2-((((9H-Fluoren-9-yl)methoxy)carbonyl)amino)-2-(4,4-difluorocyclohexyl)acetic acid and following procedures analogous to those described for Example 1, Steps 3-6. The two stereoisomers were separated via achiral HPLC, with the second eluting peak designated as the title compound. LCMS (ESI): $R_T$ (min)= 4.61, $[M+H]^+$=717.5, method=A.

Example 53: (6S,9S,12S,15S,18R,19R)-9-(Aminomethyl)-19-decyl-12-(4,4-difluorocyclohexyl)-6-((S)-1-hydroxyethyl)-15-isobutyl-16,18-dimethyl-1-oxa-4,7,10,13,16-pentaazacyclononadecane-2,5,8,11,14,17-hexaone

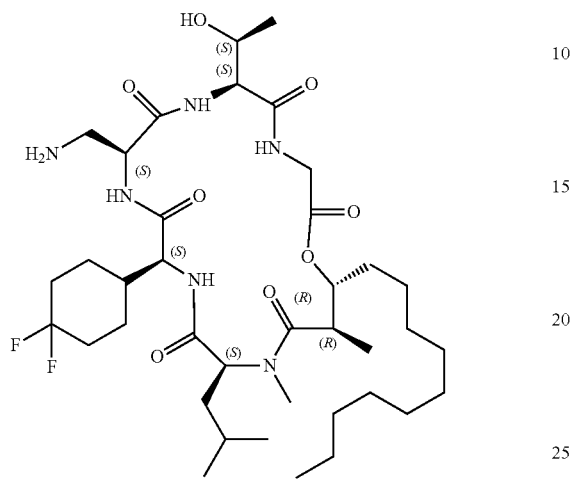

Step 1: N-((2R,3R)-3-((O-Benzyl-N-((2S)-3-(((benzyloxy)carbonyl)amino)-2-(2-((tert-butoxycarbonyl)amino)-2-(4,4-difluorocyclohexyl)acetamido)propanoyl)-L-allothreonylglycyl)oxy)-2-methyltridecanoyl)-N-methyl-L-leucine-(2-chlorotrityl resin)

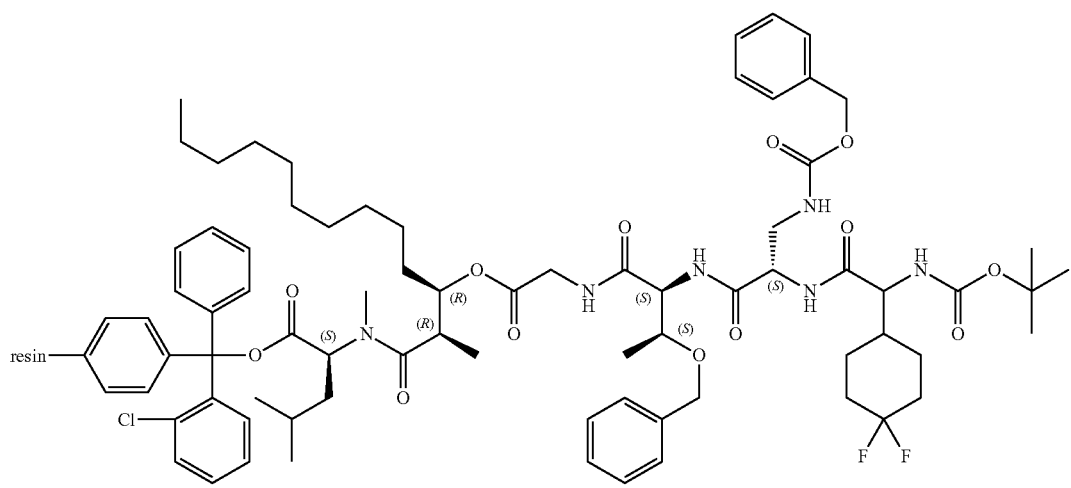

The title compound was synthesized following procedures analogous to those described for Example 28, steps 1-4 using the appropriately protected amino acids.-

Step 2: N-((2R,3R)-3-((O-Benzyl-N-((2S)-3-(((benzyloxy)carbonyl)amino)-2-(2-((tert-butoxycarbonyl)amino)-2-(4,4-difluorocyclohexyl)acetamido)propanoyl)-L-allothreonylglycyl)oxy)-2-methyltridecanoyl)-N-methyl-L-leucine

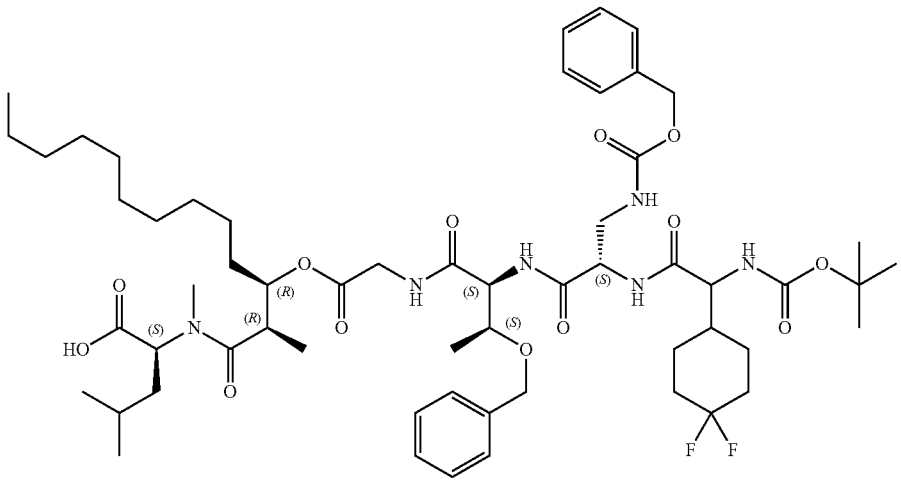

The resin-bound depsipeptide from step 1 above was treated with 8 mL of 7:2:1 DCM:AcOH:TFE. The mixture was placed on a rotator at room temperature for 3 h, and then filtered, rinsing with DCM. The combined filtrates were evaporated in vacuo, azeotroping with toluene and diethyl ether to the title compound which was taken directly into step 3 without purification. LCMS (ESI) $[M+H]^+=1115$.

Step 3: N-((2R,3R)-3-((N-((2S)-2-(2-amino-2-(4,4-difluorocyclohexyl)acetamido)-3-(((benzyloxy)carbonyl)amino)propanoyl)-O-benzyl-L-allothreonylglycyl)oxy)-2-methyltridecanoyl)-N-methyl-L-leucine

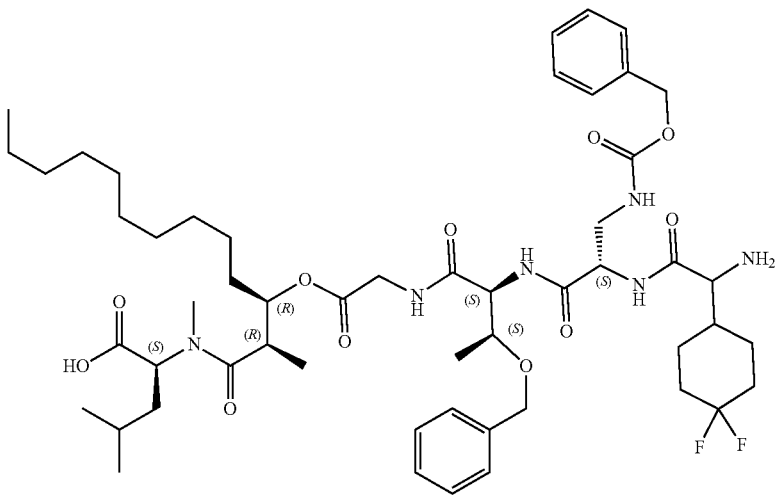

The crude residue from step 2 above was dissolved in DCM and then treated with HCl (4N in dioxane, 0.42 mL) for 3 hr. The reaction mixture was concentrated to dryness to afford crude depsipeptide. This crude material was dissolved in DCM and MP-Carbonate (3 eq, 0.30 g) was added to free-base material. The reaction was stirred on an orbital shaker for 3 h then filtered and concentrated to afford the title compound (0.32 g, 0.32 mmol, 95% crude yield) as an oil. LCMS (ESI) $[M+H]^+=1015$.

Step 4: Benzyl(((6S,9S,15S,18R,19R)-6-((S)-1-(benzyloxy)ethyl)-19-decyl-12-(4,4-difluorocyclohexyl)-15-isobutyl-16,18-dimethyl-2,5,8,11,14,17-hexaoxo-1-oxa-4,7,10,13,16-pentaazacyclononadecan-9-yl)methyl)carbamate

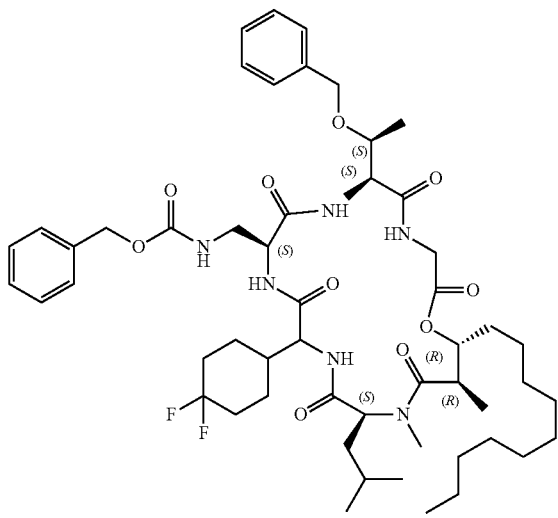

The crude material from step 3 was dissolved in DMF (40 mL) and slowly added (via dropping funnel) to a flask containing N, N'-Diisopropylcarbodiimide (4 eq, 159 mg, 1.26 mmol), HOBt (1.2 eq, 52 mg, 0.38 mmol), and DMF (185 mL). After the addition was complete, the reaction was stirred for 18 h at 45° C. whereupon the reaction was concentrated. The resulting residue was treated with saturated aqueous bicarbonate solution and extracted with DCM. The organic layer was washed with brine, dried over magnesium sulfate, filtered, and concentrated to give the title compound (245 mg, 78% crude yield) as an oil. LCMS (ESI) [M+H]$^+$=997.

Step 5: (6S,9S,12S,15S,18R,19R)-9-(Aminomethyl)-19-decyl-12-(4,4-difluorocyclohexyl)-6-((S)-1-hydroxyethyl)-15-isobutyl-16,18-dimethyl-1-oxa-4,7,10,13,16-pentaazacyclononadecane-2,5,8,11,14,17-hexaone The material from step 4 was subjected to conditions analogous to those described in Example 1, step 6 to afford 13.3 mg (20%) of the title compound following reverse phase HPLC and subsequent SFC purification (peak 2 was the active diasteromer).
SFC purification conditions:
Wavelength: 220 nm
Solvent A: 0.05% Trifluoroacetic acid
Solvent B: Acetonitrile
Initial B %: 5
Final B %: 0
Column: Luns C8 5 um
column dimensions: 100×30 mm, 5 um
flow rate: 60
run duration: 15 min
cycle time: 15 min
column temp: 25° C.
LCMS (ESI): R$_T$(min)=5.56, [M+H]$^+$=773.5, method=A; $^1$H NMR (400 MHz, DMSO-d$_6$) δ 9.10-7.17 (m, 8H), 5.46-5.22 (m, 1H), 5.13-4.58 (m, 2H), 4.39-3.36 (m, 5H), 3.05-2.63 (m, 5H), 2.11-1.14 (m, 29H), 1.14-0.75 (m, 18H).

Example 54: (6S,9S,12S,15S,18R,19R)-18-([1,1'-Biphenyl]-4-ylmethyl)-9-(aminomethyl)-12-cyclohexyl-19-hexyl-6-((S)-1-hydroxyethyl)-15-isobutyl-16-methyl-1-oxa-4,7,10,13,16-pentaazacyclononadecane-2,5,8,11,14,17-hexaone

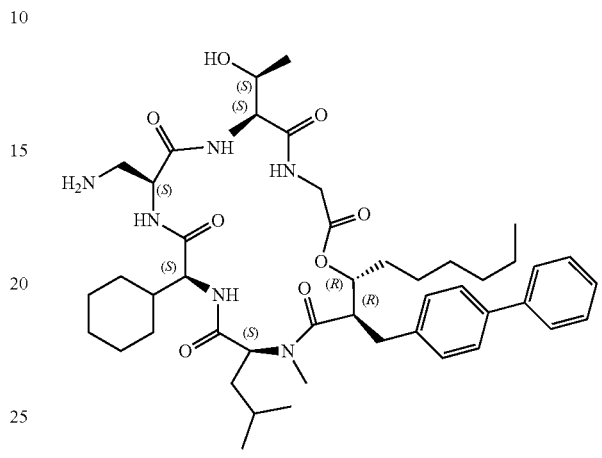

Step 1: 3-([1,1'-Biphenyl]-4-yl)-1-((3aR,6S,7aS)-8,8-dimethyl-2,2-dioxidotetrahydro-3H-3a,6-methanobenzocisothiazol-1(4H)-yl)propan-1-one

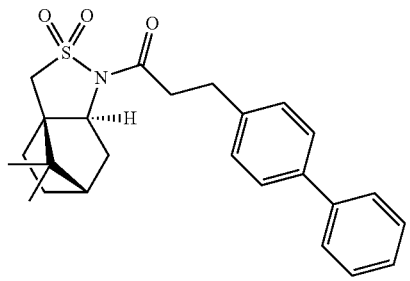 [SMILES: CC1(C)[C@H]2CC[C@@]13CS(=O)(=O)N(C(=O)CCc1ccc(-c4ccccc4)cc1)[C@H]3C2]

To a solution of 3-(4-biphenyl)propionic acid (2.5 g, 11 mmol) in DCM (20 mL) with 3 drops DMF at 0° C. was added oxalyl chloride (2.0 mol/L in DCM, 6.5 mL, 13 mmol). The reaction mixture was stirred at room temperature for 1 h, and then evaporated in vacuo to yield the corresponding acid chloride. This material was dissolved in THF (10 mL) and added to a mixture of (3aR,6S,7aS)-8,8-dimethylhexahydro-3H-3a,6-methanobenzo[c]isothiazole 2,2-dioxide (2.000 g, 9.289 mmol), DMAP (93 mg, 0.723 mmol) and triethylamine (2.5 mL, 18 mmol) in THF (20 mL) at 0° C. The reaction mixture was warmed to room temperature and allowed to stir for 17 h. The reaction mixture was evaporated in vacuo. The resulting residue was partitioned between water (100 mL) and ethyl acetate (250 mL). The organic layer was washed with saturated aqueous sodium bicarbonate, brine, dried over magnesium sulfate, filtered and evaporated in vacuo. The crude product was purified via flash chromatography on silica gel (120 g silica, solvent gradient: 0-30% ethyl acetate in heptanes) to yield 3.5965 g (91%) of the title compound as a light yellow gum. LCMS (ESI): [M+H]$^+$=424.1.

Step 2: Benzyl ((((6S,9S,12S,15S,18R,19R)-18-([1,1'-biphenyl]-4-ylmethyl)-6-((S)-1-(benzyloxy)ethyl)-12-cyclohexyl-19-hexyl-15-isobutyl-16-methyl-2,5,8,11,14,17-hexaoxo-1-oxa-4,7,10,13,16-pentaazacyclononadecan-9-yl)methyl)carbamate

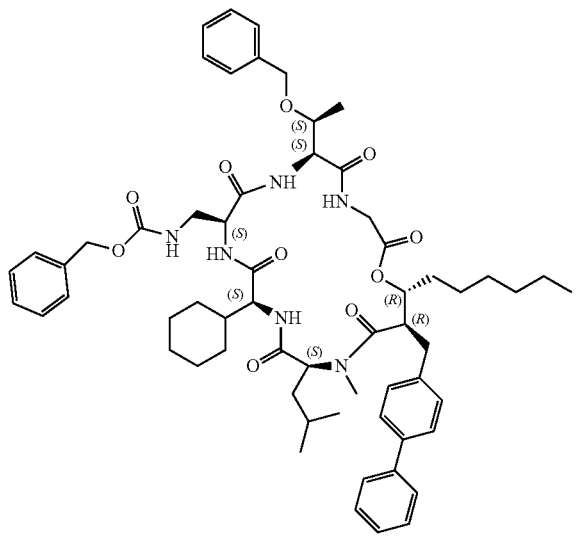

The title compound was prepared using the product from Step 1 and following procedures analogous to those described for Example 9, steps 2 and 4, and Example 1, steps 1-5, substituting the appropriately protected amino acids. LCMS (ESI) [M+H]$^+$=1057.5.

Step 3. (6S,9S,12S,15S,18R,19R)-18-([1,1'-Biphenyl]-4-ylmethyl)-9-(aminomethyl)-12-cyclohexyl-19-hexyl-6-((S)-1-hydroxyethyl)-15-isobutyl-16-methyl-1-oxa-4,7,10,13,16-pentaazacyclononadecane-2,5,8,11,14,17-hexaone A flask was charged with benzyl ((((6S,9S,12S,15S,18R,19R)-18-([1,1'-biphenyl]-4-ylmethyl)-6-((S)-1-(benzyloxy)ethyl)-12-cyclohexyl-19-hexyl-15-isobutyl-16-methyl-2,5,8,11,14,17-hexaoxo-1-oxa-4,7,10,13,16-pentaazacyclononadecan-9-yl)methyl)carbamate (39.8 mg, 0.0376 mmol) and ethyl acetate (5.0 mL), and the flask purged with nitrogen. After the addition of TFA (25 L, 0.323 mmol) and palladium (10 wt. % on carbon) (47 mg, 0.04417 mmol) the reaction mixture was evacuated and backfilled with hydrogen, and then stirred at room temperature under a hydrogen balloon for 24 h. The reaction mixture was filtered through celite, rinsing with 100 mL of 5% AcOH in methanol, and the filtrate was evaporated in vacuo, azeotroping with toluene (3×1 mL). The crude product was purified via reverse-phase HPLC and lyophilized to yield 11.95 mg (38% yield) of the title compound. LCMS (ESI): R$_T$ (m)=5.711, [M+H]$^+$=833.5, method=A; $^1$H NMR (400 MHz, DMSO-d$_6$) δ 8.77-8.34 (m, 1H), 8.21-8.09 (m, 1H), 7.95-7.74 (m, 3H), 7.70-7.39 (m, 7H), 7.39-7.31 (m, 2H), 7.24-7.17 (m, 1H), 5.28-4.49 (m, 2H), 4.42-4.05 (m, 3H), 4.03-3.55 (m, 2H), 3.21-3.05 (m, 3H), 3.00 (s, 2H), 2.89-2.61 (m, 3H), 2.06-0.61 (m, 32H), 0.60-0.44 (m, 6H).

Example 55: (6S,9S,12S,15S,18R,19R)-9-(aminomethyl)-19-hexyl-6-((S)-1-hydroxyethyl)-15-isobutyl-16,18-dimethyl-12-(spiro[3.3]heptan-2-yl)-1-oxa-4,7,10,13,16-pentaazacyclononadecane-2,5,8,11,14,17-hexaone

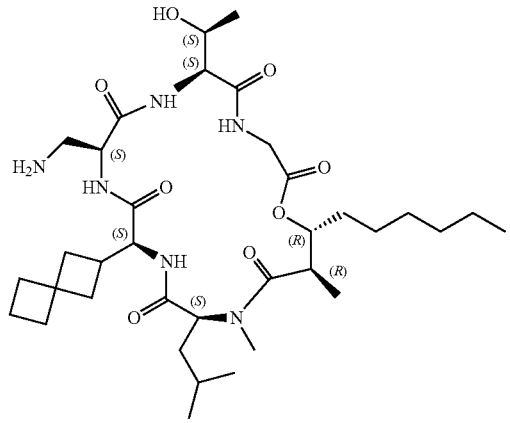

Step 1: Methyl 2-(((benzyloxy)carbonyl)amino)-2-(spiro[3.3]heptan-2-ylidene)acetate

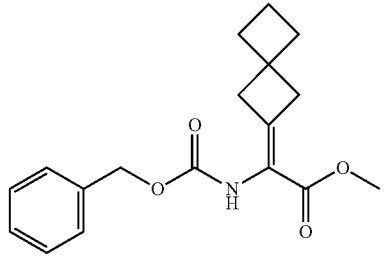 [SMILES: COC(=O)C(NC(=O)OCc1ccccc1)=C1CC2(CCC2)C1]

To a solution of methyl 2-(benzyloxycarbonylamino)-2-dimethoxyphosphoryl-acetate (1.739 g, 5.249 mmol) in ethyl acetate (15 mL) was added 1,1,3,3-tetramethylguanidine (0.85 mL, 6.8 mmol). The resulting mixture was stirred at room temperature for 30 minutes, followed by the addition of a solution of spiro[3.3]heptan-2-one (826 mg, 7.4989 mmol) in ethyl acetate (5 mL). The reaction mixture was stirred at room temperature for 3 days. The reaction mixture was quenched with the addition of 5 mL 10% aqueous citric acid and extracted with ethyl acetate (25 mL). The organic portion was washed with saturated aqueous sodium bicarbonate and brine, dried over magnesium sulfate, filtered, and evaporated in vacuo. The crude product was purified via flash chromatography on silica gel (80 g silica, solvent gradient: 0-50% ethyl acetate in heptanes) to yield 1.0857 g (66%) of the title compound as a clear, colorless oil. LCMS (ESI) [M+H]$^+$=316.05; $^1$H NMR (400 MHz, Chloroform-d) δ 7.43-7.29 (m, 5H), 6.11 (s, 1H), 5.12 (s, 2H), 3.73 (s, 3H), 3.10 (tt, J=2.0, 1.0 Hz, 2H), 2.83 (s, 2H), 2.10-1.99 (m, 5H), 1.90-1.76 (m, 2H), includes residual ethyl acetate.

Step 2: Methyl (S)-2-(((benzyloxy)carbonyl)amino)-2-(spiro[3.3]heptan-2-yl)acetate

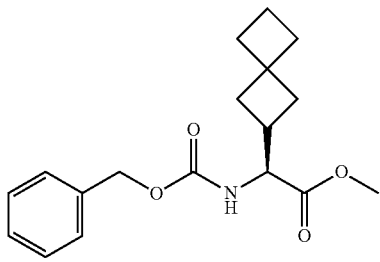 [SMILES: COC(=O)[C@@H](NC(=O)OCc1ccccc1)C1CC2(CCC2)C1]

A mixture of methyl 2-(benzyloxycarbonylamino)-2-spiro[3.3]heptan-2-ylidene-acetate (0.980 g, 3.11 mmol) and (−)-1,2-bis((2S,5S)-2,5-dimethylphospholano)ethane(1,5-cyclooctadiene)rhodium(I) tetrafluoroborate (42 mg, 0.0739996 mmol) in ethanol (8 mL) was purged with bubbling nitrogen for 10 minutes. The reaction mixture was stirred at 25° C. under 70 psi $H_2$ for 18 h. The reaction mixture was evaporated in vacuo, and the resulting residue taken up in ethyl acetate (10 mL) and filtered through celite. The filtrate was evaporated in vacuo to yield 0.956 g (97%) of the title compound. LCMS (ESI) $[M+H]^+=318.1$.

Step 3: (S)-2-(((((9H-Fluoren-9-yl)methoxy)carbonyl)amino)-2-(spiro[3.3]heptan-2-yl)acetic acid

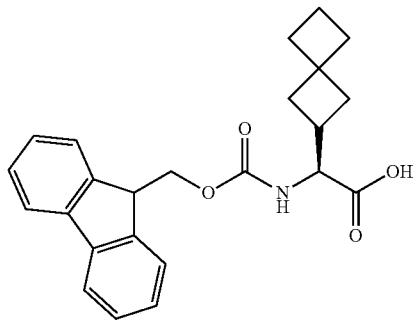 [SMILES: O=C(N[C@H](C(=O)O)C1CC2(CCC2)C1)OCC1c2ccccc2-c2ccccc21]

To a solution of methyl (2S)-2-(benzyloxycarbonylamino)-2-spiro[3.3]heptan-2-yl-acetate (1.136 g, 3.579 mmol) in THF (12 mL) was added lithium hydroxide (1.0 M in water, 7 mL, 7.0 mmol). The reaction mixture was stirred at room temperature for 16 h. The reaction mixture was poured into 10% aqueous citric acid and extracted with DCM (3×100 mL). The combined DCM extracts were dried over magnesium sulfate, filtered, and evaporated in vacuo.

The resulting material was dissolved in ethyl acetate (15 mL) with 0.75 mL TFA and the reaction vessel purged with nitrogen. Palladium (10 wt. % on carbon) (378 mg, 0.3553 mmol) was added and the reaction vessel purged again with nitrogen, then with hydrogen, and stirred under a hydrogen balloon at room temperature for 17 h. The reaction mixture was filtered through celite, rinsing with methanol, and evaporated in vacuo.

The resulting material was dissolved in water (10 mL) and 1,4-dioxane (10 mL), followed by the addition of sodium hydrogen carbonate (1.06 g, 12.6 mmol) and N-(9-fluorenylmethoxycarbonyloxy)succinimide (1.519 g, 4.503 mmol). The resulting mixture was stirred at room temperature for 19 h. The reaction mixture was poured into 10% aqueous citric acid and extracted with DCM (3×100 mL). The combined organic extracts were dried over magnesium sulfate, filtered, and evaporated in vacuo. The crude product was purified via flash chromatography on silica gel (80 g silica, solvent gradient: 0-100% ethyl acetate in DCM) to yield 0.9786 g of the title compound as a white solid (70% yield). LCMS (ESI) $[M+H]^+=392.15$.

Step 4: (6S,9S,12S,15S,18R,19R)-9-(aminomethyl)-19-hexyl-6-((S)-1-hydroxyethyl)-15-isobutyl-16,18-dimethyl-12-(spiro[3.3]heptan-2-yl)-1-oxa-4,7,10,13,16-pentaazacyclononadecane-2,5,8,11,14,17-hexaone The title compound was prepared using (S)-2-(((((9H-fluoren-9-yl)methoxy)carbonyl)amino)-2-(spiro[3.3]heptan-2-yl)acetic acid and following procedures analogous to those described for Example 1. LCMS (ESI): $R_T$ (min)=4.846, $[M+H]^+=693.3$, method=A; $^1H$ NMR (400 MHz, DMSO-$d_6$) δ 8.45-7.37 (m, 7H), 6.51 (s, 1H), 5.10-4.72 (m, 2H), 4.57-3.77 (m, 6H), 3.26-3.01 (m, 3H), 2.79-2.55 (m, 3H), 2.24-1.36 (m, 15H), 1.35-0.76 (m, 24H).

Example 56: (6S,9S,12S,15S,18R,19R)-6-((1H-1,2,3-triazol-4-yl)methyl)-9-(aminomethyl)-12-cyclohexyl-19-decyl-15-isobutyl-16,18-dimethyl-1-oxa-4,7,10,13,16-pentaazacyclononadecane-2,5,8,11,14,17-hexaone

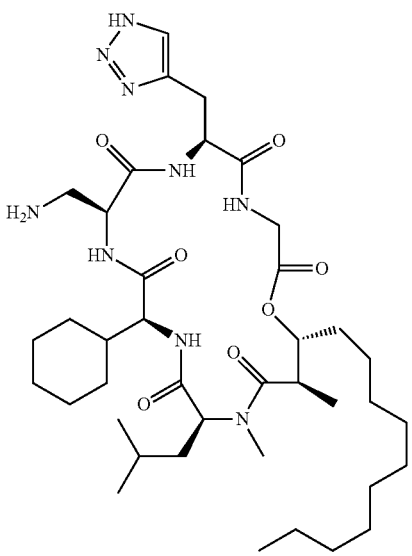 [SMILES: CCCCCCCCCC[C@H]1OC(=O)CNC(=O)[C@H](Cc2c[nH]nn2)NC(=O)[C@H](CN)NC(=O)[C@H](C2CCCCC2)NC(=O)[C@H](CC(C)C)N(C)C(=O)[C@@H]1C]

Step 1: (S)-2-((((9H-fluoren-9-yl)methoxy)carbonyl)amino)-3-(1-benzyl-1H-1,2,3-triazol-4-yl)propanoic acid

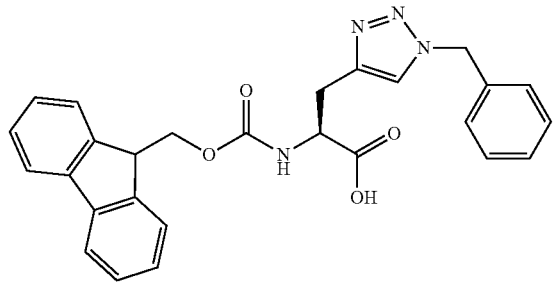 [SMILES: O=C(N[C@@H](Cc1cn(Cc2ccccc2)nn1)C(=O)O)OCC1c2ccccc2-c2ccccc21]

Following procedures from Heterocycles, 86, 2012, 735-743, (S)-3-(1-benzyl-H-1,2,3-triazol-4-yl)-2-((tert-butoxycarbonyl)amino)propanoic acid was synthesized in 56% yield from (2S)-2-(tert-butoxycarbonylamino)pent-4-ynoic acid. (S)-3-(1-benzyl-1H-1,2,3-triazol-4-yl)-2-((tert-butoxycarbonyl)amino)propanoic acid was then subjected to procedures analogous to those described in Example 1, step 2 to form (2S)-3-(1-benzyltriazol-4-yl)-2-(9H-fluoren-9-ylmethoxycarbonylamino)propanoic acid in 36% yield over 2 steps. LCMS (ESI) [M+H]$^+$=469.0.

Step 2: (6S,9S,12S,15S,18R,19R)-6-((1H-1,2,3-triazol-4-yl)methyl)-9-(aminomethyl)-12-cyclohexyl-19-decyl-15-isobutyl-16,18-dimethyl-1-oxa-4,7,10,13,16-pentaazacyclononadecane-2,5,8,11,14,17-hexaone The title compound was prepared using (S)-2-((((9H-fluoren-9-yl)methoxy)carbonyl)amino)-3-(1-benzyl-1H-1,2,3-triazol-4-yl)propanoic acid and following procedures analogous to those described for Example 28. LCMS (ESI): R$_T$ (min)=5.35, [M+H]$^+$=774.4, method=A.

Example 57: (3R,6S,9S,12S,15S,18R,19R)-9-(Aminomethyl)-12-cyclohexyl-19-hexyl-6-((S)-1-hydroxyethyl)-15-isobutyl-3,16,18-trimethyl-1-oxa-4,7,10,13,16-pentaazacyclononadecane-5,8,11,14,17-pentaone

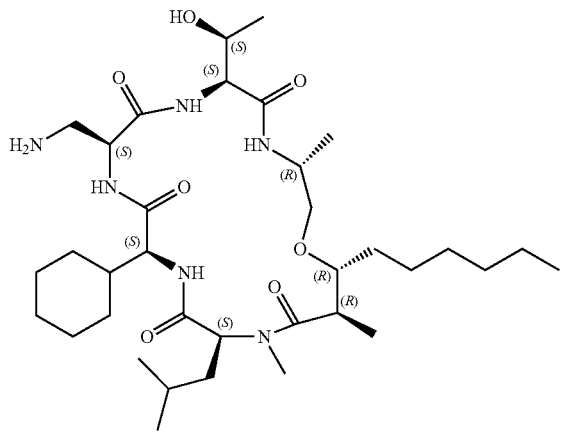

Step 1: O-Benzyl-N—((S)-3-(((benzyloxy)carbonyl)amino)-2-((S)-2-cyclohexyl-2-((6R,9R,10R,13S)-9-hexyl-13-isobutyl-2,2,6,10,12-pentamethyl-4,11-dioxo-3,8-dioxa-5,12-diazatetradecan-14-amido)acetamido)propanoyl)-L-allothreonine

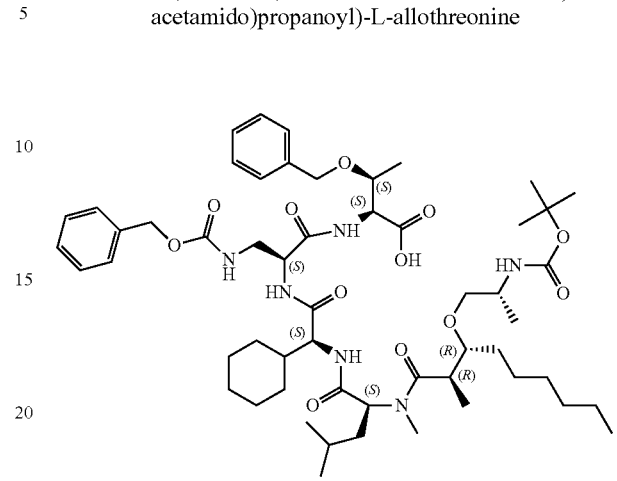

Intermediate 8 (resin loading 0.44 mmol/g, 2.0 g) was swelled with 10 mL DMF for 2 h. The resin was drained, and treated with a solution (premixed at room temperature for 15 min) of (2R,3R)-3-((R)-2-((tert-butoxycarbonyl)amino)propoxy)-2-methylnonanoic acid (Intermediate 3, 3.267 g, 7.571 mmol), HATU/HOBt (1:1) (4.4 mL, 0.4 M in DMF, 1.76 mmol), DIPEA (454 mg, 3.52 mmol) and DMF (10 mL). The resin was agitated on a shaker for 39 h, and then drained and rinsed with DMF. The resin was treated with 10 mL of 4/1 DCM/1,1,3,3,3-hexafluoropropan-2-ol. The mixture was agitated on a shaker at room temperature for 3 h, and then filtered, rinsing with 8 mL DCM. The combined filtrates were concentrated under reduced pressure, and the residue was purified by reverse phase chromatography on C18 column (acetonitrile-water 40-70/0.05% DIPEA in water) to afford the title compound as a DIPEA salt (500 mg) as a yellow solid. LCMS (ESI): [M+H]$^+$=1022.6.

Step 2. N—((S)-2-((S)-2-((S)-2-((2R,3R)-3-((R)-2-Aminopropoxy)-N,2-dimethyl nonanamido)-4-methylpentanamido)-2-cyclohexylacetamido)-3-(((benzyloxy)carbonyl)amino)propanoyl)-O-benzyl-L-allothreonine

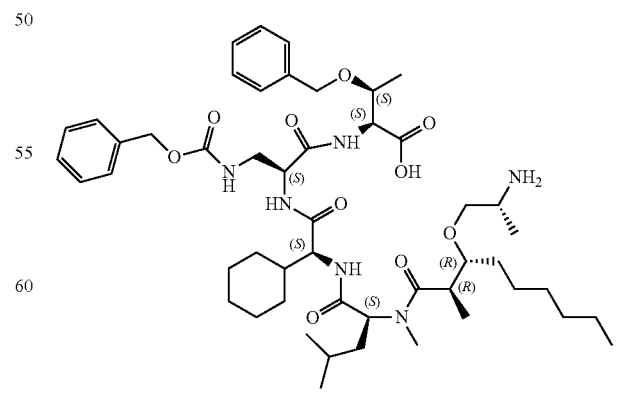

To a mixture of HCl (4 M in dioxane, 5 mL) and DCM (5 mL) was added O-benzyl-N—((S)-3-(((benzyloxy)carbonyl)amino)-2-((S)-2-cyclohexyl-2-((6R,9R,10R,13S)-9-hexyl-13-isobutyl-2,2,6,10,12-pentamethyl-4,11-dioxo-3,8-dioxa-5,12-diazatetradecan-14-amido)acetamido)propanoyl)-L-allothreonine DIPEA salt (500 mg) at 0° C. The reaction mixture was stirred for 1 h at 0° C., and concentrated under reduced pressure to afford 410 mg of the title compound as HCl salt. LCMS (ESI): [M+H]$^+$=923.

Step 3. Benzyl (((3R,6S,9S,12S,15S,18R,19R)-6-((S)-1-(benzyloxy)ethyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate

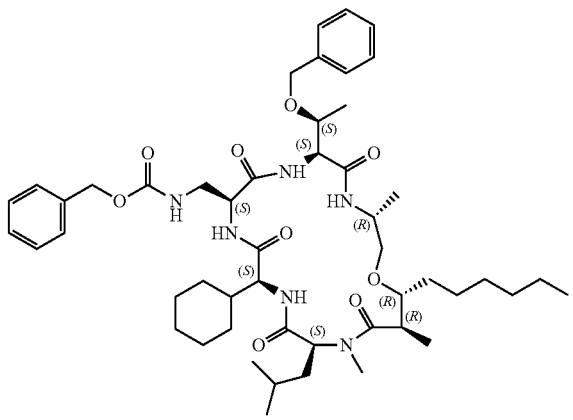

The crude product from the previous step (410 mg) was dissolved in DMF (2 mL) and added to a solution of DIPEA (189 mg, 1.47 mmol) in THF (100 mL) at 0° C. under nitrogen. Then a solution of HATU (337.7 mg, 0.89 mmol) in DMF (2 mL) was added dropwise. The reaction mixture was stirred for 1 h at 0° C., and concentrated under reduced pressure to afford the residual DMF solution, which was then added dropwise to 200 mL of water with vigorous stirring. The resulting precipitate was collected, washed by water (3×10 mL) and dried to afford the title compound (330 mg) as a yellow solid. LCMS (ESI): [M+H]$^+$=905.

Step 4. (3R,6S,9S,12S,15S,18R,19R)-9-(Aminomethyl)-12-cyclohexyl-19-hexyl-6-((S)-1-hydroxyethyl)-15-isobutyl-3,16,18-trimethyl-1-oxa-4,7,10,13,16-pentaazacyclononadecane-5,8,11,14,17-pentaone The crude product from the previous step (330 mg) was dissolved in ethyl acetate (10 mL) containing 0.5% TFA by volume. Palladium (10 wt. % on carbon) (150 mg) was added under nitrogen. The resulting mixture was evacuated and backfilled with hydrogen, and then stirred at 25° C. under a hydrogen balloon for 2 h. The catalyst was filtered off and rinsed with ethyl acetate. The filtrate was concentrated under reduced pressure. The residue was purified by reverse phase chromatography (acetonitrile-water 35-45/0.1% TFA in water) to afford the title compound (31.4 mg, 10% yield) as the TFA salt. LCMS (ESI): R$_T$=1.79 min, [M+H]$^+$=681, method=C; $^1$H NMR (400 MHz, DMSO-d$_6$) δ 8.82-8.35 (m, 1H), 8.19-7.28 (m, 6H), 4.66-3.40 (m, 11H), 3.25-2.70 (m, 5H), 2.22-1.42 (m, 9H), 1.35-0.73 (m, 32H).

Example 58: (6S,9S,12S,15S,18R,19R)-6-(((1r,3S)-3-Aminocyclobutoxy)methyl)-9-(aminomethyl)-12-cyclohexyl-19-hexyl-15-isobutyl-16,18-dimethyl-1-oxa-4,7,10,13,16-pentaazacyclononadecane-2,5,8,11,14,17-hexaone

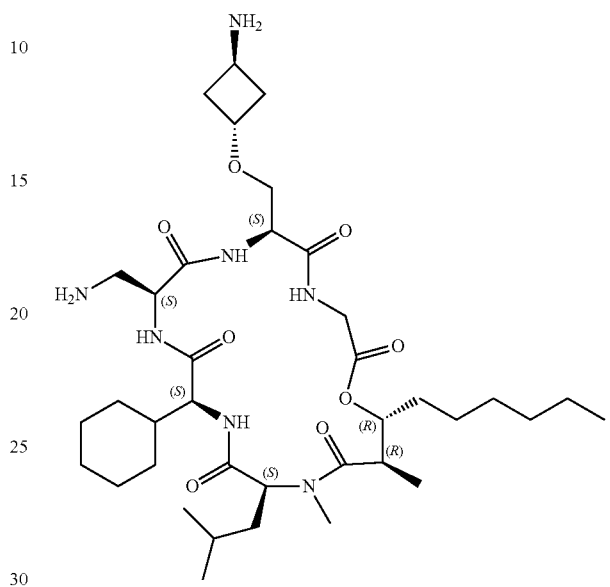

The title compound was prepared using Intermediate 6 and following procedures analogous to those described for Example 51. LCMS (ESI): R$_T$ (min)=1.53, [M+H]$^+$=736.5, method=C; $^1$H NMR (300 MHz, DMSO-d$_6$) δ 9.41-9.09 (m, 1H), 9.08-8.61 (m, 1H), 8.25-7.81 (m, 6H), 7.68-7.37 (m, 1H), 5.11-4.45 (m, 1H), 4.38-4.06 (m, 3H), 3.97-3.58 (m, 4H), 3.29-3.01 (m, 8H), 2.77-2.68 (m, 1H), 2.36-2.14 (m, 3H), 2.13-1.81 (m, 2H), 1.80-1.38 (m, 7H), 1.37-1.14 (m, 16H), 1.13-0.99 (m, 4H), 0.98-0.77 (m, 8H).

Example 59: (6S,9S,12S,15S,18R,19R)-9-(Aminomethyl)-12-cycloheptyl-19-hexyl-6-((S)-1-hydroxyethyl)-15-isobutyl-16,18-dimethyl-1-oxa-4,7,10,13,16-pentaazacyclononadecane-2,5,8,11,14,17-hexaone

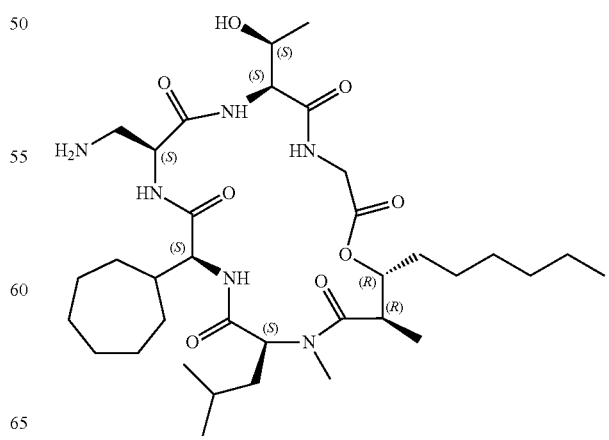

Step 1: (S)-2-((((9H-Fluoren-9-yl)methoxy)carbonyl)amino)-2-cycloheptylacetic acid

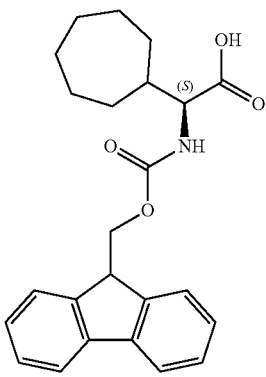

To a solution of (2S)-2-amino-2-cycloheptyl-acetic acid (1.0 g, 5.84 mmol) in DMF (25 mL) and water (25 mL) was added NaHCO$_3$ (982.0 mg, 11.69 mmol). A solution of 9-fluorenylmethylchloroformate (1.8 g, 6.98 mmol) in THF (5 mL) was added dropwise at 0° C. The reaction mixture was allowed to warm to room temperature and stirred at 25° C. for 24 h. Aqueous HCl (1 mol/L) was carefully added until pH 6. The resulting solution was extracted with ethyl acetate (3×100 mL). The organic layers were combined and washed with water (5×), dried over sodium sulfate and concentrated under reduced pressure. The residue was purified by flash chromatography on silica gel eluting with DCM/MeOH (10/1) to afford the title compound (1.77 g, 77% yield) as a white solid. LCMS (ESI): [M+H]$^+$=394.2. $^1$H NMR (400 MHz, DMSO-d$_6$) 12.58 (s, 1H), 7.89 (d, J=7.6 Hz, 2H), 7.76 (d, J=7.6 Hz, 2H), 7.59 (d, J=8.8 Hz, 1H), 7.44-7.40 (m, 2H), 7.35-7.30 (m, 2H), 4.31-3.93 (m, 4H), 1.95-1.33 (m, 13H).

Step 2: Benzyl ((((6S,9S,12S,15S,18R,19R)-6-((S)-1-(benzyloxy)ethyl)-12-cycloheptyl-19-hexyl-15-isobutyl-16,18-dimethyl-2,5,8,11,14,17-hexaoxo-1-oxa-4,7,10,13,16-pentaazacyclononadecan-9-yl)methyl)carbamate

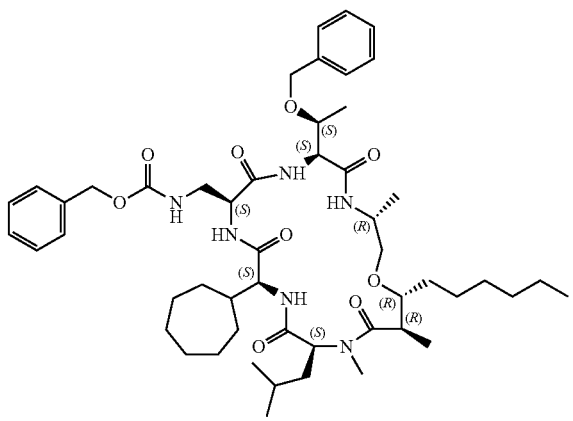

The title compound was prepared using (S)-2-((((9H-fluoren-9-yl)methoxy)carbonyl) amino)-2-cycloheptylacetic acid and following procedures analogous to those described for Example 1 LCMS (ESI): [M+H]$^+$=919.6.

Step 3: (6S,9S,12S,15S,18R,19R)-9-(Aminomethyl)-12-cycloheptyl-19-hexyl-6-((S)-1-hydroxyethyl)-15-isobutyl-16,18-dimethyl-1-oxa-4,7,10,13,16-pentaazacyclononadecane-2,5,8,11,14,17-hexaone Palladium (10 wt. % on carbon) (150 mg) was added to a solution of benzyl ((((6S,9S,12S,15S,18R,19R)-6-((S)-1-(benzyloxy)ethyl)-12-cycloheptyl-19-hexyl-15-isobutyl-16,18-dimethyl-2,5,8,11,14,17-hexaoxo-1-oxa-4,7,10,13,16-pentaazacyclononadecan-9-yl)methyl)carbamate (330 mg, 0.36 mmol) in ethyl acetate (10 mL) containing 0.5% TFA by volume under nitrogen. The mixture was evacuated and backfilled with hydrogen and stirred for 2 h at 25° C. under a hydrogen balloon.

The catalyst was filtered off and the filtrate was concentrated under reduced pressure. The resulting residue was purified by Prep-LCMS to afford the title compound (31.4 mg, 10% yield) as a TFA salt. LCMS (ESI): R$_T$ (min) 1.83, [M+1]$^+$=695.4, method=C; $^1$H NMR (400 MHz, DMSO-d$_6$) δ 8.74-8.38 (m, 1H), 8.22-7.88 (m, 3H), 7.86-7.68 (m, 1H), 7.67-7.56 (m, 1H), 7.54-6.97 (m, 1H), 5.25-4.45 (m, 3H), 4.36-3.98 (m, 4H), 3.97-3.71 (m, 2H), 3.32-3.06 (m, 4H), 2.94-2.69 (m, 2H), 2.39-2.06 (m, 1H), 2.05-1.36 (m, 15H), 1.35-0.96 (m, 16H), 0.95-0.78 (m, 9H).

Example 60: (6S,9S,12S,15S,18R,19R)-9-(Aminomethyl)-19-(2-(bicyclo[2.2.1]heptan-2-yl)ethyl)-12-cyclohexyl-6-((S)-1-hydroxyethyl)-15-isobutyl-16,18-dimethyl-1-oxa-4,7,10,13,16-pentaazacyclononadecane-2,5,8,11,14,17-hexaone

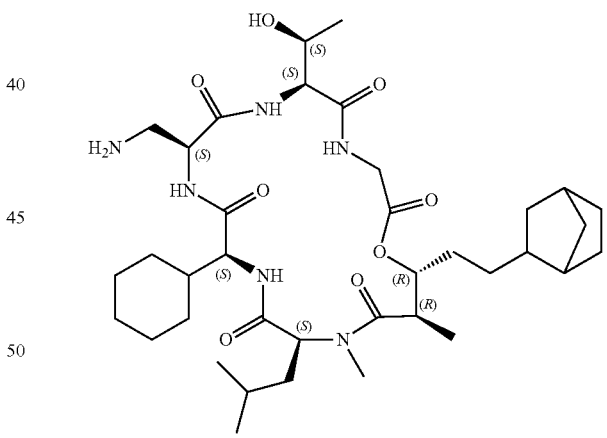

Step 1: 3-(Bicyclo[2.2.1]heptan-2-yl)propanal

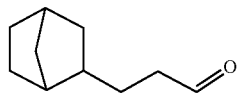 [SMILES: O=CCCC1CC2CCC1C2]

To a solution of 3-norbornan-2-ylpropan-1-ol purchased from ENAMINE (Catalog #EN300-131519) (4.06 g, 26.32 mmol) in DCM (100 mL) was added pyridinium chlorochromate (8.49 g, 39.48 mmol). The reaction mixture was stirred at ambient temperature for 2 h, filtered through celite and rinsed with DCM. The filtrate was concentrated under reduced pressure. The crude product was used for the next step without purification.

Step 2: (2R,3R)-5-(Bicyclo[2.2.1]heptan-2-yl)-3-hydroxy-2-methylpentanoic acid

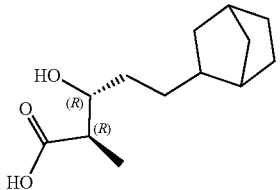

The title compound was prepared using 3-(bicyclo[2.2.1]heptan-2-yl)propanal and following procedures analogous to those described for Intermediate 1. LCMS (ESI): [M+H]$^+$=227.2.

Step 3: (6S,9S,12S,15S,18R,19R)-9-(Aminomethyl)-19-(2-(bicyclo[2.2.1]heptan-2-yl)ethyl)-12-cyclohexyl-6-((S)-1-hydroxyethyl)-15-isobutyl-16,18-dimethyl-1-oxa-4,7,10,13,16-pentaazacyclononadecane-2,5,8,11,14,17-hexaone The title compound was prepared using (2R,3R)-5-(bicyclo[2.2.1]heptan-2-yl)-3-hydroxy-2-methylpentanoic acid and following procedures analogous to those described for Example 59. LCMS (ESI): R$_T$ (min)=1.91, [M+H]$^+$=719.4, method=C; $^1$H NMR (400 MHz, DMSO-d$_6$) 8.74-8.66 (m, 1H), 8.22-7.83 (m, 3H), 7.78-7.49 (m, 2H), 7.28-6.98 (m, 1H), 5.12-4.38 (m, 2H), 4.29-4.09 (m, 3H), 4.08-3.62 (m, 2H), 3.47-3.46 (m, 1H), 3.31-3.02 (m, 7H), 2.78-2.69 (m, 1H), 2.21-1.89 (m, 4H), 1.87-1.55 (m, 8H), 1.54-1.36 (m, 5H), 1.35-1.17 (m, 6H), 1.16-0.98 (m, 9H), 0.77 (m, 7H), 0.61-0.57 (m, 1H).

Example 61: (6S,9S,12S,15S)-9-(Aminomethyl)-12-((R)-sec-butyl)-18,18-difluoro-19-hexyl-6-((S)-1-hydroxyethyl)-15-isobutyl-16-methyl-1-oxa-4,7,10,13,16-pentaazacyclononadecane-2,5,8,11,14,17-hexaone

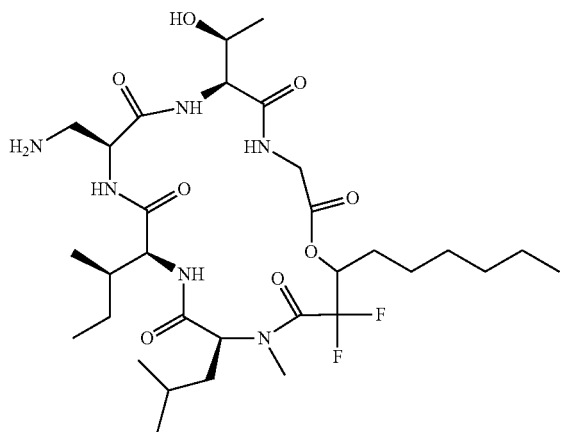 [SMILES: CCCCCCC1OC(=O)CNC(=O)[C@H]([C@H](C)O)NC(=O)[C@H](CN)NC(=O)[C@H]([C@H](C)CC)NC(=O)[C@H](CC(C)C)N(C)C(=O)C1(F)F]

Step 1: 2,2-Difluoro-3-hydroxynonanoic acid

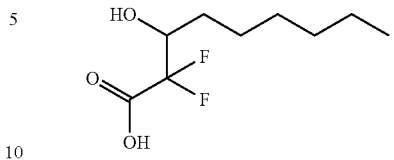

To a mixture of heptaldehyde (5.0 g, 43.79 mmol) and Zn powder (4.26 g, 65.68 mmol) in THF (200 mL) was added ethyl bromodifluoroacetate (13.33 g, 65.68 mmol). The reaction mixture was stirred at room temperature for 16 h. The mixture was quenched with 1 N HCl until pH6. The resulting solution was extracted with ethyl acetate (3×100 mL) and the organic layers were combined. The organic layer was dried over anhydrous sodium sulfate, filtered and evaporated under vacuum. The residue was purified by flash chromatography on silica gel eluting with ethyl acetate/petroleum ether (5/95) to afford ethyl 2,2-difluoro-3-hydroxy-nonanoate (5 g, 47% yield) as a colorless oil. To a solution of this material in THF (48 mL) and water (16 mL) at 0° C. was added lithium hydroxide (1.01 g, 41.96 mmol). The mixture was stirred at room temperature for 5 h. THF was distilled off under vacuum. The resulting mixture was acidified to pH=6 with aqueous hydrochloric acid (1 mol/L). The resulting solution was extracted with DCM (100 mL×3) and the organic layers were combined. The organic layer was dried over anhydrous sodium sulfate, filtered and concentrated under vacuum. The residue was purified by flash chromatography on silica gel eluting with ethyl acetate/petroleum ether (1/5) to afford the title compound (820 mg, 18% yield) as a yellow oil. LCMS (ESI): [M–H]$^-$=209.1.

Step 2: N-(2,2-Difluoro-3-hydroxynonanoyl)-N-methyl-L-leucine

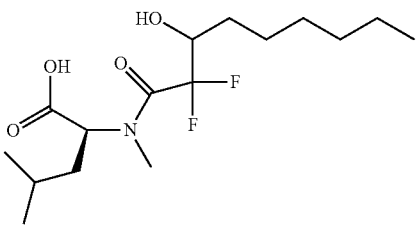 [SMILES: CCCCCCC(O)C(F)(F)C(=O)N(C)[C@@H](CC(C)C)C(=O)O]

To a solution of methyl (2S)-4-methyl-2-(methylamino)pentanoate hydrochloride (819.2 mg, 4.19 mmol), DIPEA (1.96 g, 15.22 mmol), and 2,2-difluoro-3-hydroxynonanoic acid (800.0 mg, 3.81 mmol) in DMF (10 mL) was added a solution of 1-hydroxybenzotriazole (1.03 g, 7.61 mmol) and HATU (2.89 g, 7.61 mmol) in DMF (10 mL) dropwise at 0° C. The resulting mixture was stirred at 0° C. for 3 h. The reaction mixture was then quenched with 100 mL of water. The resulting solution was extracted with 3×200 mL of ethyl acetate and the organic layers were combined. The organic layer was dried over anhydrous sodium sulfate, filtered and the filtrate was concentrated under vacuum. The resulting residue was purified by reverse phase flash chromatography with 30% CH$_3$CN in water (0.05% NH$_4$HCO$_3$) to afford methyl N-(2,2-difluoro-3-hydroxynonanoyl)-N-methyl-L-leucinate (800 mg, 59% yield) as a light yellow oil. This residue was dissolved in THF (20 mL) and water (20 mL) and treated with LiOH (163.9 mg, 6.83 mmol) at 0° C. The resulting mixture was stirred at 0° C. for 3 h. The reaction mixture was adjusted to pH=4 with HCl (1 mol/L in water) and extracted with 3×200 mL of ethyl acetate. The combined organic layers were dried over anhydrous sodium sulfate, filtered and concentrated under vacuum. The residue was purified on silica gel column eluting with 30% ethyl acetate in petroleum ether to afford the title compound (750 mg, 97% yield) as a light yellow oil. LCMS (ESI): [M+H]⁺=338.2.

Step 3. alloIsoleucine-Dap(Cbz)-allothreonine(Bzl)-glycine-(2-chlorotrityl resin)

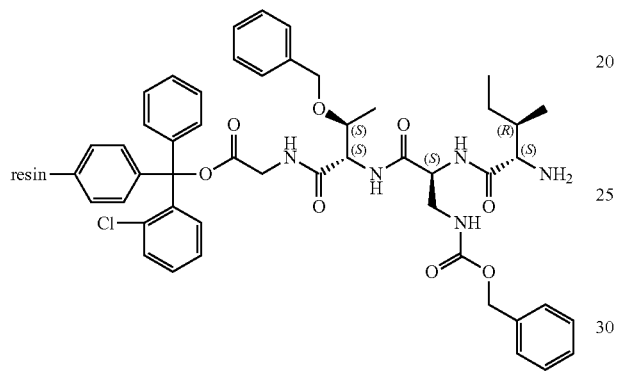

2-Chlorotrityl chloride resin (loading 0.956 mmol/g, 1 g) was swelled with the mixture of DMF:DCM (1:1, 20 mL) for 40 min. The resin was drained and then a solution of Fmoc-glycine (580.3 mg, 1.95 mmol), DMF (10 mL) and DIPEA (495.6 mg, 3.84 mmol) was added. The resin was agitated with nitrogen bubbling for 4 h, drained, and rinsed sequentially with 10 mL DCM/MeOH/DIPEA (10/10/1=V/V/V), 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL).

The resin was treated with a solution of Fmoc-allothreonine(Bzl)-OH (Example 1, Step 2) (0.86 g, 1.99 mmol), a pre-prepared stock solution of HOBt/HATU (1:1) in DMF (0.4 mmol/mL, 5 mL) and DIPEA (491 mg, 3.81 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL).

The resin was treated with a solution of (S)-2-(Fmoc-amino)-3-(((benzyloxy)carbonyl)amino)propanoic acid (0.92 g, 1.97 mmol), a pre-prepared stock solution of HOBt/HATU (1:1) in DMF (0.4 mmol/mL, 5 mL) and DIPEA (498 mg, 3.87 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL).

The resin was treated with a solution of Fmoc-L-alloisoleucine (0.71 g, 2.01 mmol), a pre-prepared stock solution of HOBt/HATU (1:1) in DMF (0.4 mmol/mL, 5 mL) and DIPEA (495 mg, 3.84 mmol). The resin was agitated with nitrogen bubbling for 2.5 h, drained and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL), to obtain the resin-bound peptide title compound.

Step 4: O-Benzyl-N-((2S)-3-(((benzyloxy)carbonyl)amino)-2-((2S,3R)-2-((2S)-2-(2,2-difluoro-3-hydroxy-N-methylnonanamido)-4-methylpentanamido)-3-methylpentanamido)propanoyl)-L-allothreonylglycine

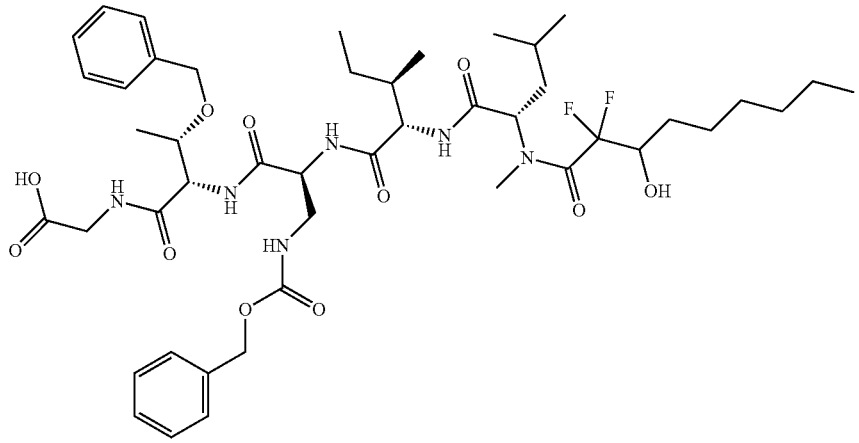 [SMILES: CCCCCCC(O)C(F)(F)C(=O)N(C)[C@@H](CC(C)C)C(=O)N[C@H](C(=O)N[C@@H](CNC(=O)OCc1ccccc1)C(=O)N[C@H](C(=O)NCC(=O)O)[C@H](C)OCc1ccccc1)[C@H](C)CC]

The resin-bound peptide from the previous step was treated with a solution of N-(2,2-difluoro-3-hydroxynonanoyl)-N-methyl-L-leucine (750 mg, 2.22 mmol), a pre-prepared stock solution of HOBt/HATU (1:1) in DMF (0.4 mmol/mL, 8 mL) and DIPEA (796 mg, 6.16 mmol). The resin was agitated with nitrogen bubbling overnight, drained and rinsed sequentially with 10 mL DMF, 10 mL DCM, 10 mL DMF. The resulting resin-bound depsipeptide was treated with 10 mL of 7:2:1 DCM:AcOH:2,2,2-trifluoroethan-1-ol. The mixture was agitated with nitrogen bubbling for 2 h, and then filtered, rinsed with 8 mL DCM. The cleavage process was repeated twice. The combined filtrates were evaporated in vacuo. The residue was purified by C18 flash chromatography with CH$_3$CN/H$_2$O (40% CH$_3$CN) to afford the title compound (354.1 mg). LCMS (ESI): [M+H]$^+$=919.5.

Step 5: (6S,9S,12S,15S)-9-(Aminomethyl)-12-((R)-sec-butyl)-18,18-difluoro-19-hexyl-6-((S)-1-hydroxyethyl)-15-isobutyl-16-methyl-1-oxa-4,7,10,13,16-pentaazacyclononadecane-2,5,8,11,14,17-hexaone Using the depsipeptide from Step 4, the title compound was prepared following procedures analogous to those described for Example 1 (steps 5-6). LCMS (ESI): R$_T$ (min)=1.84, [M+H]$^+$=677.4, method=C; $^1$H NMR (300 MHz, DMSO-d$_6$) δ 8.81-8.05 (m, 4H), 7.67-6.68 (m, 3H), 5.57-5.45 (m, 1H), 4.95-4.58 (m, 3H), 4.25-4.06 (m, 3H), 3.42-3.39 (m, 2H), 3.32-3.10 (m, 2H), 3.05-2.93 (m, 3H), 2.35-2.28 (m, 1H), 1.91-1.65 (m, 4H), 1.43-1.21 (m, 11H), 1.15-0.73 (m, 18H).

Example 62: (6S,9S,12S,15S,18R,19R)-9-(Aminomethyl)-19-(((exo)-bicyclo[2.2.1]heptan-2-yl)methyl)-12-cyclohexyl-6-((S)-1-hydroxyethyl)-15-isobutyl-16,18-dimethyl-1-oxa-4,7,10,13,16-pentaazacyclononadecane-2,5,8,11,14,17-hexaone

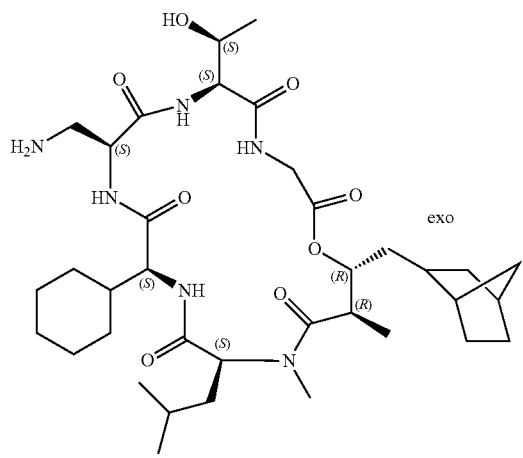

Step 1: (2R,3R)-4-(exo-Bicyclo[2.2.1]heptan-2-yl)-3-hydroxy-2-methylbutanoic acid

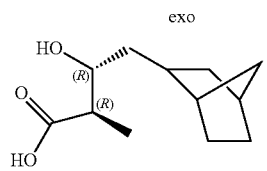

The title compound was prepared from exo-2-(bicyclo[2.2.1]heptan-2-yl)ethanol purchased from ENAMINE (Catalog #EN300-117138, CAS:70289-06-4) following procedures analogous to those described for Example 60, Steps 1-2. LCMS (ESI): [M+H]$^+$=213.1.

Step 2: (6S,9S,12S,15S,18R,19R)-9-(Aminomethyl)-19-(((exo)-bicyclo[2.2.1]heptan-2-yl)methyl)-12-cyclohexyl-6-((S)-1-hydroxyethyl)-15-isobutyl-16,18-dimethyl-1-oxa-4,7,10,13,16-pentaazacyclononadecane-2,5,8,11,14,17-hexaone The title compound was prepared following procedures analogous to those described for Example 59. LCMS (ESI): R$_T$ (min)=1.77, [M+H]$^+$=705.5, method=C; $^1$H NMR (400 MHz, DMSO-d$_6$) 8.68-8.46 (m, 1H), 8.16-7.84 (m, 4H), 7.83-7.51 (m, 2H), 5.22-4.68 (m, 2H), 4.65-4.34 (m, 1H), 4.30-4.02 (m, 3H), 3.99-3.75 (m, 2H), 3.23-3.01 (m, 4H), 2.86-2.58 (m, 1H), 2.21-1.92 (m, 4H), 1.81-1.71 (m, 2H), 1.70-1.56 (m, 4H), 1.55-1.44 (m, 4H), 1.43-1.21 (m, 6H), 1.20-0.97 (m, 12H), 0.96-0.77 (m, 8H).

Example 63: (6S,9S,12S,15S,18R,19R)-9-(aminomethyl)-12-cyclohexyl-19-(3,3-dimethylbutyl)-6-((S)-1-hydroxyethyl)-15-isobutyl-16,18-dimethyl-1-oxa-4,7,10,13,16-pentaazacyclononadecane-2,5,8,11,14,17-hexaone

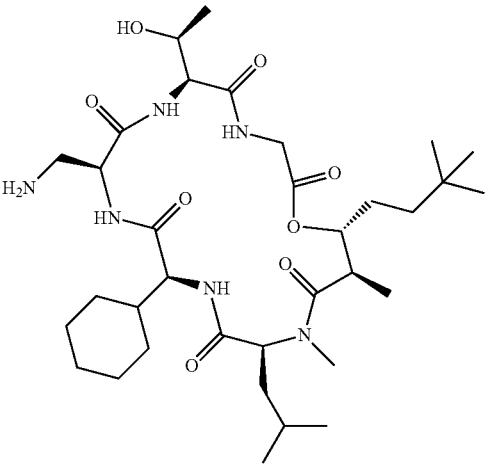 [SMILES: CC(C)C[C@H]1C(=O)N[C@@H](C2CCCCC2)C(=O)N[C@@H](CN)C(=O)N[C@@H]([C@H](C)O)C(=O)NCC(=O)O[C@H](CCC(C)(C)C)[C@@H](C)C(=O)N1C]

Step 1: 4,4-dimethylpentanal

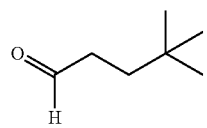

A round bottom flask was charged with ethyl 4,4-dimethylpentanoate (3.80 g, 24.0 mmol) and DCM (1.0 M) and then cooled to −78° C. Diisobutylaluminium hydride (1 mol/L in heptane, 26.0 mL, 26.0 mmol) was slowly added over 10 min. After stirring for 6 h at −78° C., the reaction was quenched with a 10% aqueous solution of Rochelle salt (200 mL) and stirred at 0° C. for 30 min. The biphasic mixture was then extracted with ethyl acetate three times and the combined organic layers were washed with brine, dried over magnesium sulfate, filtered, and concentrated.

This provided 1.4 g of the desired compound (51% yield). $^1$H NMR (400 MHz, DMSO-d$_6$) δ 9.69 (t, J=1.7 Hz, 1H), 2.44-2.35 (m, 2H), 1.49-1.38 (m, 2H), 0.86 (s, 9H).

Step 2: (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2,6,6-trimethylheptan-1-one

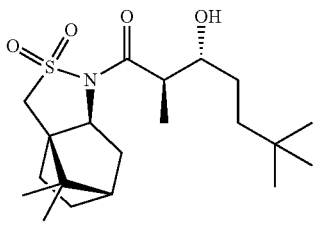 [SMILES: C[C@@H](C(=O)N1[C@H]2C[C@@H]3CC[C@@]2(CS1(=O)=O)C3(C)C)[C@H](O)CCC(C)(C)C]

The above compound was prepared using (3aR,6S,7aS)-8,8-dimethylhexahydro-3H-3a,6-methanobenzo[c]isothiazole 2,2-dioxide and the product from Step 1 and following procedures analogous to those described for Example 9, step 2. LCMS (ESI): [M+H]$^+$=386.2.

Step 3: (2R,3R)-3-((tert-butyldimethylsilyl)oxy)-2,6,6-trimethylheptanoic acid

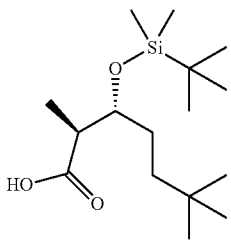 [SMILES: C[C@H](C(=O)O)[C@@H](CCC(C)(C)C)O[Si](C)(C)C(C)(C)C]

To a vial was added (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2,6,6-trimethylheptan-1-one (0.80 g, 2.1 mmol) and DMF (0.5 M), followed by imidazole (226 mg, 3.3 mmol). After 5 min tert-butyldimethylchlorosilane (451 mg, 2.9 mmol) was added. The reaction was capped and heated to 70° C. for 5.5 h then quenched with water and extracted with DCM three times. The combined organic layers were washed with brine, dried over magnesium sulfate, filtered, and concentrated. The crude residue was then treated with THF (0.2 M), water (0.4 M), and lithium hydroxide (366 mg, 8.72 mmol). The reaction was heated to 80° C. for 8 h and then left at room temperature overnight. An additional 1 eq of lithium hydroxide was added and the reaction heated to 60° C. After 6 h the reaction was quenched with 1 M aqueous hydrochloric acid to give a pH of ~3, then extracted with isopropyl acetate three times. The combined organic layers were washed with brine, dried over magnesium sulfate, filtered, and concentrated. The crude product was purified via flash chromatography on silica gel (solvent gradient: 0-100% ethyl acetate in heptanes with 1% formic acid modifier) to yield 0.254 g (39%) of the title compound. LCMS (ESI): [M+H]$^+$=303.2; $^1$H NMR (400 MHz, DMSO-d$_6$) δ 12.06 (s, 1H), 3.85 (dt, J=7.0, 4.8 Hz, 1H), 2.41 (q, J=7.0 Hz, 1H), 1.34 (dt, J=12.1, 4.9 Hz, 2H), 1.24-1.09 (m, 2H), 0.93 (d, J=7.1 Hz, 3H), 0.80 (d, J=1.6 Hz, 18H), −0.01 (d, J=8.3 Hz, 6H).

Step 4: (6S,9S,12S,15S,18R,19R)-9-(aminomethyl)-12-cyclohexyl-19-(3,3-dimethylbutyl)-6-((S)-1-hydroxyethyl)-15-isobutyl-16,18-dimethyl-1-oxa-4,7,10,13,16-pentaazacyclononadecane-2,5,8,11,14,17-hexaone The title compound was prepared following methods analogous to those described for Example 1, steps 3-6, substituting the appropriately protected amino acids and using (2R,3R)-3-((tert-butyldimethylsilyl)oxy)-2,6,6-trimethylheptanoic acid. LCMS (ESI): R$_T$ (min)=4.643, [M+H]$^+$=681.4, method=A.

Example 64: (6S,9S,12S,15S,18R,19R)-9-(Aminomethyl)-12-cyclohexyl-6-((S)-1-hydroxyethyl)-15-isobutyl-19-(7-methoxy-7-methyloctyl)-16,18-dimethyl-1-oxa-4,7,10,13,16-pentaazacyclononadecane-2,5,8,11,14,17-hexaone

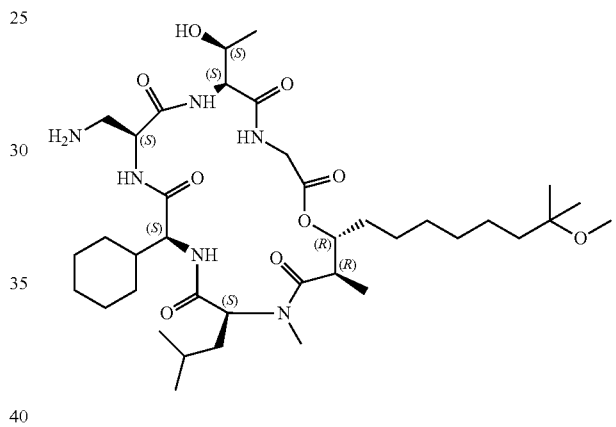

Step 1: (2R,3R,E)-3-hydroxy-10-methoxy-2,10-dimethylundec-8-enoic acid

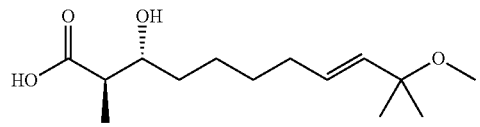 [SMILES: COC(C)(C)/C=C/CCCC[C@@H](O)[C@@H](C)C(=O)O]

To a solution of 2-methyl-3-buten-2-ol (10.62 g, 123.3 mmol) in DMF (30 mL) was added NaH (5.91 g, 195.7 mmol, 60% in mineral oil) portionwise at 0° C. Upon the completion of NaH addition, the reaction mixture was stirred at 0° C. for 10 min and then iodomethane (34.96 g, 246.3 mmol) was added. The reaction mixture was stirred at room temperature for 2 h. Water (200 mL) was added. The resulting solution was extracted with DCM (3×50 mL). The combined organic layers were dried over sodium sulfate. 3-Methoxy-3-methyl-but-1-ene (8.91 g, 72% yield) was obtained by fractional distillation.

A solution of (2R,3R)-3-hydroxy-2-methyl-non-8-enoic acid (500.3 mg, 2.69 mmol), 3-methoxy-3-methyl-but-1-ene (538.1 mg, 5.37 mmol) and benzylidene-bis(tricyclohexylphosphine)dichlororuthenium (1803.6 mg, 2.15 mmol) in DCM (2 mL) was stirred at 40° C. under nitrogen for 2 hours and then evaporated under vacuum. The residue was purified by flash chromatography on silica gel eluting with MeOH/DCM (10% MeOH) to afford the title compound (110.6 mg, 15% yield) as an oil. LCMS (ESI): [M−H]⁻=257.2.

Step 2: (2R,3R)-3-Hydroxy-10-methoxy-2,10-dimethylundecanoic acid & (2R,3R)-3-hydroxy-2,10-dimethylundecanoic acid

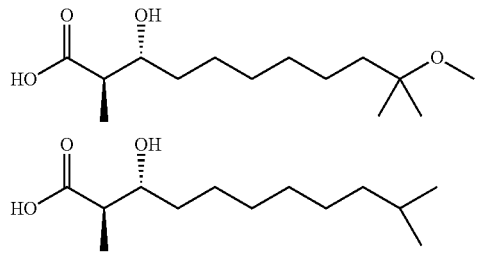

A mixture of (2R,3R)-3-hydroxy-2-methyl-non-8-enoic acid (1.3 g, 5.03 mmol) and palladium (35 mg, 10% loading on carbon) in ethyl acetate (20 mL) was stirred under a hydrogen balloon at room temperature for 5 h. The solid was removed via filtration and the filtrate was evaporated in vacuo to afford a mixture of (2R,3R)-3-hydroxy-10-methoxy-2,10-dimethylundecanoic acid & (2R,3R)-3-hydroxy-2,10-dimethylundecanoic acid (850 mg). LCMS (ESI): [M−H]⁻=259.2 & LCMS (ESI): [M−H]⁻=229.2 The mixture was used for next step without separation.

Step 3: O-Benzyl-N—((S)-3-(((benzyloxy)carbonyl)amino)-2-((S)-2-cyclohexyl-2-((S)-2-((2R,3R)-3-hydroxy-10-methoxy-N,2,10-trimethylundecanamido)-4-methylpentanamido)acetamido)propanoyl)-L-allothreonylglycine & O-Benzyl-N—((S)-3-(((benzyloxy)carbonyl)amino)-2-((S)-2-cyclohexyl-2-((S)-2-((2R,3R)-3-hydroxy-N,2,10-trimethylundecanamido)-4-methylpentanamido)acetamido)propanoyl)-L-allothreonylglycine

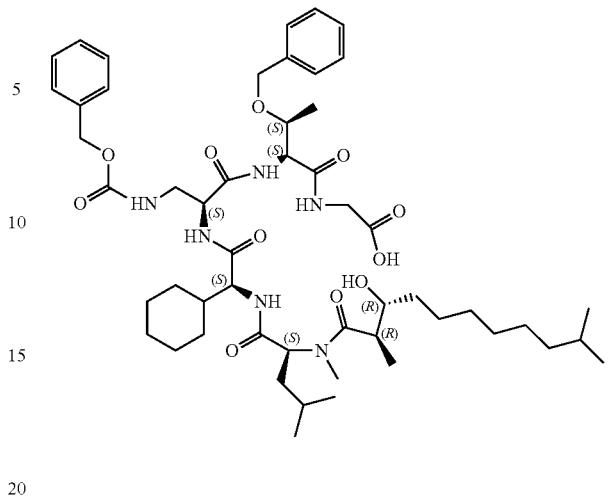

A mixture of the title compounds was prepared following procedures analogous to those described for Example 1. LCMS (ESI): [M+H]⁺=995.6 & LCMS (ESI): [M+H]⁺=965.6.

Step 4: Benzyl ((((6S,9S,12S,15S,18R,19R)-6-((S)-1-(Benzyloxy)ethyl)-12-cyclohexyl-15-isobutyl-19-(7-methoxy-7-methyloctyl)-16,18-dimethyl-2,5,8,11,14,17-hexaoxo-1-oxa-4,7,10,13,16-pentaazacyclononadecan-9-yl)methyl)carbamate & Benzyl ((((6S,9S,12S,15S,18R,19R)-6-((S)-1-(benzyloxy)ethyl)-12-cyclohexyl-15-isobutyl-16,18-dimethyl-19-(7-methyloctyl)-2,5,8,11,14,17-hexaoxo-1-oxa-4,7,10,13,16-pentaazacyclononadecan-9-yl)methyl)carbamate

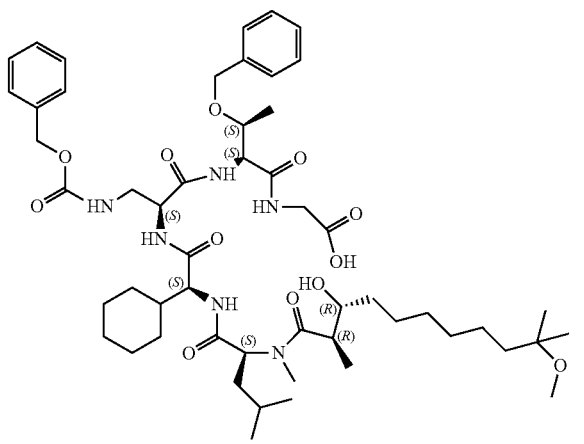

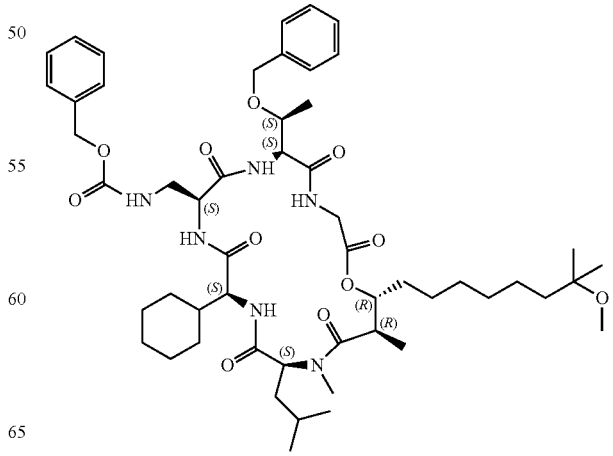

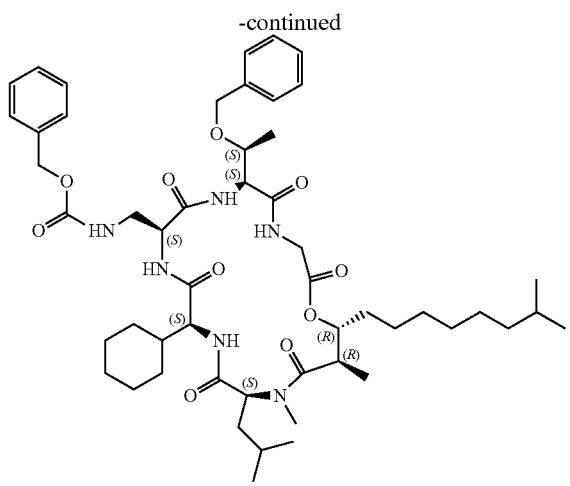

A solution of 2-methyl-6-nitrobenzoic anhydride (390.0 mg, 1.13 mmol) and 4-dimethylaminopyridine (843.4 mg, 2.44 mmol) in DCM (220 mL) was stirred at 0° C. for 10 min. Then a solution of O-benzyl-N—((S)-3-(((benzyloxy)carbonyl)amino)-2-((S)-2-cyclohexyl-2-((S)-2-((2R,3R)-3-hydroxy-10-methoxy-N,2,10-trimethylundecanamido)-4-methylpentanamido)acetamido)propanoyl)-L-allothreonylglycine & O-benzyl-N—((S)-3-(((benzyloxy)carbonyl)amino)-2-((S)-2-cyclohexyl-2-((S)-2-((2R,3R)-3-hydroxy-N,2,10-trimethylundecanamido)-4-methylpentanamido)acetamido)propanoyl)-L-allothreonylglycine (mixture, 450.0 mg, 0.45 mmol) in THF (50 mL) was added dropwise at 0° C. The resulting mixture was stirred at 40° C. for 5 h and then evaporated in vacuo. The resulting residue was dissolved in ethyl acetate (150 mL) and washed sequentially with 2×50 mL 10% aqueous citric acid and 2×50 mL 2M aqueous $Na_2CO_3$. The organic layer was dried over magnesium sulfate and filtered, and evaporated in vacuo. The residue was purified by flash chromatography on C18 column (acetonitrile-water 30-60/0.05% DIPEA in water) to afford benzyl ((((6S,9S,12S,15S,18R,19R)-6-((S)-1-(benzyloxy)ethyl)-12-cyclohexyl-15-isobutyl-19-(7-methoxy-7-methyloctyl)-16,18-dimethyl-2,5,8,11,14,17-hexaoxo-1-oxa-4,7,10,13,16-pentaazacyclononadecan-9-yl)methyl)carbamate (100.0 mg, 23% yield), LCMS (ESI): $[M+H]^+=977.6$, and benzyl(((6S,9S,12S,15S,18R,19R)-6-((S)-1-(benzyloxy)ethyl)-12-cyclohexyl-15-isobutyl-16,18-dimethyl-19-(7-methyloctyl)-2,5,8,11,14,17-hexaoxo-1-oxa-4,7,10,13,16-pentaazacyclononadecan-9-yl)methyl)carbamate (180.0 mg, 40% yield) as a yellow solid. LCMS (ESI): $[M+H]^+=947.6$.

Step 5: (6S,9S,12S,15S,18R,19R)-9-(Aminomethyl)-12-cyclohexyl-6-((S)-1-hydroxyethyl)-15-isobutyl-19-(7-methoxy-7-methyloctyl)-16,18-dimethyl-1-oxa-4,7,10,13,16-pentaazacyclononadecane-2,5,8,11,14,17-hexaone A mixture of benzyl ((((6S,9S,12S,15S,18R,19R)-6-((S)-1-(Benzyloxy)ethyl)-12-cyclohexyl-15-isobutyl-19-(7-methoxy-7-methyloctyl)-16,18-dimethyl-2,5,8,11,14,17-hexaoxo-1-oxa-4,7,10,13,16-pentaazacyclononadecan-9-yl)methyl)carbamate (100.0 mg, 0.09 mmol) and palladium (125 mg, 10% loading on carbon) in ethyl acetate (20 mL) containing 0.5% TFA was stirred under a hydrogen balloon for 4 h at room temperature. The solid was filtered off. The filtrate was evaporated in vacuo, azeotroping with toluene (5 mL). The crude product was purified by Prep-LCMS to afford the title compound (48.0 mg). LCMS (ESI): $R_T$ (min)=1.78, $[M+H]^+=753.5$, method=C; $^1$H NMR (400 MHz, DMSO-$d_6$) δ 8.71-8.52 (m, 1H), 8.18-7.88 (m, 3H), 7.82-7.55 (m, 2H), 5.11-4.81 (m, 2H), 4.68-4.45 (m, 1H), 4.33-4.02 (m, 4H), 3.97-3.78 (m, 2H), 3.21-3.17 (m, 1H), 3.15-3.07 (m, 2H), 3.05-3.01 (m, 3H), 2.79-2.69 (m, 1H), 2.29-1.88 (m, 2H), 1.82-1.32 (m, 12H), 1.31-1.12 (m, 11H), 1.11-0.98 (m, 13H), 0.95-0.78 (m, 8H).

Example 65: (6S,9S,12S,15S,18R,19R)-9-(Aminomethyl)-12-cyclohexyl-6-((S)-1-hydroxyethyl)-15-isobutyl-16,18-dimethyl-19-(7-methyloctyl)-1-oxa-4,7,10,13,16-pentaazacyclononadecane-2,5,8,11,14,17-hexaone

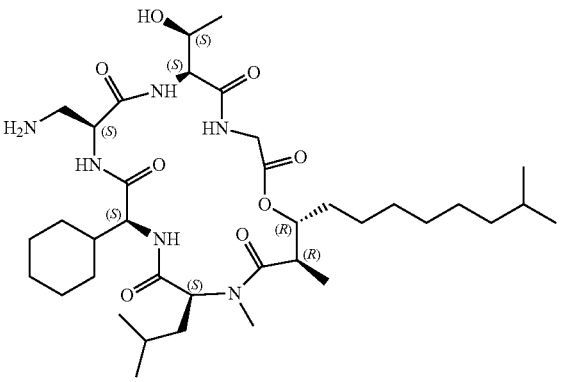

Following procedures analogous to those described in Example 64, step 5, the title compound (81 mg) was obtained from benzyl ((((6S,9S,12S,15S,18R,19R)-6-((S)-1-(benzyloxy)ethyl)-12-cyclohexyl-15-isobutyl-16,18-dimethyl-19-(7-methyloctyl)-2,5,8,11,14,17-hexaoxo-1-oxa-4,7,10,13,16-pentaazacyclononadecan-9-yl)methyl)carbamate (180.0 mg, 0.19 mmol) described in Example 64, step 4. LCMS (ESI): $R_T$ (min)=2.01, $[M+H]^+=723.5$, method=C; $^1$H NMR (400 MHz, DMSO-$d_6$) δ 8.69-8.51 (m, 1H), 8.16-7.82 (m, 3H), 7.80-7.55 (m, 2H), 5.19-4.71 (m, 2H), 4.62-4.48 (m, 1H), 4.35-3.99 (m, 4H), 3.97-3.68 (m, 2H), 3.25-3.14 (m, 2H), 3.12-3.01 (m, 3H), 2.91-2.72 (m, 2H), 2.15-1.85 (m, 2H), 1.82-1.35 (m, 10H), 1.31-1.11 (m, 12H), 1.10-0.98 (m, 7H), 0.96-0.78 (m, 13H).

Example 66: (6S,9S,12S,15S,18R,19R)-9-(Aminomethyl)-18,19-dibutyl-12-cyclohexyl-6-((S)-1-hydroxyethyl)-15-isobutyl-16-methyl-1-oxa-4,7,10,13,16-pentaazacyclononadecane-2,5,8,11,14,17-hexaone Example 67: (3R,6S,9S,12S,15S,18R,19R)-9-(Aminomethyl)-12-cyclohexyl-6-(((S)-2,3-dihydroxypropoxy)methyl)-19-hexyl-15-isobutyl-3,16,18-trimethyl-1-oxa-4,7,10,13,16-pentaazacyclononadecane-5,8,11,14,17-pentaone

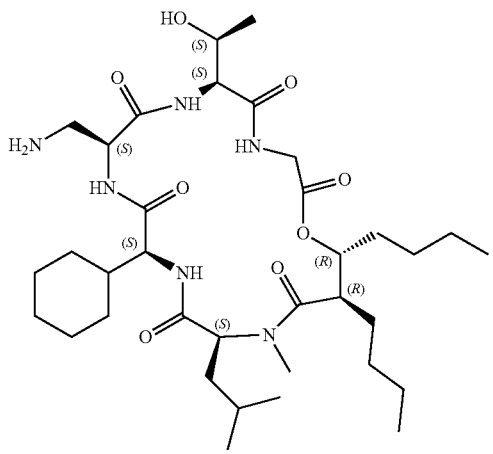

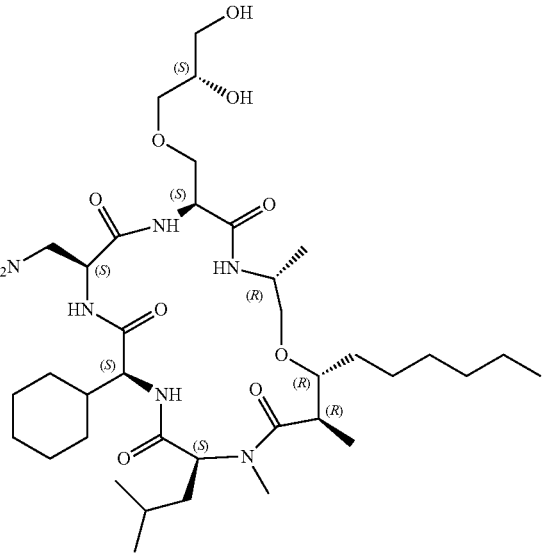

Step 1: (2R,3R)-2-Butyl-3-hydroxyheptanoic acid

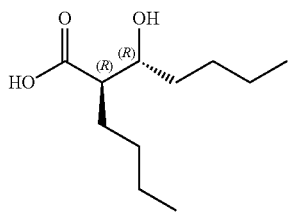

Step 1: Benzyl (((3R,6S,9S,12S,15S,18R,19R)-6-((allyloxy)methyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate The title compound was prepared following procedures analogous to those described for Intermediate 1, using pentanal instead of heptanal, and using hexanoyl chloride instead of propionyl chloride. LCMS (ESI): [M−H]⁻=201.

Step 2: (6S,9S,12S,15S,18R,19R)-9-(Aminomethyl)-18,19-dibutyl-12-cyclohexyl-6-((S)-1-hydroxyethyl)-15-isobutyl-16-methyl-1-oxa-4,7,10,13,16-pentaazacyclononadecane-2,5,8,11,14,17-hexaone The title compound was prepared following procedures analogous to those described for Example 59. LCMS (ESI): $R_T$ (min)=1.82, [M+H]+=695.5, method=C; ¹H NMR (400 MHz, DMSO-$d_6$) 8.71-7.19 (m, 7H), 5.04-4.82 (m, 1H), 4.75-4.55 (m, 1H), 4.54-4.08 (m, 4H), 3.95-3.63 (m, 2H), 3.58-3.53 (m, 1H), 3.22-3.01 (m, 4H), 2.87-2.78 (m, 1H), 2.12-1.81 (m, 2H), 1.79-1.41 (m, 10H), 1.40-1.02 (m, 16H), 0.98-0.74 (m, 14H).

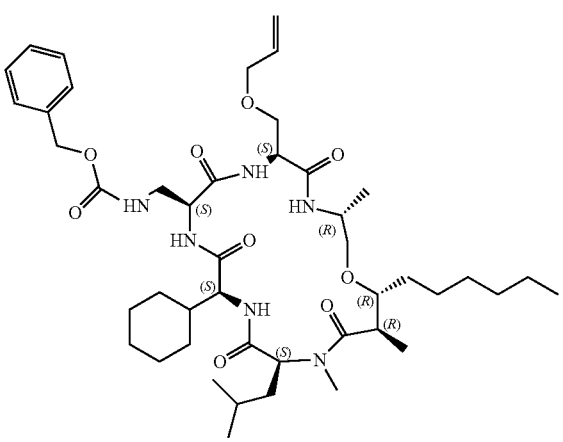

The title compound was prepared following procedures analogous to those described for Example 81, steps 2-4. LCMS (ESI): [M+H]⁺=841.5.

317

Step 2: Benzyl (((3R,6S,9S,12S,15S,18R,19R)-12-cyclohexyl-6-(((S)-2,3-dihydroxypropoxy)methyl)-19-hexyl-15-isobutyl-3,16,18-trimethyl-5,8,11,14,17-pentaoxo-1-oxa-4,7,10,13,16-pentaazacyclononadecan-9-yl)methyl)carbamate

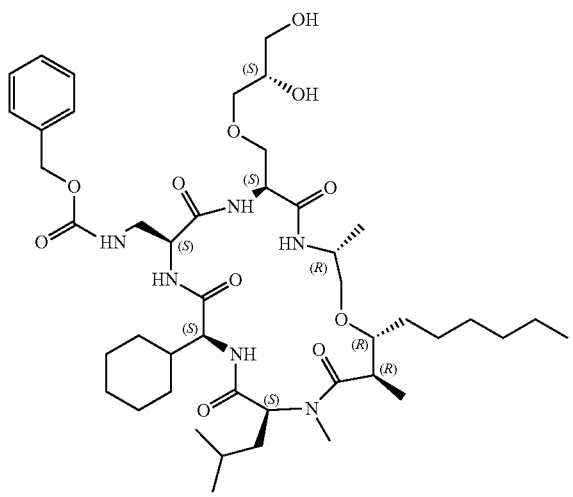

To a solution of benzyl (((3R,6S,9S,12S,15S,18R,19R)-6-((allyloxy)methyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate (150 mg, 0.17 mmol) in t-BuOH (5 mL) and H₂O (5 mL) was added AD-mix-β (1400 mg) (CAS:148618-32-0) at 0° C., followed by methanesulfonamide (70 mg, 0.73 mmol) at 0° C. The reaction mixture was stirred for 3 h at room temperature, and extracted with ethyl acetate (10 mL×3). The organic layers were combined, dried over anhydrous sodium sulfate, filtered and evaporated under vacuum to afford the title compound (130 mg, 83% yield) as a yellow solid. LCMS (ESI): [M+H]⁺=875.5.

Step 3: (3R,6S,9S,12S,15S,18R,19R)-9-(Aminomethyl)-12-cyclohexyl-6-(((S)-2,3-dihydroxypropoxy)methyl)-19-hexyl-15-isobutyl-3,16,18-trimethyl-1-oxa-4,7,10,13,16-pentaazacyclononadecane-5,8,11,14,17-pentaone A mixture of benzyl (((3R,6S,9S,12S,15S,18R,19R)-12-cyclohexyl-6-(((S)-2,3-dihydroxypropoxy)methyl)-19-hexyl-15-isobutyl-3,16,18-trimethyl-5,8,11,14,17-pentaoxo-1-oxa-4,7,10,13,16-pentaazacyclononadecan-9-yl)methyl)carbamate (130 mg, 0.17 mmol) and palladium (50 mg, 10% loading on carbon) in ethyl acetate containing 0.5% TFA (20 ml) was stirred under a hydrogen balloon for 2 h at room temperature. The solid was removed via filtration and the filtrate was evaporated under reduced pressure. The residue was purified by Prep-LCMS to afford the title compound (9.2 mg, 6% yield) as a white solid. LCMS (ESI): $R_T$ (min)=1.75, [M+H]⁺=741.5, method=C; ¹H NMR (400 MHz, DMSO-d₆) δ 8.89-7.74 (m, 5H), 7.62-6.97 (m, 1H), 4.71-4.03 (m, 4H), 3.99-3.68 (m, 3H), 3.59-3.45 (m, 9H), 3.28-2.96 (m, 8H), 2.91-2.73 (m, 2H), 2.18-1.96 (m, 1H), 1.93-1.50 (m, 5H), 1.49-1.20 (m, 15H), 1.17-0.88 (m, 15H).

318

Example 68: (6S,9S,12S,15S,18R,19R)-9-(Aminomethyl)-12-cyclohexyl-19-hexyl-6-((S)-1-hydroxyethyl)-15-isobutyl-16-methyl-18-(2,2,2-trifluoroethyl)-1-oxa-4,7,10,13,16-pentaazacyclononadecane-2,5,8,11,14,17-hexaone

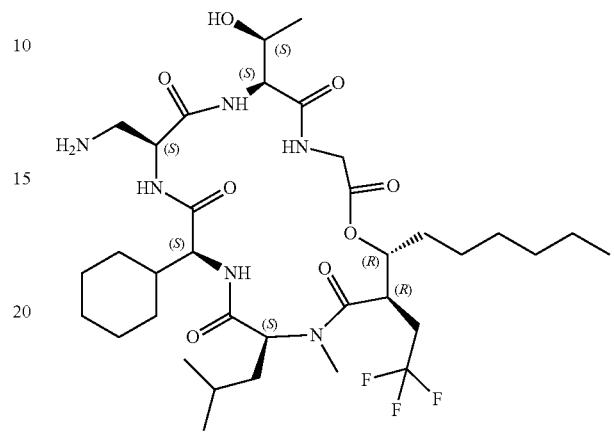

Step 1:1-((3aR,6S,7aS)-8,8-dimethyl-2,2-dioxidotetrahydro-3H-3a,6-methanobenzo[c]isothiazol-1(4H)-yl)-4,4,4-trifluorobutan-1-one

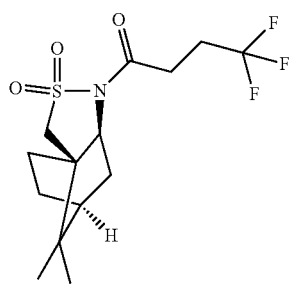 [SMILES: CC1(C)[C@H]2CC[C@@]13CS(=O)(=O)N(C(=O)CCC(F)(F)F)[C@H]3C2]

To a solution of 4,4,4-trifluorobutanoic acid (25.0 g, 175.96 mmol) in DCM (150 mL) was added oxalyl dichloride (11.91 mL, 140.77 mmol) at 0° C. under nitrogen. The reaction mixture was allowed to warm to room temperature and stirred at this temperature for 1.5 hours. The resulting mixture was evaporated under vacuum to afford 4,4,4-trifluorobutanoyl chloride (23.2 g). To a solution of (3aR,6S,7aS)-8,8-dimethylhexahydro-3H-3a,6-methanobenzo[c]isothiazole 2,2-dioxide (31.2 g, 144.53 mmol), DMAP (3.53 g) and triethylamine (131.63 g) in DCM (200 mL) was added the crude 4,4,4-trifluorobutanoyl chloride (23.2 g, 144.53 mmol) dropwise under nitrogen at 0° C. The reaction mixture was allowed to warm to room temperature and stirred at room temperature for 3 hours. The reaction mixture was washed with ice-cold 3% aqueous NH₄Cl (2×200 mL) and brine (200 mL). The organic phase was dried over Mg₂SO₄ and evaporated in vacuo. The residue was purified by flash chromatography on silica gel eluting with ethyl acetate/petroleum ether (6:94) to afford the title compound (23.9 g, yield 48.7%) as a light yellow solid. LCMS (ESI): [M+H]⁺=340.1.

Step 2: (2R,3R)-3-Hydroxy-2-(2,2,2-trifluoroethyl)nonanoic acid

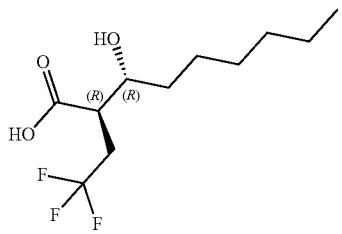

Trifluoromethanesulfonic acid (22.15 g, 147.7 mmol) was dropwise added to a solution of triethylborane (147.5 mL, 147.5 mmol, 1 mol/L in DCM) in 100 mL DCM at −10° C. The reaction mixture was stirred at room temperature for 30 min, and then cooled to 0° C. A solution of 1-((3aR,6S,7aS)-8,8-dimethyl-2,2-dioxidotetrahydro-3H-3a,6-methanobenzo[c]isothiazol-1(4H)-yl)-4,4,4-trifluorobutan-1-one (20.14 g, 59.35 mmol) in 60 mL DCM and DIPEA (26.74 mL, 153.5 mmol) was added dropwise at 0° C. The reaction mixture was stirred at 0° C. for 30 min, and then cooled to −78° C. To this mixture, titanium tetrachloride (177.9 mL, 177.9 mmol, 1 mol/L in DCM) was added dropwise at −78° C. A solution of heptaldehyde (20.19 g, 176.8 mmol) in 40 mL DCM was added dropwise at −78° C. The resulting mixture was stirred for 4 h at −50° C. and then poured into saturated aqueous NH$_4$Cl (200 mL). The phases were separated and the aqueous phase was extracted with DCM (200 mL×3). The combined organic phases were dried over Na$_2$SO$_4$, and evaporated under reduced pressure. The residue was purified by flash chromatography on silica gel eluting with petroleum ether/ethyl acetate (5/1) to afford (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-(2,2,2-trifluoroethyl)nonan-1-one (30 g, 55% yield) as a yellow oil.

To a solution of (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-(2,2,2-trifluoroethyl)nonan-1-one (80.21 g, 176.9 mmol) in acetonitrile (600 mL) and water (200 mL) was added LiOH (16.97 g, 707.1 mmol) at 0° C. The reaction mixture was stirred at 25° C. for 16 h, and acidified by 1M HCl to pH 6 and extracted with ethyl acetate (200 mL×3). The combined organic phases were evaporated under reduced pressure. The residue was purified by flash chromatography on silica gel eluting with petroleum ether/ethyl acetate (5/1) to afford the title compound (10.59 g, 23% yield) as a yellow oil. LCMS (ESI): [M−H]$^-$=255.1.

Step 3: N-((2R,3R)-3-Hydroxy-2-(2,2,2-trifluoroethyl)nonanoyl)-N-methyl-L-leucine

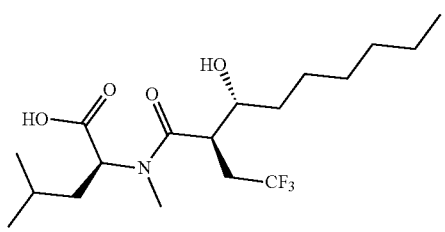 [SMILES: CCCCCC[C@@H](O)[C@@H](CC(F)(F)F)C(=O)N(C)[C@@H](CC(C)C)C(=O)O]

A solution of (2R,3R)-3-hydroxy-2-(2,2,2-trifluoroethyl)nonanoic acid (2.02 g, 7.82 mmol) and methyl (2S)-4-methyl-2-(methylamino)pentanoate (2.20 g, 13.84 mmol) in DMF (10 mL) was stirred at 0° C. Then DIPEA (4.04 g, 31.26 mmol) and a solution of HATU (5.94 g, 15.63 mmol) and 4-hydroxybenzotriazole (2.11 g, 15.63 mmol) dissolved in DMF (2 mL) was added at 0° C. and stirred for 3 hours. The reaction mixture was evaporated under vacuum. The residue was purified by flash chromatography on C18 column eluting with CH$_3$CN/H$_2$O (88% CH$_3$CN) to afford methyl (2S)-2-[[(2R,3R)-3-hydroxy-2-(2,2,2-trifluoroethyl)nonanoyl]-methyl-amino]-4-methyl-pentanoate (712.9 mg, 22% yield) as an oil. This residue was dissolved in THF (12 mL) and water (3 mL) and treated with H$_2$O$_2$ (0.1 mL, 1.89 mmol) at 0° C. for 5 min. Then LiOH (181.3 mg, 7.55 mmol) was added. The reaction mixture was stirred at 25° C. for 24 h and evaporated under vacuum. The residue was purified by flash chromatography on C18 column eluting with CH$_3$CN/H$_2$O (65% CH$_3$CN) to afford the title compound (700.3 mg, 96% yield). LCMS (ESI): [M+H]$^+$=384.2.

Step 4: (6S,9S,12S,15S,18R,19R)-9-(Aminomethyl)-12-cyclohexyl-19-hexyl-6-((S)-1-hydroxyethyl)-15-isobutyl-16-methyl-18-(2,2,2-trifluoroethyl)-1-oxa-4,7,10,13,16-pentaazacyclononadecane-2,5,8,11,14,17-hexaone The title compound was prepared following procedures analogous to those described for Example 61. LCMS (ESI): R$_T$ (min)=1.82, [M+H]$^+$=749.4, method=C; $^1$H NMR (400 MHz, DMSO-d$_6$) δ 8.45-7.89 (m, 5H), 7.47-6.92 (m, 2H), 5.28-5.09 (m, 2H), 4.56-3.95 (m, 5H), 3.67-3.37 (m, 4H), 3.30-3.15 (m, 2H), 3.06-2.95 (m, 1H), 2.93-2.68 (m, 3H), 2.18-2.03 (m, 1H), 1.84-1.47 (m, 9H), 1.36-1.17 (m, 11H), 1.13-0.94 (m, 6H), 0.91-0.72 (m, 9H).

Example 69: (6S,9S,15S,18R,19R)-9-(Aminomethyl)-12-(exo-bicyclo[2.2.1]heptan-2-yl)-19-hexyl-6-((S)-1-hydroxyethyl)-16,18-dimethyl-15-propyl-1-oxa-4,7,10,13,16-pentaazacyclononadecane-2,5,8,11,14,17-hexaone

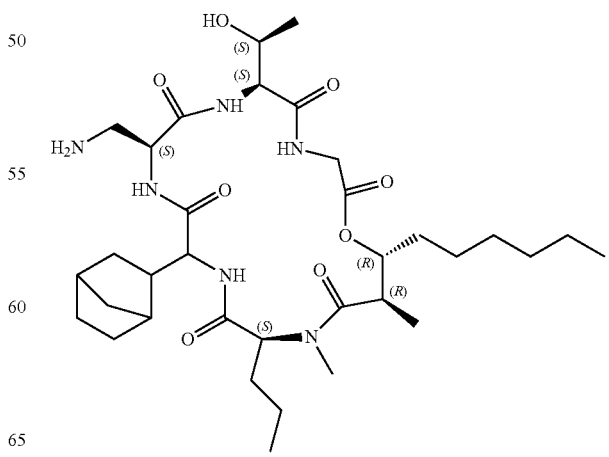

Step 1: Methyl 2-(bicyclo[2.2.1]heptan-2-yl)acetate (exo)

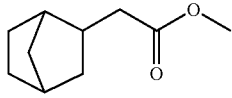

To a mixture of 2-(bicyclo[2.2.1]heptan-2-yl)acetic acid (exo) (1.400 mL), DCM (10 mL) and methanol (10 mL) was dropwise added (trimethylsilyl)diazomethane (2.0 mol/L in hexanes, 6 mL, 12 mmol). The reaction mixture was stirred at room temperature for 1 h and then evaporated in vacuo to yield 1.22 g of the title compound.

Step 2: Methyl 2-azido-2-(bicyclo[2.2.1]heptan-2-yl)acetate (exo)

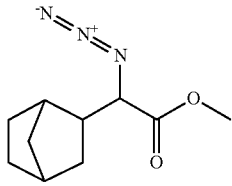

A solution of methyl 2-(bicyclo[2.2.1]heptan-2-yl)acetate (exo) (1.22 g, 7.25 mmol) in THF (15 mL) was cooled to −78° C. Potassium bis(trimethylsilyl)amide (1.0 mol/L in toluene, 10.0 mL, 10 mmol) was added slowly, and the reaction mixture stirred at −78° C. for 30 min, followed by the dropwise addition of a solution of 2,4,6-triisopropylbenzenesulfonyl azide (3.646 g, 11.31 mmol) in THF (10 mL). The reaction mixture was stirred at −78° C. for 1 h, and then quenched with 10 mL saturated aqueous ammonium chloride and warmed to room temperature. The reaction mixture was diluted with ethyl acetate, washed with saturated aqueous sodium bicarbonate and brine, dried over magnesium sulfate, filtered, and evaporated in vacuo. The crude product was purified via flash chromatography on silica gel (80 g silica, solvent gradient: 0-40% ethyl acetate in heptane) to yield 0.6587 g (43%) of the title compound, which was carried forward to the next step without purification.

Step 3: Methyl 2-((((9H-fluoren-9-yl)methoxy)carbonyl)amino)-2-(bicyclo[2.2.1]heptan-2-yl)acetate (exo)

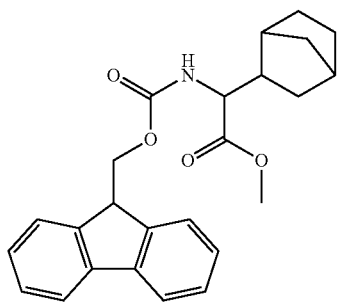 [SMILES: COC(=O)C(NC(=O)OCC1c2ccccc2-c2ccccc21)C1CC2CCC1C2]

A solution of methyl 2-azido-2-(bicyclo[2.2.1]heptan-2-yl)acetate (exo) (2.942 g, 14.06 mmol) in ethanol (30 mL) was purged with nitrogen, and then palladium (10 wt. % on carbon) (324 mg, 0.3045 mmol) was added. The reaction vessel was purged with hydrogen gas and then stirred under a hydrogen balloon at room temperature for 16 h. The reaction mixture was filtered through celite, rinsing with methanol, and evaporated in vacuo. The resulting residue was dissolved in 1,4-dioxane (18 mL) and water (10 mL) with N-(9-fluorenylmethoxycarbonyloxy)succinimide (7.18 g, 21.3 mmol) and sodium hydrogen carbonate (3.59 g, 42.6 mmol). The resulting mixture was stirred at room temperature for 3 h. The reaction mixture was diluted with ethyl acetate, washed with water and brine, dried over magnesium sulfate, filtered, and evaporated in vacuo. The crude product was purified via flash chromatography on silica gel (220 g silica, solvent gradient: 0-100% ethyl acetate in heptanes) to yield 1.9682 g of the title compound. LCMS (ESI) [M+H]$^+$=406.1.

Step 4: 2-((((9H-Fluoren-9-yl)methoxy)carbonyl)amino)-2-(bicyclo[2.2.1]heptan-2-yl)acetic acid (exo)

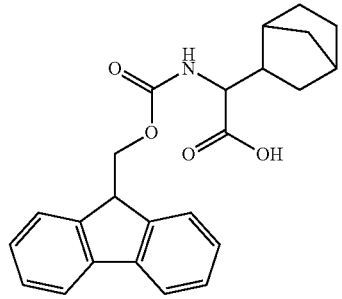 [SMILES: O=C(NC(C(=O)O)C1CC2CCC1C2)OCC1c2ccccc2-c2ccccc21]

To a solution of methyl 2-((((9H-fluoren-9-yl)methoxy)carbonyl)amino)-2-(bicyclo[2.2.1]heptan-2-yl)acetate (exo) (1.9682 g, 4.854 mmol) in 1,2-dichloroethane (12 mL) was added trimethyltin hydroxide (1.807 g, 9.793 mmol). The resulting mixture was heated at 80° C. for 5 h. To the reaction was added trimethyltin hydroxide (0.892 g) and heating continued at 80° C. for 2.5 h. The reaction mixture was diluted with ethyl acetate (150 mL) and washed with 1 M aqueous HCl, dried over magnesium sulfate, filtered, and evaporated in vacuo. The crude product was purified via flash chromatography on silica gel (40 g silica, solvent gradient: 0-100% ethyl acetate in dichloromethane) to yield 1.401 g (74%) of the title compound as a white foam. LCMS (ESI) [M+H]$^+$=392.1.

Step 5: (6S,9S,15S,18R,19R)-9-(Aminomethyl)-12-(exo-bicyclo[2.2.1]heptan-2-yl)-19-hexyl-6-((S)-1-hydroxyethyl)-16,18-dimethyl-15-propyl-1-oxa-4,7,10,13,16-pentaazacyclononadecane-2,5,8,11,14,17-hexaone The title compound was prepared using the material from Step 4 and following procedures analogous to those described for Example 1. Two products were separated using achiral HPLC, assumed to be either R or S at the backbone carbon and both peaks as a mixture of exo diastereomers. Peak 2: LCMS (ESI): $R_T$ (min)=4.508, [M+H]$^+$=679.5, method=A; $^1$H NMR (400 MHz, DMSO-d$_6$) δ 8.68 (dd, J=44.0, 6.8 Hz, 0H), 8.27-7.69 (m, 6H), 4.95-4.83 (m, 1H), 4.62-4.38 (m, 1H), 4.25-3.61 (m, 6H), 3.16-2.61 (m, 5H), 2.27-0.78 (m, 39H).

Example 70: (3R,6S,9S,12S,15S,18R,19R)-9-(Aminomethyl)-6-((S)-1-(3-aminopropoxy)ethyl)-12-cyclohexyl-19-hexyl-15-isobutyl-3,16,18-trimethyl-1-oxa-4,7,10,13,16-pentaazacyclononadecane-5,8,11,14,17-pentaone

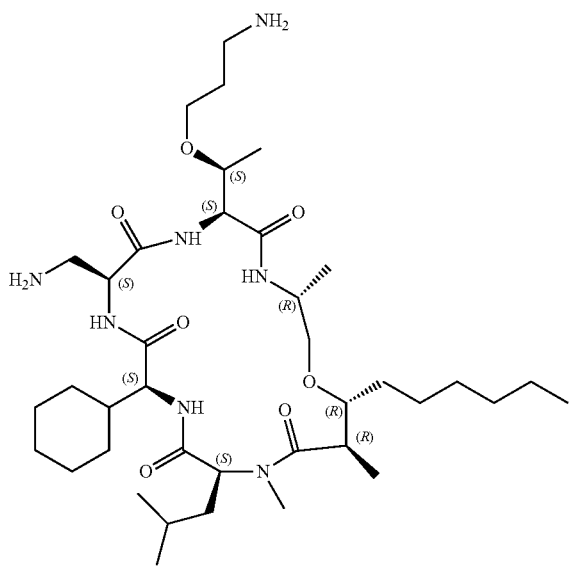

Step 1: tert-Butyl (tert-butoxycarbonyl)-L-allothreoninate

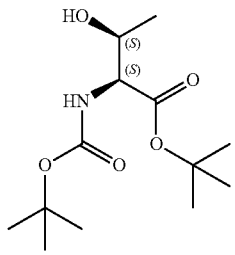

To a solution of (tert-butoxycarbonyl)-L-allothreonine (10.0 g, 45.61 mmol) in DCM (450 mL) was added (E)-(tert-butoxy)-N,N-bis(propan-2-yl)methanimidamide (27.41 g, 136.83 mmol) at 25° C. The resulting solution was stirred for 16 h at 25° C. The reaction mixture was concentrated under vacuum. The residue was purified by flash chromatography on silica gel eluting with ethyl acetate/petroleum ether (1:2) to afford the title compound (6.42 g, 51% yield) as a colorless oil. LCMS (ESI): [M+H]$^+$=276.2.

Step 2: tert-Butyl O-(3-(((benzyloxy)carbonyl)amino)propyl)-N-(tert-butoxycarbonyl)-L-allothreoninate

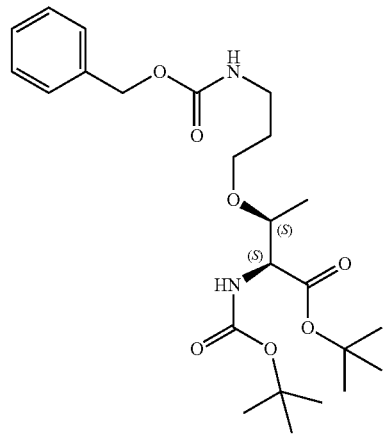

To a solution of tert-butyl (tert-butoxycarbonyl)-L-allothreoninate (6.41 g, 23.29 mmol) in THF (200 mL) was added benzyl N-(3-bromopropyl)carbamate (9.53 g, 35.03 mmol) and tetrabutylammonium fluoride (35 mL, 1 mol/L in THF). The resulting mixture was cooled to 0° C. and NaH (3.75 g, 93.75 mmol, 60% in mineral oil) was added at 0° C. under nitrogen. The reaction mixture was stirred at 0° C. for 1 h and quenched with HCl (0.5 M in water) to pH 6. The resulting solution was extracted with ethyl acetate (200 mL×3). The organic layers were combined and dried over anhydrous sodium sulfate, filtered and evaporated under vacuum. The residue was purified by flash chromatography on silica gel eluting with ethyl acetate/petroleum ether (1:4) to afford the title compound (2.50 g, 23% yield) as a colorless oil. LCMS (ESI): [M+H]$^+$=467.2.

Step 3: N-(((9H-Fluoren-9-yl)methoxy)carbonyl)-O-(3-(((benzyloxy)carbonyl)amino)propyl)-L-allothreonine

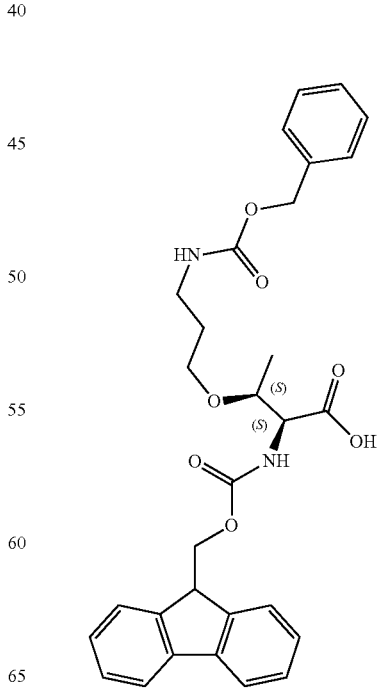

To a solution of tert-butyl O-(3-(((benzyloxy)carbonyl)amino)propyl)-N-(tert-butoxycarbonyl)-L-allothreoninate (2.78 g, 5.96 mmol) in DCM (25 mL) was added HCl (25 mL, 4 mol/L in dioxane) at 25° C. The reaction was stirred for 1 h at 25° C. The resulting solution was evaporated under vacuum to afford O-(3-(((benzyloxy)carbonyl)amino)propyl)-L-allothreonine HCl salt (1.38 g) as a yellow solid. This residue was dissolved in 1,4-dioxane (9 mL) and treated with sodium carbonate (1.14 g, 4.47 mmol) in water (11 mL) at room temperature. Then 9-fluorenylmethylchloroformate (1.39 g, 5.36 mmol) in 1,4-dioxane (11 mL) was added dropwise and the resulting mixture stirred at 0° C. for 1 h. The reaction was quenched with HCl (1M in water) to pH 6. The resulting solution was extracted with ethyl acetate (100 mL×3) and the organic layers were combined. The organic layer was dried over anhydrous sodium sulfate, filtered and evaporated under vacuum. The residue was purified by flash chromatography on silica gel eluting with MeOH/DCM (1:20) to afford the title compound (1.10 g, 46% yield) as a colorless oil. LCMS (ESI): [M+H]$^+$=533.2.

Step 4: ((3R,6S,9S,12S,15S,18R,19R)-9-(Aminomethyl)-6-((S)-1-(3-aminopropoxy)ethyl)-12-cyclohexyl-19-hexyl-15-isobutyl-3,16,18-trimethyl-1-oxa-4,7,10,13,16-pentaazacyclononadecane-5,8,11,14,17-pentaone The title compound was prepared using N-(((9H-fluoren-9-yl)methoxy)carbonyl)-O-(3-(((benzyloxy)carbonyl)amino)propyl)-L-allothreonine and following procedures analogous to those described for Example 57. LCMS (ESI): R$_T$ (min)=1.54, [M+H]f=738.5, method=L; $^1$H NMR (400 MHz, DMSO-d$_6$) δ 8.51-7.22 (m, 10H), 5.16-4.32 (m, 4H), 3.89-3.36 (m, 7H), 3.31-2.79 (m, 8H), 1.79-1.54 (m, 10H), 1.52-1.18 (m, 13H), 1.11-1.02 (m, 6H), 0.98-0.89 (m, 15H).

Example 71: (2S,6S,9S,12S,15S,18R,19R)-9-(Aminomethyl)-12-cyclohexyl-19-hexyl-6-((S)-1-hydroxyethyl)-15-isobutyl-2,16,18-trimethyl-1-oxa-4,7,10,13,16-pentaazacyclononadecane-5,8,11,14,17-pentaone

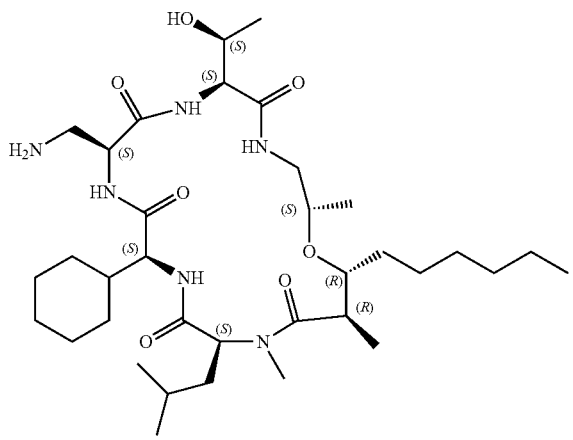

Step 1: Benzyl (R)-2-methylaziridine-1-carboxylate

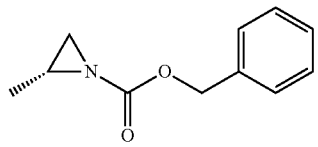

To a solution of benzyl (1R)-2-hydroxy-1-methylethylcarbamate (5.0 g, 23.9 mmol) and triethylamine (9.99 mL, 71.7 mmol) in DCM (40 mL) was added p-toluenesulfonylchloride (5.01 g, 26.29 mmol) in small portions at 0° C. under nitrogen. The resulting solution was stirred for 16 h at room temperature. The reaction was quenched with water. The resulting solution was extracted with ethyl acetate (200 mL×2) and the organic layers were combined. The organic layer was dried over anhydrous sodium sulfate and concentrated under vacuum. The residue was purified by flash chromatography on silica gel eluting with EA/PE (1/2) to afford [(2R)-2-(benzyloxycarbonylamino)propyl] 4-methylbenzenesulfonate (6.7 g) as a colorless oil.

To a mixture of NaH (530.9 mg, 13.25 mmol, 60% in mineral oil) and THF (150 mL) was added a solution of [(2R)-2-(benzyloxycarbonylamino)propyl] 4-methylbenzenesulfonate (6.7 g, 18.44 mmol) in THF (60 mL) dropwise at 60° C. The resulting solution was stirred for 4 h at 60° C., and then cooled to room temperature and quenched with 30 mL of water. The resulting solution was extracted with ethyl acetate (200 mL×2) and the organic layers were combined. The organic layer was dried over anhydrous sodium sulfate and evaporated under vacuum. The residue was purified by flash chromatography on silica gel eluting with ethyl acetate/petroleum ether (1/9) to afford the title compound (1.12 g). LCMS (ESI): [M+H]$^+$=192.1.

Step 2: (2R,3R)-3-(((S)-1-(((Benzyloxy)carbonyl)amino)propan-2-yl)oxy)-2-methylnonanoic acid

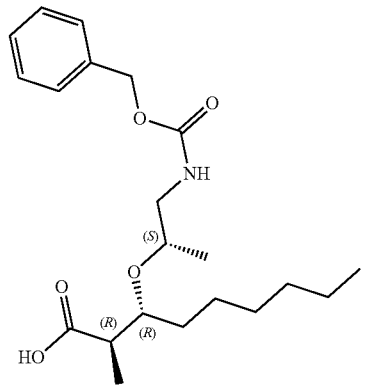

To a solution of benzyl (R)-2-methylaziridine-1-carboxylate (1.12 g, 5.86 mmol) and (2R,3R)-1-((3aR,6S,7aS)-8,8-dimethyl-2,2-dioxidotetrahydro-3H-3a,6-methanobenzo[c]isothiazol-1(4H)-yl)-3-hydroxy-2-methylnonan-1-one (2.26 g, 5.86 mmol) in chloroform (15 mL) was added boron trifluoride diethyl etherate (0.72 mL, 5.71 mmol) at 0° C. The resulting solution was stirred for 16 h at room temperature. The mixture was evaporated under vacuum. The residue was purified by flash chromatography on silica gel eluting with with ethyl acetate/petroleum ether (5/95) to afford benzyl ((S)-2-(((2R,3R)-1-((3aR,6S,7aS)-8,8-dimethyl-2,2-dioxidotetrahydro-3H-3a,6-methanobenzo[c]isothiazol-1(4H)-yl)-2-methyl-1-oxononan-3-yl)oxy)propyl) carbamate (2.6 g). This material was dissolved in THF (30 mL) and water (10 mL) and treated with hydrogen peroxide (0.4 mL, 30% in water) and lithium hydroxide (432.7 mg, 18.03 mmol) 0° C. The mixture was stirred for 4 h at 0° C. and saturated aqueous sodium sulfite was added at 0° C. The reaction mixture was then quenched with HCl (2 mol/L in water) to pH4. The resulting solution was extracted with ethyl acetate (3×200 mL) and the organic layers were combined. The organic layer was dried over anhydrous sodium sulfate and evaporated under vacuum. The residue was purified by flash chromatography on silica gel eluting with petroleum ether/ethyl acetate (1/5) to afford the title compound (1 g, 58% yield) as a solid. LCMS (ESI): $[M+H]^+$=380.2.

Step 3: (2R,3R)-3-(((S)-1-((((9H-Fluoren-9-yl)methoxy)carbonyl)amino)propan-2-yl)oxy)-2-methylnonanoic acid

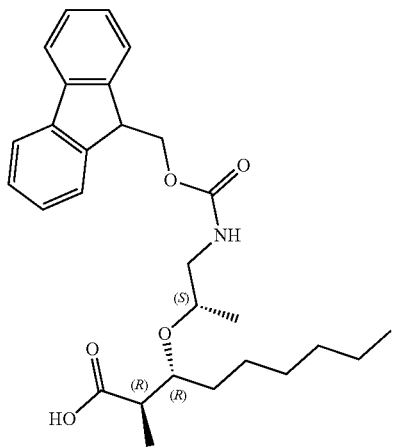

To a solution of (2R,3R)-3-(((S)-1-(((Benzyloxy)carbonyl)amino)propan-2-yl)oxy)-2-methylnonanoic acid (205.2 mg, 0.54 mmol) in ethyl acetate (10 mL) was added palladium (104 mg, 10% loading on carbon). The mixture was stirred for 1 h under a hydrogen balloon at room temperature. Then the solid was removed via filtration and the filtrate was evaporated under vacuum to afford (2R,3R)-3-[(1S)-2-amino-1-methyl-ethoxy]-2-methyl-nonanoic acid (120.4 mg, 90% yield). This residue was dissolved in 1,4-dioxane (2 mL) and treated with $Na_2CO_3$ (80.3 mg, 0.76 mmol) in water (2 mL) at room temperature. Then 9-fluorenylmethylchloroformate (161.5 mg, 0.62 mmol) in 1,4-dioxane (2 mL) was added at 0° C. The mixture was stirred at 0° C. for 1 h. Then the reaction was quenched with HCl (1M in water) to pH6 and extracted with ethyl acetate (3×100 mL). The combined organic layers were dried over anhydrous sodium sulfate and evaporated under vacuum. The residue was purified by flash chromatography on silica gel eluting with ethyl acetate/petroleum ether (1/5) to afford the title compound (100.4 mg, 43% yield) as a colorless oil. LCMS (ESI): $[M+H]^+$=468.2.

Step 4: (2S,6S,9S,12S,15S,18R,19R)-9-(Aminomethyl)-12-cyclohexyl-19-hexyl-6-((S)-1-hydroxyethyl)-15-isobutyl-2,16,18-trimethyl-1-oxa-4,7,10,13,16-pentaazacyclononadecane-5,8,11,14,17-pentaone The title compound was prepared using (2R,3R)-3-(((S)-1-((((9H-fluoren-9-yl)methoxy)carbonyl)amino)propan-2-yl)oxy)-2-methylnonanoic acid and following procedures analogous to those described for Example 57. LCMS (ESI): $R_T$ (min)=1.70, $[M+H]^+$=681.5, method=L; $^1H$ NMR (400 MHz, DMSO-$d_6$) δ 8.81-7.76 (m, 5H), 7.52-6.80 (m, 1H), 5.35-4.41 (m, 2H), 4.38-3.41 (m, 10H), 3.28-3.20 (m, 4H), 2.95-2.61 (m, 6H), 2.38-1.62 (m, 6H), 1.45-1.12 (m, 13H), 1.09-0.68 (m, 17H).

Example 72: N-(((6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)azetidine-3-carboxamide

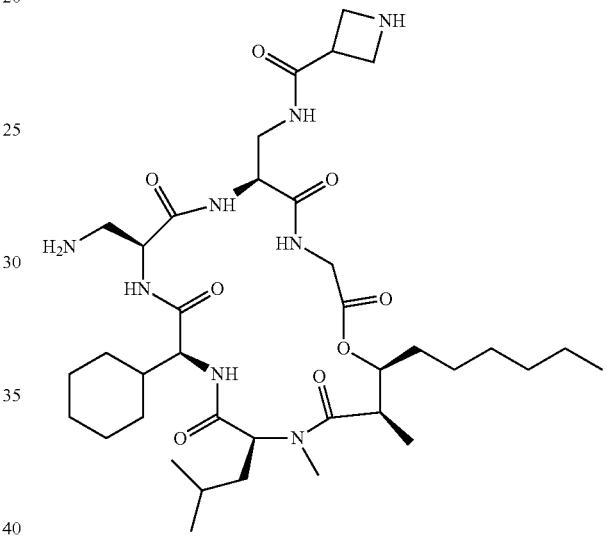

Step 1: tert-Butyl ((((6S,9S,12S,15S,18R,19R)-9-((((benzyloxy)carbonyl)amino)methyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)carbamate

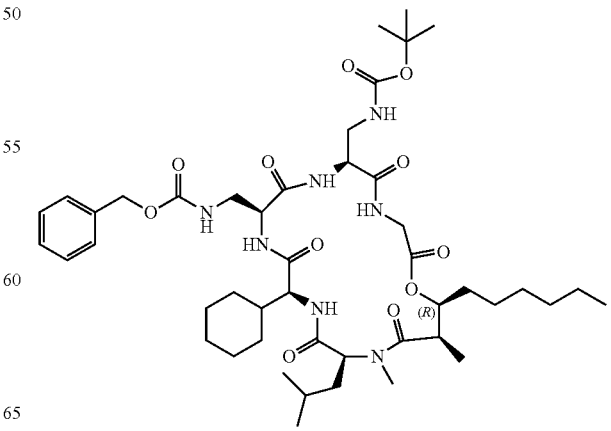

The title compound was prepared using procedures analogous to those described for Example 1, steps 1-5. LCMS (ESI) [M+H]⁺=900.5.

Step 2: Benzyl ((((6S,9S,12S,15S,18R,19R)-6-(aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-9-yl)methyl)carbamate

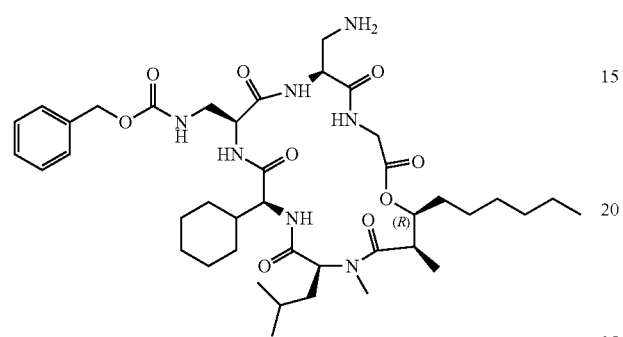

tert-Butyl ((((6S,9S,12S,15S,18R,19R)-9-(((((benzyloxy)carbonyl)amino)methyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)carbamate (90 mg, 0.1 mmol) was dissolved in 1 mL of DCM and charged with 150 uL of TFA. The mixture was then agitated at room temperature for 3 hours. After cooling to 0° C., 300 uL of triethylamine was added and the mixture was diluted with ethyl acetate. The organic was then washed with water, dried over magnesium sulfate, and concentrated in vacuo to afford the title compound (80 mg, 100% yield). LCMS (ESI) [M+H]⁺=800.5.

Step 3: tert-Butyl 3-(((((6S,9S,12S,15S,18R,19R)-9-(((((benzyloxy)carbonyl)amino)methyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)carbamoyl)azetidine-1-carboxylate

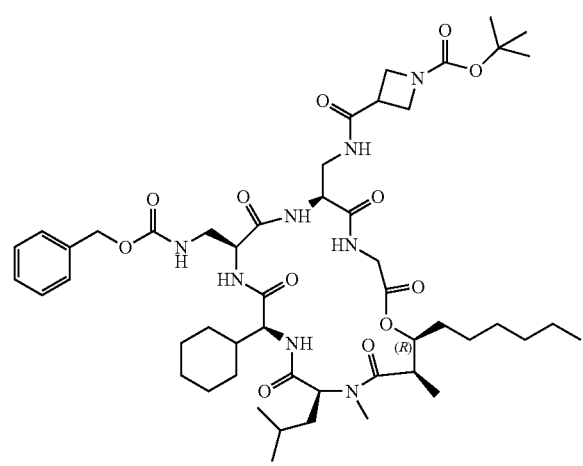

1-(tert-Butoxycarbonyl)azetidine-3-carboxylic acid (80 mg, 0.4 mmol) was dissolved in 1 mL of dimethylacetamide and charged with HATU (152 mg, 0.4 mmol) and DIPEA (174 uL, 1 mmol). The mixture was then agitated at room temperature for 5 minutes. The mixture was then added to benzyl ((((6S,9S,12S,15S,18R,19R)-6-(aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-9-yl)methyl)carbamate (80 mg). After agitating at room temperature for 30 minutes, the mixture was diluted with ethyl acetate. The organic was then washed with water twice, dried over magnesium sulfate, and concentrated in vacuo to afford the title compound, which was carried forward without purification (105 mg). LCMS (ESI) [M+H]+=983.5.

Step 4: tert-Butyl 3-(((((6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)carbamoyl)azetidine-1-carboxylate

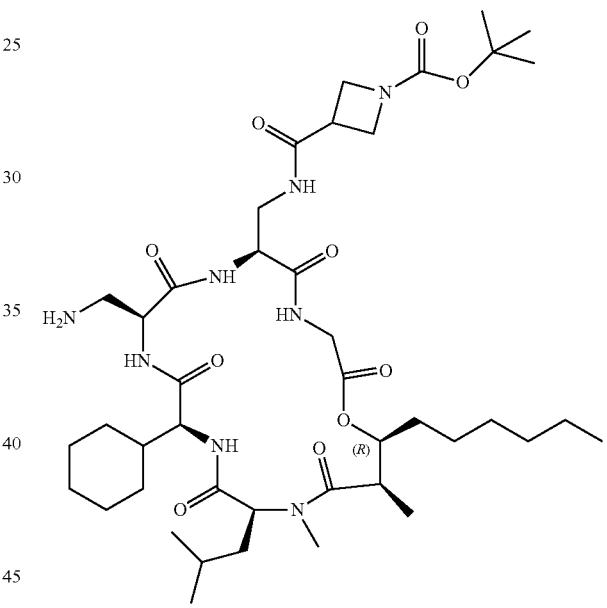

tert-Butyl 3-(((((6S,9S,12S,15S,18R,19R)-9-(((((benzyloxy)carbonyl)amino)methyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)carbamoyl)azetidine-1-carboxylate (105 mg, 0.11 mmol) was dissolved in 10 mL of 7:2:1-ethyl acetate:methanol:acetic acid and passed through immobilized 10% Pd/C under hydrogen using an Hcube hydrogenation instrument (50 psi, 37C). The eluent was then concentrated in vacuo to afford the title compound (84 mg, 90% yield). LCMS (ESI) [M+H]⁺=849.5.

Step 5: N-(((6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)azetidine-3-carboxamide tert-Butyl 3-(((((6S,9S,12S,15S,18R,19R)-9-(aminomethyl)-12-cyclohexyl-19-hexyl-15-isobutyl-16,18-dimethyl- 2,5,8,11,14,17-hexaoxo-1-oxa-4,7,10,13,16-pentaazacyclononadecan-6-yl)methyl)carbamoyl)azetidine-1-carboxylate (84 mg, 0.1 mmol) was dissolved in 1 mL of DCM and charged with 200 uL of triisopropylsilane and 150 uL of TFA. The mixture was then agitated for 1 hour at room temperature. The mixture was then diluted with dioxane and concentrated in vacuo. The residue was then purified by reverse-phase HPLC (5-50% Acetonitrile in 0.05% TFA in Water, 250×30 mm 10 um Luna C18) to afford the title compound as a TFA salt (12 mg, 0.016 mmol, 16% yield). LCMS (ESI): $R_T$ (min)=4.20, [M+H]$^+$=749.5, method=A; $^1$H NMR (400 MHz, DMSO-d$_6$) δ 8.91-8.55 (m, 3H), 8.19-7.79 (m, 5H), 7.69-7.52 (m, 1H), 5.03-4.85 (m, 1H), 4.51-4.31 (m, 1H), 4.23-3.90 (m, 7H), 3.90-3.51 (m, 6H), 3.23-2.90 (m, 5H), 2.71 (s, 1H), 2.05-1.33 (m, 10H), 1.34-0.75 (m, 25H).

Example 73: (3R,6S,9S,12S,15S,18R,19R)-6-((4-Aminobutoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone Step 1: N—((S)-2-((S)-2-((S)-2-((2R,3R)-3-((R)-2-Aminopropoxy)-N,2-dimethylnonan amido)-4-methylpentanamido)-2-cyclohexylacetamido)-3-((tert-butoxycarbonyl)amino)propanoyl)-O-(4-((tert-butoxycarbonyl)amino)butyl)-L-serine

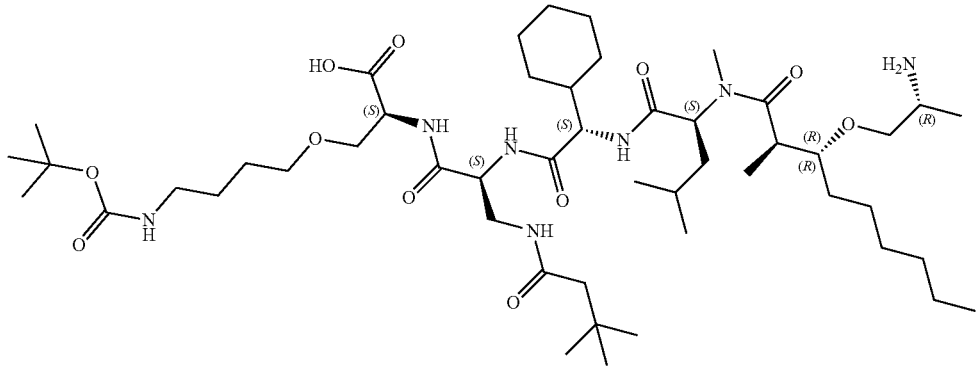

The title compound was prepared from N-(((9H-fluoren-9-yl)methoxy)carbonyl)-O-(4-((tert-butoxycarbonyl)amino)butyl)-L-serine (intermediate P2C) following procedures analogous to those described for Example 57, steps 1 and 2. LCMS (ESI): [M+H]$^+$=956.7.

Step 2: tert-Butyl(4-(((3R,6S,9S,12S,15S,18R,19R)-9-(((tert-butoxycarbonyl)amino)methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)butyl)carbamate

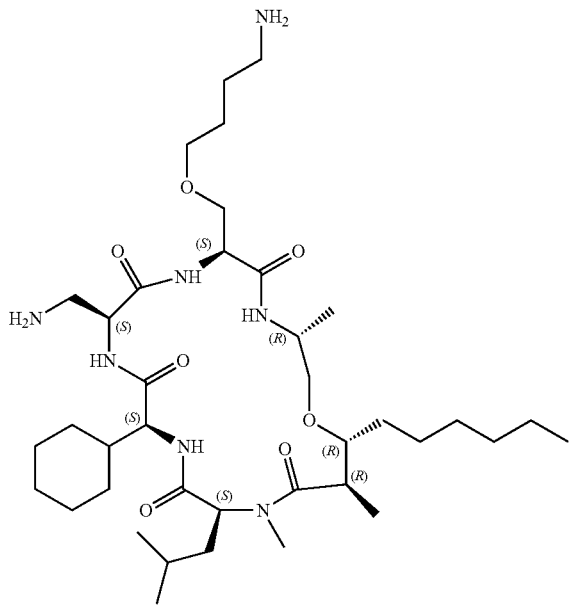

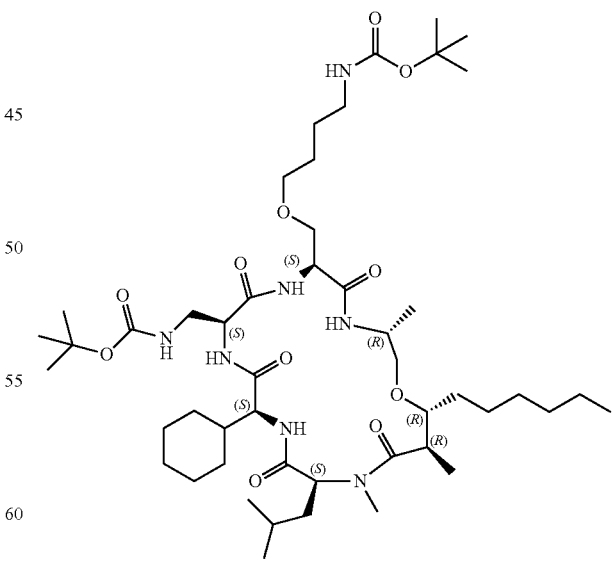

A solution of HATU/HOBt (0.4 M in DMF, 0.65 mL) was diluted with DMF (2 mL) and THF (20 mL). The resulting solution was added dropwise to a solution of DIPEA (165.5 mg, 1.28 mmol) and N—((S)-2-((S)-2-((S)-2-((2R,3R)-3-

((R)-2-aminopropoxy)-N,2-dimethylnonan amido)-4-methylpentanamido)-2-cyclohexylacetamido)-3-((tert-butoxycarbonyl)amino)propanoyl)-O-(4-((tert-butoxycarbonyl)amino)butyl)-L-serine (245.5 mg, 0.26 mmol) in THF (180 ml) at 0° C. The reaction mixture was stirred at 0° C. for 1 h and concentrated under reduced pressure. The residual solution was diluted with DMF (2 mL), and the resulting solution was added dropwise to water (200 mL) with vigorous stirring. The precipitate was collected by filtration, washed with water (10 mL) and dried to afford the title compound (230 mg, 95% yield). LCMS (ESI): [M+H]$^+$=938.7.

Step 3: (3R,6S,9S,12S,15S,18R,19R)-6-((4-Aminobutoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone A solution of the product from the previous step (216.3 mg, 0.23 mmol) in TFA (20 mL) was stirred at 0° C. for 1 h. Toluene (5 mL) was added to the mixture and the resulting mixture was concentrated under reduced pressure to dryness. The crude product was purified via reverse phase HPLC to afford the title compound (108 mg) as a TFA salt. LCMS (ESI): R$_T$ (min)=1.62, [M+H]$^+$=738.5, method=C; $^1$H NMR (400 MHz, DMSO-d$_6$) 8.75-8.17 (m, 2H), 8.16-7.85 (m, 4H), 7.84-7.49 (m, 3H), 4.78-4.61 (m, 1H), 4.49-4.32 (m, 1H), 4.25-4.01 (m, 1H), 3.99-3.85 (m, 1H), 3.80-3.65 (m, 2H), 3.38-2.89 (m, 9H), 2.85-2.69 (m, 4H), 2.11-1.94 (m, 1H), 1.92-1.43 (m, 13H), 1.42-1.16 (m, 12H), 1.15-0.75 (m, 18H).

Example 74: (3R,6S,9S,12S,15S,18R,19R)-19-(((1r,3R,5S)-Adamantan-1-yl)methyl)-9-(aminomethyl)-12-cyclohexyl-6-((S)-1-hydroxyethyl)-15-isobutyl-3,16,18-trimethyl-1-oxa-4,7,10,13,16-pentaazacyclononadecane-5,8,11,14,17-pentaone

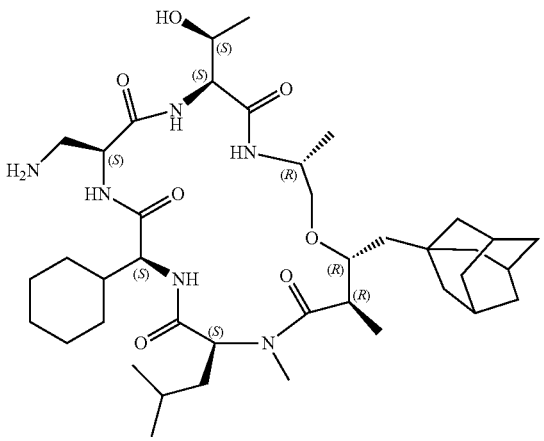

Step 1. (2R,3R)-4-((1r,3R,5S)-Adamantan-1-yl)-3-((R)-2-((tert-butoxycarbonyl)amino) propoxy)-2-methylbutanoic acid

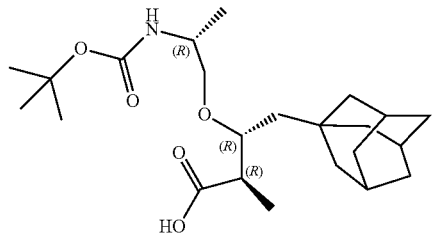

The title compound was prepared from Intermediate T8 following procedures analogous to those described for Intermediate 3. LCMS (ESI): [M+H]$^+$=410.3.

Step 2. (3R,6S,9S,12S,15S,18R,19R)-19-(((1r,3R,5S)-Adamantan-1-yl)methyl)-9-(aminomethyl)-12-cyclohexyl-6-((S)-1-hydroxyethyl)-15-isobutyl-3,16,18-trimethyl-1-oxa-4,7,10,13,16-pentaazacyclononadecane-5,8,11,14,17-pentaone The title compound was prepared following procedures analogous to those described for Example 57. LCMS (ESI): R$_T$ (min)=2.02, [M+H]+=745.5, method=C; $^1$H NMR (400 MHz, DMSO-d$_6$) 8.91-7.72 (m, 5H), 7.63-7.35 (m, 1H), 7.34-7.02 (m, 1H), 5.27-4.40 (m, 2H), 4.39-4.18 (m, 1H), 4.16-3.68 (m, 7H), 3.67-3.51 (m, 1H), 3.50-3.41 (m, 1H), 3.32-3.14 (m, 2H), 3.13-3.07 (m, 1H), 3.06-2.97 (m, 2H), 2.78-2.75 (m, 1H), 2.22-2.03 (m, 1H), 1.96-1.82 (m, 4H), 1.78-1.55 (m, 10H), 1.54-1.34 (m, 8H), 1.33-0.65 (m, 21H).

Example 75: (6S,9S,12S,15S,18R,19R)-9-(Aminomethyl)-6-((3-aminopropoxy)methyl)-12-cyclohexyl-19-(5,5-dimethylhexyl)-15-isobutyl-16,18-dimethyl-1-oxa-4,7,10,13,16-pentaazacyclononadecane-2,5,8,11,14,17-hexaone

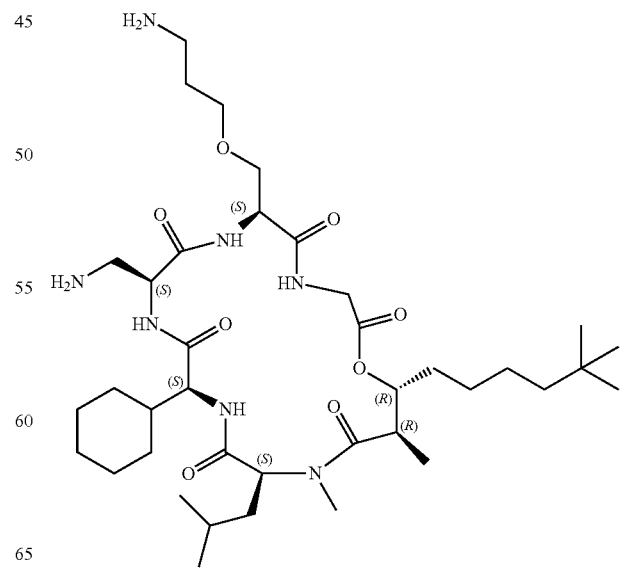

The title compound was prepared using Intermediate T5 and Intermediate 5 following procedures analogous to those described for Example 3. LCMS (ESI): $R_T$ (min)=1.59, [M+H]$^+$=752.6, method=C; $^1$H NMR (400 MHz, DMSO-d$_6$) 9.17-8.65 (m, 1H), 8.32-7.89 (m, 5H), 7.88-7.42 (m, 4H), 5.16-4.89 (m, 1H), 4.77-4.25 (m, 4H), 4.21-3.87 (m, 2H), 3.86-3.78 (m, 1H), 3.77-3.55 (m, 2H), 3.54-3.31 (m, 3H), 3.30-2.97 (m, 4H), 2.94-2.76 (m, 2H), 2.75-2.68 (m, 1H), 2.09-1.34 (m, 13H), 1.32-1.08 (m, 8H), 1.07-0.75 (m, 20H).

Example 76: (3R,6S,9S,12S,15S,18R,19R)-9-(Aminomethyl)-6-((4-(aminomethyl)phenoxy)methyl)-12-cyclohexyl-19-hexyl-15-isobutyl-3,16,18-trimethyl-1-oxa-4,7,10,13,16-pentaazacyclononadecane-5,8,11,14,17-pentaone

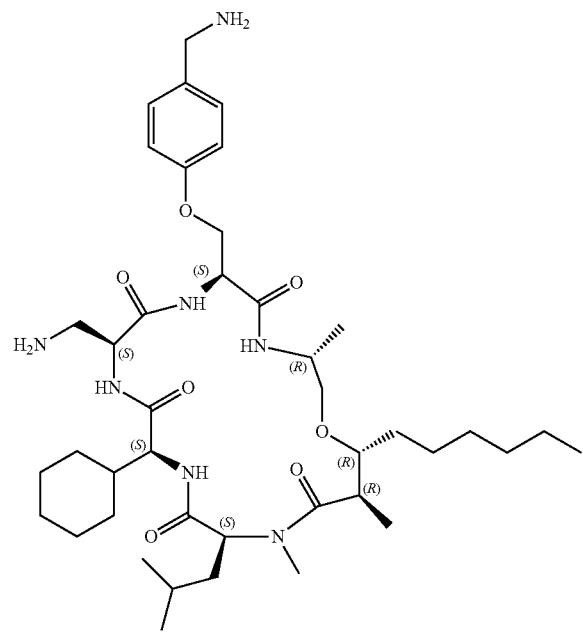

Step 1: Benzyl (S)-(3-hydroxy-1-(methoxy(methyl)amino)-1-oxopropan-2-yl)carbamate

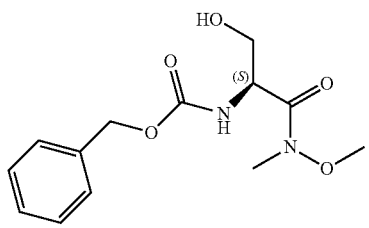

To a solution of (2S)-2-(benzyloxycarbonylamino)-3-hydroxy-propanoic acid (2.0 g, 8.36 mmol) in DMF (40 mL) was added HATU (4.77 g, 12.55 mmol), DIPEA (2.16 g, 16.7 mmol) and N,O-dimethylhydroxylamine hydrochloride (1.22 g, 12.51 mmol). The reaction was stirred at room temperature for 3 h. The resulting solution was diluted with ethyl acetate (200 mL), washed with 0.5 M aqueous NaOH (50 mL×2) and brine (50 mL×2). The organic layer was concentrated under reduced pressure. The residue was purified by flash chromatography on silica gel eluting with petroleum ether/ethyl acetate (2/3) to afford the title compound (960 mg, 40% yield) as yellow oil. LCMS (ESI): [M+H]$^+$=283.1.

Step 2: tert-Butyl (S)-(4-(2-(((benzyloxy)carbonyl)amino)-3-(methoxy(methyl)amino)-3-oxopropoxy)benzyl)carbamate

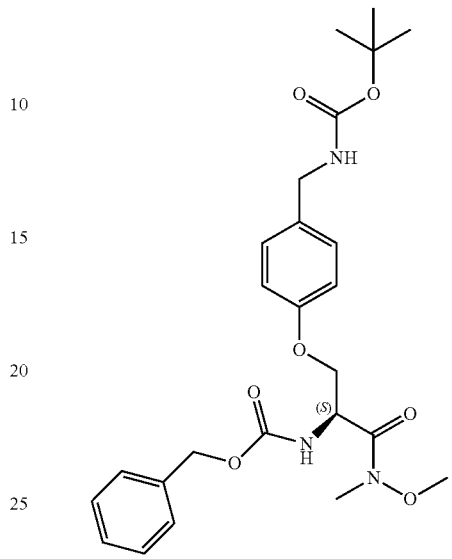

To a solution of tert-butyl N-[(4-bromophenyl)methyl]carbamate (1.0 g, 3.50 mmol) and benzyl (S)-(3-hydroxy-1-(methoxy(methyl)amino)-1-oxopropan-2-yl)carbamate (990.0 mg, 3.51 mmol) in toluene (14 mL) was added t-BuBrettphos (169.3 mg, 0.35 mmol) under nitrogen, followed by [Pd(allyl)Cl]$_2$ (64.0 mg, 0.18 mmol) and Cs$_2$CO$_3$ (2.29 g, 7.02 mmol). The reaction mixture was stirred at 60° C. for 3 h. A duplicate reaction with same scale was repeated in parallel. The combined reaction mixtures were cooled to ambient temperature and concentrated under reduced pressure. The residue was purified by flash chromatography on silica gel eluting with petroleum ether/ethyl acetate (2/3) to afford the title compound (906 mg, 27% yield) as a yellow solid. LCMS (ESI): [M+H]$^+$=488.2.

Step 3: tert-Butyl (S)-(4-(2-amino-3-(methoxy(methyl)amino)-3-oxopropoxy)benzyl)carbamate

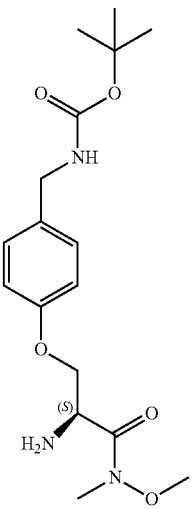

To a solution of tert-butyl (S)-(4-(2-(((benzyloxy)carbonyl)amino)-3-(methoxy(methyl)amino)-3-oxopropoxy)benzyl)carbamate (735.0 mg, 1.51 mmol) in ethyl acetate (30 mL) was added palladium (10 wt. % on carbon) (500 mg) under nitrogen. The reaction mixture was evacuated and backfilled with hydrogen, and stirred under a hydrogen balloon at ambient temperature for 45 min. The catalyst was filtered off and rinsed with ethyl acetate. The filtrate was concentrated under reduced pressure to afford the title compound (500 mg, 93% yield) as yellow oil. LCMS (ESI): [M+H]$^+$=354.2.

Step 4: N-(((9H-Fluoren-9-yl)methoxy)carbonyl)-O-(4-((((tert-butoxycarbonyl)amino) methyl)phenyl)-L-serine

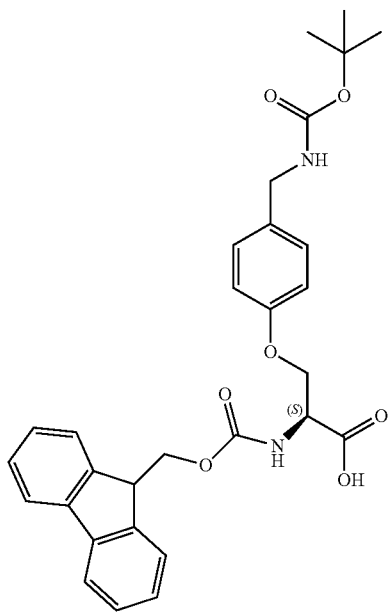

To a solution of tert-butyl (S)-(4-(2-amino-3-(methoxy(methyl)amino)-3-oxopropoxy)benzyl)carbamate (376 mg, 1.05 mmol) in water (4 mL) and THF (12 mL) was added LiOH (51 mg, 2.1 mmol). The reaction mixture was stirred at 25° C. overnight. Then 9-fluorenylmethylchloroformate (329 mg, 1.05 mmol) was added. The reaction mixture was stirred at 25° C. for 1 h and concentrated under reduced pressure. The residue was diluted with water (10 mL). Aqueous HCl solution (1 mol/L) was carefully added until pH6. The resulting solution was extracted with ethyl acetate (100 mL×5) and the organic layers were combined. The combined organic layers were dried over anhydrous sodium sulfate, and concentrated under reduced pressure. The residue was purified by flash chromatography on silica gel eluting with petroleum ether/ethyl ester (2/1), then DCM/methanol (10/1) to afford the title compound (360 mg, 68% yield) as a white solid. LCMS (ESI): [M+H]$^+$=533.2.

Step 5: (3R,6S,9S,12S,15S,18R,19R)-9-(Aminomethyl)-6-((4-(aminomethyl)phenoxy)methyl)-12-cyclohexyl-19-hexyl-15-isobutyl-3,16,18-trimethyl-1-oxa-4,7,10,13,16-pentaazacyclononadecane-5,8,11,14,17-pentaone The title compound was prepared following procedures analogous to those described for Example 73. LCMS (ESI): Rt (min)=1.64, [M+H]$^+$=772.5, method=C; $^1$H NMR (400 MHz, DMSO-d$_6$) 9.02-7.95 (m, 8H), 7.67-7.29 (m, 2H), 7.05-6.91 (m, 2H), 4.78-4.48 (m, 1H), 4.47-4.16 (m, 3H), 4.15-3.71 (m, 5H), 3.69-3.45 (m, 3H), 3.31-3.15 (m, 3H), 3.14-3.09 (m, 1H), 3.08-2.89 (m, 1H), 2.85-2.65 (m, 2H), 1.14-1.84 (m, 2H), 1.83-1.43 (m, 8H), 1.83-1.43 (m, 11H), 1.42-0.76 (m, 17H).

Example 77: (3R,6S,9S,12S,15S,18R,19R)-9-(Aminomethyl)-18,19-dibutyl-12-cyclohexyl-6-((S)-1-hydroxyethyl)-3,16-dimethyl-15-propyl-1-oxa-4,7,10,13,16-pentaazacyclononadecane-5,8,11,14,17-pentaone

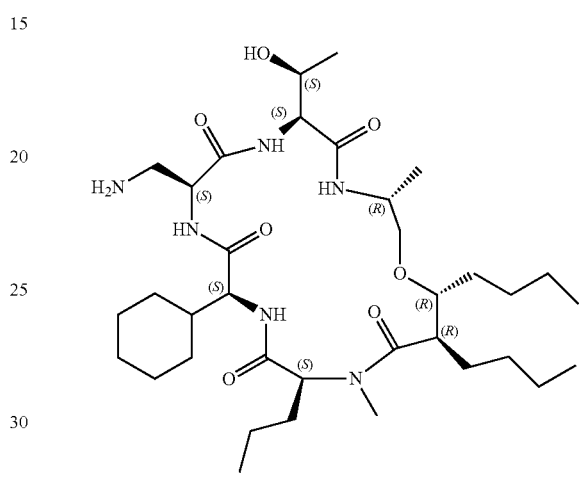

Step 1: 1-((3aR,6S,7aS)-8,8-Dimethyl-2,2-dioxidotetrahydro-3H-3a,6-methanobenzo[c]isothiazol-1(4H)-yl)hex-5-en-1-one

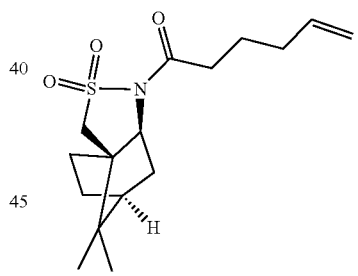

To a solution of 5-hexenoic acid (10.0 g, 87.61 mmol) in DCM (200 mL) was added oxalyl dichloride (16.6 g, 130.78 mmol) at 0° C. The reaction mixture was stirred at room temperature for 3 h and concentrated under reduced pressure. The crude product (hex-5-enoyl chloride, 9.67 g) was carried forward without purification. To a solution of (2r)-bornane-10,2-sultam (15.7 g, 72.92 mmol), triethylamine (44.0 g, 435.64 mmol) and DMAP (1.78 g, 14.59 mmol) in DCM (200 mL) was added dropwise a solution of hex-5-enoyl chloride (9.67 g) in 10 mL of DCM at 0° C. The reaction mixture was stirred at room temperature overnight. Water (50 mL) was added and the phases were separated. The aqueous phase was extracted with DCM. The combined organic phases were washed with HCl (1 mol/L in water, 30 mL), brine, dried over sodium sulfate and evaporated under reduced pressure. The residue was purified by flash chromatography on silica gel eluting with petroleum ether/ethyl acetate (5/1) to afford the title compound (8.01 g, 35% yield) as a yellow oil. LCMS (ESI): [M+H]$^+$=312.2.

Step 2: (2R,3R)-2-(But-3-en-1-yl)-3-hydroxyhept-6-enoic acid

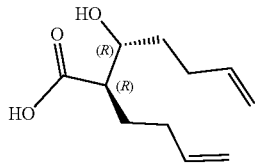

To a solution of 1-((3aR,6S,7aS)-8,8-dimethyl-2,2-dioxidotetrahydro-3H-3a,6-methanobenzo[c]isothiazol-1(4H)-yl)hex-5-en-1-one (2.01 g, 6.45 mmol) in DCM (30 mL) was added calcium hydride (100 mg), followed by triethylamine (783.1 mg, 7.74 mmol) and tert-butyldimethylsilyl trifluoromethanesulfonate (1.87 g, 7.09 mmol) at room temperature. The reaction mixture was stirred at 30° C. overnight under nitrogen and evaporated under reduced pressure. The residue was dissolved in DCM (100 mL). The solution was added dropwise to a solution of pent-4-enal (702.8 mg, 8.35 mmol) and titanium tetrachloride (8.3 mL, 8.3 mmol) in anhydrous DCM (20 mL) at −78° C. under nitrogen. The reaction was stirred at −78° C. for 30 minutes and then saturated aqueous ammonium chloride solution (50 mL) was added and the phases were separated. The aqueous phase was extracted with DCM (2×100 mL). The combined organic phases were dried over sodium sulfate, filtered and evaporated in vacuo. The residue was purified by flash chromatography on silica gel eluting with EA/PE (1:10) to afford (2R,3R)-2-(but-3-en-1-yl)-1-((3aR,6S,7aS)-8,8-dimethyl-2,2-dioxidotetrahydro-3H-3a,6-methanobenzo[c]isothiazol-1(4H)-yl)-3-hydroxyhept-6-en-1-one (1.2 g, 47% yield) as a light yellow oil.

Lithium hydroxide (193 mg, 8.39 mmol) was added to a solution of (2R,3R)-2-(but-3-en-1-yl)-1-((3aR,6S,7aS)-8,8-dimethyl-2,2-dioxidotetrahydro-3H-3a,6-methanobenzo[c]isothiazol-1(4H)-yl)-3-hydroxyhept-6-en-1-one (0.81 g, 2.05 mmol) in acetonitrile (10 mL) and water (10 mL). The reaction mixture was stirred for 3 h at 0° C. and acidified with HCl (1 mol/L in water) to pH 4. The resulting solution was extracted with ethyl acetate (3×50 mL). The organic layer was dried over anhydrous sodium sulfate and evaporated under vacuum. The residue was purified on silica gel eluting with 30% ethyl acetate in petroleum ether to afford the title compound (331 mg, 81% yield) as an oil. LCMS (ESI): [M−H]⁻=197.1.

Step 3: (2R,3R)-2-(But-3-en-1-yl)-3-((R)-2-((tert-butoxycarbonyl)amino)propoxy)hept-6-enoic acid

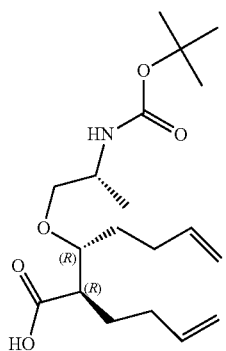

To a solution of (2R,3R)-2-but-3-enyl-3-hydroxy-hept-6-enoic acid (3.12 g, 15.74 mmol), tert-butyl(4R)-4-methyl-2,2-dioxo-oxathiazolidine-3-carboxylate (10.89 g, 45.9 mmol) and tetrabutylammonium fluoride (23.2 mL, 1M in THF) in THF (100 mL) was added NaH (2.52 g, 63.0 mmol, 60% in mineral oil) portionwise at 0° C. The reaction mixture was stirred for 3 h at room temperature and quenched with 10 mL of water and diluted hydrochloric acid (0.5 mol/L in water) to pH6. The resulting solution was extracted with ethyl acetate (3×). The combined organic layers were dried over anhydrous sodium sulfate and evaporated under vacuum. The residue was purified on silica gel eluting with 30% ethyl acetate in petroleum ether to afford [(2R)-2-(tert-butoxycarbonylamino)propyl](2R,3R)-2-but-3-enyl-3-[(2R)-2-(tert-butoxycarbonylamino)propoxy]hept-6-enoate (4.21 g) as a white solid.

To a solution of [(2R)-2-(tert-butoxycarbonylamino)propyl](2R,3R)-2-but-3-enyl-3-[(2R)-2-(tert-butoxycarbonylamino)propoxy]hept-6-enoate (3.03 g, 5.91 mmol) in MeOH (30 mL) and water (30 mL) was added LiOH (1.64 g, 71.3 mmol). The reaction mixture was stirred for 2 days at room temperature and acidified with diluted hydrochloric acid (1 mol/L) to pH 4. The resulting solution was extracted with ethyl acetate (3×). The combined organic layers were dried over anhydrous sodium sulfate and concentrated under vacuum. The residue was purified via silica gel chromatography eluting with 35% ethyl acetate in petroleum ether to afford the title compound (1.83 g, 87% yield) as a white solid. LCMS (ESI): [M−H]⁻=354.2.

Step 4: Benzyl(((3R,6S,9S,12S,15S,18R,19R)-6-((S)-1-(benzyloxy)ethyl)-18,19-di(but-3-en-1-yl)-12-cyclohexyl-3,16-dimethyl-5,8,11,14,17-pentaoxo-15-propyl-1-oxa-4,7,10,13,16-pentaazacyclononadecan-9-yl)methyl)carbamate

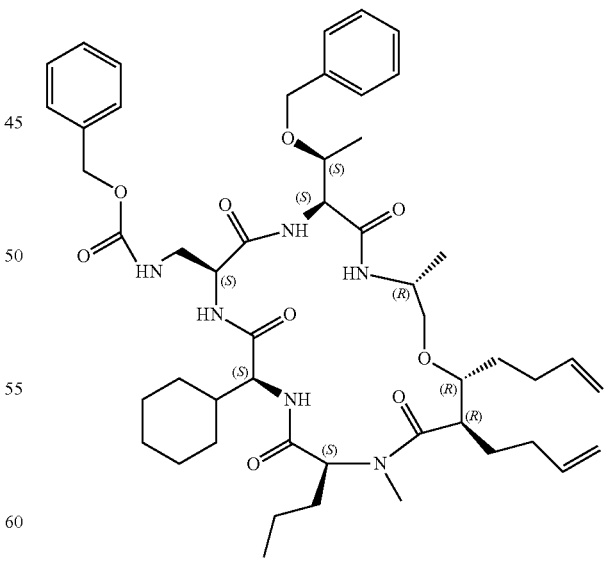

The title compound was prepared following procedures analogous to those described for Example 57. LCMS (ESI): [M+H]⁺=901.5.

Step 5: (3R,6S,9S,12S,15S,18R,19R)-9-(Aminomethyl)-18,19-dibutyl-12-cyclohexyl-6-((S)-1-hydroxyethyl)-3,16-dimethyl-15-propyl-1-oxa-4,7,10,13,16-pentaazacyclononadecane-5,8,11,14,17-pentaone A mixture of benzyl (((3R,6S,9S,12S,15S,18R,19R)-6-((S)-1-(benzyloxy)ethyl)-18,19-di(but-3-en-1-yl)-12-cyclohexyl-3,16-dimethyl-5,8,11,14,17-pentaoxo-15-propyl-1-oxa-4,7,10,13,16-pentaazacyclononadecan-9-yl)methyl) carbamate (201.5 mg, 0.22 mmol) and palladium (150 mg, 10% loading on carbon) in ethyl acetate containing 0.5% TFA (20 mL) was stirred under a hydrogen balloon for 3 h at room temperature. The solid was removed via filtration and the filtrate was evaporated under reduced pressure. The resulting residue was purified by Prep-HPLC to afford the title compound (9.1 mg, 5% yield) as a white solid. LCMS (ESI): $R_T$ (min)=1.71, [M+H]$^+$=681.5, method=L; $^1$H NMR (400 MHz, DMSO-$d_6$) δ 8.86-8.12 (m, 2H), 8.05-6.88 (m, 5H), 4.81-3.95 (m, 5H), 3.91-3.62 (m, 3H), 3.32-3.08 (m, 6H), 3.01-2.60 (m, 4H), 2.07-1.88 (m, 1H), 1.85-1.52 (m, 7H), 1.49-1.07 (m, 18H), 1.03-0.92 (m, 7H), 0.90-0.83 (m, 7H).

Example 78: (3R,6S,9S,12S,15S,18R,19R)-9-(Aminomethyl)-12-cyclohexyl-6-((3-(dimethylamino)propoxy)methyl)-19-hexyl-15-isobutyl-3,16,18-trimethyl-1-oxa-4,7,10,13,16-pentaazacyclononadecane-5,8,11,14,17-pentaone

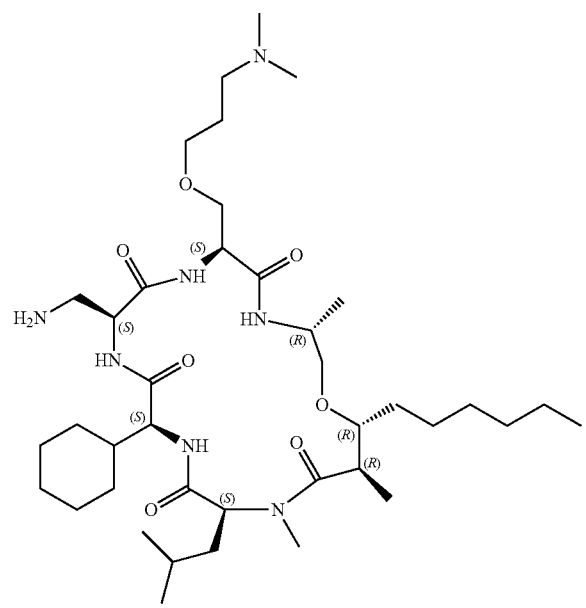

Step 1: tert-Butyl (3-(((3R,6S,9S,12S,15S,18R,19R)-9-((((benzyloxy)carbonyl)amino)methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)propyl) carbamate

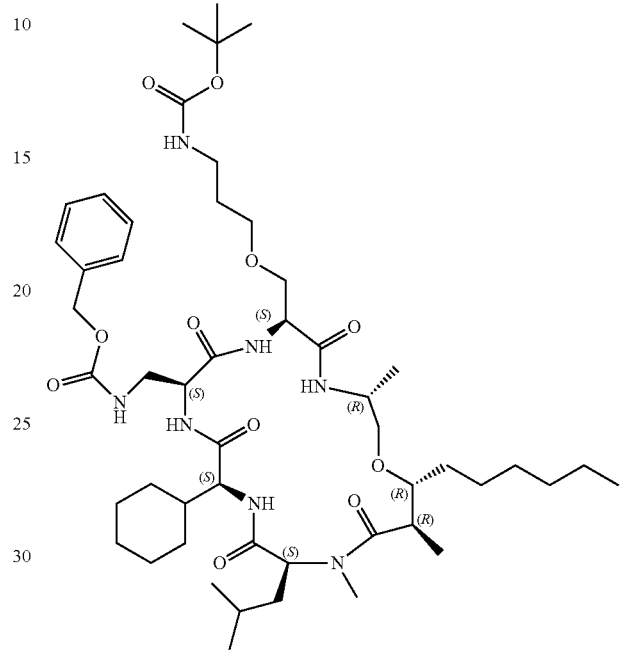

The title compound was prepared following procedures analogous to those described for Example 81 (steps 2-4) LCMS (ESI): [M+H]$^+$=958.6.

Step 2: Benzyl (((3R,6S,9S,12S,15S,18R,19R)-6-((3-aminopropoxy)methyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate

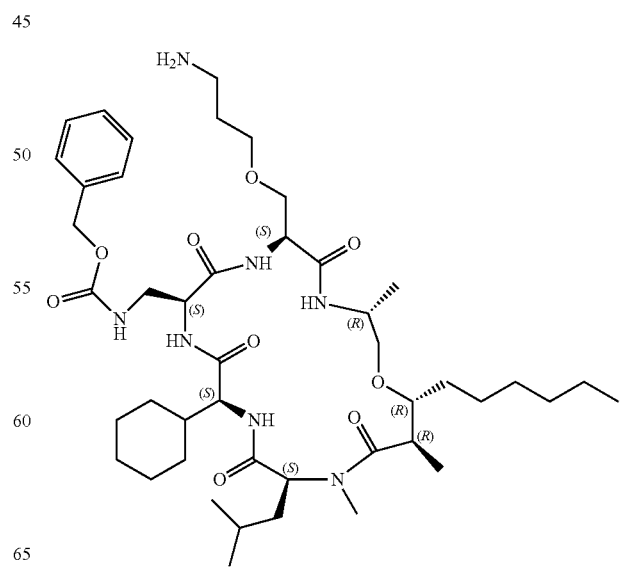

A solution of tert-butyl (3-(((3R,6S,9S,12S,15S,18R,19R)-9-((((benzyloxy)carbonyl)amino)methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)propyl)carbamate (481.0 mg, 0.50 mmol) in TFA (5 mL) was stirred at 0° C. for 30 min. Toluene (10 mL) was added and the resulting mixture was evaporated under reduced pressure to afford the title compound (409.3 mg) as a TFA salt. LCMS (ESI): [M+H]⁺=858.6.

Step 3: Benzyl (((3R,6S,9S,12S,15S,18R,19R)-12-cyclohexyl-6-((3-(dimethylamino)propoxy)methyl)-19-hexyl-15-isobutyl-3,16,18-trimethyl-5,8,11,14,17-pentaoxo-1-oxa-4,7,10,13,16-pentaazacyclononadecan-9-yl)methyl)carbamate

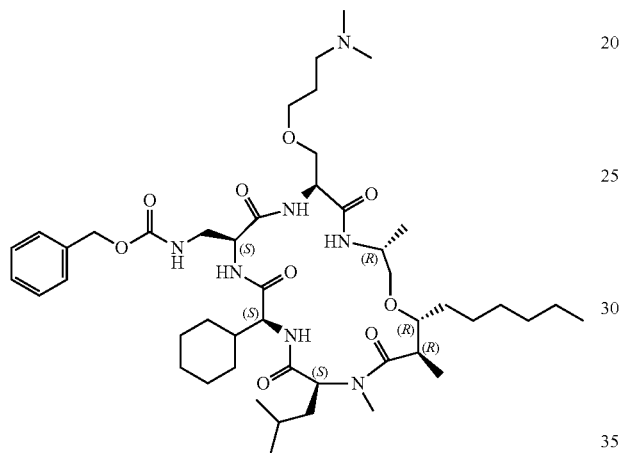

To a solution of benzyl (((3R,6S,9S,12S,15S,18R,19R)-6-((3-aminopropoxy)methyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate (180.6 mg, 0.18 mmol) in DCM (10 mL) was added (HCHO)$_n$ (80.9 mg) and DIPEA (0.13 mL, 0.75 mmol) at 0° C. The reaction mixture was stirred at room temperature for 2 h. Then NaBH(OAc)$_3$ (92.6 mg, 0.44 mmol) was added and the reaction mixture was stirred at room temperature for an additional 2 h. The reaction mixture was partitioned between DCM (100 mL) and water (50 mL). The organic layer was dried over anhydrous sodium sulfate and evaporated under reduced pressure to afford the title compound (180.3 mg) as a yellow solid. LCMS (ESI): [M+H]⁺=886.6.

Step 4: (3R,6S,9S,12S,15S,18R,19R)-9-(Aminomethyl)-12-cyclohexyl-6-((3-(dimethylamino)propoxy)methyl)-19-hexyl-15-isobutyl-3,16,18-trimethyl-1-oxa-4,7,10,13,16-pentaazacyclononadecane-5,8,11,14,17-pentaone A mixture of benzyl (((3R,6S,9S,12S,15S,18R,19R)-12-cyclohexyl-6-((3-(dimethylamino)propoxy)methyl)-19-hexyl-15-isobutyl-3,16,18-trimethyl-5,8,11,14,17-pentaoxo-1-oxa-4,7,10,13,16-pentaazacyclononadecan-9-yl)methyl)carbamate (180.6 mg, 0.20 mmol) and palladium (205.3 mg, 10% loading on carbon) in ethyl acetate containing 0.5% TFA (20 mL) was stirred under a hydrogen balloon for 3 h at room temperature. The reaction mixture was diluted with ethyl acetate (50 ml).

The solid was removed via filtration and the filtrate was evaporated under reduced pressure. The residue was purified by prep-LCMS to afford the title compound (54.2 mg, 30% yield). LCMS (ESI): R$_T$ (m)=1.61, [M+H]⁺=752.6, method=L; ¹H NMR (400 MHz, DMSO-d$_6$) δ 9.68-8.57 (m, 2H), 8.34-7.82 (m, 5H), 7.68-6.67 (m, 1H), 4.66-3.89 (m, 5H), 3.78-3.62 (m, 3H), 3.59-3.35 (m, 9H), 3.15-2.94 (m, 4H), 2.88-2.72 (m, 8H), 2.13-1.45 (m, 12H), 1.40-1.23 (m, 11H), 1.19-1.06 (m, 4H), 1.01-0.94 (m, 5H), 0.90-0.82 (m, 6H).

Example 79: (6S,9S,12S,15S,18R,19R)-9-(Aminomethyl)-19-(bicyclo[2.2.2]octan-2-ylmethyl)-12-cycloheptyl-6-((S)-1-hydroxyethyl)-16,18-dimethyl-15-propyl-1-oxa-4,7,10,13,16-pentaazacyclononadecane-2,5,8,11,14,17-hexaone

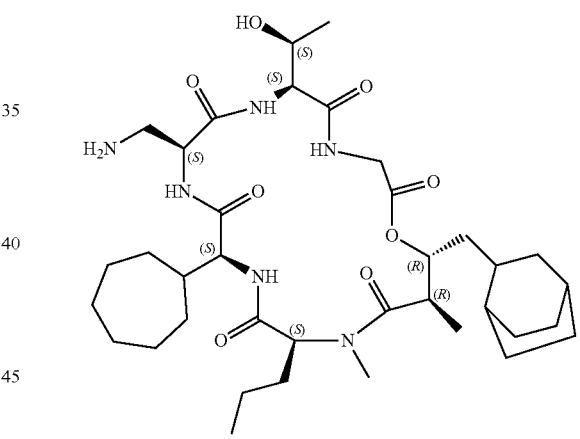

The title compound was prepared using Intermediate T9 following procedures analogous to those described for Example 59. LCMS (ESI): R$_T$ (min)=1.77, [M+H]⁺=719.4, method=C; ¹H NMR (400 MHz, DMSO-d$_6$) 8.74-7.01 (m, 7H), 5.12-4.79 (m, 1H), 4.51-4.20 (m, 2H), 4.19-4.01 (m, 2H), 3.99-3.79 (m, 3H), 3.58-3.41 (m, 2H), 3.39-3.24 (m, 2H), 2.23-3.03 (m, 3H), 3.01-2.66 (m, 2H), 2.32-2.19 (m, 1H), 2.05-1.75 (m, 2H), 1.74-1.14 (m, 27H), 1.13-0.98 (m, 6H), 0.97-0.83 (m, 3H).

Example 80: (6S,9S,12S,15S,18R,19R)-6-(((1r,3S)-3-Aminocyclobutoxy)methyl)-9-(aminomethyl)-12-cycloheptyl-19-hexyl-16,18-dimethyl-15-propyl-1-oxa-4,7,10,13,16-pentaazacyclononadecane-5,8,11,14,17-pentaone

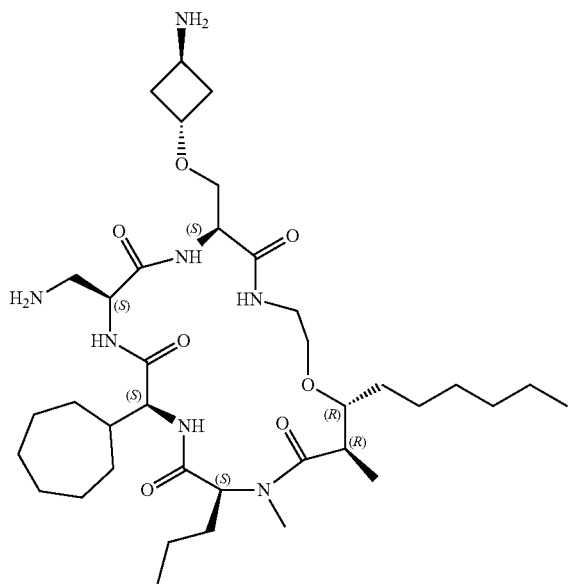

Step 1: 2-((tert-Butoxycarbonyl)amino)ethyl (2R,3R)-3-(2-((tert-butoxycarbonyl)amino) ethoxy)-2-methylnonanoate

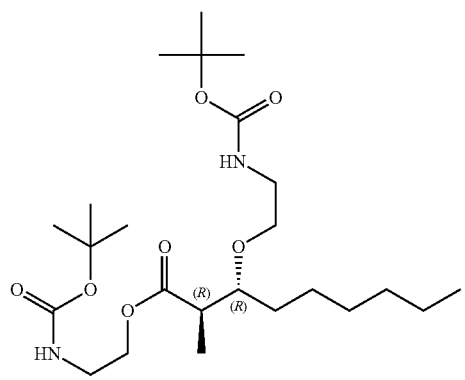

To a solution of (2R,3R)-3-hydroxy-2-methyl-nonanoic acid (3.0 g, 15.96 mmol) and tert-butyl 2,2-dioxooxathiazolidine-3-carboxylate (10.7 g, 47.87 mmol) in THF (100 mL) was added tetrabutylammonium fluoride (24 mL, 1 M in THF, Aldrich) at room temperature under nitrogen. Then sodium hydride (60% in oil, 2.55 g, 63.84 mmol) was added at 0° C. in small portions. The reaction mixture was stirred at room temperature for 4 h. The reaction was quenched with aqueous HCl solution (1 M in water). The resulting solution was extracted with ethyl acetate (3×200 mL) and the organic layers were combined. The combined organic layers were dried over anhydrous sodium sulfate, filtered and concentrated under reduced pressure. The residue was purified by flash chromatography on silica gel eluting with ethyl acetate/petroleum ether (1/9) to afford the title compound (5.4 g, 71% yield) as colorless oil. LCMS (ESI): [M+H]$^+$=475.3.

Step 2: (2R,3R)-3-(2-((tert-Butoxycarbonyl)amino)ethoxy)-2-methylnonanoic acid

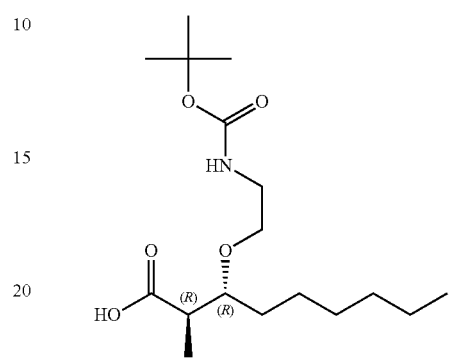

To a solution of 2-((tert-butoxycarbonyl)amino)ethyl (2R,3R)-3-(2-((tert-butoxycarbonyl)amino)ethoxy)-2-methylnonanoate (5.40 g, 11.37 mmol) in THF (60 mL) and water (20 mL) was added H$_2$O$_2$ (7 mL, 30% in water) and lithium hydroxide (2.73 g, 113.7 mmol). The reaction mixture was stirred at room temperature for 3 days. Then saturated sodium sulfite solution (10 ml) was added. After stirring for 10 min, aqueous HCl (1 mol/L) was added until pH6. The mixture was diluted with EtOAc (200 mL) and the phases were separated. The aqueous phase was extracted with ethyl acetate (2×). The combined organic layers were washed with brine, dried with sodium sulfate, filtered and concentrated under reduced pressure. The residue was purified by flash chromatography on silica gel eluting with ethyl acetate/petroleum ether (1/4) to afford the title compound (3.4 g, 90% yield) as colorless oil. LCMS (ESI): [M+H]$^+$=332.2.

Step 3. (2R,3R)-3-(2-((((9H-Fluoren-9-yl)methoxy)carbonyl)amino)ethoxy)-2-methylnonanoic acid

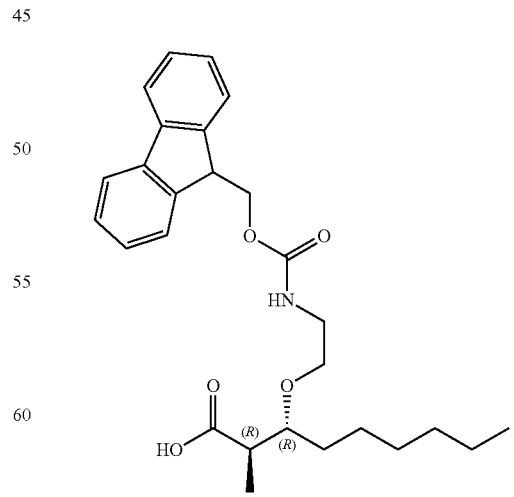

To a solution of HCl in dioxane (40 mL, 4 mol/L) at room temperature was added (2R,3R)-3-(2-((tert-butoxycarbonyl)amino)ethoxy)-2-methylnonanoic acid (2.92 g, 8.79 mmol).

The reaction mixture was stirred at room temperature for 3 h and concentrated under reduced pressure to afford (2R,3R)-3-(2-aminoethoxy)-2-methyl-nonanoic acid (2.0 g, crude) as a white solid. A solution of Na₂CO₃ (2.30 g, 21.78 mmol) in dioxane (20 mL) and water (10 mL) was added to the crude (2R,3R)-3-(2-aminoethoxy)-2-methyl-nonanoic acid (2.0 g). The resulting mixture was stirred at 0° C. for 5 min. Then 9-fluorenylmethylchloroformate (3.37 g, 13.05 mmol) was added at this temperature. The reaction mixture was stirred at room temperature for 2 h and diluted with water (20 mL) and acidified to pH 6 with 1 N HCl. The resulting solution was extracted with ethyl acetate (3×100 mL). The organic combined layers were dried over anhydrous sodium sulfate, filtered and concentrated under reduced pressure. The residue was purified by flash chromatography on silica gel eluting with ethyl acetate/petroleum ether (1/4) to afford (2R,3R)-3-[2-(9H-fluoren-9-yl-methoxycarbonylamino)ethoxy]-2-methyl-nonanoic acid (3.52 g, 89% yield for 2 steps) as a colorless oil. LCMS (ESI): [M+H]⁺=454.3.

Step 4: (6S,9S,12S,15S,18R,19R)-6-(((1r,3S)-3-Aminocyclobutoxy)methyl)-9-(aminomethyl)-12-cycloheptyl-19-hexyl-16,18-dimethyl-15-propyl-1-oxa-4,7,10,13,16-pentaazacyclononadecane-5,8,11,14,17-pentaone The title compound was prepared following procedures analogous to those described for Example 73. LCMS (ESI): R$_T$ (min)=1.56, [M+H]⁺=722.5, method=C; ¹H NMR (400 MHz, DMSO-d₆) 9.03-7.16 (m, 10H), 4.73-3.82 (m, 5H), 4.75-3.56 (m, 3H), 3.53-3.43 (m, 2H), 3.25-3.22 (m, 1H), 3.21-3.19 (m, 1H), 3.08-2.94 (m, 2H), 2.93-2.86 (m, 1H), 2.71-2.66 (m, 2H), 2.32-2.17 (m, 4H), 2.16-1.94 (m, 2H), 1.83-1.47 (m, 9H), 1.46-1.38 (m, 6H), 1.37-1.08 (m, 12H), 1.02-0.76 (m, 9H).

Example 81: (3R,6S,9S,12S,15S,18R,19R)-6-((3-Amino-2,2-difluoropropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone

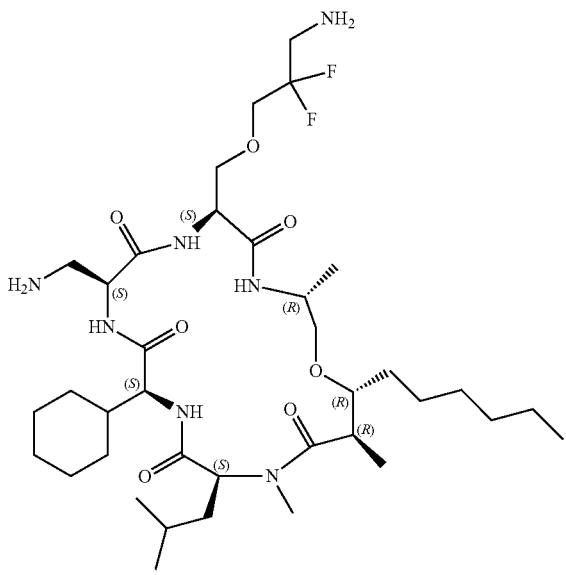

Step 1: N-Me-Leucine-cyclohexylglycine-(S)-2-amino-3-((tert-butoxycarbonyl)amino)propanoic acid)-(2-chlorotrityl resin)

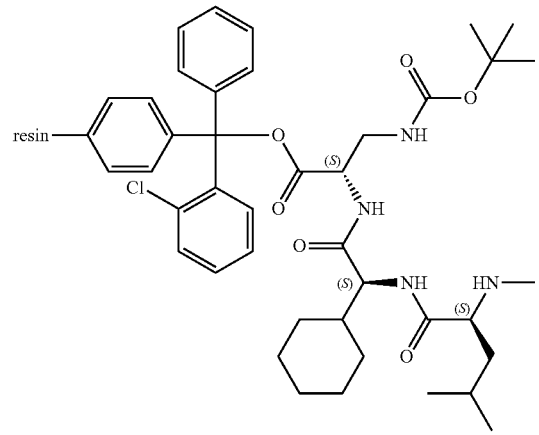

2-Chlorotrityl chloride resin (loading 0.956 mmol/g, 1.5 g) was swelled with the mixture of DMF:DCM (1:1, 20 mL) for 40 min. The resin was drained and then a solution of (S)-2-((((9H-fluoren-9-yl)methoxy)carbonyl)amino)-3-((tert-butoxycarbonyl)amino)propanoic acid (1.62 g, 3.82 mmol), DMF (10 mL) and DIPEA (491 mg, 3.82 mmol) was added. The resin was agitated with nitrogen bubbling for 4 h, drained and rinsed sequentially with 10 mL DCM/MeOH/DIPEA (10/10/1=V/V/V), 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (S)-2-((((9H-fluoren-9-yl)methoxy)carbonyl)amino)-2-cyclohexylacetic acid (1.81 g, 4.76 mmol), a premixed solution of HOBt/HATU (1:1) in DMF (0.4 mmol/mL, 10 mL) and DIPEA (1.22 g, 9.46 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL). The resin was treated with a solution of (2S)-2-{[(9H-fluoren-9-ylmethoxy)carbonyl](methyl)amino}-4-methylpentanoic acid (1.74 g, 4.75 mmol), HOBt/HATU (1:1) in DMF (0.4 mmol/mL, 10 mL) and DIPEA (1.23 g, 9.47 mmol). The resin was agitated with nitrogen bubbling for 2.5 h, drained, and rinsed sequentially with 10 mL DMF, 10 mL DCM, 10 mL DMF. The resin was treated with 25 mL of 20% piperidine in DMF, and agitated with nitrogen bubbling for 1.5 h. The resin was drained and rinsed sequentially with DMF (3×25 mL) and DCM (3×25 mL).

Step 2: (11S,14S,17S,18S,21R,24S,27R)-11-Amino-27-(((tert-butoxycarbonyl)amino) methyl)-24-cyclohexyl-7,7-difluoro-17-hexyl-21-isobutyl-2,2,14,18,20-pentamethyl-4,12,19,22,25-pentaoxo-3,9,16-trioxa-5,13,20,23,26-pentaazaoctacosan-28-oic acid

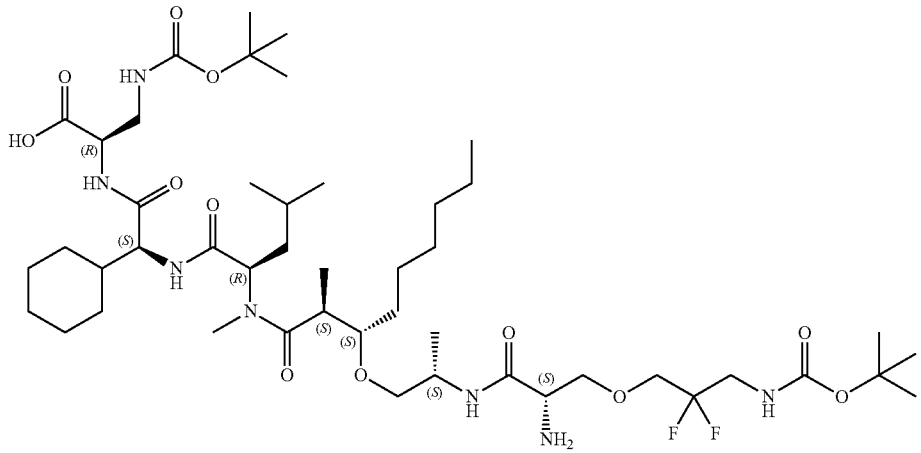

To the resin-bound peptide from Step 1 (2.05 g, 0.57 mmol/g loading) was added a premixed solution of Intermediate 4 (1.35 g, 2.89 mmol), HATU (1.09 g, 2.87 mmol), 4-hydroxybenzotriazole (389.4 mg, 2.88 mmol) and DIPEA (1 mL, 5.75 mmol) in DMF (20 mL). The resin was agitated with nitrogen bubbling for 2 h, drained, and rinsed successively with 20 mL DMF, 20 mL DCM and 20 mL DMF. The resin was treated with 20 mL of 20% piperidine in DMF, and agitated with nitrogen bubbling for 60 min. The resin was drained and rinsed with DMF (3×20 mL) and DCM (3×20 mL). The resin was treated with a solution (premixed at room temperature for 15 min) of N-(((9H-fluoren-9-yl)methoxy)carbonyl)-O-(3-((tert-butoxycarbonyl)amino)-2,2-difluoropropyl)-L-serine (Intermediate P2D) (905.1 mg, 1.74 mmol), HATU (1.33 g, 3.49 mmol), 4-hydroxybenzotriazole (470.2 mg, 3.48 mmol) and DIPEA (1.21 mL, 6.95 mmol) in DMF (20 mL). The resin was agitated with nitrogen bubbling for 2 h., and then drained and rinsed sequentially with DMF (2×20 mL) and DCM (3×20 mL). The resin was treated with 20 mL of 20% piperidine in DMF, and agitated with nitrogen bubbling for 60 min. The resin was drained and rinsed with DMF (3×20 mL) and DCM (3×20 mL). The resin was treated with a solution of 1,1,1,3,3,3-hexafluoropropan-2-ol/DCM (1/4, 20 mL) and agitated with nitrogen bubbling for 1 h. The reaction solution was collected via filtration. The treatment of resin with 20 mL of 1,1,1,3,3,3-hexafluoropropan-2-ol/DCM (1/4) was repeated, and the solution collected via filtration. The resin was rinsed with DCM (2×). The organic solutions were combined and concentrated under reduced pressure. The residue was purified by flash chromatography on C18 eluting with $CH_3CN/H_2O$ (40%) to afford the title compound (547.2 mg, 48% yield) as a yellow solid. LCMS (ESI): $[M+H]^+=978.6$.

Step 4: tert-Butyl (3-(((3R,6S,9S,12S,15S,18R,19R)-9-(((tert-butoxycarbonyl)amino) methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)-2,2-difluoropropyl)carbamate

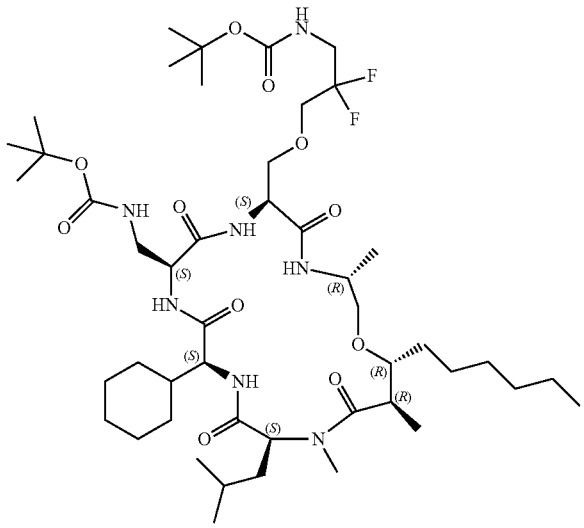

A solution of HATU (307.4 mg, 0.81 mmol) and 4-hydroxybenzotriazole (109.2 mg, 0.81 mmol) in DCM (50 mL) was added dropwise to a solution of (11S,14S,17S,18S,21R,24S,27R)-11-amino-27-(((tert-butoxycarbonyl)amino) methyl)-24-cyclohexyl-7,7-difluoro-17-hexyl-21-isobutyl-2,2,14,18,20-pentamethyl-4,12,19,22,25-pentaoxo-3,9,16-trioxa-5,13,20,23,26-pentaazaoctacosan-28-oic acid (527.5 mg, 0.54 mmol) and DIPEA (0.28 mL, 1.62 mmol) in DCM (50 mL) at 0° C. dropwise. The reaction mixture was stirred at 0° C. for 1 h. Water (100 mL) was added and the phases were separated. The organic phase was washed with water, brine, dried over anhydrous sodium sulfate, and concentrated under reduced pressure to afford the title compound (423 mg, crude) as a yellow solid, which was carried forward without purification. LCMS (ESI): [M+H]⁺=960.6.

Step 5: (3R,6S,9S,12S,15S,18R,19R)-6-((3-Amino-2,2-difluoropropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone The crude product from the previous step (410 mg, 0.43 mmol) was dissolved with TFA (4 mL) at 0° C. The reaction mixture was stirred for 30 min at this temperature, diluted with toluene (10 mL) and concentrated under reduced pressure. The residue was purified by prep-LCMS to afford the title compound (83.8 mg) as a TFA salt. LCMS (ESI): $R_T$ (min)=1.73, [M+H]⁺=760.5, method=C; ¹H NMR (400 MHz, DMSO-$d_6$) 8.91-6.98 (m, 8H), 5.33-4.73 (m, 2H), 4.68-4.63 (m, 1H), 4.51-4.38 (m, 1H), 4.22-4.09 (m, 1H), 4.05-3.77 (m, 4H), 3.74-3.68 (m, 1H), 3.63-3.19 (m, 6H), 3.18-3.03 (m, 2H), 3.02-2.92 (m, 1H), 2.82-2.65 (m, 2H), 2.54-2.48 (m, 6H), 2.18-1.99 (m, 1H), 1.98-1.46 (m, 7H), 1.45-1.15 (m, 10H), 1.14-0.75 (m, 16H).

Example 82: 1-(3-(((3R,6S,9S,12S,15S,18R,19R)-9-(Aminomethyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)propyl)guanidine

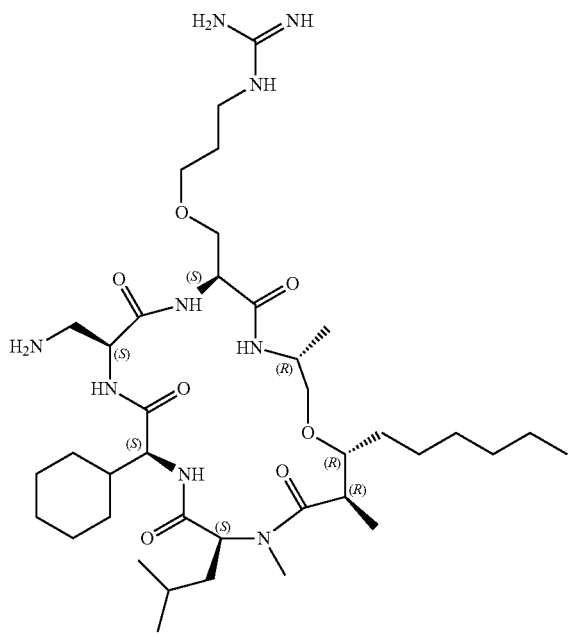

Step 1: tert-Butyl (3-(((3R,6S,9S,12S,15S,18R,19R)-9-((((benzyloxy)carbonyl)amino)methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)propyl)carbamate

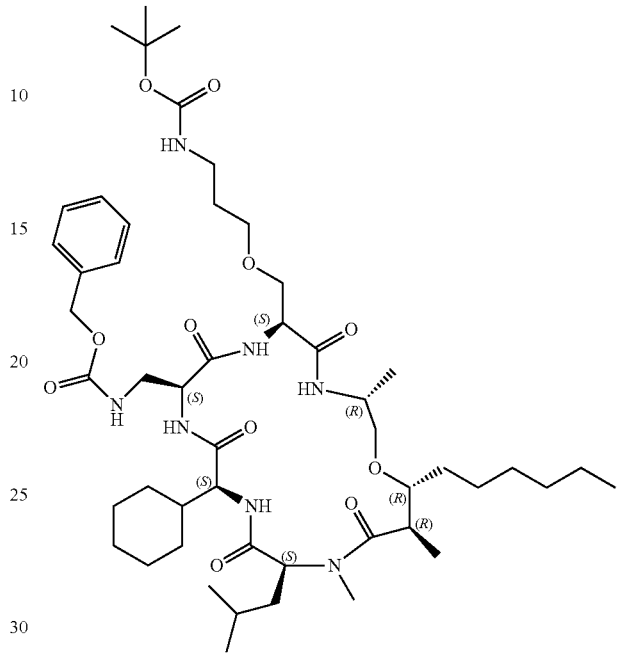

The title compound was prepared following procedures analogous to those described for Example 57, steps 1-3. LCMS (ESI): [M+H]⁺=958.6.

Step 2: tert-Butyl N—[N'-[3-[[(3R,6S,9S,12S,15S,18R,19R)-9-(benzyloxycarbonylaminomethyl)-12-cyclohexyl-19-hexyl-15-isobutyl-3,16,18-trimethyl-5,8,11,14,17-pentaoxo-1-oxa-4,7,10,13,16-pentazacyclononadec-6-yl]methoxy]propyl]-N-tert-butoxycarbonyl-carbamimidoyl]carbamate

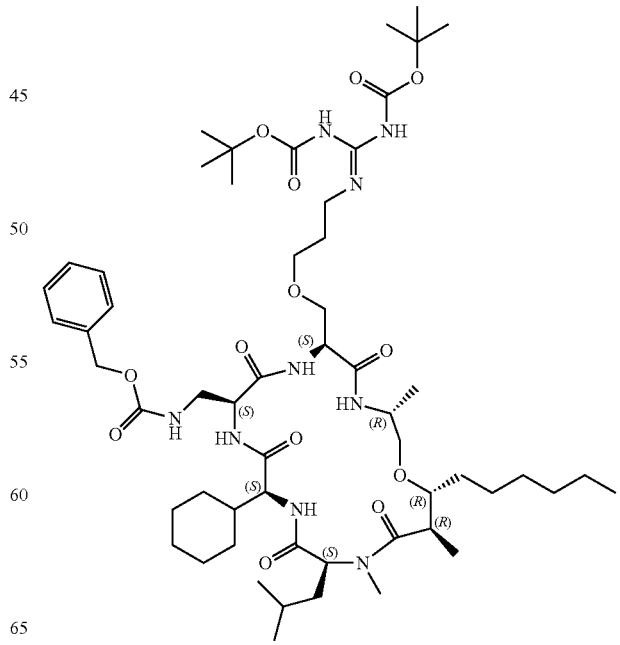

To a solution of tert-butyl (3-(((3R,6S,9S,12S,15S,18R, 19R)-9-((((benzyloxy)carbonyl)amino)methyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl)methoxy)propyl)carbamate (200 mg, 0.21 mmol) in DCM (10 mL) was added TFA (10 mL) at 0° C. The resulting mixture was stirred for 2 h at room temperature and concentrated under vacuum. The resulting residue was dissolved with DIPEA (144.2 mg, 1.12 mmol) in ethanol (5 mL) and treated with tert-butyl (((tert-butoxycarbonyl) amino)(1H-pyrazol-1-yl)methylene)carbamate (105.6 mg, 0.3400 mmol). The reaction mixture was stirred at room temperature for 4 hours and evaporated under vacuum. The residue was partitioned between DCM (100 mL) and water (50 mL). The organic layer was dried over anhydrous sodium sulfate, filtered and concentrated under vacuum to afford the title compound (180.7 mg) as a yellow solid. LCMS (ESI): [M+H]⁺=1100.7.

Step 3: 1-(3-(((3R,6S,9S,12S,15S,18R,19R)-9-(Aminomethyl)-12-cyclohexyl-19-hexyl-15-isobutyl-3,16,18-trimethyl-5,8,11,14,17-pentaoxo-1-oxa-4,7,10,13,16-pentaazacyclononadecan-6-yl) methoxy)propyl)guanidine To a solution of tert-butyl N—[N'-[3-[[(3R,6S,9S,12S, 15S,18R,19R)-9-(benzyloxycarbonylaminomethyl)-12-cyclohexyl-19-hexyl-15-isobutyl-3,16,18-trimethyl-5,8,11,14, 17-pentaoxo-1-oxa-4,7,10,13,16-pentazacyclononadec-6-yl]methoxy]propyl]-N-tert-butoxycarbonyl-carbamimidoyl] carbamate (180.7 mg) in ethyl acetate (20 mL) containing 0.5% TFA was added palladium (200 mg, 10% loading on carbon). The mixture was stirred for 3 h under a hydrogen balloon at room temperature and diluted with ethyl acetate (50 mL). The solid was removed via filtration and the filtrate was evaporated under reduced pressure. The residue was purified by flash chromatography on C18 column to afford tert-butyl N—[N'-[3-[[(3R,6S,9S,12S,15S,18R,19R)-9-(aminomethyl)-12-cyclohexyl-19-hexyl-15-isobutyl-3,16, 18-trimethyl-5,8,11,14,17-pentaoxo-1-oxa-4,7,10,13,16-pentazacyclononadec-6-yl]methoxy]propyl]-N-tert-butoxycarbonyl-carbamimidoyl]carbamate (102.3 mg, 64% yield) as a yellow solid.

This material (91.1 mg, 0.09 mmol) was added to TFA (3 mL) at 0° C. The mixture was stirred at 0° C. for 30 min and diluted with toluene (10 mL). The mixture was concentrated under vacuum. The residue was purified by prep-HPLC to afford the title compound (13.5 mg, 16% yield) as a white solid. LCMS (ESI): R_T (min)=1.75, [M+H]⁺=766.5, method=H; ¹H NMR (400 MHz, DMSO-d₆) δ 8.89-7.78 (m, 5H), 7.67-6.81 (m, 6H), 4.68-4.06 (m, 3H), 3.97-3.41 (m, 7H), 3.28-3.06 (m, 9H), 2.82-2.75 (m, 2H), 2.12-1.98 (m, 1H), 1.85-1.47 (m, 10H), 1.40-1.32 (m, 11H), 1.18-0.85 (m, 18H).

Example 83: (6S,9S,12S,15S,18R,19R)-9-(Aminomethyl)-19-(((1R,3s,5S)-bicyclo[3.2.1]octan-3-yl) methyl)-12-cycloheptyl-6-((S)-1-hydroxyethyl)-16, 18-dimethyl-15-propyl-1-oxa-4,7,10,13,16-pentaazacyclononadecane-2,5,8,11,14,17-hexaone

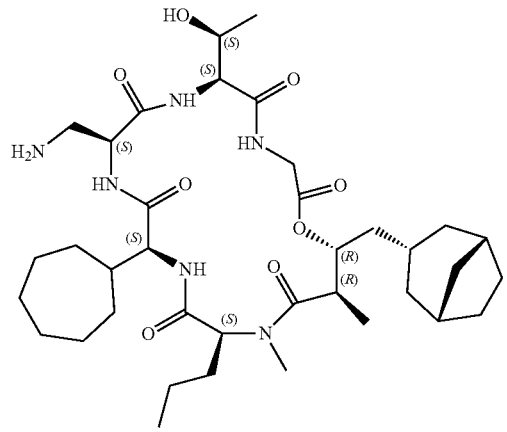

Step 1: 2-((1R,3s,5S)-Bicyclo[3.2.1]octan-3-yl) ethan-1-ol

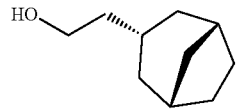 [SMILES: OCC[C@H]1C[C@H]2CC[C@@H](C1)C2]

To a suspension of NaH (1.93 g, 48.3 mmol, 60% in mineral oil) in 1,2-dimethoxyethane (30 ml) was added triethyl phosphonoacetate (11.7 g, 52.3 mmol) at 0° C. The resulting mixture was stirred for 15 min at 0° C. Then a solution of bicyclo[3.2.1]octan-3-one (4.06 g, 32.7 mmol) in 1,2-dimethoxyethane (20 mL) was added. The resulting solution was stirred for 15 min at 0° C. and stirred for 3 days at room temperature, poured into an ice cold solution of HCl (1 mol/L in water, 100 ml). The resulting solution was extracted with ethyl acetate (100 ml×4) and the organic layers were combined. The organic layer was dried over anhydrous sodium sulfate and concentrated under vacuum. The residue was purified by flash chromatography on silica gel eluting with EA/PE (1/4) to afford ethyl 2-(3-bicyclo [3.2.1]octanylidene)acetate (2.51 g). This material was dissolved in ethyl acetate (100 mL). A drop of TFA was added, then the flask was evacuated and flushed 3 times with nitrogen. Palladium (1.3 g, 10% loading on carbon) was added. The system was evacuated and charged with hydrogen. The mixture was stirred under a hydrogen balloon overnight at room temperature. The solid was filtered off and the filtrate was concentrated under vacuum to afford crude ethyl 2-(3-bicyclo[3.2.1]octanyl)acetate (6.53 g). This material was dissolved in THF (120 mL) and treated with lithium aluminum hydride (2.31 g, 60.7 mmol) in small portions at 0° C. under nitrogen. The reaction mixture was allowed to warm to room temperature and stirred at this temperature for 2 hours, cooled over ice bath, and quenched by careful addition of 2.3 mL water, 2.3 mL aqueous sodium hydroxide solution (25%) and 2.3 mL water sequentially. The precipitate was removed via filtration and the filtrate was evaporated under vacuum. The residue was purified by flash chromatography on silica gel eluting with ethyl acetate/petroleum ether (11-15% ethyl acetate) to afford the title compound (2.66 g, 84% yield) as a colorless oil. $^1$H NMR (400 MHz, DMSO-$d_6$) δ 4.24 (t, J=5.2 Hz, 1H), 3.39-3.34 (m, 2H), 2.13-2.12 (m, 2H), 1.75-1.56 (m, 3H), 1.48-1.32 (m, 5H), 1.29-1.24 (m, 3H), 1.01-0.94 (m, 2H). 1H NMR suggested a ratio of endo and exo isomers of 6:1.

Step 2: 2-((1R,3s,5S)-Bicyclo[3.2.1]octan-3-yl)acetaldehyde

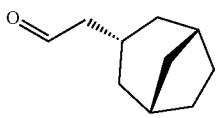 [SMILES: O=CC[C@H]1C[C@H]2CC[C@@H](C1)C2]

To a solution of 2-(3-bicyclo[3.2.1]octanyl)ethanol (4.21 g, 27.29 mmol) in DCM (150 mL) was added pyridinium chlorochromate (8.86 g, 41.21 mmol). The reaction mixture was stirred at room temperature for 3 h. The solid was removed via filtration and the filtrate was evaporated under reduced pressure. The crude product was used directly in the next step without purification. TLC R$_f$=0.5, PE/EA=4/1.

Step 3: (2R,3R)-4-((1R,3s,5S)-bicyclo[3.2.1]octan-3-yl)-3-hydroxy-2-methylbutanoic acid

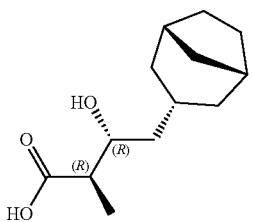

Trifluoromethanesulfonic acid (3.66 g, 24.4 mmol) was added dropwise to triethyl borane (24.9 mL, 24.9 mmol, 1 M in THF) in DCM (30 mL) at −10° C., the reaction mixture was stirred at room temperature for 30 min. Then a solution of 1-((3aR,6S,7aS)-8,8-dimethyl-2,2-dioxidotetrahydro-3H-3a,6-methanobenzo[c]isothiazol-1(4H)-yl)propan-1-one (5.95 g, 21.92 mmol) and DIPEA (3.63 g, 28.14 mmol) in DCM (30 mL) was added at 0° C. The reaction mixture was stirred at 0° C. for 30 min. Then the reaction mixture was stirred at −78° C. Titanium tetrachloride (28.4 mL, 1 M in DCM) was added. Then a solution of 2-(3-bicyclo[3.2.1] octanyl)acetaldehyde (3.96 g, 26.01 mmol) in DCM (40 mL) was added. The reaction mixture was stirred at −78° C. for 2 h. The reaction mixture was poured into saturated aqueous ammonium chloride (100 mL) and extracted with DCM (150 ml×3). The combined organic phases were dried over Na$_2$SO$_4$ and evaporated under reduced pressure. The residue was purified by flash chromatography on silica gel eluting with petroleum ether/ethyl acetate (5/1) to afford (2R,3R)-4-((1R,5S)-bicyclo[3.2.1]octan-3-yl)-1-((3aR,6S,7aS)-8,8-dimethyl-2,2-dioxidotetrahydro-3H-3a,6-methanobenzo[c]isothiazol-1(4H)-yl)-3-hydroxy-2-methylbutan-1-one (7.45 g, 17.6 mmol, 80.2% yield) as a yellow oil.

A solution of LiOH (1.67 g, 69.52 mmol) in H$_2$O (40 mL) was added to a solution of (2R,3R)-4-((1R,5S)-bicyclo [3.2.1]octan-3-yl)-1-((3aR,6S,7aS)-8,8-dimethyl-2,2-dioxidotetrahydro-3H-3a,6-methanobenzo[c]isothiazol-1(4H)-yl)-3-hydroxy-2-methylbutan-1-one (7.37 g, 17.39 mmol) in acetonitrile (120 mL) at 0° C. The reaction mixture was stirred at room temperature for 16 h and then acidified by the addition of HCl (1 mol/L in water) to pH6 and extracted with ethyl acetate (100 mL×3). The combined organic phases were dried over Na$_2$SO$_4$ and evaporated under reduced pressure. The residue was purified by flash chromatography on silica gel eluting with petroleum ether/ethyl acetate (5/1) to afford the title compound (2.96 g, 75% yield, endo/exo=6/1) as a light red solid. The mixture (2.96 g) was dissolved in petroleum ether/ethyl acetate (5/1, 100 ml) at 60° C., and cooled to 0° C. The resulting crystalline solid was collected by filtration to afford the title compound as pure endo isomer (1.05 g). LCMS (ESI): [M−H]$^-$=225.2.

Step 4: (6S,9S,12S,15S,18R,19R)-9-(Aminomethyl)-19-(((1R,3s,5S)-bicyclo[3.2.1]octan-3-yl) methyl)-12-cycloheptyl-6-((S)-1-hydroxyethyl)-16, 18-dimethyl-15-propyl-1-oxa-4,7,10,13,16-pentaazacyclononadecane-2,5,8,11,14,17-hexaone The title compound was prepared using (2R,3R)-4-((1R, 3s,5S)-bicyclo[3.2.1]octan-3-yl)-3-hydroxy-2-methylbutanoic acid and following procedures analogous to those described for Example 1. LCMS (ESI): R$_T$ (min)=1.77, [M+H]$^+$=719.4, method=L; $^1$H NMR (400 MHz, DMSO-$d_6$) δ 8.72-7.37 (m, 6H), 4.95-4.72 (m, 1H), 4.46-4.03 (m, 4H), 3.95-3.45 (m, 7H), 3.28-2.91 (m, 4H), 2.66-2.56 (m, 2H), 2.21-2.02 (m, 3H), 1.96-1.74 (m, 1H), 1.69-1.23 (m, 19H), 1.22-1.08 (m, 5H), 1.06-0.93 (m, 6H), 0.87-0.73 (m, 4H).

Example 84: (6S,9S,12S,15S,18R,19R)-9-(Aminomethyl)-12-cycloheptyl-6-((S)-1-hydroxyethyl)-16,18-dimethyl-15-propyl-19-(spiro[3.3]heptan-2-ylmethyl)-1-oxa-4,7,10,13,16-pentaazacyclononadecane-2,5,8,11,14,17-hexaone

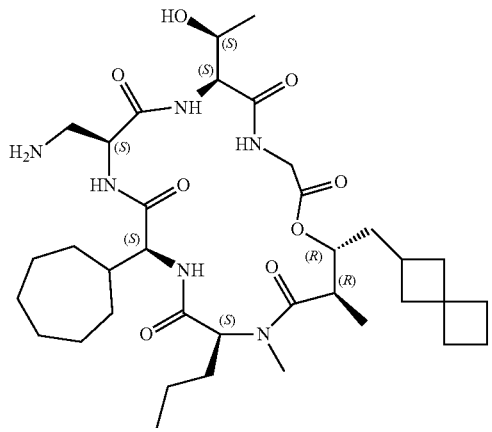

Step 1: 2-(Spiro[3.3]heptan-2-yl)ethan-1-ol

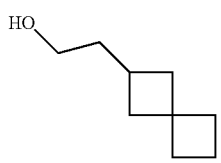

To a solution of triethyl phosphonoacetate (11.47 g, 51.18 mmol) in THF (150 mL) was added NaH (2.23 g, 55.84 mmol, 60% in mineral oil) at 0° C. The reaction mixture was stirred at room temperature for 1 h and cooled to 0° C. Spiro[3.3]heptan-2-one (5.13 g, 46.53 mmol) was added portionwise at 0° C. The reaction mixture was stirred at room temperature for 2 h and then quenched by the addition of HCl (100 mL, 1 mol/L in water). The mixture was extracted with ethyl acetate (100 mL×3) and the combined organic phases were dried over sodium sulfate and evaporated under reduced pressure. The residue was purified by flash chromatography on silica gel eluting with petroleum ether/ethyl acetate (5/1) to afford ethyl 2-spiro[3.3]heptan-2-ylideneacetate (8.02 g, 95% yield) as a yellow oil.

To a solution of ethyl 2-spiro[3.3]heptan-2-ylideneacetate (8.02 g, 44.47 mmol) in ethyl acetate (150 mL) was added palladium (0.8 g, 10% loading on carbon) at 0° C. The mixture was evacuated and recharged with hydrogen and stirred at room temperature under a hydrogen balloon for 5 h. The mixture was filtered and the filtrate was evaporated under reduced pressure. The resulting residue was dissolved in THF (150 mL), then LiAlH$_4$ (2.48 g, 65.19 mmol) was added at 0° C. The reaction mixture was stirred at room temperature for 3 h and quenched by careful addition of water (50 mL). The solid was removed via filtration and the filtrate was extracted with DCM (100 mL×3). The combined organic phases were dried over sodium sulfate and concentrated under reduced pressure. The residue was purified by flash chromatography on silica gel eluting with petroleum ether/ethyl acetate (2/1) to afford the title compound (5.52 g, 90% yield) as a colorless oil. TLC R$_f$=0.4, PE/EA=2/1.

Step 2: 2-(Spiro[3.3]heptan-2-yl)acetaldehyde

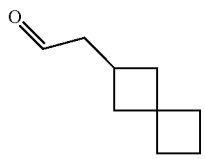

To a solution of 2-spiro[3.3]heptan-2-ylethanol (5.52 g, 39.37 mmol) in DCM (300 mL) was added pyridinium chlorochromate (12.63 g, 58.74 mmol). The reaction mixture was stirred at room temperature for 3 h. The solid was removed via filtration. The filtrate was evaporated under reduced pressure and the crude product was used directly for the next step. TLC R$_f$=0.5, PE/EA=4/1.

Step 3: (2R,3R)-3-Hydroxy-2-methyl-4-(spiro[3.3]heptan-2-yl butanoic acid

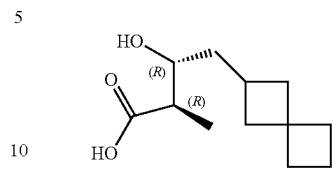

The title compound was prepared using 2-(spiro[3.3]heptan-2-yl)acetaldehyde instead of heptaldehyde and following procedures analogous to those described for Intermediate 1. LCMS (ESI): [M−H]$^-$=211.1.

Step 4: (6S,9S,12S,15S,18R,19R)-9-(Aminomethyl)-12-cycloheptyl-6-((S)-1-hydroxyethyl)-16,18-dimethyl-15-propyl-19-(spiro[3.3]heptan-2-ylmethyl)-1-oxa-4,7,10,13,16-pentaazacyclononadecane-2,5,8,11,14,17-hexaone The title compound was prepared using (2R,3R)-3-hydroxy-2-methyl-4-(spiro[3.3]heptan-2-yl)butanoic acid and following procedures analogous to those described for Example 1. LCMS (ESI): R$_T$ (min)=1.76, [M+H]$^+$=705.4, method=L; $^1$H NMR (400 MHz, DMSO-d$_6$) δ 8.79-7.13 (m, 7H), 4.95-4.53 (m, 3H), 4.42-4.08 (m, 3H), 3.98-3.45 (m, 3H), 3.30-2.97 (m, 4H), 2.68 (s, 2H), 2.40-1.88 (m, 6H), 1.87-1.36 (m, 20H), 1.35-1.12 (m, 5H), 1.08-0.97 (m, 5H), 0.93-0.77 (m, 3H).

Example 85: (6S,9S,12S,15S,18R,19R)-9-(Aminomethyl)-19-(((2R)-bicyclo[2.2.1]heptan-2-yl)methyl)-12-cycloheptyl-6-((S)-1-hydroxyethyl)-16,18-dimethyl-15-propyl-1-oxa-4,7,10,13,16-pentaazacyclononadecane-2,5,8,11,14,17-hexaone (endo)

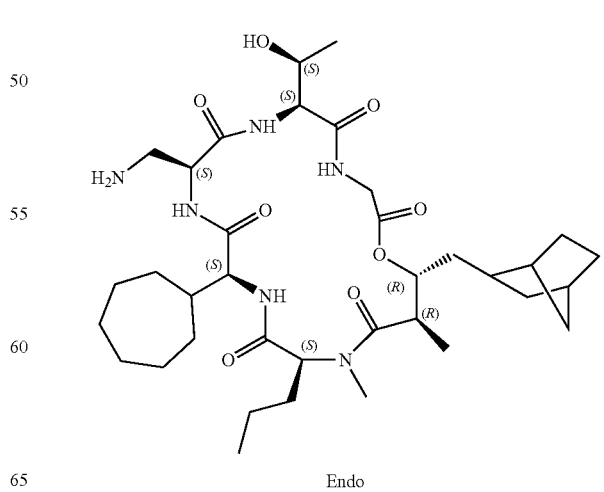

Endo

Step 1: (endo) 2-Norbornan-2-ylethanol

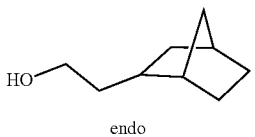

endo

To a solution of triethyl phosphonoacetate (23.81 g, 106.2 mmol) in THF (220 mL) was added NaH (4.37 g, 96.5 mmol, 60% in mineral oil) portionwise at 0° C. The resulting solution was stirred at room temperature for 1 h. Then a solution of norcamphor (10.63 g, 96.5 mmol) in THF (90 mL) was added dropwise at 0° C. The reaction mixture was stirred at room temperature for 1.5 h and quenched by the addition of HCl (1 mol/L in water, 100 ml). The resulting solution was extracted with ethyl acetate (200 mL×3). The combined organic layers were dried over anhydrous sodium sulfate and concentrated under vacuum. The residue was purified by flash chromatography on silica gel eluting with ethyl acetate/petroleum ether (1/10) to afford ethyl (2E)-2-norbornan-2-ylideneacetate (12.32 g, 70% yield) as a colorless oil.

To a solution of ethyl (2E)-2-norbornan-2-ylideneacetate (12.32 g, 68.35 mmol) in ethyl acetate (400 mL) was added palladium (1.54 g, 10% loading on carbon) at 25° C. The resulting solution was stirred under a hydrogen balloon for 16 h at 25° C. The solid was removed via filtration and the filtrate was evaporated under reduced pressure. The residue was purified by flash chromatography on silica gel eluting with ethyl acetate/petroleum ether (1:10) to afford ethyl 2-norbornan-2-ylacetate (11.52 g, 92% yield) as a colorless oil.

To a solution of ethyl 2-norbornan-2-ylacetate (12.55 g, 68.86 mmol) in THF (150 mL) was added LiAlH$_4$ (2.61 g, 68.79 mmol) portionwise at 0° C. The reaction mixture was stirred for 16 h at 25° C. and quenched by the sequential addition of water (2.6 mL), NaOH (10% in water) (2.6 mL) and water (2.6 mL). The precipitate was removed via filtration and the filtrate was evaporated under reduced pressure. The residue was purified by flash chromatography on silica gel eluting with ethyl acetate/petroleum ether (1:1) to afford 2-norbornan-2-ylethanol (endo) (7.3 g, 75% yield) as a colorless oil. TLC R$_f$=0.4, PE/EA=2/1.

Step 2: 2-Norbornan-2-ylacetaldehyde (endo)

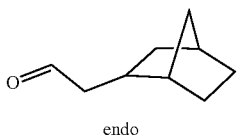

endo

To a solution of 2-norbornan-2-ylethanol (endo) (8.42 g, 60.06 mmol) in DCM (200 mL) was added pyridinium chlorochromate (19.33 g, 90.08 mmol) at 25° C. The reaction mixture was stirred for 2 h at 25° C. The solid was removed via filtration. The filtrate was concentrated under reduced pressure. The residue was purified by flash chromatography on silica gel eluting with DCM to afford 2-norbornan-2-ylacetaldehyde (endo) (5.64 g, 68% yield) as a colorless oil. TLC R$_f$=0.5, PE/EA=4/1.

Step 3: (2R,3R)-4-((1S,2S,4R)-bicyclo[2.2.1]heptan-2-yl)-3-hydroxy-2-methylbutanoic acid (endo)

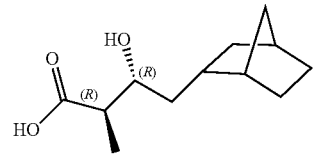

The title compound was prepared using 2-norbornan-2-ylacetaldehyde instead of heptaldehyde and following procedures analogous to those described for Intermediate 1. LCMS (ESI): [M−H]$^-$=211.1.

Step 4: (6S,9S,12S,15S,18R,19R)-9-(Aminomethyl)-19-(((2R)-bicyclo[2.2.1]heptan-2-yl)methyl)-12-cycloheptyl-6-((S)-1-hydroxyethyl)-16,18-dimethyl-15-propyl-1-oxa-4,7,10,13,16-pentaazacyclononadecane-2,5,8,11,14,17-hexaone (endo)

The title compound was prepared following procedures analogous to those described for Example 1. LCMS (ESI): R$_T$ (min)=1.71, [M+H]$^+$=705.4, method=L; $^1$H NMR (400 MHz, DMSO-d$_6$) δ 8.76-7.47 (m, 6H), 5.11-4.82 (m, 1H), 4.55-4.02 (m, 4H), 3.99-3.36 (m, 8H), 3.30-2.98 (m, 4H), 2.81-2.69 (m, 2H), 2.35-2.11 (m, 2H), 2.03-1.91 (m, 1H), 1.88-1.63 (m, 8H), 1.58-1.16 (m, 13H), 1.11-0.98 (m, 8H), 0.96-0.83 (m, 3H).

Example 86: (3R,6S,9S,12S,15S,17aR,23aR)-9-(Aminomethyl)-12-cyclohexyl-6-((S)-1-hydroxyethyl)-3,16-dimethyl-15-propyloctadecahydrocyclooctα[r][1]oxa[4,7,10,13,16]pentaazacyclononadecine-5,8,11,14,17(2H)-pentaone

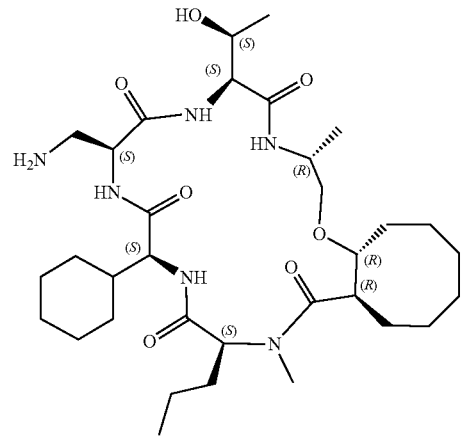

Step 1: Benzyl (((3R,6S,9S,12S,15S,17aR,23aR,Z)-6-((S)-1-(benzyloxy)ethyl)-12-cyclohexyl-3,16-dimethyl-5,8,11,14,17-pentaoxo-15-propyl-2,3,4,5,6,7,8,9,10,11,12,13,14,15,16,17,17a,18,19,22,23,23a-docosahydrocyclooocta[r][1l]oxa[4,7,10,13,16]pentaazacyclononadecin-9-yl)methyl)carbamate

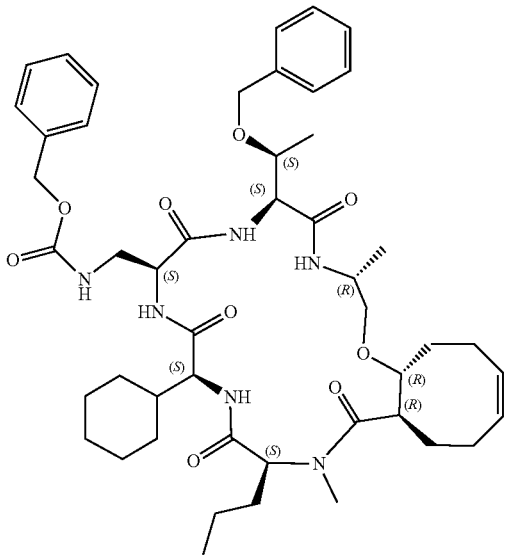

To a solution of benzyl (((3R,6S,9S,12S,15S,18R,19R)-6-((S)-1-(benzyloxy)ethyl)-18,19-di(but-3-en-1-yl)-12-cyclohexyl-3,16-dimethyl-5,8,11,14,17-pentaoxo-15-propyl-1-oxa-4,7,10,13,16-pentaazacyclononadecan-9-yl)methyl)carbamate (described in Example 77, step 4) (280.3 mg, 0.31 mmol) in 1,2-dichloroethane (300 mL) was added a solution of dichloro-[(2-isopropoxyphenyl)methylene]-(tricyclohexyl-λˆ{5}-phosphanyl)ruthenium (203.5 mg, 0.34 mmol) (CAS:203714-71-0) in 1,2-dichloroethane (2 mL) at 0° C. dropwise under nitrogen. The reaction mixture was stirred for 5 h at 60° C. and then evaporated under reduced pressure. The residue was dissolved with 1,2-dichloroethane (4 mL), and the resulting solution was added dropwise to hexane (70 mL) with stirring. The solids were collected and washed with hexane (10 ml×3) to afford the title compound (220 mg, 81% yield) as a brown solid, which was carried forward without purification. LCMS (ESI): [M+H]$^+$=873.5.

Step 2: (3R,6S,9S,12S,15S,17aR,23aR)-9-(Aminomethyl)-12-cyclohexyl-6-((S)-1-hydroxyethyl)-3,16-dimethyl-15-propyloctadecahydrocyclooocta[r][1]oxa[4,7,10,13,16]pentaazacyclononadecine-5,8,11,14,17(2H)-pentaone A solution of benzyl (((3R,6S,9S,12S,15S,17aR,23aR,Z)-6-((S)-1-(benzyloxy)ethyl)-12-cyclohexyl-3,16-dimethyl-5,8,11,14,17-pentaoxo-15-propyl-2,3,4,5,6,7,8,9,10,11,12,13,14,15,16,17,17a,18,19,22,23,23a-docosahydrocyclooocta[r][1]oxa[4,7,10,13,16]pentaazacyclononadecin-9-yl)methyl)carbamate (200.2 mg, 0.23 mmol) and palladium (150 mg, 10% loading on carbon) in ethyl acetate containing 0.5% TFA (10 mL) was stirred under a hydrogen balloon for 2 h at room temperature. The solid was removed via filtration and the filtrate was evaporated under reduced pressure. The crude product was purified by Prep-LCMS to afford the title compound (4.6 mg, 3% yield) as a white solid. LCMS (ESI): R$_T$ (min)=2.55, [M+H]$^+$=651.5, method=L; $^1$H NMR (400 MHz, DMSO-d$_6$) δ 8.51-7.72 (m, 5H), 7.39-6.95 (m, 2H), 4.84-4.07 (m, 4H), 4.02-3.40 (m, 5H), 3.30-3.12 (m, 3H), 3.03-2.61 (m, 3H), 2.23-2.07 (m, 1H), 1.85-1.74 (m, 5H), 1.72-1.64 (m, 7H), 1.63-1.36 (m, 8H), 1.31-1.10 (m, 7H), 1.07-0.92 (m, 9H).

Example 148: (3R,6S,9S,12S,15S,18R,19R)-9-(Aminomethyl)-19-hexyl-6-((S)-1-hydroxyethyl)-15-isobutyl-3,16,18-trimethyl-12-(1-phenylpiperidin-4-yl)-1-oxa-4,7,10,13,16-pentaazacyclononadecane-5,8,11,14,17-pentaone

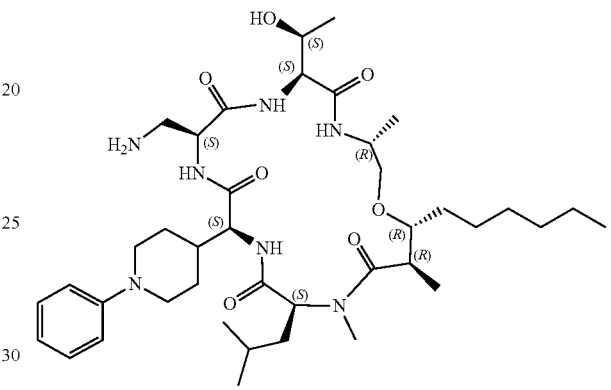

Step 1: (2S)-2-(Benzyloxycarbonylamino)-2-(1-tert-butoxycarbonyl-4-piperidyl)acetic acid

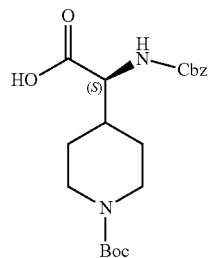

To a solution of (2S)-2-amino-2-(1-tert-butoxycarbonyl-4-piperidyl)acetic acid (1.63 g, 6.31 mmol) and Na$_2$CO$_3$ (1.31 g, 12.2 mmol) in THF (30 mL) and water (13 mL) was added dropwise benzyl chloroformate (1.62 g, 9.51 mmol) at 0° C. The reaction mixture was stirred at room temperature for 2 h.

LC-MS showed the starting material was consumed. Aqueous hydrochloric acid solution (1 mol/L) was carefully added until the solution reached pH 6. The resulting solution was concentrated under reduced pressure to remove THF, and extracted with ethyl acetate (3×). The combined organic layers were dried over anhydrous sodium sulfate and evaporated under vacuum. The residue was purified by flash chromatography on silica gel eluting with petroleum ether: ethyl acetate (gradient 2:1 to 1:1) to afford the title compound (1.90 g, 76.7% yield) as an off-white solid. LCMS (ESI): [M+H]$^+$=393.1.

Step 2: tert-Butyl 4-[(1S)-1-(benzyloxycarbonylamino)-2-methoxy-2-oxo-ethyl]piperidine-1-carboxylate

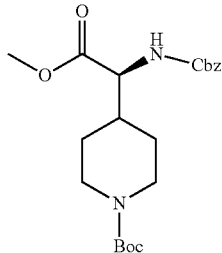 [SMILES: COC(=O)[C@@H](NC(=O)OCc1ccccc1)C1CCN(C(=O)OC(C)(C)C)CC1]

To a solution of (2S)-2-(benzyloxycarbonylamino)-2-(1-tert-butoxycarbonyl-4-piperidyl)acetic acid (1.7 g, 4.33 mmol) in DCM (30 mL) and MeOH (15 mL) was added dropwise trimethylsilyldiazomethane (4.8 mL, 9.6 mmol, 2M in hexane) at 0° C. under $N_2$. The resulting solution was stirred at room temperature for 2 h and evaporated under reduced pressure. The residue was purified by flash chromatography on silica gel eluting with petroleum ether/ethyl acetate (3/1) to afford the title compound (1.45 g, 82.5% yield) as a colorless oil. LCMS (ESI): $[M+H]^+$=407.2.

Step 3: Methyl (2S)-2-(benzyloxycarbonylamino)-2-(4-piperidyl)acetate

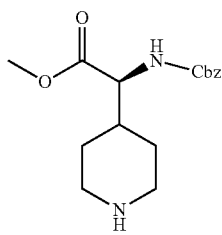 [SMILES: COC(=O)[C@@H](NC(=O)OCc1ccccc1)C1CCNCC1]

A mixture of tert-butyl 4-[(1S)-1-(benzyloxycarbonylamino)-2-methoxy-2-oxo-ethyl]piperidine-1-carboxylate (1.452 g, 3.57 mmol) and HCl/dioxane solution (4.0 M, 30 mL, 120 mmol) was stirred for 2 h at room temperature. The reaction mixture was evaporated under vacuum to afford methyl (2S)-2-(benzyloxycarbonylamino)-2-(4-piperidyl)acetate as its HCl salt (1.02 g) as a white solid. LCMS (ESI): $[M+H]^+$=307.1. The crude product was used in the next step without further purification.

Step 4: Methyl (2S)-2-(benzyloxycarbonylamino)-2-(1-phenyl-4-piperidyl)acetate

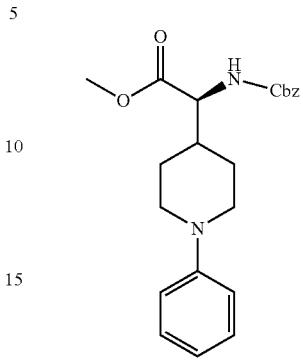

To a mixture of crude methyl (2S)-2-(benzyloxycarbonylamino)-2-(4-piperidyl)acetate HCl salt (811 mg) in 1,2-dichloroethane (50 mL) was added triethylamine (1.34 g, 13.2 mmol), pyridine (2.09 mg, 26.4 mmol), phenylboronic acid (647 mg, 5.30 mmol) and $Cu(OAc)_2$ (960 mg, 5.22 mmol). The resulting solution was stirred at room temperature for 24 h and evaporated under vacuum. Ethyl acetate (200 mL) was added to the residue. The resulting mixture was washed with brine (3×50 mL). The organic layer was dried over anhydrous sodium sulfate and evaporated under vacuum. The residue was purified by flash chromatography on silica gel eluting with petroleum ether:ethyl acetate (4:1) to afford the title compound (542 mg, 53.5% yield) as a colorless oil. LCMS (ESI): $[M+H]^+$=383.2.

Step 5: Methyl (2S)-2-amino-2-(1-phenyl-4-piperidyl)acetate

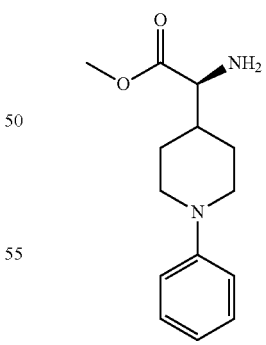

A mixture of methyl (2S)-2-(benzyloxycarbonylamino)-2-(1-phenyl-4-piperidyl)acetate (271 mg, 0.770 mmoL) and Pd (1.5 g, 10% loading on carbon) in ethyl acetate (54 mL) was stirred at 25° C. for 30 min under $H_2$(3 atm). The solid was removed via filtration and the filtrate was evaporated under vacuum to afford the title compound (255 mg, 72.5% yield) as a yellow oil. LCMS (ESI): $[M+H]^+$=249.2.

365

Step 6: (2S)-2-(9H-fluoren-9-ylmethoxycarbonylamino)-2-(1-phenyl-4-piperidyl) acetic acid

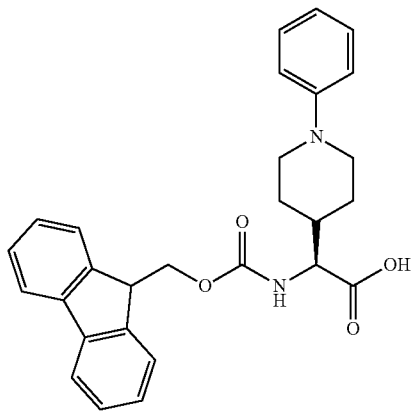 [SMILES: O=C(N[C@H](C(=O)O)C1CCN(c2ccccc2)CC1)OCC1c2ccccc2-c2ccccc21]

To a solution of methyl (2S)-2-amino-2-(1-phenyl-4-piperidyl)acetate (255 mg, 1.03 mmol) in THF (15 mL) and water (5 mL) was added a solution of LiOH (49.0 mg, 2.04 mmol) in water (5.0 mL) at 0° C. The mixture was stirred at 25° C. for 1 h and a solution of 9-fluorenylmethoxycarbonyl chloride (318 mg, 1.23 mmol) in THF was added at 0° C. The reaction mixture was stirred at 25° C. for 1 h. THF was evaporated under reduced pressure, and the residual aqueous solution was diluted with water (3 mL) and acidified with 1 N HCl until pH 6. The resulting solution was evaporated under vacuum. The residue was purified by flash chromatography on silica gel eluting with DCM/MeOH (10/1) to afford the title compound (418 mg, 89.1% yield) as a white solid. LCMS (ESI): [M+H]$^+$=457.2. $^1$H NMR (400 MHz, DMSO-d$_6$) δ 12.67 (s, 1H), 7.89 (d, J=8.4 Hz, 2H), 7.75 (m, J=8.4 Hz, 2H), 7.70-7.60 (m, 1H), 7.44-7.39 (m, 2H), 7.36-7.27 (m, 2H), 7.21-7.17 (m, 2H), 6.93 (d, J=8.4 Hz, 2H), 6.76-6.73 (m, 1H), 4.32-4.20 (m, 3H), 3.95-3.92 (m, 1H), 3.73-3.65 (m, 2H), 2.63-2.57 (m, 2H), 1.90-1.85 (m, 1H), 1.66-1.52 (m, 2H), 1.44-1.36 (m, 2H).

Step 7: (3R,6S,9S,12S,15S,18R,19R)-9-(Aminomethyl)-19-hexyl-6-((S)-1-hydroxyethyl)-15-isobutyl-3,16,18-trimethyl-12-(1-phenylpiperidin-4-yl)-1-oxa-4,7,10,13,16-pentaazacyclononadecane-5,8,11,14,17-pentaone The title compound was prepared following procedures analogous to those described for compound 73. LCMS (ESI): R$_T$ (min)=2.60, [M+H]$^+$=758.5, method=H; $^1$H NMR (400 MHz, DMSO-d$_6$) δ 8.79-8.52 (m, 1H), 8.32-8.15 (m, 1H), 8.02-7.22 (m, 7H), 7.01-6.81 (m, 3H), 4.72-4.59 (m, 1H), 4.33-4.25 (m, 1H), 4.13-4.01 (m, 7H), 3.46-3.09 (m, 6H), 3.01-2.85 (m, 2H), 2.76-2.65 (m, 4H), 2.25-1.82 (m, 3H), 1.79-1.40 (m, 6H), 1.39-1.21 (m, 9H), 1.07-0.84 (m, 17H).

366

Example 150: (3R,6S,9S,12S,15S,18R,19R)-9-(Aminomethyl)-12-cyclohexyl-18-hexyl-6-((S)-1-hydroxyethyl)-3,16,19-trimethyl-15-propyl-1-oxa-4,7,10,13,16-pentaazacyclononadecane-5,8,11,14,17-pentaone

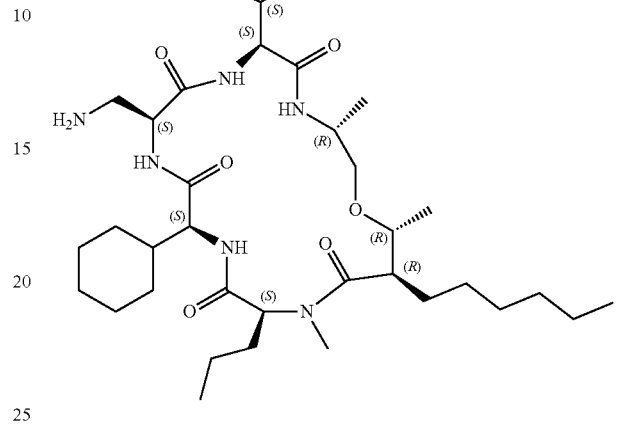

Step 1: (2R)-2-[(1R)-1-Hydroxyethyl]octanoic acid

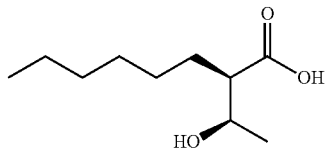

The title compound was prepared following procedures analogous to those described for Intermediate 1, using acetaldehyde instead of heptanal, and using octanoyl chloride instead of propionyl chloride. LCMS (ESI): [M−H]$^-$=187.2; $^1$H NMR (300 MHz, DMSO-d$_6$) δ 11.91 (s, 1H), 4.64 (br, 1H), 3.75-3.66 (m, 1H), 2.18-2.09 (m, 1H), 1.42-1.39 (m, 2H), 1.33-1.14 (m, 8H), 1.02 (d, J=6.3 Hz, 3H), 0.84 (t, J=6.6 Hz, 3H).

Step 2: (2R)-2-[(1R)-1-[(2R)-2-(tert-Butoxycarbonylamino)propoxy]ethyl]octanoic acid

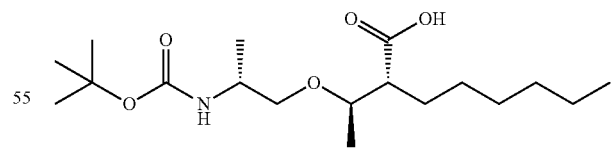

The title compound was prepared following procedures analogous to those described for Intermediate 3, using (2R)-2-[(1R)-1-hydroxyethyl]octanoic acid instead of (2R,3R)-3-hydroxy-2-methyl-nonanoic acid. LCMS (ESI): [M+H]$^+$=346.3; $^1$H NMR (300 MHz, DMSO-d$_6$) δ 12.04 (s, 1H), 6.54 (d, J=8.4 Hz, 1H), 3.49-3.36 (m, 3H), 3.00-2.95 (m, 1H), 2.29-2.24 (m, 1H), 1.36 (s, 9H), 1.22-1.10 (m, 8H), 1.03 (d, J=6.3 Hz, 3H), 0.96 (d, J=6.6 Hz, 3H), 0.84-0.80 (m, 5H).

Step 3: (3R,6S,9S,12S,15S,18R,19R)-9-(Aminomethyl)-12-cyclohexyl-18-hexyl-6-((S)-1-hydroxyethyl)-3,16,19-trimethyl-15-propyl-1-oxa-4,7,10,13,16-pentaazacyclononadecane-5,8,11,14,17-pentaone The title compound was prepared following procedures analogous to those described for compound 57. LCMS (ESI): $R_T$ (min)=2.92, [M+H]$^+$=667.5, method=H; $^1$H NMR (400 MHz, DMSO-d$_6$) δ 8.82-8.35 (m, 1H), 8.19-7.28 (m, 6H), 4.66-3.40 (m, 11H), 3.25-2.70 (m, 5H), 2.22-1.42 (m, 9H), 1.35-0.73 (m, 32H).

Example 151: (3R,6S,9S,12S,15S,18R,19R)-6,9-Bis(aminomethyl)-12-cycloheptyl-19-hexyl-15-isobutyl-3,16,18-trimethyl-1-oxa-4,7,10,13,16-pentazacyclononadecane-5,8,11,14,17-pentone

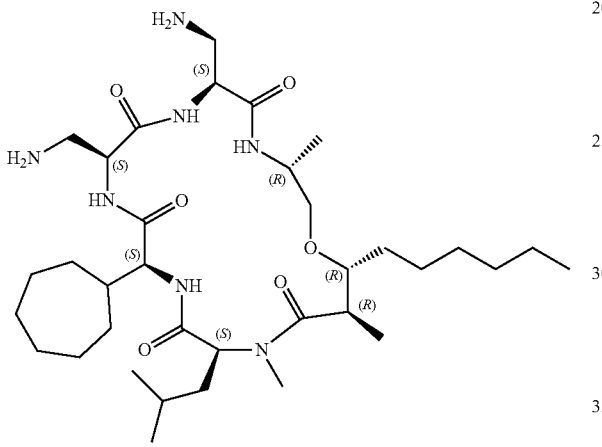

Step 1: tert-Butyl N-[[(3R,6S,9S,12S,15S,18R,19R)-9-(benzyloxycarbonylaminomethyl)-12-cycloheptyl-19-hexyl-15-isobutyl-3,16,18-trimethyl-5,8,11,14,17-pentaoxo-1-oxa-4,7,10,13,16-pentazacyclononadec-6-yl]methyl]carbamate

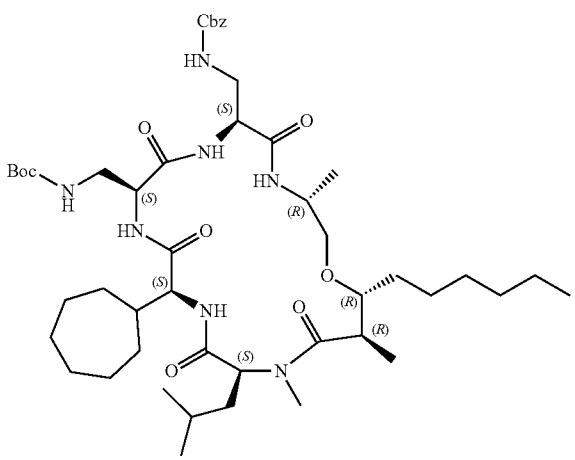

The title compound was prepared following procedures analogous to those described for Intermediate 8 (substituting the relevant Fmoc-protected amino acids), and compound 57, steps 1-3. LCMS (ESI): [M+H]$^+$=914.6.

Step 2: tert-Butyl N-[[(3R,6S,9S,12S,15S,18R,19R)-9-(aminomethyl)-12-cycloheptyl-19-hexyl-15-isobutyl-3,16,18-trimethyl-5,8,11,14,17-pentaoxo-1-oxa-4,7,10,13,16-pentazacyclononadec-6-yl]methyl]carbamate

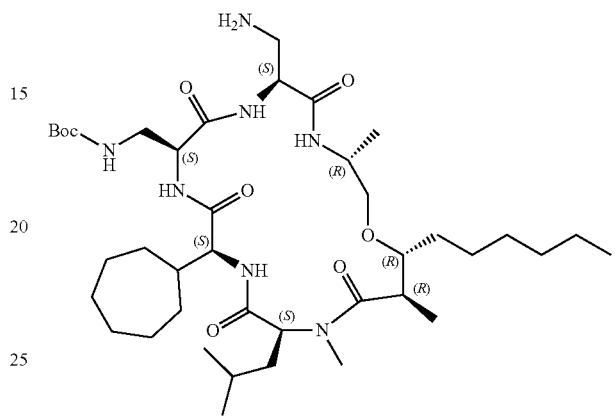

To a solution of tert-butyl N-[[(3R,6S,9S,12S,15S,18R,19R)-9-(benzyloxycarbonylaminomethyl)-12-cycloheptyl-19-hexyl-15-isobutyl-3,16,18-trimethyl-5,8,11,14,17-pentaoxo-1-oxa-4,7,10,13,16-pentazacyclononadec-6-yl]methyl]carbamate (150 mg, 0.160 mmol) in ethyl acetate with 0.5% TFA (20 mL) was added palladium (10% loading on carbon, 25 mg) under nitrogen.

The flask was evacuated and backfilled with hydrogen, and then was stirred for 4 h at 25° C. under a hydrogen balloon (3 atm). The reaction mixture was filtered through celite, rinsing with ethyl acetate. The filtrate was evaporated under vacuum to give the title compound which was used to next step without further purification. LCMS (ESI): [M+H]$^+$=780.5.

Step 3: (3R,6S,9S,12S,15S,18R,19R)-6,9-Bis(aminomethyl)-12-cycloheptyl-19-hexyl-15-isobutyl-3,16,18-trimethyl-1-oxa-4,7,10,13,16-pentazacyclononadecane-5,8,11,14,17-pentone A mixture tert-butyl N-[[(3R,6S,9S,12S,15S,18R,19R)-9-(aminomethyl)-12-cycloheptyl-19-hexyl-15-isobutyl-3,16,18-trimethyl-5,8,11,14,17-pentaoxo-1-oxa-4,7,10,13,16-pentazacyclononadec-6-yl]methyl]carbamate (98.0 mg) and TFA (20 mL) was stirred for 1 h at 0° C. The reaction mixture was evaporated under vacuum. The crude product was purified by reverse-phase HPLC to afford the title compound as its TFA salt (20.8 mg, 20.9% yield) as a white solid. LCMS (ESI): $R_T$=2.73 min, [M+H]+=680.5, method=H; $^1$H NMR (400 MHz, DMSO-d$_6$) δ 8.82-8.35 (m, 1H), 8.19-7.28 (m, 6H), 4.66-3.40 (m, 11H), 3.25-2.70 (m, 5H), 2.22-1.42 (m, 9H), 1.35-0.73 (m, 32H).

Example 161: (3R,6S,9S,12S,15S,18R,19R)-6-[(2-Aminoethylamino)methyl]-9-(aminomethyl)-12-cycloheptyl-19-hexyl-15-isobutyl-3,16,18-trimethyl-1-oxa-4,7,10,13,16-pentazacyclononadecane-5,8,11,14,17-pentone

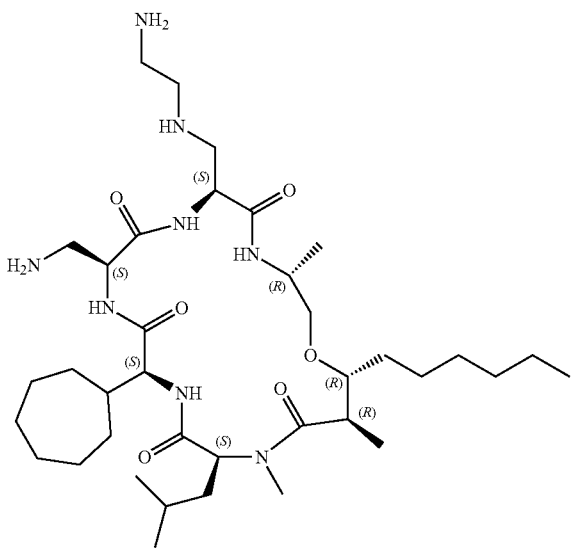

Step 1: tert-Butyl N-[[(3R,6S,9S,2S,15S,18R,9R)-6-[[2-tert-butoxycarbonylamino)ethylamino]methyl]-12-cycloheptyl-19-hexyl-15-isobutyl-3,16,18-trimethyl-5,8,11,14,17-pentaoxo-1-oxa-4,7,10,13,16-pentazacyclononadec-9-yl]methyl]carbamate

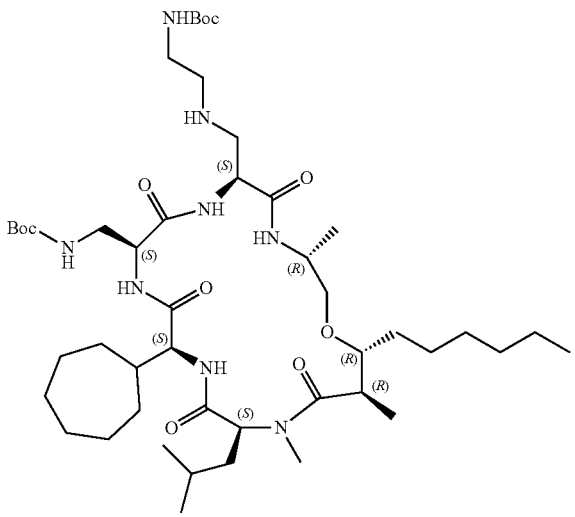

To a solution of tert-butyl N-[[(3R,6S,9S,12S,15S,18R,19R)-6-(aminomethyl)-12-cycloheptyl-19-hexyl-15-isobutyl-3,16,18-trimethyl-5,8,11,14,17-pentaoxo-1-oxa-4,7,10,13,16-pentazacyclononadec-9-yl]methyl]carbamate (described in the synthesis of compound 151, step 2) (220 mg, 0.282 mmol) in DCM (200 mL) was added tert-butyl N-(2-oxoethyl)carbamate (46.5 mg, 0.292 mmol). The mixture was stirred at room temperature for 2 h. Then NaBH(OAc)$_3$ (122 mg, 0.575 mmol) was added. The reaction was stirred at room temperature for 2 h and quenched with 10% aqueous NH$_4$Cl (200 mL). The phases were separated and the aqueous phase was extracted with DCM (200 mL). The organic layer was dried over anhydrous sodium sulfate and evaporated under vacuum. The residue was purified by reverse phase flash chromatography to afford the title compound (170 mg, 65.4% yield) as a white solid. LCMS (ESI): [M+H]$^+$=923.6.

Step 2: (3R,6S,9S,12S,15S,18R,19R)-6-[(2-Aminoethylamino)methyl]-9-(aminomethyl)-12-cycloheptyl-19-hexyl-15-isobutyl-3,16,18-trimethyl-1-oxa-4,7,10,13,16-pentazacyclononadecane-5,8,11,14,17-pentone A mixture of tert-butyl N-[[(3R,6S,9S,12S,15S,18R,19R)-6-[[2-(tert-butoxycarbonylamino)ethylamino]methyl]-12-cycloheptyl-19-hexyl-15-isobutyl-3,16,18-trimethyl-5,8,11,14,17-pentaoxo-1-oxa-4,7,10,13,16-pentazacyclononadec-9-yl]methyl]carbamate (165 mg, 0.179 mmol) in 2,2,2-trifluoroacetic acid (4.0 mL) was stirred at 0° C. for 30 min. The reaction mixture was diluted with toluene (10 mL) and evaporated under vacuum. The residue was purified by reverse-phase HPLC to afford the title compound as its TFA salt (14.4 mg, 9.6% yield) as a white solid. LCMS (ESI): R$_T$ (min)=1.65, [M+H]$^+$=723.6, method=M; $^1$H NMR (400 MHz, DMSO-d$_6$) δ 8.22-7.58 (m, 9H), 4.72-4.58 (m, 1H), 4.11-4.05 (m, 1H), 3.92-3.85 (m, 1H), 3.15-2.77 (m, 13H), 2.19-1.27 (m, 30H), 1.05-0.85 (m, 15H).

Example 164: (3R,6S,9S,12S,15S,18R,19R)-6-(((1r,3S)-3-Aminocyclobutoxy)methyl)-9-(aminomethyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone

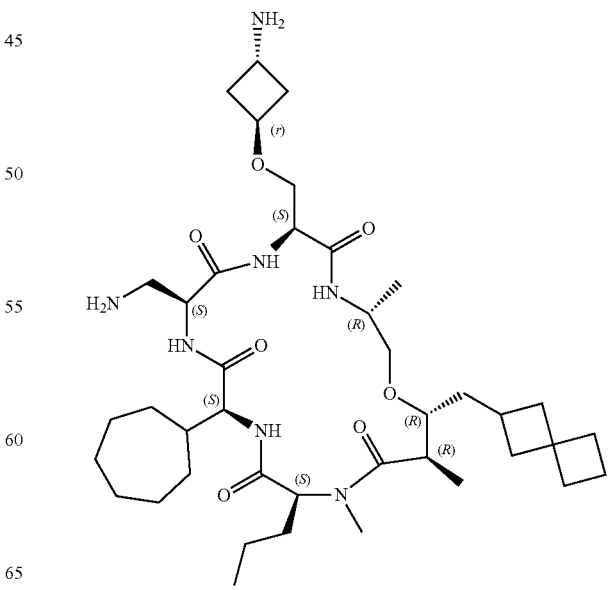

371

Step 1: (2R,3R)-3-((R)-2-((((9H-fluoren-9-yl)methoxy)carbonyl)amino) propoxy)-2-methyl-4-(spiro[3.3]heptan-2-yl)butanoic acid

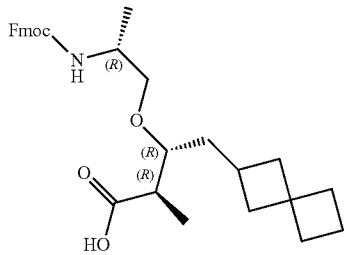

The title compound was prepared following procedures analogous to those described for Intermediates 3 and 4, using (2R,3R)-3-hydroxy-2-methyl-4-(spiro[3.3]heptan-2-yl)butanoic acid (Example 84, step 3) instead of (2R,3R)-3-hydroxy-2-methyl-nonanoic acid. LCMS (ESI): [M+H]$^+$ =492.3.

Step 2: (3R,6S,9S,12S,15S,18R,19R)-6-(((1r,3S)-3-Aminocyclobutoxy)methyl)-9-(aminomethyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone The title compound was prepared using (2R,3R)-3-((R)-2-((((9H-fluoren-9-yl)methoxy)carbonyl)amino) propoxy)-2-methyl-4-(spiro[3.3]heptan-2-yl)butanoic acid and following procedures analogous to those described for compound 73. LCMS (ESI): R$_T$(min)=2.75, [M+H]$^+$=760.5, method=H; $^1$H NMR (400 MHz, DMSO-d$_6$) δ 8.53-8.24 (m, 1H), 8.21-8.01 (m, 1H), 7.93 (d, J=21.9 Hz, 6H), 7.48-7.29 (m, 1H), 4.61-4.25 (m, 1H), 4.26-3.99 (m, 2H), 3.96-3.40 (m, 6H), 3.27-2.89 (m, 6H), 2.73 (s, 2H), 2.30-2.14 (m, 5H), 2.14-1.87 (m, 5H), 1.87-1.16 (m, 26H), 1.07-0.84 (m, 8H).

Example 166: (3R,6S,9S,12S,15S,18R,19R)-9-(Aminomethyl)-6-(((6-aminospiro[3.3]heptan-2-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone (single unknown stereoisomer 1)

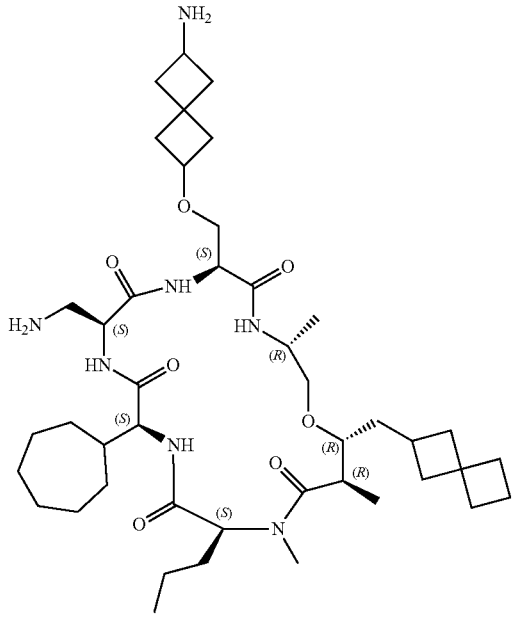

372

Step 1: Methyl (2S)-2-(benzyloxycarbonylamino)-3-[6-(tert-butoxycarbonylamino)spiro[3.3]heptan-2-yl]oxy-propanoate

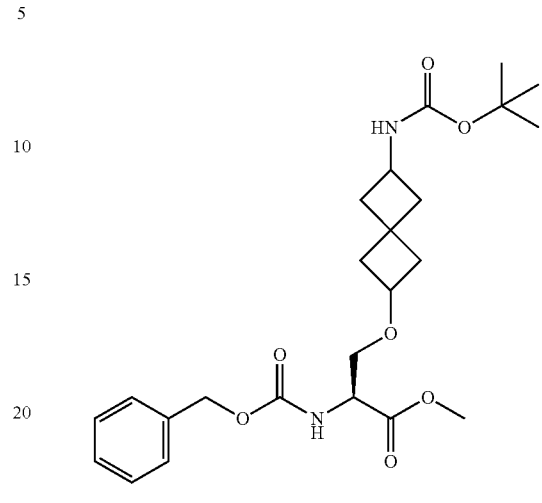

To a solution of tert-butyl N-(2-hydroxyspiro[3.3]heptan-6-yl)carbamate (2.13 g, 9.37 mmol) in CHCl$_3$ (30 mL) was added BF$_3$.Et$_2$O (270 mg, 1.87 mmol). Then a solution of (S)-1-benzyl 2-methyl aziridine-1,2-dicarboxylate (2.20 g, 9.35 mmol) in chloroform (5.0 mL) was added dropwise at 25° C. The reaction mixture was stirred at 25° C. for 8 h, and then evaporated under vacuum. The residue was purified by flash chromatography on silica gel eluting with petroleum ether/ethyl ester (2/1) to afford the title compound (811 mg, 18.7% yield). LCMS (ESI): [M+H]$^+$=463.2.

Step 2: Methyl (2S)-2-amino-3-[6-(tert-butoxycarbonylamino)spiro[3.3]heptan-2-yl]oxy-propanoate

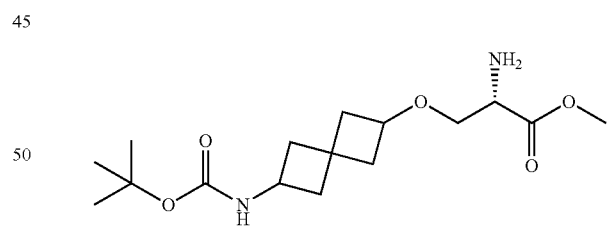

A mixture of methyl (2S)-2-(benzyloxycarbonylamino)-3-[6-(tert-butoxycarbonylamino)spiro[3.3]heptan-2-yl]oxy-propanoate (811 mg, 1.75 mmol) and palladium (200 mg, 10% loading on carbon) in ethyl acetate (30 mL) was stirred at 25° C. for 1 h under H$_2$(3 atm). The mixture was filtered through celite and the filtrate was evaporated under vacuum to afford the title compound (557 mg, 96.7% yield) as a yellow oil. LCMS (ESI): [M+H]$^+$=329.2.

Step 3: Methyl (2S)-3-[6-(tert-butoxycarbonylamino)spiro[3.3]heptan-2-yl]oxy-2-(9H-fluoren-9-ylmethoxycarbonylamino)propanoate

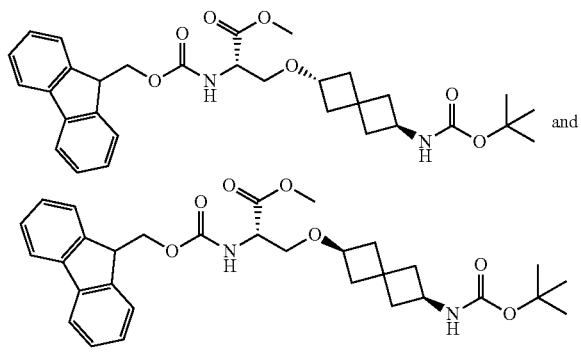

and

To a solution of methyl (2S)-2-amino-3-[6-(tert-butoxycarbonylamino)spiro[3.3]heptan-2-yl]oxy-propanoate (557 mg, 1.70 mmol) in DMF (28 mL) and water (28 mL) was added a solution of NaHCO$_3$ (285 mg, 3.39 mmol) in water (10 mL) at 0° C. Then a solution of 9-fluorenylmethoxycarbonyl chloride (525 mg, 2.04 mmol) in DMF (5.0 mL) was added at 0° C. The reaction mixture was stirred at 25° C. for 1 h and then acidified with 1 N HCl solution to pH 6 and extracted with ethyl acetate (3×150 mL).

The combined organic layers were washed with water (50 mL×5) and evaporated under vacuum. The residue was purified by flash chromatography on silica gel eluting with PE/EA (2/1) to afford the title compound (930 mg) as a white solid as a mixture of two diastereomers. LCMS (ESI): [M+H]$^+$=551.2. The mixture was separated by the following conditions to yield two single unknown stereoisomers: Column: CHIRALPAK AD-H SFC, 5*25 cm, 5 um; Mobile Phase A: CO2:60, Mobile Phase B: IPA (2 mM NH3-MEOH):40; Flow rate: 150 mL/min; 220 nm: First peak: R$_T$ 6.7 min, 270 mg. Second peak: R$_T$ 7.9 min, 304 mg.

Step 4: (2S)-3-[6-(tert-butoxycarbonylamino)spiro[3.3]heptan-2-yl]oxy-2-(9H-fluoren-9-ylmethoxycarbonylamino)propanoic acid (single unknown stereoisomer 1)

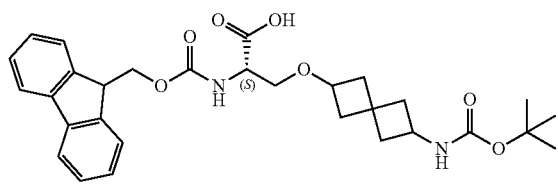

To a solution of methyl (2S)-3-[6-(tert-butoxycarbonylamino)spiro[3.3]heptan-2-yl]oxy-2-(9H-fluoren-9-ylmethoxycarbonylamino)propanoate (peak 1 from Step 3) (250 mg, 0.450 mmol) in THF (30 mL) and water (10 mL) was added LiOH (21.8 mg, 0.910 mmol) in water (2.0 mL) at 0° C. The reaction mixture stirred at 25° C. for 1h and then evaporated under vacuum to remove THF. The residual solution was diluted with water (3.0 mL) and acidified with 1 N HCl solution to pH6. The resulting solution was evaporated to dryness under vacuum. The residue was purified by flash chromatography on silica gel eluting with DCM/MeOH (10/1) to afford the title compound (237 mg, 97.3% yield) as a white solid. LCMS (ESI): [M+H]$^+$=537.3. $^1$H NMR (300 MHz, DMSO-d$_6$) δ 7.90 (d, J=8.4 Hz, 2H), 7.75 (d, J=8.7 Hz, 2H), 7.53 (d, J=8.7 Hz, 1H), 7.45-7.40 (m, 2H), 7.36-7.30 (m, 2H), 7.07 (d, J=8.1 Hz, 1H), 4.30-4.22 (m, 3H), 4.15-4.10 (m, 1H), 3.87-3.80 (m, 2H), 3.51 (d, J=6.9 Hz, 2H), 2.31-2.08 (m, 3H), 1.91-1.77 (m, 5H), 1.36 (s, 9H).

Step 5: (3R,6S,9S,12S,15S,18R,19R)-9-(Aminomethyl)-6-(((6-aminospiro[3.3]heptan-2-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone (single unknown stereoisomer 1)

The title compound was prepared following procedures analogous to those described for compound 73. LCMS (ESI): R$_T$(min)=2.11, [M+H]$^+$=800.6, method=M; $^1$H NMR (400 MHz, DMSO-d$_6$) δ 8.54-8.18 (m, 1H), 8.05-7.63 (m, 6H), 7.35-7.29 (m, 1H), 4.56-4.19 (m, 2H), 4.09-4.01 (m, 1H), 3.83-3.72 (m, 2H), 3.57-3.50 (m, 2H), 3.38-3.06 (m, 7H), 2.92-2.86 (m, 1H), 2.80-2.73 (m, 2H), 2.33-1.95 (m, 13H), 1.87-1.24 (m, 26H), 1.01-0.87 (m, 9H).

Example 167: (3R,6S,9S,12S,15S,18R,19R)-9-(Aminomethyl)-6-((3-(aminomethyl)phenoxy)methyl)-12-cyclohexyl-19-hexyl-15-isobutyl-3,16,18-trimethyl-1-oxa-4,7,10,13,16-pentaazacyclononadecane-5,8,11,14,17-pentaone

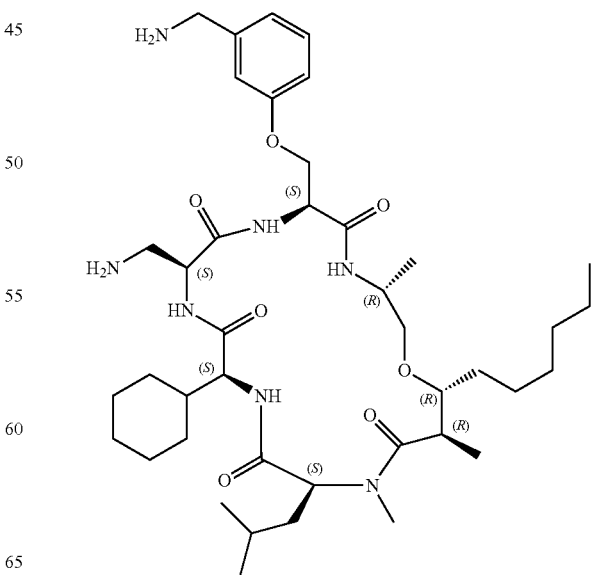

Step 1: (2S)-3-[3-[(tert-Butoxycarbonylamino)methyl]phenoxy]-2-(9H-fluoren-9-ylmethoxycarbonylamino)propanoic acid

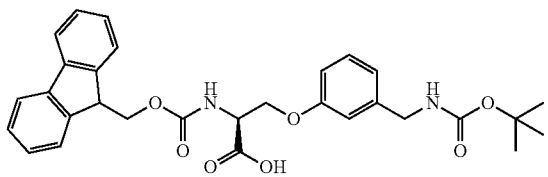 [SMILES: CC(C)(C)OC(=O)NCc1cccc(OC[C@H](NC(=O)OCC2c3ccccc3-c3ccccc32)C(=O)O)c1]

The title compound was prepared following procedures analogous to those described for the synthesis of compound 76, steps 1-4, using tert-butyl N-[(3-bromophenyl)methyl]carbamate instead of tert-butyl N-[(4-bromophenyl)methyl]carbamate. LCMS (ESI): [M+H]$^+$=533.4; $^1$H NMR (400 MHz, DMSO-d$_6$) δ 7.89 (d, J=8.4 Hz, 2H), 7.75-7.66 (m, 3H), 7.45-7.37 (m, 3H), 7.33-7.28 (m, 2H), 7.24-7.20 (m, 1H), 6.83-6.75 (m, 3H), 4.38-4.34 (m, 1H), 4.31-4.29 (m, 2H), 4.25-4.21 (m, 3H), 4.10 (d, J=4.8 Hz, 2H), 1.39 (s, 9H).

Step 2: (3R,6S,9S,12S,15S,18R,19R)-9-(Aminomethyl)-6-((3-(aminomethyl)phenoxy)methyl)-12-cyclohexyl-19-hexyl-15-isobutyl-3,16,18-trimethyl-1-oxa-4,7,10,13,16-pentaazacyclononadecane-5,8,11,14,17-pentaone The title compound was prepared following procedures analogous to those described for compound 73. LCMS (ESI): R$_T$(min)=2.15, [M+H]$^+$=772.5, method=M; $^1$H NMR (400 MHz, DMSO-d$_6$) δ 8.72-8.13 (m, 9H), 7.63-7.57 (m, 1H), 7.34-7.30 (m, 1H), 7.06-7.02 (m, 2H), 6.96-6.90 (m, 1H), 4.64-4.58 (m, 1H), 4.40-4.12 (m, 3H), 4.00-3.60 (m, 8H), 3.32-3.15 (m, 5H), 3.10-2.92 (m, 2H), 2.80-2.71 (m, 2H), 2.02-1.53 (m, 9H), 1.49-0.85 (m, 27H).

Example 168: (3R,6S,9S,12S,15S,18R,19R)-9-(Aminomethyl)-6-(((1r,3S)-3-(aminomethyl)cyclobutoxy)methyl)-12-cycloheptyl-19-hexyl-3,16,18-trimethyl-15-propyl-1-oxa-4,7,10,13,16-pentaazacyclononadecane-5,8,11,14,17-pentaone

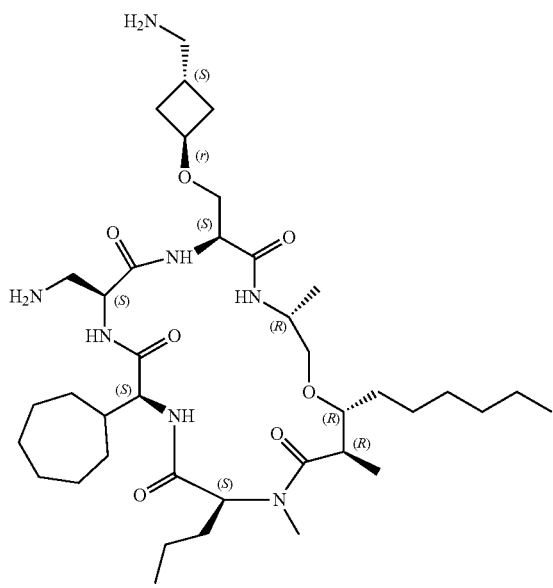

The title compound was prepared following procedures analogous to those described for compound 73, using intermediate P2L. LCMS (ESI): R$_T$ (min)=1.95, [M+1]*=750.6, method=M; $^1$H NMR (400 MHz, DMSO-d$_6$) δ 8.66-8.39 (m, 1H), 8.36-8.09 (m, 1H), 8.02-7.82 (m, 4H), 7.75-7.57 (m, 3H), 7.36 (d, J=8.5 Hz, 1H), 4.69-4.13 (m, 2H), 4.14-3.58 (m, 5H), 3.30-2.83 (m, 9H), 2.75 (s, 2H), 2.43-2.14 (m, 2H), 2.12-1.84 (m, 6H), 1.85-1.16 (m, 25H), 1.06-0.74 (m, 12H).

Example 169: (3R,6S,9S,12S,15S,18R,19R)-9-(Aminomethyl)-12-cycloheptyl-19-hexyl-6-(((2-hydroxyethyl)amino)methyl)-15-isobutyl-3,16,18-trimethyl-1-oxa-4,7,10,13,16-pentaazacyclononadecane-5,8,11,14,17-pentaone

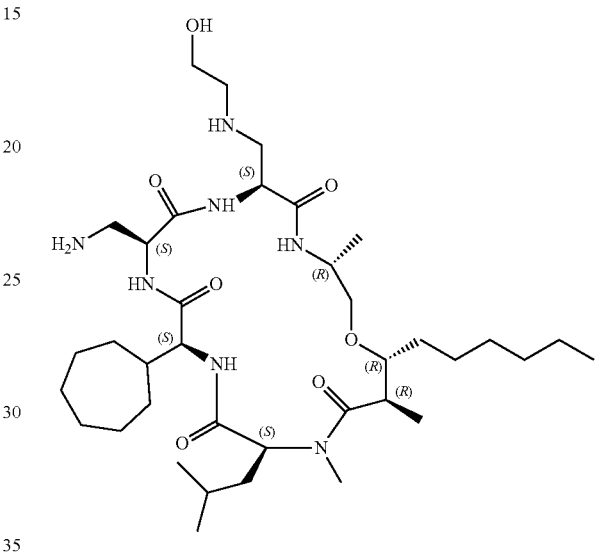

Step 1: tert-Butyl N-[[(3R,6S,9S,12S,15S,18R,19R)-6-[[2-[tert-butyl(dimethyl)silyl]oxyethylamino]methyl]-12-cycloheptyl-19-hexyl-15-isobutyl-3,16,18-trimethyl-5,8,11,14,17-pentaoxo-1-oxa-4,7,10,13,16-pentazacyclononadec-9-yl]methyl]carbamate

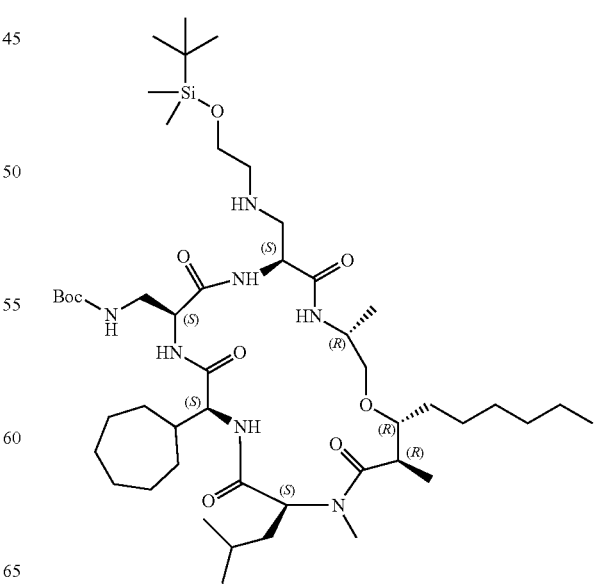

A solution of tert-butyl N-[[(3R,6S,9S,12S,15S,18R, 19R)-6-(aminomethyl)-12-cycloheptyl-19-hexyl-15-isobutyl-3,16,18-trimethyl-5,8,11,14,17-pentaoxo-1-oxa-4,7,10,13,16-pentazacyclononadec-9-yl]methyl]carbamate (206 mg, 0.264 mmol) (synthesis of compound 151, step 2) and 2-((tert-butyldimethylsilyl)oxy)acetaldehyde (48.6 mg, 0.279 mmol) in DCM (200 mL) was stirred at room temperature for 2 h. Then NaBH(OAc)$_3$ (109 mg, 0.517 mmol) was added. The reaction mixture was stirred at room temperature for additional 2 h and then evaporated under vacuum. The residue was purified by reverse phase flash chromatography eluting with acetonitrile/water (90/10) to afford the title compound (103.4 mg, 41.6% yield) as a white solid. LCMS (ESI): [M+H]$^+$=938.6.

Step 2: (3R,6S,9S,12S,15S,18R,19R)-9-(Aminomethyl)-12-cycloheptyl-19-hexyl-6-(((2-hydroxyethyl)amino)methyl)-15-isobutyl-3,16,18-trimethyl-1-oxa-4,7,10,13,16-pentaazacyclononadecane-5,8,11,14,17-pentaone Ice cold TFA (10 mL) was added to tert-butyl N-[[(3R, 6S,9S,12S,15S,18R,19R)-6-[[2-[tert-butyl(dimethyl)silyl] oxyethylamino]methyl]-12-cycloheptyl-19-hexyl-15-isobutyl-3,16,18-trimethyl-5,8,11,14,17-pentaoxo-1-oxa-4,7,10,13,16-pentazacyclononadec-9-yl]methyl]carbamate (93.2 mg, 0.100 mmol). The resulting mixture was stirred at 0° C. for 4 h and then evaporated under vacuum. The residue was purified by reverse-phase HPLC to afford the title compound (23.8 mg, 25.2% yield) as a white solid. LCMS (ESI): R$_T$(min)=2.11, [M+H]$^+$=724.5, method=M; $^1$H NMR (400 MHz, DMSO-d$_6$) δ 8.75-8.61 (m, 2H), 8.59-8.31 (m, 2H), 8.19-7.87 (m, 4H), 7.52-7.39 (m, 1H), 4.69-4.51 (m, 2H), 4.29-4.19 (m, 1H), 4.11-4.05 (m, 1H), 3.90-3.83 (m, 2H), 3.71-3.55 (m, 4H), 3.30-3.21 (m, 9H), 3.14-3.06 (m, 7H), 2.95-2.75 (m, 3H), 2.14-1.97 (m, 1H), 1.78-1.18 (m, 20H), 1.08-0.81 (m, 12H).

Example 170: (3R,6S,9S,12S,15S,18R,19R)-9-(Aminomethyl)-6-(((6-aminospiro[3.3]heptan-2-yl)oxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone (single unknown stereoisomer 2)

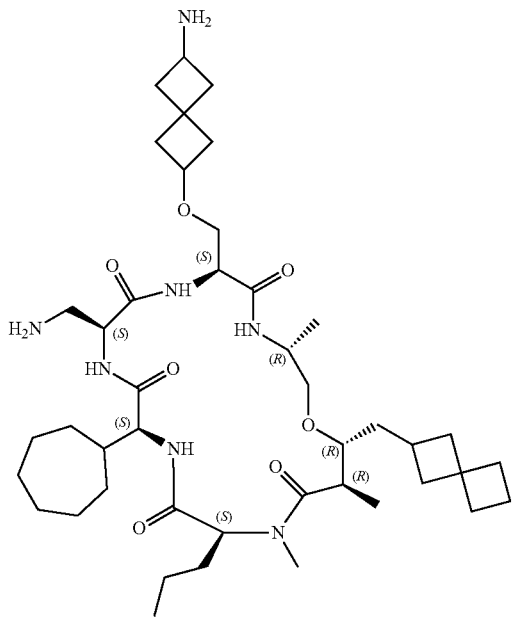

Step 1. (2S)-3-[6-(tert-Butoxycarbonylamino)spiro [3.3]heptan-2-yl]oxy-2-(9H-fluoren-9-ylmethoxycarbonylamino)propanoic acid (Single unknown stereoisomer 2)

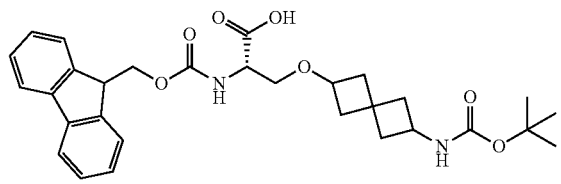 [SMILES: CC(C)(C)OC(=O)NC1CC2(C1)CC(OC[C@H](NC(=O)OCC1c3ccccc3-c3ccccc31)C(=O)O)C2]

Methyl (2S)-3-[6-(tert-butoxycarbonylamino)spiro[3.3] heptan-2-yl]oxy-2-(9H-fluoren-9-ylmethoxycarbonylamino)propanoate (peak 2 from compound 166, Step 3) (285 mg, 0.520 mmol) was hydrolyzed following the same method described in the synthesis of compound 166, step 4 to afford the title compound (206 mg, 74.2% yield) as a white solid. LCMS (ESI): [M+H]$^+$=537.3; $^1$H NMR (300 MHz, DMSO-d$_6$) δ 7.90 (d, J=8.4 Hz, 2H), 7.73 (d, J=8.7 Hz, 2H), 7.45-7.40 (m, 2H), 7.36-7.30 (m, 2H), 7.20 (br, 1H), 7.07 (d, J=8.1 Hz, 1H), 4.35-4.22 (m, 3H), 4.07-4.00 (m, 1H), 3.85-3.77 (m, 2H), 3.51 (d, J=6.9 Hz, 2H), 2.31-2.08 (m, 3H), 1.91-1.77 (m, 5H), 1.35 (s, 9H).

Step 2: (3R,6S,9S,12S,15S,18R,19R)-9-(Aminomethyl)-6-(((6-aminospiro[3.3]heptan-2-yl)oxy) methyl)-12-cycloheptyl-3,16,18-trimethyl-15-propyl-19-(spiro[3.3]heptan-2-ylmethyl)-1-oxa-4,7,10, 13,16-pentaazacyclononadecane-5,8,11,14,17-pentaone (single unknown stereoisomer 2)

The title compound was prepared following procedures analogous to those described for compound 73. LCMS (ESI): R$_T$(min)=2.10, [M+H]$^+$=800.5, method=M; $^1$H NMR (400 MHz, DMSO-d$_6$) δ 8.54-8.18 (m, 1H), 8.08-7.65 (m, 7H), 7.35-7.30 (m, 1H), 4.56-4.22 (m, 2H), 4.12-4.05 (m, 1H), 3.87-3.80 (m, 2H), 3.57-3.53 (m, 1H), 3.38-3.14 (m, 7H), 2.94-2.92 (m, 1H), 2.86-2.73 (m, 2H), 2.33-1.96 (m, 13H), 1.89-1.24 (m, 26H), 1.01-0.87 (m, 9H).

Example 173: (3R,6S,9S,12S,15S,18R,19R)-6-((3-Amino-2-hydroxypropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone

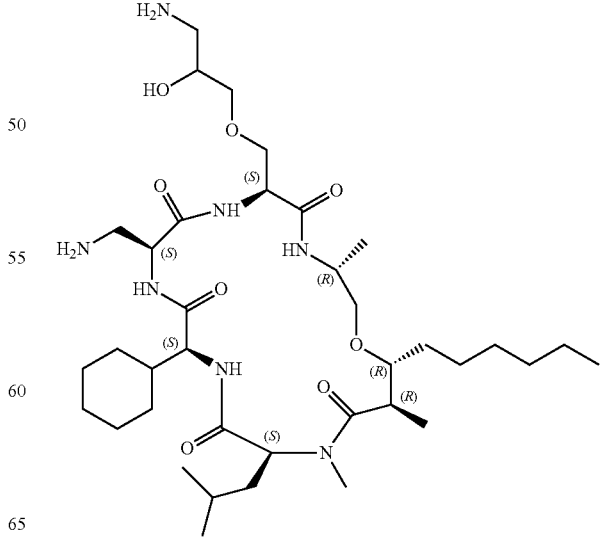

Step 1: tert-Butyl (((3R,6S,9S,12S,15S,18R,19R)-6-((allyloxy)methyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate

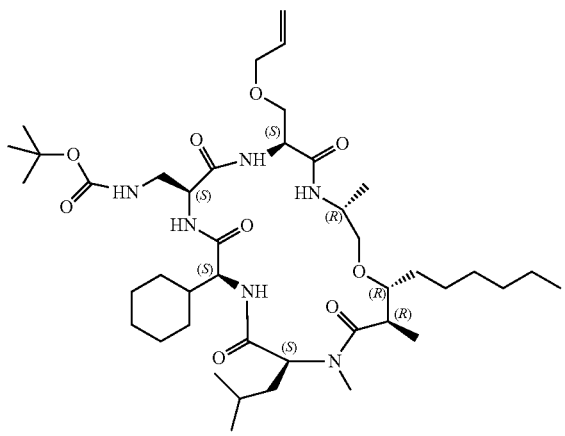

The title compound was prepared following procedures analogous to those described for Example 81, steps 2-4, substituting commercially available Fmoc-L-Ser(O-allyl)-OH instead of Intermediate P2D. LCMS (ESI): [M+H]⁺=807.4.

Step 2: tert-Butyl N-[[(3R,6S,9S,12S,15S,18R,19R)-12-cyclohexyl-19-hexyl-15-isobutyl-3,16,18-trimethyl-6-(oxiran-2-ylmethoxymethyl)-5,8,11,14,17-pentaoxo-1-oxa-4,7,10,13,16-pentazacyclononadec-9-yl]methyl]carbamate

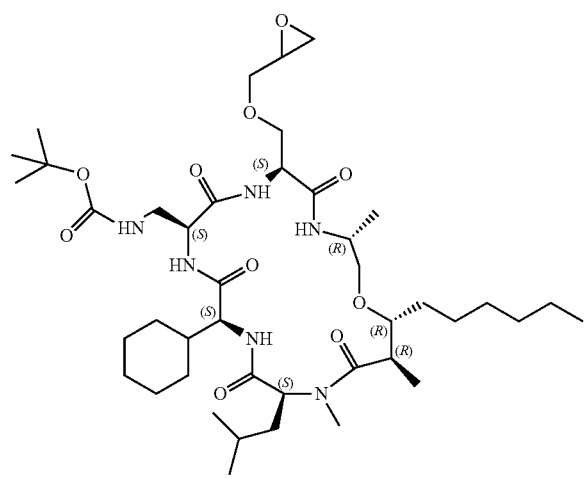

To a solution of tert-butyl (((3R,6S,9S,12S,15S,18R,19R)-6-((allyloxy)methyl)-12-cyclohexyl-19-hexyl-15-isobutyl-3,16,18-trimethyl-5,8,11,14,17-pentaoxo-1-oxa-4,7,10,13,16-pentaazacyclononadecan-9-yl)methyl)carbamate (200 mg, 0.250 mmol) in 1,2-dichloroethane (15 mL) was added a solution of 3-chloroperoxybenzoic acid (427.8 mg, 2.48 mmol) in 1,2-dichloroethane (1.0 mL) at 0° C. The reaction mixture was stirred overnight at 25° C. An additional amount of 3-chloroperoxybenzoic acid (428 mg, 2.48 mmol) was added and the reaction mixture was stirred for another 6 h at 25° C. Saturated aqueous Na₂CO₃ solution (10 mL) was added at 0° C. The resulting solution was extracted with DCM (30 mL×3). The organic layers were combined and dried over anhydrous sodium sulfate and evaporated under vacuum to afford the title compound (165 mg), which was carried forward to the next step without purification. LCMS (ESI): [M+H]⁺=823.5.

Step 3: tert-Butyl N-[[(3R,6S,9S,12S,15S,18R,19R)-6-[(3-azido-2-hydroxy-propoxy)methyl]-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate

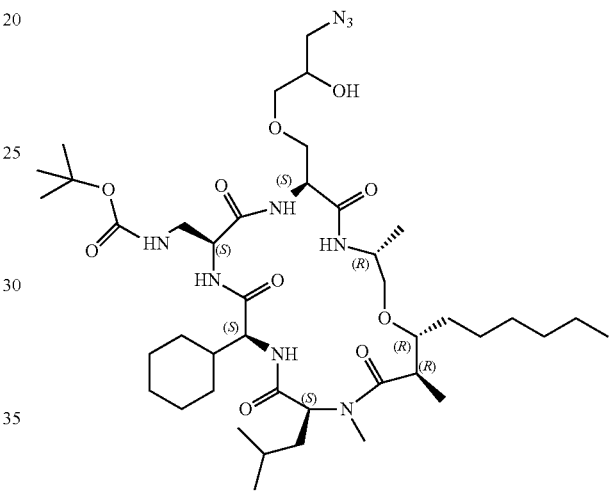

To a solution of tert-butyl N-[[(3R,6S,9S,12S,15S,18R,19R)-12-cyclohexyl-19-hexyl-15-isobutyl-3,16,18-trimethyl-6-(oxiran-2-ylmethoxymethyl)-5,8,11,14,17-pentaoxo-1-oxa-4,7,10,13,16-pentazacyclononadec-9-yl]methyl]carbamate (165 mg) in DMF (10 mL) was added NaN₃ (67.6 mg, 1.04 mmol). The reaction mixture was stirred for 20 h at 70° C. The reaction mixture was cooled to 0° C. and water (60 mL) was added dropwise to reaction mixture. The resulting solution was extracted with DCM (30 mL×3) and the organic layers were combined, dried over sodium sulfate, and evaporated under reduced pressure to give the title compound (130 mg) as a yellow oil, which was carried forward to the next step without purification. LCMS (ESI): [M+H]⁺=866.5.

Step 4: tert-Butyl N-[[(3R,6S,9S,12S,15S,18R, 19R)-6-[(3-amino-2-hydroxy-propoxy)methyl]-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate

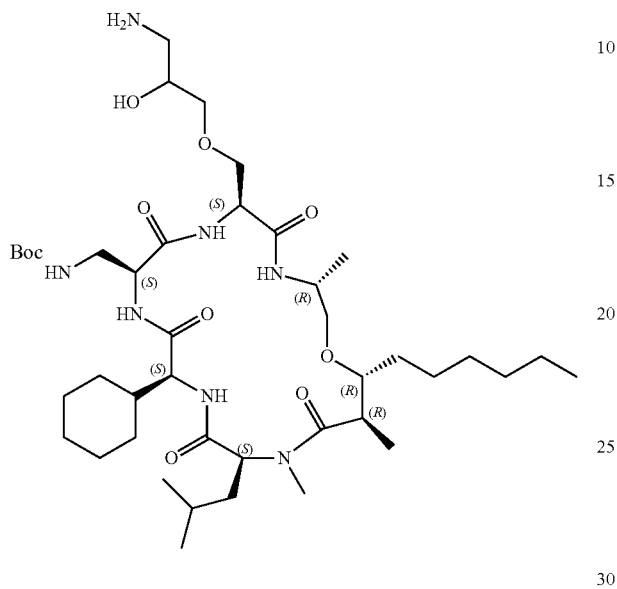

To a solution of tert-butyl N-[[(3R,6S,9S,12S,15S,18R, 19R)-6-[(3-azido-2-hydroxy-propoxy)methyl]-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate (120 mg, 0.138 mmol) in ethanol (20 mL) was added palladium (136 mg, 10% loading on carbon) under nitrogen. Then the mixture was stirred for 2 h under $H_2$ (3 atm) at room temperature. The reaction mixture was diluted with EtOH (20 mL) and filtered. The filtrate was evaporated under reduced pressure to afford the title compound (36.2 mg) as a brown solid. LCMS (ESI): $[M+H]^+=840.5$.

Step 5: (3R,6S,9S,12S,15S,18R,19R)-6-((3-Amino-2-hydroxypropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone A mixture of tert-butyl N-[[(3R,6S,9S,12S,15S,18R, 19R)-6-[(3-amino-2-hydroxy-propoxy)methyl]-12-cyclohexyl-19-hexyl-15-isobutyl-3,16,18-trimethyl-5,8,11,14,17-pentaoxo-1-oxa-4,7,10,13,16-pentazacyclononadec-9-yl]methyl]carbamate (31.2 mg, 0.0371 mmol) and 2,2,2-trifluoroacetic acid (2 mL) was stirred at 0° C. for 30 min. The resulting mixture was concentrated under vacuum. The residue was purified by reverse-phase HPLC to afford the title compound as the TFA salt (3.7 mg, 10.3% yield) as a white solid. LCMS (ESI): $R_T=2.70$ min, $[M+H]^+=740.6$, method=H; $^1H$ NMR (400 MHz, DMSO-$d_6$) δ 8.82-8.74 (m, 1H), 8.32-8.25 (m, 1H), 8.09-7.95 (m, 4H), 7.79-7.70 (m, 3H), 5.60-5.52 (m, 1H), 4.49-4.38 (m, 1H), 4.16-3.96 (m, 4H), 3.94-3.62 (m, 5H), 3.32-3.20 (m, 6H), 3.09-2.67 (m, 8H), 2.13-2.01 (m, 2H), 1.95-1.51 (m, 7H), 1.33-1.07 (m, 12H), 0.98-0.86 (m, 17H).

Example 174: (3R,6S,9S,12S,15S,18R,19R)-6-((4-(2-Aminoethyl)phenoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone

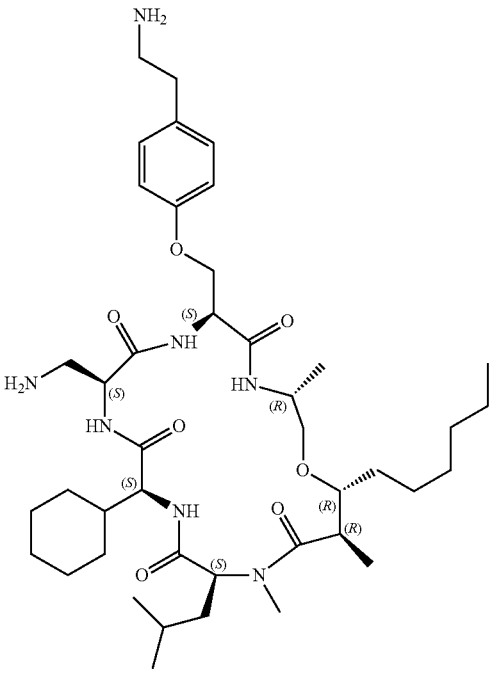

Step 1: (S)-2-(((((9H-fluoren-9-yl)methoxy)carbonyl) amino)-3-(4-(2-((tert-butoxycarbonyl)amino)ethyl) phenoxy)propanoic acid

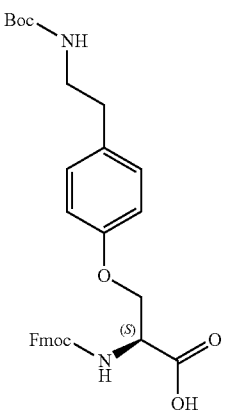

The title compound was prepared following procedures analogous to those described for the synthesis of compound 76, Steps 1-4, using tert-butyl 4-bromophenethylcarbamate instead of tert-butyl N-[(4-bromophenyl)methyl]carbamate. LCMS (ESI): $[M+H]^+=547.2$; $^1H$ NMR (400 MHz, DMSO-$d_6$) δ 7.88 (d, J=8.4 Hz, 2H), 7.72 (d, J=8.4 Hz, 2H), 7.42-7.38 (m, 3H), 7.34-7.26 (m, 2H), 7.08 (d, J=8.4 Hz, 2H), 6.86-6.82 (m, 3H), 4.31-4.17 (m, 6H), 3.10-3.05 (m, 2H), 2.61 (t, J=6.9 Hz, 2H), 1.36 (s, 9H).

Step 2: (3R,6S,9S,12S,15S,18R,19R)-6-((4-(2-Aminoethyl)phenoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone The title compound was prepared following procedures analogous to those described for compound 73. LCMS (ESI): $R_T$(min)=2.12, [M+H]$^+$=786.5, method=M; $^1$H NMR (400 MHz, DMSO-d$_6$) δ 8.30-7.56 (m, 8H), 7.16 (d, J=8.4 Hz, 2H), 6.91-6.88 (m, 2H), 4.74-4.62 (m, 1H), 4.39-4.12 (m, 3H), 4.08-3.72 (m, 3H), 3.16-2.72 (m, 10H), 2.18-1.53 (m, 11H), 1.48-1.25 (m, 12H), 1.08-0.85 (m, 19H).

The Examples listed in Table 5 were prepared following procedures analogous to those described in the above Examples, substituting the appropriate Fmoc-protected amino acids, one or more of Intermediates 1-8, and/or the indicated Intermediate #.

TABLE 5

| Example | Structure/Name | LCMS [M + H]$^+$ | LCMS $R^T$ (min), method | Synthesis Method/ Example # (Intermediate #) |
|---|---|---|---|---|
| 18 | 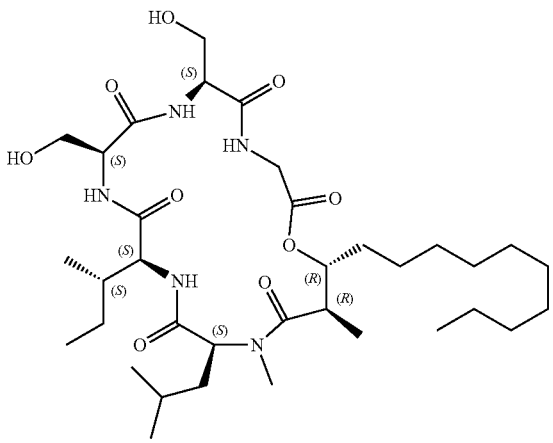<br>(6S,9S,12S,15S,18R,19R)-12-((S)-sec-butyl)-19-decyl-6,9-bis(hydroxymethyl)-15-isobutyl-16,18-dimethyl-1-oxa-4,7,10,13,16-pentaazacyclononadecane-2,5,8,11,14,17-hexaone | 698.4 | 6.747, A | 1 |
| 19 | 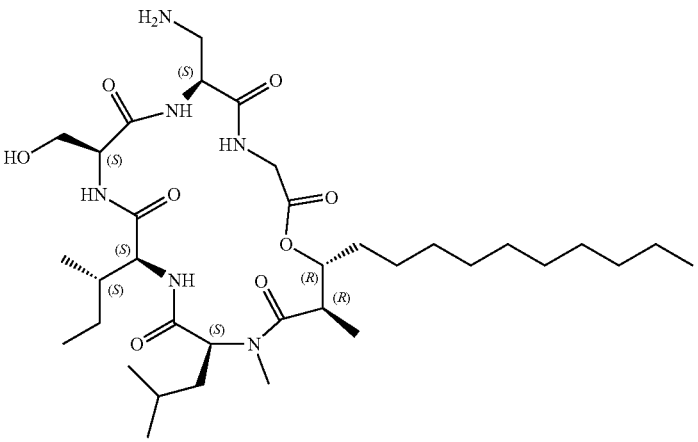<br>(6S,9S,12S,15S,18R,19R)-6-(aminomethyl)-12-((S)-sec-butyl)-19-decyl-9-(hydroxymethyl)-15-isobutyl-16,18-dimethyl-1-oxa-4,7,10,13,16-pentaazacyclononadecane-2,5,8,11,14,17-hexaone | 697.4 | 14.28, F | 8 |

TABLE 5-continued
| Example | Structure/Name | LCMS [M + H]+ | LCMS R$^T$ (min), method | Synthesis Method/ Example # (Intermediate #) |
|---|---|---|---|---|
| 20 | 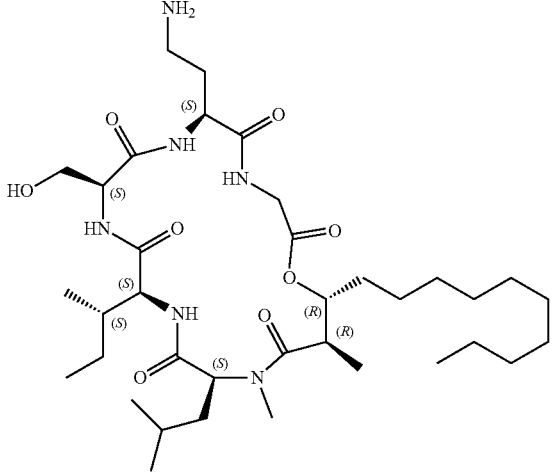<br>(6S,9S,12S,15S,18R,19R)-6-(2-aminoethyl)-12-((S)-sec-butyl)-19-decyl-9-(hydroxymethyl)-15-isobutyl-16,18-dimethyl-1-oxa-4,7,10,13,16-pentaazacyclononadecane-2,5,8,11,14,17-hexaone | 711.5 | 14.34, F | 8 |
| 21 | 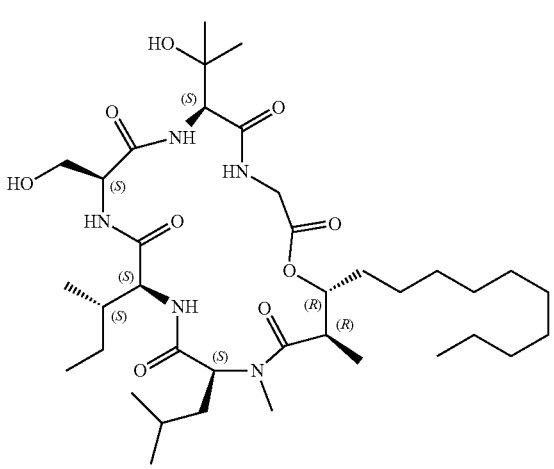<br>(6S,9S,12S,15S,18R,19R)-12-((S)-sec-butyl)-19-decyl-9-(hydroxymethyl)-6-(2-hydroxypropan-2-yl)-15-isobutyl-16,18-dimethyl-1-oxa-4,7,10,13,16-pentaazacyclononadecane-2,5,8,11,14,17-hexaone | 726.5 | 7.161, A | 1 |

TABLE 5-continued
| Example | Structure/Name | LCMS [M + H]+ | LCMS R$^T$ (min), method | Synthesis Method/ Example # (Intermediate #) |
|---|---|---|---|---|
| 22 | 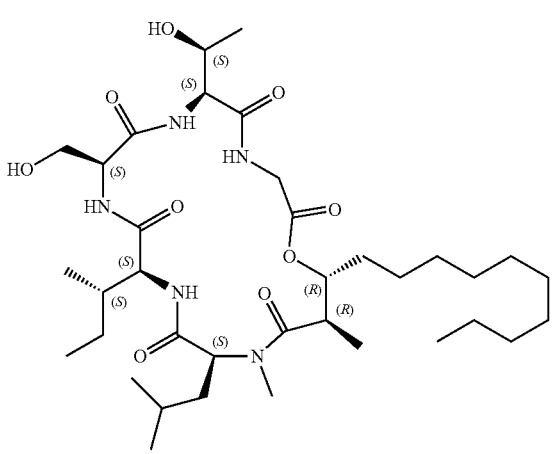(6S,9S,12S,15S,18R,19R)-12-((S)-sec-butyl)-19-decyl-6-((S)-1-hydroxyethyl)-9-(hydroxymethyl)-15-isobutyl-16,18-dimethyl-1-oxa-4,7,10,13,16-pentaazacyclononadecane-2,5,8,11,14,17-hexaone | 712.4 | 6.923, A | 8 |
| 23 | 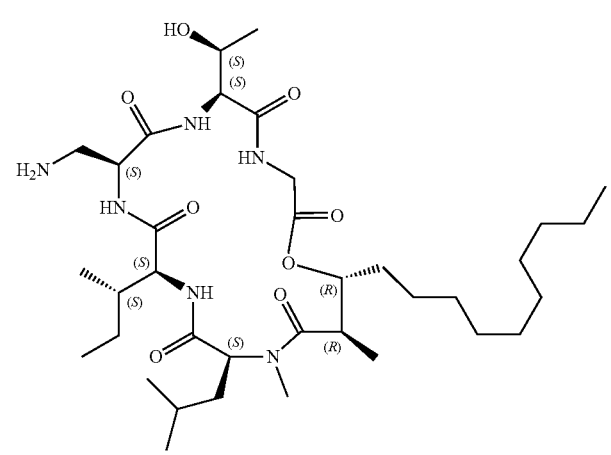(6S,9S,12S,15S,18R,19R)-9-(aminomethyl)-12-((S)-sec-butyl)-19-decyl-6-((S)-1-hydroxyethyl)-15-isobutyl-16,18-dimethyl-1-oxa-4,7,10,13,16-pentaazacyclononadecane-2,5,8,11,14,17-hexaone | 711.4 | 5.37, A | 28 (steps 1-5) & 3 (step 3) |

TABLE 5-continued
| Example | Structure/Name | LCMS [M + H]⁺ | LCMS $R^T$ (min), method | Synthesis Method/ Example # (Intermediate #) |
|---|---|---|---|---|
| 24 | 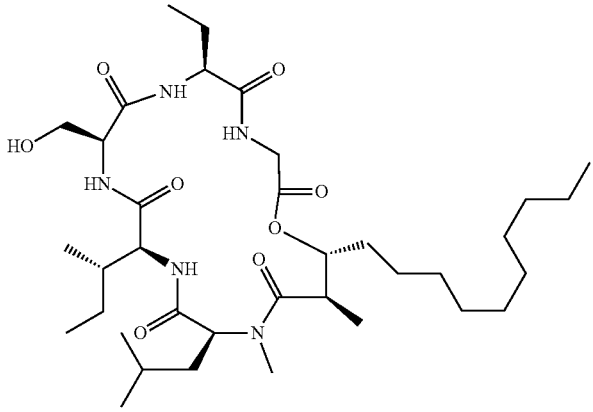 (6S,9S,12S,15S,18R,19R)-12-((S)-sec-butyl)-19-decyl-6-ethyl-9-(hydroxymethyl)-15-isobutyl-16,18-dimethyl-1-oxa-4,7,10,13,16-pentaazacyclononadecane-2,5,8,11,14,17-hexaone | 696.4 | 19.32, F | 28 |
| 25 | 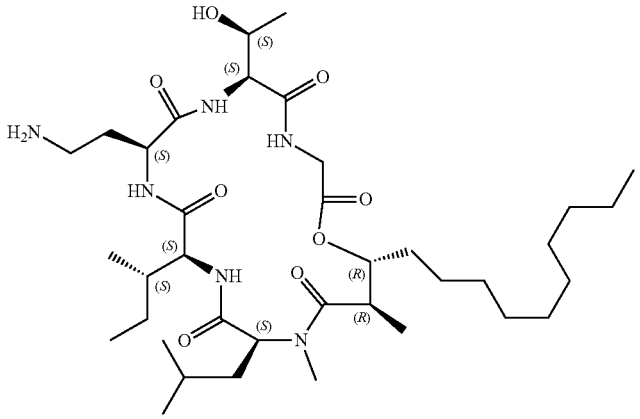 (6S,9S,12S,15S,18R,19R)-9-(2-aminoethyl)-12-((S)-sec-butyl)-19-decyl-6-((S)-1-hydroxyethyl)-15-isobutyl-16,18-dimethyl-1-oxa-4,7,10,13,16-pentaazacyclononadecane-2,5,8,11,14,17-hexaone | 725.5 | 5.43, A | 26 |

TABLE 5-continued

| Example | Structure/Name | LCMS [M + H]+ | LCMS $R^T$ (min), method | Synthesis Method/ Example # (Intermediate #) |
|---|---|---|---|---|
| 26 | 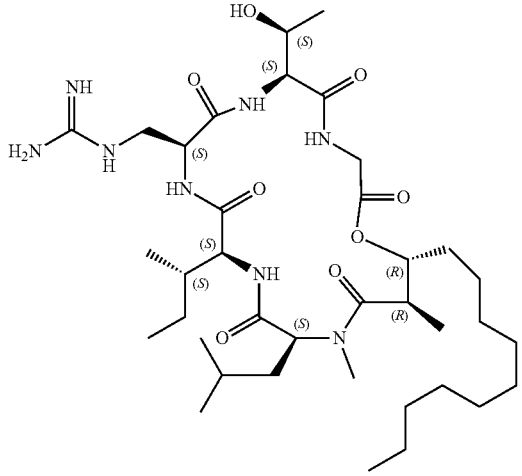<br>1-((((6S,9S,12S,15S,18R,19R)-12-((S)-sec-butyl)-19-decyl-6-((S)-1-hydroxyethyl)-15-isobutyl-16,18-dimethyl-2,5,8,11,14,17-hexaoxo-1-oxa-4,7,10,13,16-pentaazacyclononadecan-9-yl)methyl)guanidine | 753.5 | 5.46, A | 28 (steps 1-5) & 3 (step 3) |
| 27 | 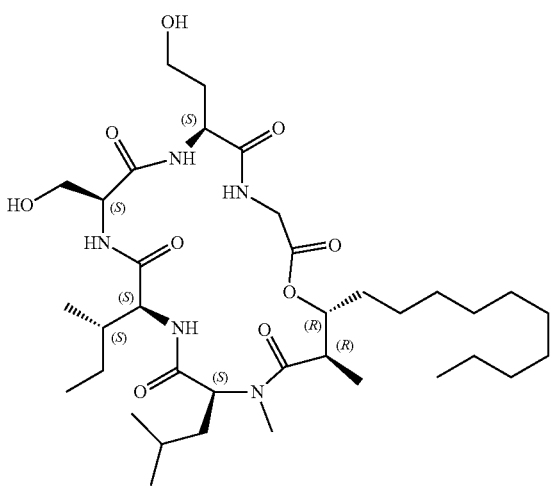<br>(6S,9S,12S,15S,18R,19R)-12-((S)-sec-butyl)-19-decyl-6-(2-hydroxyethyl)-9-(hydroxymethyl)-15-isobutyl-16,18-dimethyl-1-oxa-4,7,10,13,16-pentaazacyclononadecane-2,5,8,11,14,17-hexaone | 712.4 | 6.747, A | 1 |

TABLE 5-continued
| Example | Structure/Name | LCMS [M + H]⁺ | LCMS $R^T$ (min), method | Synthesis Method/ Example # (Intermediate #) |
|---|---|---|---|---|
| 29 | 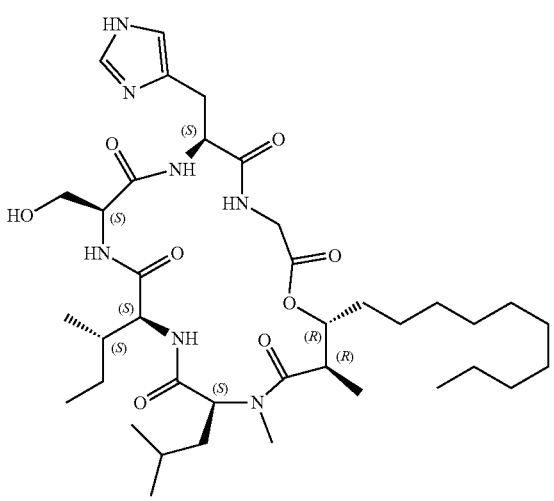<br>(6S,9S,12S,15S,18R,19R)-6-((1H-imidazol-4-yl)methyl)-12-((S)-sec-butyl)-19-decyl-9-(hydroxymethyl)-15-isobutyl-16,18-dimethyl-1-oxa-4,7,10,13,16-pentaazacyclononadecane-2,5,8,11,14,17-hexaone | 748.5 | 1.94, C | 1 |
| 30 | 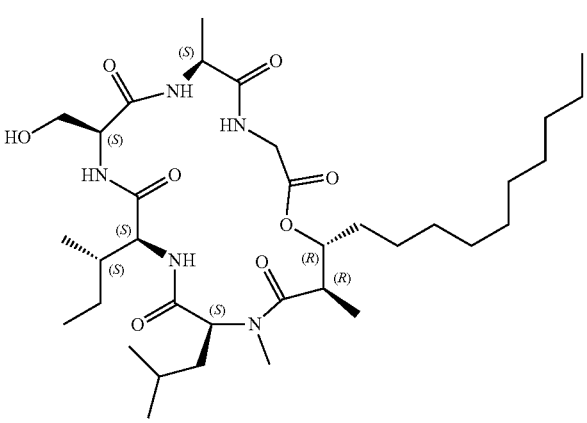<br>(6S,9S,12S,15S,18R,19R)-12-((S)-sec-butyl)-19-decyl-9-(hydroxymethyl)-15-isobutyl-6,16,18-trimethyl-1-oxa-4,7,10,13,16-pentaazacyclononadecane-2,5,8,11,14,17-hexaone | 682.6 | 2.18, G | 1 |

TABLE 5-continued
| Example | Structure/Name | LCMS [M + H]+ | LCMS R$^T$ (min), method | Synthesis Method/ Example # (Intermediate #) |
|---|---|---|---|---|
| 31 | 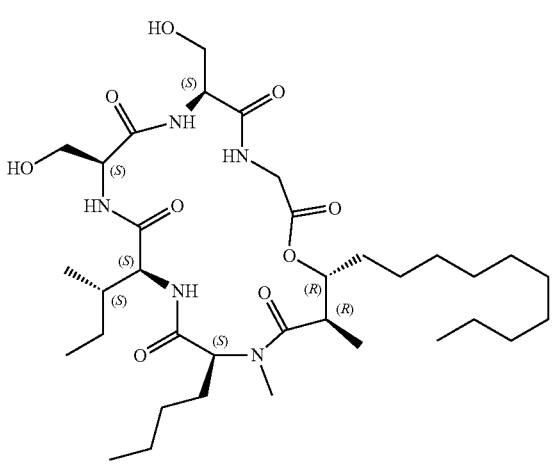<br>(6S,9S,12S,15S,18R,19R)-12-((S)-sec-butyl)-15-butyl-19-decyl-6,9-bis(hydroxymethyl)-16,18-dimethyl-1-oxa-4,7,10,13,16-pentaazacyclononadecane-2,5,8,11,14,17-hexaone | 698.5 | 6.726, A | 1 |
| 32 | 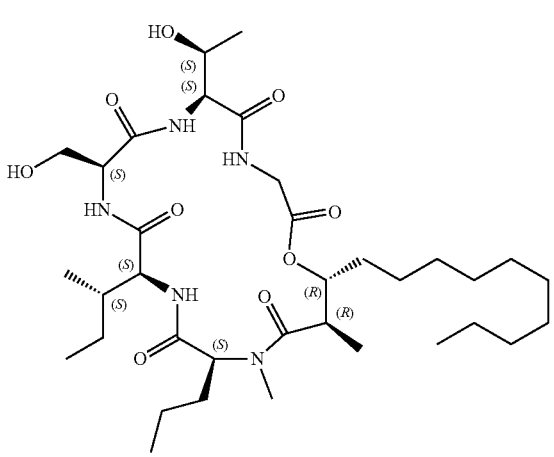<br>(6S,9S,12S,15S,18R,19R)-12-((S)-sec-butyl)-19-decyl-6-((S)-1-hydroxyethyl)-9-(hydroxymethyl)-16,18-dimethyl-15-propyl-1-oxa-4,7,10,13,16-pentaazacyclononadecane-2,5,8,11,14,17-hexaone | 698.5 | 2.28, C | 1 |

TABLE 5-continued

| Example | Structure/Name | LCMS [M + H]⁺ | LCMS R$^T$ (min), method | Synthesis Method/ Example # (Intermediate #) |
|---|---|---|---|---|
| 33 | (6S,9S,12S,15S,18R,19R)-12-((S)-sec-butyl)-19-dodecyl-6-((S)-1-hydroxyethyl)-9-(hydroxymethyl)-15-isobutyl-16,18-dimethyl-1-oxa-4,7,10,13,16-pentaazacyclononadecane-2,5,8,11,14,17-hexaone | 726.5 | 2.38, C | 1 |
| 34 | (6S,9S,12S,15S,18R,19R)-9-(aminomethyl)-12-((R)-sec-butyl)-19-hexyl-6-((S)-1-hydroxyethyl)-15-isobutyl-16,18-dimethyl-1-oxa-4,7,10,13,16-pentaazacyclononadecane-2,5,8,11,14,17-hexaone | 655.5 | 4.53, A | 26 |

TABLE 5-continued
| Example | Structure/Name | LCMS [M + H]+ | LCMS R$^T$ (min), method | Synthesis Method/ Example # (Intermediate #) |
|---|---|---|---|---|
| 35 | 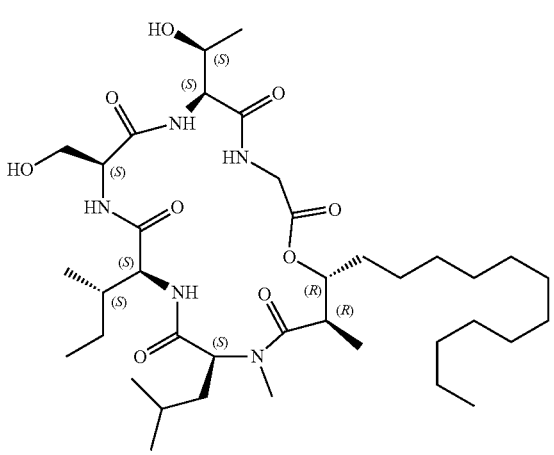 (6S,9S,12S,15S,18R,19R)-12-((S)-sec-butyl)-19-dodecyl-6-((S)-1-hydroxyethyl)-9-(hydroxymethyl)-15-isobutyl-16,18-dimethyl-1-oxa-4,7,10,13,16-pentaazacyclononadecane-2,5,8,11,14,17-hexaone | 740.5 | 3.05, I | 1 (T3) |
| 36 | 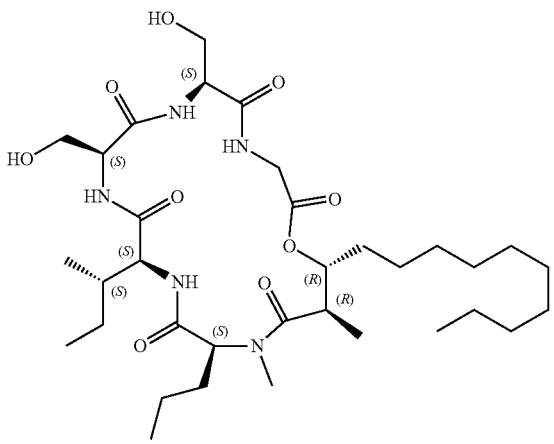 (6S,9S,12S,15S,18R,19R)-12-((S)-sec-butyl)-19-decyl-6,9-bis(hydroxymethyl)-16,18-dimethyl-15-propyl-1-oxa-4,7,10,13,16-pentaazacyclononadecane-2,5,8,11,14,17-hexaone | 684.5 | 2.23, C | 1 |

TABLE 5-continued

| Example | Structure/Name | LCMS [M + H]+ | LCMS R$^T$ (min), method | Synthesis Method/ Example # (Intermediate #) |
|---|---|---|---|---|
| 37 | 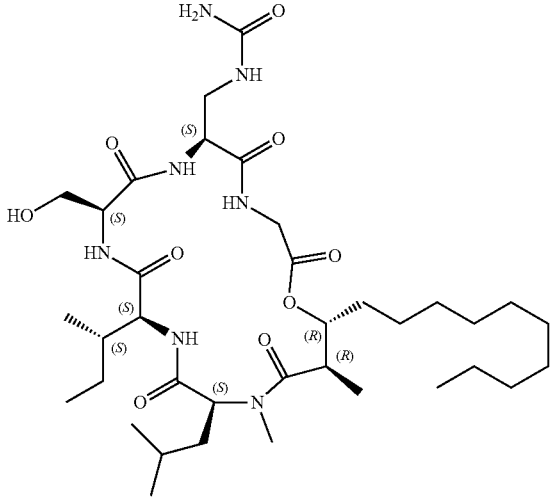<br>1-((((6S,9S,12S,15S,18R,19R)-12-((S)-sec-butyl)-19-decyl-9-(hydroxymethyl)-15-isobutyl-16,18-dimethyl-2,5,8,11,14,17-hexaoxo-1-oxa-4,7,10,13,16-pentaazacyclononadecan-6-yl)methyl)urethyl acetate | 740.5 | 2.27 C | 3 |
| 38 | 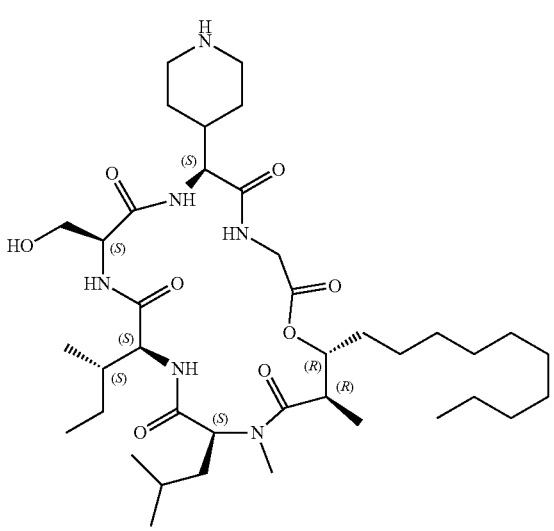<br>(6S,9S,12S,15S,18R,19R)-12-((S)-sec-butyl)-19-decyl-9-(hydroxymethyl)-15-isobutyl-16,18-dimethyl-6-(piperidin-4-yl)-1-oxa-4,7,10,13,16-pentaazacyclononadecane-2,5,8,11,14,17-hexaone | 751.6 | 1.97, C | 1 |

TABLE 5-continued
| Example | Structure/Name | LCMS [M + H]+ | LCMS R^T (min), method | Synthesis Method/ Example # (Intermediate #) |
|---|---|---|---|---|
| 39 | 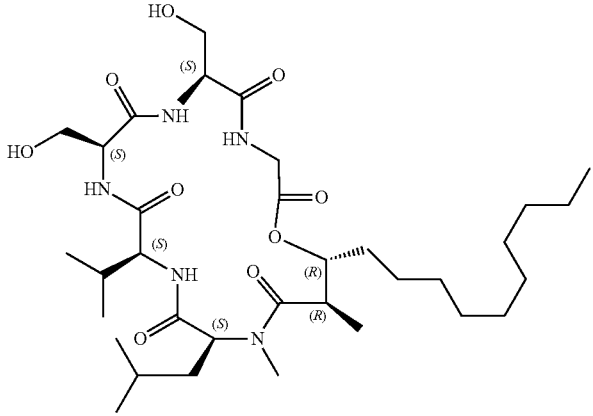<br>(6S,9S,12S,15S,18R,19R)-19-decyl-6,9-bis(hydroxymethyl)-15-isobutyl-12-isopropyl-16,18-dimethyl-1-oxa-4,7,10,13,16-pentaazacyclononadecane-2,5,8,11,14,17-hexaone | 684.5 | 6.53, A | 1 |
| 41 | 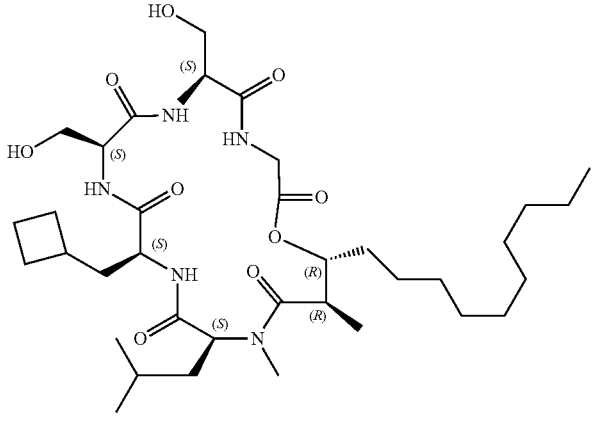<br>(6S,9S,12S,15S,18R,19R)-12-(cyclobutylmethyl)-19-decyl-6,9-bis(hydroxymethyl)-15-isobutyl-16,18-dimethyl-1-oxa-4,7,10,13,16-pentaazacyclononadecane-2,5,8,11,14,17-hexaone | 710.47 | 6.63, E | 1 |

TABLE 5-continued
| Example | Structure/Name | LCMS [M + H]+ | LCMS R$^T$ (min), method | Synthesis Method/ Example # (Intermediate #) |
|---|---|---|---|---|
| 42 | 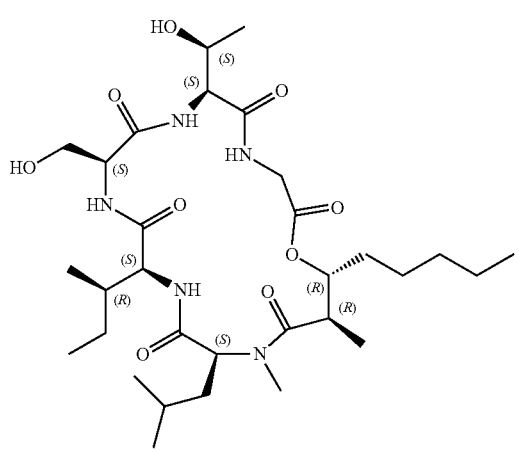<br>(6S,9S,12S,15S,18R,19R)-12-((R)-sec-butyl)-6-((S)-1-hydroxyethyl)-9-(hydroxymethyl)-15-isobutyl-16,18-dimethyl-19-(2-propylpentyl)-1-oxa-4,7,10,13,16-pentaazacyclononadecane-2,5,8,11,14,17-hexaone | 684.5 | 2.09, J | 1 (T7) |
| 43 | 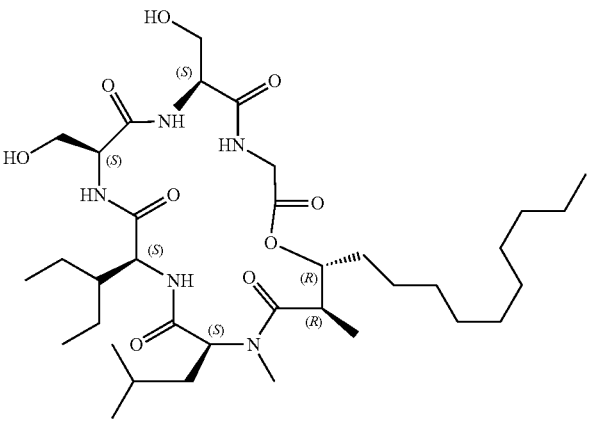<br>(6S,9S,12S,15S,18R,19R)-19-decyl-6,9-bis(hydroxymethyl)-15-isobutyl-16,18-dimethyl-12-(pentan-3-yl)-1-oxa-4,7,10,13,16-pentaazacyclononadecane-2,5,8,11,14,17-hexaone | 712.48 | 6.78, E | 1 |

TABLE 5-continued

| Example | Structure/Name | LCMS [M + H]⁺ | LCMS $R^T$ (min), method | Synthesis Method/ Example # (Intermediate #) |
|---|---|---|---|---|
| 44 | (6S,9S,12S,15S,18R,19R)-12-((S)-sec-butyl)-19-(5,5-dimethylhexyl)-6-((S)-1-hydroxyethyl)-9-(hydroxymethyl)-15-isobutyl-16,18-dimethyl-1-oxa-4,7,10,13,16-pentaazacyclononadecane-2,5,8,11,14,17-hexaone | 684.5 | 2.11, C | 1 (T5) |
| 45 | (6S,9S,12S,15S,18R,19R)-9-(aminomethyl)-12-cyclopentyl-19-decyl-6-((S)-1-hydroxyethyl)-15-isobutyl-16,18-dimethyl-1-oxa-4,7,10,13,16-pentaazacyclononadecane-2,5,8,11,14,17-hexaone | 723.5 | 5.43, E | 53 |

TABLE 5-continued
| Example | Structure/Name | LCMS [M + H]+ | LCMS R$^T$ (min), method | Synthesis Method/ Example # (Intermediate #) |
|---|---|---|---|---|
| 46 | 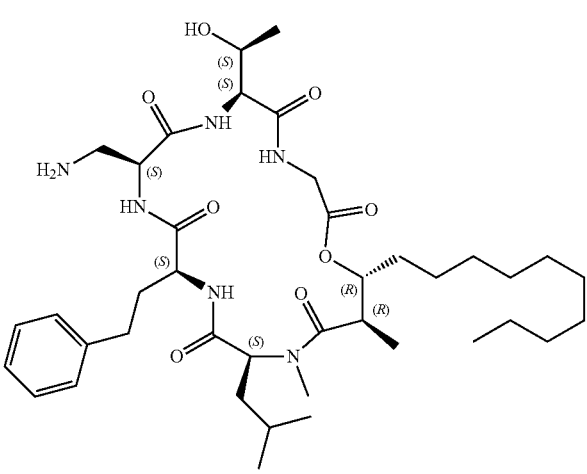 (6S,9S,12S,15S,18R,19R)-9-(aminomethyl)-19-decyl-6-((S)-1-hydroxyethyl)-15-isobutyl-16,18-dimethyl-12-phenethyl-1-oxa-4,7,10,13,16-pentaazacyclononadecane-2,5,8,11,14,17-hexaone | 759.5 | 2.09, C | 1 |
| 47 | 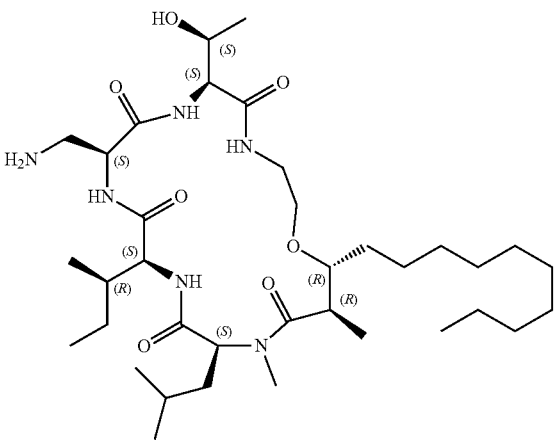 (6S,9S,12S,15S,18R,19R)-9-(aminomethyl)-12-((R)-sec-butyl)-19-decyl-6-((S)-1-hydroxyethyl)-15-isobutyl-16,18-dimethyl-1-oxa-4,7,10,13,16-pentaazacyclononadecane-5,8,11,14,17-pentaone | 697.6 | 2.06, C | 57 |

TABLE 5-continued

| Example | Structure/Name | LCMS [M + H]⁺ | LCMS $R^T$ (min), method | Synthesis Method/ Example # (Intermediate #) |
|---|---|---|---|---|
| 48 | 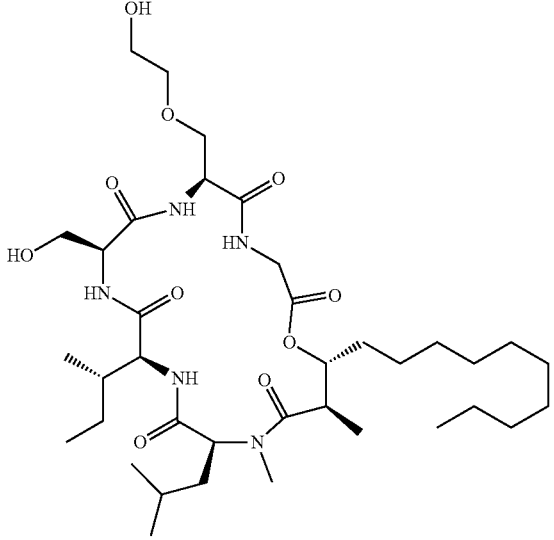<br>(6S,9S,12S,15S,18R,19R)-12-((S)-sec-butyl)-19-decyl-6-((2-hydroxyethoxy)methyl)-9-(hydroxymethyl)-15-isobutyl-16,18-dimethyl-1-oxa-4,7,10,13,16-pentaazacyclononadecane-2,5,8,11,14,17-hexaone | 742.5 | 2.26, C | 1 (P2A) |
| 49 | 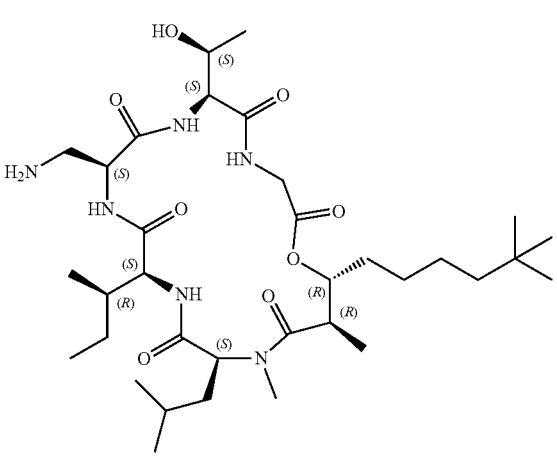<br>(6S,9S,12S,15S,18R,19R)-9-(aminomethyl)-12-((R)-sec-butyl)-19-(5,5-dimethylhexyl)-6-((S)-1-hydroxyethyl)-15-isobutyl-16,18-dimethyl-1-oxa-4,7,10,13,16-pentaazacyclononadecane-2,5,8,11,14,17-hexaone | 683.6 | 1.86, C | 1 (T5) |

TABLE 5-continued
| Example | Structure/Name | LCMS [M + H]+ | LCMS R$^T$ (min), method | Synthesis Method/ Example # (Intermediate #) |
|---|---|---|---|---|
| 50 | 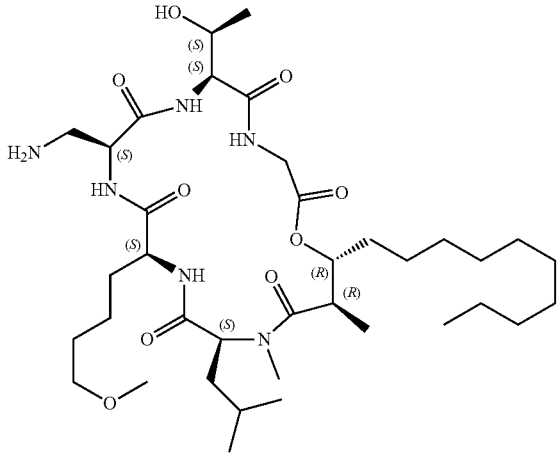 (6S,9S,12S,15S,18R,19R)-9-(aminomethyl)-19-decyl-6-((S)-1-hydroxyethyl)-15-isobutyl-12-(4-methoxybutyl)-16,18-dimethyl-1-oxa-4,7,10,13,16-pentaazacyclononadecane-2,5,8,11,14,17-hexaone | 741.6 | 1.99, C | 1 |
| 87 | 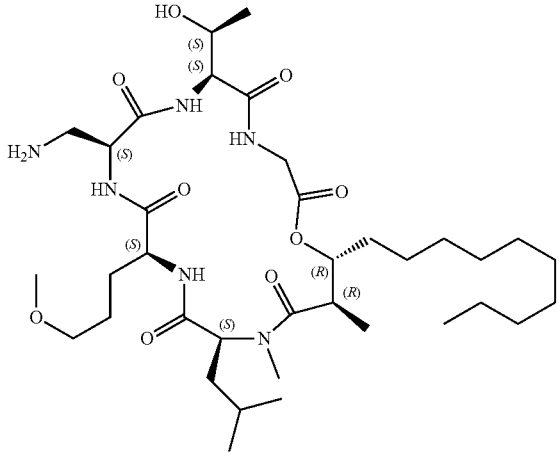 (6S,9S,12S,15S,18R,19R)-9-(aminomethyl)-19-decyl-6-((S)-1-hydroxyethyl)-15-isobutyl-12-(3-methoxypropyl)-16,18-dimethyl-1-oxa-4,7,10,13,16-pentaazacyclononadecane-2,5,8,11,14,17-hexaone | 727.5 | 1.96, C | 1 |

TABLE 5-continued
| Example | Structure/Name | LCMS [M + H]+ | LCMS R$^T$ (min), method | Synthesis Method/ Example # (Intermediate #) |
|---|---|---|---|---|
| 88 | 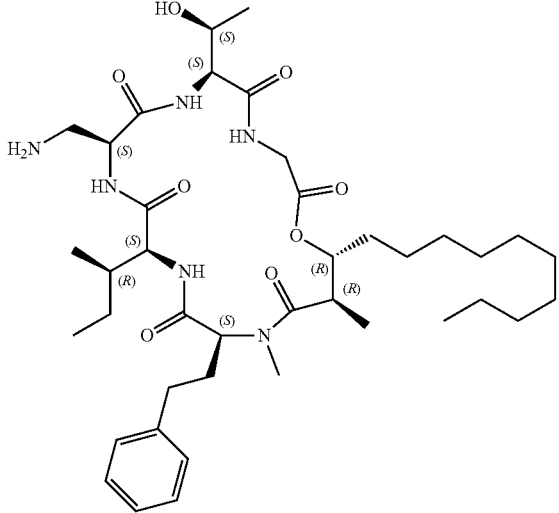 (6S,9S,12S,15S,18R,19R)-9-(aminomethyl)-12-((R)-sec-butyl)-19-decyl-6-((S)-1-hydroxyethyl)-16,18-dimethyl-15-phenethyl-1-oxa-4,7,10,13,16-pentaazacyclononadecane-2,5,8,11,14,17-hexaone | 759.5 | 2.12, C | 1 |
| 89 | 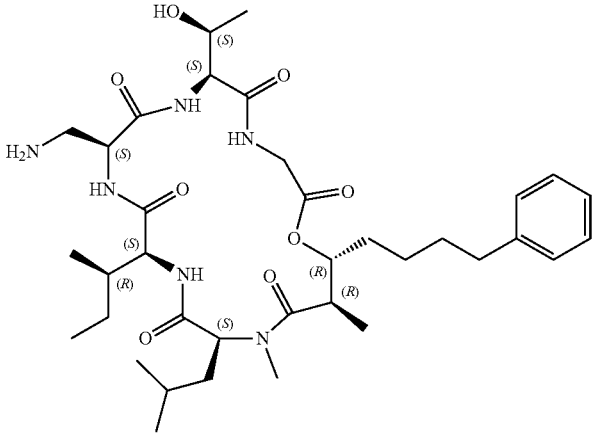 (6S,9S,12S,15S,18R,19R)-9-(aminomethyl)-12-((R)-sec-butyl)-6-((S)-1-hydroxyethyl)-15-isobutyl-16,18-dimethyl-19-(4-phenylbutyl)-1-oxa-4,7,10,13,16-pentaazacyclononadecane-2,5,8,11,14,17-hexaone | 703.4 | 1.75, C | 1 |

TABLE 5-continued
| Example | Structure/Name | LCMS [M + H]+ | LCMS R^T (min), method | Synthesis Method/ Example # (Intermediate #) |
|---|---|---|---|---|
| 90 | 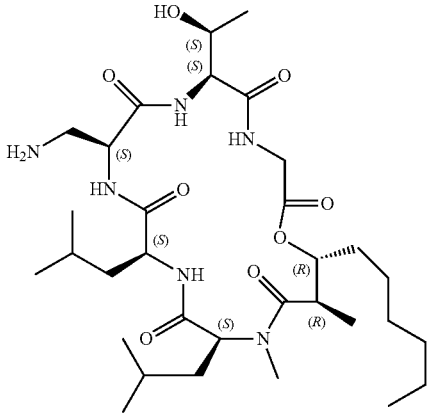<br>(6S,9S,12S,15S,18R,19R)-9-(aminomethyl)-19-hexyl-6-((S)-1-hydroxyethyl)-12,15-diisobutyl-16,18-dimethyl-1-oxa-4,7,10,13,16-pentaazacyclononadecane-2,5,8,11,14,17-hexaone | 55.5 | 4.57 A | 1 |
| 91 | 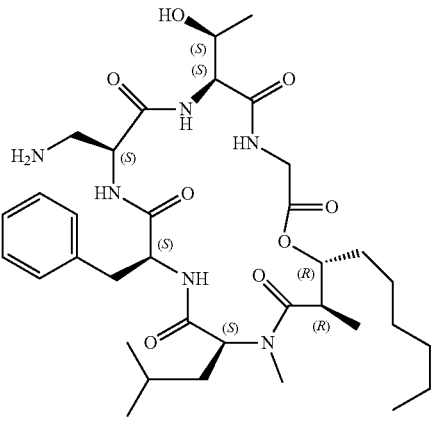<br>(6S,9S,12S,15S,18R,19R)-9-(aminomethyl)-12-benzyl-19-hexyl-6-((S)-1-hydroxyethyl)-15-isobutyl-16,18-dimethyl-1-oxa-4,7,10,13,16-pentaazacyclononadecane-2,5,8,11,14,17-hexaone | 89.5 | 4.56 A | 1 |

TABLE 5-continued

| Example | Structure/Name | LCMS [M + H]+ | LCMS R$^T$ (min), method | Synthesis Method/ Example # (Intermediate #) |
|---|---|---|---|---|
| 92 | 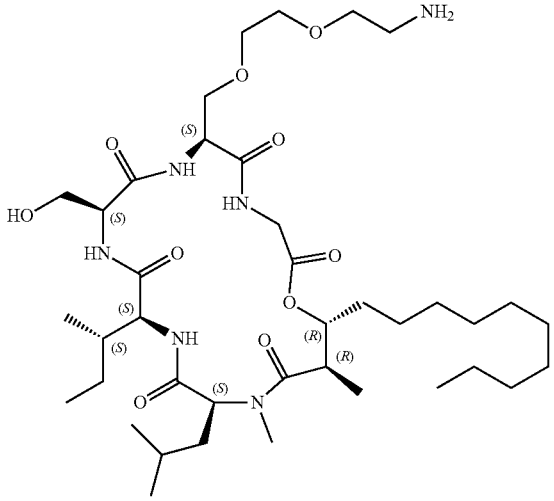<br>(6S,9S,12S,15S,18R,19R)-6-((2-(2-aminoethoxy)ethoxy)methyl)-12-((S)-sec-butyl)-19-decyl-9-(hydroxymethyl)-15-isobutyl-16,18-dimethyl-1-oxa-4,7,10,13,16-pentaazacyclononadecane-2,5,8,11,14,17-hexaone | 785.5 | 1.98, C | 3 (P2G) |
| 93 | 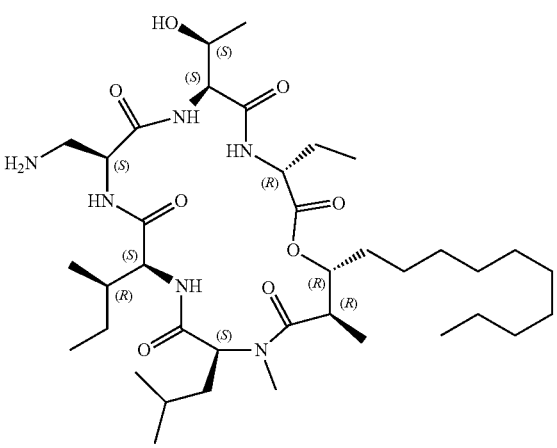<br>(3R,6S,9S,12S,15S,18R,19R)-9-(aminomethyl)-12-((R)-sec-butyl)-19-decyl-3-ethyl-6-((S)-1-hydroxyethyl)-15-isobutyl-16,18-dimethyl-1-oxa-4,7,10,13,16-pentaazacyclononadecane-2,5,8,11,14,17-hexaone | 739.6 | 2.13 C | 1 |

TABLE 5-continued

| Example | Structure/Name | LCMS [M + H]+ | LCMS R$^T$ (min), method | Synthesis Method/ Example # (Intermediate #) |
|---|---|---|---|---|
| 94 | 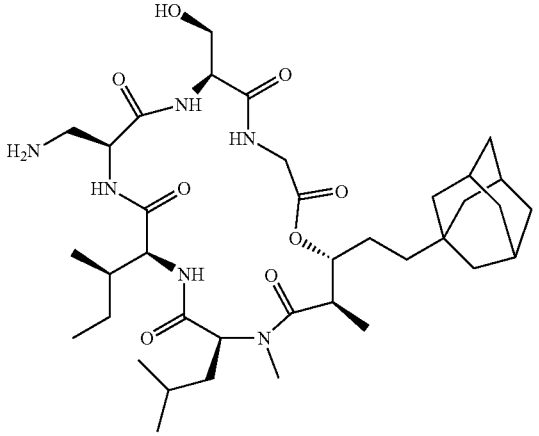<br>(6S,9S,12S,15S,18R,19R)-19-(2-((1r,3S)-adamantan-1-yl)ethyl)-9-(aminomethyl)-12-((R)-sec-butyl)-6-(hydroxymethyl)-15-isobutyl-16,18-dimethyl-1-oxa-4,7,10,13,16-pentaazacyclononadecane-2,5,8,11,14,17-hexaone | 719.5 | 5.059, A | 63 |
| 95 | 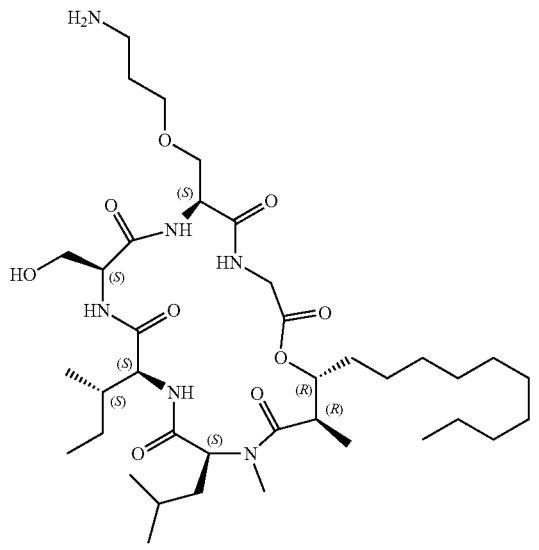<br>(6S,9S,12S,15S,18R,19R)-6-((3-aminopropoxy)methyl)-12-((S)-sec-butyl)-19-decyl-9-(hydroxymethyl)-15-isobutyl-16,18-dimethyl-1-oxa-4,7,10,13,16-pentaazacyclononadecane-2,5,8,11,14,17-hexaone | 755.5 | 2.00, C | 3 |

TABLE 5-continued

| Example | Structure/Name | LCMS [M + H]+ | LCMS R^T (min), method | Synthesis Method/ Example # (Intermediate #) |
|---|---|---|---|---|
| 96 | 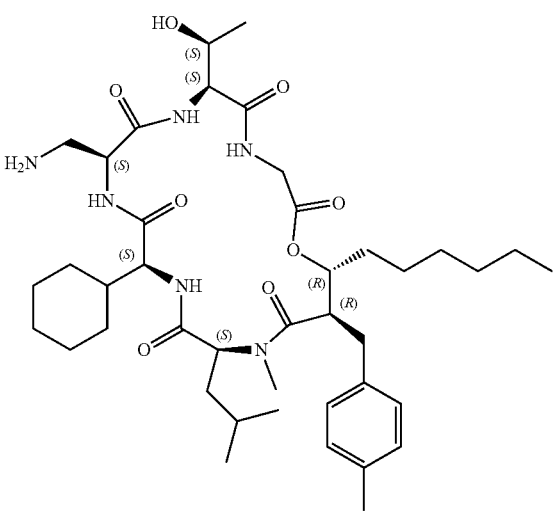<br>(6S,9S,12S,15S,18R,19R)-9-(aminomethyl)-12-cyclohexyl-19-hexyl-6-((S)-1-hydroxyethyl)-15-isobutyl-16-methyl-18-(4-methylbenzyl)-1-oxa-4,7,10,13,16-pentaazacyclononadecane-2,5,8,11,14,17-hexaone | 771.4 | 5.384, A | 54 |
| 97 | 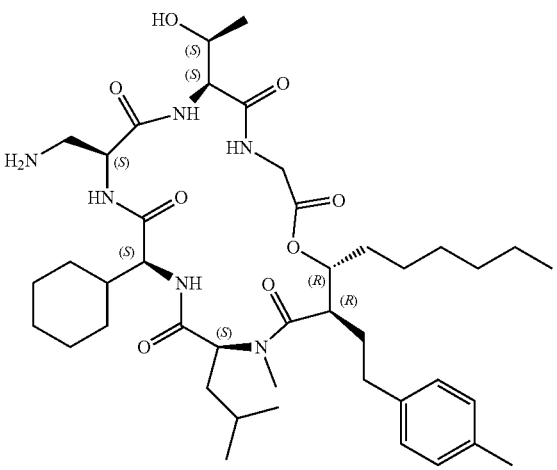<br>(6S,9S,12S,15S,18R,19R)-9-(aminomethyl)-12-cyclohexyl-19-hexyl-6-((S)-1-hydroxyethyl)-15-isobutyl-16-methyl-18-(4-methylphenethyl)-1-oxa-4,7,10,13,16-pentaazacyclononadecane-2,5,8,11,14,17-hexaone | 785.4 | 5.56, A | 54 |

TABLE 5-continued
| Example | Structure/Name | LCMS [M + H]⁺ | LCMS R$^T$ (min), method | Synthesis Method/ Example # (Intermediate #) |
|---|---|---|---|---|
| 98 | 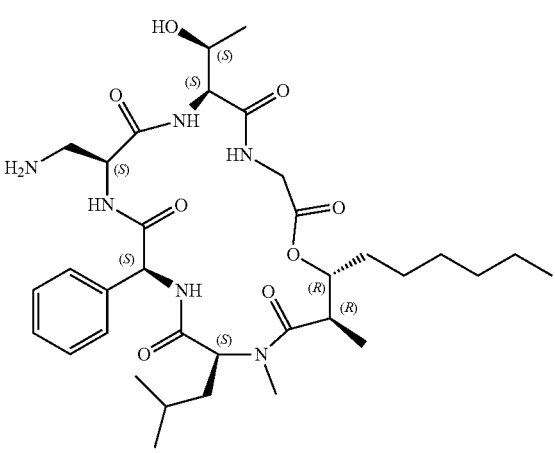<br>(6S,9S,12S,15S,18R,19R)-9-(aminomethyl)-19-hexyl-6-((S)-1-hydroxyethyl)-15-isobutyl-16,18-dimethyl-12-phenyl-1-oxa-4,7,10,13,16-pentaazacyclononadecane-2,5,8,11,14,17-hexaone | 675.4 | 1.77 C | 1 |
| 99 | 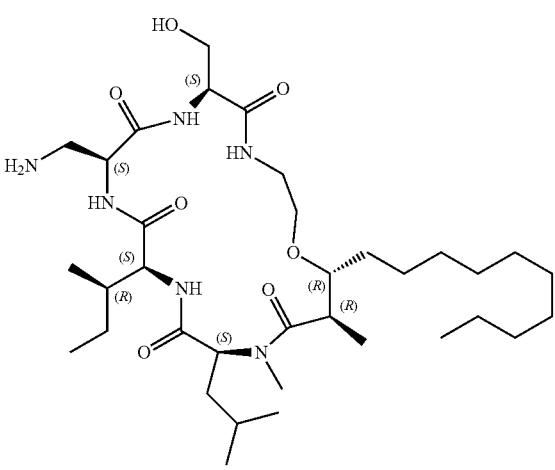<br>(6S,9S,12S,15S,18R,19R)-6-(aminomethyl)-12-((R)-sec-butyl)-19-decyl-6-(hydroxymethyl)-15-isobutyl-16,18-dimethyl-1-oxa-4,7,10,13,16-pentaazacyclononadecane-5,8,11,14,17-pentaone | 683.6 | 2.10, C | 57 |

TABLE 5-continued
| Example | Structure/Name | LCMS [M + H]+ | LCMS R$^T$ (min), method | Synthesis Method/ Example # (Intermediate #) |
|---|---|---|---|---|
| 100 | 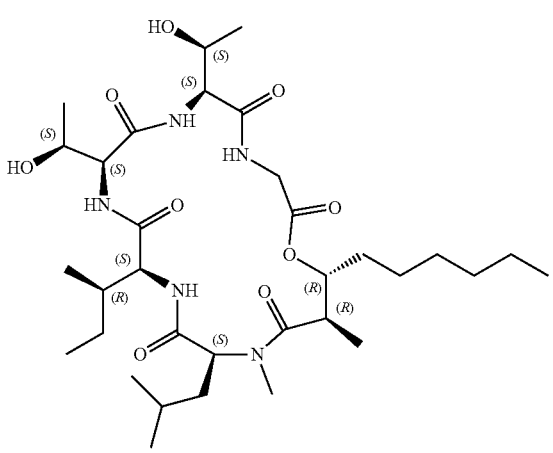<br>(6S,9S,12S,15S,18R,19R)-12-((R)-sec-butyl)-19-hexyl-6,9-bis((S)-1-hydroxyethyl)-15-isobutyl-16,18-dimethyl-1-oxa-4,7,10,13,16-pentaazacyclononadecane-2,5,8,11,14,17-hexaone | 670.4 | 1.98, C | 1 |
| 101 | 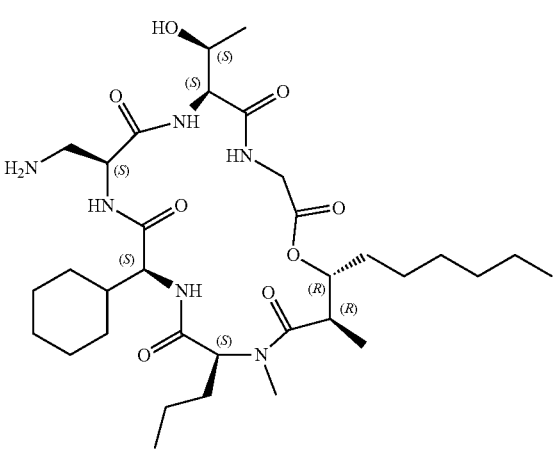<br>(6S,9S,12S,15S,18R,19R)-9-(aminomethyl)-12-cyclohexyl-19-hexyl-6-((S)-1-hydroxyethyl)-16,18-dimethyl-15-propyl-1-oxa-4,7,10,13,16-pentaazacyclononadecane-2,5,8,11,14,17-hexaone | 667.5 | 1.72, C | 1 |

TABLE 5-continued

| Example | Structure/Name | LCMS [M + H]⁺ | LCMS $R^T$ (min), method | Synthesis Method/ Example # (Intermediate #) |
|---|---|---|---|---|
| 102 | 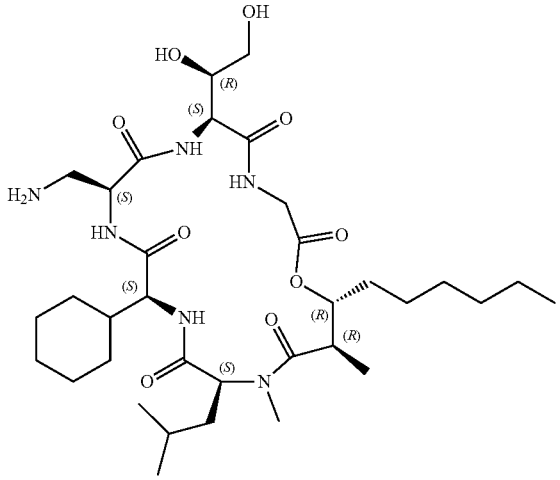<br>(6S,9S,12S,15S,18R,19R)-9-(aminomethyl)-12-cyclohexyl-6-((R)-1,2-dihydroxyethyl)-19-hexyl-15-isobutyl-16,18-dimethyl-1-oxa-4,7,10,13,16-pentaazacyclononadecane-2,5,8,11,14,17-hexaone | 697.4 | 1.72, C | 3 (P2J) |
| 103 | 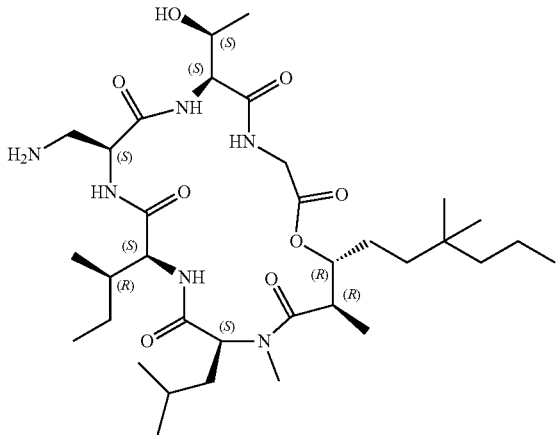<br>(6S,9S,12S,15S,18R,19R)-9-(aminomethyl)-12-((R)-sec-butyl)-19-(3,3-dimethylhexyl)-6-((S)-1-hydroxyethyl)-15-isobutyl-16,18-dimethyl-1-oxa-4,7,10,13,16-pentaazacyclononadecane-2,5,8,11,14,17-hexaone | 683.5 | 1.85, C | 1 (T6) |

TABLE 5-continued

| Example | Structure/Name | LCMS [M + H]+ | LCMS R$^T$ (min), method | Synthesis Method/ Example # (Intermediate #) |
| --- | --- | --- | --- | --- |
| 104 | 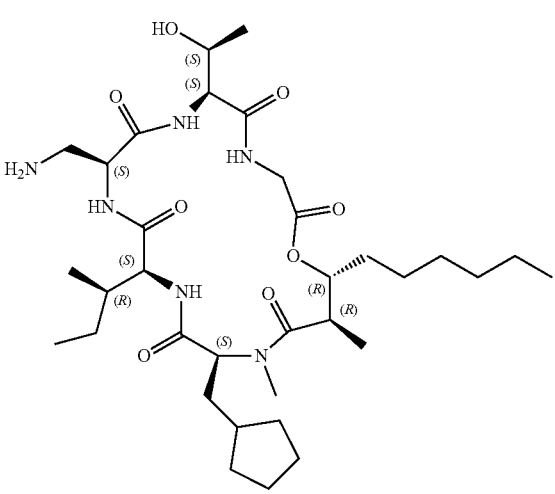<br>(6S,9S,12S,15S,18R,19R)-9-(aminomethyl)-12-((R)-sec-butyl)-15-(cyclopentylmethyl)-19-hexyl-6-((S)-1-hydroxyethyl)-16,18-dimethyl-1-oxa-4,7,10,13,16-pentaazacyclononadecane-2,5,8,11,14,17-hexaone | 681.4 | 1.83, C | 1 |
| 105 | 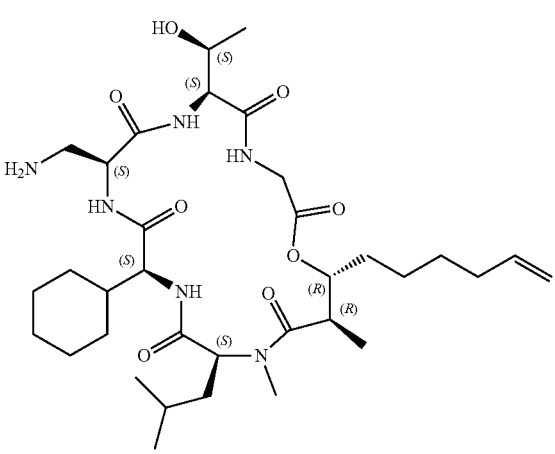<br>(6S,9S,12S,15S,18R,19R)-9-(aminomethyl)-12-cyclohexyl-19-(hex-5-en-1-yl)-6-((S)-1-hydroxyethyl)-15-isobutyl-16,18-dimethyl-1-oxa-4,7,10,13,16-pentaazacyclononadecane-2,5,8,11,14,17-hexaone | 679.4 | 1.73, C | 3 |

TABLE 5-continued

| Example | Structure/Name | LCMS [M + H]⁺ | LCMS $R^T$ (min), method | Synthesis Method/ Example # (Intermediate #) |
|---|---|---|---|---|
| 106 | 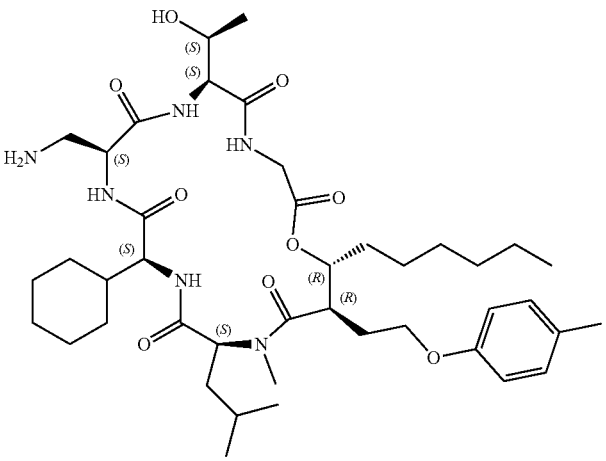<br>(6S,9S,12S,15S,18R,19R)-9-(aminomethyl)-12-cyclohexyl-19-hexyl-6-((S)-1-hydroxyethyl)-15-isobutyl-16-methyl-18-(2-(p-tolyloxy)ethyl)-1-oxa-4,7,10,13,16-pentaazacyclononadecane-2,5,8,11,14,17-hexaone | 801.4 | 5.545, A | 54 |
| 107 | 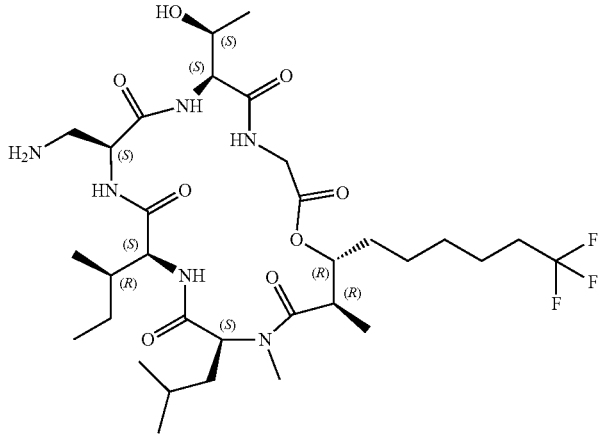<br>(6S,9S,12S,15S,18R,19R)-9-(aminomethyl)-12-((R)-sec-butyl)-6-((S)-1-hydroxyethyl)-15-isobutyl-16,18-dimethyl-19-(6,6,6-trifluorohexyl)-1-oxa-4,7,10,13,16-pentaazacyclononadecane-2,5,8,11,14,17-hexaone | 709.4 | 1.69, C | 1 (T4) |

TABLE 5-continued

| Example | Structure/Name | LCMS [M + H]+ | LCMS $R^T$ (min), method | Synthesis Method/ Example # (Intermediate #) |
|---|---|---|---|---|
| 108 | 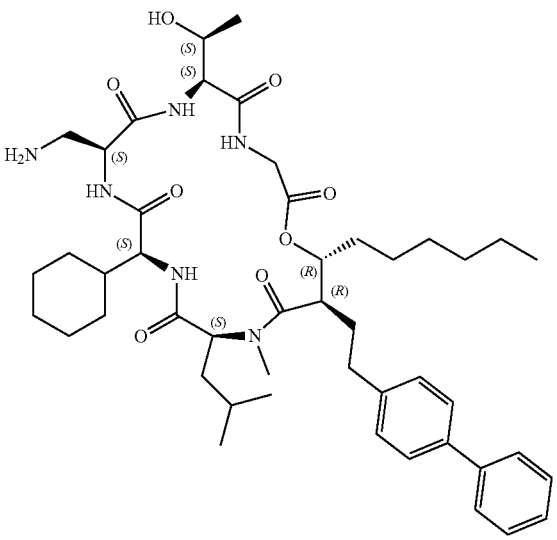<br>(6S,9S,12S,15S,18R,19R)-18-(2-([1,1'-biphenyl]-4-yl)ethyl)-9-(aminomethyl)-12-cyclohexyl-19-hexyl-6-((S)-1-hydroxyethyl)-15-isobutyl-16-methyl-1-oxa-4,7,10,13,16-pentaazacyclononadecane-2,5,8,11,14,17-hexaone | 847.4 | 5.846, A | 54 |
| 109 | 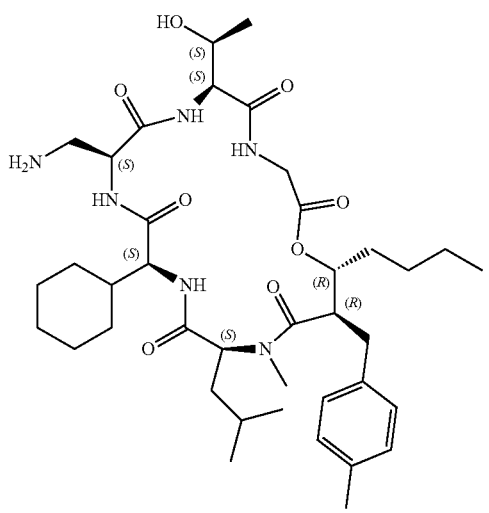<br>(6S,9S,12S,15S,18R,19R)-9-(aminomethyl)-19-butyl-12-cyclohexyl-6-((S)-1-hydroxyethyl)-15-isobutyl-16-methyl-18-(4-methylbenzyl)-1-oxa-4,7,10,13,16-pentaazacyclononadecane-2,5,8,11,14,17-hexaone | 743.3 | 4.961, A | 54 |

437	438

TABLE 5-continued

| Example | Structure/Name | LCMS [M + H]+ | LCMS R$^T$ (min), method | Synthesis Method/ Example # (Intermediate #) |
|---|---|---|---|---|
| 110 | 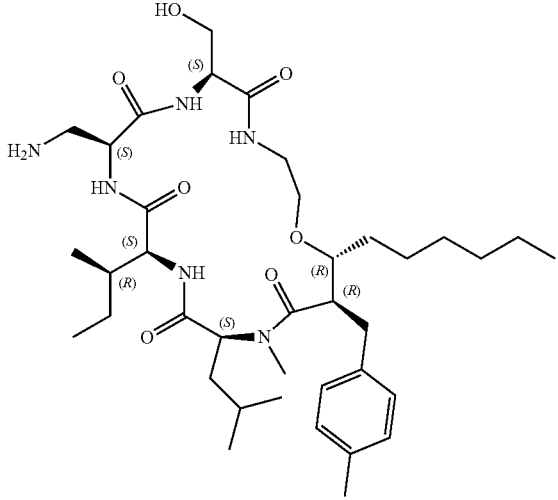<br>(6S,9S,12S,15S,18R,19R)-9-(aminomethyl)-12-((R)-sec-butyl)-19-hexyl-6-(hydroxymethyl)-15-isobutyl-16-methyl-18-(4-methylbenzyl)-1-oxa-4,7,10,13,16-pentaazacyclononadecane-5,8,11,14,17-pentaone | 717.4 | 5.266, A | 57 and 54 |
| 111 | 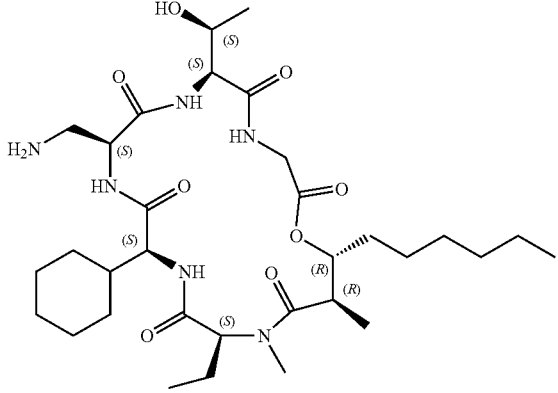<br>(6S,9S,12S,15S,18R,19R)-9-(aminomethyl)-12-cyclohexyl-15-ethyl-19-hexyl-6-((S)-1-hydroxyethyl)-16,18-dimethyl-1-oxa-4,7,10,13,16-pentaazacyclononadecane-2,5,8,11,14,17-hexaone | 653.4 | 1.64, C | 1 |

TABLE 5-continued

| Example | Structure/Name | LCMS [M + H]+ | LCMS R$^T$ (min), method | Synthesis Method/ Example # (Intermediate #) |
|---|---|---|---|---|
| 112 | (6S,9S,12S,15S,18R,19R)-9-(aminomethyl)-12-cyclohexyl-6-((S)-1-hydroxyethyl)-15-isobutyl-16-methyl-18-(4-methylbenzyl)-19-(3,3,3-trifluoropropyl)-1-oxa-4,7,10,13,16-pentaazacyclononadecane-2,5,8,11,14,17-hexaone | 783.3 | 4.832, A | 54 |
| 113 | (6S,9S,12S,15S,18R,19R)-9-(aminomethyl)-12-((R)-sec-butyl)-19-hexyl-6-(hydroxymethyl)-15-isobutyl-16,18-dimethyl-1-oxa-4,7,10,13,16-pentaazacyclononadecane-5,8,11,14,17-pentaone | 627.4 | 1.69, C | 57 |

TABLE 5-continued

| Example | Structure/Name | LCMS [M + H]⁺ | LCMS R$^T$ (min), method | Synthesis Method/ Example # (Intermediate #) |
|---|---|---|---|---|
| 114 | (6S,9S,12S,15S,18R,19R)-9-(aminomethyl)-12-cyclohexyl-19-(7-hydroxy-7-methyloctyl)-6-((S)-1-hydroxyethyl)-15-isobutyl-16,18-dimethyl-1-oxa-4,7,10,13,16-pentaazacyclononadecane-2,5,8,11,14,17-hexaone | 739.5 | 1.61, C | 1 |
| 115 | (6S,9S,12S,15S,18R,19R)-9-(aminomethyl)-12-cyclohexyl-19-hexyl-6-((S)-1-hydroxyethyl)-15-isobutyl-16,18-dimethyl-1-oxa-4,7,10,13,16-pentaazacyclononadecane-5,8,11,14,17-pentaone | 667.5 | 1.84, K | 57 |

TABLE 5-continued
| Example | Structure/Name | LCMS [M + H]+ | LCMS R$^T$ (min), method | Synthesis Method/ Example # (Intermediate #) |
|---|---|---|---|---|
| 116 | 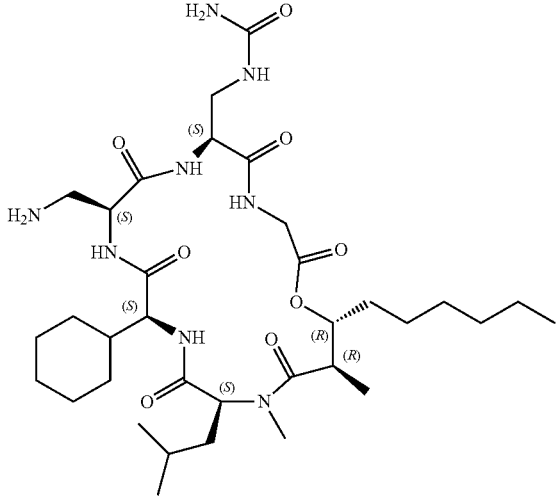<br>1-(((6S,9S,12S,15S,18R,19R)-9-(aminomethyl)-12-cyclohexyl-19-hexyl-15-isobutyl-16,18-dimethyl-2,5,8,11,14,17-hexaona-1-oxa-4,7,10,13,16-pentaazacyclononadecan-6-yl)methyl)urea | 709.4 | 1.72, C | 1 |
| 117 | 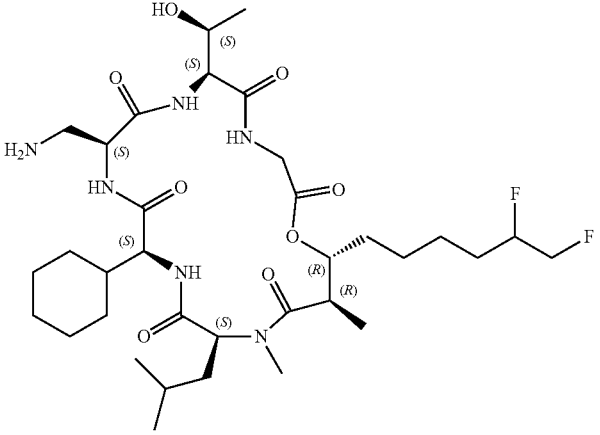<br>(6S,9S,12S,15S,18R,19R)-9-(aminomethyl)-12-cyclohexyl-19-(5,6-difluorohexyl)-6-((S)-1-hydroxyethyl)-15-isobutyl-16,18-dimethyl-1-oxa-4,7,10,13,16-pentaazacyclononadecane-2,5,8,11,14,17-hexaone | 717.4 | 2.62, H | 1 (T10) |

TABLE 5-continued

| Example | Structure/Name | LCMS [M + H]$^+$ | LCMS R$^T$ (min), method | Synthesis Method/ Example # (Intermediate #) |
| --- | --- | --- | --- | --- |
| 118 | 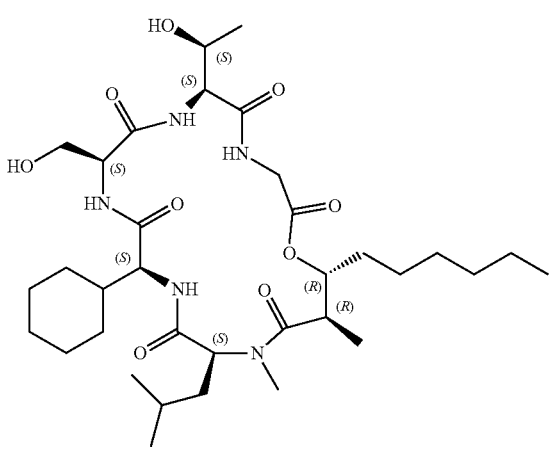<br>(6S,9S,12S,15S,18R,19R)-12-cyclohexyl-19-hexyl-6-((S)-1-hydroxyethyl)-9-(hydroxymethyl)-15-isobutyl-16,18-dimethyl-1-oxa-4,7,10,13,16-pentaazacyclononadecane-2,5,8,11,14,17-hexaone | 682.4 | 2.04, C | 1 |
| 119 | 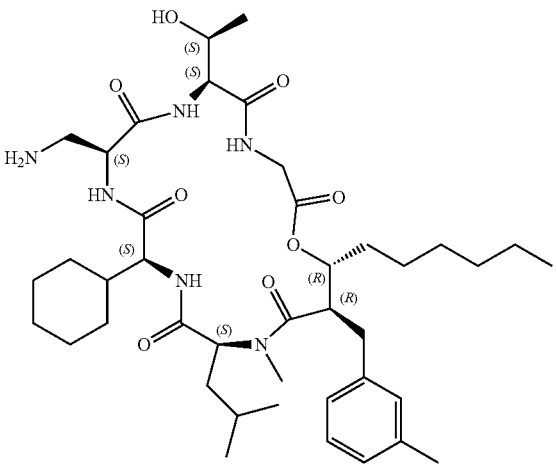<br>(6S,9S,12S,15S,18R,19R)-9-(aminomethyl)-12-cyclohexyl-19-hexyl-6-((S)-1-hydroxyethyl)-15-isobutyl-16-methyl-18-(3-methylbenzyl)-1-oxa-4,7,10,13,16-pentaazacyclononadecane-2,5,8,11,14,17-hexaone | 771.4 | 5.35, A | 54 |

TABLE 5-continued

| Example | Structure/Name | LCMS [M + H]⁺ | LCMS $R^T$ (min), method | Synthesis Method/ Example # (Intermediate #) |
|---|---|---|---|---|
| 120 | 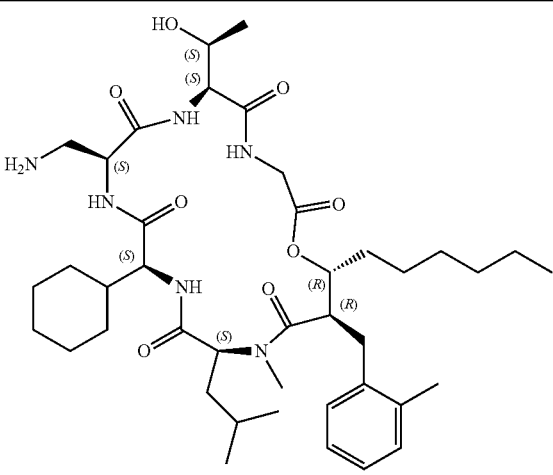<br>(6S,9S,12S,15S,18R,19R)-9-(aminomethyl)-12-cyclohexyl-19-hexyl-6-((S)-1-hydroxyethyl)-15-isobutyl-16-methyl-18-(2-methylbenzyl)-1-oxa-4,7,10,13,16-pentaazacyclononadecane-2,5,8,11,14,17-hexaone | 771.4 | 5.34, A | 54 |
| 121 | 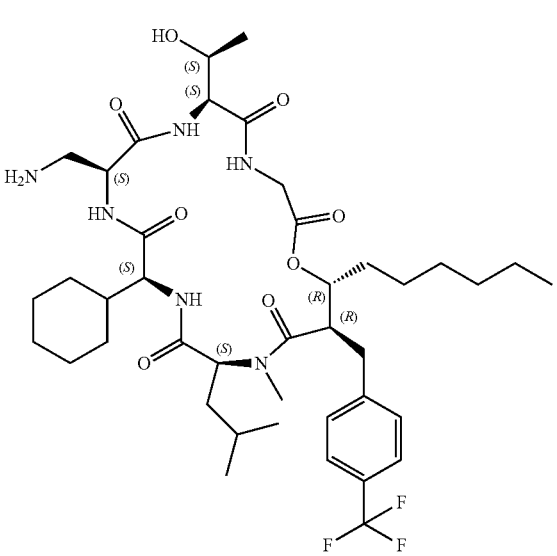<br>(6S,9S,12S,15S,18R,19R)-9-(aminomethyl)-12-cyclohexyl-19-hexyl-6-((S)-1-hydroxyethyl)-15-isobutyl-16-methyl-18-(4-(trifluoromethyl)benzyl)-1-oxa-4,7,10,13,16-pentaazacyclononadecane-2,5,8,11,14,17-hexaone | 825.3 | 5.39, A | 54 |

TABLE 5-continued

| Example | Structure/Name | LCMS [M + H]+ | LCMS $R^T$ (min), method | Synthesis Method/ Example # (Intermediate #) |
|---|---|---|---|---|
| 122 | 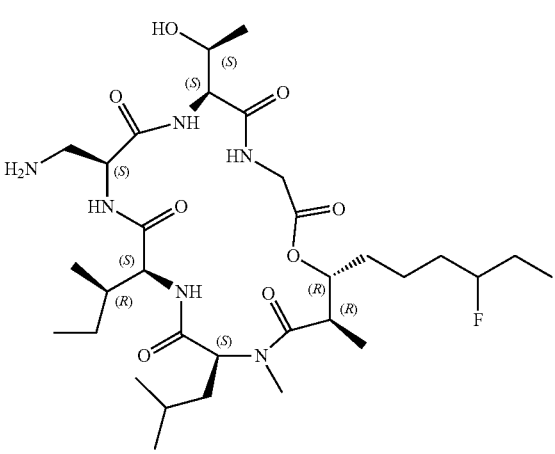<br>(6S,9S,12S,15S,18R,19R)-9-(aminomethyl)-12-((R)-sec-butyl)-19-(4-fluorohexyl)-6-((S)-1-hydroxyethyl)-15-isobutyl-16,18-dimethyl-1-oxa-4,7,10,13,16-pentaazacyclononadecane-2,5,8,11,14,17-hexaone | 673.4 | 1.60, C | 1 (T12) |
| 123 | 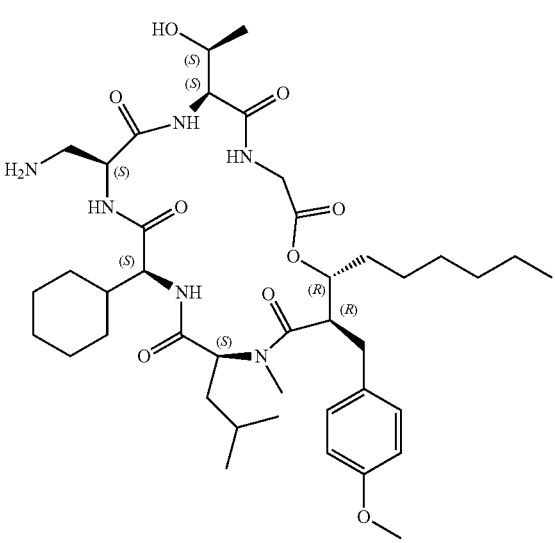<br>(6S,9S,12S,15S,18R,19R)-9-(aminomethyl)-12-cyclohexyl-19-hexyl-6-((S)-1-hydroxyethyl)-15-isobutyl-18-(4-methoxybenzyl)-16-methyl-1-oxa-4,7,10,13,16-pentaazacyclononadecane-2,5,8,11,14,17-hexaone | 787.4 | 5.11, A | 54 |

TABLE 5-continued
| Example | Structure/Name | LCMS [M + H]+ | LCMS R$^T$ (min), method | Synthesis Method/ Example # (Intermediate #) |
|---|---|---|---|---|
| 124 | 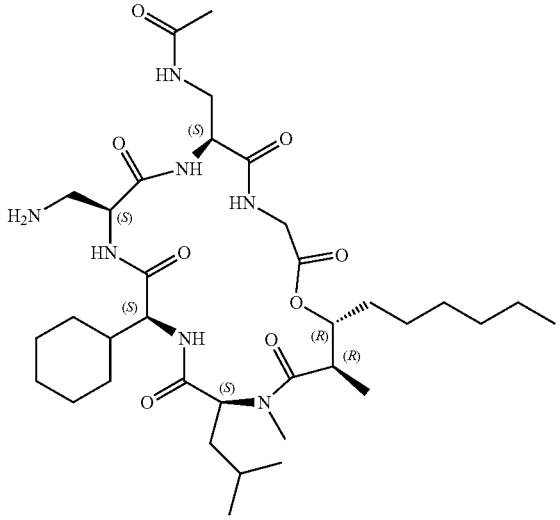<br>N-(((6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)acetamide | 708.4 | 1.75, C | 1 (P2K) |
| 125 | 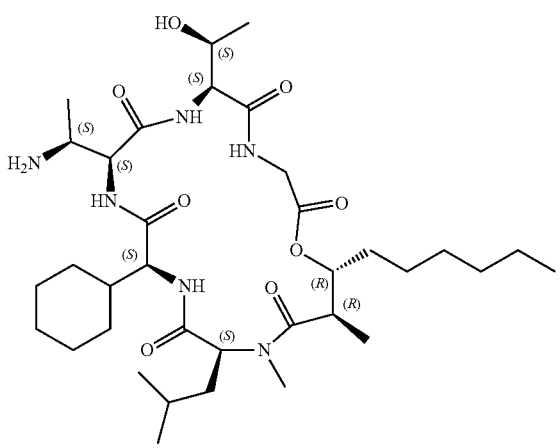<br>(6S,9S,12S,15S,18R,19R)-9-((S)-1-aminoethyl)-12-cyclohexyl-19-hexyl-6-((S)-1-hydroxyethyl)-15-isobutyl-16,18-dimethyl-1-oxa-4,7,10,13,16-pentaazacyclononadecane-2,5,8,11,14,17-hexaone | 695.4 | 1.79, C | 1 |

TABLE 5-continued

| Example | Structure/Name | LCMS [M + H]+ | LCMS R$^T$ (min), method | Synthesis Method/ Example # (Intermediate #) |
|---|---|---|---|---|
| 126 | 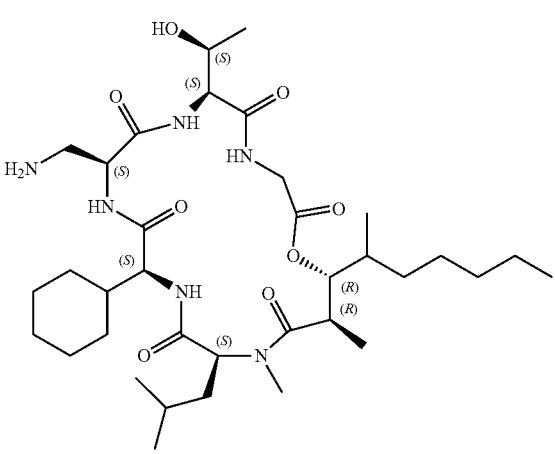<br>(6S,9S,12S,15S,18R,19R)-9-(aminomethyl)-12-cyclohexyl-19-(heptan-2-yl)-6-((S)-1-hydroxyethyl)-15-isobutyl-16,18-dimethyl-1-oxa-4,7,10,13,16-pentaazacyclononadecane-2,5,8,11,14,17-hexaone (single unknown stereoisomer) | 695.4 | 1.85, C | 1 (T13) |
| 127 | 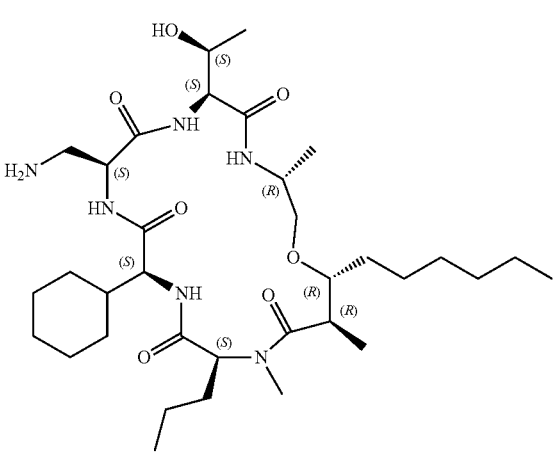<br>(3R,6S,9S,12S,15S,18R,19R)-9-(aminomethyl)-12-cyclohexyl-19-hexyl-6-((S)-1-hydroxyethyl)-3,16,18-trimethyl-15-propyl-1-oxa-4,7,10,13,16-pentaazacyclononadecane-5,8,11,14,17-pentaone | 667.5 | 1.75, C | 57 |

TABLE 5-continued

| Example | Structure/Name | LCMS [M + H]⁺ | LCMS R$^T$ (min), method | Synthesis Method/ Example # (Intermediate #) |
|---|---|---|---|---|
| 128 | 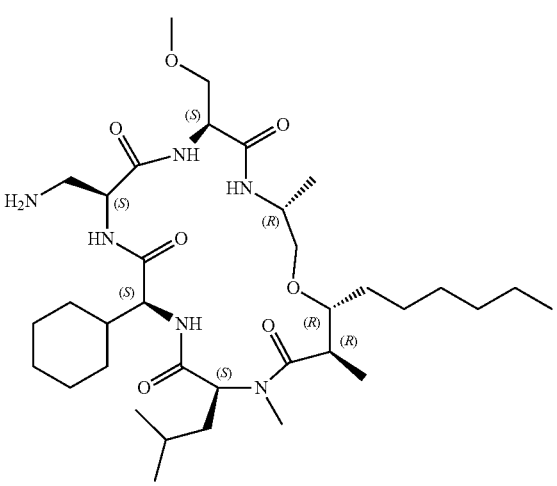<br>(3R,6S,9S,12S,15S,18R,19R)-9-(aminomethyl)-12-cyclohexyl-19-hexyl-15-isobutyl-6-(methoxymethyl)-3,16,18-trimethyl-1-oxa-4,7,10,13,16-pentaazacyclononadecane-5,8,11,14,17-pentaone | 681.5 | 1.89, C | 57 |
| 129 | 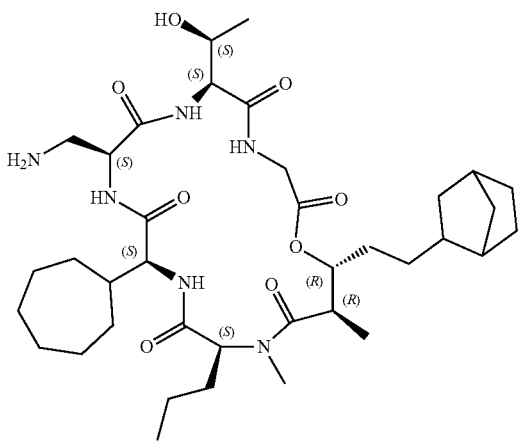<br>(6S,9S,12S,15S,18R,19R)-9-(aminomethyl)-19-(2-(bicyclo[2.2.1]heptan-2-yl)ethyl)-12-cycloheptyl-6-((S)-1-hydroxyethyl)-16,18-dimethyl-15-propyl-1-oxa-4,7,10,13,16-pentaazacyclononadecane-2,5,8,11,14,17-hexaone | 719.4 | 1.78 C | 60 |

TABLE 5-continued

| Example | Structure/Name | LCMS [M + H]+ | LCMS R^T (min), method | Synthesis Method/ Example # (Intermediate #) |
|---|---|---|---|---|
| 130 | 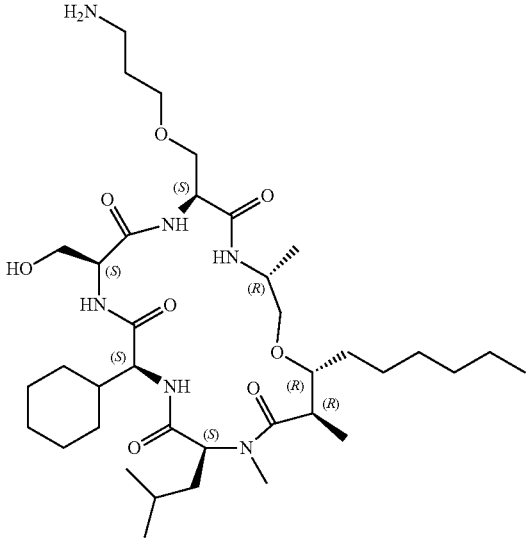<br>(3R,6S,9S,12S,15S,18R,19R)-6-((3-aminopropoxy)methyl)-12-cyclohexyl-19-hexyl-9-(hydroxymethyl)-3,16,18-trimethyl-15-propyl-1-oxa-4,7,10,13,16-pentaazacyclononadecane-5,8,11,14,17-pentaone | 711.5 | 1.72, C | 81 |
| 131 | 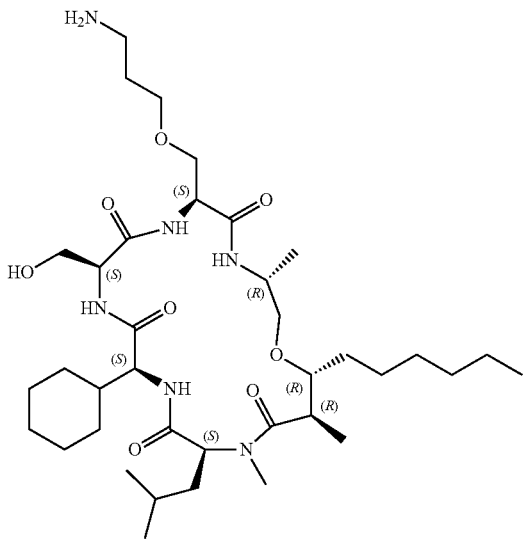<br>(3R,6S,9S,12S,15S,18R,19R)-9-(aminomethyl)-6-((3-aminopropoxy)methyl)-12-cyclohexyl-19-hexyl-15-isobutyl-3,16,18-trimethyl-1-oxa-4,7,10,13,16-pentaazacyclononadecane-5,8,11,14,17-pentaone | 724.5 | 1.60 C | 81 |

TABLE 5-continued
| Example | Structure/Name | LCMS [M + H]+ | LCMS R$^T$ (min), method | Synthesis Method/ Example # (Intermediate #) |
| --- | --- | --- | --- | --- |
| 132 | 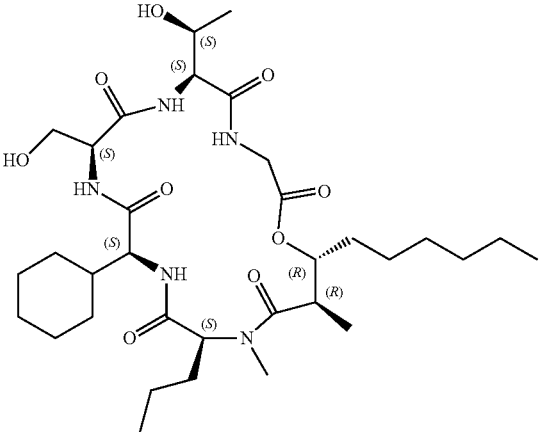<br>(6S,9S,12S,15S,18R,19R)-12-cyclohexyl-19-hexyl-6-((S)-1-hydroxyethyl)-9-(hydroxymethyl)-16,18-dimethyl-15-propyl-1-oxa-4,7,10,13,16-pentazaacyclononadecane-2,5,8,11,14,17-hexaone | 668.4 | 1.94, C | 1 |
| 133 | 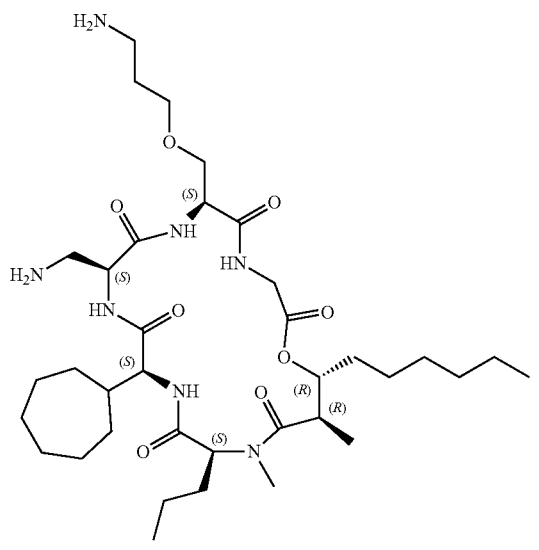<br>(6S,9S,12S,15S,18R,19R)-9-(aminomethyl)-6-((3-aminopropoxy)methyl)-12-cycloheptyl-19-hexyl-16,18-dimethyl-15-propyl-1-oxa-4,7,10,13,16-pentaazacyclononadecane-2,5,8,11,14,17-hexaone | 724.5 | 1.56, C | 51 |

TABLE 5-continued

| Example | Structure/Name | LCMS [M + H]+ | LCMS R$^T$ (min), method | Synthesis Method/ Example # (Intermediate #) |
|---|---|---|---|---|
| 134 | 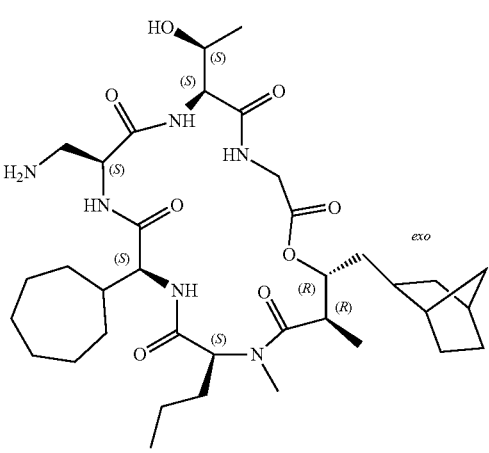(6S,9S,12S,15S,18R,19R)-9-(aminomethyl)-19-(exo-bicyclo[2.2.1]heptan-2-ylmethyl)-12-cycloheptyl-6-((S)-1-hydroxyethyl)-16,18-dimethyl-15-propyl-1-oxa-4,7,10,13,16-pentaazacyclononadecane-2,5,8,11,14,17-hexaone | 705.4 | 1.76, C | 62 |
| 135 | 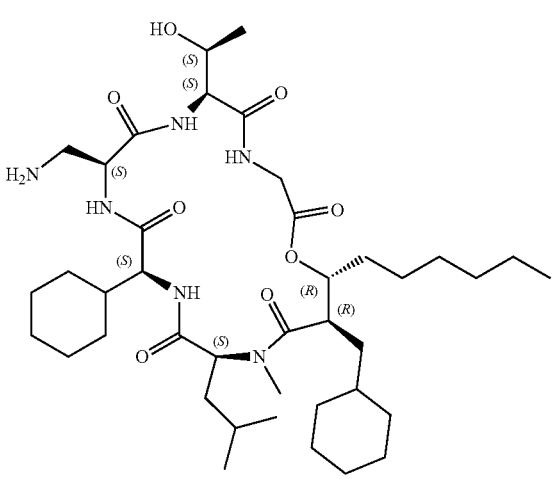(6S,9S,12S,18R,19R)-9-(aminomethyl)-12-cyclohexyl-18-(cyclohexylmethyl)-19-hexyl-6-((S)-1-hydroxyethyl)-15-isobutyl-16-methyl-1-oxa-4,7,10,13,16-pentaazacyclononadecane-2,5,8,11,14,17-hexaone | 763.5 | 2.16, C | 1 |

TABLE 5-continued

| Example | Structure/Name | LCMS [M + H]+ | LCMS R$^T$ (min), method | Synthesis Method/ Example # (Intermediate #) |
|---|---|---|---|---|
| 136 | 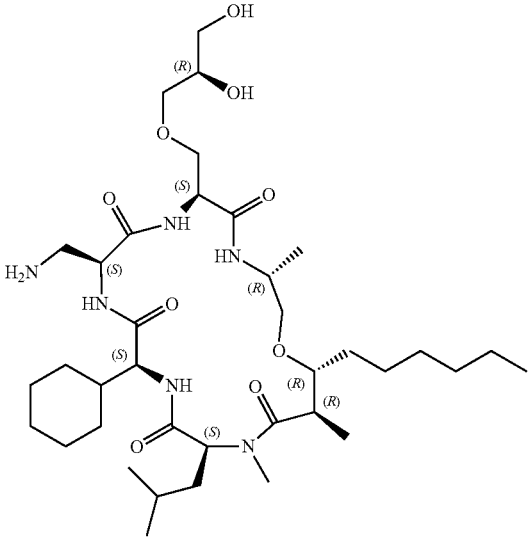 (3R,6S,9S,12S,15S,18R,19R)-9-(aminomethyl)-12-cyclohexyl-6-(((R)-2,3-dihydroxypropoxy)methyl)-19-hexyl-15-isobutyl-3,16,18-trimethyl-1-oxa-4,7,10,13,16-pentaazacyclononadecane-5,8,11,14,17-pentaone | 741.5 | 1.75, C | 67 |
| 137 | 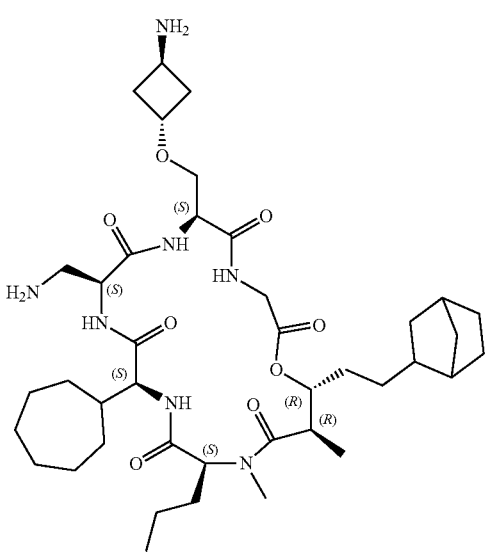 (6S,9S,12S,15S,18R,19R)-6-(((1r,3S)-3-aminocyclobutoxy)methyl)-9-(aminomethyl)-19-(2-(bicyclo[2.2.1]heptan-2-yl)ethyl)-12-cycloheptyl-16,18-dimethyl-15-propyl-1-oxa-4,7,10,13,16-pentaazacyclononadecane-2,5,8,11,14,17-hexaone | 774.5 | 1.60 C | 58 & 60 |

TABLE 5-continued

| Example | Structure/Name | LCMS [M + H]⁺ | LCMS R$^T$ (min), method | Synthesis Method/ Example # (Intermediate #) |
|---|---|---|---|---|
| 138 | 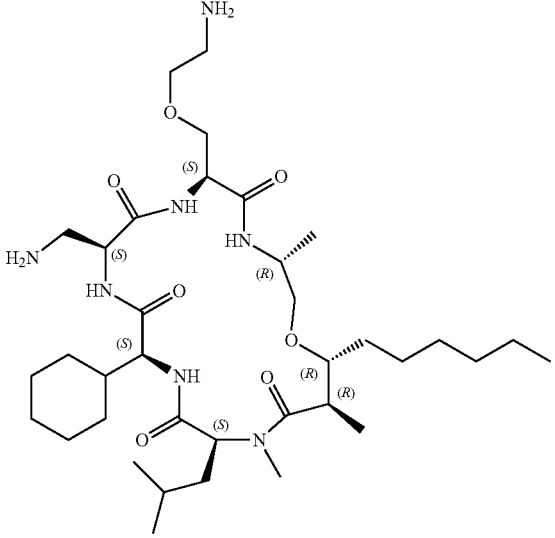<br>(3R,6S,9S,12S,15S,18R,19R)-6-((2-aminoethoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone | 710.5 | 1.60, C | 81 (P2B) |
| 139 | 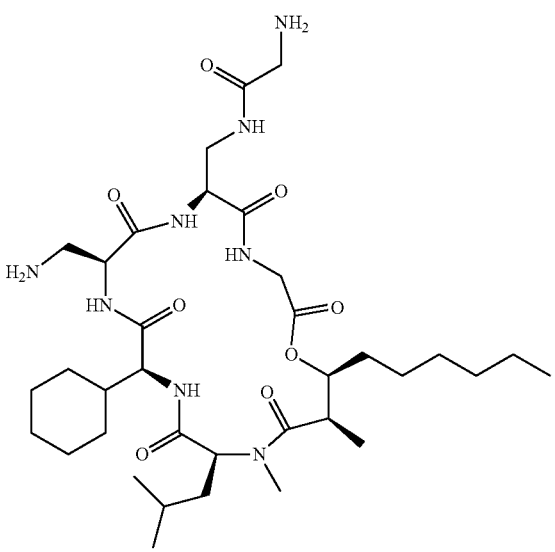<br>2-amino-N-(((6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)acetamide | 723.4 | 4.00, A | 72 |

TABLE 5-continued

| Example | Structure/Name | LCMS [M + H]+ | LCMS R$^T$ (min), method | Synthesis Method/ Example # (Intermediate #) |
|---|---|---|---|---|
| 140 | 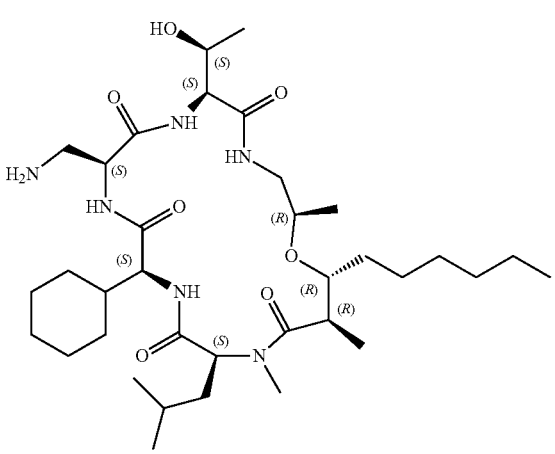<br>(2R,6S,9S,12S,15S,18R,19R)-9-(aminomethyl)-12-cyclohexyl-19-hexyl-6-((S)-1-hydroxyethyl)-15-isobutyl-2,16,18-trimethyl-1-oxa-4,7,10,13,16-pentaazacyclononadecane-5,8,11,14,17-pentaone | 681.5 | 1.72, L | 71 |
| 141 | 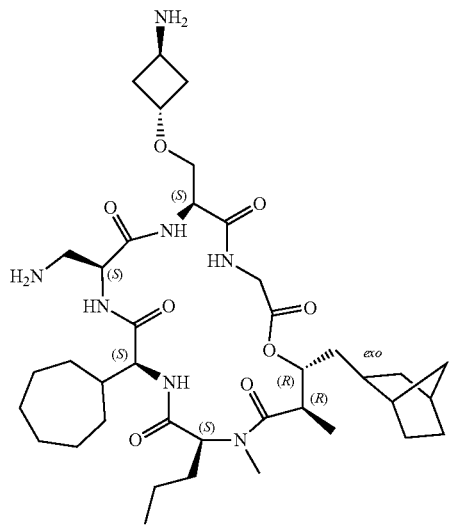<br>(6S,9S,12S,15S,18R,19R)-6-(((1r,3S)-3-aminocyclobutoxy)methyl)-9-(aminomethyl)-19-(exo-bicyclo[2.2.1]heptan-2-ylmethyl)-12-cycloheptyl-16,18-dimethyl-15-propyl-1-oxa-4,7,10,13,16-pentaazacyclononadecane-2,5,8,11,14,17-hexaone | 760.5 | 1.53 C | 58 & 62 |

TABLE 5-continued

| Example | Structure/Name | LCMS [M + H]+ | LCMS R$^T$ (min), method | Synthesis Method/ Example # (Intermediate #) |
|---|---|---|---|---|
| 142 | 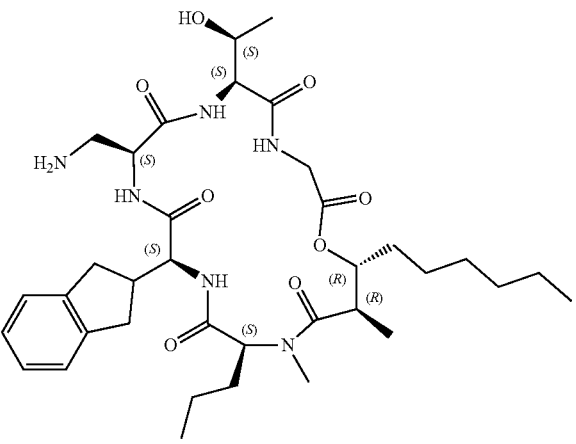<br>(6S,9S,12S,15S,18R,19R)-9-(aminomethyl)-12-(2,3-dihydro-1H-inden-2-yl)-19-hexyl-6-((S)-1-hydroxyethyl)-16,18-dimethyl-15-propyl-1-oxa-4,7,10,13,16-pentaazacyclononadecane-2,5,8,11,14,17-hexaone | 701.4 | 1.65, L | 1 |
| 143 | 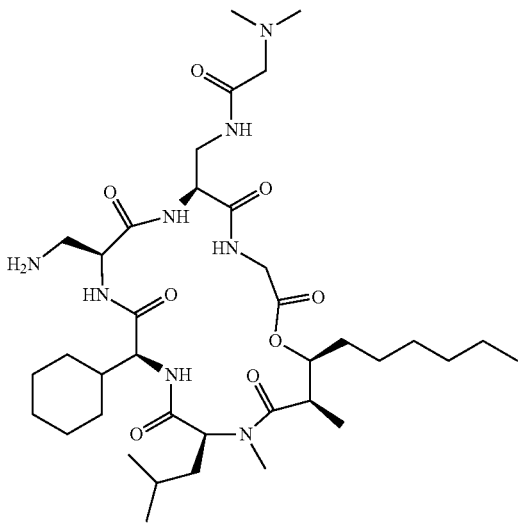<br>N-((((6S,9S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentaazacyclononadecan-6-yl)methyl)-2-(dimethylamino)acetamide | 751.5 | 4.17, A | 72 |

TABLE 5-continued

| Example | Structure/Name | LCMS [M + H]⁺ | LCMS $R^T$ (min), method | Synthesis Method/ Example # (Intermediate #) |
|---|---|---|---|---|
| 144 | 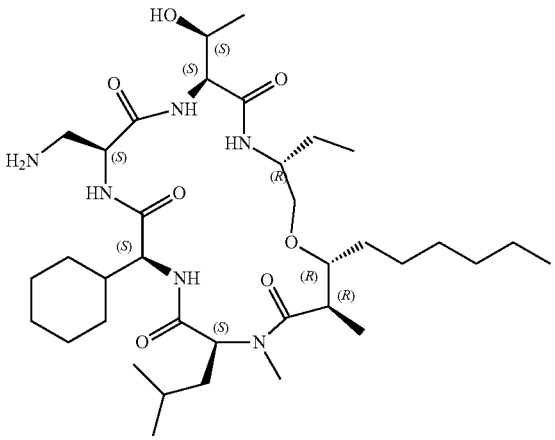<br>(3R,6S,9S,12S,15S,18R,19R)-9-(aminomethyl)-12-cyclohexyl-3-ethyl-19-hexyl-6-((S)-1-hydroxyethyl)-15-isobutyl-16,18-dimethyl-1-oxa-4,7,10,13,16-pentaazacyclononadecane-5,8,11,14,17-pentaone | 695.5 | 1.80, L | 57 |
| 145 | 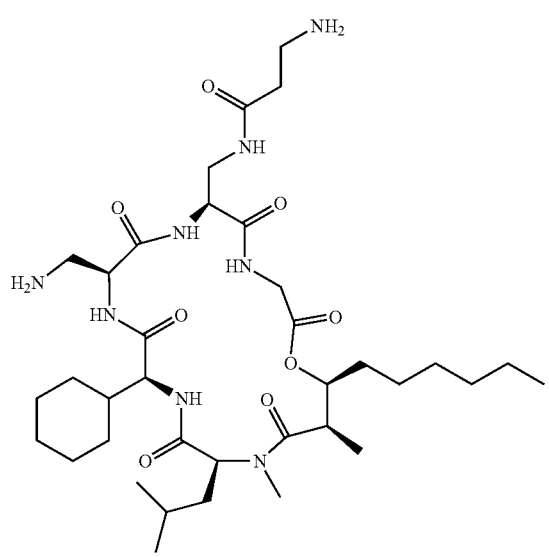<br>3-amino-N-(((6S,9S,12S,15S,18R,19R)-9-(aminomethyl)-12-cyclohexyl-19-hexyl-15-isobutyl-16,18-dimethyl-2,5,8,11,14,17-hexaoxo-1-oxa-4,7,10,13,16-pentazaacyclononadecan-6-yl)methyl)propanamide | 737.5 | 4.00, A | 72 |

TABLE 5-continued

| Example | Structure/Name | LCMS [M + H]+ | LCMS R$^T$ (min), method | Synthesis Method/ Example # (Intermediate #) |
| --- | --- | --- | --- | --- |
| 146 | 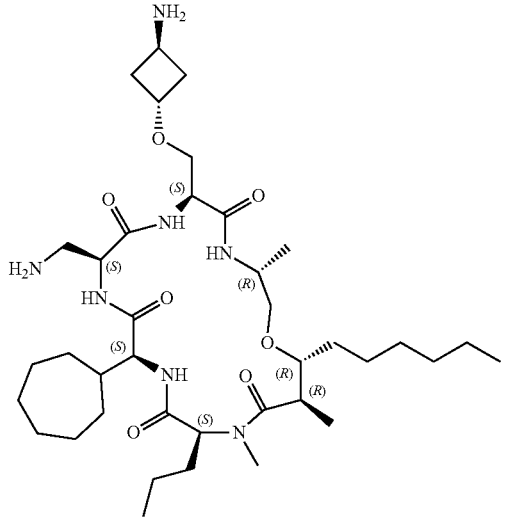<br>(3R,6S,9S,12S,15S,18R,19R)-6-(((1r,3S)-3-aminocyclobutoxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone | 736.6 | 1.52 C | 73 |
| 147 | 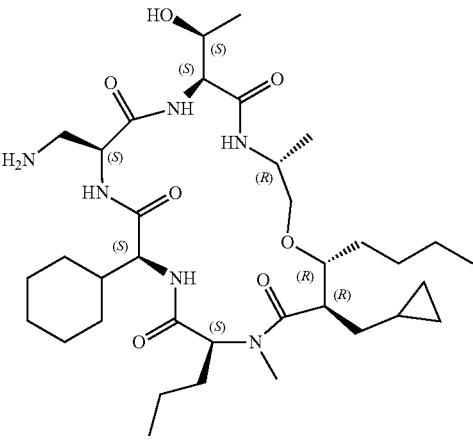<br>(3R,6S,9S,12S,15S,18R,19R)-9-(Aminomethyl)-19-butyl-12-cyclohexyl-18-(cyclopropylmethyl)-6-((S)-1-hydroxyethyl)-3,16-dimethyl-15-propyl-1-oxa-4,7,10,13,16-pentaazacyclononadecane-5,8,11,14,17-pentaone | 679.5 | 2.82, H | 57 |

TABLE 5-continued

| Example | Structure/Name | LCMS [M + H]+ | LCMS R$^T$ (min), method | Synthesis Method/ Example # (Intermediate #) |
|---|---|---|---|---|
| 149 | 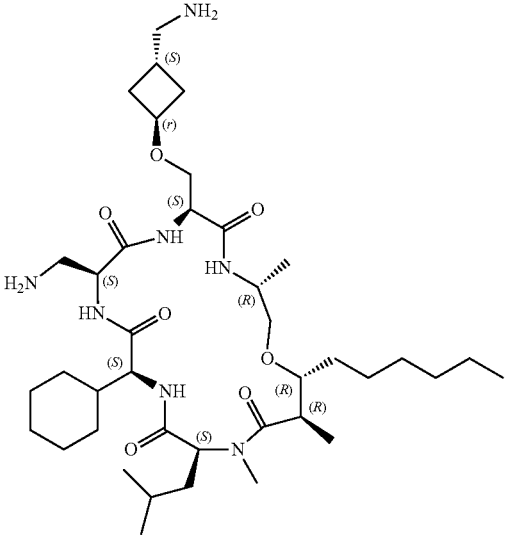<br>(3R,6S,9S,12S,15S,18R,19R)-9-(Aminomethyl)-6-(((1r,3S)-3-(aminomethyl)cyclobutoxy)methyl)-12-cyclohexyl-19-hexyl-15-isobutyl-3,16,18-trimethyl-1-oxa-4,7,10,13,16-pentaazacyclononadecane-5,8,11,14,17-pentaone | 750.6 | 2.69, H | 73 (P2L) |
| 152 | 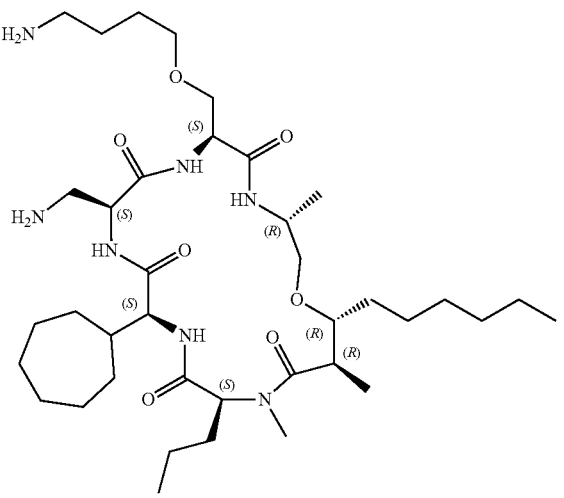<br>(3R,6S,9S,12S,15S,18R,19R)-6-((4-Aminobutoxy)methyl)-9-(aminomethyl)-12-cycloheptyl-19-hexyl-3,16,18-trimethyl-15-propyl-1-oxa-4,7,10,13,16-pentaazacyclononadecane-5,8,11,14,17-pentaone | 738.5 | 2.68, H | 73 |

TABLE 5-continued

| Example | Structure/Name | LCMS [M + H]+ | LCMS R$^T$ (min), method | Synthesis Method/ Example # (Intermediate #) |
|---|---|---|---|---|
| 153 | (3R,6S,9S,12S,15S,19R)-9-(Aminomethyl)-12-cyclohexyl-19-(heptan-2-yl)-6-((S)-1-hydroxyethyl)-15-isobutyl-3,16,18-trimethyl-1-oxa-4,7,10,13,16-pentaazacyclononadecane-5,8,11,14,17-pentaone (mixture of diastereomers) | 695.5 | 3.28, H | 57 |
| 154 | (3R,6S,9S,12S,15S,18R,19R)-6-(((R)-3-Amino-2-fluoropropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone | 742.5 | 2.7, H | 73 |

TABLE 5-continued

| Example | Structure/Name | LCMS [M + H]+ | LCMS R^T (min), method | Synthesis Method/ Example # (Intermediate #) |
|---|---|---|---|---|
| 155 | 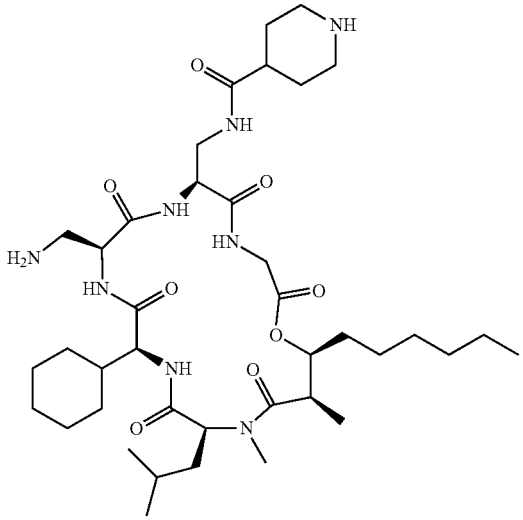<br>N-[[(6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]piperidine-4-carboxamide | 777.5 | 10.2, F | 72 |
| 156 | 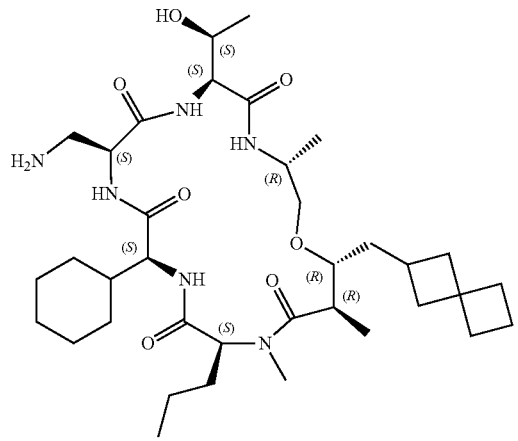<br>(3R,6S,9S,12S,15S,18R,19R)-9-(Aminomethyl)-12-cyclohexyl-6-((S)-1-hydroxyethyl)-3,16,18-trimethyl-15-propyl-19-(spiro[3.3]heptan-2-ylmethyl)-1-oxa-4,7,10,13,16-pentaazacyclononadecane-5,8,11,14,17-pentaone | 691.5 | 3.0, H | 57 |

TABLE 5-continued

| Example | Structure/Name | LCMS [M + H]⁺ | LCMS $R^T$ (min), method | Synthesis Method/ Example # (Intermediate #) |
|---|---|---|---|---|
| 157 | 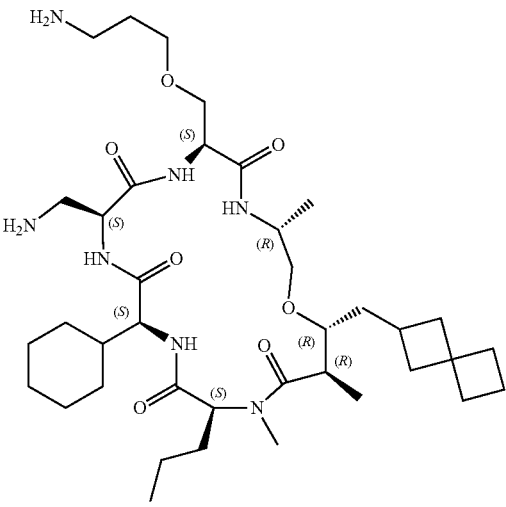<br>(3R,6S,9S,12S,15S,18R,19R)-9-(Aminomethyl)-6-((3-aminopropoxy)methyl)-12-cyclohexyl-3,16,18-trimethyl-15-propyl-19-(spiro[3.3]heptan-2-ylmethyl)-1-oxa-4,7,10,13,16-pentaazacyclononadecane-5,8,11,14,17-pentaone | 734.5 | 2.65, H | 73 |
| 158 | 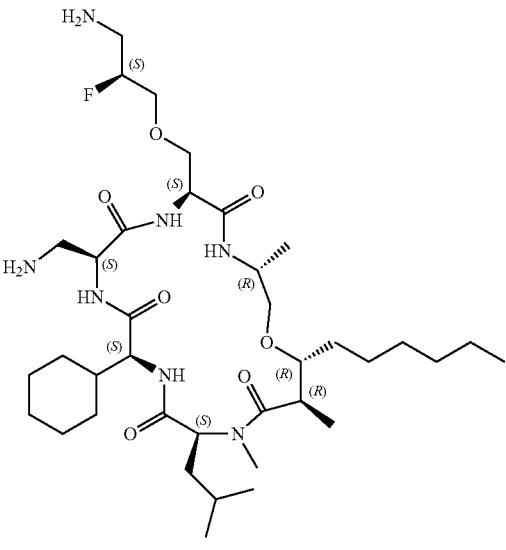<br>(3R,6S,9S,12S,15S,18R,19R)-6-(((S)-3-Amino-2-fluoropropoxy)methyl)-9-(aminomethyl)-12-cyclohexyl-19-hexyl-15-isobutyl-3,16,18-trimethyl-1-oxa-4,7,10,13,16-pentaazacyclononadecane-5,8,11,14,17-pentaone | 742.5 | 2.7, H | 73 |

TABLE 5-continued

| Example | Structure/Name | LCMS [M + H]+ | LCMS R$^T$ (min), method | Synthesis Method/ Example # (Intermediate #) |
|---|---|---|---|---|
| 159 | 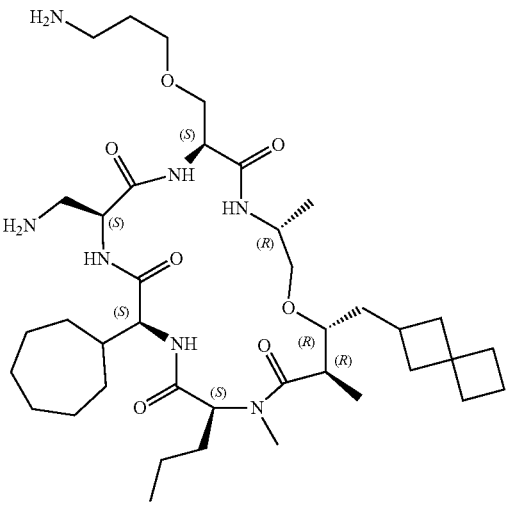<br>(3R,6S,9S,12S,15S,18R,19R)-9-(Aminomethyl)-6-((3-aminopropoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone | 748.5 | 2.73, H | 164 |
| 160 | 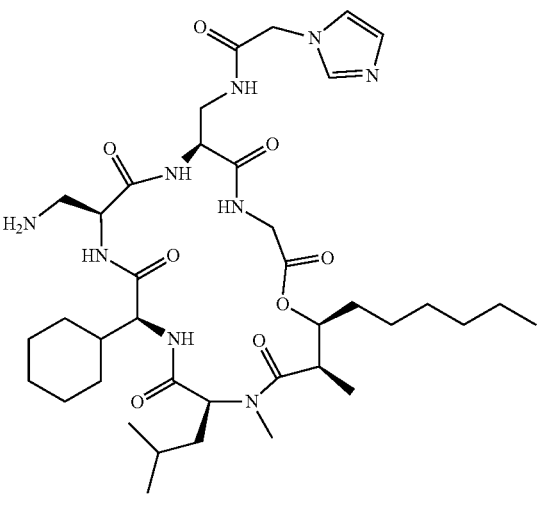<br>N-[[(6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]-2-imidazol-1-yl-acetamide | 774.5 | 10.8, F | 72 |

TABLE 5-continued

| Example | Structure/Name | LCMS [M + H]+ | LCMS R$^T$ (min), method | Synthesis Method/ Example # (Intermediate #) |
| --- | --- | --- | --- | --- |
| 162 | 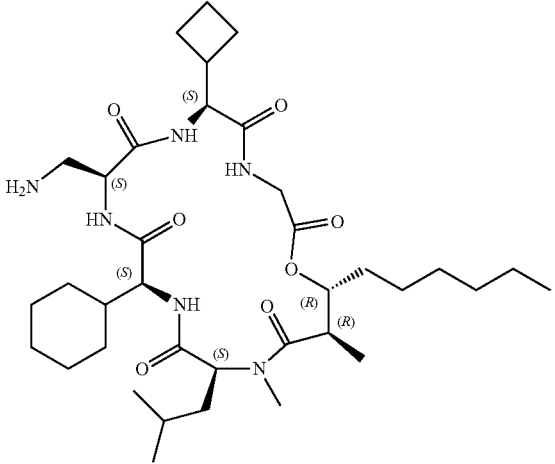<br>(6S,9S,12S,15S,18R,19R)-9-(Aminomethyl)-6-cyclobutyl-12-cyclohexyl-19-hexyl-15-isobutyl-16,18-dimethyl-1-oxa-4,7,10,13,16-pentaazacyclononadecane-2,5,8,11,14,17-hexaone | 691.5 | 1.91, N | 1 |
| 163 | 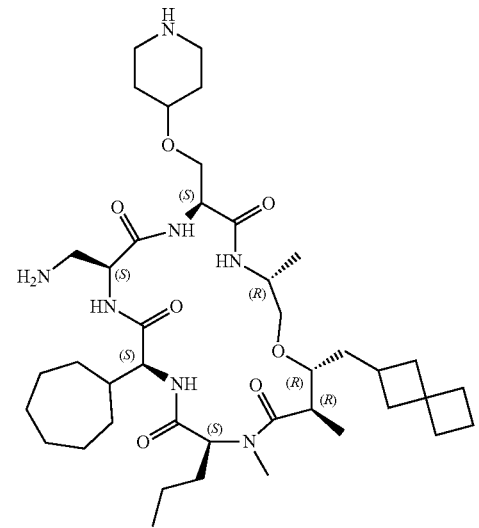<br>(3R,6S,9S,12S,15S,18R,19R)-9-(Aminomethyl)-12-cycloheptyl-3,16,18-trimethyl-6-((piperidin-4-yloxy)methyl)-15-propyl-19-(spiro[3.3]heptan-2-ylmethyl)-1-oxa-4,7,10,13,16-pentaazacyclononadecane-5,8,11,14,17-pentaone | 774.6 | 2.78, H | 164 (P2I) |

TABLE 5-continued

| Example | Structure/Name | LCMS [M + H]+ | LCMS R$^T$ (min), method | Synthesis Method/ Example # (Intermediate #) |
|---|---|---|---|---|
| 165 | 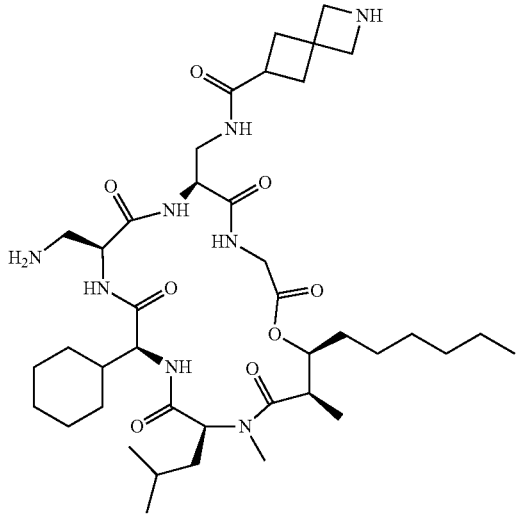<br>N-[[(6S,9S,12S,15S,18R,19R)-9-(Aminomethyl)-12-cyclohexyl-19-hexyl-15-isobutyl-16,18-dimethyl-2,5,8,11,14,17-hexaoxo-1-oxa-4,7,10,13,16-pentazacyclononadec-6-yl]methyl]-2-azaspiro[3.3]heptane-6-carboxamide | 789.5 | 9.9, F | 72 |
| 171 | 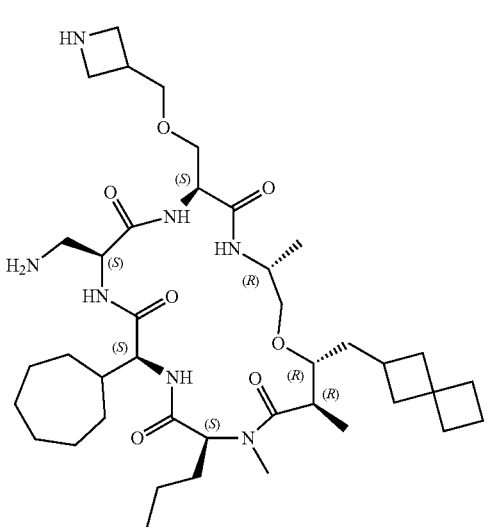<br>(3R,6S,9S,12S,15S,18R,19R)-9-(Aminomethyl)-6-((azetidin-3-ylmethoxy)methyl)-12-cycloheptyl-3,16,18-trimethyl-15-propyl-19-(spiro[3.3]heptan-2-ylmethyl)-1-oxa-4,7,10,13,16-pentaazacyclononadecane-5,8,11,14,17-pentaone | 760.6 | 2.14, M | 164 (P2H) |

TABLE 5-continued

| Example | Structure/Name | LCMS [M + H]⁺ | LCMS $R^T$ (min), method | Synthesis Method/ Example # (Intermediate #) |
|---|---|---|---|---|
| 172 | 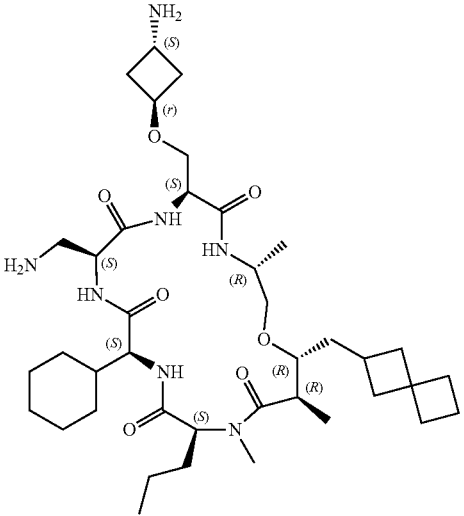<br>(3R,6S,9S,12S,15S,18R,19R)-6-(((1r,3S)-3-Aminocyclobutoxy)methyl)-9-(aminomethyl)-12-cyclohexyl-3,16,18-trimethyl-15-propyl-19-(spiro[3.3]heptan-2-ylmethyl)-1-oxa-4,7,10,13,16-pentaazacyclononadecane-5,8,11,14,17-pentaone | 746.5 | 1.65, H | 164 |

Biological Assays

Example B1: Determination of Minimum Inhibitory Concentration

In vitro antimicrobial activity of each compound was determined by measuring minimal inhibitor concentrations (MICs) using the broth micro-dilution technique as approved by the Clinical and Laboratory Standards Institute (CLSI) (Methods for Dilution Antimicrobial Susceptibility Tests for Bacteria that Grow Aerobically; Approved Standard—Eighth Edition. CLSI document M07-A8. Wayne, Pa.: Clinical and Laboratroy Standards; 2009). Antibacterial activity was measure against *Escherichia coli* (*E. coli*) strain CFT073 ATCC 700928, which is a clinically relevant Gram-negative strain. Cells were inoculated onto plates of Mueller Hinton Agar and grown at 37° C. for 16-18 hours. Inocula suspensions were prepared by scraping cells into 1 mL of testing media (Mueller Hinton II cation adjusted Broth supplemented with 0.002% v/v Tween-80) and diluting to a final $OD_{600\ nm}$ of 0.01.

Test compounds were prepared in DMSO at a concentration of 100 uM The compounds were tested under several different dilution formats and the data are reported in Tables 6, 7 and 8. In protocol 1, the compound stocks were diluted into testing media at a concentration of 64 µg/ml and serial 2-fold dilutions were made in the same media, in 96-well U bottom microtiter dishes, for a total of 10 compound concentrations. In protocol 2, the compound stocks were diluted into testing media at a concentration of 4 µg/mL and serial 2-fold dilutions were made in the same media, in 96-well U bottom microtiter dishes, for a total of 10 compound concentrations. In protocol 3, compound stocks were diluted into testing media at a concentration of 0.5 µg/mL, with serial 2-fold dilutions conducted as described above. In protocol 4, compound stocks were diluted into testing media at a concentration of 0.13 µg/mL, with serial 2-fold dilutions conducted as described above. Inocula suspensions were added to the 2-fold serial dilutions of test compounds to a final density of OD $OD_{600\ nm}$ of 0.0005 and incubated at 35° C. for 22 hours. After incubation the plates were examined visually and the lowest concentration of test compound that completely prevented bacterial growth were recorded as the MICs. The results are listed in Table 6.

TABLE 6

| | MIC (µM) |
|---|---|
| 1 | 3.1 |
| 2 | 3.1 |
| 3 | 3.1 |
| 4 | 13 |
| 5 | 4.7 |
| 5 | 3.1 |
| 7 | 3.1 |
| 8 | 25 |
| 9 | 6.3 |
| 10 | 6.3 |
| 11 | 25 |
| 12 | 4.7 |
| 13 | 50 |
| 14 | 3.1 |
| 15 | 6.3 |
| 16 | 6.3 |
| 17 | 25 |
| 18 | 19 |
| 19 | 25 |
| 20 | 50 |
| 21 | 50 |
| 22 | 13 |
| 23 | 3.1 |
| 24 | 13 |
| 25 | 25 |
| 26 | 50 |

TABLE 6-continued

| | MIC (μM) |
|---|---|
| 27 | 13 |
| 28 | 25 |
| 29 | 13 |
| 30 | 13 |
| 31 | 13 |
| 32 | 9.4 |
| 33 | 13 |
| 34 | 9.4 |
| 35 | 6.3 |
| 36 | 25 |
| 37 | 25 |
| 38 | 50 |
| 39 | 25 |
| 40 | 50 |
| 41 | 25 |
| 42 | 50 |
| 43 | 13 |
| 44 | 25 |
| 45 | 25 |
| 46 | 25 |
| 47 | 3.1 |
| 48 | 50 |
| 49 | 3.1 |
| 50 | 25 |
| 51 | 8.7 |
| 52 | 12 |
| 53 | 25 |
| 54 | 8.7 |
| 55 | 18 |
| 56 | 4.4 |
| 57 | 2.9 |
| 58 | 6.3 |
| 59 | 1.1 |
| 60 | 0.73 |
| 61 | 6.3 |
| 62 | 1.6 |
| 63 | 4.4 |
| 64 | 2.2 |
| 65 | 0.78 |
| 66 | 1.3 |
| 67 | 8.8 |
| 68 | 3.1 |
| 69 | 8.8 |
| 70 | 15 |
| 71 | 12 |
| 72 | 12 |
| 73 | 6.3 |
| 74 | 1.6 |
| 75 | 3.1 |
| 76 | 6.3 |
| 77 | 4.4 |
| 78 | 25 |
| 79 | 0.78 |
| 80 | 12 |
| 81 | 12 |
| 82 | 4.4 |
| 83 | 0.39 |
| 84 | 0.78 |
| 85 | 0.78 |
| 86 | 50 |
| 87 | 50 |
| 88 | 50 |
| 89 | 12 |
| 90 | 21 |
| 91 | 50 |
| 92 | 19 |
| 93 | 10 |
| 94 | 4.4 |
| 95 | 14 |
| 96 | 5.3 |
| 97 | 3.7 |
| 98 | 71 |
| 99 | 17 |
| 100 | 35 |
| 101 | 4.1 |
| 102 | 3.1 |
| 103 | 3.1 |
| 104 | 6.3 |

TABLE 6-continued

| | MIC (μM) |
|---|---|
| 105 | 5.2 |
| 106 | 6.3 |
| 107 | 25 |
| 108 | 35 |
| 109 | 25 |
| 110 | 25 |
| 111 | 8.8 |
| 112 | 71 |
| 113 | 50 |
| 114 | 15 |
| 115 | 8.7 |
| 116 | 50 |
| 117 | 25 |
| 118 | 4.4 |
| 119 | 3.1 |
| 120 | 3.1 |
| 121 | 6.3 |
| 122 | 25 |
| 123 | 12 |
| 124 | 18 |
| 125 | 3.2 |
| 126 | 3.1 |
| 127 | 4.4 |
| 128 | 3.1 |
| 129 | 0.66 |
| 130 | 44 |
| 131 | 11 |
| 132 | 6.1 |
| 133 | 3.1 |
| 134 | 0.78 |
| 135 | 3.7 |
| 136 | 8.8 |
| 137 | 0.78 |
| 138 | 12 |
| 139 | 18 |
| 140 | 35 |
| 141 | 2.2 |
| 142 | 8.8 |
| 143 | 25 |
| 144 | 2.2 |
| 145 | 12 |
| 146 | 6.3 |
| 147 | 12 |
| 148 | 8.8 |
| 149 | 8.8 |
| 150 | 25 |
| 151 | 6.3 |
| 152 | 6.3 |
| 153 | 1.6 |
| 154 | 12 |
| 155 | 18 |
| 156 | 2.2 |
| 157 | 12 |
| 158 | 12 |
| 159 | 3.1 |
| 160 | 71 |
| 161 | 6.3 |
| 162 | 3.1 |
| 163 | 4.4 |
| 164 | 2.2 |
| 165 | 4.4 |
| 166 | 1.1 |
| 167 | 1.6 |
| 168 | 3.1 |
| 169 | 6.3 |
| 170 | 0.78 |
| 171 | 6.3 |
| 172 | 4.4 |
| 173 | 12 |
| 174 | 1.6 |

Pharmaceutical Compositions

Example C1: Parenteral Composition

To prepare a parenteral pharmaceutical composition suitable for administration by injection, 100 mg of a compound of Formula (I), (Ia)-(Ic), (II), (IIa)-(IIc), (III), (IIIa)-(IIIc), (IV), (IVa)-(IVc), (V), or (Va)-(Vc) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I), (Ia)-(Ic), (II), (IIa)-(IIc), (III), (IIIa)-(IIIc), (IV), (IVa)-(IVc), (V), or (Va)-(Vc) | 1.2 g |
| sodium acetate buffer solution (0.4M) | 2.0 mL |
| HCl (1N) or NaOH (1M) | q.s. to suitable pH |
| water (distilled, sterile) | q.s.to 20 mL |

All of the above ingredients, except water, are combined and stirred and if necessary, with slight heating if necessary. A sufficient quantity of water is then added.

Example C2: Oral Composition

To prepare a pharmaceutical composition for oral delivery, 100 mg of a compound of Formula (I), (Ia)-(Ic), (II), (IIa)-(IIc), (III), (IIIa)-(IIIc), (IV), (IVa)-(IVc), (V), or (Va)-(Vc) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I), (Ia)-(Ic), (II), (IIa)-(IIc), (III), (IIIa)-(IIIc), (IV), (IVa)-(IVc), (V), or (Va)-(Vc) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I), (Ia)-(Ic), (II), (IIa)-(IIc), (III), (IIIa)-(IIIc), (IV), (IVa)-(IVc), (V), or (Va)-(Vc) | 200 |
| lactose, spray-dried | 148 |
| magnesium stearate | 2 |

In yet another embodiment, the following ingredients are mixed to form a solution/suspension for oral administration:

| Ingredient | Amount |
| --- | --- |
| Compound of Formula (I), (Ia)-(Ic), (II), (IIa)-(IIc), (III), (IIIa)-(IIIc), (IV), (IVa)-(IVc), (V), or (Va)-(Vc) | 1 g |
| Anhydrous Sodium Carbonate | 0.1 g |
| Ethanol (200 proof), USP | 10 mL |
| Purified Water, USP | 90 mL |
| Aspartame | 0.003 g |

Example 3: Topical Gel Composition

To prepare a pharmaceutical topical gel composition, 100 mg of a compound of Formula (I), (Ia)-(Ic), (II), (IIa)-(IIc), (III), (IIIa)-(IIIc), (IV), (IVa)-(IVc), (V), or (Va)-(Vc) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein may be employed in practicing the invention. It is intended that the following claims define the scope of the disclosure and that methods and structures within the scope of these claims and their equivalents be covered thereby.

What is claimed is:
1. A compound of Formula (I):

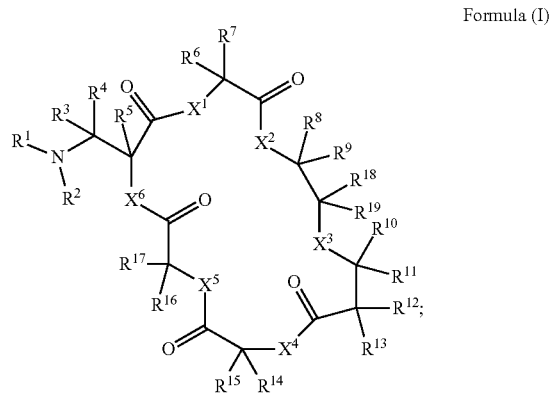

Formula (I)

wherein:
$X^1$ is —O— or —NR$^{1a}$—;
$X^2$ is —O— or —NR$^{2a}$—;
$X^3$ is —O— or —NR$^{3a}$—;
$X^4$ is —O— or —NR$^{4a}$—;
$X^5$ is —O— or —NR$^{5a}$—;
$X^6$ is —O— or —NR$^{6a}$—;
provided that at least one of $X^1$, $X^2$, $X^3$, $X^4$, $X^5$, or $X^6$ is —O—;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-

$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, optionally substituted ($C_1$-$C_6$ alkyl)heteroaryl, —S(=O)$_2$R$^a$, —S(=O)$_2$NR$^b$R$^c$, —C(=O)R$^a$, —C(=O)OR$^b$, —C(=O)NR$^b$R$^c$, or —(C=NR$^b$)NR$^b$R$^c$;

or R$^1$ and R$^2$ are taken together with the nitrogen atom to which they are attached to form an optionally substituted heterocycloalkyl;

R$^3$ and R$^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or R$^3$ and R$^4$ are taken together with the carbon atom to which they are attached to form an oxo;

R$^5$ is hydrogen, halogen, optionally substituted $C_1$-$C_6$ alkyl, optionally substituted $C_2$-$C_6$ alkenyl, or optionally substituted $C_2$-$C_6$ alkynyl;

R$^6$ and R$^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^8$ and R$^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{10}$ and R$^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{12}$ and R$^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{10}$ and R$^{12}$ are taken together to form an optionally substituted cycloalkyl or an optionally substituted cycloalkenyl;

R$^{14}$ and R$^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{14}$ and R$^{4a}$ are taken together with the atoms to which they are attached to form an optionally substituted heterocycloalkyl;

R$^{16}$ and R$^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

R$^{18}$ and R$^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or R$^{18}$ and R$^{19}$ are taken together with the carbon atom to which they are attached to form an oxo;

each R$^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each R$^b$ and R$^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or R$^b$ and R$^c$ are taken together with the nitrogen atom to which they are attached to form an optionally substituted heterocycloalkyl;

or a pharmaceutically acceptable salt, solvate, or stereoisomer thereof.

2. The compound of claim 1, wherein R$^{18}$ and R$^{19}$ are taken together with the carbon atom to which they are attached to form an oxo.

3. The compound of claim 1, wherein R$^{18}$ and R$^{19}$ are hydrogen.

4. The compound of claim 1, having the structure of Formula (Ia):

Formula (Ia)

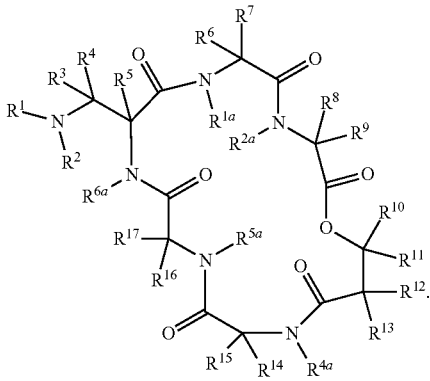

5. The compound of claim 1, wherein $R^1$, $R^2$, $R^5$, $R^7$, $R^9$, $R^{11}$, $R^{13}$, $R^{15}$ and $R^{17}$ are hydrogen.

6. The compound of claim 1, having the structure of Formula (Ib):

Formula (Ib)

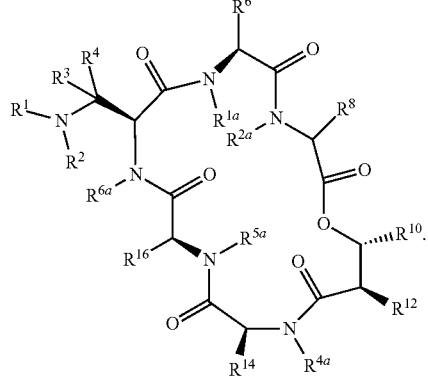

7. The compound of claim 1, wherein $R^{1a}$, $R^{2a}$, $R^{5a}$ and $R^{6a}$ are hydrogen.

8. The compound of claim 1, having the structure of Formula (Ic):

Formula (Ic)

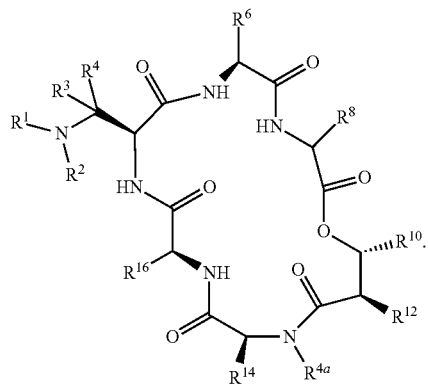

9. The compound of claim 1, wherein $R^3$ and $R^4$ are hydrogen and $R^{4a}$ is hydrogen or $C_1$-$C_6$alkyl.

10. The compound of claim 1, wherein $R^6$ is $C_1$-$C_6$ alkyl optionally substituted with one, two, or three halogen, —$OR^b$, —$NR^bR^c$, —$NC(=NR^b)NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$NR^bC(=O)[(R^d)_2]_{1-4}NR^bR^c$, —$OC[(R^d)_2]_{2-4}OR^b$, —$OC[(R^d)_2]_{2-4}NR^bR^c$, —$OC[(R^d)_2]_{2-4}OC[(R^d)_2]_{2-4}NR^bR^c$, —$OC[(R^d)_2]_{2-4}NC(=NR^b)NR^bR^c$, —$OC(=O)NR^bR^c$, —$NR^bC(=O)NR^bR^c$, —$NR^bC(=O)R^a$, —$NR^bC(=O)OR^b$, —O-(optionally substituted heterocycloalkyl), —O-(optionally substituted aryl), —O-(optionally substituted heteroaryl), or heteroaryl; and each $R^d$ is independently hydrogen, halogen, —OH, —$OCH_3$, or $C_1$-$C_6$ alkyl.

11. The compound of claim 1, wherein $R^6$ is $C_1$-$C_6$ alkyl optionally substituted with one, two, or three —$OR^b$.

12. The compound of claim 1, wherein $R^6$ is selected from:

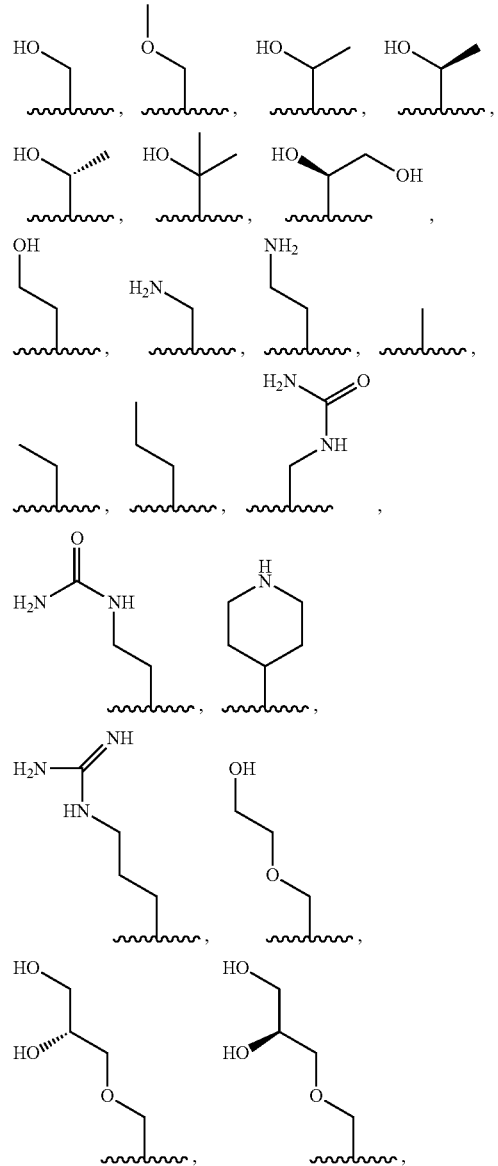

-continued

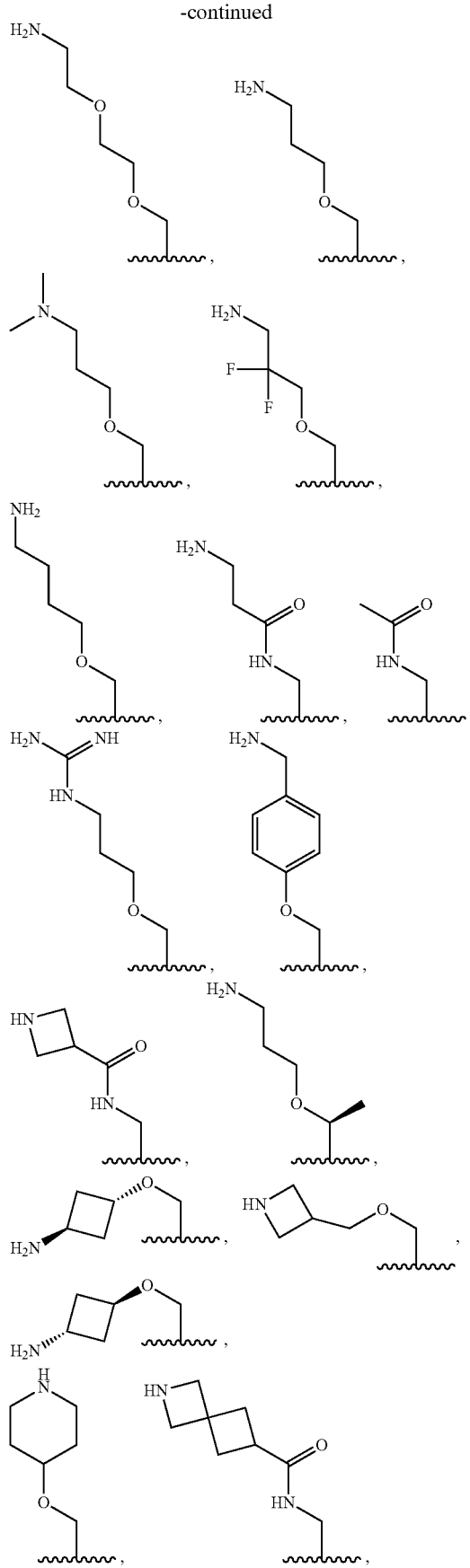

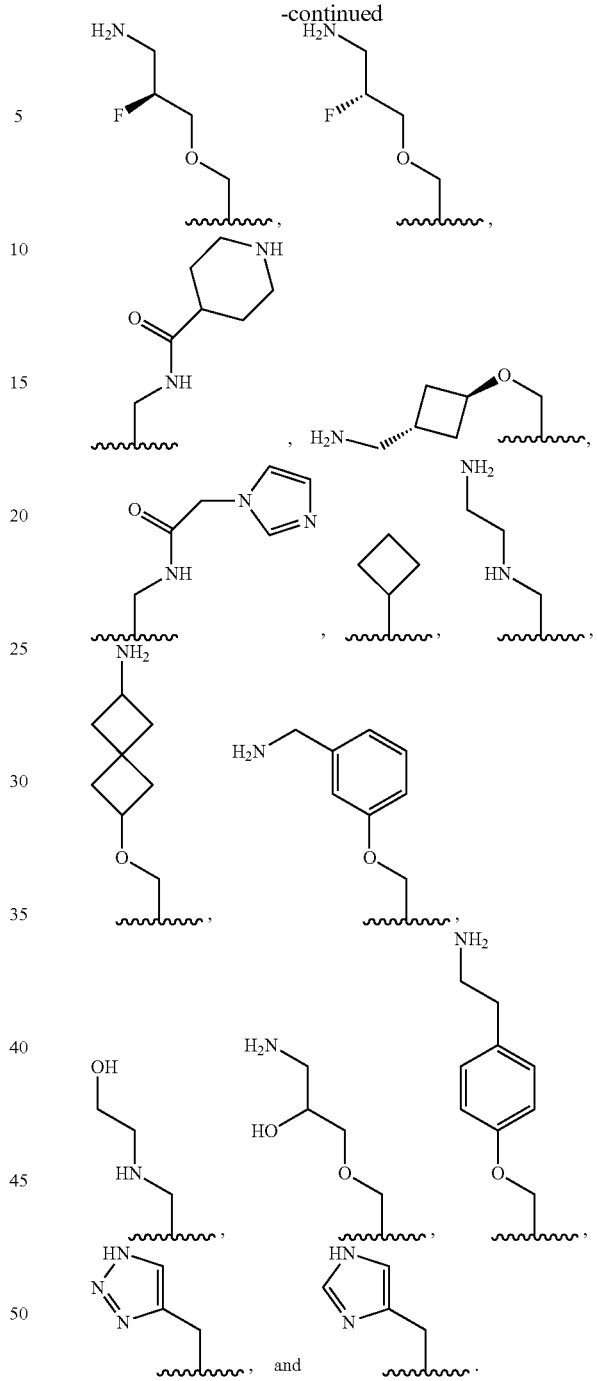

13. The compound of claim 1, wherein $R^8$ is hydrogen or $C_1$-$C_6$ alkyl.

14. The compound of claim 1, wherein $R^{10}$ is $C_8$-$C_{12}$ alkyl optionally substituted with one, two, or three halogen, —OH, or —OCH$_3$.

15. The compound of claim 1, wherein $R^{12}$ is $C_1$-$C_6$ alkyl, $C_1$-$C_6$ haloalkyl, ($C_1$-$C_6$ alkyl)aryl, or ($C_1$-$C_6$ alkyl)cycloalkyl; wherein the aryl is optionally substituted with one, two, or three halogen, $C_1$-$C_6$ alkyl, $C_1$-$C_6$ haloalkyl, —OH, —OCH$_3$, or aryl.

16. The compound of claim 1, wherein $R^{14}$ is $C_1$-$C_6$ alkyl, $C_1$-$C_6$ haloalkyl, or ($C_1$-$C_6$ alkyl)cycloalkyl.

17. The compound of claim 1, wherein $R^{14}$ is selected from:

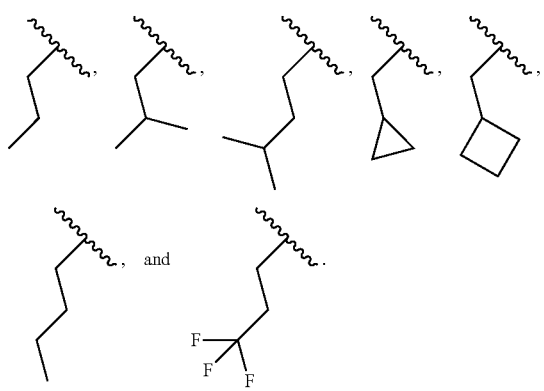

18. The compound of claim 1, wherein $R^{14}$ and $R^{4a}$ are taken together with the atoms to which they are attached to form an optionally substituted 5- or 6-membered heterocycloalkyl.

19. The compound of claim 1, wherein $R^{16}$ is $C_1$-$C_6$ alkyl, ($C_1$-$C_6$ alkyl)cycloalkyl, cycloalkyl, ($C_1$-$C_6$ alkyl)aryl, or aryl, each optionally substituted with one, two, or three halogen, —$OR^b$, —$NR^bR^c$, —$S(=O)_2R^a$, —$NR^bS(=O)_2R^a$, —$S(=O)_2NR^bR^c$, —$C(=O)R^a$, —$OC(=O)R^a$, —$C(=O)OR^a$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, or aryl.

20. The compound of claim 1, wherein $R^{16}$ is selected from:

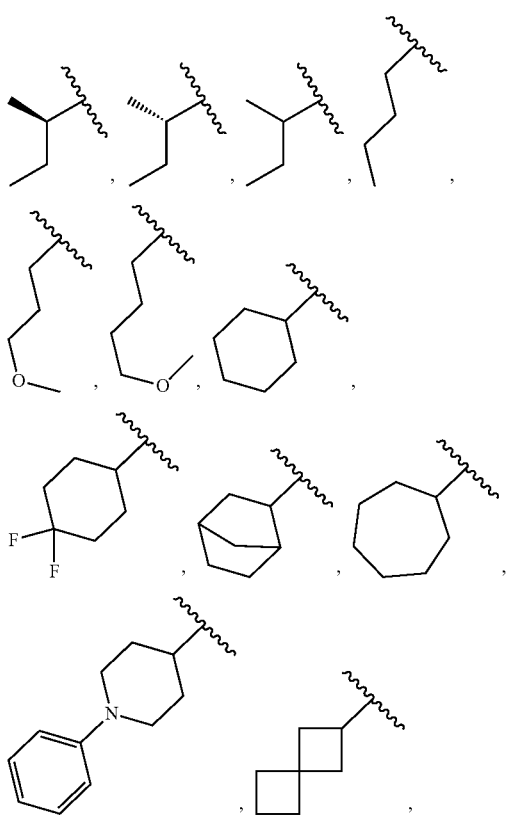

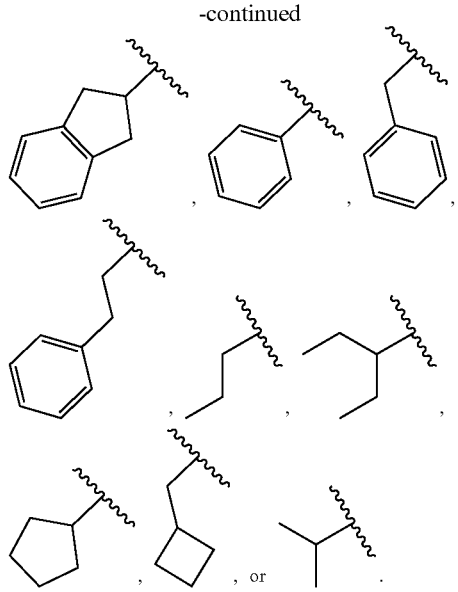

21. The compound of claim 1, wherein each $R^a$ is independently $C_1$-$C_6$ alkyl, and each $R^b$ and $R^c$ is independently hydrogen or $C_1$-$C_6$ alkyl.

22. A compound of Formula (III):

Formula (II)

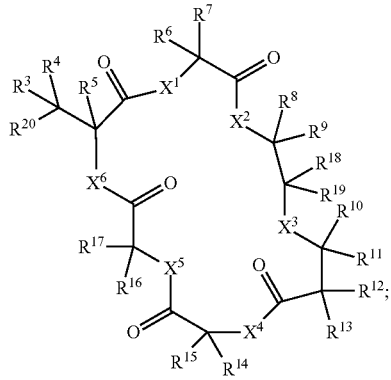

wherein:
$X^1$ is —O— or —$NR^{1a}$—;
$X^2$ is —O— or —$NR^{2a}$—;
$X^3$ is —O— or —$NR^{3a}$—;
$X^4$ is —O— or —$NR^{4a}$—;
$X^5$ is —O— or —$NR^{5a}$—;
$X^6$ is —O— or —$NR^{6a}$—;
provided that at least one of $X^1$, $X^2$, $X^3$, $X^4$, $X^5$, or $X^6$ is —O—;
Y is a bond or optionally substituted $C_1$-$C_6$ alkylene;
$R^{2a}$, $R^{3a}$, $R^{4a}$, $R^{5a}$, and $R^{6a}$ are each independently hydrogen or optionally substituted $C_1$-$C_6$ alkyl;
$R^1$ and $R^2$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, optionally substituted ($C_1$-$C_6$ alkyl)heteroaryl, —$S(=O)_2R^a$, —$S(=O)_2NR^bR^c$, —$C(=O)R^a$, —$C(=O)OR^b$, or —$C(=O)NR^bR^c$;

or $R^1$ and $R^2$ are taken together with the nitrogen atom to which they are attached to form an optionally substituted heterocycloalkyl;

$R^3$ and $R^4$ are each independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted heterocycloalkyl, optionally substituted ($C_1$-$C_6$ alkyl)aryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;

$R^{10}$ and $R^{11}$ are each independently hydrogen, halogen, optionally substituted $C_1$-$C_{20}$ alkyl, optionally substituted $C_2$-$C_{20}$ alkenyl, optionally substituted $C_2$-$C_{20}$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;

$R^{12}$ and $R^{13}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;

or $R^{10}$ and $R^{12}$ are taken together to form an optionally substituted cycloalkyl or an optionally substituted cycloalkenyl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{17}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted ($C_1$-$C_6$ alkyl)heterocycloalkyl, optionally substituted ($C_1$-$C_6$ alkyl)aryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

$R^{20}$ is hydroxyl or —$NR^1R^2$;

$R^{21}$ is optionally substituted cycloalkyl;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

23. A compound of Formula (V):

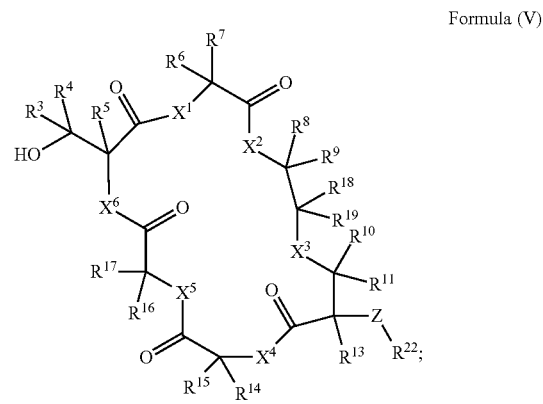

Formula (V)

wherein:
$X^1$ is —O— or —$NR^{1a}$—;
$X^2$ is —O— or —$NR^{2a}$—;
$X^3$ is —O— or —$NR^{3a}$—;
$X^4$ is —O— or —$NR^{4a}$—;
$X^5$ is —O— or —$NR^{5a}$—;
$X^6$ is —O— or —$NR^{6a}$—;
$R^{1a}$, $R^{2a}$, $R^{3a}$, $R^{4a}$, $R^{5a}$, and $R^{6a}$ are each independently hydrogen or optionally substituted $C_1$-$C_6$ alkyl;
$R^3$ and $R^4$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^3$ and $R^4$ are taken together with the carbon atom to which they are attached to form an oxo;

$R^5$ is hydrogen, halogen, optionally substituted $C_1$-$C_6$ alkyl, optionally substituted $C_2$-$C_6$ alkenyl, or optionally substituted $C_2$-$C_6$ alkynyl;

$R^6$ and $R^7$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{10}$ is optionally substituted $C_2$-$C_{20}$ alkyl;

$R^{11}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

Z is —$CR^{23}R^{24}$—, —O—, or —$NR^{25}$—;

$R^{22}$ is optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{23}$, $R^{24}$, and $R^{25}$ are each independently hydrogen or optionally substituted $C_1$-$C_6$ alkyl;

$R^{13}$ is hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{14}$ and $R^{15}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{14}$ and $R^{4a}$ are taken together with the atoms to which they are attached to form an optionally substituted heterocycloalkyl;

$R^{16}$ and $R^{17}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

$R^{18}$ and $R^{19}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted ($C_1$-$C_6$ alkyl)cycloalkyl, optionally substituted heterocycloalkyl, optionally substituted ($C_1$-$C_6$ alkyl)heterocycloalkyl, optionally substituted aryl, optionally substituted ($C_1$-$C_6$ alkyl)aryl, optionally substituted heteroaryl, or optionally substituted ($C_1$-$C_6$ alkyl)heteroaryl;

or $R^{18}$ and $R^{19}$ are taken together with the carbon atom to which they are attached to form an oxo;

each $R^a$ is independently optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

each $R^b$ and $R^c$ is independently hydrogen, optionally substituted $C_1$-$C_6$ alkyl, optionally substituted $C_2$-$C_6$ alkenyl, optionally substituted $C_2$-$C_6$ alkynyl, optionally substituted cycloalkyl, optionally substituted heterocycloalkyl, optionally substituted aryl, or optionally substituted heteroaryl;

or $R^b$ and $R^c$ are taken together with the nitrogen atom to which they are attached to form an optionally substituted heterocycloalkyl;

or a pharmaceutically acceptable salt, solvate, or stereoisomer thereof.

24. A compound selected from:

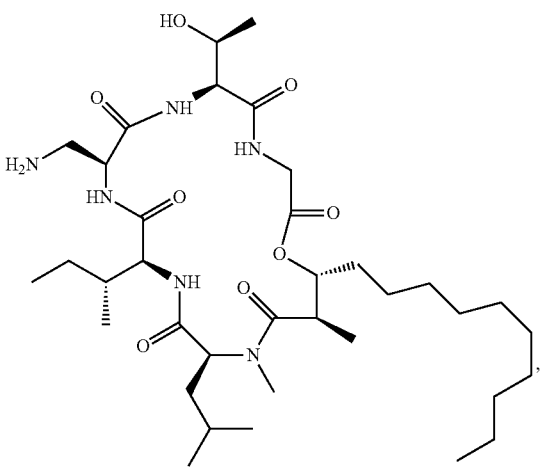

507
-continued
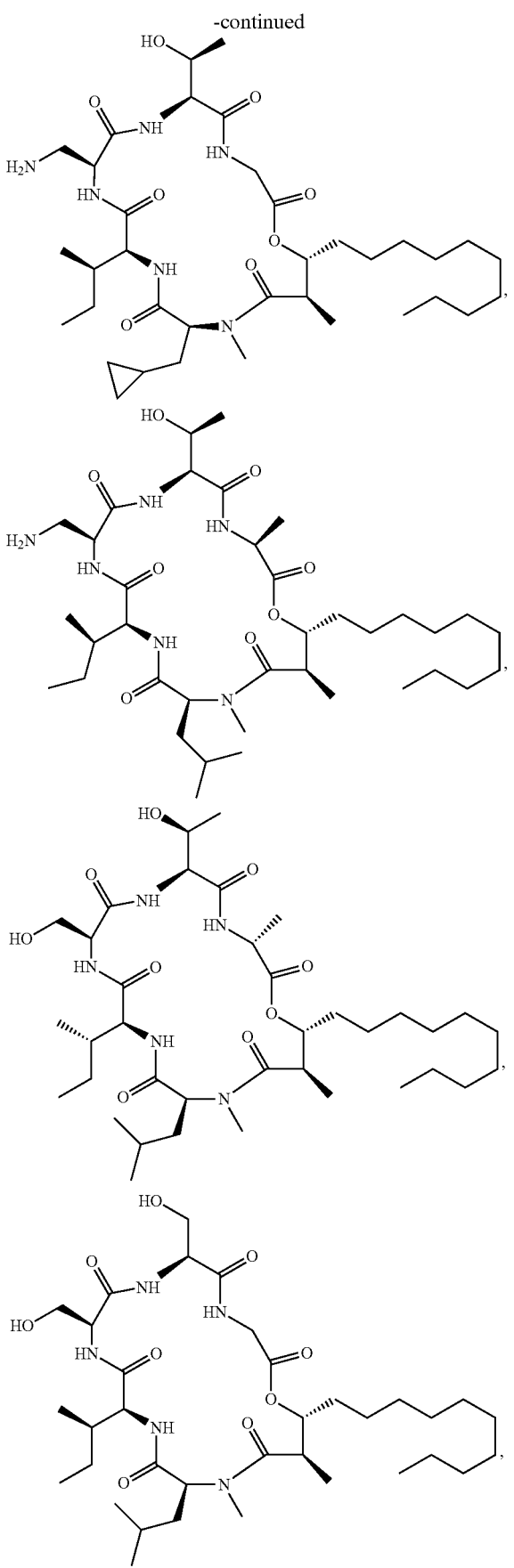
508
-continued
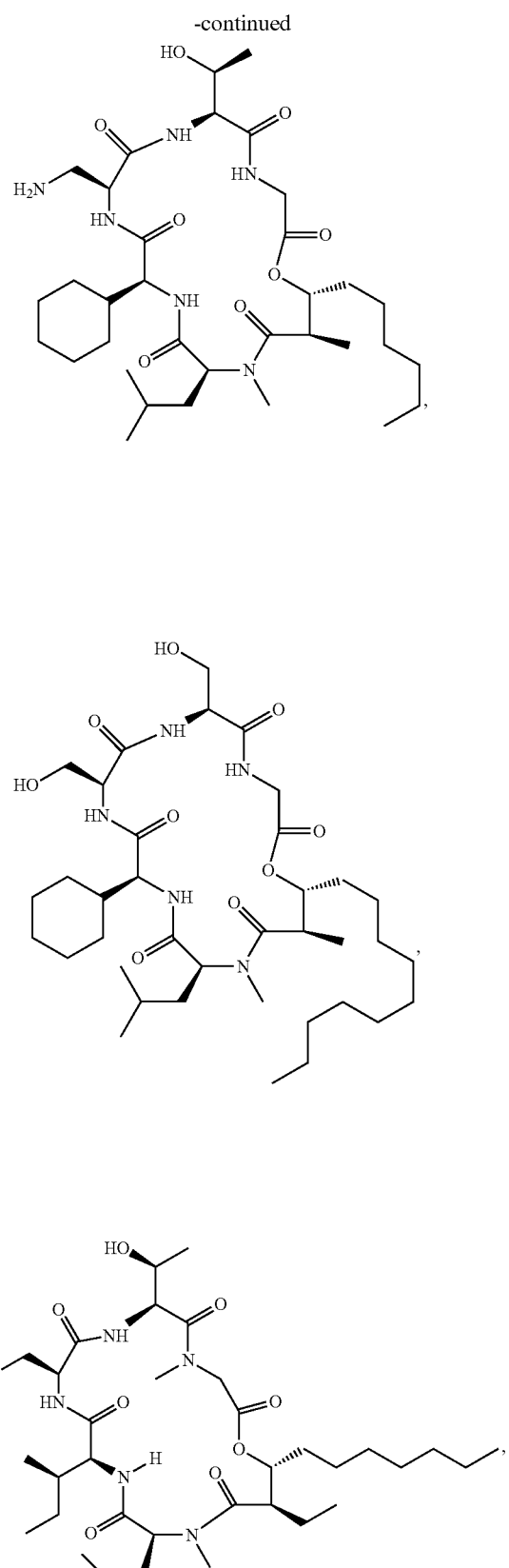

509
-continued
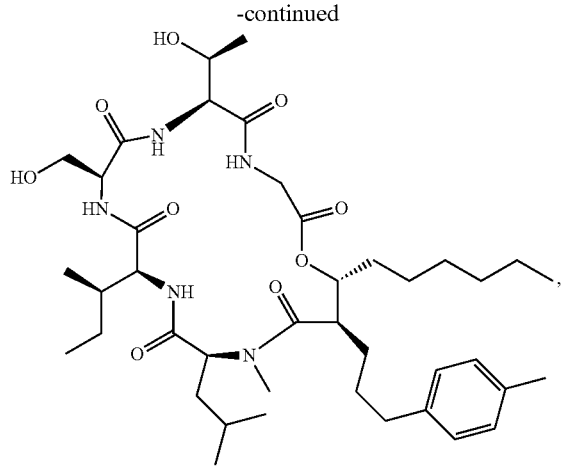
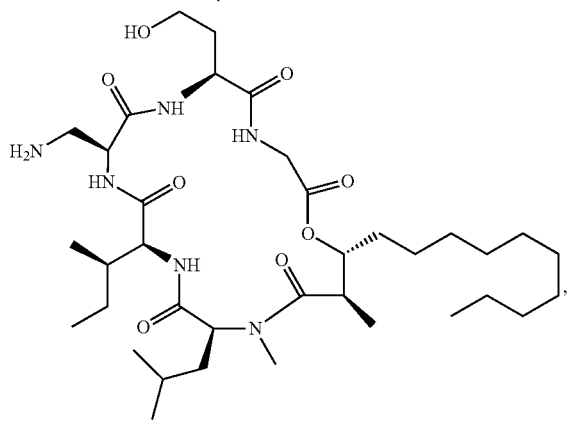
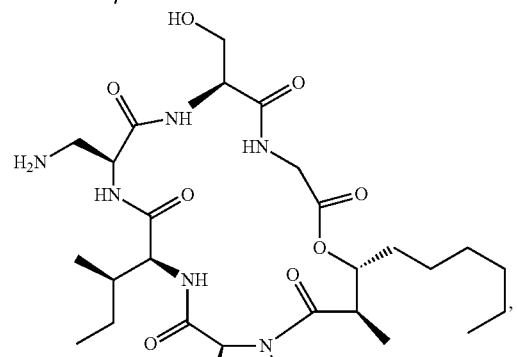
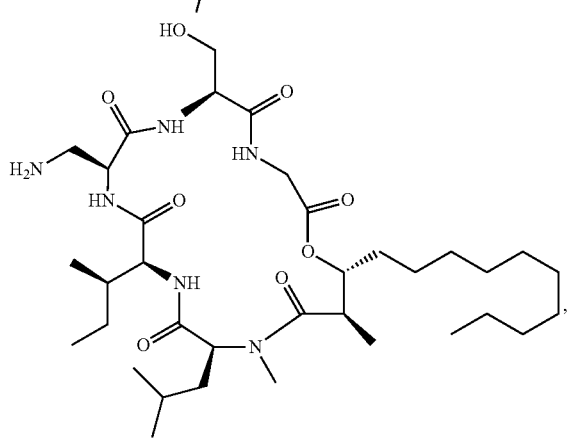
510
-continued
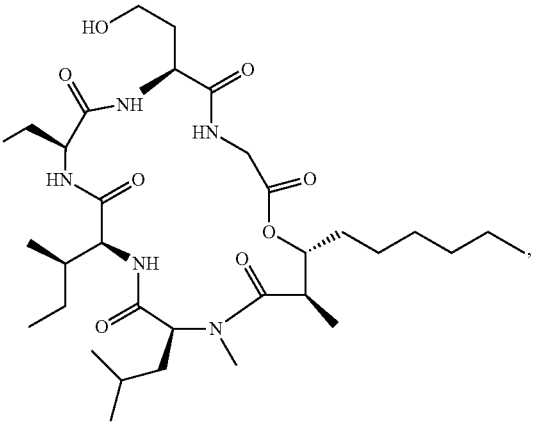
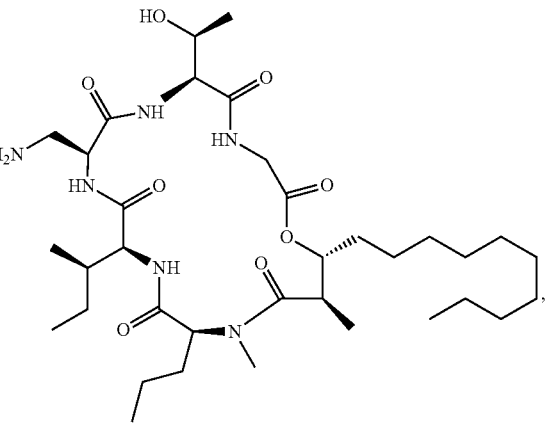
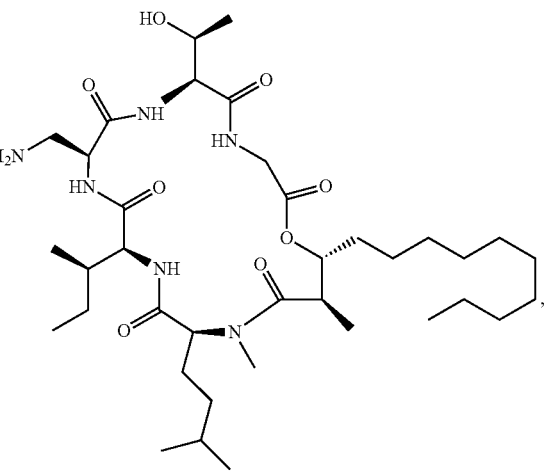

511
-continued
512
-continued
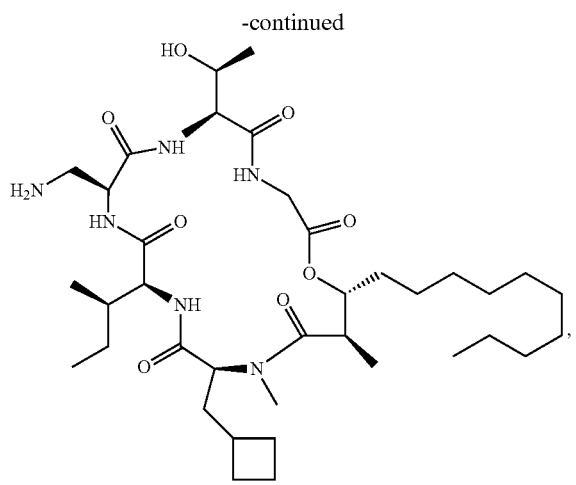
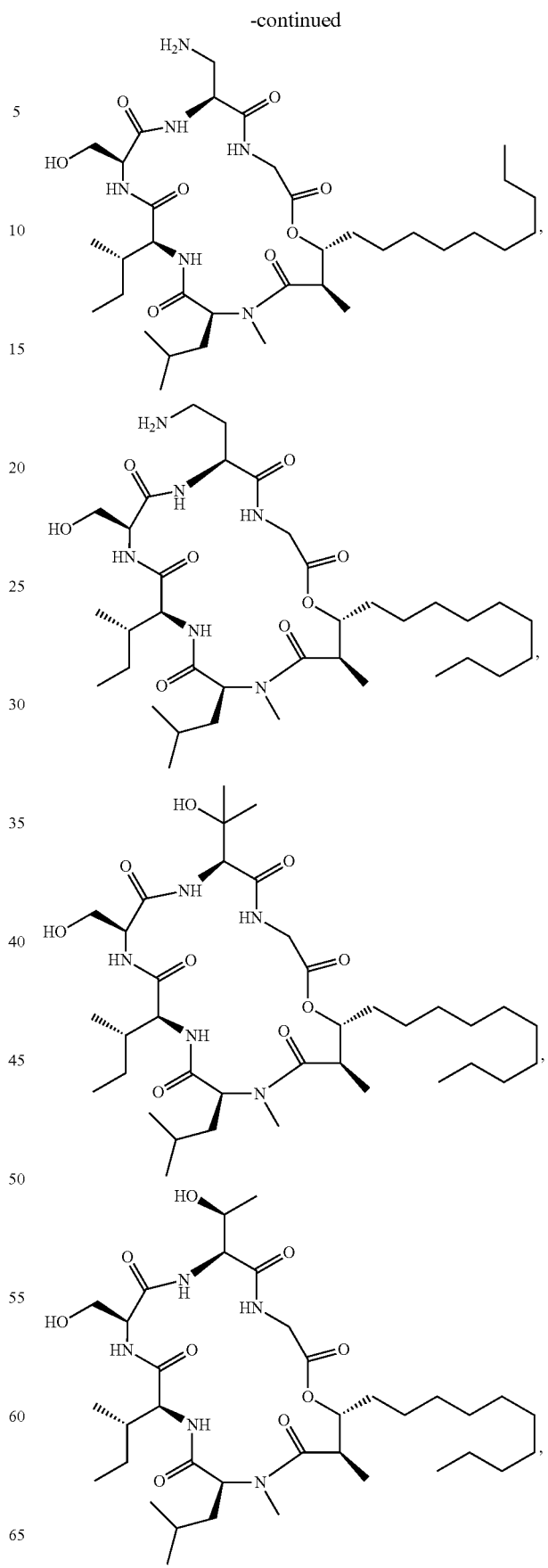

513
-continued
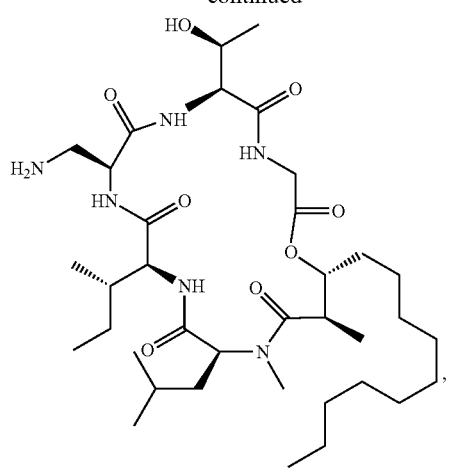
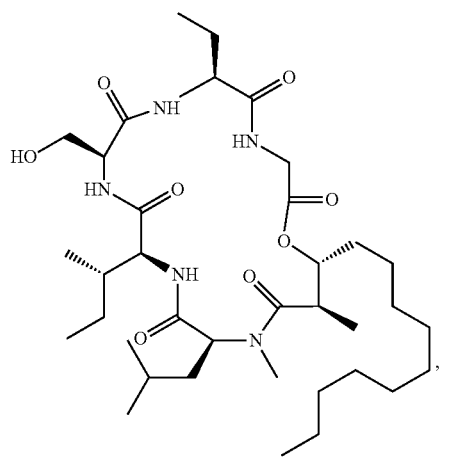
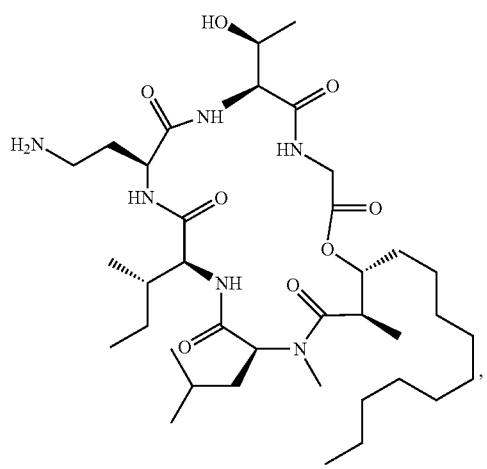
514
-continued
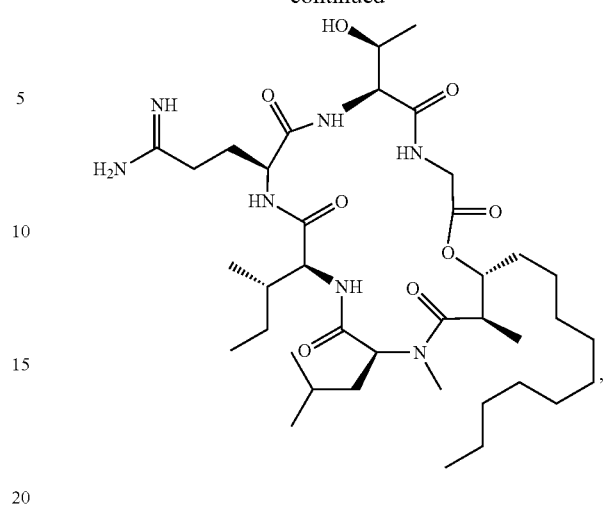
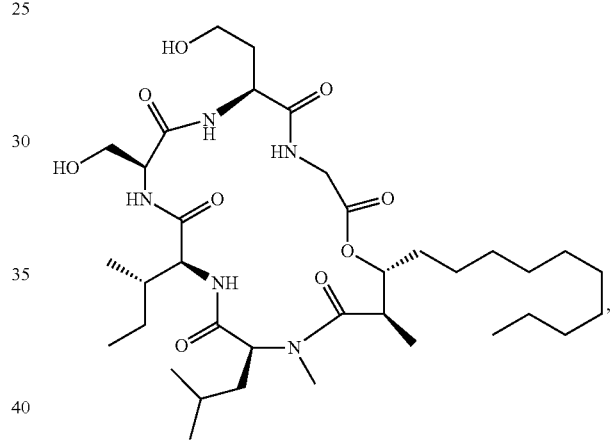
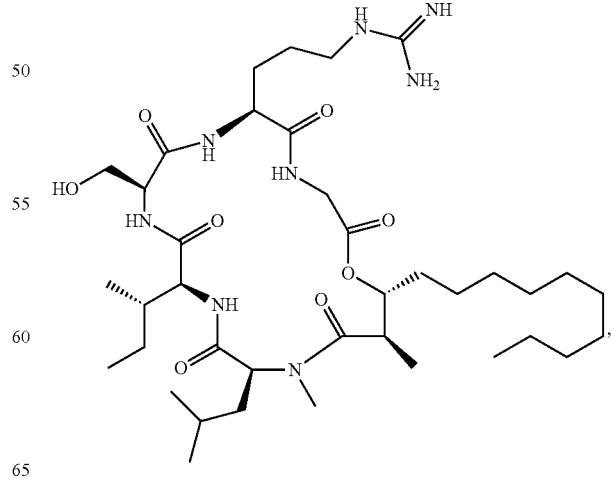

515
-continued
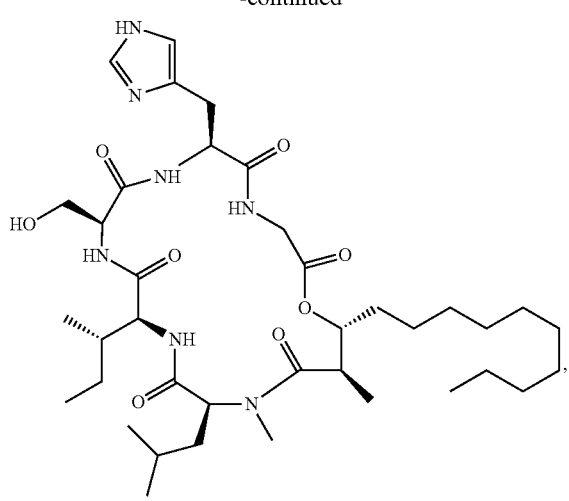
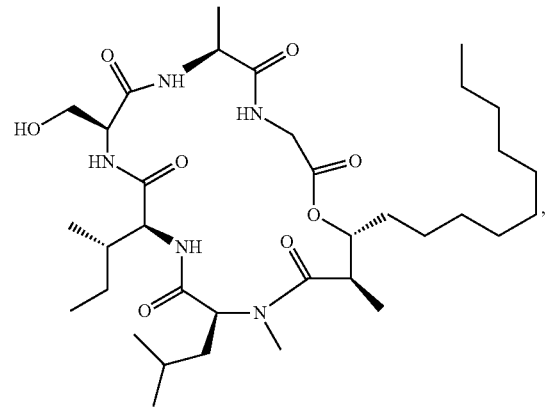
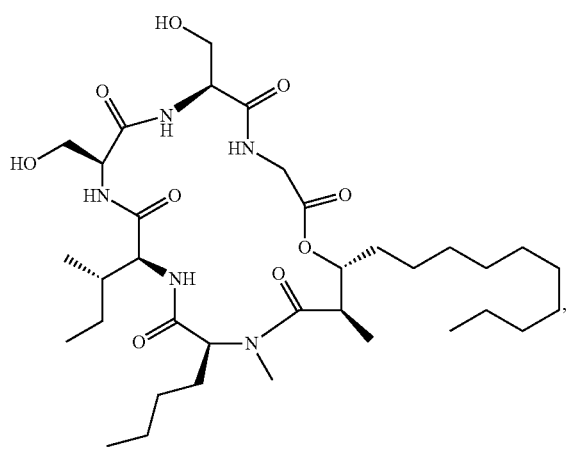
516
-continued
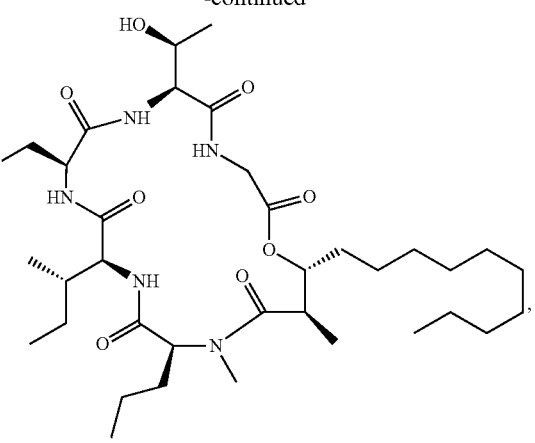
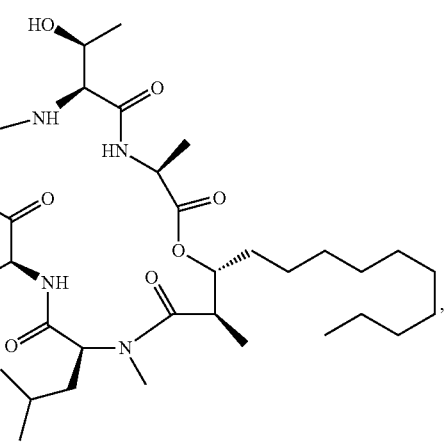
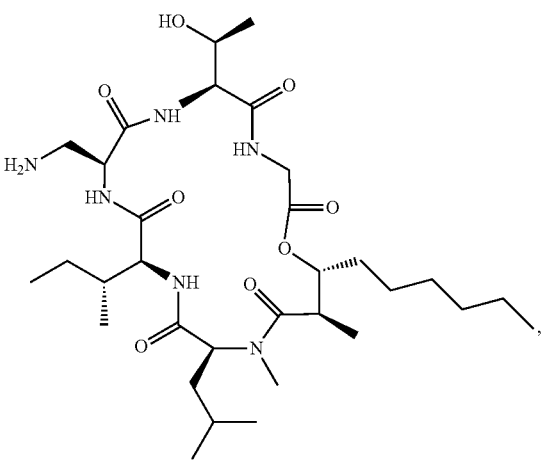

517
-continued
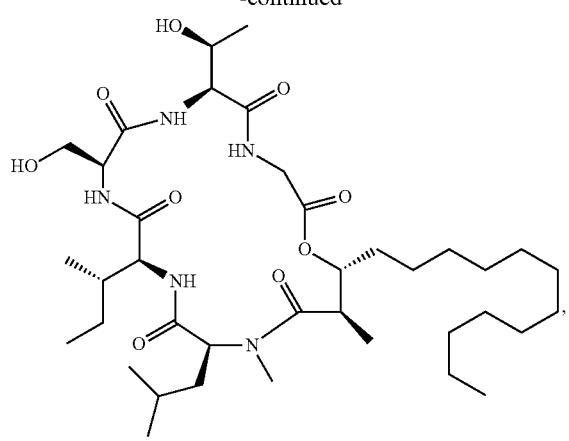
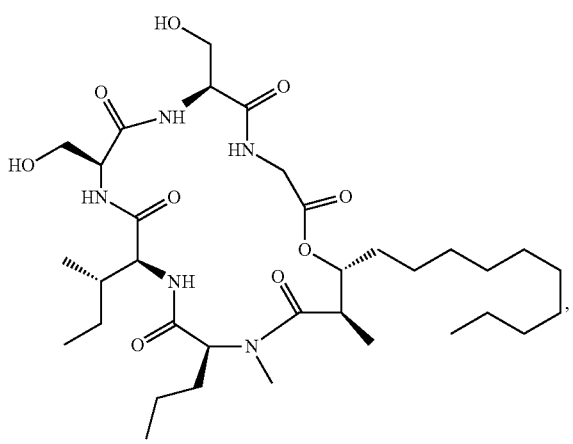
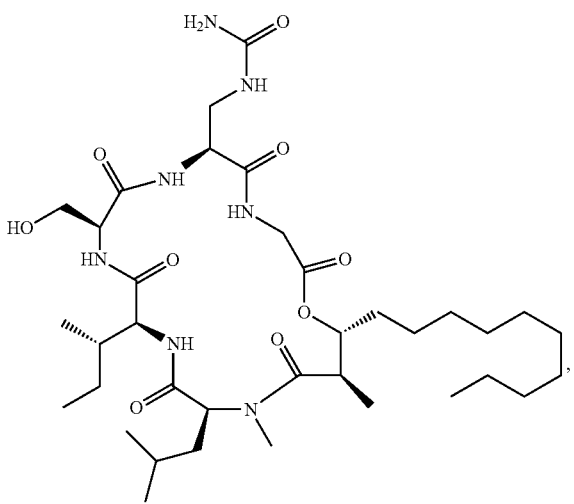
518
-continued
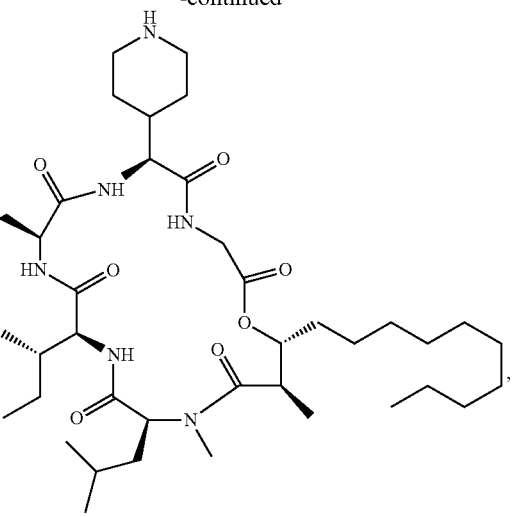
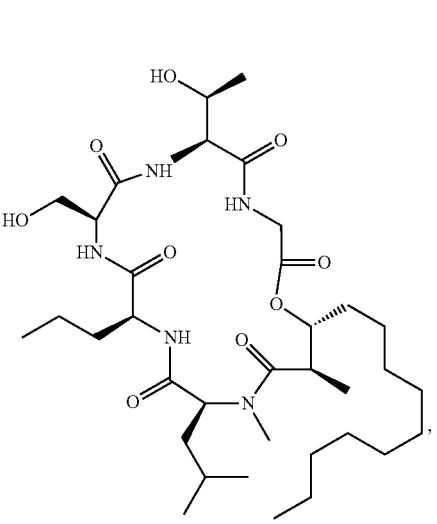

519
-continued
520
-continued
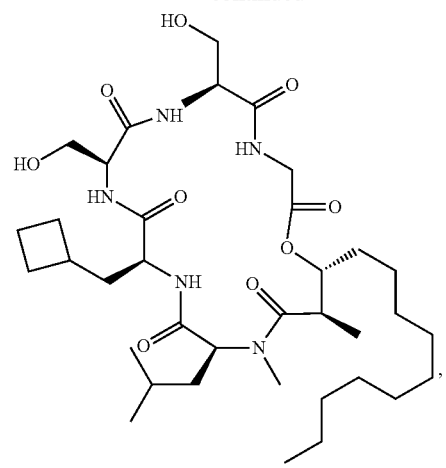
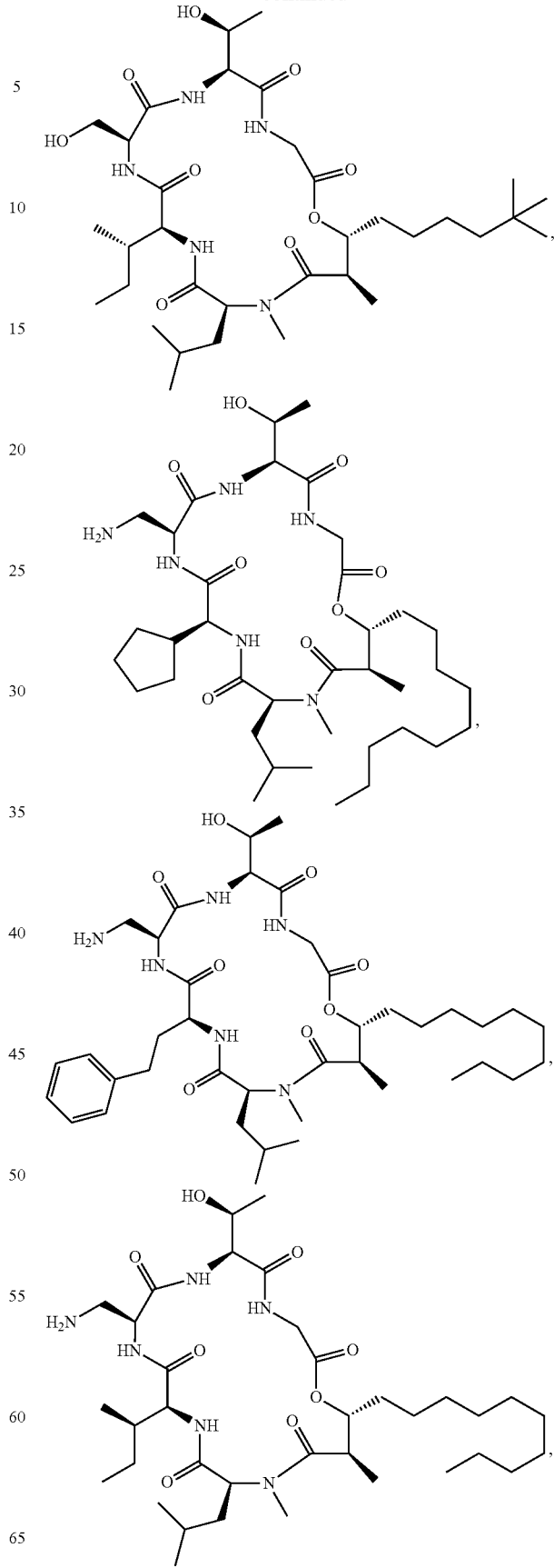

521
-continued
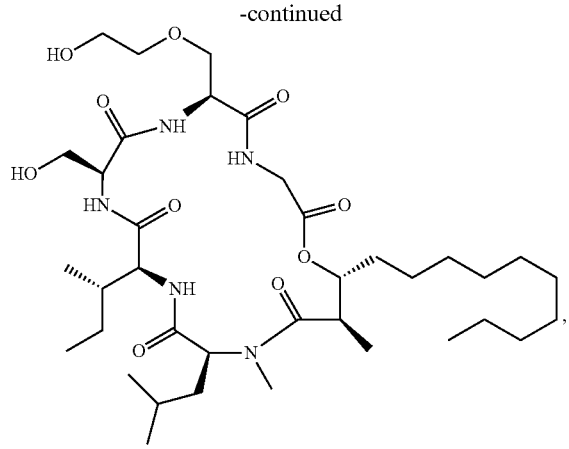
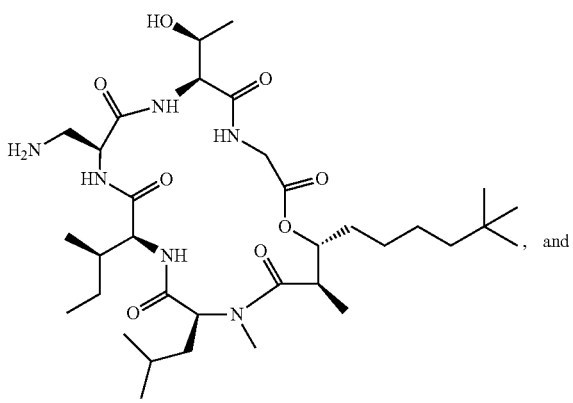, and
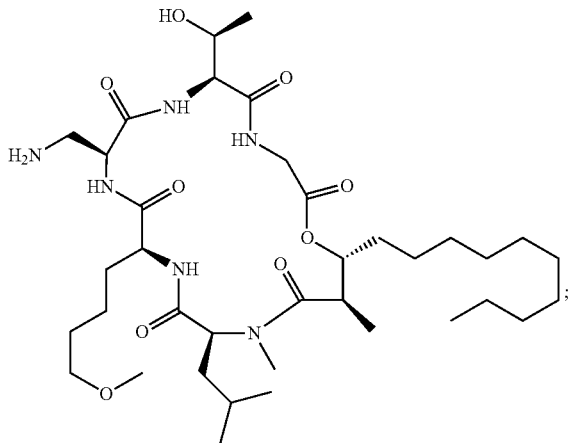;
or a pharmaceutically acceptable salt, solvate, or stereoisomer thereof.
25. A pharmaceutical composition comprising the compound of claim 1, or a pharmaceutically acceptable salt, solvate, or stereoisomer thereof, and a pharmaceutically acceptable excipient.
522
26. The compound of claim 25, selected from:
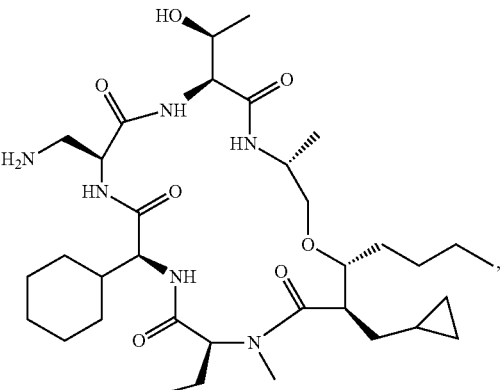,
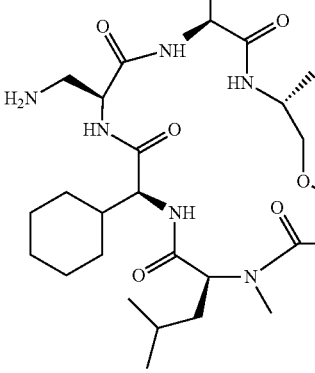,
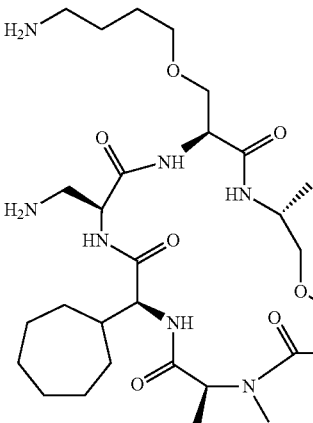, 523
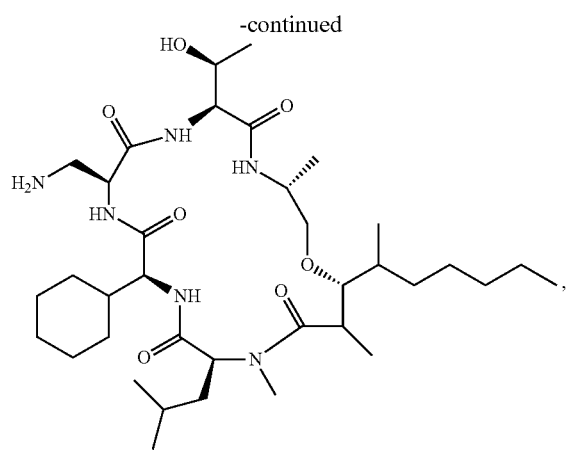
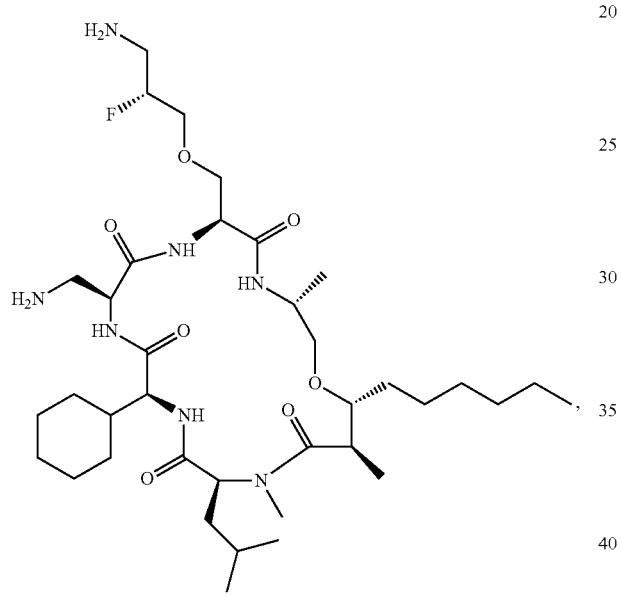
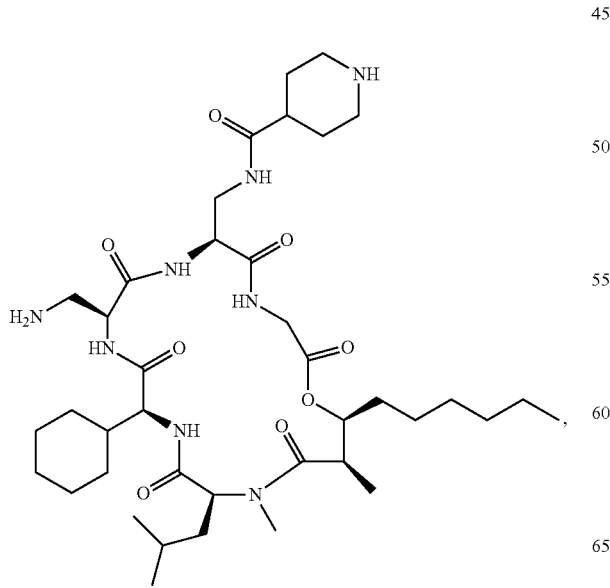
524
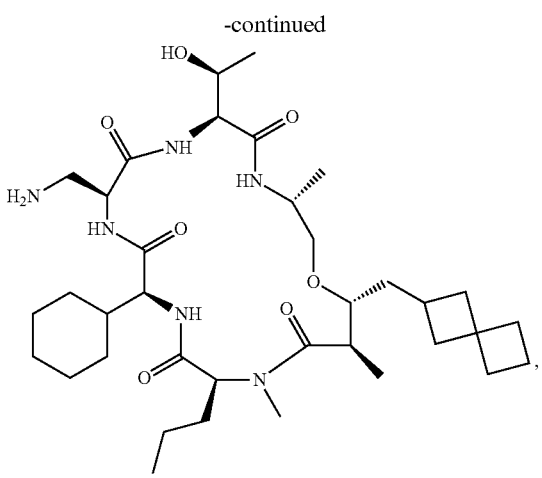
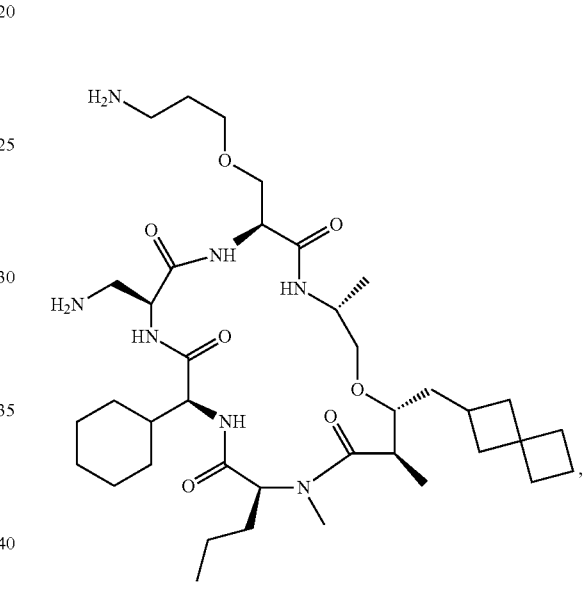
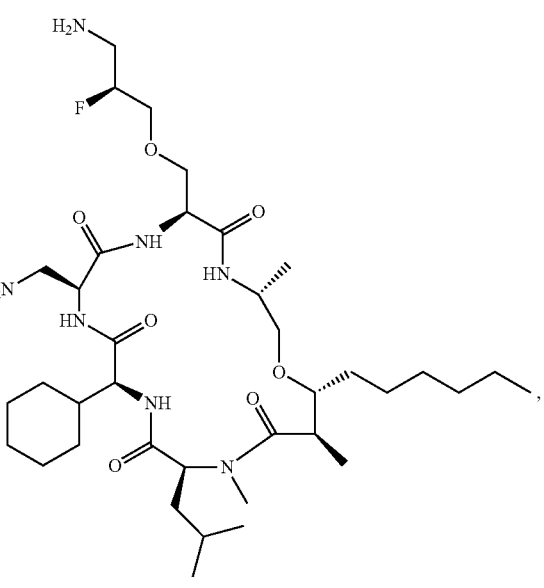

525
-continued
526
-continued
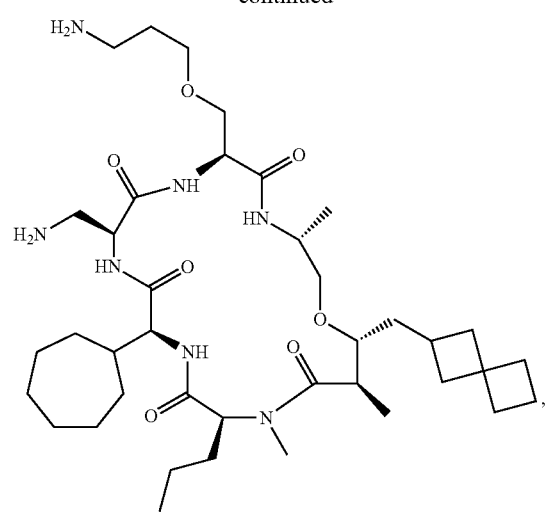
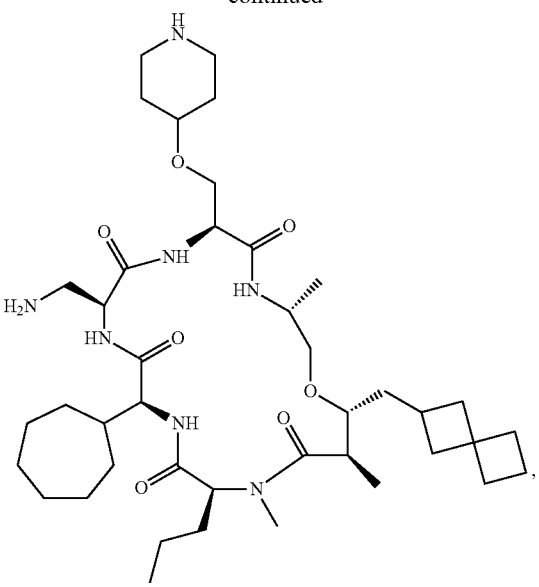
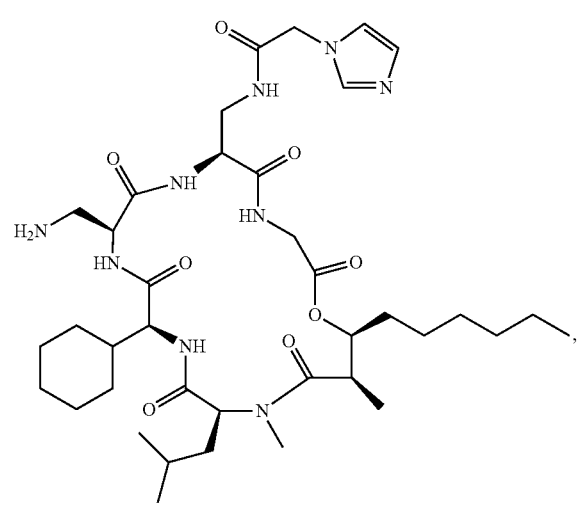
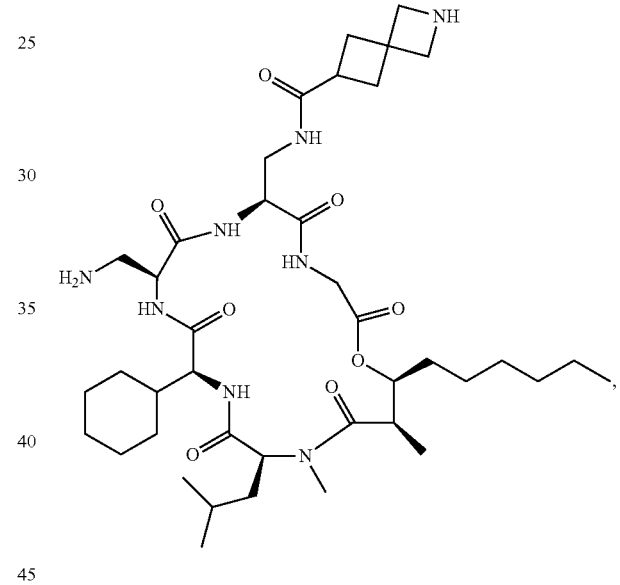
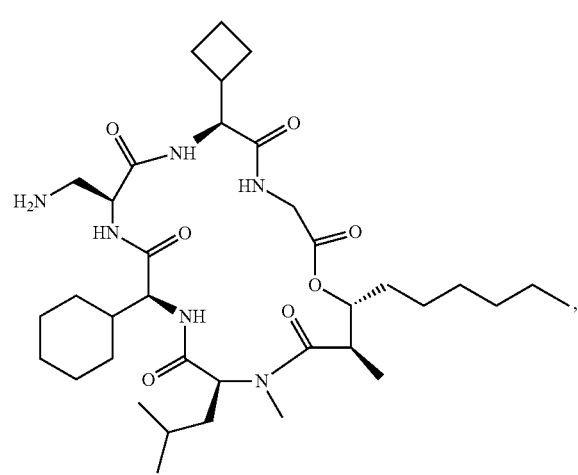
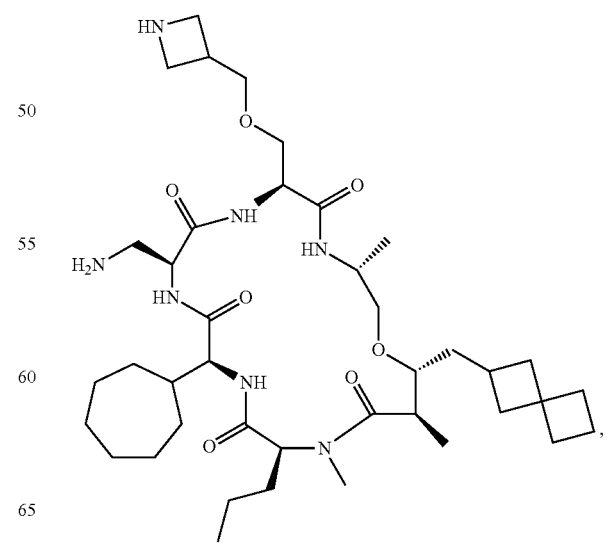

527
-continued
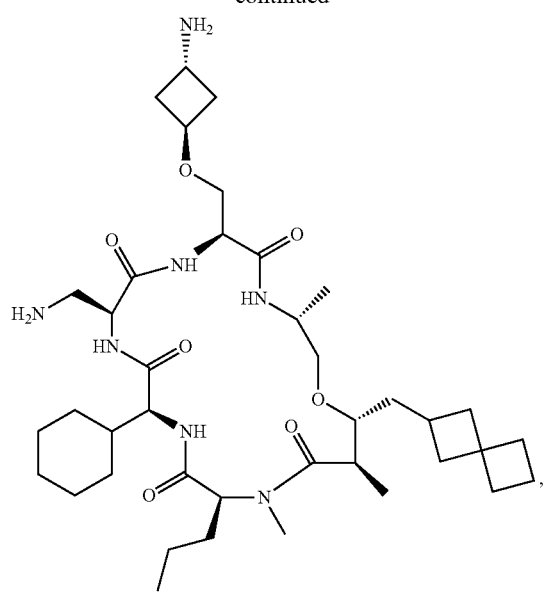
or a pharmaceutically acceptable salt, solvate, or stereoisomer thereof.
27. The compound of claim 25, selected from:
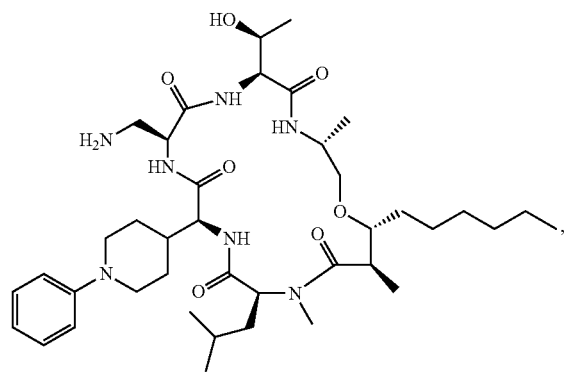
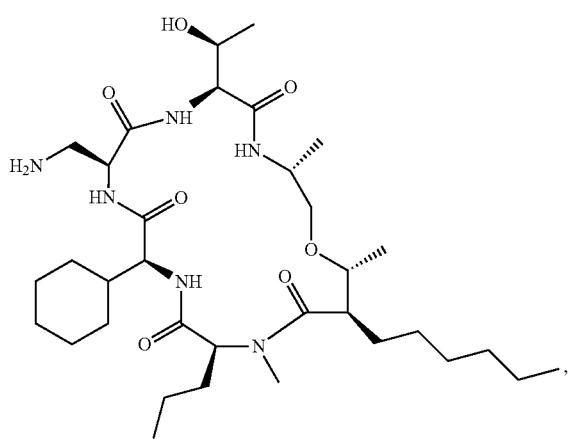
528
-continued
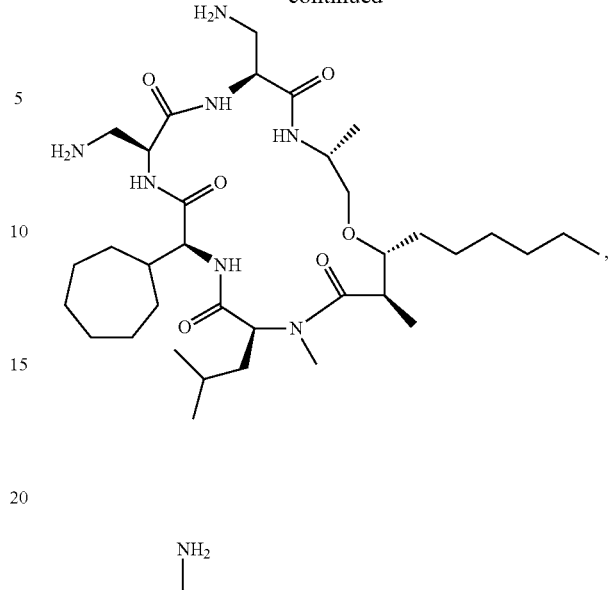
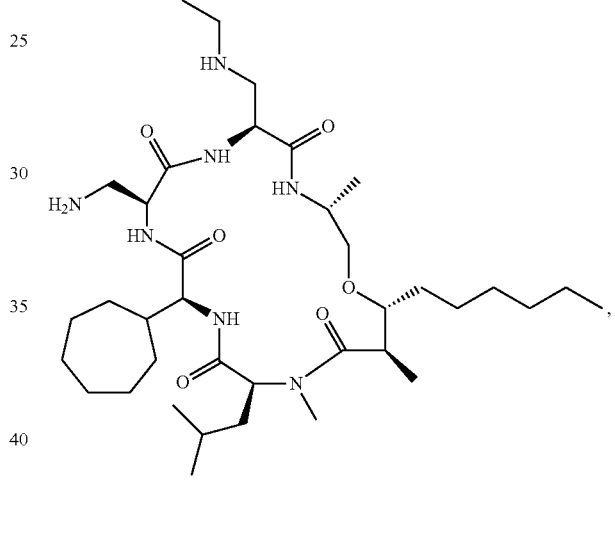
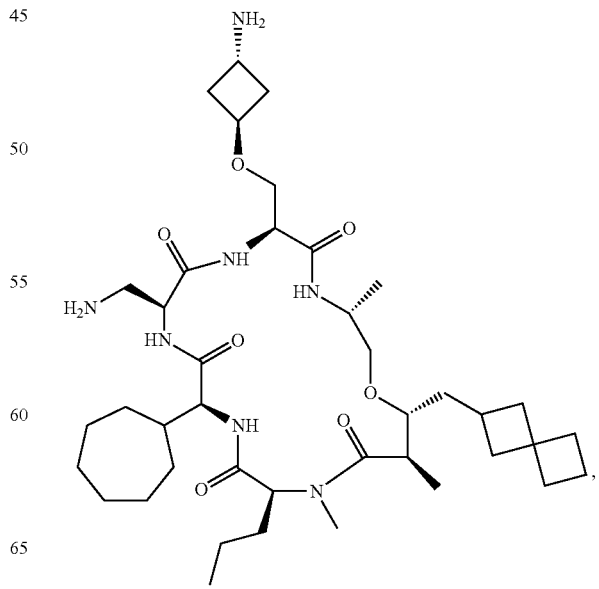

529
-continued
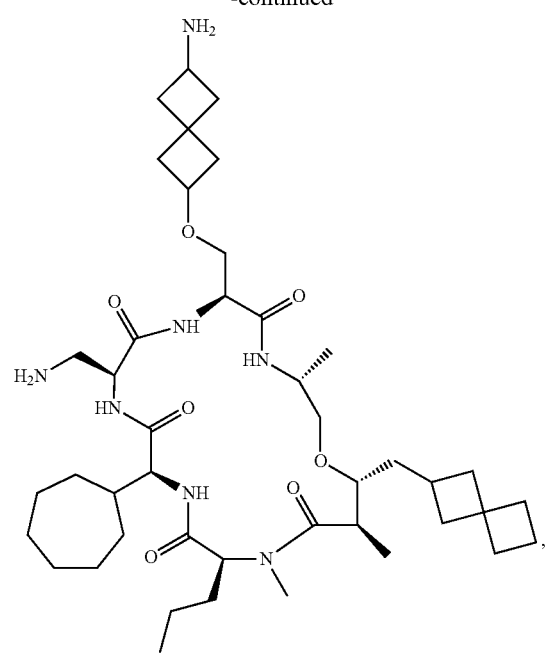
530
-continued
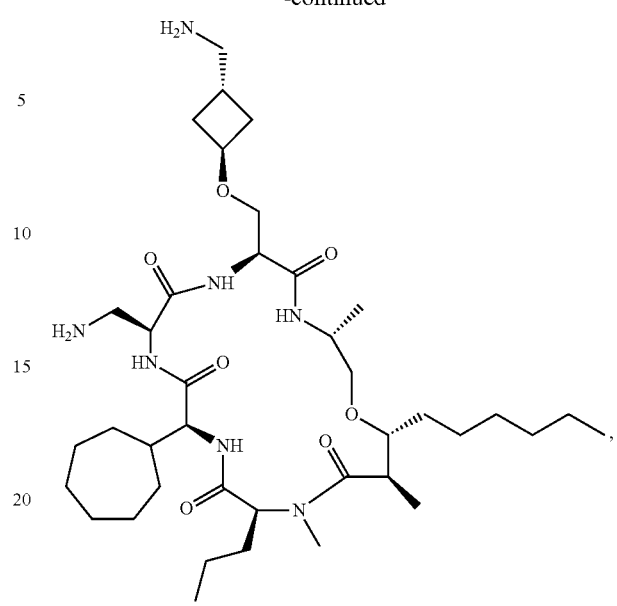
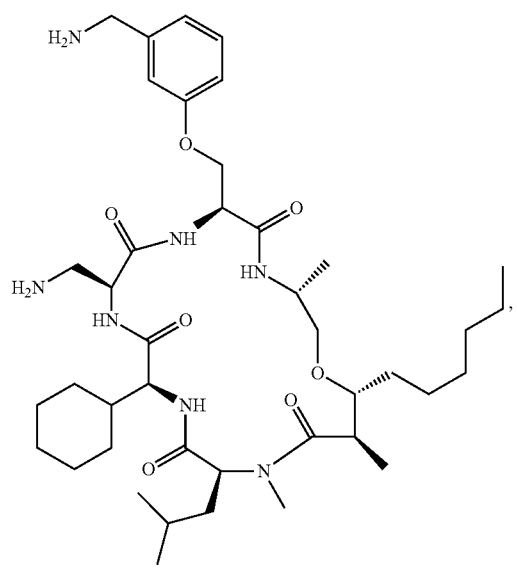
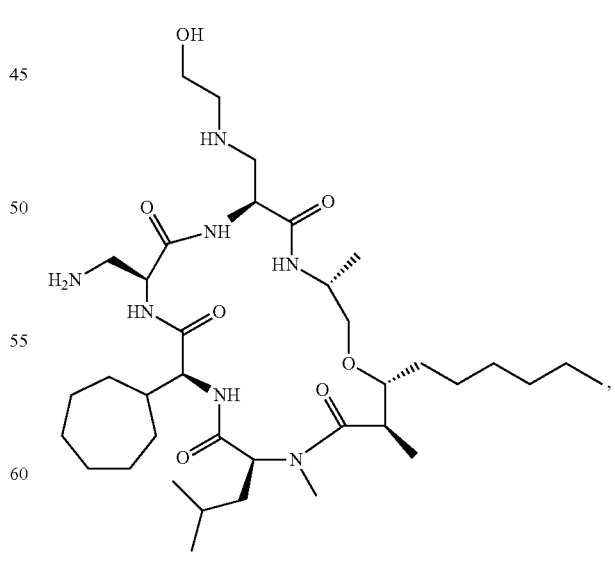

531
-continued
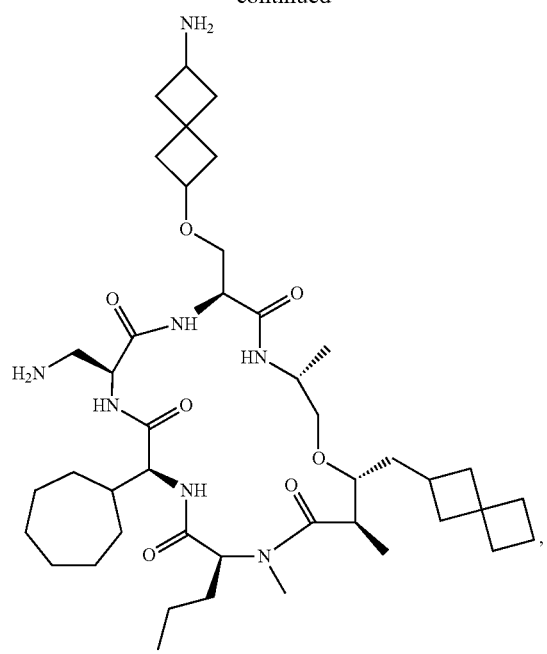
532
-continued
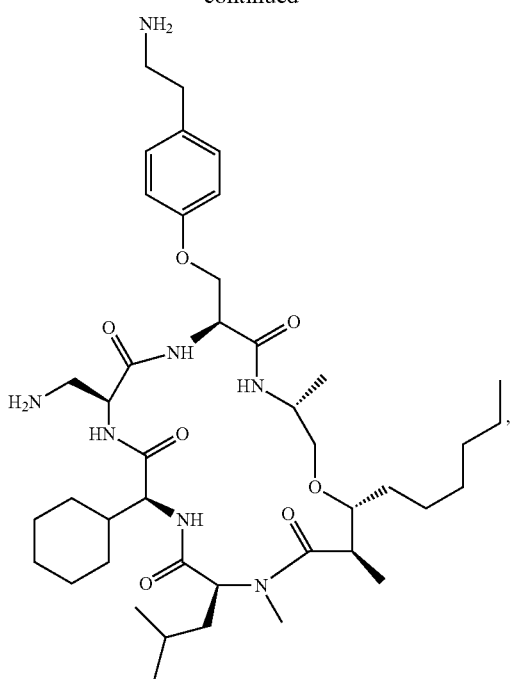
or a pharmaceutically acceptable salt, solvate, or stereoisomer thereof.
28. The compound of claim 1, selected from:
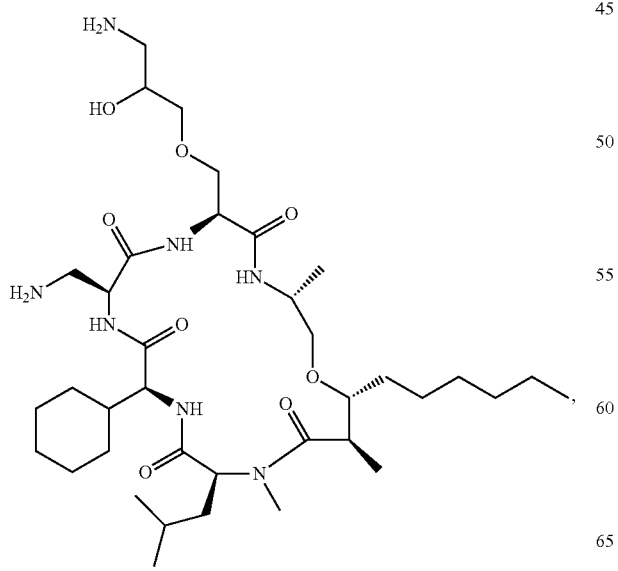
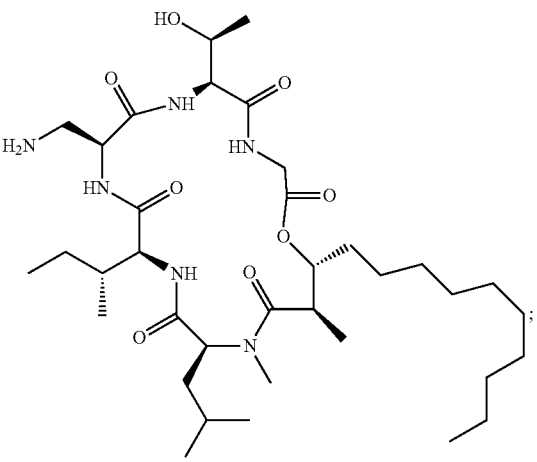

533
-continued
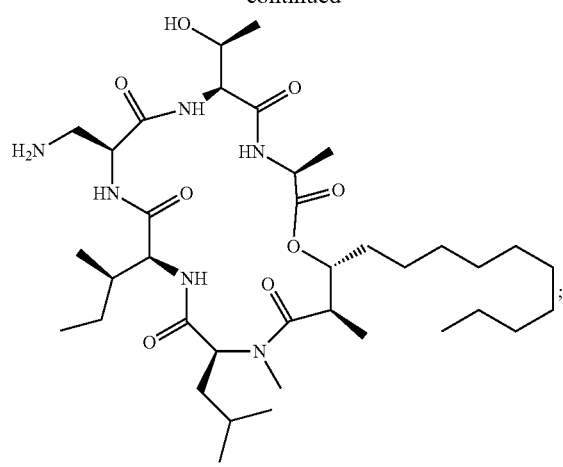
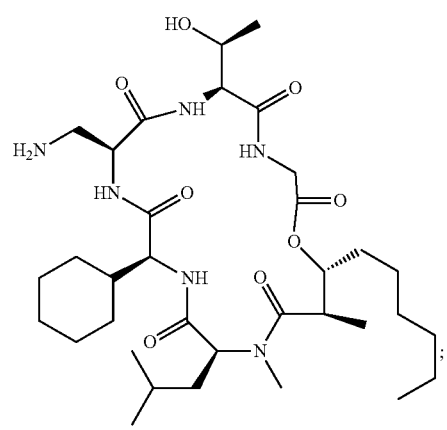
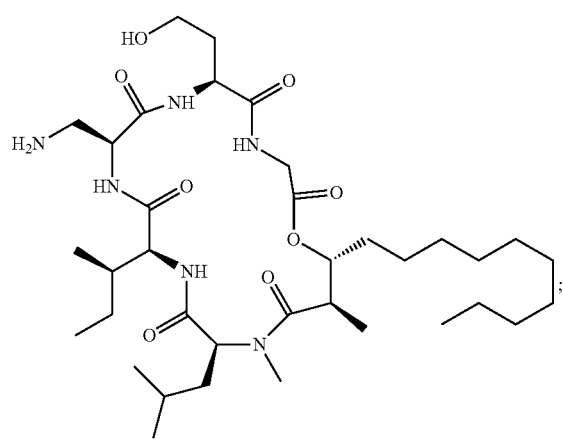
534
-continued
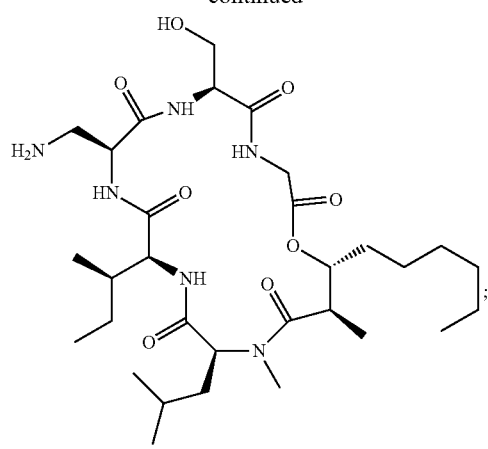
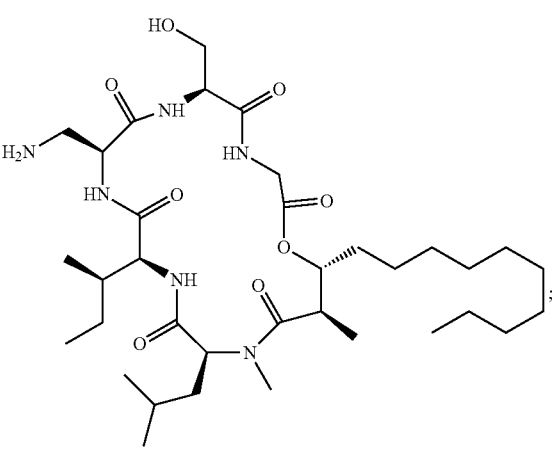
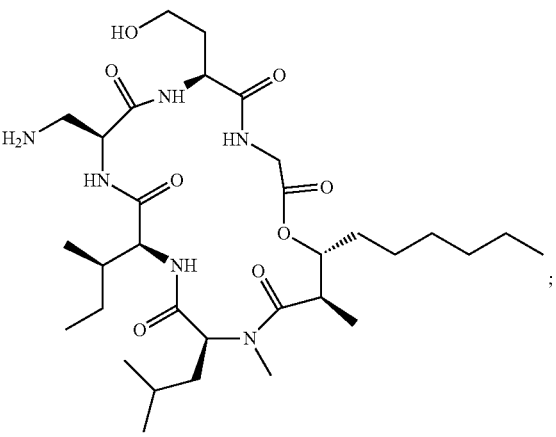

-continued
535
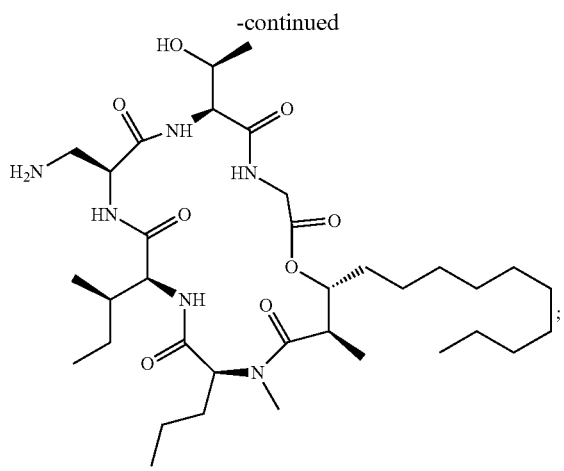
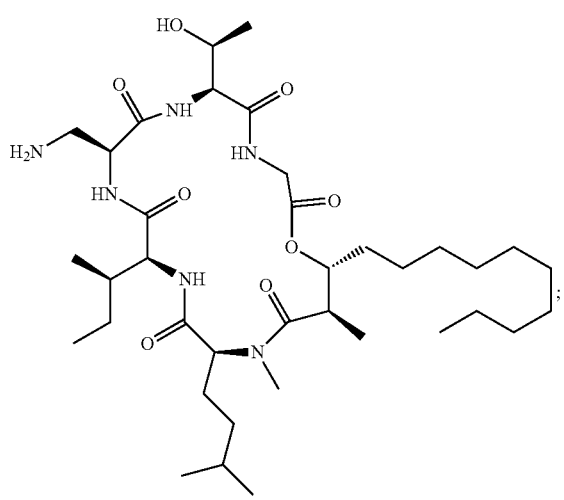
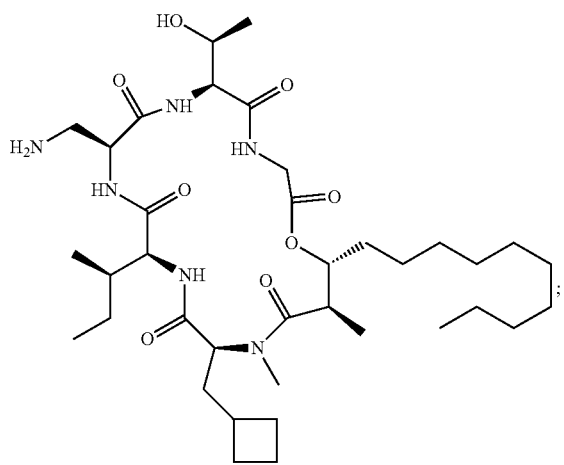
536
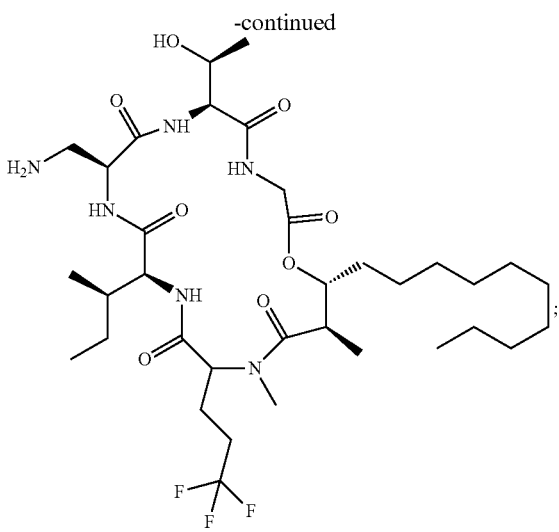
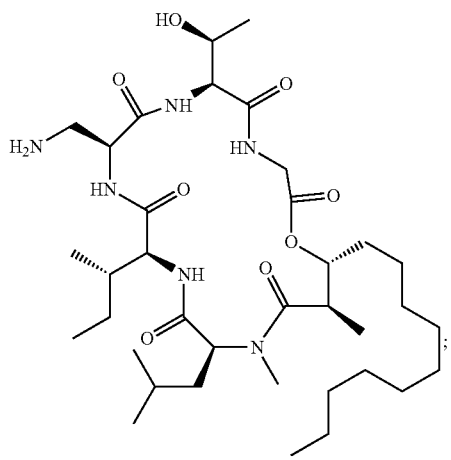
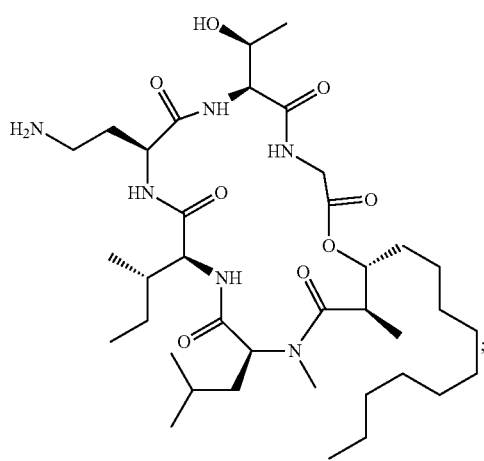

537
-continued
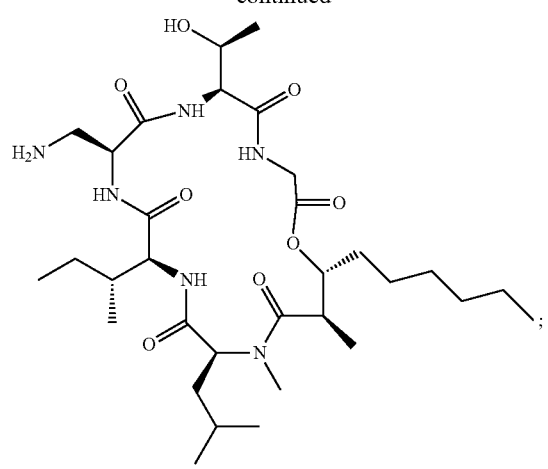
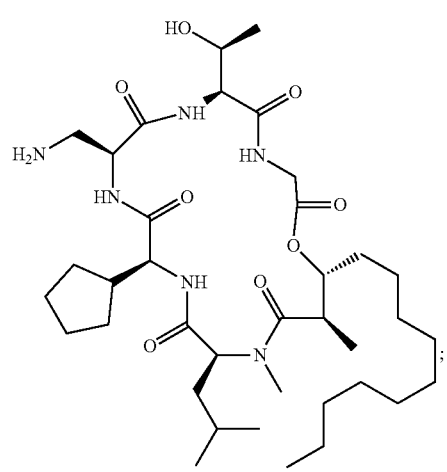
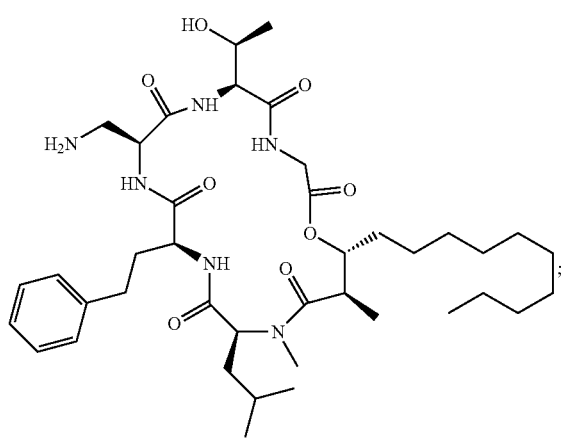
538
-continued
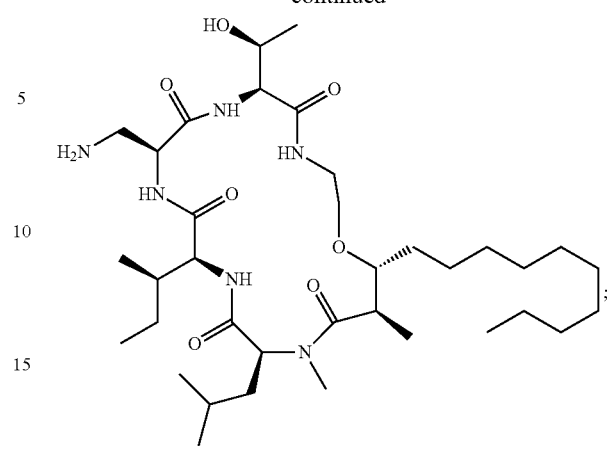
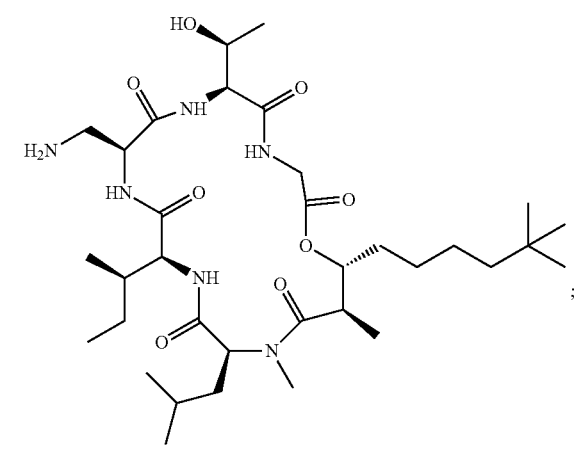
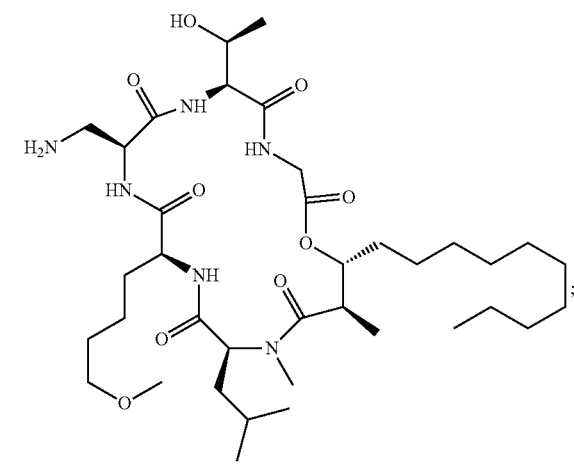

539
-continued
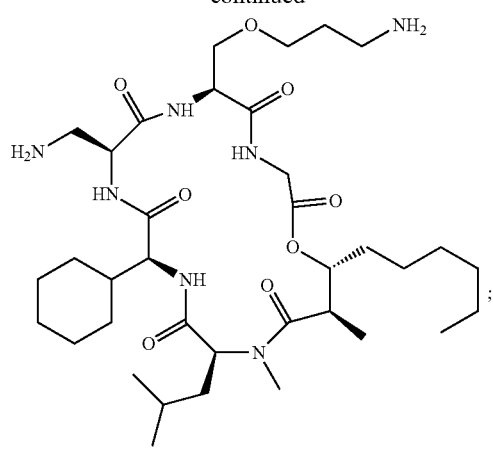
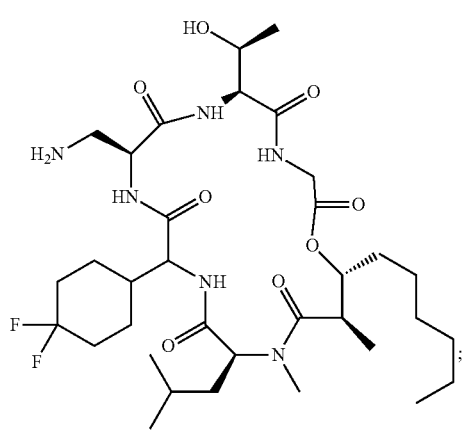
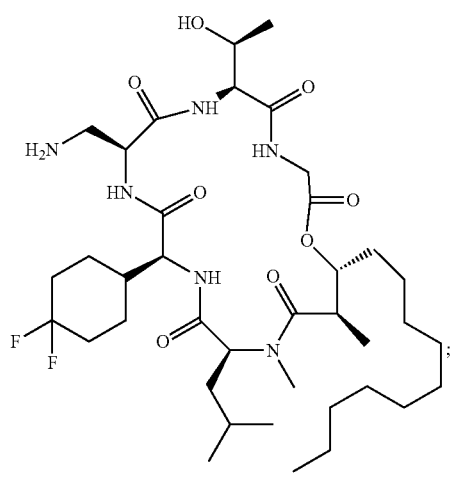
540
-continued
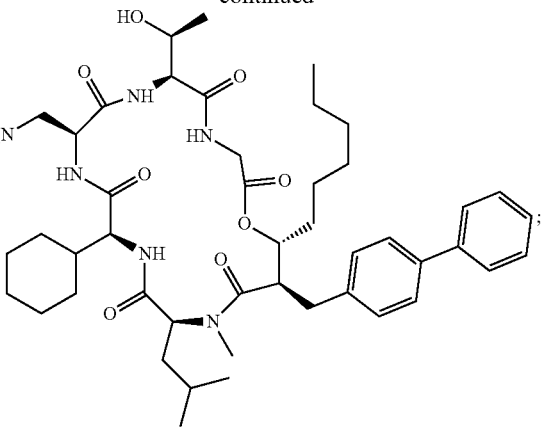
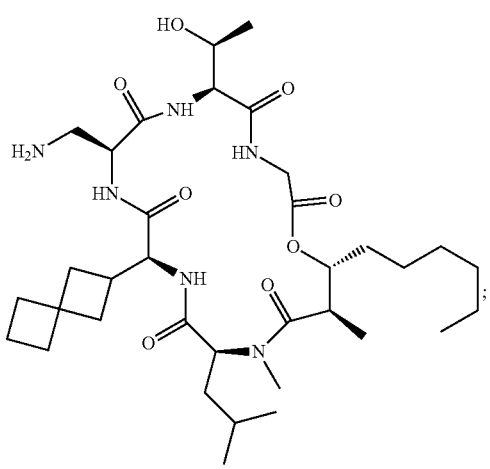
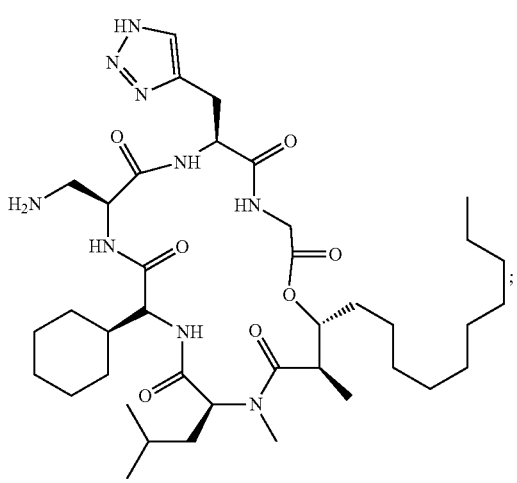

541
-continued
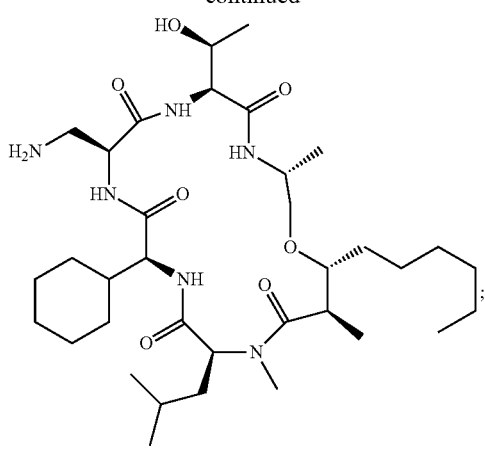
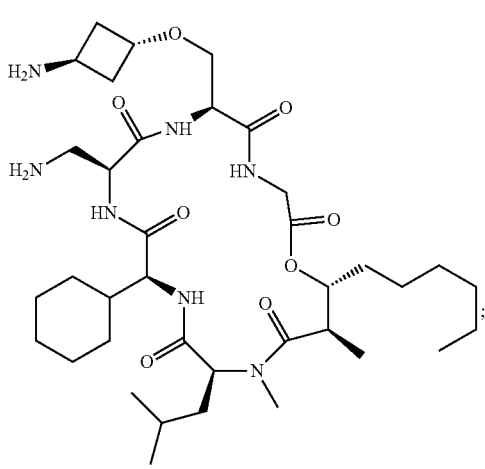
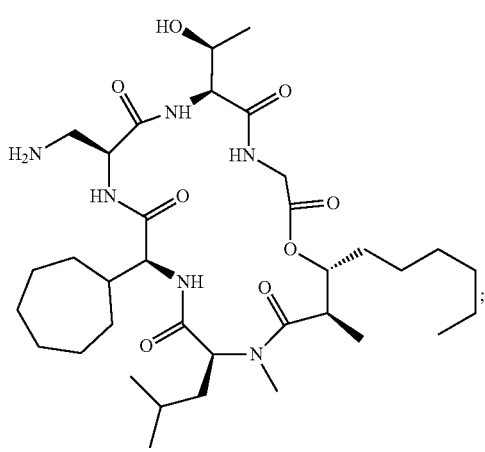
542
-continued
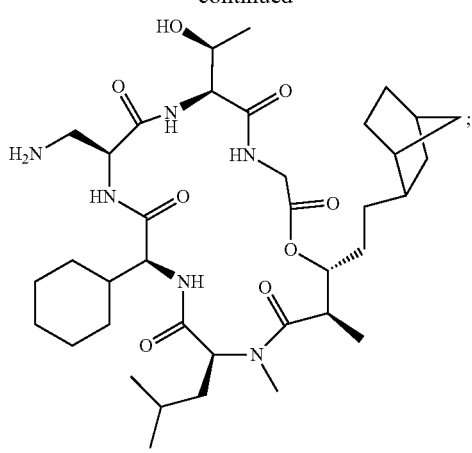
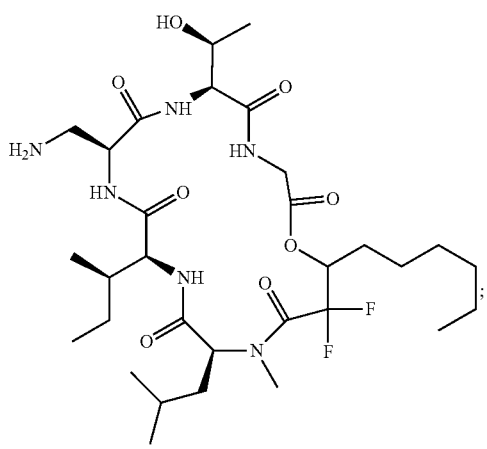
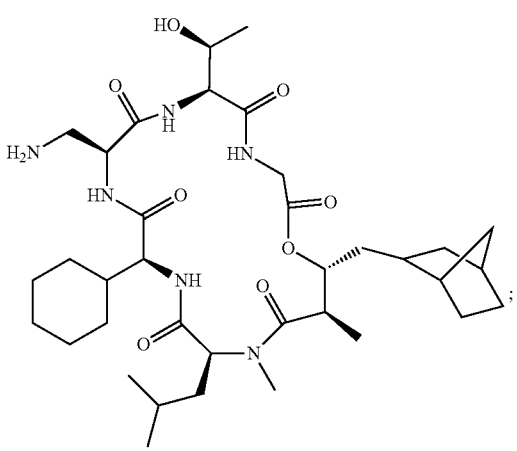

543
-continued
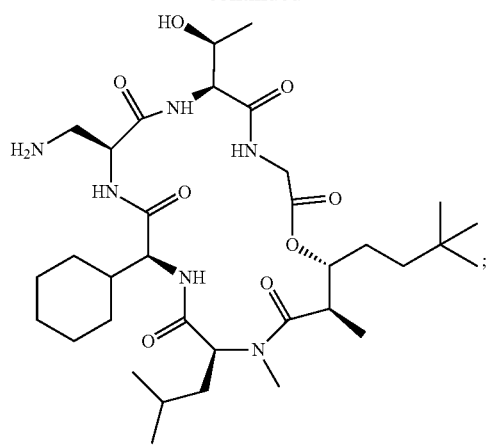
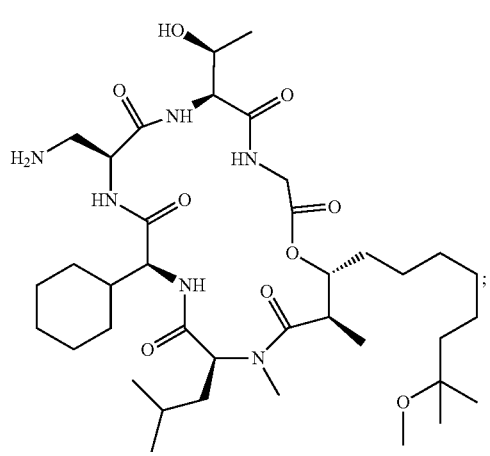
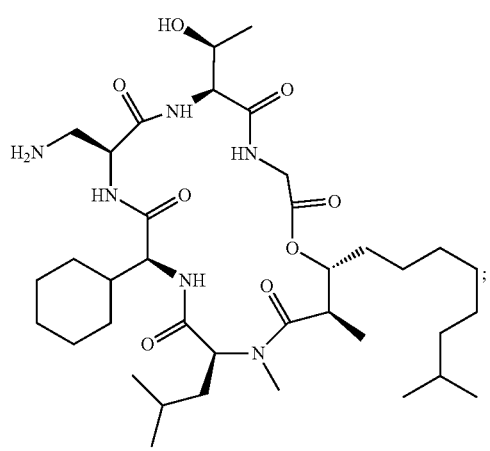
544
-continued
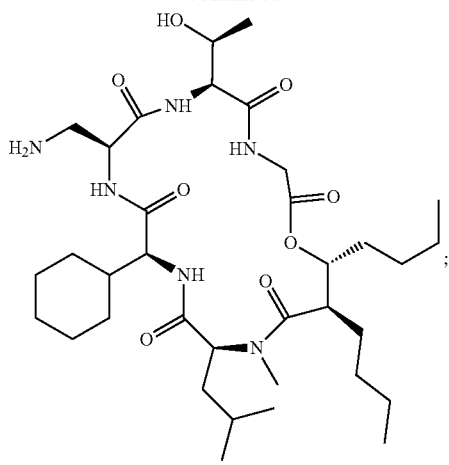
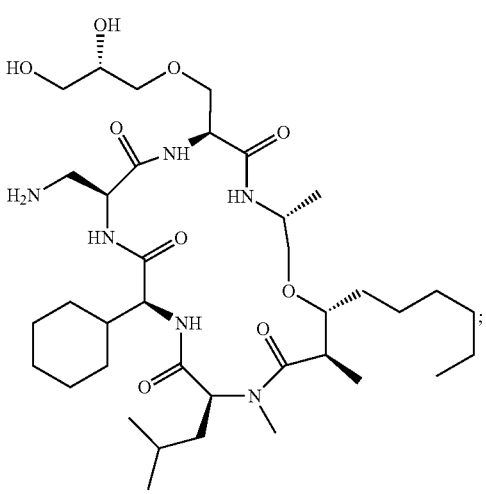
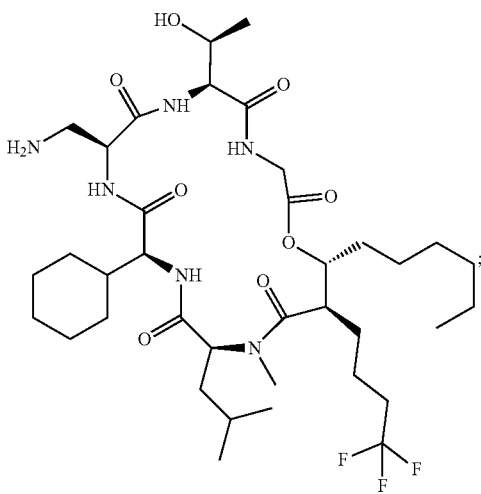

545
-continued
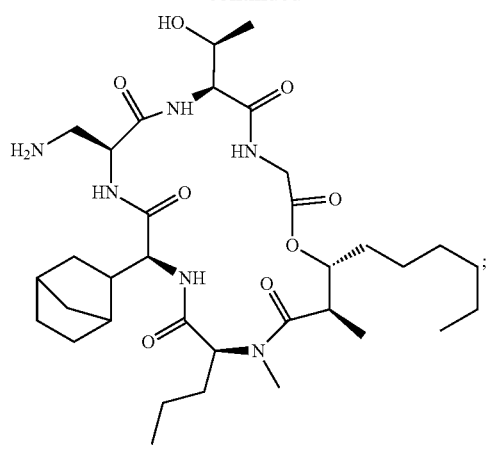
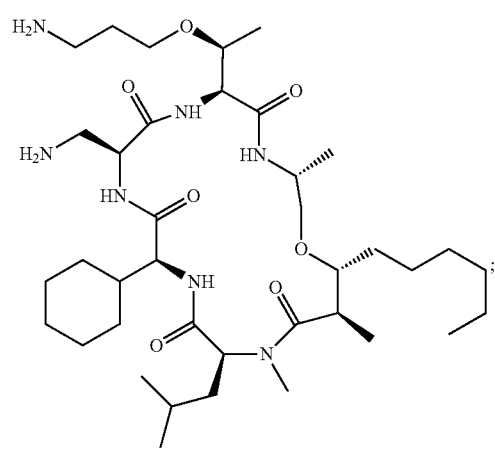
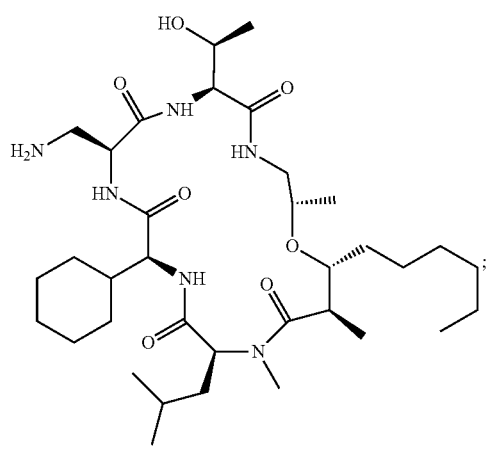
546
-continued
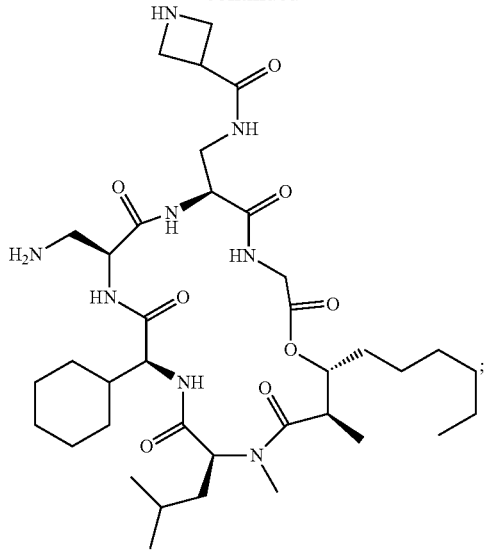
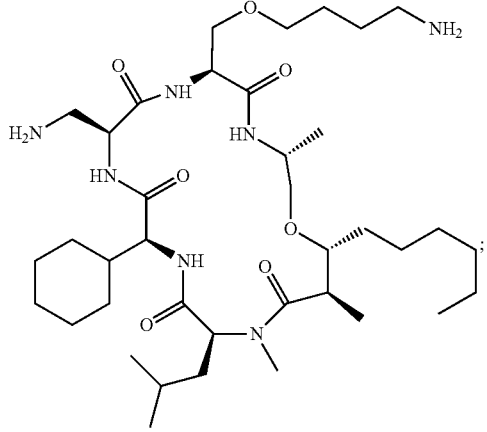
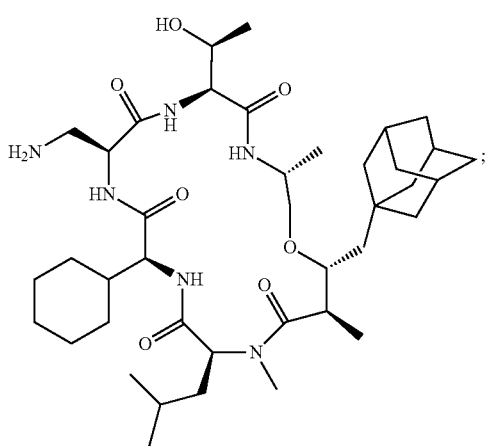

547
-continued
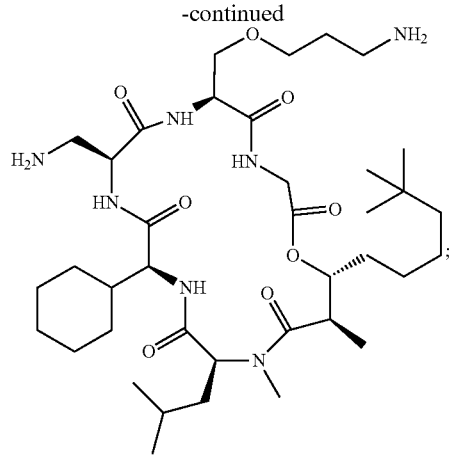
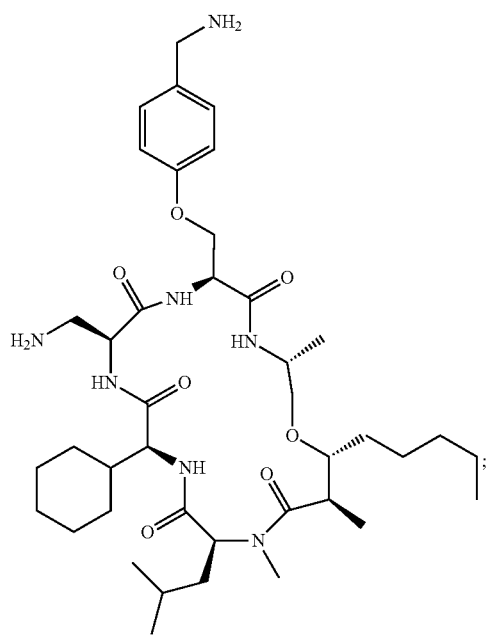
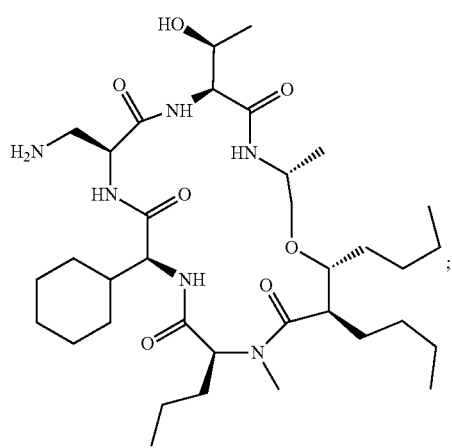
548
-continued
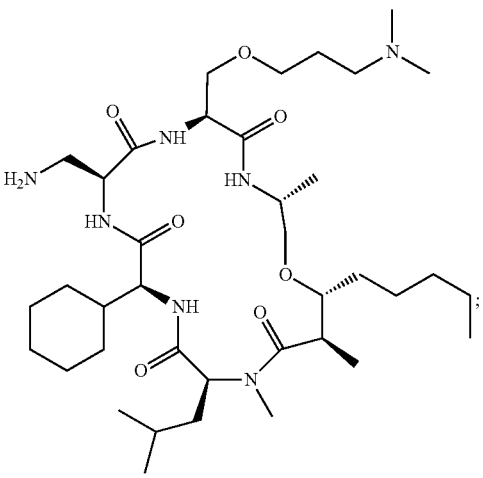
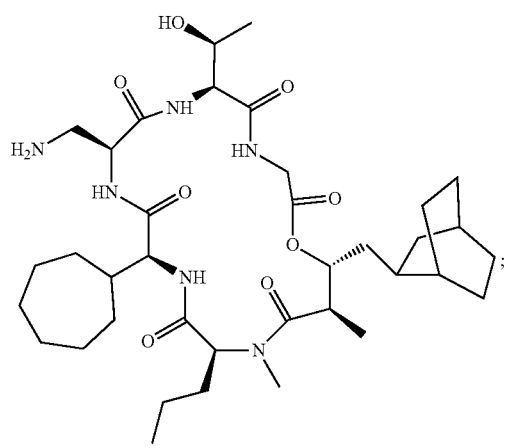
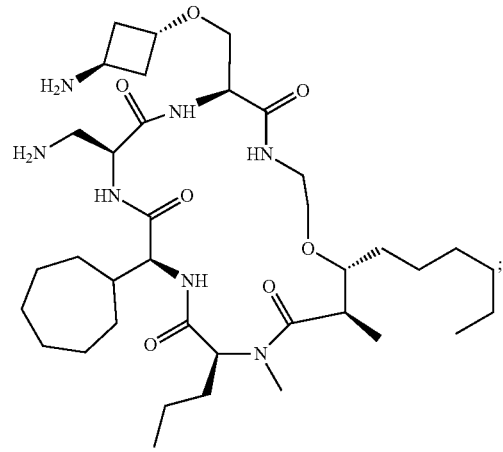

549
-continued
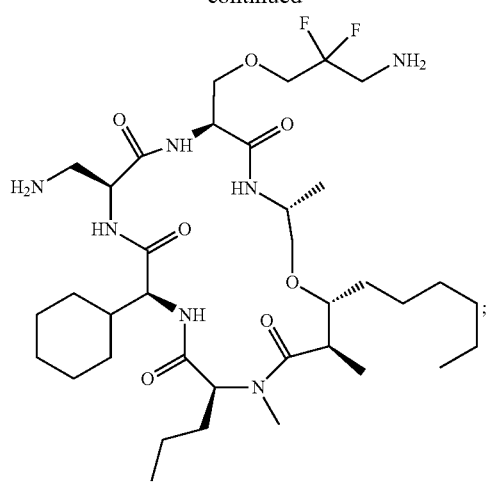
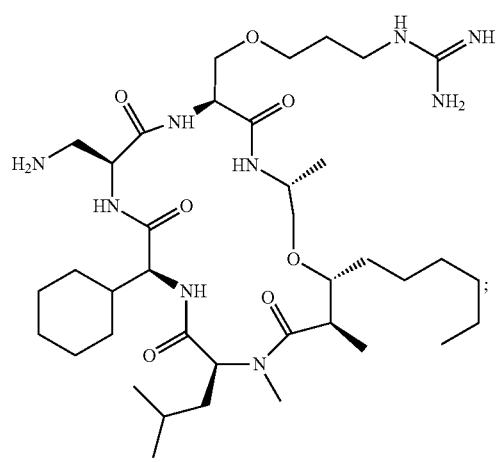
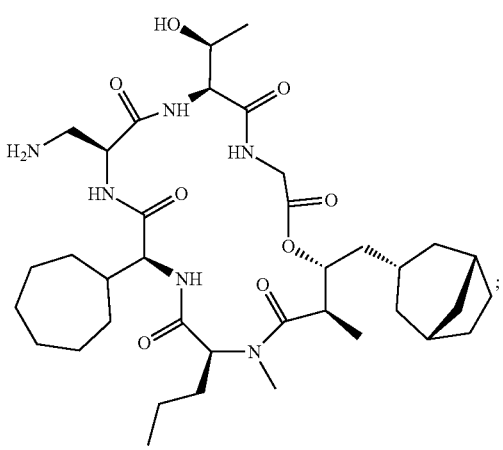
550
-continued
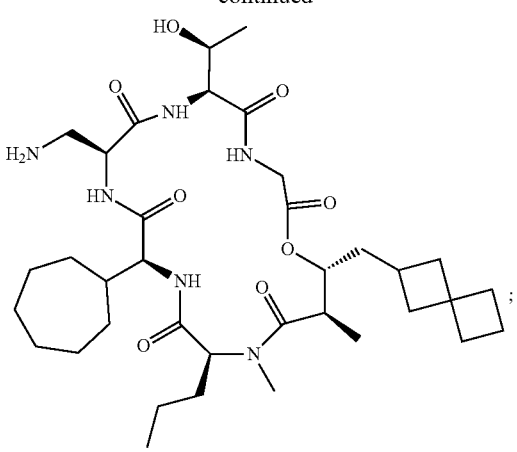
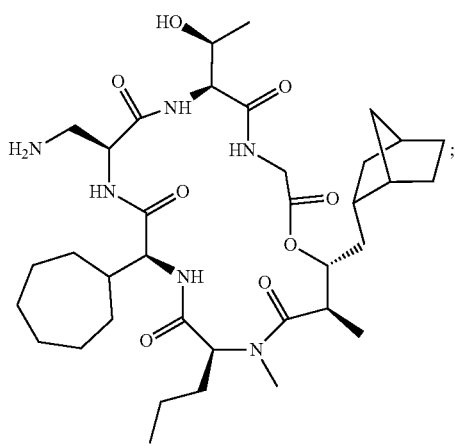
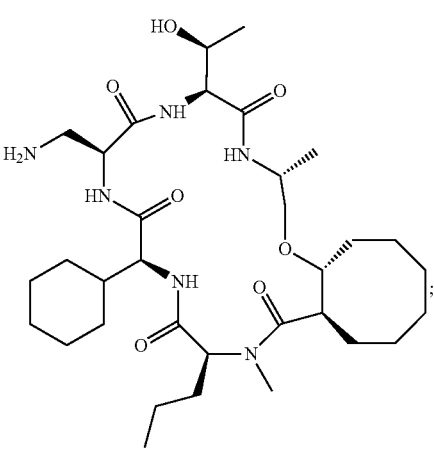

551
-continued
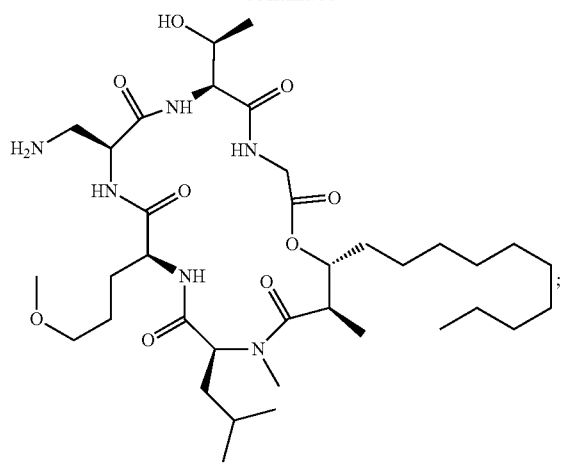
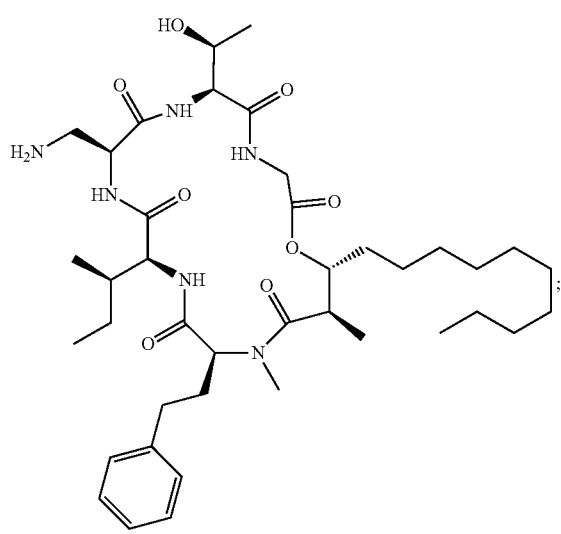
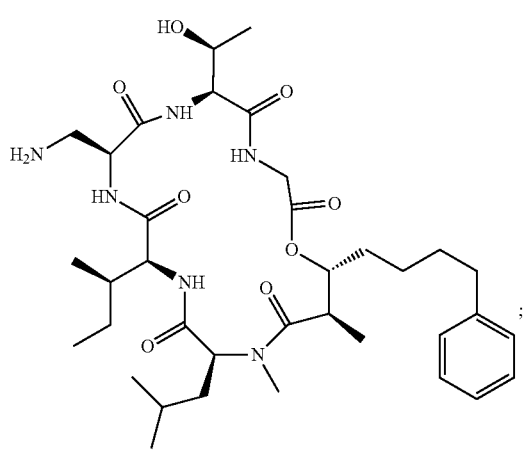
552
-continued
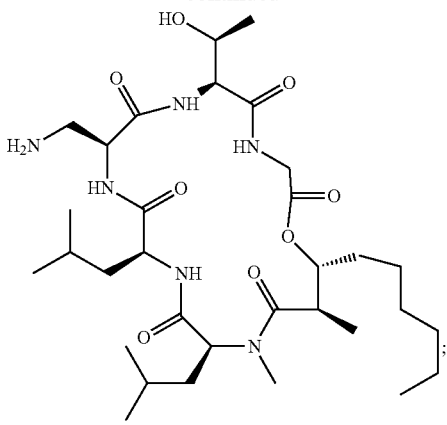
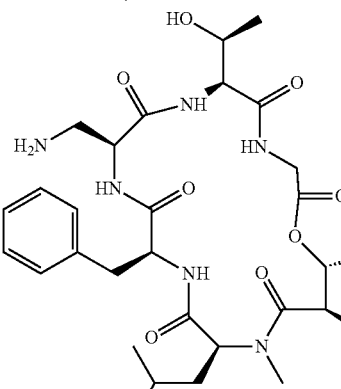
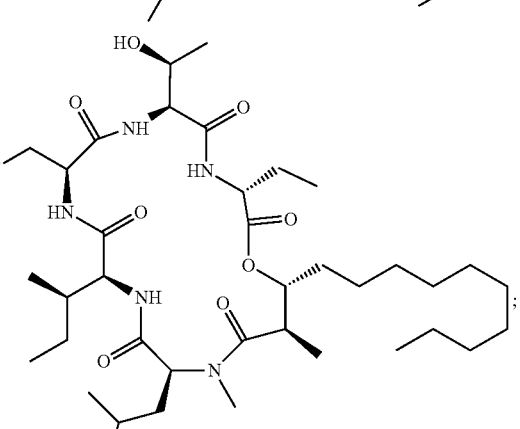
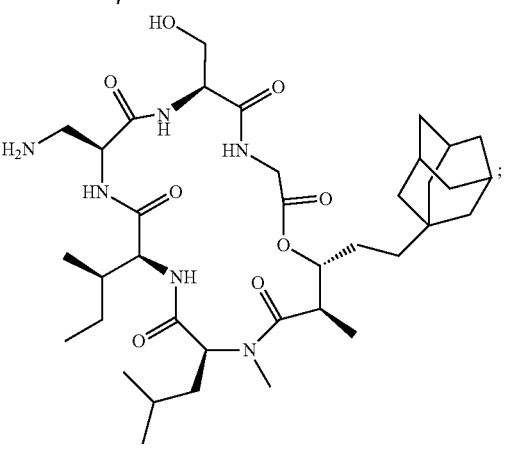

553
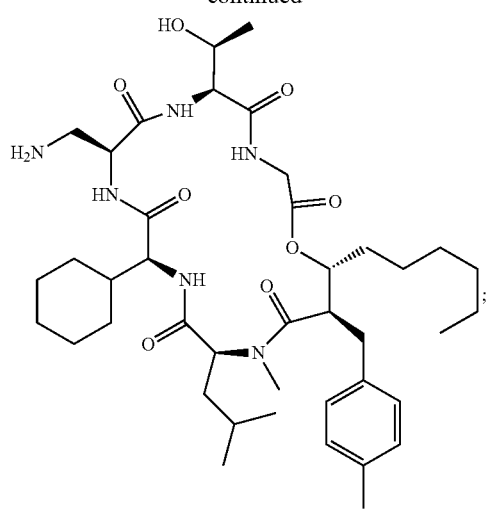
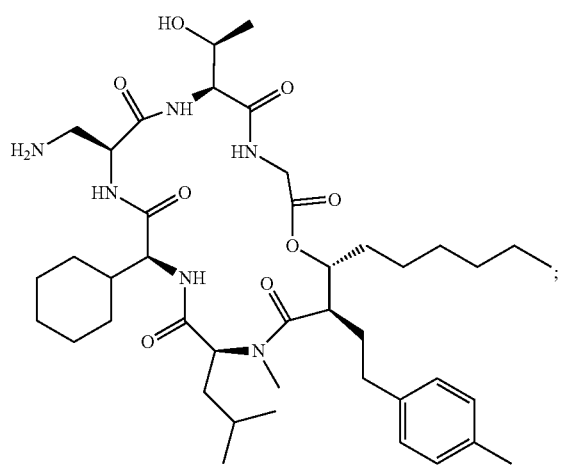
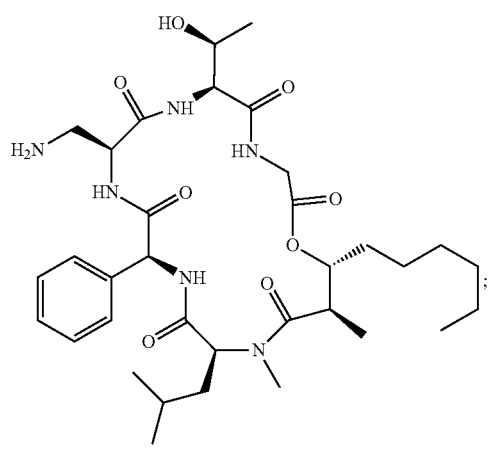
554
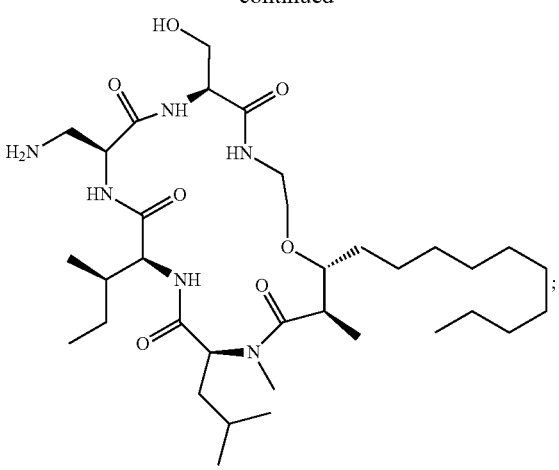
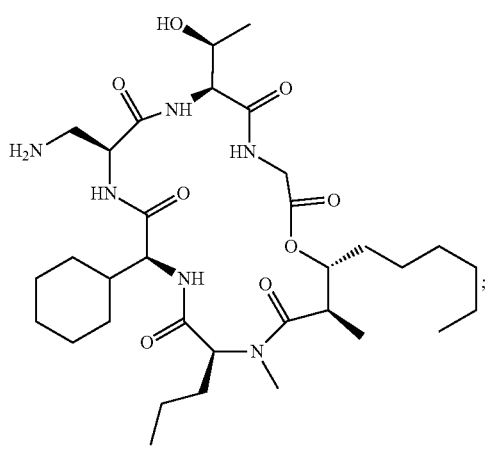
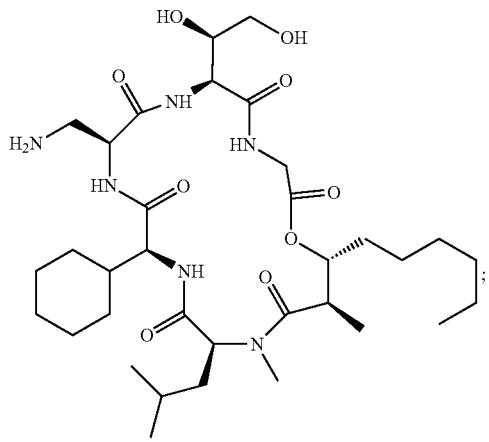

555
-continued
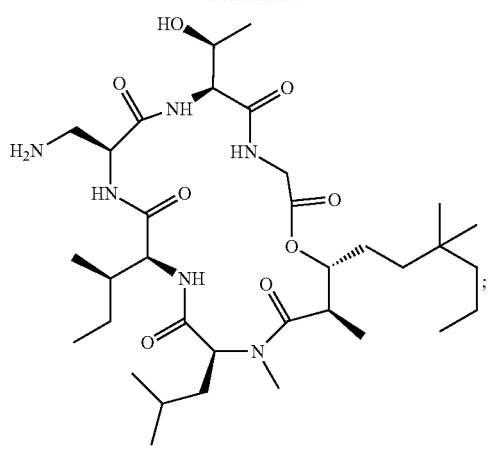
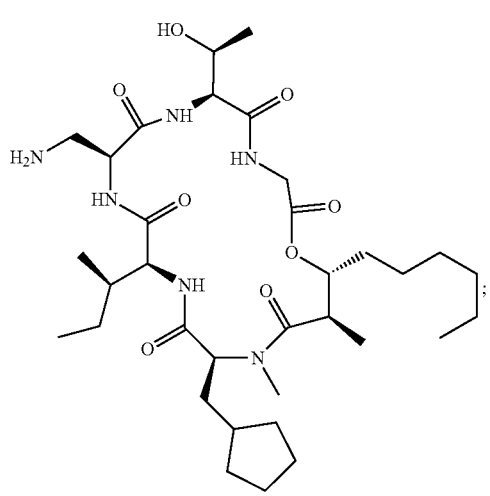
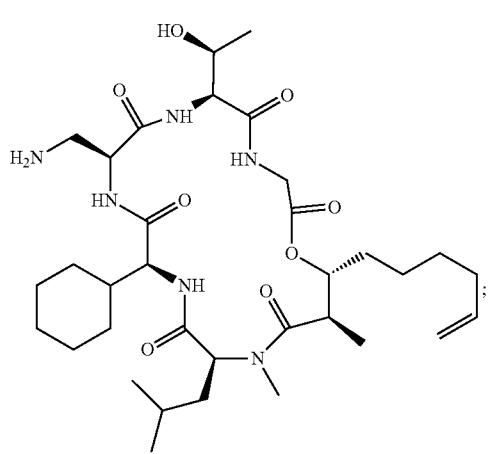
556
-continued
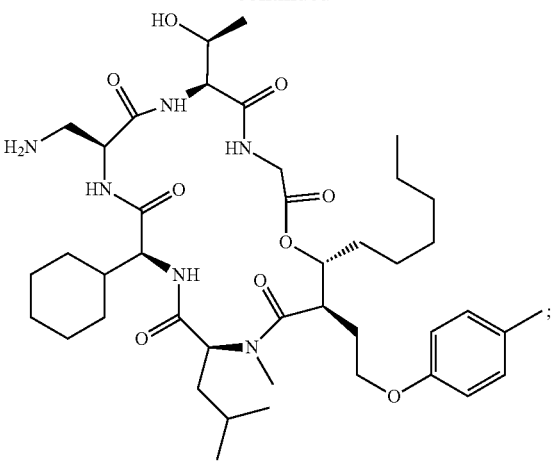
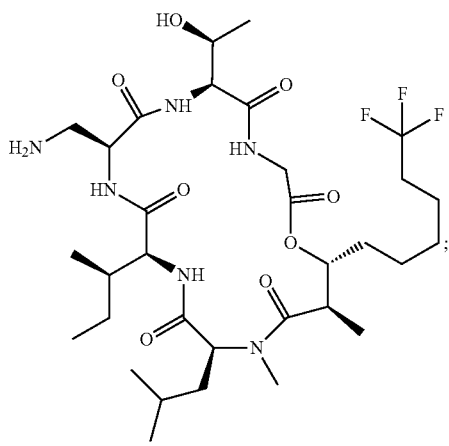
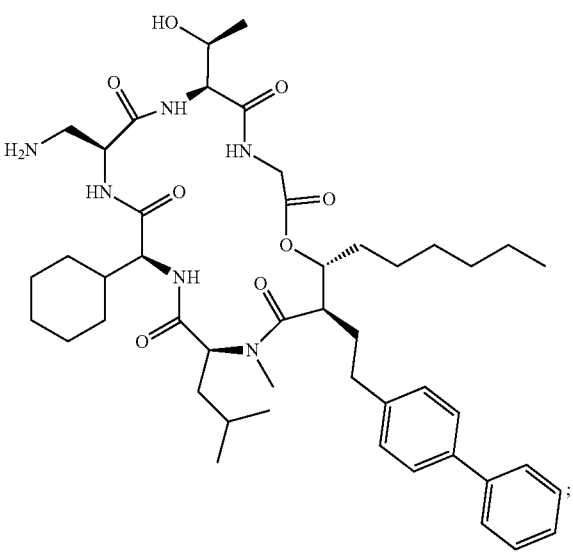

557
-continued
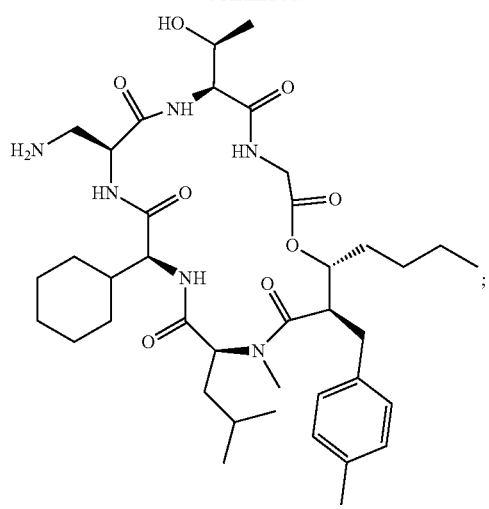
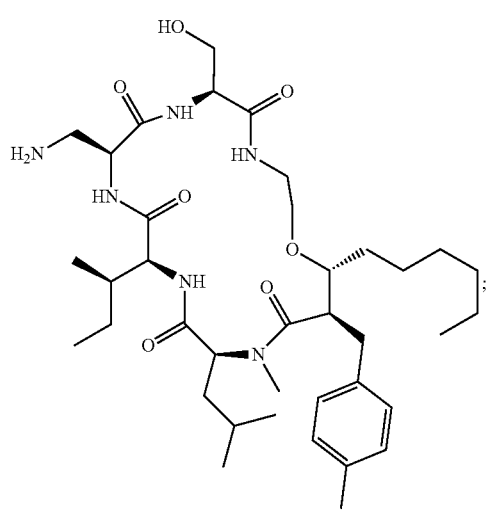
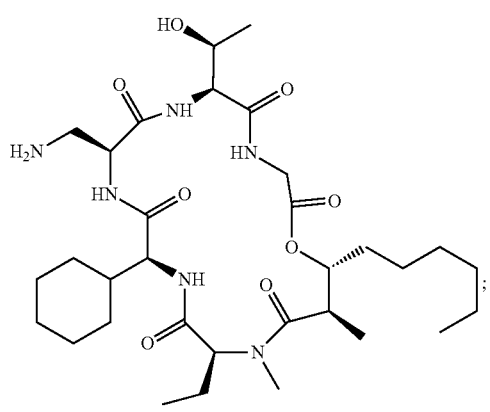
558
-continued
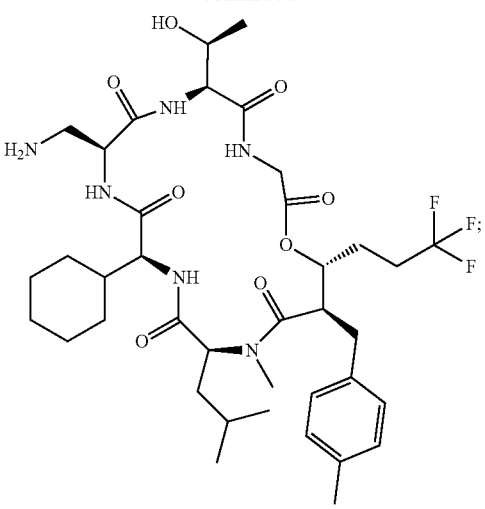
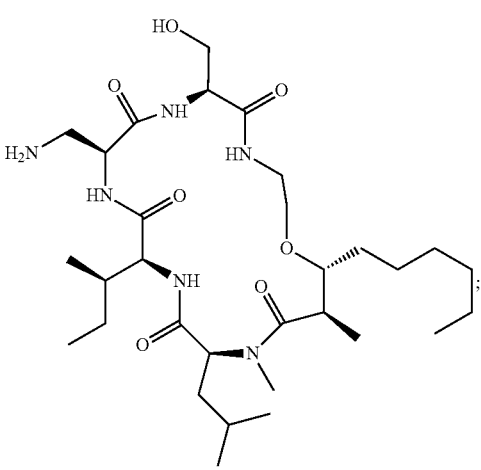
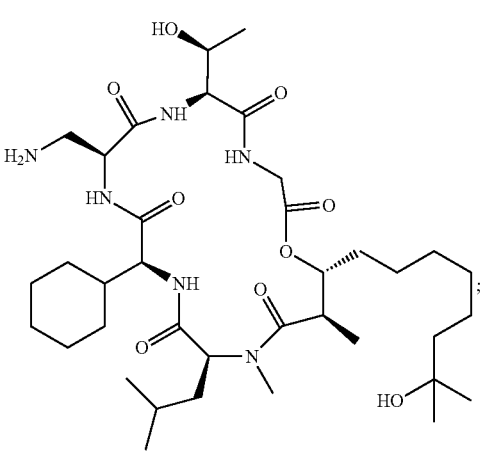

559
-continued
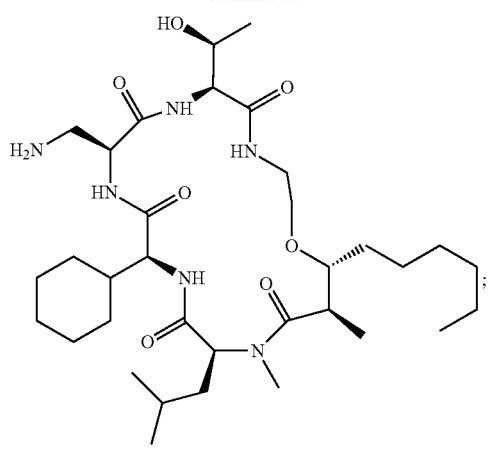
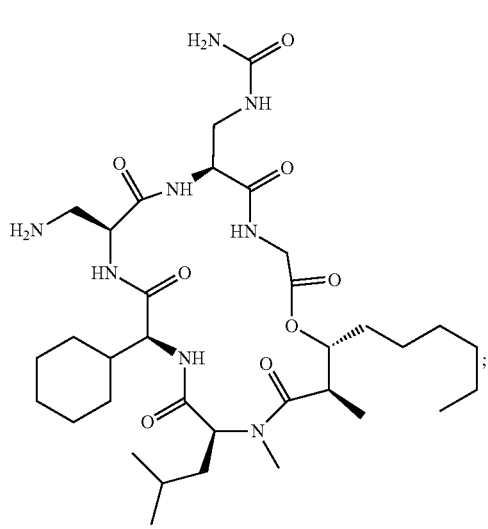
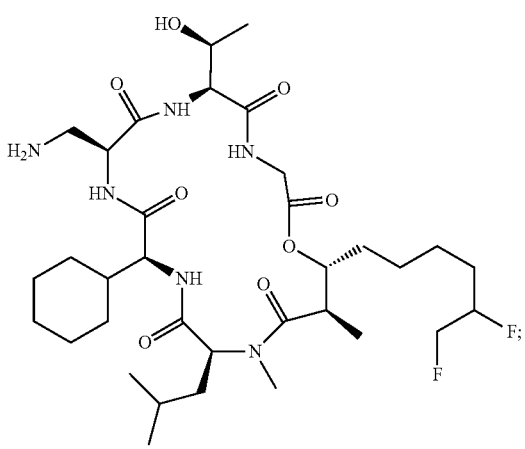
560
-continued
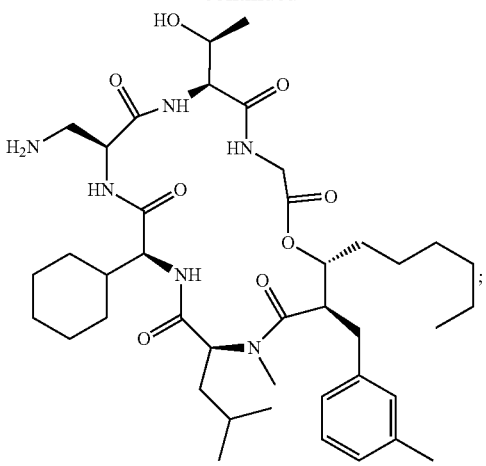
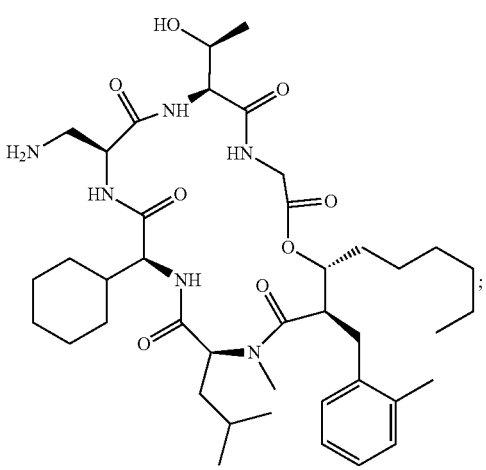
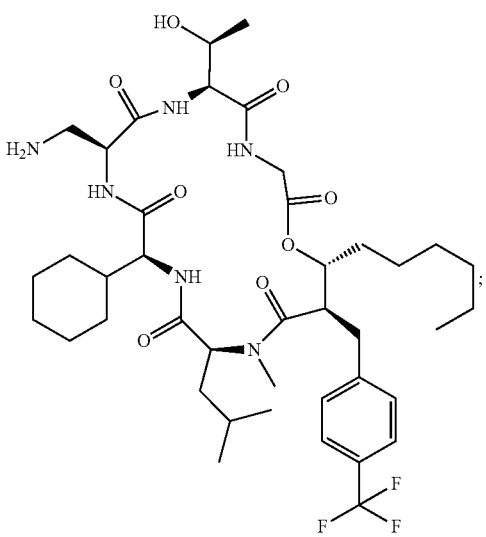

561
-continued
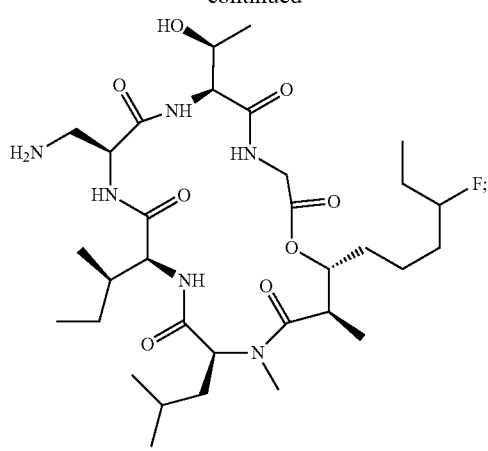
562
-continued
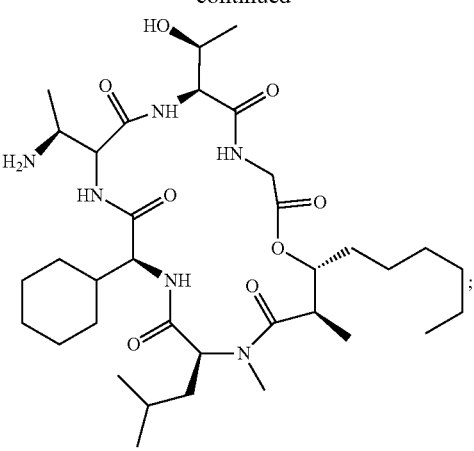
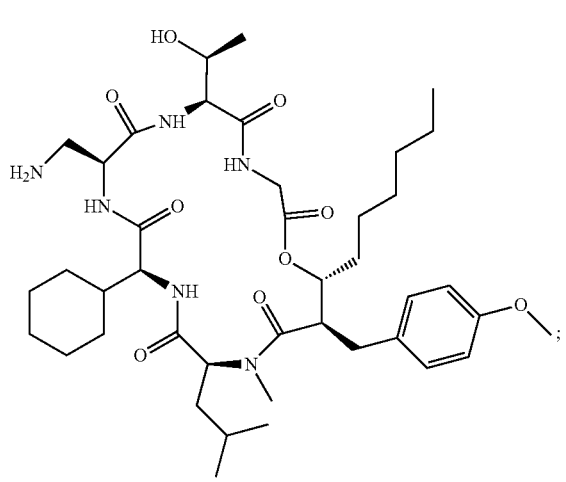
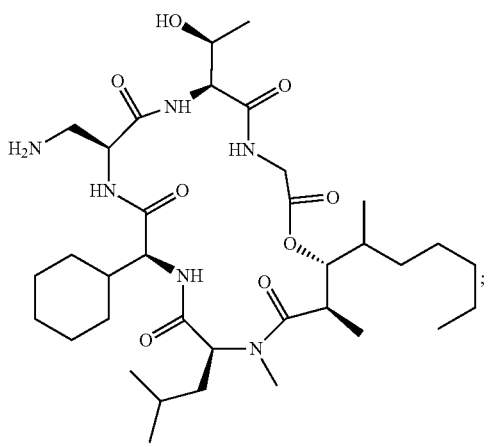
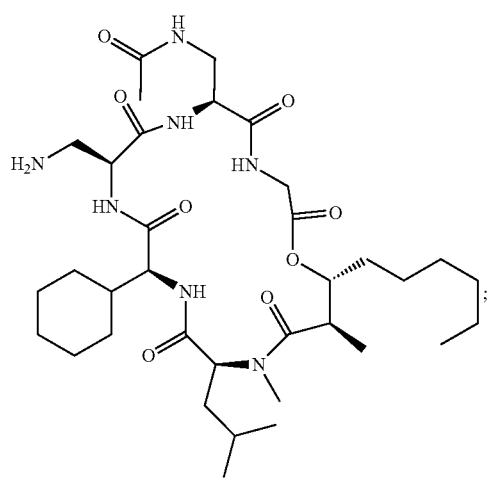
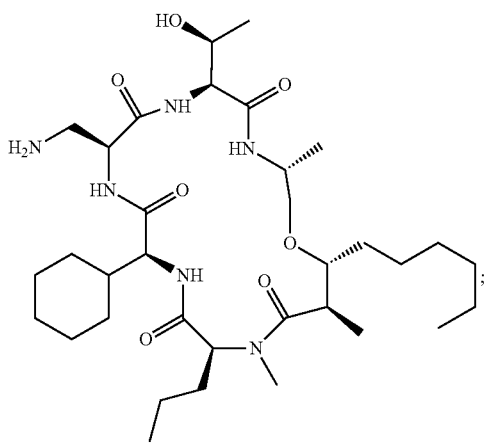

563
-continued
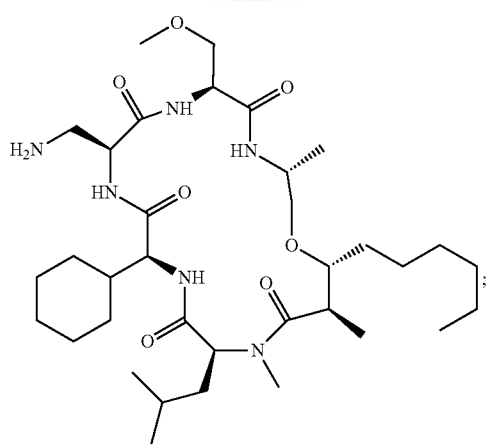
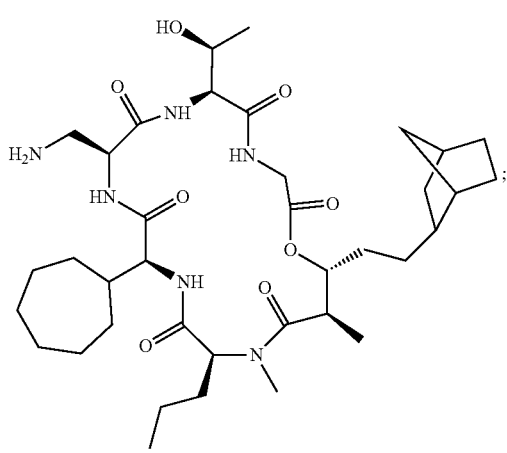
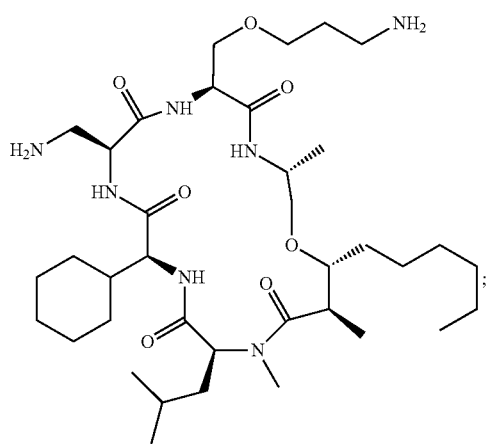
564
-continued
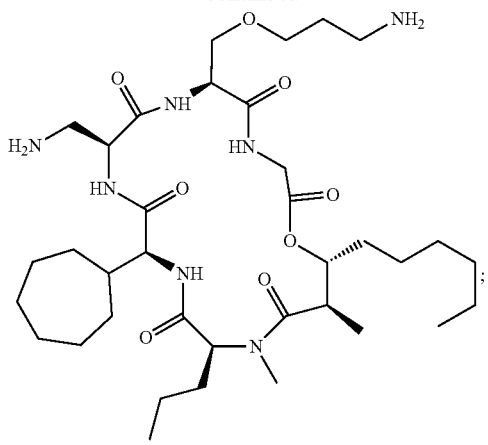
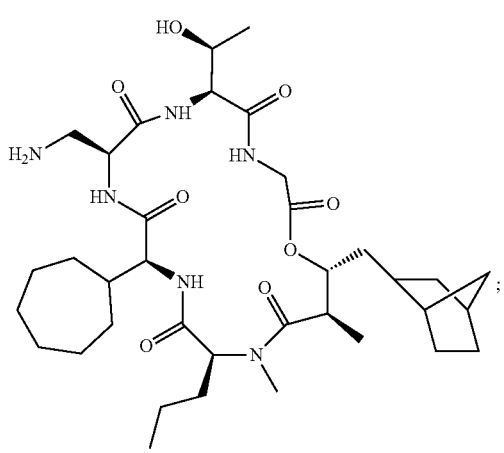
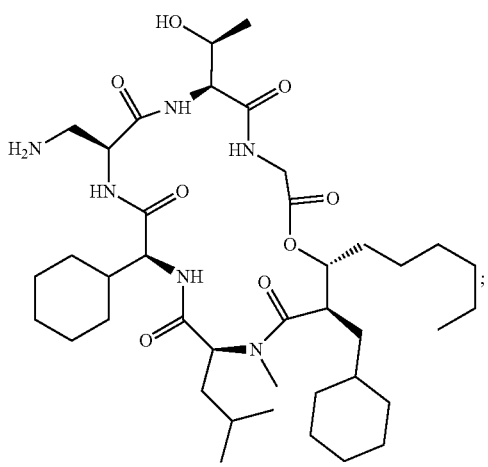

565
-continued
566
-continued
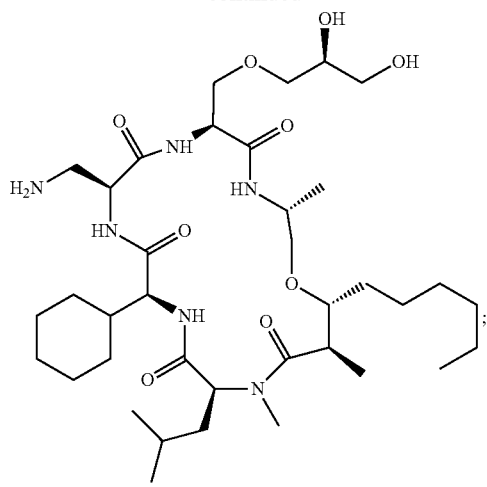
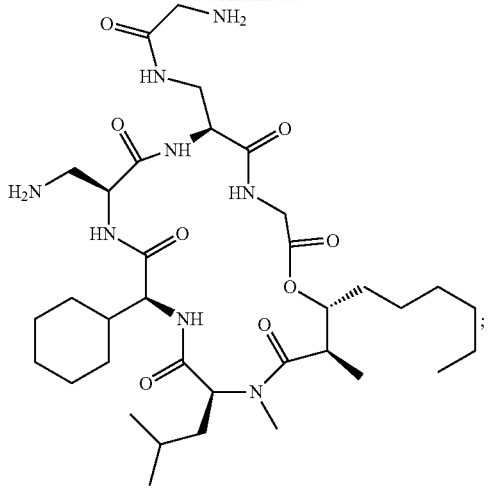
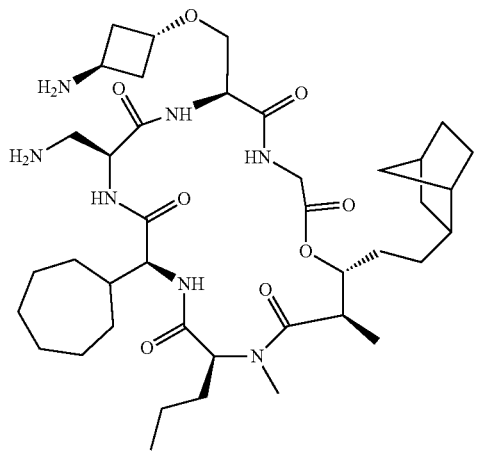
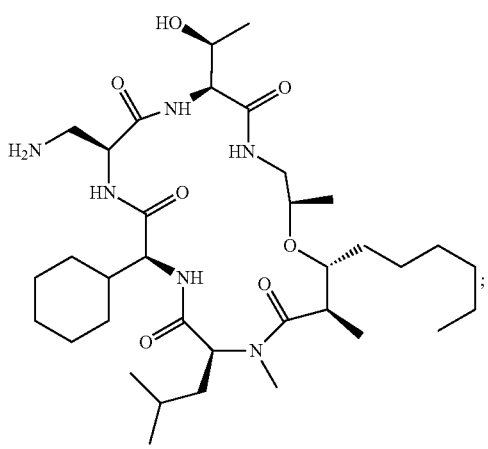
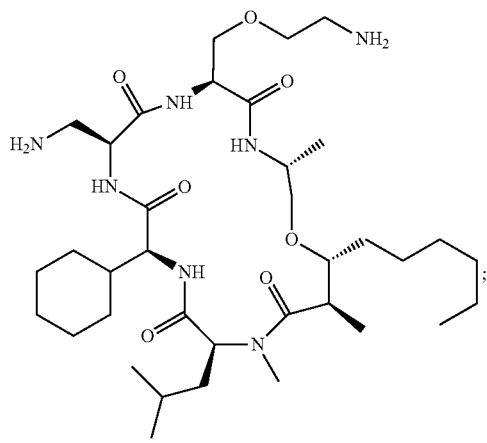

567
-continued
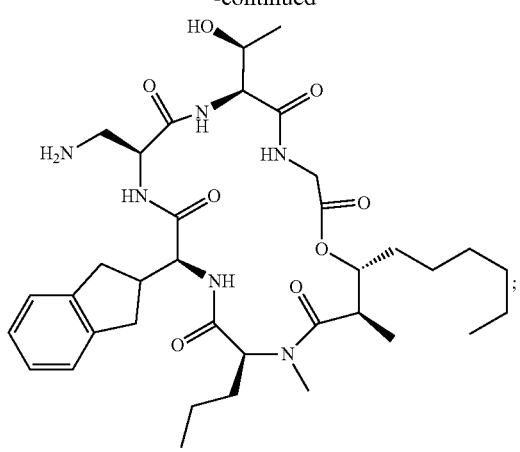
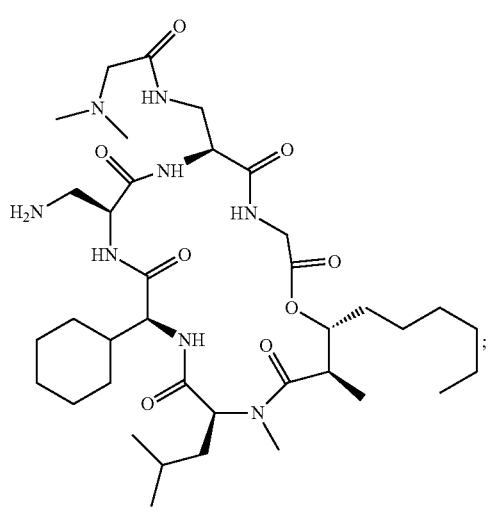
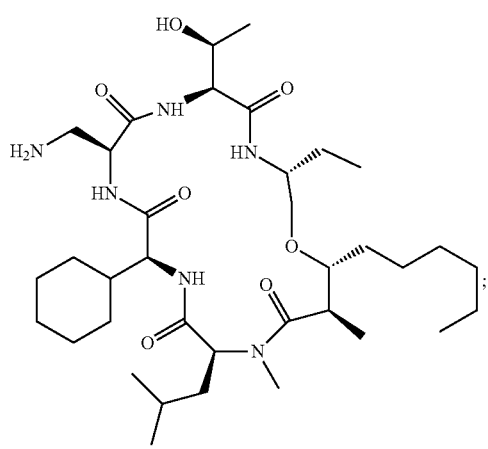
568
-continued
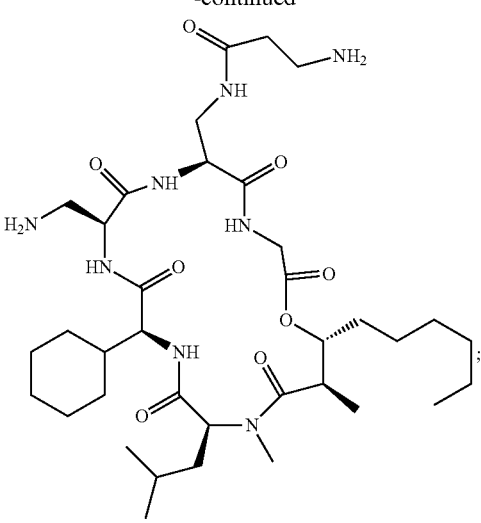
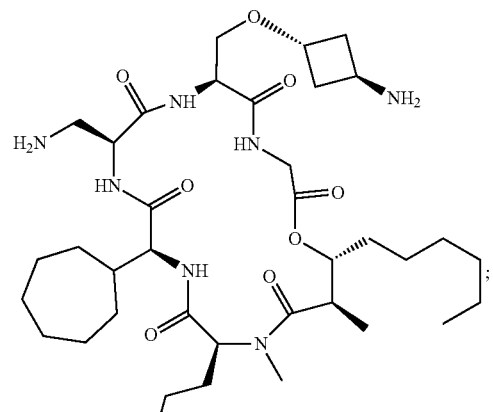
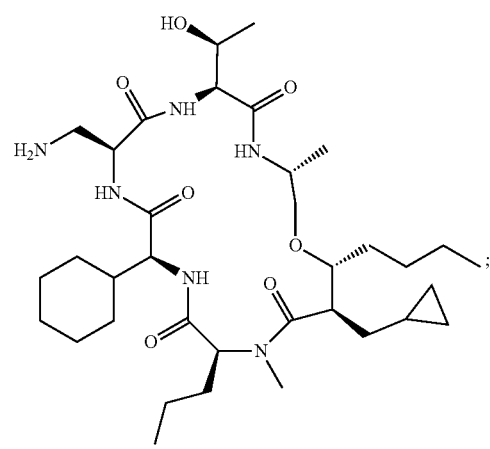

569
-continued
570
-continued
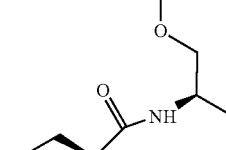

571
-continued
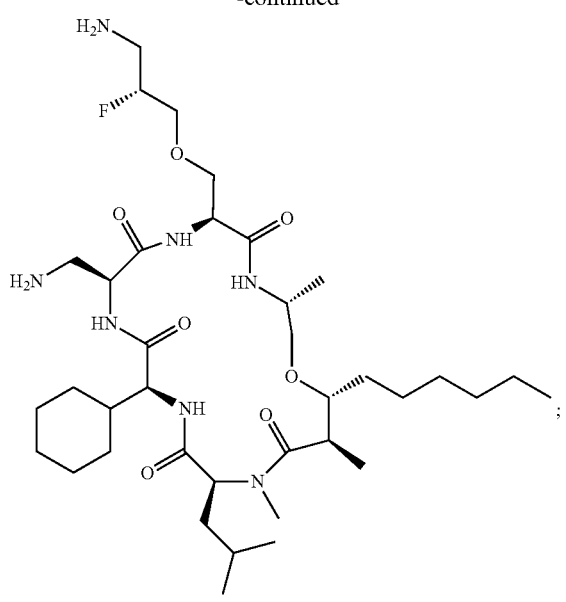
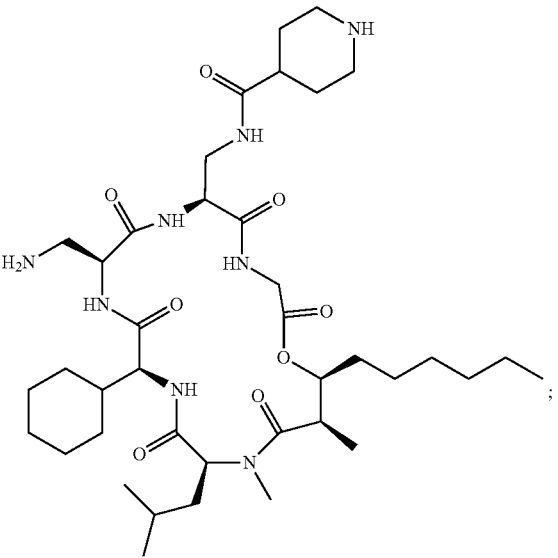
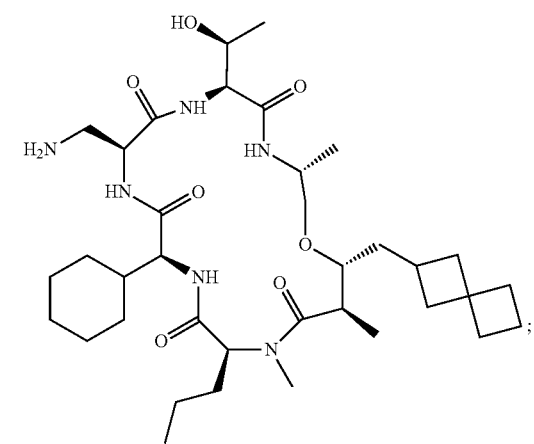
572
-continued
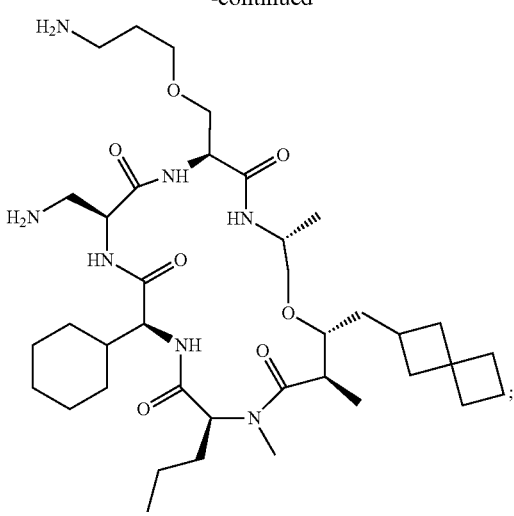
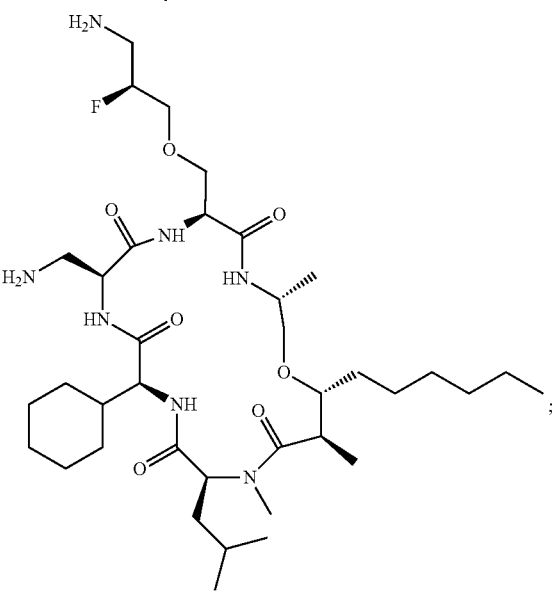
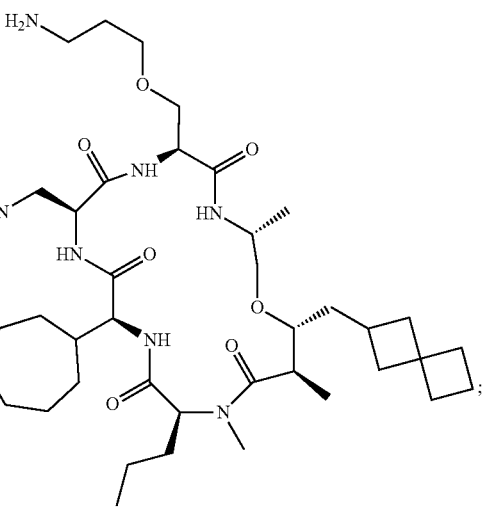

573
-continued
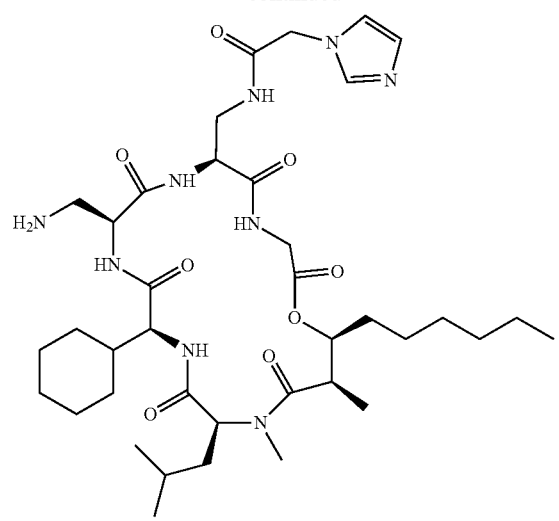
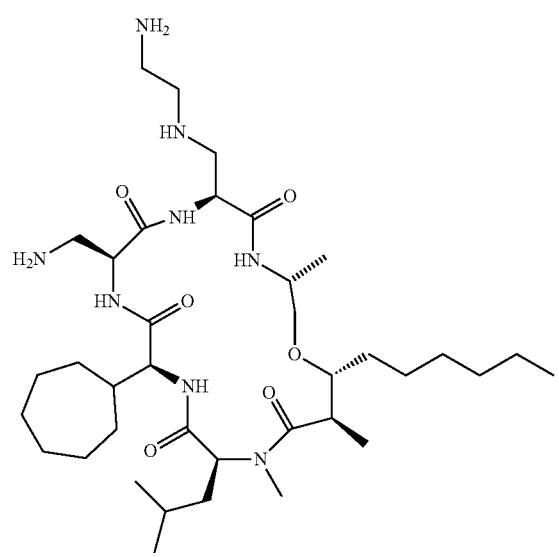
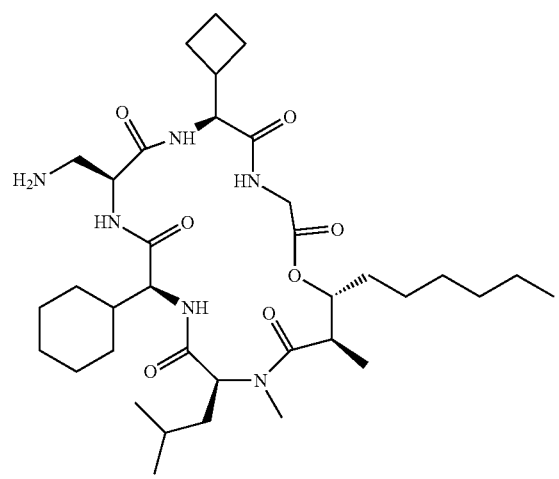
574
-continued
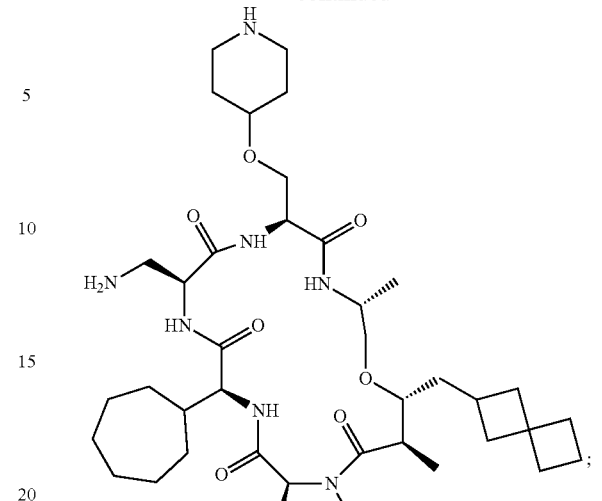
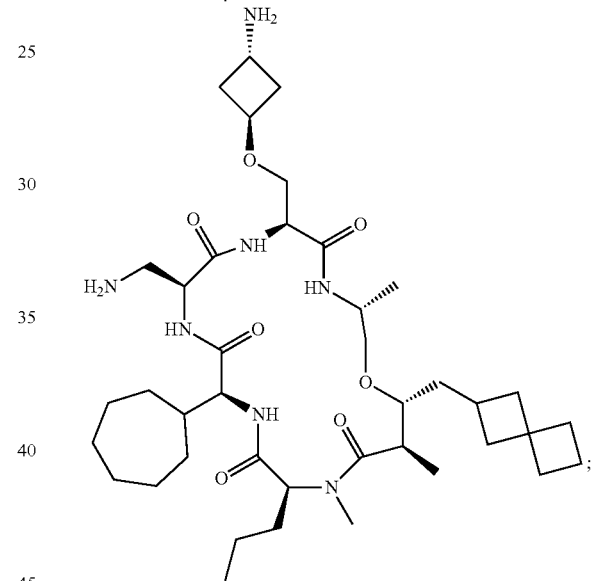
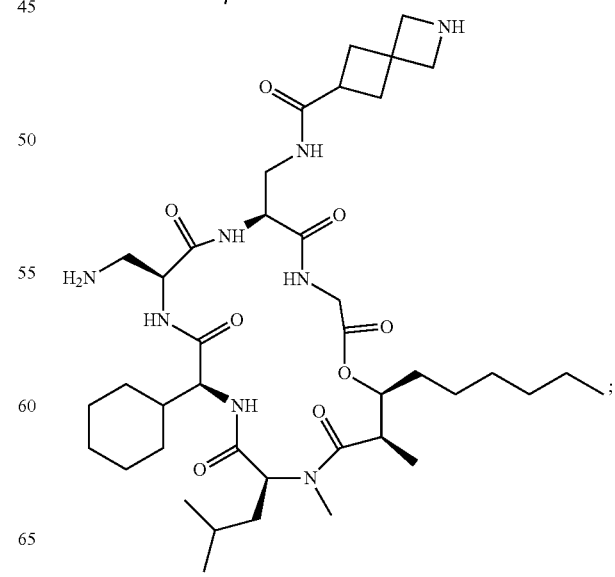

575
-continued
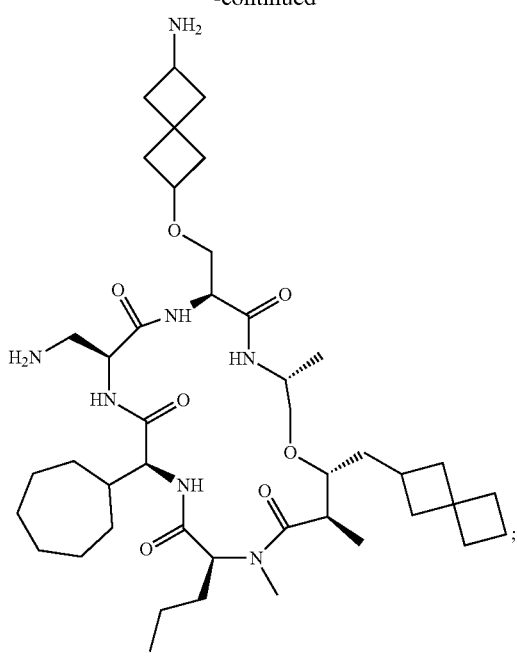
576
-continued
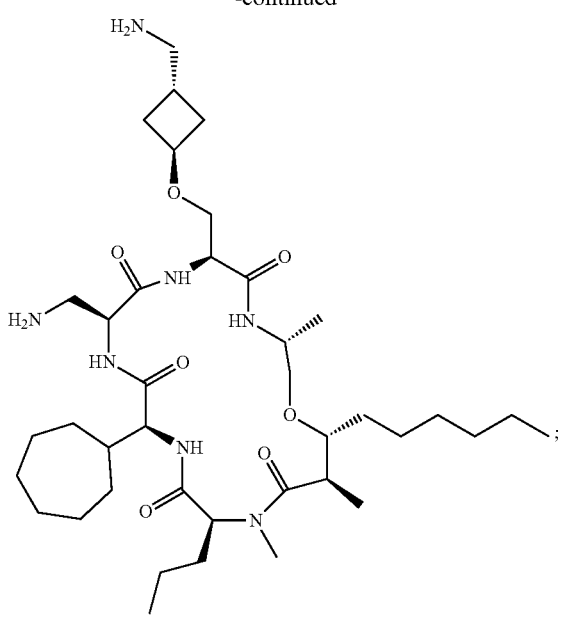
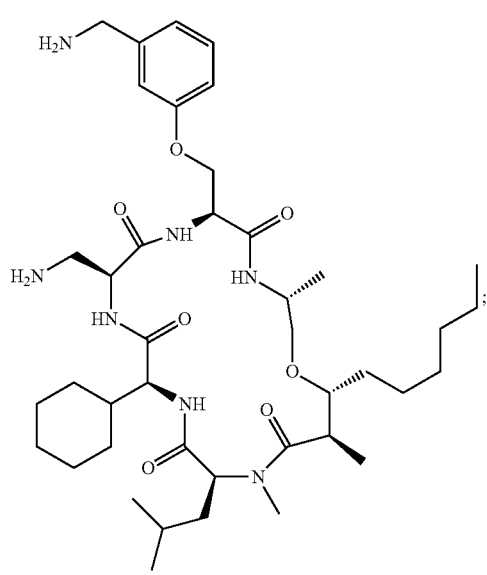
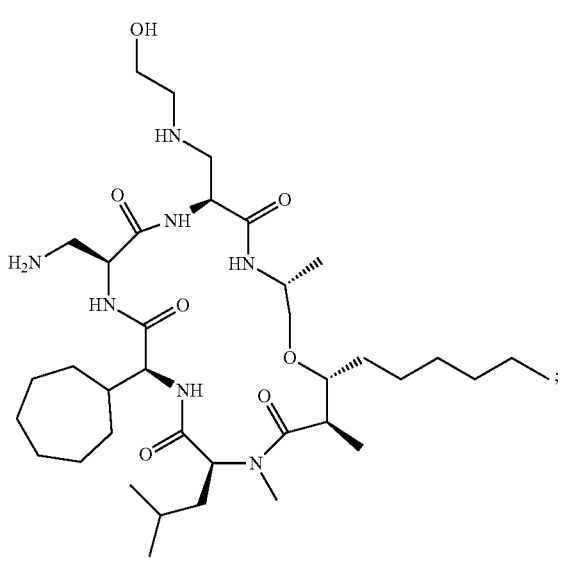

577
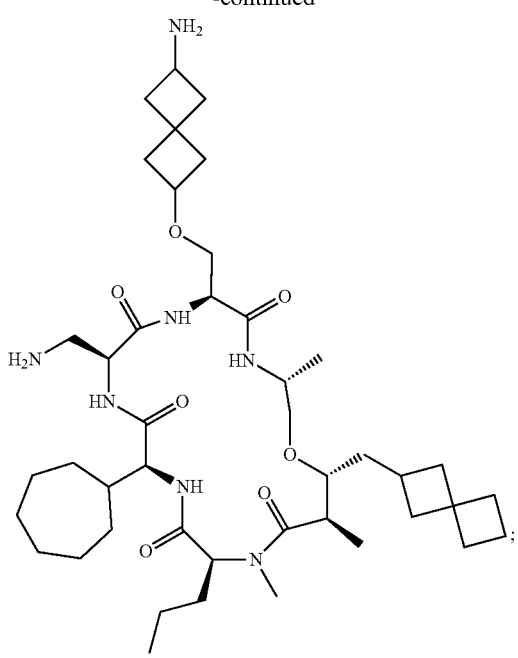
578
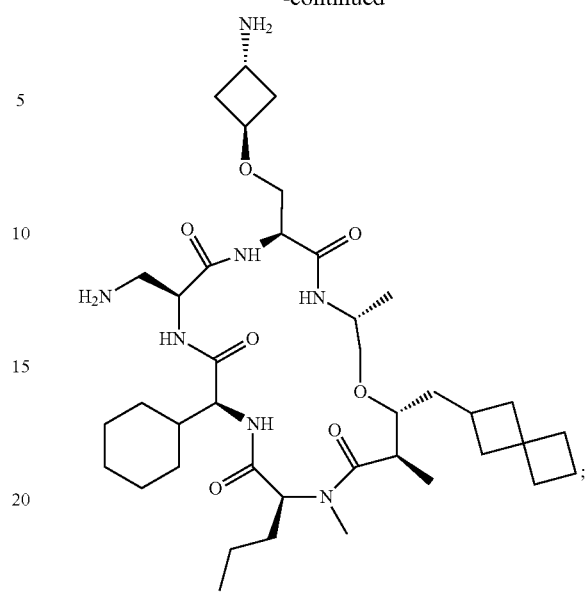
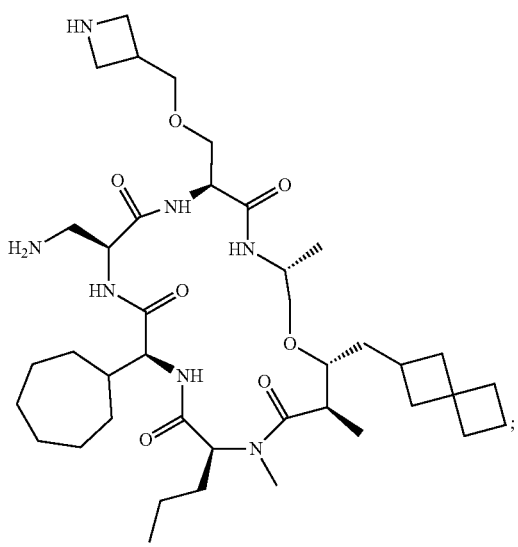
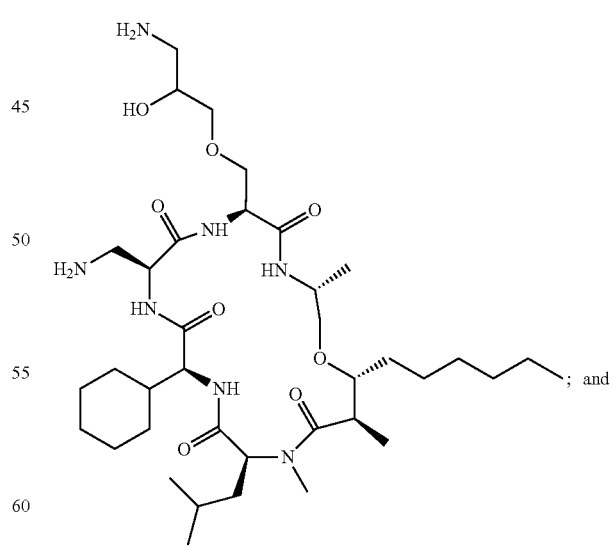
; and

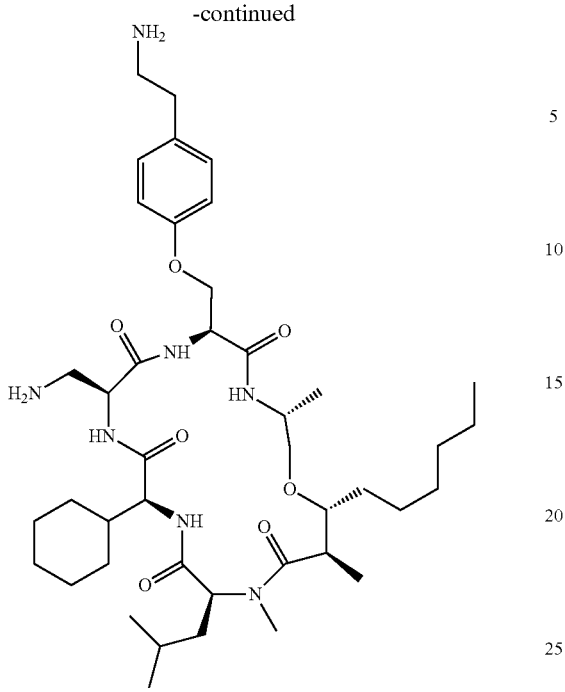
or an enantiomer or pharmaceutically acceptable salt thereof.
* * * * *